(12) United States Patent
Bramble, Jr. et al.

(10) Patent No.: US 8,003,398 B2
(45) Date of Patent: Aug. 23, 2011

(54) METHODS AND COMPOSITIONS FOR DETECTING GLYPHOSATE AND METABOLITES THEREOF

(75) Inventors: Frederick Q. Bramble, Jr., Rehoboth Beach, DE (US); Anne M. Pentz, Landenberg, PA (US)

(73) Assignee: E.I. de Pont de Nemours and Company, Wilmington, DE (US)

( * ) Notice: Subject to any disclaimer, the term of this patent is extended or adjusted under 35 U.S.C. 154(b) by 303 days.

(21) Appl. No.: 12/051,220

(22) Filed: Mar. 19, 2008

(65) Prior Publication Data

US 2008/0280370 A1 Nov. 13, 2008

Related U.S. Application Data

(60) Provisional application No. 60/908,336, filed on Mar. 27, 2007.

(51) Int. Cl.
*G01N 33/00* (2006.01)
(52) U.S. Cl. ......... 436/104; 436/103; 436/161; 436/173
(58) Field of Classification Search ........................ None
See application file for complete search history.

(56) References Cited

U.S. PATENT DOCUMENTS 4,517,303 A * 5/1985 Freytag et al. ................. 436/501
2005/0054871 A1 3/2005 Coleman

OTHER PUBLICATIONS

Alferness, P., et al. "Touchdown: Determination of Glyphosate and Aminomethylphosphonic Acid in Corn Grain, Corn Forage, and Corn Fodder by Gas Chromatography and Mass-Selective Detection", *Zeneca Ag Products Analytical Method RR 92-042B*, issued Apr. 3, 1993.
Castle, L. et al., "Discovery and Directed Evolution of a Glyphosate Tolerance Gene", *Science*, vol. 304, (2004), pp. 1151-1154.
Cowell, J., et al. "Validation of an Analytical Residue Method for Analysis of Glyphosate and Metabolite: An Interlaboratory Study",*J. Agric. Food Chem.*, vol. 34, (1986), pp. 955-960.

(Continued)

*Primary Examiner* — Yelena G Gakh
*Assistant Examiner* — David Weisz
(74) *Attorney, Agent, or Firm* — Alston & Bird LLP

(57) ABSTRACT

The present invention provides various methods and compositions which allow for determining the presence or amount of glyphosate, N-acetylglyphosate, N-acetyl AMPA or aminomethyl phosphoric acid (AMPA) and its various metabolites in a variety of test matrices. In one method, determining the presence or amount of N-acetylglyphosate and/or N-acetyl AMPA in a test sample comprises providing the test sample suspected of containing N-acetylglyphosate and/or N-acetyl AMPA; extracting the N-acetylglyphosate and/or N-acetyl AMPA from the test sample; and, detecting the N-acetylglyphosate and/or N-acetyl AMPA in the extract. In other methods, the presence or amount of at least one of glyphosate, N-acetylglyphosate, N-acetyl AMPA or aminomethyl phosphonic acid (AMPA) or a metabolite thereof in a test sample is determined. The method comprises providing the test sample suspected of containing at least one of glyphosate, N-acetylglyphosate, N-acetyl AMPA or AMPA or a metabolite thereof, extracting from the test sample at least one of the glyphosate, N-acetylglyphosate, N-acetyl AMPA or AMPA; and, detecting at least one of the glyphosate, the N-acetylglyphosate, the N-acetyl AMPA and the AMPA from the test sample; wherein detection of the glyphosate, N-acetylglyphosate, N-acetyl AMPA or AMPA occurs without derivatization of the glyphosate, the N-acetylglyphosate, N-acetyl AMPA or the AMPA.

60 Claims, 85 Drawing Sheets

OTHER PUBLICATIONS

Granby, K., et al., "Investigation of the Herbicide Glyphosate and the Plant GrowthRegulators Chlormequat and Mepiquat in Cereals Produced in Denmark", *Food Additives and Contaminants*, vol. 18, No. 10, Jan. 1, 2001, pp. 898-905.

Roos, C., "Bestimmung von Pestiziden in Flusswasser im ng/L- und sub-ng/L-Bereich mittals Flussigchromatographic-Tandem-Massenspektrometrie (LC-MS/MS)-Verfahrensentwicklung, Validierung und Anwendung fur die Untersuchung der Elbe", *GKSS* [*Online*], 2003, http://dvsun3.gkss.de/berichte/gkss_berichte_2003/GKSS_2003_29.pdf Their, H.-P, and Kirchhoff, J., "Manual of Pesticide Residue Analysis vol. I and II", [Online], 1989, ISBN 3-527-27017-5, www.bfr.bund.de/cd/1652.

* cited by examiner

N-ACETYLGLYPHOSATE FULL-SCAN SPECTRUM

N-ACETYLGLYPHOSATE FULL-SCAN MRM SPECTRA

N-Acetyl AMPA Full-Scan Spectrum

N-Acetyl AMPA Full-Scan MRM Spectrum

*Glyphosate, N-acetylglyphosate, and N-acetyl AMPA Calibration Standards, 0.5–50 ng/mL*

*AMPA Calibration Standards, 0.5–50 ng/mL*

*Soybean Meal LOQ Fortification Sample (SM-032406-2 LOQ 1)*

*Glyphosate (34/1, s/n)*

$$\frac{3/1}{34/1} \times 0.045 \text{ mg/kg found} = 0.004 \text{ mg/kg}$$

*N-acetyl AMPA*

$$\frac{3/1}{48/1} \times 0.103 \text{ mg/kg found} = 0.006 \text{ mg/kg}$$

*N-acetylglyphosate (20/1, s/n)*

$$\frac{3/1}{20/1} \times 0.037 \text{ mg/kg found} = 0.006 \text{ mg/kg}$$

*AMPA (18/1, s/n)*

$$\frac{3/1}{18/1} \times 0.043 \text{ mg/kg found} = 0.007 \text{ mg/kg}$$

N-acetyl AMPA Full-Scan Spectrum

N-acetyl AMPA Full-Scan MRM Spectrum 0.25-20 ng/mL CALIBRATION STANDARDS FROM (25-JUN-07)

0.5-50 ng/mL CALIBRATION STANDARDS (17-APR-07)

Muscle Validation LOQ Fort (Sciex API-5000, negative ion mode

Muscle Validation 10 x LOQ Fort (Sciex API-5000, negative ion mode)

*Milk Matrix*

*Egg Matrix*

Glyphosate $$\frac{3/1}{22.06/1} \times 0.022 \text{ mg/kg} = 0.003 \text{ mg/kg}$$

N-acetylglyphosate $$\frac{3/1}{9.67/1} \times 0.026 \text{ mg/kg} = 0.008 \text{ mg/kg}$$

AMPA $$\frac{3/1}{14.17/1} \times 0.027 \text{ mg/kg} = 0.006 \text{ mg/kg}$$

N-acetyl AMPA $$\frac{3/1}{10.40/1} \times 0.025 \text{ mg/kg} = 0.007 \text{ mg/kg}$$

Liver Matrix

Glyphosate $$\frac{3/1}{17.80/1} \times 0.052 \text{ mg/kg} = 0.009 \text{ mg/kg}$$

N-acetylglyphosate $$\frac{3/1}{8.36/1} \times 0.049 \text{ mg/kg} = 0.018 \text{ mg/kg}$$

AMPA $$\frac{3/1}{7.93/1} \times 0.050 \text{ mg/kg} = 0.019 \text{ mg/kg}$$

N-acetyl AMPA $$\frac{3/1}{16.47/1} \times 0.046 \text{ mg/kg} = 0.008 \text{ mg/kg}$$

*Kidney Matrix*

Glyphosate $$\frac{3/1}{43.18/1} \times 0.058 \text{ mg/kg} = 0.004 \text{ mg/kg}$$

N-acetylglyphosate $$\frac{3/1}{10.73/1} \times 0.049 \text{ mg/kg} = 0.014 \text{ mg/kg}$$

AMPA $$\frac{3/1}{12.30/1} \times 0.038 \text{ mg/kg} = 0.009 \text{ mg/kg}$$

N-acetyl AMPA $$\frac{3/1}{17.08/1} \times 0.046 \text{ mg/kg} = 0.008 \text{ mg/kg}$$

*Fat Matrix*

Glyphosate $$\frac{3/1}{11.26/1} \times 0.030 \text{ mg/kg} = 0.008 \text{ mg/kg}$$

*N*-acetylglyphosate $$\frac{3/1}{10.98/1} \times 0.056 \text{ mg/kg} = 0.015 \text{ mg/kg}$$

AMPA $$\frac{3/1}{9.97/1} \times 0.049 \text{ mg/kg} = 0.015 \text{ mg/kg}$$

*N*-acetyl AMPA $$\frac{3/1}{16.37/1} \times 0.048 \text{ mg/kg} = 0.009 \text{ mg/kg}$$

*Muscle Matrix*

Glyphosate $$\frac{3/1}{17.71/1} \times 0.022 \text{ mg/kg} = 0.004 \text{ mg/kg}$$

N-acetylglyphosate $$\frac{3/1}{12.31/1} \times 0.026 \text{ mg/kg} = 0.006 \text{ mg/kg}$$

AMPA $$\frac{3/1}{17.68/1} \times 0.050 \text{ mg/kg} = 0.008 \text{ mg/kg}$$

N-acetyl AMPA $$\frac{3/1}{10.72/1} \times 0.023 \text{ mg/kg} = 0.006 \text{ mg/kg}$$

_US 8,003,398 B2_

METHODS AND COMPOSITIONS FOR DETECTING GLYPHOSATE AND METABOLITES THEREOF

CROSS-REFERENCE TO RELATED APPLICATIONS

The application claims priority to U.S. Provisional Application No. 60/908,336 filed Mar. 27, 2007, which is herein incorporated by reference.

FIELD OF THE INVENTION

The invention relates to the detection of the presence or the amount of glyphosate and/or its metabolites in a variety of test matrices.

BACKGROUND OF THE INVENTION

Glyphosate (DPX-B2856) is an active ingredient in nonselective herbicides which are widely used on crops that have been genetically modified for resistance to the herbicidal activity. Glyphosate inhibits the EPSPS (enolpyruvylshikimate-3-phosphate synthase) enzyme required for the biosynthesis of aromatic amino acids in plants. Crop tolerance to glyphosate herbicides has been achieved by genetic modification of the plant with microbially derived EPSPS (enolpyruvylshikimate-3-phosphate synthase), GOX (glyphosate oxidoreductase), and glyat (glyphosate N-acetyltransferase) enzyme variants in plants. EPSPS variants disrupt the activity of glyphosate on the EPSPS enzyme, leaving intact glyphosate in the plant. GOX variants detoxify glyphosate by decarboxylation to AMPA. Glyat variants provide a new mode of glyphosate detoxification through enzymatic acetylation of the glyphosate molecule to form the non-phytotoxic metabolite N-acetylglyphosate. See, for example, Castle et al. (2004) *Science* 304:1151-1154. Regulatory monitoring for the presence and amount of glyphosate and glyphosate metabolites in a variety of test matrices including various animal and plant matrices are needed.

BRIEF SUMMARY OF THE INVENTION

The present invention provides methods and compositions which allow for the determination of the presence or the amount of glyphosate and its metabolites, derivatives or degradate residues in a variety of test matrices. The relevant glyphosate metabolites degradates included in the analytical method are N-acetylglyphosate, N-acetylaminomethylphosphonic acid (N-acetyl AMPA) and aminomethyl phosphonic acid (AMPA). N-acetylglyphosate and N-acetyl AMPA are novel glyphosate metabolites found in genetically modified plants containing a glyat (glyphosate N-acetyltransferase) gene. In one method, determining the presence or amounts of N-acetylglyphosate and/or N-acetyl AMPA in a test sample comprises providing the test sample suspected of containing N-acetylglyphosate and/or N-acetyl AMPA; extracting a composition comprising the N-acetylglyphosate and/or N-acetyl AMPA from the test sample; and, detecting the N-acetylglyphosate and/or N-acetyl AMPA in the composition.

In other methods, the presence or amount of at least one of glyphosate, N-acetylglyphosate, N-acetyl AMPA and/or AMPA or a metabolite thereof in a test sample is determined. This method comprises providing the test sample suspected of containing at least one of glyphosate, N-acetylglyphosate, N-acetyl AMPA or AMPA or a metabolite thereof; extracting from the test sample a composition comprising at least one of the glyphosate, N-acetylglyphosate, N-acetyl AMPA or AMPA, or a metabolite thereof, and, detecting at least one of the glyphosate, N-acetylglyphosate, N-acetyl AMPA or AMPA or a metabolite thereof. In specific embodiments, the detection of the glyphosate, N-acetylglyphosate, N-acetyl AMPA or AMPA occurs without derivatization of the glyphosate, N-acetylglyphosate, N-acetyl AMPA or AMPA.

DETAILED DESCRIPTION OF THE INVENTION

Figure 1:
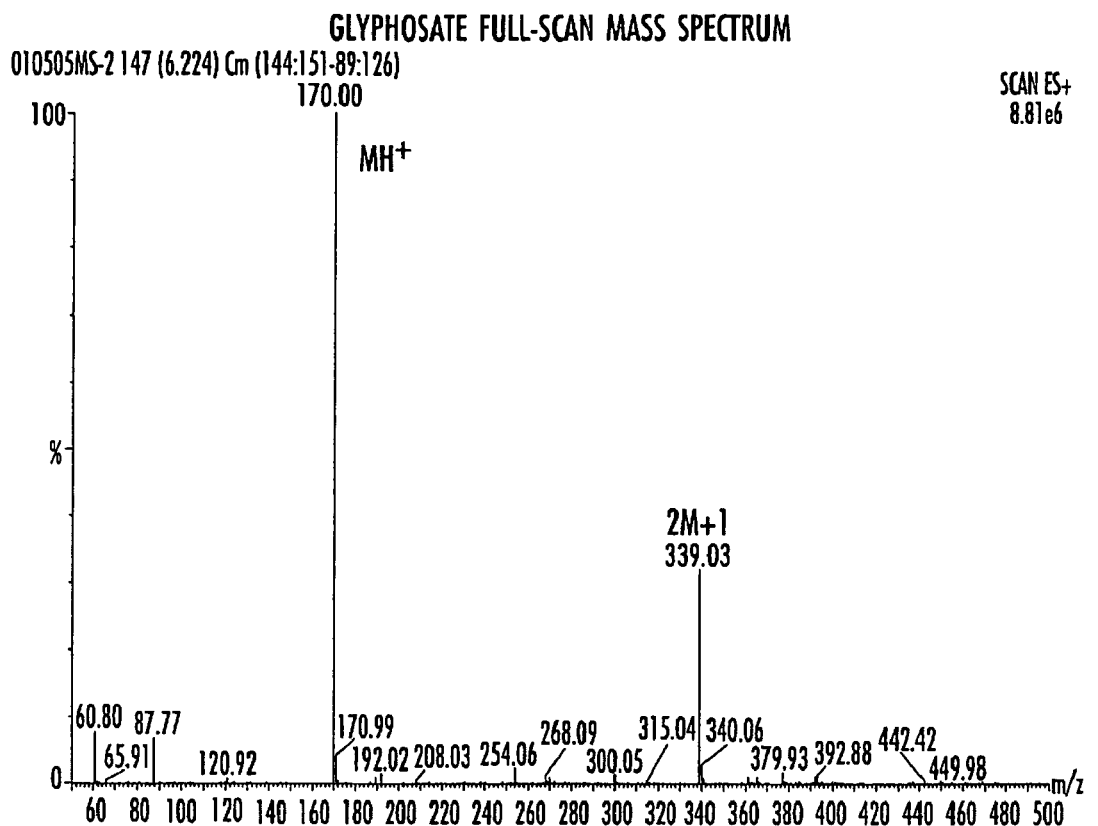
FIG. 1 provides representative glyphosate mass spectra.
Figure 1:
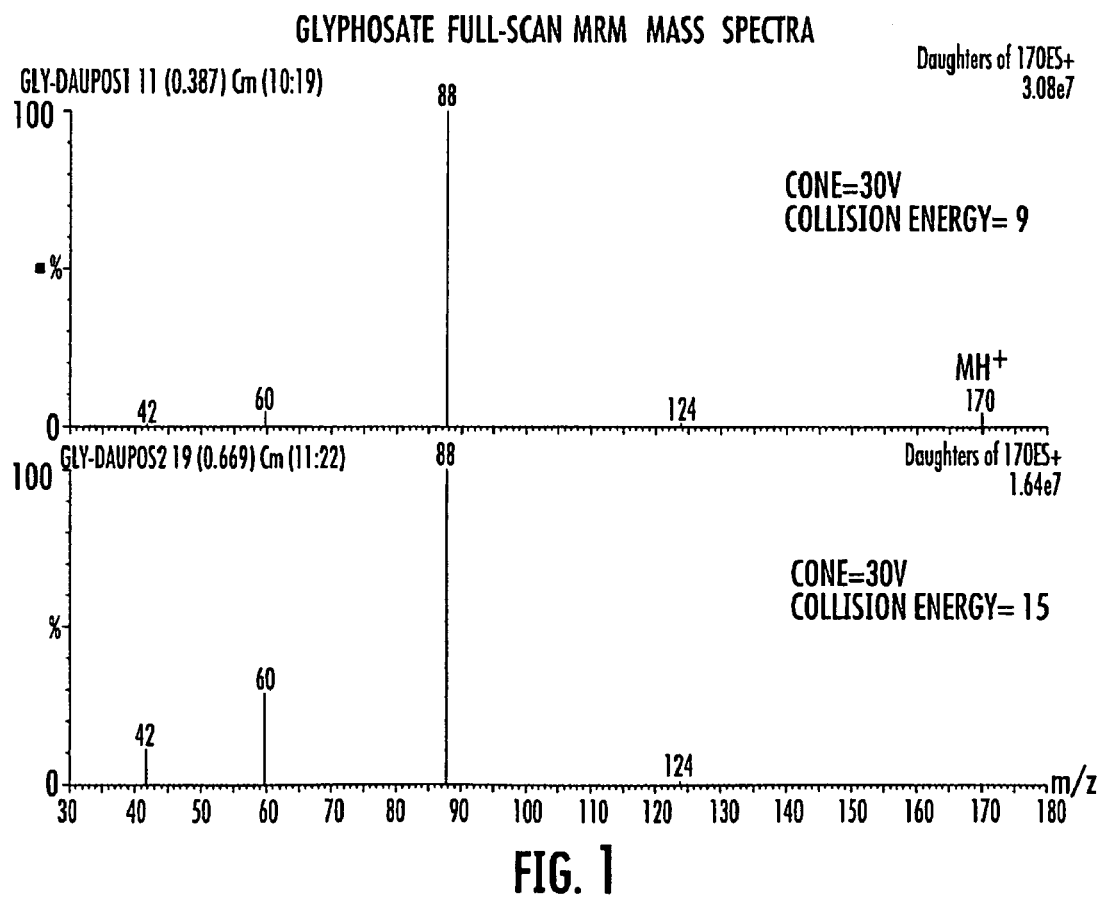

The presently disclosed subject matter now will be described more fully hereinafter with reference to the accompanying drawings, in which some, but not all embodiments of the presently disclosed subject matter are shown. Indeed, the presently disclosed subject matter can be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims. Although specific terms are employed herein, they are used in a generic and descriptive sense only and not for purposes of limitation.

I. Overview

The present invention provides methods and compositions which allow for the determination of the presence or the amount of glyphosate and its metabolites and/or degradate residues in a variety of test matrices. Analytical methods exist for the analysis of glyphosate and AMPA in plants. See, for example, Cowell et al. (1986) *J. Agric. Food Chem.* 34:955-960; Alferness et al. (Apr. 3, 1993) "Touchdown: Determination of Glyphosate and Aminomethylphosphonic Acid in Corn Grain, Corn Forage, and Corn Fodder by Gas Chromatography and Mass-Selective Detection." Zeneca Ag Products Analytical Method RR 92-042B, available at U.S. EPA Pesticides: Analytical Methods & Procedures website (www.epa.gov/oppbead1/methods/ram12b.htm); and, Method No. 405 in Manual of Pesticide Residue Analysis Volume I and II available from BfR Federal Institute for Risk Assessment, official analytical methods for residues of plant protection products and pesticides (L 00.00 16) (www.bfr.bund.de/cd/1652). Such methods analyze glyphosate and AMPA only and further require analyte derivatization for detection. The methods and compositions of the present invention allow for the detection and/or quantitation of the new glyat metabolites, N-acetylglyphosate and N-acetyl AMPA, and further provide a combined, highly specific residue method for the quantitative and confirmatory analysis of glyphosate and relevant metabolites using LC/MS/MS technology without analyte derivatization. Further provided are novel methods for purifying glyphosate from various metabolites, such as from AMPA. Moreover, the methods and compositions of the instant invention further improve the overall response and linearity of glyphosate detection and/or its metabolites by employing a weak ion-pairing reagent, such as phosphoric acid, to prepare the final samples and standard solutions employed in the LC/MS/MS technology. In addition, the methods can employ extraction methods using an aqueous methanol/dilute acid solution that allow for an acceptable analyte extraction efficiency and can further employ the use of mass spectroscopy in positive ion mode. And finally, commercially available stable isotopes for glyphosate and AMPA can be used in the methods and compositions of the present invention as internal standards to normalize LC/MS/MS response for matrix effects. Thus, the novel methods and compositions of the present invention offer robust quantitative analysis of glyphosate, N-acetylglyphosate, N-acetyl AMPA and AMPA without matrix effects.

As used herein, an analyte of interest comprises at least one of glyphosate, N-acetylglyphosate, AMPA, and/or N-acetyl AMPA. As used herein the terms "glyphosate" or "N-(phosphonomethyl)glycine" refers to a compound having formula (I) as set forth below.

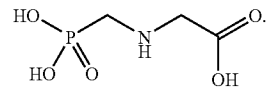

The term "N-acetylglyphosate" or "N-Acetyl-N-(phosphonomethyl)glycine" refers to a compound having formula (II) as set forth below.

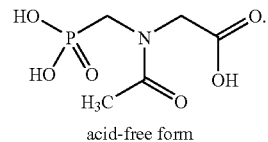

acid-free form

The term "AMPA" or "aminomethyl phosphonic acid" or "1-aminomethylphosphonic acid" refers to a compound having formula (III) as set forth below.

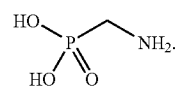

The term "N-acetyl AMPA" or "(Acetamidomethyl)phosphonic acid" or "N-Acetylaminomethylphosphonic acid" refers to a compound having formula (IV) as set forth below.

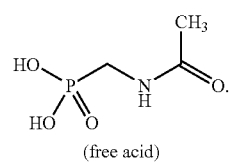

(free acid)

Thus, the various methods and compositions for detecting the presence or quantity of glyphosate, N-acetylglyphosate, AMPA, and/or N-acetyl AMPA in a test sample are provided. The methods and compositions of the invention find use in monitoring the level of glyphosate, N-acetylglyphosate, N-acetyl AMPA, and/or AMPA in a variety of test samples including crops, crop raw agricultural commodities, and crop process fractions.

II. Determining the Presence or Amount of at least one of Glyphosate, N-acetylglyphosate, N-acetyl AMPA, or AMPA in a Test Sample Methods and compositions are provided for determining the presence or amount of N-acetylglyphosate and/or N-acetyl AMPA in a test sample. The method comprises providing a test sample suspected of containing N-acetylglyphosate and/or N-acetyl AMPA, extracting a composition comprising the N-acetylglyphosate and/or N-acetyl AMPA from the test sample; and, detecting the N-acetylglyphosate and/or N-acetyl AMPA in the extract.

Methods and compositions are further provided for determining the presence or amount of at least one of glyphosate, N-acetylglyphosate, N-acetyl AMPA and/or AMPA or a metabolite thereof in a test sample. The methods comprise providing the test sample suspected of containing at least one of glyphosate, N-acetylglyphosate, N-acetyl AMPA and/or AMPA or a metabolite thereof; extracting from the test sample a composition comprising at least one of the glyphosate, N-acetylglyphosate, N-acetyl AMPA or AMPA or a metabolite thereof; and, detecting at least one of the glyphosate, N-acetylglyphosate, N-acetyl AMPA or AMPA or a metabolite thereof in the extract, where in specific embodiments, the detection of the glyphosate, the N-acetylglyphosate, the N-acetyl AMPA or the AMPA occurs without derivatization of the glyphosate, N-acetylglyphosate, N-acetyl AMPA and/or AMPA. In each matrix tested, such methods have a target limit of quantitation (LOQ) of the analytes of interest of 0.050 mg/kg (ppm) or 0.025 mg/kg (depending on the sample matrix) and are validated at 0.050 mg/kg and 0.50 mg/kg.

As used herein, a "test sample" can include any sample that can contain one or more of the target analytes of interest. In some embodiments, the test sample comprises a biological sample or an environmental sample. Thus, test samples can be from an animal (such as a mammal, including, but not limited to an agricultural animal, a domestic animal, a dog, a cat, a horse, a human, and the like). In other embodiments, the test sample is not a bacterium, such as *E. coli*. In other embodiments, the test sample is from a plant.

As used herein, the term "plant" includes plant cells, plant protoplasts, plant cell tissue cultures from which plants can be regenerated, plant calli, plant clumps, explants, plant tissues, forage, stover, hay, hulls, grits, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Accordingly, a sample from a plant can be derived from any one part or multiple parts of the plant.

Test samples derived from the plant can further comprise raw agricultural commodities (RAC) or can comprise a sample obtained during the manufacture of a plant or part thereof. Exemplary corn RACs include, for example, forage, grain and stover, while exemplary soybean RACs include, for example, forage, seed and hulls. In other embodiments, a test sample comprises a crop process fraction including solid process fractions or meal process fractions. Additional test samples can include flour, starch, grits, oils, refined oils, or meal obtained from the plant. Exemplary corn process fractions include flour, grits, meal and starch. Exemplary soy process fractions include meal and hulls. In one embodiment, the test sample is derived from a plant expressing a glyphosate acetyltransferase (GLYAT) polypeptide. See, for example, WO 02/36782, WO 2005/012515, U.S. Application Publication No. 2004/0082770, and U.S. application Ser. No. 11/507,751, all of which are herein incorporated by reference.

In specific embodiments, the test sample comprises a solid matrix fraction from a plant. As used herein, the term "solid matrix sample" refers to any matrix in a solid state, such as, but not limited to, flour, grits, meal, starch, tissue, etc.

Test samples can be obtained from any plant species, including, but not limited to, monocots and dicots or watery crops or acid crops. Examples of plant species of interest include, but are not limited to, corn (*Zea mays*, also referred to herein as "maize"), *Brassica* spp. (e.g., *B. napus*, *B. rapa*, *B. juncea*), particularly those *Brassica* species useful as sources of seed oil (also referred to as "canola"), flax (*Linum* spp.), alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, fruits, ornamentals (flowers), sugar cane, conifers, *Arabidopsis*.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Any tree can also be employed. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Hardwood trees can also be employed including ash, aspen, beech, basswood, birch, black cherry, black walnut, buckeye, American chestnut, cottonwood, dogwood, elm, hackberry, hickory, holly, locust, magnolia, maple, oak, poplar, red alder, redbud, royal paulownia, sassafras, sweetgum, sycamore, tupelo, willow, yellow-poplar.

In specific embodiments, test samples are from crop plants (for example, corn (also referred to as "maize"), alfalfa, sunflower, *Brassica*, soybean, cotton, safflower, peanut, sorghum, wheat, millet, tobacco, etc.).

Other plants of interest that test samples can be derived from include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Test samples can also be derived from other plants of interest including Turfgrasses such as, for example, turfgrasses from the genus *Poa, Agrostis, Festuca, Lolium*, and *Zoysia*. Additional turfgrasses can come from the subfamily Panicoideae. Turfgrasses can further include, but are not limited to, Blue gramma (*Bouteloua gracilis* (H.B.K.) Lag. Ex Griffiths); Buffalograss (*Buchloe dactyloids* (Nutt.) Engelm.); Slender creeping red fescue (*Festuca rubra* ssp. *Litoralis*); Red fescue (*Festuca rubra*); Colonial bentgrass (*Agrostis tenuis* Sibth.); Creeping bentgrass (*Agrostis palustris* Huds.); Fairway wheatgrass (*Agropyron cristatum* (L.)

Gaertn.); Hard fescue (*Festuca longifolia* Thuill.); Kentucky bluegrass (*Poa pratensis* L.); Perennial ryegrass (*Lolium perenne* L.); Rough bluegrass (*Poa trivialis* L.); Sideoats grama (*Bouteloua curtipendula* Michx. Torr.); Smooth bromegrass (*Bromus inermis* Leyss.); Tall fescue (*Festuca arundinacea* Schreb.); Annual bluegrass (*Poa annua* L.); Annual ryegrass (*Lolium multiflorum* Lam.); Redtop (*Agrostis alba* L.); Japanese lawn grass (*Zoysia japonica*); bermudagrass (*Cynodon dactylon; Cynodon* spp. L.C. Rich; *Cynodon transvaalensis*); Seashore paspalum (*Paspalum vaginatum* Swartz); Zoysiagrass (*Zoysia* spp. Willd; *Zoysia japonica* and *Z. matrella* var. *matrella*); Bahiagrass (*Paspalum notatum* Flugge); Carpetgrass (*Axonopus affinis* Chase); Centipedegrass (*Eremochloa ophiuroides* Munro Hack.); Kikuyugrass (*Pennisetum clandesinum* Hochst Ex Chiov); Browntop bent (*Agrostis tenuis* also known as *A. capillaris*); Velvet bent (*Agrostis canina*); Perennial ryegrass (*Lolium perenne*); and, St. Augustinegrass (*Stenotaphrum secundatum* Walt. Kuntze). Additional grasses of interest include switchgrass (*Panicum virgatum*).

In other embodiments, the test sample can be from an animal. Any animal can be used including, for example, agricultural animals, such as, cops, pigs, poultry (chickens, ducks, etc.) pigs, sheep, etc. Such samples can be derived from any part of the animal including, but not limited to, milk (whole milk, skim milk, cream), eggs (whole eggs, egg yolks, egg whites), or any meat commodity, such as, muscle, kidney, liver, fat, etc.

III. Extracting Glyphosate, N-acetylglyphosate, N-acetyl AMPA, AMPA, and Other Metabolites From the Test Sample By "extracting" is intended any method that allows for the removal of the analyte of interest from the sample matrix or a sample derived therefrom. As used herein, the term "extraction" or derivations thereof does not necessarily refer to the removal of all materials or constituents other than the analyte(s) of interest from a sample matrix or a sample derived therefrom. Instead, in some embodiments, the term "extraction" refers to a procedure that enriches the amount of one or more analytes of interest relative to one or more other components present in the sample matrix or in a sample derived therefrom. In some embodiments, an "extraction" procedure can be used to remove one or more components of a sample that could interfere with the detection of the analyte, for example, one or more components that could interfere with detection of an analyte ion by mass spectrometry. In other embodiments, the extraction procedure is used to remove the analyte of interest from the test sample matrix, and in still other embodiments, the extraction procedure is used to purify a first analyte of interest away from a second analyte of interest in a sample or to purify an analyte of interest away from an interfering substance.

Various extractions can be employed to extract or purify at least one of the analytes of interest (i.e., glyphosate, AMPA, N-acetyl AMPA and/or N-acetylglyphosate) from the sample. Various dilute acids can be used including, for example, solutions comprising dilute formic acid solutions, dilute hydrochloric acid solutions, or dilute phosphoric acid solutions. In particular embodiments, the extraction employs, for example, solutions comprising about 96% aqueous 0.1% formic acid/ 4% methanol or about 96% aqueous 0.025N hydrochloric acid/4% methanol or about 0.1N HCL in 96% water/4% methanol or about 0.02M phosphoric acid. In still other embodiments, the extraction solution can comprise a dilute formic acid solution comprising about 0.01% to about 10% formic acid, about 0.01% to about 1% formic acid, about 0.1% to about 1% formic acid, or about 0.1% to about 5% formic acid. In still other embodiments, the extraction solution can comprise a dilute hydrochloric acid solution comprising about 0.0025N to about 0.25N hydrochloric acid, about 0.025N to about 0.25N hydrochloric acid, about 0.0025N to about 0.025N hydrochloric acid. In further embodiments, the dilute phosphoric acid solution can comprise about 0.002M to about 0.2M phosphoric acid, about 0.002M to about 0.02M phosphoric acid, or about 2M to about 0.02M phosphoric acid. The extraction solution employed can vary depending on the test sample. For example, dilute hydrochloric acid can be used instead of formic acid to increase the acidity for more efficient extraction of N-acetylglyphosate, glyphosate, AMPA and/or N-acetyl AMPA from various matrixes, such as corn flour and meal process fractions. Alternatively, dilute phosphoric acid can be used for an efficient extraction of N-acetylglyphosate, glyphosate N-acetyl AMPA and/or AMPA from an oil test sample.

In specific embodiments, the extraction is performed with an aqueous dilute acid/methanol solution. In further embodiments, the extraction method employed will be sufficient to allow for an analyte extraction efficiency from the matrix of at least 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100%. In specific embodiments, the extraction efficiencies of the various analytes of interest are established through metabolism studies and not through surface application studies.

Multiple liquid-liquid extractions can be performed to extract the analyte(s) of interest from the test sample, including 1, 2, 3, 4, 5, or more. As outlined in further detail in the experimental section, it is further recognized that the extraction volume employed can vary depending on the moisture content of the matrix. For example, test samples with lower moisture content (i.e., stover, hay, hull, etc) may need larger extraction solution volumes and an increased number of extractions.

Following the dilute acidic extraction, an additional extraction step can be employed to further purify the analytes of interest from various contaminates remaining in the sample. For example, an aqueous-organic extraction step can be performed, such as a dilute acid/methylene chloride partition. In such an extraction, the analytes of interest remain in the aqueous phase which can be subsequently applied to an extraction column. In specific embodiments, the dilute acid employed with the methylene chloride extraction comprises a dilute formic acid solution, a dilute hydrochloric acid solution, or a dilute phosphoric acid solution, as described above.

One or more of the analytes of interest can further be extracted or purified from other components of the test sample or from one another by employing a solid phase extraction (SPE) column. As used herein, an "extraction column" is used to extract retained materials from non-retained materials and thus allows one to obtain a "purified" sample for further purification or analysis. Multiple extraction columns can also be used, including, 1, 2, 3, 4, 5 or more. In specific embodiments, the extracting or purifying step includes: (a) disposing the sample onto an extraction column; (b) washing the extraction column under conditions whereby the analyte(s) of interest is retained on the extraction column; and, (c) eluting the retained analyte(s) from the extraction column. In some embodiments, one or more of the extraction columns employed is a hydrophobic silica-based bonded phase extraction column (i.e., a C-18 column), a cation exchange extraction column (i.e., an m-divinylbenzene & N-vinylpyrrolidone copolymer, with sulfonic acid substituents) or an anion exchange extraction column (i.e., m-divinylbenzene & N-vinylpyrrolidone copolymer, with quaternary amine substituents) or a combination thereof. In one embodiment, one or more of the analytes of interest are extracted from the sample matrix employing a liquid-liquid extraction, an extraction column, or any combination thereof.

Depending on the test sample employed and the analyte of interest, different extraction columns can be used to extract the analyte of interest (i.e., glyphosate, AMPA, N-acetyl AMPA and/or N-acetylglyphosate) from the test sample matrix. For example, for the analysis of solid matrix sample extracts, following an aqueous-organic liquid-liquid extraction, as described above, a hydrophobic silica-based bonded phase extraction column can be used for the purification of glyphosate, AMPA, N-acetyl AMPA and N-acetylglyphosate. In specific embodiments, the hydrophobic silica-based bonded phase extraction column comprises a $C_{18}$ extraction column. Additional extraction columns can be employed following the hydrophobic silica-based extraction column to further purify the analyte of interest.

For some sample matrices, the use of a solid phase extraction step can occur with the dilute acid/methanol extraction step. For example, with a meat commodity matrix, a solid phase extraction sorbent (such as $C_{18}$) can be added to the homogenized tissue sample. The homogenized tissue is mixed with the solid phase extraction sorbent and a dilute acid/methanol solution is added. Steps can be taken to elute and collect the analytes bound by the solid phase extraction sorbent.

In still other embodiments, for milk and egg commodities, the test samples are mixed with aqueous 0.1% formic acid/methanol (96/4, v/v). Hexane is then added followed by centrifugation. A methylene chloride extraction is then performed on the aqueous layer. Two additional 0.1% formic acid/methanol (96/4, v/v) extractions are then performed.

In specific embodiments, prior to chromatographically separating the analyte of interest from the extracted test sample, a sufficient concentration of a weak-ion pairing reagent is added to the extract. A sufficient concentration of a weak-ion pairing reagent is a concentration that allows for an improved response and linearity of glyphosate, N-acetylglyphosate, N-acetyl AMPA and/or AMPA. In specific embodiments, the weak-ion pairing reagent is phosphoric acid. In specific embodiments, final extracts are prepared in aqueous 0.02M phosphoric acid and filtered prior to LC/MS/MS analysis. Glyphosate and AMPA stable isotopes can be added to final extract solutions as internal standards to normalize for matrix effects.

i. Extracting AMPA from a Solid Matrix or an Animal Commodity

In specific embodiments, an aliquot of the eluate from the hydrophobic silica-based extraction column is processed for the analysis of AMPA by disposing the hydrophobic silica-based extraction column eluate onto a cation exchange extraction column. In specific embodiments, the cation exchange extraction column has a surface functionality comprising a m-divinylbenzene & N-vinylpyrrolidone copolymer with sulfonic acid substituents. Non-limiting examples of cation exchange extraction columns that can be used include an MCX SPE column (Waters Oasis). As outlined in further detail elsewhere herein, various methods can be used to dispose the eluate of the hydrophobic silica-based extraction column onto the cation exchange extraction column.

Accordingly, methods to extract or purify AMPA from a solid sample matrix can comprise: (a) extracting a composition comprising the AMPA from the test sample by liquid-liquid extraction; (b) disposing the composition comprising the AMPA of step (a) onto a hydrophobic silica-based bonded phase extraction column; (c) obtaining the elute comprising the AMPA from the extraction column of step (b); (d) disposing the eluate of step (c) onto a cation exchange column; (e) washing the extraction column under conditions whereby the AMPA is retained on the extraction column; and, (f) eluting the retained AMPA from the cation exchange extraction column. In specific embodiments, the extraction of the AMPA from the solid matrix sample comprises a dilute acid extraction followed by a methylene chloride partition.

In one non-limiting embodiment, the test sample extraction is performed as follows. AMPA is extracted from a plant solid matrix into dilute aqueous acid (0.1% formic acid or 0.025N hydrochloric acid)/methanol (96/4) using a probe homogenizer. Multiple extractions (1, 2, 3, 4 or more) are made for quantitative recovery of the analyte of interest. An aliquot of the filtered aqueous fraction is partitioned with methylene chloride and the aqueous fraction is recovered and filtered to remove particulates. An aliquot of the extract is then filtered through a $C_{18}$ solid phase extraction (SPE) cartridge. An aliquot of the eluate collected from the $C_{18}$ SPE cartridge is diluted and applied to a cation exchange Oasis™ MCX SPE cartridge, diluted, and filtered.

In another non-limiting embodiment, the test sample comprises a meat tissue commodity, and the extraction is performed as follows. AMPA is extracted from a meat tissue commodity by (a) homogenizing the tissue; (b) adding a solid phase extraction sorbent, such as $C_{18}$, to the homogenized tissue; (c) adding 0.1N HCL in 96% water/4% methanol; (d) centrifuging the sample and collecting the $C_{18}$ pellet; (e) eluting the analyte from the solid phase extraction sorbent with water. An aliquot of the eluate is then applied to a cation Oasis™ MCX SPE cartridge.

In another non-limiting embodiment, the test sample comprises a milk or egg commodity and the extraction is performed as follows. An aqueous 0.1% formic acid/methanol (96/4, v/v) solution is added to the sample. A hexane extraction is performed. A methylene chloride extraction is performed on the aqueous layer. Additional formic acid/methanol extractions (at least 1, 2, 3 or more) are performed on the aqueous layer. An aliquot of the eluate is then applied to a cation Oasis™ MCS SPE cartridge.

ii. Extracting Glyphosate, N-acetyl AMPA and/or N-acetylglyphosate from a Solid Matrix or an Animal Commodity In other embodiments, an aliquot of the eluate from the hydrophobic silica-based extraction column is processed for the analysis of glyphosate, N-acetyl AMPA and/or N-acetylglyphosate from a solid matrix. In specific embodiments, an aliquot of the hydrophobic silica-based extraction eluate is disposed onto an anion exchange extraction column. The anion exchange extraction column can comprise a surface functionality comprising a m-divinylbenzene & N-vinylpyrrolidone copolymer with quaternary amine substituents. Non-limiting examples of such anion exchange extraction columns include, a MAX SPE column. As outlined in further detail elsewhere herein, various methods can be used to dispose the eluate of the hydrophobic silica-based extraction column onto the anion exchange extraction column. Briefly, an m-divinylbenzene & N-vinylpyrrolidone copolymer with quaternary amine substituents extraction column can be employed following an extract (adjusted to basic pH) in methanol for corn matrices, soybean forage, and hay matrices. In other methods, an m-divinylbenzene & N-vinylpyrrolidone copolymer with quaternary amine substituents extraction column following an extract dilution in water procedure can be used for the analysis of soybean seed, meal, and hull matrices.

Accordingly, methods to extract or purify glyphosate, N-acetyl AMPA and/or N-acetylglyphosate from a plant solid sample matrix can comprise: (a) extracting a composition comprising the glyphosate, N-acetyl AMPA and/or N-acetylglyphosate from the test sample by liquid-liquid extraction; (b) disposing the composition of step (a) onto a hydrophobic silica-based bonded phase extraction column; (c) obtaining the elute comprising the glyphosate, N-acetyl AMPA and/or N-acetylglyphosate from the extraction column of step (b); (d) disposing the eluate of step (c) onto an anion exchange column; (e) washing the extraction column under conditions whereby the glyphosate, N-acetyl AMPA and/or N-acetylglyphosate are retained on the extraction column; and, (f) eluting the retained glyphosate, N-acetyl AMPA and/or N-acetylglyphosate from the extraction column. In specific embodiments, the aqueous extraction of the glyphosate, N-acetyl AMPA and/or N-acetylglyphosate from the solid matrix sample is followed by a methylene chloride partition.

In one non-limiting embodiment, the test sample extraction is performed as follows. Glyphosate, N-acetyl AMPA and/or N-acetylglyphosate are extracted from a plant solid matrix or a milk or egg commodity into dilute aqueous acid (0.1% formic acid or 0.025N hydrochloric acid)/methanol (96/4) using a probe homogenizer. Multiple extractions (1, 2, 3, 4 or more) are made for quantitative recovery of analytes. When employing a plant solid matrix sample extract, an aliquot of extract can be partitioned with methylene chloride and the aqueous fraction is recovered and filtered to remove particulates. When employing an egg or milk commodity, a hexane extraction step can be performed before the methylene chloride extraction. An aliquot of the extract is then filtered through a $C_{18}$ solid phase extraction (SPE) cartridge. An aliquot of the eluate collected from the $C_{18}$ SPE is diluted and applied to an anion exchange Oasis™ MAX SPE cartridge. The analytes are eluted from the MAX cartridge with 1% trifluoroacetic acid in methanol/water (9/1) solution following several solution rinses. The MAX eluate is evaporated to dryness and redissolved in aqueous 0.02M aqueous phosphoric acid, filtered, and analyzed for glyphosate, N-acetyl AMPA and/or N-acetylglyphosate. For the analysis of soybean samples (i.e., seed and meal) following partitioning, extract samples can be heated in a steam bath for approximately 15 minutes to precipitate additional material in the extract prior to particulate filtration.

In another non-limiting embodiment, the test sample is a meat commodity, and the sample extraction is performed as follows. Glyphosate, N-acetyl AMPA, and/or N-acetylglyphosate are extracted from the meat commodity by the homogenization of the tissue and the subsequent addition of the solid phase extraction sorbent, such as $C_{18}$. 0.1N HCL in 96% water/4% methanol is added to the sample. The sample is centrifuged, and the supernant is removed. The analyte is eluted from the solid phase extraction sorbent by the addition of water to the pellet. TEA is added to the sample, followed by an acetonitrile extraction. The sample is then loaded onto an Oasis™ MAX SPE cartridge. The column is washed and the analytes are eluted from the column using 1% TFA in methanol/water, 90/10. The MAX eluate is evaporated to dryness and redissolved in aqueous 0.02M aqueous phosphoric acid.

iii. Extracting Glyphosate, N-acetylglyphosate, N-acetyl AMPA and/or AMPA from an Oil Sample In still other embodiments, when the test sample comprises an oil sample, a single procedure can be employed for the extraction and purification of all analytes of interest (glyphosate, N-acetylglyphosate, N-acetyl AMPA, and AMPA). In such embodiments, an extraction column need not be employed. For example, the test sample can undergo a series of aqueous-organic extractions, such as, with a dilute acid or a weak ion-pairing reagent (such as 0.02M phosphoric acid) and methylene chloride. Following a sufficient number of extractions, the aqueous fraction is ready for the detection of the analyte of interest. The extraction can be repeated 2, 3, 4, 5 or more times for quantitative transfer of the analytes. Centrifugation can be used to define phase separation after each partition.

Accordingly, methods are provided to extract glyphosate, N-acetylglyphosate, N-acetyl AMPA and/or AMPA from an oil sample matrix comprising: (a) performing an aqueous-organic extraction of the test sample comprising (i) adding a sufficient concentration of a weak-ion pairing reagent or a dilute acid, such as phosphoric acid, to the test sample, wherein the sufficient concentration of the weak-ion pairing reagent or dilute acid allows for the improved response and linearity of glyphosate, N-acetylglyphosate, N-acetyl AMPA or AMPA; and, (ii) adding an organic solvent; (b) extracting the analyte of interest from the aqueous phase of the aqueous-organic partition; and, (c) repeating either of step (a) and/or step (b) a sufficient number of times to allow for the quantitative transfer of the analytes. In specific embodiments, the aqueous-organic extraction comprises a phosphoric acid/methylene chloride partition.

IV. Determining the Presence or Amount of Glyphosate, N-acetylglyphosate, N-acetyl AMPA, AMPA, and other Metabolites in a Test Sample Following the extraction of one or more of the analyte(s) of interest from the test sample, any method can be employed that allows for the detection of one or more of the analytes of interest. In one embodiment, detecting one or more of the analytes of interest comprises separating (and in specific embodiments, chromatographically separating) at least one of the analytes of interest from the extracted test sample and analyzing at least one of the chromatographically separated analytes to determine the presence or amount of at least one of glyphosate, N-acetylglyphosate, N-acetyl AMPA and/or AMPA in the test sample.

i. Separating at Least One of Glyphosate, N-acetylglyphosate, N-acetyl AMPA and/or AMPA from the Extracted Test Sample As used herein, "chromatographically separating" employs an "analytical column" or a "chromatography column" having sufficient chromatographic plates to effect a separation of the components of a test sample matrix. Preferably, the components eluted from the analytical column are separated in such a way to allow the presence or amount of an analyte(s) of interest to be determined. "Analytical columns" can be distinguished from "extraction columns," which typically are used to purify or extract retained materials from non-retained materials to obtain a "purified" sample for further purification or analysis.

In specific embodiments, each of the analytes of interest (i.e., glyphosate, AMPA, N-acetyl AMPA or N-acetylglyphosate) is chromatographically separated from one another prior to detection. It is, however, recognized that depending on the method of detection employed, it may not be necessary to separate each of the analytes of interest from one another by chromatography. Such methods of detection allow each of the analytes of interest to be detected when present as a mixture.

In specific embodiments, following the extraction step described in further detail above, chromatographically separating the analytes of interest includes: (a) disposing the composition comprising the extracted analyte(s) onto an analytical column; and (b) eluting the analyte(s) from the analytical column. In one embodiment, chromatographically separating the analytes of interest from one another or other constituents of the test sample comprises the use of a high performance liquid chromatography (HPLC) column. Any HPLC column that can sufficiently resolve the analytes of interest and allow for their detection and/or quantitation can be employed. In specific embodiments, the HPLC column comprises a phenyl phase which employs a hexyl alkyl linker.

ii. Detecting Glyphosate, N-acetylglyphosate, AMPA, N-acetyl AMPA and other Metabolites By "detecting" is intended determining the presence or amount of an analyte of interest (i.e., glyphosate, N-acetylglyphosate, N-acetyl AMPA and/or AMPA) in a test sample. The method of detection is not restricted and may be either qualitative or quantitative. In one embodiment, detecting the glyphosate, N-acetylglyphosate, N-acetyl AMPA and/or AMPA comprises analyzing the chromatographically separated analytes by a mass spectrometer. In some non-limiting embodiments, separation and/or detection does not require the derivatization of the analyte of interest. In specific embodiments, positive ion mass spectroscopy is performed to detect the analyte of interest.

The term "mass spectrometry" or "MS" as used herein generally refer to methods of filtering, detecting, and measuring ions based on their mass-to-charge ratio, or "m/z." In MS techniques, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,107,623, entitled "Methods and Apparatus for Tandem Mass Spectrometry," which is hereby incorporated by reference in its entirety.

In a "quadrupole" or "quadrupole ion trap" mass spectrographic instrument, ions in an oscillating radio frequency (RF) field experience a force proportional to the direct current (DC) potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

Further, the resolution of the MS technique can be enhanced by using "tandem mass spectrometry," or "MS/MS." Tandem mass spectrometry (MS/MS) is the name given to a group of mass spectrometric methods wherein "parent" ions generated from a sample are fragmented to yield one or more "daughter" ions, which are subsequently mass analyzed by a second MS procedure. MS/MS methods are useful for the analysis of complex mixtures, especially biological samples, in part because the specificity of MS/MS can minimize the need for extensive sample clean-up prior to mass spectral analysis. In an example of an MS/MS method, parent ions are generated from a sample and passed through a first mass filter to select those ions having a particular mass-to-charge ratio. These ions are then fragmented, typically by collisions with neutral gas molecules in a suitable ion collision cell, to yield daughter ions, the mass spectrum of which is recorded by a second mass analyzer. The daughter ion spectra so produced are indicative of the structure of the parent ion, and the two stages of mass filtering can eliminate ions from interfering species present in the conventional mass spectrum of a complex mixture.

The most common type of MS/MS instrument is the triple quadrupole (see, for example, Yost, Enke in Ch. 8 of Tandem Mass Spectrometry, Ed. McLafferty, pub. John Wiley and Sons, 1983). Triple quadrupole MS/MS instruments typically consist of two quadrupole mass filters separated by a fragmentation means (i.e., a colison cell), (usually a quadrupole mass filter operated in the RF only mode as an ion containment device and containing a collision gas at a pressure of between 1 and 10 millitorr). Many other types of "hybrid" tandem mass spectrometers are also known, however, including various combinations of magnetic sector analyzers and quadrupole filters. These hybrid instruments often comprise high resolution magnetic sector analyzers (i.e., analyzers comprising both magnetic and electrostatic sectors arranged in a double-focusing combination) as either or both of the mass filters. Use of high resolution mass filters is highly effective in reducing chemical noise to very low levels.

The term "electron ionization" as used herein refers to methods in which one or more analytes of interest in a gaseous or vapor phase is interacted with a flow of electrons. Impact of the electrons with the analyte(s) produces analyte ions, which are then be subjected to a mass spectroscopy technique.

The term "chemical ionization" as used herein refers to methods in which a reagent gas (e.g., ammonia) is subjected to electron impact, and analyte ions are formed by the interaction of reagent gas ions and analyte molecules.

The term "fast atom bombardment" as used herein refers to methods in which a beam of high energy atoms (often Xe or Ar) impacts a non-volatile test sample, desorbing and ionizing molecules contained in the sample. Samples are dissolved in a viscous liquid matrix, such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

The term "field desorption" as used herein refers to methods in which a non-volatile test sample is placed on an ionization surface, and an intense electric field is used to generate analyte ions.

The term "matrix-assisted laser desorption ionization," or "MALDI" as used herein refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

The term "surface enhanced laser desorption ionization," or "SELDI" as used herein refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

The term "electrospray ionization," or "ESI," as used herein refers to methods in which a solution is passed along a short length of capillary tube, to the end of which is applied a high positive or negative electric potential. Solution reaching the end of the tube, is vaporized (nebulized) into a jet or spray of very small droplets of solution in solvent vapor. This mist of droplets flows through an evaporation chamber which is heated slightly to prevent condensation and to evaporate solvent. As the droplets get smaller the electrical surface charge density increases until such time that the natural repulsion between like charges causes ions as well as neutral molecules to be released.

The term "Atmospheric Pressure Chemical Ionization," or "APCI," as used herein refers to mass spectroscopy methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "Atmospheric Pressure Photoionization" ("APPI") as used herein refers to the form of mass spectroscopy where the mechanism for the photoionization of molecule M is photon absorption and electron ejection to form the molecular M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. Robb, D. B., Covey, T. R. and Bruins, A. P. (2000): See, e.g., Robb et al., Atmospheric pressure photoionization: An ionization method for liquid chromatography-mass spectrometry. *Anal. Chem.* 72(15): 3653-3659.

The term "inductively coupled plasma" as used herein refers to methods in which a sample is interacted with a partially ionized gas at a sufficiently high temperature to atomize and ionize most elements.

The term "ionization" and "ionizing" as used herein refers to the process of generating an analyte ion having a net electrical charge equal to one or more electron units. Negative ions are those ions having a net negative charge of one or more electron units, while positive ions are those ions having a net positive charge of one or more electron units.

The term "desorption" as used herein refers to the removal of an analyte from a surface and/or the entry of an analyte into a gaseous phase.

In those embodiments, such as MS/MS, where precursor ions are isolated for further fragmentation, collision-induced dissociation ("CID") is often used to generate the fragment ions for further detection. In CID, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

In some embodiments, one or more of the purification or separation steps can be preformed "online." As used herein, the term "online" refers to purification or separation steps that are performed in such a way that the test sample is disposed, e.g., injected, into a system in which the various components of the system are operationally connected and, in some embodiments, in fluid communication with one another. Representative components of such online systems include, but are not limited to: an autosampler; one or more injection ports; one or more columns, including but not limited to, an extraction column, including an extraction column, and in some embodiments, an analytical column; a detection system, e.g., a mass spectrometer system; one or more pumps; one or more valves; and necessary plumbing. In such "online" systems, the test sample and/or analytes of interest can be passed from one component of the system to another without exiting the system, e.g., without having to be collected and then disposed into another component of the system.

In some embodiments, the online purification or separation method can be automated. In such embodiments, the steps can be performed without the need for operator intervention once the process is set-up and initiated. One of ordinary skill in the art also would appreciate that an online, automated procedure can include the use of software for controlling the various components of the system, including pumps, valves, autosamplers, and the like. Such software can be used to optimize the extraction process through the precise timing of sample and solute additions and flow rate.

In contrast, the term "offline" refers to a purification, separation, or extraction procedure that is performed separately from subsequent purification or separation steps and/or analysis steps. In such offline procedures, the analytes of interests typically are separated, for example, on an extraction column or by liquid-liquid extraction, from the other components in the sample matrix and then collected for subsequent introduction into another chromatographic or detector system. Offline procedures typically require manual intervention on the part of the operator.

V. Specific Embodiments of the Invention

In non-limiting embodiments, determining the presence or amount of N-acetylglyphosate in a test sample comprises: (a) providing a test sample suspected of containing N-acetylglyphosate; (b) extracting a composition comprising the N-acetylglyphosate from the test sample by liquid-liquid extraction; (c) disposing the composition of step (b) comprising the N-acetylglyphosate onto a $C_{18}$ extraction column and eluting the N-acetylglyphosate therefrom; (d) disposing the eluted N-acetylglyphosate from step (c) onto an anion exchange column having a surface functionally of m-divinylbenzene and N-vinylpyrrolidone copolymer with quaternary amines and eluting the N-acetylglyphosate therefrom; (e) adding a sufficient concentration of phosphoric acid to said eluted N-acetylglyphosate of step (d), wherein said sufficient concentration allows for an improved response and linearity of N-acetylglyphosate during detection or wherein said sufficient concentration comprises a final concentration of about 0.02M phosphoric acid; (f) chromatographically separating the N-acetylglyphosate from other constituents in the composition of step (e) using a phenyl-hexyl high performance liquid chromatography (HPLC) analytical column; and, (g) analyzing the chromatographically separated sample of step (f) to determine the presence or amount of the N-acetylglyphosate in the test sample by a tandem quadrupole mass spectrometer operated in positive ion mode. In specific embodiments, the liquid-liquid extraction comprises a dilute acid and methylene chloride extraction. In further embodiments, the test sample comprises a solid matrix sample from a plant or is a milk or egg commodity sample.

In non-limiting embodiments, determining the presence or amount of N-acetylglyphosate in a test sample comprises: (a) providing a test sample suspected of containing N-acetylglyphosate; (b) mixing the test sample with a solid phase extraction sorbent under conditions that allow the solid phase extraction sorbent to bind the N-acetylglyphosate; (c) extracting the solid phase extraction sorbent and the bound N-acetylglyphosate from the sample by liquid/liquid extraction; (d) eluting said N-acetylglyphosate from the solid phase extraction sorbent; (e) extracting a composition comprising the N-acetylglyphosate from the eluate of step (d) by liquid-liquid extraction; (f) disposing the eluted N-acetylglyphosate from step (e) onto an anion exchange column having a surface functionally of m-divinylbenzene and N-vinylpyrrolidone copolymer with quaternary amines and eluting the N-acetylglyphosate therefrom; (g) adding a sufficient concentration of phosphoric acid to said eluted N-acetylglyphosate of step (f), wherein said sufficient concentration allows for an improved response and linearity of N-acetylglyphosate during detection or wherein said sufficient concentration comprises a final concentration of about 0.02M phosphoric acid; (h) chromatographically separating the N-acetylglyphosate from other constituents in the composition of step (g) using a phenyl-hexyl high performance liquid chromatography (HPLC) analytical column; and, (i) analyzing the chromatographically separated sample of step (h) to determine the presence or amount of the N-acetylglyphosate in the test sample by a tandem quadrupole mass spectrometer operated in positive ion mode. In specific embodiments, the liquid-liquid extraction of step (c) comprises a dilute acid and methanol extraction. In further embodiments, the test sample comprises a meat tissue commodity.

In other non-limiting embodiments, the method of determining the presence or amount of glyphosate in a test sample comprises: (a) providing a test sample suspected of containing glyphosate; (b) extracting a composition comprising the glyphosate from the test sample by liquid-liquid extraction; (c) disposing the composition comprising the glyphosate of step (b) onto a $C_{18}$ extraction column and eluting the glyphosate therefrom; (d) disposing the eluted glyphosate from step (c) onto an anion exchange column comprising a surface functionally of m-divinylbenzene and N-vinylpyrrolidone copolymer with quaternary amines and eluting the glyphosate therefrom; (e) adding a sufficient concentration of phosphoric acid to said eluted glyphosate of step (d), wherein said sufficient concentration allows for an improved response and linearity of glyphosate during detection or wherein the sufficient concentration comprises a final concentration of about 0.02M phosphoric acid; (f) chromatographically separating the glyphosate from other constituents of step (e) using a phenyl-hexyl high performance liquid chromatography (HPLC) column; and, (g) analyzing the chromatographically separated sample of step (f) to determine the presence or amount of glyphosate in the test sample by a tandem quadrupole mass spectrometer operated in positive ion mode; wherein detection of said glyphosate occurs without derivatization of said glyphosate. In specific embodiments, the liquid-liquid extraction comprises a dilute aqueous acid/methanol solution and/or a dilute acid and methylene chloride extraction. In further embodiments, the test sample comprises a solid matrix sample from a plant or an egg or a milk commodity.

In non-limiting embodiments, determining the presence or amount of glyphosate in a test sample comprises: (a) providing a test sample suspected of containing glyphosate; (b) mixing the test sample with a solid phase extraction sorbent under conditions that allow the solid phase extraction sorbent to bind the glyphosate; (c) extracting the solid phase extraction sorbent and the bound glyphosate from the sample by liquid/liquid extraction; (d) eluting the glyphosate from the solid phase extraction sorbent; (e) extracting a composition comprising the glyphosate from the eluate of step (d) by liquid-liquid extraction; (f) disposing the eluted glyphosate from step (e) onto an anion exchange column having a surface functionally of m-divinylbenzene and N-vinylpyrrolidone copolymer with quaternary amines and eluting the glyphosate therefrom; (g) adding a sufficient concentration of phosphoric acid to said eluted glyphosate of step (f), wherein said sufficient concentration allows for an improved response and linearity of glyphosate during detection or wherein said sufficient concentration comprises a final concentration of about 0.02M phosphoric acid; (h) chromatographically separating the glyphosate from other constituents in the composition of step (g) using a phenyl-hexyl high performance liquid chromatography (HPLC) analytical column; and, (i) analyzing the chromatographically separated sample of step (h) to determine the presence or amount of the glyphosate in the test sample by a tandem quadrupole mass spectrometer operated in positive ion mode. In specific embodiments, the liquid-liquid extraction of step (c) comprises a dilute acid and methanol extraction. In further embodiments, the test sample comprises a meat tissue commodity.

In other non-limiting embodiments, the method of determining the presence or amount of aminomethyl phosphonic acid (AMPA) in a test sample comprises: (a) providing the test sample suspected of containing AMPA; (b) extracting a composition comprising the AMPA from the test sample by liquid-liquid extraction; (c) disposing the composition of step (b) onto a $C_{18}$ extraction column and eluting the AMPA therefrom; (d) disposing the eluted AMPA from step (c) onto a cation exchange column comprising a surface functionally of m-divinylbenzene and N-vinylpyrrolidone copolymer with sulfonic acid substituents and eluting the AMPA therefrom; (e) adding a sufficient concentration of phosphoric acid to said eluate AMPA of step (d), wherein said sufficient concentration allows for an improved response and linearity of AMPA during detection or wherein said sufficient concentration comprises a final concentration of about 0.02M phosphoric acid; (f) chromatographically separating the AMPA from other constituents of step (e) using a phenyl-hexyl high performance liquid chromatography (HPLC) analytical column; and, (g) analyzing the chromatographically separated sample of step (f) to determine the presence or amount of AMPA in the test sample by a tandem quadrupole mass spectrometer operated in positive ion mode; wherein detection of the AMPA occurs without derivatization of the AMPA. In specific embodiments, the liquid-liquid extraction comprises a dilute aqueous acid/methanol solution and/or a dilute acid and methylene chloride extraction. In further embodiments, the test sample comprises a solid matrix sample from a plant or a milk or egg commodity.

In another non-limiting embodiment, a method of determining the presence or amount of aminomethyl phosphonic acid (AMPA) in a test sample comprises: (a) providing the test sample suspected of containing AMPA; (b) mixing the test sample with a solid phase extraction sorbent under conditions that allow the solid phase extraction sorbent to bind the AMPA; (c) extracting the solid phase extraction sorbent and the bound AMPA from the sample by liquid/liquid extraction; (d) eluting the AMPA from the solid phase extraction sorbent; (e) disposing the eluted AMPA from step (d) onto a cation exchange column comprising a surface functionally of m-divinylbenzene and N-vinylpyrrolidone copolymer having sulfonic acid substituents and eluting the AMPA therefrom; (f) adding a sufficient concentration of phosphoric acid to said eluted AMPA of step (d), wherein said sufficient concentration allows for an improved response and linearity of AMPA during detection; (g) chromatographically separating the AMPA from other constituents in the eluate of step (f) using a phenyl-hexyl high performance liquid chromatography (HPLC) analytical column; and, (h) analyzing the chromatographically separated sample of step (g) to determine the presence or amount of AMPA in the test sample by a tandem quadrupole mass spectrometer operated in positive ion mode. In further embodiments, the test sample comprises a meat tissue commodity.

In other non-limiting embodiments, the method of determining the presence or amount of N-acetyl AMPA in a test sample comprises: (a) providing a test sample suspected of containing N-acetyl AMPA; (b) extracting a composition comprising the N-acetyl AMPA from the test sample by liquid-liquid extraction; (c) disposing the composition of step (b) comprising the N-acetyl AMPA onto a $C_{18}$ extraction column and eluting the N-acetyl AMPA therefrom; (d) disposing the eluted N-acetyl AMPA from step (c) onto an anion exchange column having a surface functionally of m-divinylbenzene and N-vinylpyrrolidone copolymer with quaternary amines and eluting the N-acetyl AMPA therefrom; (e) adding a sufficient concentration of phosphoric acid to said eluted N-acetyl AMPA of step (d), wherein said sufficient concentration allows for an improved response and linearity of N-acetyl AMPA during detection or wherein said sufficient concentration comprises a final concentration of about 0.02M phosphoric acid; (f) chromatographically separating the N-acetyl AMPA from other constituents in the composition of step (e) using a phenyl-hexyl high performance liquid chromatography (HPLC) analytical column; and, (g) analyzing the chromatographically separated sample of step (f) to determine the presence or amount of the N-acetyl AMPA in the test sample by a tandem quadrupole mass spectrometer operated in positive ion mode. In specific embodiments, the liquid-liquid extraction comprises a dilute aqueous acid/methanol solution and/or a dilute acid and methylene chloride extraction. And in further embodiments, the test sample comprises a solid matrix sample from a plant or a milk or egg commodity.

In non-limiting embodiments, determining the presence or amount of N-acetyl AMPA in a test sample comprises: (a) providing a test sample suspected of containing N-acetyl AMPA; (b) mixing the test sample with a solid phase extraction sorbent under conditions to allow the solid phase extraction sorbent to bind the N-acetyl AMPA; (c) extracting the solid phase extraction sorbent and the bound N-acetyl AMPA from the sample by liquid/liquid extraction; (d) eluting the N-acetyl AMPA from the solid phase extraction sorbent; (e) extracting a composition comprising the N-acetyl AMPA from the composition comprising the N-acetyl AMPA from step (d) by liquid-liquid extraction; (f) disposing the eluted N-acetyl AMPA from step (e) onto an anion exchange column having a surface functionally of m-divinylbenzene and N-vinylpyrrolidone copolymer with quaternary amines and eluting the N-acetyl AMPA therefrom; (g) adding a sufficient concentration of phosphoric acid to said eluted glyphosate of step (f), wherein said sufficient concentration allows for an improved response and linearity of N-acetyl AMPA during detection or wherein said sufficient concentration comprises a final concentration of about 0.02M phosphoric acid; (h) chromatographically separating the N-acetyl AMPA from other constituents in the composition of step (g) using a phenyl-hexyl high performance liquid chromatography (HPLC) analytical column; and, (i) analyzing the chromatographically separated sample of step (h) to determine the presence or amount of the N-acetyl AMPA in the test sample by a tandem quadrupole mass spectrometer operated in positive ion mode. In specific embodiments, the liquid-liquid extraction comprises a dilute acid and methylene chloride extraction. In further embodiments, the test sample comprises a meat tissue commodity.

In other non-limiting embodiments, a method for determining the presence or amount of at least one of glyphosate, N-acetylglyphosate, N-acetyl AMPA or AMPA in an oil test sample comprises: (a) providing the oil test sample suspected of containing at least one of the glyphosate, the N-acetylglyphosate, the N-acetyl AMPA or the AMPA; (b) adding a sufficient concentration of phosphoric acid to said test sample of (a) wherein said sufficient concentration allows for an improved response and linearity of N-acetylglyphosate, AMPA, glyphosate, or N-acetyl AMPA during detection or wherein said sufficient concentration comprises a final concentration of about 0.02M phosphoric acid; (c) extracting a composition from said test sample comprising at least one of the AMPA, the N-acetylglyphosate, the N-acetyl AMPA or the glyphosate by a aqueous-organic extraction; (d) chromatographically separating at least one of the AMPA, N-acetylglyphosate, N-acetyl AMPA or glyphosate of step (c) using a high performance liquid chromatography (HPLC) column comprising a phenyl-hexyl analytical column; and, (e) analyzing the chromatographically separated sample of step (d) to determine the presence or amount of at least one of AMPA, glyphosate, N-acetyl AMPA or N-acetylglyphosate in the test sample by a tandem quadrupole mass spectrometer operated in electrospray ionization mode.

In other non-limiting embodiments, a method of purifying at least glyphosate, N-acetyl AMPA or N-acetylglyphosate from AMPA is provided. The method comprises: (a) providing a test sample suspected of containing at least one of the glyphosate, the N-acetyl AMPA, the N-acetylglyphosate, or the AMPA; (b) extracting a composition comprising at least one of the N-acetylglyphosate, the glyphosate, the N-acetyl AMPA or the AMPA from said test sample; (c) disposing the composition of step (b) onto an anion exchange extraction column and eluting at least one of the N-acetylglyphosate, N-acetyl AMPA and glyphosate therefrom and thereby purifying the glyphosate, N-acetyl AMPA and N-acetylglyphosate from the AMPA; or, disposing the composition of step (b) onto a cation exchange extraction column and eluting the AMPA therefrom and thereby purifying the glyphosate, N-acetyl AMPA and the N-acetylglyphosate from the AMPA.

EXPERIMENTAL

Example 1

In one embodiment, an analytical method was developed for the determination of glyphosate and relevant metabolites or degradate residues in transgenic crop and crop fraction matrices. The glyphosate metabolites or analytes are N-acetylglyphosate, aminomethyl phosphonic acid (AMPA) and N-acetyl AMPA. N-acetylglyphosate is a metabolite associated with transgenic crops containing the glyphosate N-acetyltransferase (glyat) enzyme. The method target limit of quantitation (LOQ) in each matrix examined was 0.050 mg/kg (ppm). The method was validated at 0.050 mg/kg and 0.50 mg/kg using a LC/MS/MS system operating with an electrospray interface (ESI) in positive ion mode detection. This analytical method was developed to support residue data collection required for registration of genetically modified crops.

Raw agricultural and solid process fraction commodities derived from plants expressing GLYAT were extracted 3 times in acidic (0.1% formic acid or 0.025N hydrochloric acid) water/methanol (96/4) solution. An aliquot of extract was partitioned with methylene chloride and the aqueous fraction was recovered and filtered. An aliquot of the aqueous fraction was filtered through a $C_{18}$ SPE cartridge. An aliquot of the eluate from the $C_{18}$ SPE was diluted and applied to a MAX SPE cartridge. The analytes were eluted from the MAX sorbent in 1% TFA in methanol/water (9/1) solution following several solution rinses. The MAX eluate was evaporated to dryness and redissolved in aqueous 0.02M phosphoric acid, filtered, and analyzed for glyphosate, N-acetylglyphosate, N-acetyl AMPA. A separate aliquot of the eluate from the $C_{18}$ SPE was processed on a MCX SPE cartridge, diluted, filtered, and analyzed for AMPA.

Processed oil commodities were partitioned with methylene chloride and aqueous 0.02M phosphoric acid. The solution was centrifuged to resolve organic and aqueous fractions, and the aqueous fraction was collected. The remaining matrix and methylene chloride fraction were partitioned again with aqueous 0.02M phosphoric acid, and the aqueous fraction was collected and combined with the first aqueous fraction for quantitative recovery of the analytes. The combined aqueous extract was diluted, filtered, and analyzed for glyphosate, N-acetylglyphosate, N-acetyl AMPA and AMPA.

Final extracts were analyzed using HPLC with reverse phase chromatography and a triple quadrupole mass spectrometer with an electrospray source, operating in positive ion LC/MS/MS (liquid chromatograph/mass spectrometry/mass spectrometry) mode. Stable isotope standards of glyphosate ($1,2\text{-}^{13}C_2^{15}N$) and AMPA ($^{13}C^{15}N$) were added just prior to LC/MS/MS analysis as needed for internal standards to normalize response for matrix effects.

The recoveries from samples of various corn and soybean matrices fortified at 0.050 mg/kg (LOQ) and 0.50 mg/kg (10×LOQ) support the satisfactory performance of this method. Tables 17A, B and C, 18A and B, 19, 20, and 21 summarize the average recovery results for each analyte in sample matrices.

TABLE 17A

Corn Matrices

| MATRIX | FORTIFICATION LEVEL IN PPM (MG/KG) | SAMPLE SIZE (N) | RECOVERIES (%) | MEAN ± SD (% ± %) |
|---|---|---|---|---|
| GLYPHOSATE | | | | |
| Corn Forage | 0.050 | 13 | 100, 87, 95, 92, 95, 74, 74, 72, 79, 73, 82, 77, 83 | 83 ± 10 |
| | 0.50 | 12 | 100, 83, 85, 90, 88, 66, 69, 73, 75, 75, 78, 76 | 80 ± 10 |
| Corn Grain | 0.050 | 12 | 88, 78, 95, 77, 73, 74, 71, 77, 75, 73, 75, 71 | 77 ± 7 |
| | 0.50 | 12 | 80, 90, 87, 97, 97, 72, 73, 74, 72, 71, 70, 70 | 79 ± 10 |
| Corn Stover | 0.050 | 10 | 74, 86, 78, 73, 91, 90, 78, 77, 87, 83 | 82 ± 7 |
| | 0.50 | 10 | 79, 84, 88, 87, 84, 79, 81, 84, 83, 76 | 83 ± 4 |
| Corn Oil | 0.050 | 10 | 93, 100, 102, 99, 98, 96, 98, 98, 106, 103 | 99 ± 4 |
| | 0.50 | 10 | 96, 103, 95, 103, 101, 99, 107, 97, 104, 107 | 99 ± 2 |
| Corn Flour | 0.050 | 5 | 86, 101, 83, 87, 100 | 91 ± 8 |
| | 0.50 | 5 | 93, 90, 72, 69, 73 | 79 ± 12 |
| Corn Grits | 0.050 | 5 | 82, 93, 88, 80, 88 | 86 ± 5 |
| | 0.50 | 5 | 81, 79, 74, 99, 75 | 82 ± 10 |
| Corn Starch | 0.050 | 5 | 81, 83, 74, 74, 76 | 78 ± 4 |
| | 0.50 | 5 | 88, 85, 71, 77, 77 | 80 ± 7 |
| Corn Meal | 0.050 | 5 | 100, 116, 98, 83, 100 | 99 ± 12 |
| | 0.50 | 5 | 100, 99, 85, 91, 86 | 92 ± 7 |

TABLE 17B

Corn Matrices

| MATRIX | FORTIFICATION LEVEL IN PPM (MG/KG) | SAMPLE SIZE (N) | RECOVERIES (%) | MEAN ± SD (% ± %) |
|---|---|---|---|---|
| N-ACETYLGLYPHOSATE | | | | |
| Corn Forage | 0.050 | 13 | 92, 93, 97, 82, 84, 93, 95, 93, 87, 75, 93, 95, 95 | 90 ± 6 |
| | 0.50 | 12 | 89, 92, 82, 83, 78, 71, 91, 83, 96, 91, 90, 89 | 86 ± 7 |
| Corn Grain | 0.050 | 12 | 85, 83, 84, 83, 91, 92, 93, 78, 95, 82, 98, 81 | 87 ± 6 |
| | 0.50 | 12 | 83, 83, 86, 84, 86, 91, 92, 98, 91, 90, 94, 91 | 89 ± 5 |
| Corn Stover | 0.050 | 10 | 92, 89, 94, 86, 92, 81, 90, 92, 96, 97 | 91 ± 5 |
| | 0.50 | 10 | 92, 84, 91, 87, 102, 89, 90, 91, 90, 87 | 90 ± 5 |
| Corn Oil | 0.050 | 10 | 101, 100, 100, 99, 93, 100, 99, 98, 97, 99 | 99 ± 2 |
| | 0.50 | 10 | 103, 102, 98, 101, 98, 99, 102, 91, 102, 102 | 100 ± 4 |
| Corn Flour | 0.050 | 5 | 80, 82, 81, 89, 95 | 85 ± 7 |
| | 0.50 | 5 | 78, 72, 86, 91, 85 | 83 ± 7 |
| Corn Grits | 0.050 | 5 | 79, 79, 83, 81, 81 | 81 ± 2 |
| | 0.50 | 5 | 88, 75, 78, 106, 76 | 85 ± 13 |
| Corn Starch | 0.050 | 5 | 95, 90, 99, 96, 94 | 95 ± 3 |
| | 0.50 | 5 | 93, 94, 93, 95, 94 | 94 ± 1 |
| Corn Meal | 0.050 | 5 | 82, 65, 73, 89, 91 | 80 ± 11 |
| | 0.50 | 5 | 78, 81, 84, 83, 79 | 81 ± 13 |
| AMPA | | | | |
| Corn Forage | 0.050 | 10 | 89, 94, 93, 88, 87, 96, 117, 100, 102, 109 | 98 ± 10 |
| | 0.50 | 10 | 98, 93, 83, 85, 87, 93, 92, 90, 93, 94 | 91 ± 4 |
| Corn Grain | 0.050 | 12 | 97, 109, 104, 106, 115, 129, 105, 113, 102, 103, 120, 107 | 109 ± 9 |
| | 0.50 | 12 | 85, 83, 89, 93, 103, 102, 102, 102, 101, 101, 106, 95 | 97 ± 8 |

TABLE 17B-continued

Corn Matrices

| MATRIX | FORTIFICATION LEVEL IN PPM (MG/KG) | SAMPLE SIZE (N) | RECOVERIES (%) | MEAN ± SD (% ± %) |
|---|---|---|---|---|
| Corn Stover | 0.050 | 10 | 96, 102, 106, 86, 94, 93, 97, 103, 99, 95 | 97 ± 6 |
| | 0.50 | 10 | 97, 96, 83, 76, 76, 90, 92, 99, 100, 92 | 90 ± 9 |
| Corn Oil | 0.050 | 10 | 85, 109, 107, 130, 94, 87, 126, 84, 120, 77 | 102 ± 19 |
| | 0.50 | 10 | 92, 99, 93, 91, 88, 87, 92, 77, 90, 98 | 90 ± 6 |
| Corn Flour | 0.050 | 5 | 86, 86, 74, 89, 100 | 87 ± 9 |
| | 0.50 | 5 | 76, 77, 71, 81, 77 | 76 ± 4 |
| Corn Grits | 0.050 | 5 | 87, 90, 89, 87, 94 | 90 ± 3 |
| | 0.50 | 5 | 82, 78, 79, 83, 77 | 80 ± 3 |
| Corn Starch | 0.050 | 5 | 103, 94, 95, 100, 101 | 98 ± 4 |
| | 0.50 | 5 | 94, 92, 88, 94, 93 | 92 ± 2 |
| Corn Meal | 0.050 | 5 | 105, 113, 111, 86, 80 | 99 ± 15 |
| | 0.50 | 5 | 91, 89, 75, 74, 78 | 81 ± 8 |

TABLE 17C

Corn Matrices

| MATRIX | FORTIFICATION LEVEL IN PPM (MG/KG) | SAMPLE SIZE (N) | RECOVERIES (%) | MEAN ± SD (% ± %) |
|---|---|---|---|---|
| | | | N-ACETYL AMPA | |
| Corn Forage | 0.050 | 22 | 84, 90, 93, 114, 94, 122, 93, 69, 83, 83, 80, 87, 78, 87, 90, 78, 81, 87, 82, 69, 70, 90 | 87 ± 13 |
| | 0.50 | 2 | 73, 91 | 82 |
| | 5.00 | 21 | 91, 99, 83, 92, 88, 102, 112, 87, 93, 83, 99, 86, 81, 95, 95, 101, 72, 86, 86, 81, 92 | 91 ± 9 |
| Corn Grain | 0.050 | 11 | 77, 74, 100, 75, 79, 89, 91, 90, 91, 94, 86 | 87 ± 8 |
| | 0.50 | 10 | 80, 80, 79, 81, 88, 85, 82, 97, 84, 77 | 85 ± 7 |
| Corn Stover | 0.050 | 24 | 98, 86, 87, 85, 88, 96, 80, 89, 82, 82, 66, 75, 84, 74, 87, 80, 87, 89, 82, 68, 85, 76, 88, 84 | 83 ± 8 |
| | 0.50 | 2 | 85, 89 | 87 |
| | 10.0 | 17 | 95, 88, 85, 94, 91, 94, 81, 85, 95, 97, 92, 89, 93, 89, 97, 75, 92 | 90 ± 6 |

TABLE 18A

Soybean Matrices

| MATRIX | FORTIFICATION LEVEL IN PPM (MG/KG) | SAMPLE SIZE (N) | RECOVERIES (%) | MEAN ± SD (% ± %) |
|---|---|---|---|---|
| | | | GLYPHOSATE | |
| Soybean Forage | 0.050 | 8 | 88, 86, 91, 124, 90, 87, 115, 106 | 98 ± 15 |
| | 0.50 | 7 | 92, 89, 94, 103, 89, 98, 94 | 94 ± 5 |
| Soybean Seed | 0.050 | 5 | 88, 89, 91, 80, 78 | 85 ± 6 |
| | 0.50 | 5 | 85, 80, 72, 81, 73 | 78 ± 5 |
| Soybean Hay | 0.050 | 5 | 90, 99, 83, 91, 107 | 94 ± 9 |
| | 0.50 | 5 | 76, 78, 83, 78, 86 | 80 ± 4 |
| Soybean Oil | 0.050 | 5 | 100, 102, 91, 105, 96 | 99 ± 6 |
| | 0.50 | 5 | 95, 83, 101, 101, 85 | 93 ± 9 |
| Soybean Meal | 0.050 | 5 | 91, 102, 89, 87, 96 | 93 ± 6 |
| | 0.50 | 5 | 78, 81, 77, 79, 78 | 79 ± 2 |
| Soybean Hulls | 0.050 | 5 | 92, 93, 87, 75, 72 | 84 ± 10 |
| | 0.50 | 5 | 78, 71, 74, 77, 74 | 75 ± 3 |

TABLE 18B

Soybean Matrices

| MATRIX | FORTIFICATION LEVEL IN PPM (MG/KG) | SAMPLE SIZE (N) | RECOVERIES (%) | MEAN ± SD (% ± %) |
|---|---|---|---|---|
| N-ACETYLGLYPHOSATE | | | | |
| Soybean | 0.050 | 8 | 89, 92, 108, 89, 93, 85, 84, 85 | 91 ± 8 |
| Forage | 0.50 | 7 | 96, 98, 97, 98, 100, 80, 80 | 93 ± 9 |
| Soybean | 0.050 | 5 | 97, 96, 94, 100, 98 | 97 ± 2 |
| Seed | 0.50 | 5 | 92, 92, 96, 94, 99 | 95 ± 3 |
| Soybean | 0.050 | 5 | 92, 105, 88, 87, 100 | 94 ± 8 |
| Hay | 0.50 | 5 | 85, 84, 85, 87, 88 | 86 ± 2 |
| Soybean | 0.050 | 5 | 94, 92, 93, 94, 97 | 94 ± 2 |
| Oil | 0.50 | 5 | 101, 98, 98, 96, 97 | 98 ± 2 |
| Soybean | 0.050 | 5 | 97, 90, 75, 92, 90 | 89 ± 8 |
| Meal | 0.50 | 5 | 96, 100, 93, 89, 88 | 93 ± 5 |
| Soybean | 0.050 | 5 | 104, 95, 98, 93, 104 | 99 ± 5 |
| Hulls | 0.50 | 5 | 100, 99, 102, 95, 102 | 100 ± 3 |
| AMPA | | | | |
| Soybean | 0.050 | 8 | 90, 72, 85, 105, 91, 93, 90, 91 | 90 ± 9 |
| Forage | 0.50 | 7 | 72, 75, 99, 94, 95, 80, 78 | 85 ± 11 |
| Soybean | 0.050 | 5 | 93, 77, 108, 102, 90 | 94 ± 12 |
| Seed | 0.50 | 5 | 85, 74, 83, 77, 73 | 78 ± 5 |
| Soybean | 0.050 | 5 | 113, 95, 95, 94, 98 | 99 ± 8 |
| Hay | 0.50 | 5 | 76, 74, 80, 82, 85 | 79 ± 5 |
| Soybean | 0.050 | 5 | 98, 100, 118, 101, 116 | 107 ± 9 |
| Oil | 0.50 | 5 | 95, 95, 94, 96, 96 | 95 ± 1 |
| Soybean | 0.050 | 5 | 84, 76, 87, 82, 90 | 84 ± 5 |
| Meal | 0.50 | 5 | 74, 75, 72, 73, 76 | 74 ± 2 |
| Soybean | 0.050 | 5 | 84, 96, 84, 84, 90 | 87 ± 5 |
| Hulls | 0.50 | 5 | 81, 83, 84, 72, 81 | 80 ± 5 |
| N-ACETYL AMPA | | | | |
| Soybean | 0.050 | 4 | 92, 96, 83, 88, 80, 77 | 86 ± 7 |
| Forage | 0.50 | 10 | 96, 82, 89, 91, 81, 82, 87, 87, 74, 82 | 85 ± 6 |
| Soybean Seed | 0.050 | 17 | 111, 116, 98, 96, 100, 86, 87, 82, 96, 88, 82, 105, 113, 92, 87, 66, 83 | 89 ± 13 |
| | 0.50 | 10 | 115, 106, 95, 91, 81, 79, 70, 71, 75, 73 | 85 ± 16 |
| Soybean Hay | 0.050 | 23 | 79, 72, 78, 78, 83, 77, 86, 73, 78, 71, 70, 61, 77, 62, 80, 73, 68, 80, 92, 71, 67, 71, 66 | 75 ± 7 |
| | 0.50 | 6 | 82, 83, 81, 74, 75, 71 | 78 ± 5 |

TABLE 19

Oil Matrix (N-acetyl AMPA only)

| MATRIX | FORTIFICATION LEVEL IN PPM (MG/KG) | SAMPLE SIZE (N) | RECOVERIES (%) | MEAN ± SD (% ± %) |
|---|---|---|---|---|
| N-ACETYL AMPA | | | | |
| Corn Oil | 0.050 | 2 | 101, 109 | 105 |
| | 0.50 | 2 | 97, 100 | 99 |
| Soybean Oil | 0.050 | 4 | 108, 96, 97, 97 | 100 ± 6 |
| | 0.50 | 4 | 100, 105, 99, 104 | 102 ± 3 |
| Combined Oil | 0.050 | 6 | 101, 109, 108, 96, 97, 97 | 101 ± 6 |
| | 0.50 | 6 | 97, 100, 100, 105, 99, 104 | 101 ± 3 |

TABLE 20

Plum Matrix

| MATRIX | FORTIFICATION LEVEL IN PPM (MG/KG) | SAMPLE SIZE (N) | RECOVERIES (%) | MEAN ± SD (% ± %) |
|---|---|---|---|---|
| GLYPHOSATE | | | | |
| Plums | 0.050 | 5 | 90, 96, 95, 99, 98 | 95 ± 4 |
|  | 0.50 | 5 | 91, 94, 96, 89, 85 | 91 ± 4 |
| N-ACETLYGLYPHOSATE | | | | |
| Plums | 0.050 | 5 | 110, 91, 93, 105, 110 | 102 ± 9 |
|  | 0.50 | 5 | 98, 100, 97, 87, 82 | 93 ± 8 |
| AMPA | | | | |
| Plums | 0.050 | 5 | 93, 88, 90, 96, 108 | 95 ± 8 |
|  | 0.50 | 5 | 93, 95, 107, 112, 92 | 100 ± 9 |
| N-ACETYL AMPA | | | | |
| Plums | 0.050 | 5 | 99, 106, 109, 98, 100 | 102 ± 5 |
|  | 0.05 | 5 | 112, 100, 102, 89, 99 | 100 ± 8 |

TABLE 21

Lime Matrix

| MATRIX | FORTIFICATION LEVEL IN PPM (MG/KG) | SAMPLE SIZE (N) | RECOVERIES (%) | MEAN ± SD (% ± %) |
|---|---|---|---|---|
| GLYPHOSATE | | | | |
| Limes | 0.050 | 5 | 96, 88, 110, 100, 105 | 100 ± 8 |
|  | 0.50 | 5 | 97, 90, 98, 107, 103 | 99 ± 6 |
| N-ACETLYGLYPHOSATE | | | | |
| Limes | 0.050 | 5 | 78, 91, 78, 84, 99 | 86 ± 9 |
|  | 0.50 | 5 | 85, 91, 96, 98, 87 | 91 ± 6 |
| AMPA | | | | |
| Limes | 0.050 | 5 | 100, 96, 91, 85, 104 | 95 ± 7 |
|  | 0.50 | 5 | 101, 101, 101, 90, 98 | 98 ± 5 |
| N-ACETYL AMPA | | | | |
| Limes | 0.050 | 5 | 79, 93, 105, 104, 89 | 94 ± 11 |
|  | 0.50 | 5 | 95, 121, 107, 112, 100 | 107 ± 10 |

Materials

TABLE 22

Equipment

| EQUIPMENT DESCRIPTION | PRODUCT ID | SUPPLIER |
|---|---|---|
| Freezer | Labline ® Frigid-Cab ® | Labline Instruments, Inc. (Melrose Park, IL) |
| Refrigerator | 6FAR | Marvel Industries, Inc. (Richmond, IN) |
| Analytical Balance | AE163 Dual Range Balance PM460 Toploading Balance | Mettler Instrument Corp. (Hightstown, NJ) |
| Homogenizer | Tissumizer ® Homogenizer Model SDT-20 equipped with Model SDT-182EN shaft (Teflon ® bearing) | Tekmar Company (Cincinnati, OH) |
| Sonication | Bransonic ® 52-H, 0.75 gal. capacity | Branson Ultrasonics Corp. (Danbury, CT) |
| Vortex Mixer | Vortex Genie ® K-550-G or Vortex-2 Genie ® | VWR, Inc. (West Chester, PA) |
| Filtration | Pall Acrodisc ® Nylon Syringe Filters: 13 mm × 0.2-μm (#4427T Whatman ® Puradisc ™ 25 GD 1.0 μm × 25 mm GMF-150 Filter | VWR (Bridgeport, NJ) |
| Centrifuge | Sorvall ® Centrifuge, Model RT7 with a RTH750 rotor | Sorvall Instruments (Wilmington, DE) |
|  | RC5C with Super-Lite ™ GSA Model SLA-1500 Rotor | Sorvall Instruments (Wilmington, DE) |
| Solid Phase Extraction | Oasis ™ MAX SPE Cartridge, 500 mg/6 ml, Cat. No. 186000865 | Waters Corporation (Milford, MA) |
|  | Oasis ™ MCX SPE Cartridge, 500 mg/6 ml, Cat. No. 186000776 | Waters Corporation (Milford, MA) |
|  | Bond Elut ™ SPE Cartridge: $C_{18}$, 500 mg/6 cc, Cat. No. 12102052; Reservoir Adapters, Cat. No. 12131003. | Varian, Inc. (Palo Alto, CA) |
|  | Supelco Visiprep ™ SPE Vacuum Manifold Standard, 12-port Model, Cat. No. 57030-U Supelco Disposable Flow Control Valve Liners for Visiprep ™-DL, Cat. No. 57059 | Supelco (Bellefonte, PA) |
| Analytical Evaporator | N-Evap ® Model 112 (with stainless steel luer fit needles) | Organomation Assoc. (South Berlin, MA) |
| Labware | 250 ml, Nalgene ® Cat. No. 16129 028 Polypropylene Centrifuge Bottles; Borosilicate Glass Scintillation Vials with Cap, 20 ml, Cat. No. 66022-004; Class B (calibrated to contain) Metric Scale Graduated Cylinders, 50-ml, 100-ml, and 250-ml capacity; Disposable PET Transfer Pipettes. | VWR (Bridgeport, NJ) |
|  | Falcon ® 2098 (50 ml), 2096 (15 ml) Polypropylene Centrifuge Tubes; 3-ml Disposable Syringe, Cat. No. BD309585; 5-ml Disposable Syringe, Cat. No. BD301027 | Becton Dickinson (Franklin Lakes, NJ) |
| Variable Volume Pipettors | Electronic 10-ml variable volume Pipettor Mechanical, positive displacement, 100-μL, 250-μL, and 1000-μL Pipettors | Rainin (Walnut Creek, CA) Gilson, Inc. (Middletown, WI) |

TABLE 23

| EQUIPMENT DESCRIPTION | PRODUCT ID | SUPPLIER |
|---|---|---|
| HPLC/MS SYSTEM | | |
| HPLC | HP1100: G1322A Degasser, G1311A Quaternary Pump; G1330A Chilled Well Plate Autosampler; G1316A Column Unit; G1314A Variable Wavelength Detector | Agilent Technologies, Inc. (Palo Alto, CA) |
| Autosampler Vials | Target DP Amber Kit, T/S/T Septa, 100 PK, Cat. No. 5182-0556; Clear Screw Cap Vial, Cat. No. 5182-0724 | Agilent Technologies, Inc. (Palo Alto, CA) |
| HPLC Guard Column | Nova-Pak ® Sentry ™ $C_{18}$ Guard Column, 3.9 × 20 mm, 4-µm particle size, Cat. No. WAT044380 (Holder Cat. No. WAT046910) | Waters Corporation (Milford, MA) |
| HPLC Column | Luna ® Phenyl-Hexyl; 4.6 mm × 150 mm, 3-µm Particle Size Diameter | Phenomenex ® (Torrance, CA) |
| Triple Quadrupole MS | MicroMass Quattro Premier Triple Quadrupole Mass Spectrometer using an Electrospray (ESI) Interface and MassLynx XP Version 4.0 Software | Waters Corporation (Milford, MA) |

TABLE 24

Reagents

| REAGENTS | PRODUCT DESCRIPTION | PRODUCT ID | SUPPLIER |
|---|---|---|---|
| Formic Acid | GR, ACS, 98% | FX0440-11 | EMD Chemicals (Gibbstown, NJ) |
| Glacial Acetic Acid | OmniTrace ®, Ultra High Purity, 99% | AX0077-1 | EMD Chemicals (Gibbstown, NJ) |
| Hydrochloric Acid | Hydrochloric Acid GR ACS (36.5-38% assay) | HX0603-4 | EMD Chemicals (Gibbstown, NJ) |
| Phosphoric Acid | 'Baker Analyzed', 500 ml | 0260-02 | JT Baker (Phillipsburg, NJ) |
| Trifluoroacetic Acid | 'Baker Analyzed', 100 ml | W729-05 | JT Baker (Phillipsburg, NJ.) |
| Methanol | OmniSolv ®, 4 L | MX0488-1 | EMD Chemicals (Gibbstown, NJ) |
| Water | OmniSolv ® HPLC grade, 4 L | WX0004-1 | EMD Chemicals (Gibbstown, NJ) |
| Methylene Chloride | OmniSolv ®, 1 L | DX0831-6 | EMD Chemicals (Gibbstown, NJ) |
| Ammonium Hydroxide Solution | EM SupraPur ®, min 25%, 250 ml or EM GR ACS, 28-30%, 500 ml | 5428-1 AX1303-13 | EMD Chemicals (Gibbstown, NJ) |
| Trietylamine (TEA) | Sigma-Aldrich Triethylamine, ≧99.5% | 471283-100 ml | VWR (Bridgeport, NJ) |

Reference Analytical Standards

Reference analytical standards of glyphosate (DPX-B2856-011, 96% pure) and N-acetylglyphosate, sodium salt (IN-MCX20-000, 67.4% pure as free acid) were obtained from Sigma Aldrich. Reference analytical standard of AMPA (IN-YB726-001, 99.53% pure) was obtained from Alfa Aesar. Reference analytical standard of N-acetyl AMPA was synthesized at E. I. du Pont de Nemours and Company, DuPont Agricultural Products, Wilmington, Del. Characterization data are archived by DuPont Agricultural Products, E.I. du Pont de Nemours and Company, Wilmington, Del.

Internal Standards

Glyphosate 1,2-$^{13}C_2$$^{15}$N and aminomethyl phosphonic acid $^{13}$C $^{15}$N (AMPA) stable isotope standards were obtained from GmbH for use as internal standards. Structures and specific information follow.

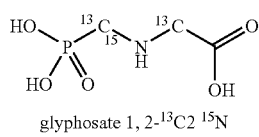

glyphosate 1, 2-$^{13}C_2$ $^{15}$N

Product Number: 14050100
Lot: 41012WA  Purity: 99 ± 1%
Molecular weight = 172.06 g/mole
Monoisotopic Mass = 172.02 g/mole

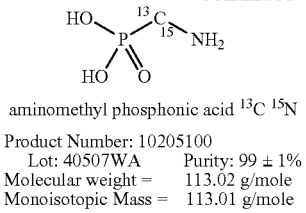

aminomethyl phosphonic acid $^{13}$C $^{15}$N

Product Number: 10205100
Lot: 40507WA  Purity: 99 ± 1%
Molecular weight = 113.02 g/mole
Monoisotopic Mass = 113.01 g/mole Example 2

Principle of Analytical Method

Glyphosate, N-acetylglyphosate, AMPA, and N-acetyl AMPA were extracted from plant tissue and solid process fraction matrices of various crops into dilute aqueous acid (0.1% formic acid or 0.025N hydrochloric acid)/methanol (96/4) using a probe homogenizer. Dilute hydrochloric acid was substituted for formic acid to increase acidity for more efficient extraction of N-acetylglyphosate from corn flour and meal process fractions. Multiple extractions (3) were made for quantitative recovery of analytes and to eliminate moisture content in the matrix as a recovery factor. Additional extraction solution volumes were necessary for stover, hay, and hulls because of the lower moisture content in those matrices.

Purification of Glyphosate, N-acetylglyphosate and N-acetyl AMPA in Solid Matrix Sample Extracts:

An aliquot of extract was partitioned with methylene chloride and the aqueous fraction was recovered and filtered (0.2-1.0 µm) to remove particulates. Approximately 10 ml of the aqueous fraction was collected following filtration through a $C_{18}$ SPE cartridge. An aliquot of the eluate collected from the $C_{18}$ SPE was diluted and applied to a MAX SPE cartridge. The analytes were eluted from the MAX sorbent in 1% TFA in methanol/water (9/1) solution following several solution rinses. The MAX eluate was evaporated to dryness and redissolved in aqueous 0.02M aqueous phosphoric acid, filtered, and analyzed for glyphosate and N-acetylglyphosate. A minor modification was made to this procedure for the analysis of soybean samples. For soybean seed and meal following partitioning, extract samples were heated in a steam bath for approximately 15 minutes to precipitate additional material in the extract prior to particulate filtration.

Purification of AMPA in Solid Matrix Sample Extracts:

A second aliquot of the eluate collected from the $C_{18}$ SPE described above was processed through a MCX SPE cartridge, diluted, filtered and analyzed for AMPA. A separate analyte purification procedure was required for AMPA due to low recoveries using MAX SPE purification.

Analysis of Glyphosate, N-acetylglyphosate, AMPA and N-acetyl AMPA in Oil Samples:

An aliquot of the sample was diluted with methylene chloride and the analytes were liquid-liquid partitioned into 0.02M aqueous phosphoric acid. The sample was partitioned twice for quantitative transfer of the analytes. Centrifugation was used to define phase separation in each partition.

All final extracts were filtered (0.2 µm) prior to LC/MS/MS analysis to remove particulates as preventive maintenance measure for the HPLC system. The use of phosphoric acid in the final sample solution was shown to improve the overall response and linearity of glyphosate. The use of glyphosate and AMPA stable isotopes as internal standards in final extract solutions was required to normalize for matrix effects in the analysis of soybean matrices and is recommended for general use to improve method ruggedness. The stable isotope internal standards were initially added to final extracts just prior to LC/MS/MS analysis, but the procedure was modified for addition just prior to SPE purification to normalize for SPE performance and matrix effects. The stable isotope forms of glyphosate and AMPA used as internal standards behave identically to glyphosate and AMPA. The analytes were resolved by HPLC reverse-phase chromatography using a phenyl-hexyl analytical column coupled to electrospray ionization in positive ion mode with MS/MS detection. The same chromatography conditions were used for glyphosate, N-acetylglyphosate, AMPA, and N-acetyl AMPA analysis. Two molecular ion transitions were acquired for each analyte, except for AMPA (only 1 molecular ion transition was available in positive ion mode). Quantitative analysis was accomplished using a single molecular ion transition for each analyte. With the exception of AMPA, the relative abundance of the 2 detected MS/MS fragment ions provides confirmatory evidence for each analyte.

Analytical Procedure
Reagent Solutions

Extraction Solution A: 96% aqueous 0.1% formic acid/4% methanol.

Extraction Solution B: 96% aqueous 0.025N hydrochloric acid/4% methanol.

80% or 95% Methanol in Water Solution 0.1M Acetic Acid in 80% Methanol/Water Solution 0.25% Ammonium Hydroxide in 95% Methanol/5% Water 0.25% Ammonium Hydroxide in Water: Per liter volume, 10 ml of ammonium hydroxide solution (minimum 25%) was added to small volume of HPLC grade purified water, then diluted to final volume with HPLC grade purified water. This is a conditioning solution for MAX SPE (12 ml/sample, dilution in water procedure). Note: 1 ml of 25% ammonium hydroxide diluted to 100 ml≈0.25% $NH_4OH$.

Elution Solution, 1% TFA in 90% methanol/10% water.

1.0M Phosphoric Acid Solution: Per 10 ml volume, 0.67 ml of concentrated phosphoric acid (min. 85%) was added to HPLC grade purified water in a 15-ml polypropylene centrifuge tube and dilute to final volume using gradations on tube with HPLC grade purified water.

Sample and Standard Final Solution, aqueous 0.02M phosphoric acid

Aqueous 0.2M Formic Acid, aqueous mobile phase

Stock Standard Preparation and Stability

Standards with purity of greater than 95% were used. A minimum of approximately 10 mg of standard was weighed on an analytical balance that provides a weight precision to three significant figures, or the amount of standard was increased to satisfy this condition.

Since residue tolerances are established in glyphosate free-acid equivalents, stock standard solutions for each analyte are prepared in glyphosate free-acid equivalents so that fortifications and recoveries can be determined in parent free acid equivalents. As needed, individual free-acid equivalent stock standards solutions were prepared were prepared for glyphosate, N-acetylglyphosate, AMPA or N-acetyl AMPA by adding appropriate amounts of standard to a 100-ml volumetric flask and diluting to final volume with water (water refers to HPLC grade or equivalent water). The following calculation and Table 25 provide guidance for the preparation of 100 ml of a 100 µg/ml (ppm) in glyphosate free-acid equivalents for each analyte.

$$\text{mg analyte} = \left(\frac{100 \ \mu g/mL}{1000 \ \mu g/mL}\right) \times 100 \ mL \times \left(\frac{\text{MW analyte}}{\text{MW parent free acid}}\right) / (\% \ \text{Purity}/100)$$

TABLE 25

| Analyte | Avg. MW (g/mole) | Purity | Target Weight (mg) | Parent free-acid eq. (µg/mL) |
|---|---|---|---|---|
| glyphosate free acid | 169.07 | 97.0% | 10.31 | 100.0 |
| AMPA | 111.04 | 99.0% | 6.63 | 100.0 |
| N-acetylglyphosate free acid | 211.11 | 63.0% | 19.82 | 100.0 |
| N-acetyl AMPA free acid | 153.08 | 76.0% | 11.91 | 100.0 |

Amounts weighed for each analyte were at least 10 mg and, therefore, individual analyte stock solution concentrations can exceed 100 µg/ml in parent free-acid equivalents. Stock standard solutions may be prepared at higher concentrations (not to exceed 1 mg/ml). A minimum standard weight of approximately 10 mg and final standard volume of at least 10 ml were observed. These solutions were stored at or below 4° C. and are stable for at least 9 months.

Internal Standard Preparation and Stability

Glyphosate 1,2-$^{13}C_2{}^{15}N$ and aminomethyl phosphonic acid $^{13}C^{15}N$ (AMPA) stable isotope standards were supplied in amber ampules containing 1.1 ml of aqueous solution at a nominal concentration of 100 mg/L (μg/ml). Each standard solution was transferred to an individual amber vial and stored at or below 20° C. in the dark. The isotopic purity was verified for each standard by analysis of an approximately 500 ng/ml solution following protocol outlined below.

An intermediate 100 ng/ml internal standard solution containing glyphosate and AMPA isotopes was prepared by diluting 100 μg/ml stock solution at a rate of 0.1 ml in 100 ml of aqueous 0.02M phosphoric acid or HPLC grade purified water. Internal standards were included in final extract and calibration standard solutions at a rate of 50 μL/ml or 5 ng/ml in the final solution volume. Each 100 ml of a 100 ng/ml standard solution can be used in up to 400 samples when 250 μL of internal standard is applied in 5 ml of final extract.

Figure 25:
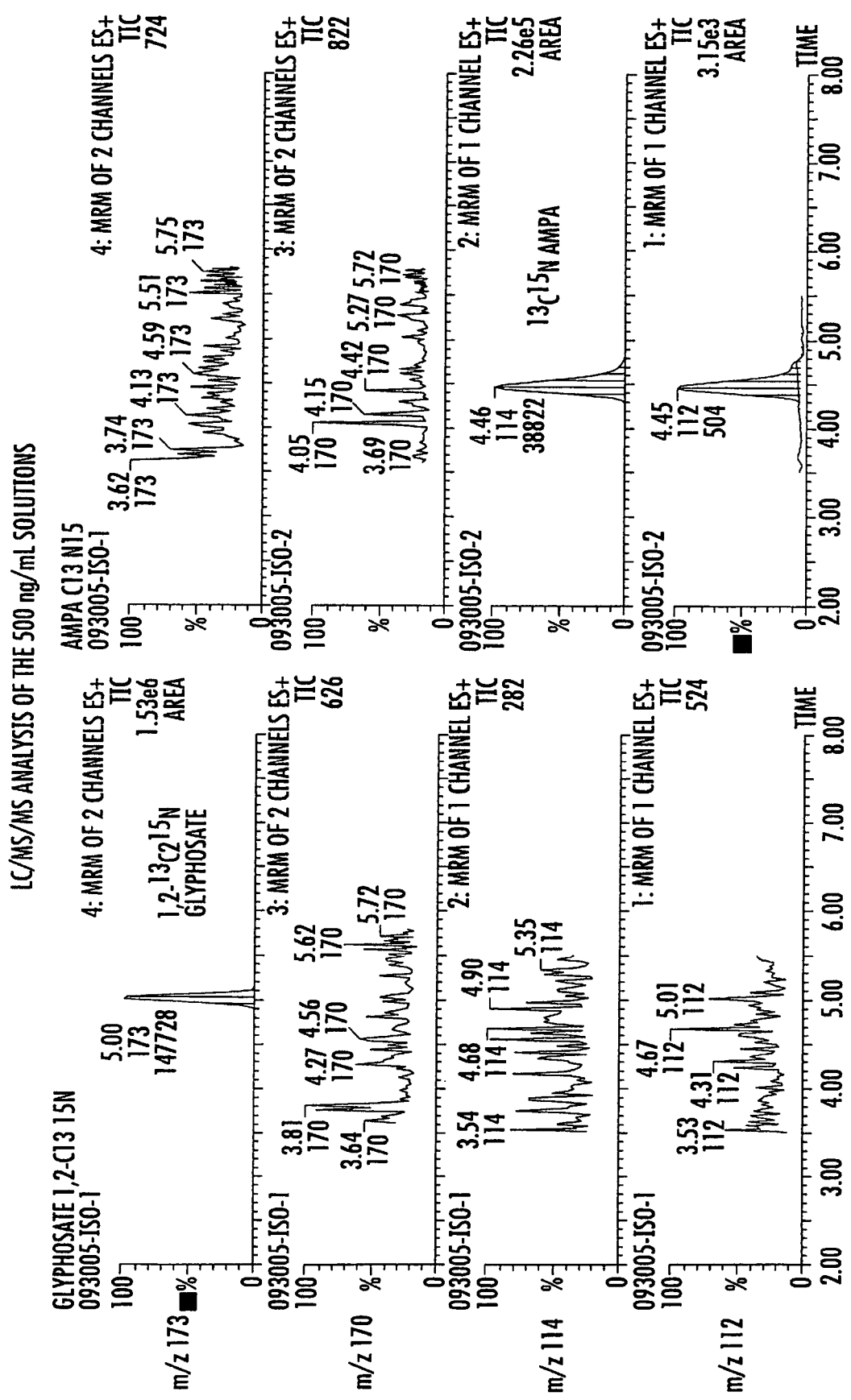
FIG. 25 provides an LC/MS/MS analysis showing the isotopic purity evaluation of glyphosate 1,2-$^{13}$C2$^{15}$N and AMPA $^{13}$C$^{15}$N standards.

The 100 μg/ml standards (Glyphosate 1,2-$^{13}C_2{}^{15}N$, 100 μg/ml×1.1 ml and Aminomethyl phosphonic acid $^{13}C^{15}N$ (AMPA), 100 μg/ml×1.1 ml) were individually transferred to screw cap amber autosampler vials using glass transfer pipet. A 0.025 ml aliquot of the 100 μg/ml standard was transferred to a 15 ml polypropylene centrifuge tube and diluted with 5 ml of 0.02M $H_3PO_4$ to prepare separate solutions at 500 ng/ml. A 0.10 ml aliquot of each 100 μg/ml standard was combined in a single 100 ml volumetric flask and diluted to volume with 0.02M $H_3PO_4$ to prepare a mixed solution at 100 ng/ml. This solution was divided into 2×50 ml polypropylene centrifuge tubes. All standards were stored in refrigerator. The LC/MS/MS analysis of the 500 ng/ml solutions is shown in FIG. 25.

Intermediate and Fortification Standards Preparation and Stability

Fortification solutions were prepared in glyphosate free-acid equivalent concentrations from dilutions of the individual stock solutions. If glyphosate, N-acetylglyphosate, AMPA or N-acetyl AMPA fortifications are required at levels greater than 0.5 mg/kg (10×LOQ), the individual stock standard solutions should be used to fortify samples. 10.0 μg/ml and 1.0 μg/ml fortification solutions were prepared for sample fortification at the 10×LOQ and LOQ, respectively. Alternative concentrations may be prepared as needed for other fortification levels.

10.0 μg/ml Fortification Solution: The stock solution for each analyte was dilated appropriately into a common volumetric flask, diluted to volume with HPLC grade purified water, cap, and mix well. For example, 1.00 ml of a 100 μg/ml stock solution was combined for each required analyte in a 10-ml volumetric flask and diluted to final volume with water, cap, and mix well.

Stock solutions concentrations will vary and the required volume of each analyte stock solution used to prepare fortification solution is adjusted for correct final concentration as determined using the following calculation.

$$\frac{\text{Final Concentration, μg/mL} \times \text{Final Volume, mL}}{\text{Stock Solution Concentration, μg/mL}} = \text{Aliquot(mL) of Stock Solution added}$$

For example, to prepare 50 ml of a 10 μg/ml fortification solution from glyphosate, N-acetylglyphosate, and AMPA stock solutions prepared respectively at 115 μg/ml, 186 μg/ml, and 206 μg/ml in glyphosate free-acid equivalent concentrations the following stock solution volumes was added to a 50-ml volumetric flask.

Glyphosate=10 μg/ml×50 ml/115 μg/ml=4.35 ml stock solution

N-acetylglyphosate=10 μg/ml×50 ml/186 μg/ml=2.69 ml stock solution

AMPA=10 μg/ml×50 ml/206 μg/ml=2.42 ml stock solution 10 ml Fortification Solution: The 10.0 μg/ml fortification solution (preferred) or the stock solution for each analyte was diluted appropriately with HPLC grade purified water into a common volumetric flask. For example, 1.0 ml of the 10.0 μg/ml fortification solution was transferred to a 10 ml volumetric flask, dilute to volume with water, cap, and mix well. Store at or below 4° C. and replace monthly.

Chromatographic Standard Preparation and Stability

Calibration standards were prepared in glyphosate free-acid equivalent concentrations from dilutions of fortification standards or individual stock standards. Glyphosate and AMPA stable isotopes can be used as internal standards in calibration standards and final extract solutions to normalize recoveries for matrix effects for sample analysis. A minimum of 5 or more calibration standards over a range from approximately 50% of LOQ equivalent final concentration to ≧120% of the highest expected final sample concentration are recommended for quantification. AMPA analysis was conducted separately and had an LOQ equivalent final concentration of 2.0 ng/ml. The LOQ equivalent final concentration for glyphosate, N-acetylglyphosate and N-acetyl AMPA was 1.0 ng/ml.

For example, intermediate standard solutions of 10.0 ng/ml and 100 ng/ml were prepared from the 1.0 and 10.0 μg/ml fortification solutions, respectively, by diluting a 250 μL aliquot to final volume of 25.0 ml in standard prep solution (aqueous 0.02M phosphoric acid). Calibration standards were prepared from serial dilutions of these intermediate standards with the addition of internal standards as indicated in the following Table 26.

TABLE 26

| Diluting Standard (ng/mL) | Diluting Standard Aliquot (mL) | 100 ng/mL Internal Standard (mL) | Final Volume (mL) | Final Concentration (ng/mL) |
| --- | --- | --- | --- | --- |
| 100.0 | 5.0 | 0.5 | 10.0 | 50 |
| 100.0 | 2.0 | 0.5 | 10.0 | 20 |
| 100.0 | 1.0 | 0.5 | 10.0 | 10 |
| 10.0 | 5.0 | 0.5 | 10.0 | 5 |
| 10.0 | 2.0 | 0.5 | 10.0 | 2 |
| 10.0 | 1.0 | 0.5 | 10.0 | 1 |
| 10.0 | 0.5 | 0.5 | 10.0 | 0.5 |

Concentrations are glyphosate free-acid equivalents.

Calibration standards were kept at or below 4° C. and replaced at least biweekly. Calibration standards use may be extended if supported by stability test data.

Source (& Characterization) of Samples

Corn forage, grain, and stover matrix test samples were collected from transgenic hybrid maize that contained the glyphosate acetyl transferase gene (glyat). Corn flour, starch, grits, refined oil (wet milled), meal (dry milled), and refined oil (dry milled) samples were processed and also collected. Soybean forage, seed, and hay were from soybean line containing glyat and collected from greenhouse plants. Soybean hulls were processed and soybean meal from a soybean line containing glyat was also prepared. Plums and limes were purchased at local supermarkets.

Storage & Preparation of Samples

All samples were stored at −20±5° C. prior to sample preprocessing, extraction, and analysis. In preparation for analysis, the RAC samples were removed from frozen storage and ground frozen with dry ice using a Hobart® Food Processor (Model #84145) for forage and stover and a Quaker Grinding Mill (Model 4E) for grain. Samples were mixed extensively during the grinding process to ensure homogeneity. Most of the dry ice was allowed to sublime, and then the samples were returned to the freezer for storage until extraction and analysis. Process Fraction samples were homogenous when received and require no further preprocessing.

Sample Fortification Procedure

Untreated matrix control samples are fortified in extraction containers (250-ml bottles or 50-ml centrifuge tubes) as required in glyphosate free-acid equivalent concentrations. The 10.0 and 1.0 µg/ml Fortification Standards containing a mixture of test analytes were used to fortify test samples. Table 27 provides exemplary fortifications suitable for use with the presently disclosed methods.

TABLE 27

| SAMPLE IDENTIFICATION | AMOUNT (G) | FORTIFICATION SOLUTION | | FORTIFICATION (MG/KG) |
|---|---|---|---|---|
| | | µG/ML | ML | |
| Forage, grain, seed, plum, lime, or solid process fractions LOQ Fort | 5.0 ± 0.05 | 1.0 | 0.250 | 0.050 |
| Forage, grain, seed, plum, lime, or solid process fractions 10 × LOQ Fort | 5.0 ± 0.05 | 10.0 | 0.250 | 0.50 |
| Stover, hay, or hulls LOQ Fort | 10.0 ± 0.1 | 1.0 | 0.500* | 0.050 |
| Stover, hay, or hulls 10 × LOQ Fort | 10.0 ± 0.1 | 10.0 | 0.500* | 0.50 |
| Crop Oil LOQ Fort | 2.0 ± 0.02 | 1.0 | 0.100 | 0.050 |
| Crop Oil 10 × LOQ Fort | 2.0 ± 0.02 | 10.0 | 0.100 | 0.50 |

Concentrations are glyphosate free-acid equivalents.
*Dilute fortification aliquot in 5 ml of water prior to application for better distribution of analytes on very dry matrices.

For each solid matrix sample, the appropriate amount was weighed into a clean 250-ml PPCO centrifuge bottle. For each oil sample, 2.0±0.02 g of sample was weighed into a clean 50-ml glass or polypropylene centrifuge tube. For dry commodities (e.g., stover, hay, hulls), the fortification aliquot should be diluted in 5 ml of HPLC grade purified water in a vial or tube prior to fortification for better dispersion of the analytes in the matrix. After fortification, the solid matrix samples are allowed to stand in a fume hood for approximately 15 minute to allow the fortification solution to dissipate.

Example 3

Analyte Extraction Procedures

Analyte extractions procedures are provided for solid matrices including corn RACs (forage, grain, stover), corn process fractions (flour, grits, meal, starch), soybean RACs (forage, seed, hulls), and soybean process fractions (meal, hulls). Sample amount, extraction solution, and extraction solution volumes vary by commodity. Stover, hay, and hulls require 2× sample amount (10.0 g) and extract volume (200 ml) to compensate for dry commodity. Corn and soybean oil process fraction procedures are provided elsewhere herein.

Solid Matrix Samples
First Extraction
1.0 Correct amount of sample was weighed into the appropriate container as indicated above.
2.0 Samples were fortified as indicated above and solid matrices allowed to air dry in hood for 15 minutes.
3.1 For forage, grain, seed, grits, starch, or soy meal samples, 50 ml of Extraction Solution A (96% aq. 0.1% formic acid/4% methanol) was added to sample. This step was applied to watery (e.g. plums) and acid (e.g. lime) crop types.
3.2 For stover, hay, or hulls, 100 ml of Extraction Solution A (96% aq. 0.1% formic acid/4% methanol) was added to the sample. The tube or vial used to dilute the fortification solution to 5 ml was rinsed with the extraction solution for quantitative transfer of the analytes to the sample during this step for dry matrix samples.
3.3 For corn meal or flour, 50 ml of Extraction Solution B (96% aq. 0.025N hydrochloric acid/4% methanol) was added to sample.
4.0 The sample was capped and allowed to stand for 15 minutes so extraction solution can soak into matrix.
5.0 The sample was uncapped and homogenized using a Tissumizer® for 2 minutes at 40-50% of total motor speed or at a speed that efficiently homogenizes the samples without overheating or foaming.
6.0 The samples were capped and centrifuged for 15 minutes at 13,000 rpm to achieve sufficient clarification of supernatant.
7.0 The supernatants were decanted into clean graduated cylinders (100 ml or 250 ml as needed for final volume capacity). The supernatant may be decanted through paper filters to clarify extract solutions. Hulls were pressed with spoon or spatula when decanting to recover additional extraction solution (30-40 ml may be retained in the pellet).

Second Extraction
8.1 For forage, grain, seed, grits, starch, meal, or flour samples, 25 ml of Extraction Solution A (96% aq. 0.1% formic acid/4% methanol) was added to sample. Apply this step to watery (e.g. plum) and acid (e.g. lime) crop types. Note: the second and third extractions of meal and flour matrices use Extraction Solution A.
8.2 For stover, hay, or hulls samples 50 ml of Extraction Solution A (96% aq. 0.1% formic acid/4% methanol) was added to sample.
9.0 Samples were homogenized using a Tissumizer® for 2 minutes at 40-50% of total motor speed or at a speed that efficiently homogenizes the samples without overheating or foaming.
10.0 Samples were capped and centrifuged for 15 minutes at 13,000 rpm to achieve sufficient clarification of supernatant. The supernatant was decanted through paper filters to clarify extract solutions.
11.0 Supernatants were decanted and combined to respective graduated cylinders.

Third Extraction
12.0 Repeat steps 8.1 thru 11.0
13.1 For forage, grain, seed, grits, starch, meal, or flour samples the final extract volumes were adjusted to 100 ml with HPLC grade water or determine exact volume in excess of 100 ml. Apply this step to watery (e.g. plum) and acid (e.g. lime) crop types.
13.2 For stover, hay, or hulls samples final extract volumes were adjusted to 200 ml with HPLC grade water or determine exact volume in excess of 200 ml.
14.0 The supernatants were transferred to clean polypropylene bottles. The sample was poured back and forth from graduated cylinder to bottle to mix solution. Cap filled bottles. Raw extracts may be stored at or below 4° C.

Example 4

Analyte Purification Procedures

For the analysis of solid matrix sample extracts, methylene chloride partition and $C_{18}$ SPE filtration procedures (as outlined below) were initially used for the purification of all analytes. An aliquot of the $C_{18}$ SPE eluate was processed for the analysis of AMPA by strong cation exchange MCX SPE (as outlined below). A separate aliquot of the $C_{18}$ SPE eluate was processed for the analysis of glyphosate and N-acetylglyphosate and N-acetyl AMPA by strong anion exchange MAX SPE (as outlined below). Separate procedures were required due to the characteristics and behavior of analytes on SPE stationery phases selected. For the analysis of oil process fractions, a single procedure was used for the extraction and purification of all analytes (see below).

A. Glyphosate, N-acetylglyphosate, and AMPA and N-acetyl AMPA Initial Purification Procedure in Solid Matrix Samples
Methylene Chloride Partition
1.0 30 ml sample extract was transferred to a 50-ml polypropylene centrifuge tube and 10 ml of methylene chloride was added to sample aliquot which was capped and shook or vortexed for at least 30 seconds (use gradations on tube for volume measurements). For soybean seed or meal, 20 ml of methylene chloride was used. Samples were centrifuged 10 minutes at sufficient rpm (e.g., 3000 rpm) to form distinct layers (aqueous above protein and methylene chloride). Smaller extract aliquots may be used to accommodate the individual analyte purification procedures (e.g., 15 ml of extract and 5 ml of methylene chloride when AMPA analysis not needed or to separate the 2 purification procedures).
2.1 For all solid matrices except soybean seed and meal, as much of the aqueous fraction was recovered as possible without disturbing the precipitate or methylene chloride layers and filtered through a 1.0 μm or smaller hydrophilic filter (nylon or glass microfiber) into a clean 50-ml polypropylene centrifuge tube. (The original centrifuge tubes were emptied and saved to collect waste extract in $C_{18}$ SPE Filtration step 4.0). At least 15 ml of the aqueous fraction was recovered and filtered to use 14 ml for the following $C_{18}$ SPE purification. Processing a smaller volume of extract may be helpful if filtration is difficult. Filtration is an important precondition for the ion exchange SPE performance.
2.2 For soybean seed and meal samples, as much of the aqueous fraction was recovered as possible without disturbing the precipitate or methylene chloride layers and added to a clean glass tube. (The original centrifuge tubes were emptied and saved to collect waste extract in $C_{18}$ SPE Filtration step 4.0). The aqueous extract samples were placed in a steam bath for at least 15 minutes to further precipitate matrix, then filtered through a 1.0-μm or smaller hydrophilic filter (nylon or glass microfiber) into a clean 50-ml polypropylene centrifuge tube.

$C_{18}$ SPE Filtration
1.0 Waste collection tubes were installed in vacuum manifold to collect initial sample load volume. Note: waste collection tubes were used to prevent cross-contamination in the vacuum manifold during step 3.0.
2.0 $C_{18}$ SPE (6 cc/500 mg, Varian #12102052) cartridges were conditioned with 1 ml of methanol, followed by 2 CV's (CV=6 ml) of Extraction Solution A (96% aq. 0.1% HCOOH/4% MeOH). Vacuum or positive pressure was applied as needed for slow drip rate (1-2 ml/min). Note: aqueous 0.2M formic acid may be substituted for Extraction Solution A for $C_{18}$ SPE conditioning.
3.0 As last of conditioning solution enters the sorbent, 4.0 ml of aqueous sample extract from Methylene Chloride Partition Purification step 2.0 was added onto SPE column.
4.0 After dripping stops, the waste collection tubes were moved and clean 15-ml centrifuge tubes were installed. 10.0 ml of aqueous sample extract from step 2.0 was added, eluted, and eluate collected. Extract solution may be stored at or below 4° C.

B. AMPA Purification Procedures for Solid Matrix Samples
Two procedures were used for MCX SPE purification of AMPA. A MCX SPE Filtration Purification procedure was originally developed for corn matrices to filter matrix from extract with no retention of AMPA. Subsequently, a MCX SPE Purification procedure was developed to reduce matrix suppression with soybean matrices. The MCX SPE Purification Procedure is suitable for use with for all solid matrix samples. Purification procedure is also used for watery (e.g. plum) and acid (e.g. lime) crop types.

AMPA MCX SPE Filtration Purification
1.0 Oasis MCX SPE cartridge sequentially was conditioned with 1 CV (CV=6 ml) of methanol and 1 CV Extraction Solution A (96% Aq. 0.1% HCOOH/4% MeOH). Slight vacuum can be applied to control elution at slow drip (1-2 ml/min). Slight vacuum was applied or continued just until dripping stopped.
2.0 15 ml centrifuge tubes were installed under SPE cartridges in vacuum manifold and 0.25 ml of 100 ng/ml internal standard was applied to top of sorbent bed in each SPF cartridge.
3.0 4.0 ml of the $C_{18}$ filtered extract was applied to MCX SPE cartridge. After dripping stopped, 4.0 ml of methanol was applied to MCX SPE cartridge. Slight vacuum may be applied, if necessary. Positive pressure or vacuum can be applied to recover methanol remaining on SPE cartridge.
4.0 Samples were recovered from vacuum manifold and were evaporated to less than 4 ml on N-Evap at 45-50° C.
5.0 0.1 ml of aqueous 1M phosphoric acid then diluted to final volume of 5.0 ml with water. Cap and vortex final extract.
6.0 An aliquot of the final extract for LC/MS/MS analysis was filtered (0.2 μm nylon). Final solution may be stored at or below 4° C.

AMPA MCX SPE Purification
1.0 4 ml of the $C_{18}$ filtered extract was diluted to 20 ml with methanol in 50-ml centrifuge tube containing 0.25 ml of 100 ng/ml internal standard and applied to MCX SPE cartridge. Slight vacuum may be applied, if necessary. Note: Precipitate may be observed in the dilute methanol/aqueous extract solution of some matrices.
2.0 Oasis MCX SPE cartridge was conditioned sequentially with 1 CV (CV=6 ml) of methanol and 1 CV of Extraction Solution A (96% Aq. 0.1% HCOOH/4% MeOH):methanol (1:4, v:v) solution. Slight vacuum may be applied to control elution at slow drip (1-2 ml/min). Slight vacuum was applied or continued just until dripping stops.
3.0 The dilute extracted sample (step 1.0) is applied to MCX SPE cartridge. Slight vacuum may be applied if necessary.
4.0 2 ml of methanol was added to sample tube, mixed and added to SPE cartridge for quantitative transfer and sorbent rinse. Vacuum or positive pressure was applied just until dripping stops.
5.0 15-ml centrifuge tubes were installed under SPE cartridges in vacuum manifold.
6.0 4.0 ml of HPLC grade water was applied to MCX SPE cartridge. After dripping stopped, 4.0 ml of methanol was applied to MCX SPE cartridge. Slight vacuum may be applied, if necessary. Positive pressure or vacuum was applied to recover methanol remaining on SPE cartridge.
7.0 Samples from vacuum manifold were recovered and samples were evaporated to less than 4 ml on N-Evap at 45-50° C.
8.0 0.1 ml of aqueous 1M phosphoric acid+0.25 ml of 100 ng/ml internal standard was added to sample, then diluted to final volume of 5.0 ml with water. Cap and vortex final extract.
9.0 An aliquot of the final extract was filtered (0.2 μm nylon) for LC/MS/MS analysis. Final solution may be stored at or below 4° C.

C. Glyphosate and N-acetylglyphosate and N-acetyl AMPA Analyte Purification Procedures in Solid Matrix Samples
Two procedures were applied to MAX SPE extracts purification for glyphosate and N-acetylglyphosate and N-acetyl AMPA analysis. A MAX SPE purification following extract (adjusted to basic pH) dilution in methanol procedure was generally used for corn matrices and soybean forage and hay matrices. MAX SPE purification with dilution in methanol can be used for acid (e.g. lime) crop types. A MAX SPE purification following extract dilution in water procedure was used for the analysis of soybean seed, meal, and hull matrices. A MAX SPE purification with dilution in water procedure was used for water (e.g. plum) crop types.

MAX SPE Purification (Extract Dilution in Methanol Procedure 1.0a Except for acid crops, 2.0 ml of $C_{18}$ purified extract was transferred (from $C_{18}$ SPE Filtration, Step 4.0) to a 50-ml graduated centrifuge tube containing 80 µL ammonium hydroxide solution (minimum 25%) and 0.25 ml of 100 ng/ml internal standard, then dilute to approximately 20 ml with methanol.

1.0b For acid crops, 2.0 ml of $C_{18}$ purified extract (from $C_{18}$ SPE Filtration, Step 4.0) was transferred to a 50-ml graduated centrifuge tube containing 0.1 ml Triethylamine (TEA) and 0.25 ml of 100 ng/ml internal standard, then diluted to approximately 20 ml with methanol. Note: The volume of extract applied to the MAX SPE cartridge may be varied over range of 1.0 to 4.0 ml. The amount of base added (ammonium hydroxide or TEA) should be adjusted appropriately and the amount of 100 ng/ml internal standard should be adjusted for any change to final extract volume in Step 8.0 (0.05 ml internal standard/ml of final extract volume), but the dilution to 20 ml with methanol, rinse volumes, and 8 ml elution should not be changed.

2.0a Except for acid crops, MAX SPE (6 cc/500 mg) cartridges were conditioned with 1 CV (CV=6 ml) of methanol, followed by 2 CV's of 0.25% ammonium hydroxide in 95% methanol/water solution. Vacuum was applied as needed to control flow to 2-5 ml/min.

2.0b For acid crops, MAX SPE (6 cc/500 mg) cartridges were conditioned with 1 CV (CV=6 ml) of methanol, followed by 2 CV's of 0.1% TEA in 80% methanol/water solution. Vacuum was applied as needed to control flow to 2-5 ml/min.

3.0 As the last of the conditioning solution enters the sorbent, the base-adjusted sample extract solution was loaded (Step 1.0). May need to apply slight vacuum for grain samples, but keep drip rate slow.

4.0 After the last of the sample solution enters the sorbent, sequentially 15 ml of 80% methanol/water, 10 ml of 0.1M acetic acid in 80% methanol/water, and 10 ml of 95% methanol/water was added to rinse the SPE cartridge. Note: The 15 ml of 80% methanol/water and the 10 ml of 0.1M acetic acid were sequentially added to and dispensed from respective emptied sample extract tubes for quantitative transfer of sample extract to the SPE cartridges. The final 10 ml of 95% methanol/water rinse were applied directly to the SPE cartridge in 2×5 ml aliquots.

5.0 After dripping stops, vacuum was increased briefly to remove excess solution from SPE sorbent, and collection vial or tubes in vacuum manifold were installed. Note: 50-ml glass centrifuge tubes (reused) or 20-ml glass scintillation vials (discarded after use) were used for sample collection. Collection container with flat, rounded, or gently sloped bottom for fastest evaporation were used.

6.0 Analytes were eluted in 2×4 ml aliquots of Elution Solution (1% TFA in methanol/water, 90/10). Elute was performed by gravity feed. At least 5 minutes after first aliquot passes through SPE cartridge was waited before adding the second aliquot. Positive pressure or vacuum was applied to recover methanol remaining on SPE cartridge.

7.0 Samples were removed from SPE tank and evaporated to complete dryness on N-Evap at 45-50° C. Note: An additional 15 minutes of drying to insure TFA was completely evaporated was allowed.

8.0 5.0 ml of aqueous 0.02M phosphoric acid was added to sample. Sample were capped, vortex mixed, sonicated at least 5 min, and vortex mixed. Note: If other volume of $C_{18}$ extract was used (Step 1.0), the final extract volume and composition should be adjusted so concentration of analytes are consistent (e.g., if 1.0 ml of extract from $C_{18}$ SPE were processed through this purification procedure, the final extract samples should be reconstituted in 2.5 ml with the addition of 0.125 ml of 100 ng/ml internal standard in Step 1.0).

9.0 An aliquot of the final extract solutions were filtered (0.2-µm nylon) into an autosampler vial for LC/MS/MS analysis.

MAX SPE Purification (Extract Dilution in Water Procedure 1.0 2.0 ml of $C_{18}$ purified extract was transferred to a 50-ml graduated centrifuge tube containing 0.25 ml of 100 ng/ml internal standard and diluted to approximately 20 ml with HPLC grade water. Note: The volume of extract applied to the MAX SPE cartridge may be varied over range of 1.0 to 4.0 ml. The amount of 100 ng/ml internal standard should be adjusted for any change to final extract volume in Step 8.0 (0.05-ml internal standard/ml of final extract volume), but the dilution to 20 ml with water, rinse volumes, and 8-ml elution should not be changed).

2.0 MAX SPE (6 cc/500 mg) cartridges were conditioned with 1 CV (CV=6 ml) of methanol, followed by 2 CV's of 0.25% ammonium hydroxide in HPLC grade water. Vacuum was applied as needed to control flow to 2-5 ml/min.

3.0 As the last of the conditioning solution entered the sorbent, the sample extract solution was loaded. May need to apply slight vacuum for grain samples, but keep drip rate slow.

4.0 After the last of the sample solution entered the sorbent, sequentially 15 ml of 80% methanol/water, 10 ml of 0.1M acetic acid in 80% methanol/water, and 10 ml of 95% methanol/water was added to rinse the SPE cartridge. Note: The 15 ml of 80% methanol/water and the 10 ml of 0.1M acetic acid should be sequentially added to and dispensed from respective emptied sample extract tubes for quantitative transfer of sample extract to the SPE cartridges. The final 10 ml of 95% methanol/water rinse should be applied directly to the SPE cartridge in 2×5 ml aliquots.

5.0 After dripping stops, vacuum was increased briefly to remove excess solution from SPE sorbent, then collection vials or tubes were installed in vacuum manifold. Note: 50-ml glass centrifuge tubes (reused) or 20 ml glass scintillation vials (discarded after use) were used for sample collection. Use collection container with flat, rounded, or gently sloped bottom for fastest evaporation.

6.0 Analytes were eluted in 2×4 ml aliquots of Elution Solution (1% TFA in methanol/water, 90/10). Elution was by gravity feed. At least 5 minutes passed after first aliquot passed through SPE cartridge before the second aliquot was added. Positive pressure or vacuum was applied to recover methanol remaining on SPE cartridge.

7.0 Samples were removed from SPE tank and evaporated to complete dryness on N-Evap at 45-50° C. Note: Allow additional 15 minutes of drying to insure TFA is completely evaporated.

8.0 5 ml of aqueous 0.02M phosphoric acid was added to sample. Sample was capped, vortex mixed, sonicated at least 5 min, and vortex mixed. Note: If other volume of $C_{18}$ extract was used (step 1.0), the final extract volume and composition should be adjusted so concentration of analytes are consistent (e.g., if 1.0 ml of extract from $C_{18}$ SPE were processed through this purification procedure, the final extract samples should be reconstituted in 2.5 ml with the addition of 1.25 ml of 100 ng/ml internal standard).

9.0 An aliquot of the final extract solutions was filtered (0.2 μm nylon) into an autosampler vial for LC/MS/MS analysis.

D. Glyphosate, N-acetylglyphosate, and AMPA and N-acetyl AMPA Extraction and Purification Procedure in Oil Matrix Samples 1.0 For each sample 2.0±0.02 g of sample was weighed into a clean 50-ml glass or polypropylene centrifuge tube.

2.0 For Fortified Samples, samples were fortified appropriately as indicated above.

3.0 15.0 ml of aqueous 0.02M phosphoric acid was added to sample.

4.0 15.0 ml of methylene chloride was added to sample, which was then capped, vortex mixed for at least 30 seconds.

5.0 Sample was centrifuged at 3000 rpm for approximately 10 minutes.

6.0 Aqueous fraction was transferred to clean 50-ml graduated cylinder. (As much of the fraction as possible was recovered without disturbing the organic layer.)

7.0 Another 15.0 ml of aqueous 0.02M phosphoric acid was added to sample, which was then capped, vortex mixed for at least 30 seconds.

8.0 Sample was centrifuged at 3000 rpm for approximately 10 minutes.

9.0 Aqueous fraction were combined with 1st partition in respective 50-ml graduated cylinder. (As much of the fraction as possible was recovered without disturbing the organic layer.

10.0 Aqueous sample was diluted to 40 ml final volume with aqueous 0.02M phosphoric acid.

11.0 Final sample extract was transferred to clean bottle. (Sample was poured back and forth between graduated cylinder and bottle to insure homogeneity.)

12.0 If stable isotope glyphosate and AMPA internal standards were used, the final sample was prepared by combining 4 ml of extract+0.25 ml of 100 ng/ml IS+0.75 ml of aqueous 0.02M phosphoric acid and sample was filtered (0.2 μm) prior to LC/MS/MS analysis. If stable isotope internal standards are not used, dilute 4 ml of the extract with 1 ml of aqueous 0.02 M phosphoric acid and filter (0.2 μm) prior to LC/MS/MS analysis.

Example 5

Detection of Analytes

An Agilent HP1100 HPLC and a Waters Quattro Premier triple quadrupole mass spectrometer were used for LC/MS/MS analysis. Typical equipment components and operating conditions follow:

| | |
|---|---|
| Agilent HP1100 HPLC: | G1322A vacuum degasser, G1311A quaternary pump, G1367A chilled autosampler, G1330A chiller, G1316A column compartment |
| Injection Volume: | 25 μL (may be varied to correct for MS sensitivity) |
| Guard Column (optional, preferred): | Waters Nova-Pak $C_{18}$ (3.9 mm i.d. × 20 mm, 4 μm diameter particle) |
| HPLC Column: | Phenomenex Luna Phenyl-Hexyl (15.0 cm × 4.6 mm i.d., 3 μm diameter particle) |
| Column Temperature: | 40° C. |
| Mobile Phases: | A = aqueous 0.2M formic acid<br>B = methanol |
| Waters Quattro Premier: | ESI interface, MassLynx Version 4 SP4 software |
| Interface: | electrospray (ESI) |
| Polarity: | positive ion |
| Mode: | MRM |

TABLE 28

HPLC Conditions:

| TIME | FLOWRATE (ML/MIN) | % A | % B | COMMENTS |
|---|---|---|---|---|
| Initial | 0.5 | 95 | 5 | No post-column split to MS |
| 0.0 | 0.35 | 95 | 5 | HPLC effluent directed to |
| 10.0 | 0.35 | 40 | 60 | waste until ~3.3 min and |
| 10.1 | 0.5 | 1 | 99 | after ~8.2 min |
| 13.0 | 0.5 | 1 | 99 | |
| 13.1 | 0.5 | 95 | 5 | Column re-equilibration |
| 18.0 | 0.5 | 95 | 5 | End Run (time may be extended fro column equilibration) |

The Approximate Analyte Retention Times (ordered by retention time) shown in table 28 are as follows:
AMPA = 4.6 min
glyphosate = 5.3 min
N-acetyl AMPA = 7.1 min
N-acetylglyphosate = 7.4 min Note: Analyte retention times can shift based on condition of the HPLC column and formic acid mobile phase. Expect retention times to shorten with column deterioration. Lower concentration of formic acid in the mobile phase extends the retention times and broadens the peak shape of the analytes.

TABLE 29

Mass Spectrometer Conditions:
Tune File: Gly050205pos.IPR Ionization Mode: ESI+

| Voltages | | | Temperatures | | Gas Flow | |
|---|---|---|---|---|---|---|
| Capillary (kV) | Extractor (V) | RF Lens (V) | Source (° C.) | Desolv. (° C.) | Desolv. (L/hr) | Cone (L/hr) |
| 1.00 | 4.2 | 0.1 | 125 | 350 | 700 | 100 |

| Q1 | Q2 | Q3 |
|---|---|---|
| LM Res 12.0<br>HM Res 12.0<br>Ion Energy 0.3 | Entrance<br>1 | Exit<br>1 | 12.0 LM Res<br>12.0 HM Res<br>3.0 Ion Energy |

Collison Cell: 0.35 mL/min 3.10E−03 mbar
MRM Functions

| Analyte (acquisition_time) | Parent (m/z) | Daughter (m/z) | Dwell (secs) | Cone (volts) | Coil Energy (eV) |
|---|---|---|---|---|---|
| AMPA (3.3-6.0 min) | 111.80 | 30.00 | 0.30 | 12.00 | 8.00 |
| AMPA 13C 15N | 113.80 | 32.00 | 0.30 | 12.00 | 8.00 |
| Glyphosate (3.6-6.0 min) | 170.00 | 60.10 | 0.10 | 14.00 | 17.00 |
| | 170.00 | 87.70 | 0.10 | 14.00 | 9.00 |
| Glyphosate 1,2-13C 15N | 173.00 | 90.70 | 0.10 | 14.00 | 9.00 |
| N-acetyl AMPA (5.8-7.8 min) | 154.00 | 30.00 | 0.10 | 14.00 | 15.00 |
| | 154.00 | 111.90 | 0.10 | 14.00 | 9.00 |
| N-acetylglyphosate (5.8-8.5 min) | 212.00 | 87.70 | 0.10 | 17.00 | 17.00 |
| | 212.00 | 169.90 | 0.10 | 17.00 | 10.00 |

Mass assignment on other instruments may vary ± 0.5 amu.
Dwell time may be adjusted to optimize response.

Calibration Procedures

Standard mass spectrometer tuning and calibration techniques were used. If confidence in the mass calibration needed to be established (modern mass spectrometers under digital control generally do not need frequent mass calibration, especially for quantitative modes), vendor recommended calibrating solution was used. Optimization tuning of MS system may be accomplished by infusion of one or more of the test analytes. This method uses internal and external calibration standards, prepared as described above.

Instrument calibration was based on the average response factor (analyte peak area response/analyte concentration) of external calibration standards using Excel® functions AVERAGE, STDEV (standard deviation), and RSD (relative standard deviation StDev/mean). For average response factor calibration, a % RSD of less than or equal to 20% should be observed. The linear regression response of external calibration standards using Excel® functions SLOPE, INTERCEPT, and RSQ (r-squared; the square of the Pearson product moment correlation coefficient determined using Excel® function RSQ) were monitored to establish calibration curve linearity. Acceptance criteria for valid quantitation are: (1) RSQ value>0.99 for calibration curve and (2) the % RSD≦20% for the individual calibration standard response factors. Alternative approaches including linear regression with or without weighting (e.g., 1/X) may be used if they provide an equivalent or more consistent fit of sample response to the response of calibration standards.

The nominal LC/MS/MS calibrated range for glyphosate and N-acetylglyphosate and N-acetyl AMPA was 0.5-20.0 ng/ml and for AMPA was 1.0-50.0 ng/ml. The LOQ equivalent final extract concentration for glyphosate and N-acetylglyphosate analysis is 1.0 ng/ml. The LOQ equivalent final extract concentration for AMPA analysis is 2.0 ng/ml. Generally, 5 calibration solutions were analyzed for quantitative LC/MS/MS analysis (a minimum of 4 calibration solutions are required).

Net recoveries may be calculated for fortified samples only (not acceptable for field samples). Net recoveries may be calculated and reported only when residues in the control sample are integrable and <50% of the LOQ. When the control residues are >50% of the LOQ, the recovery samples prepared at the LOQ using that control are invalidated. When the control residues are <50% of the LOQ, corrected ppm (mg/kg) found in fortified samples are calculated by subtracting area counts found in the control from area counts found in fortified samples. If net recoveries are calculated, those results must be uniquely identified or presented in a separate spreadsheet column heading for corrected ppm (mg/kg).

Sample Analysis

Preliminary runs of at least 2 calibration standards were routinely made to demonstrate adequate instrument response and insure the LC/MS/MS system was equilibrated. If multiple sets were analyzed, a solvent blank injection was made between the last and first injections of the sets to minimize risk of carryover between sets. Calibration standard analyses preceded the first sample analysis and follow the last sample analysis so sample analyses were contained within the external standard calibration. Generally, the injection sequence was organized from lowest to highest expected analyte concentrations. Calibration standard runs were intermixed with the test samples and can be analyzed before and after every 1-3 samples in each analytical set. Extracts and calibration standards were be refrigerated if stored. Generally, fortification sample recoveries (70-120%) are required for acceptable quantitation results in an analysis set.

Calculations

Methods

Glyphosate, N-acetylglyphosate, and AMPA and N-acetyl AMPA residues were measured as mg/kg (ppm) glyphosate free-acid equivalents in crop matrices. Quantitation was based on an average response factor determined from the multiple calibration standards concurrently analyzed with sample extracts. All calculations were made using unrounded values that were reported to two significant figures. Fortified sample recoveries were reported to the nearest whole number percentage (%).

The calculation to determine mg/kg found in residue samples by average response factor analysis follows:

Without internal standard calibration:

$$\text{mg/kg glyphosate free-acid equivalents found} = \frac{PA \times FV \times XV}{ARF \times AF \times SW} \times UC$$

With internal standard calibration:

$$\text{mg/kg glyphosate free-acid equivalents found} = \frac{(PA/IS) \times FV \times XV}{ARF_{IS} \times AF \times SW} \times UC$$

where,

PA is Analyte Peak Area,

FV is Final extract Volume (ml),

XV is total eXtract Volume (ml),

ARF is Average Response Factor $$\left(\frac{\text{peak area}}{\text{ng/mL}}\right),$$

IS is peak area of Internal Standard in sample extract, $ARF_{IS}$ is Average Response Factor with Internal Standard $$\left(\frac{\text{peak area/IS peak area}}{\text{ng/mL}}\right),$$

AF is Aliquot Factor (ml of XV diluted to FV),

SW is Sample Weight (5.0 g) of sample aliquot extracted, and

UC Units Conversions $$\mu g/1000 \text{ ng} \times \text{mg}/1000 \text{ g} \times 1000 \text{ g/kg} = \text{mg} \cdot \text{g}/1000 \text{ ng} \cdot \text{kg}$$

Percent recoveries (reported to the nearest whole number) from fortified samples were calculated as follows:

$$\% \text{ Recovery} = \frac{\text{mg/kg analyte found}}{\text{mg/kg analyte fortified}} \times 100$$

Examples Without Internal Standard

Figure 8:
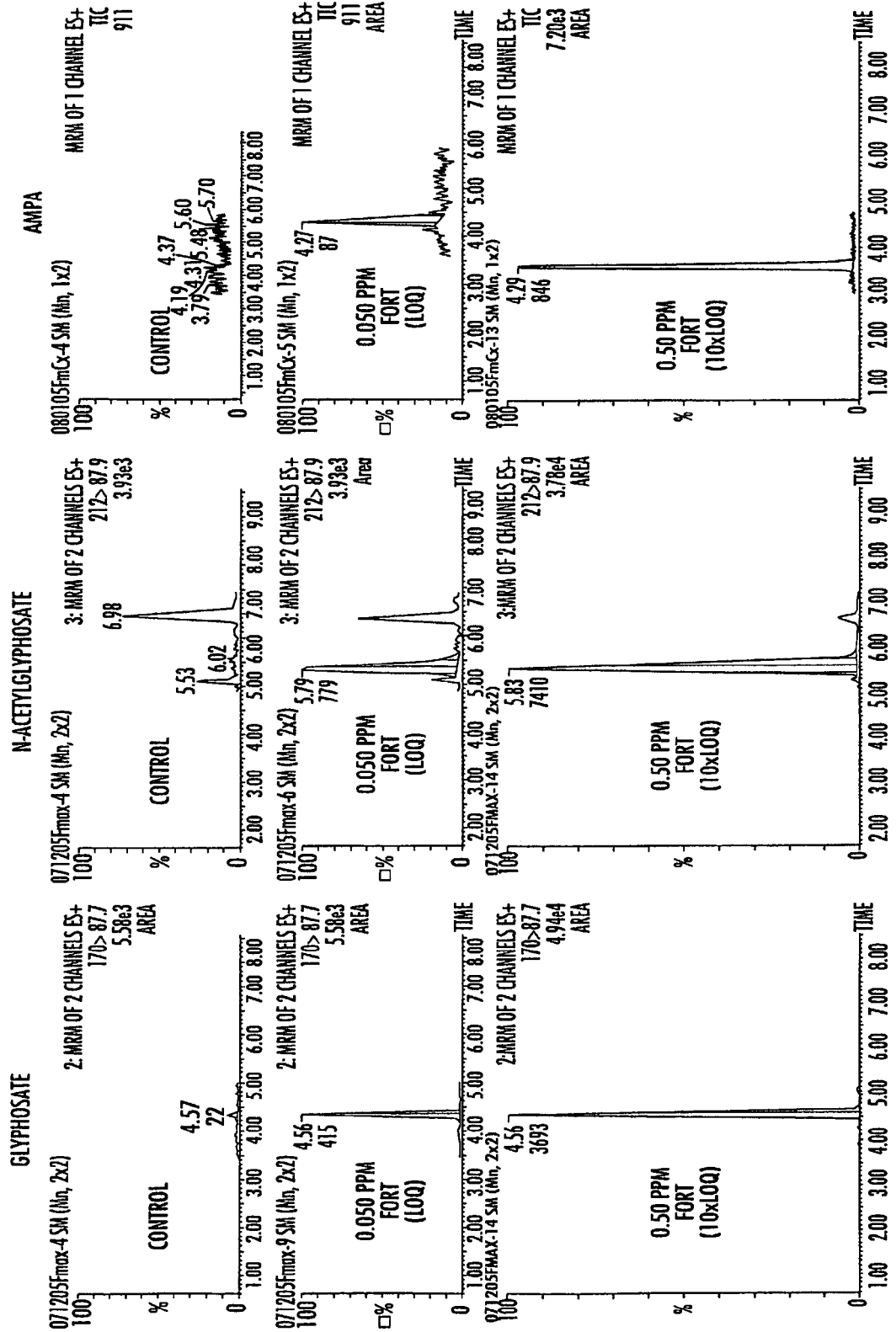
FIG. 8 provides representative corn forage chromatograms.
Figure 9:
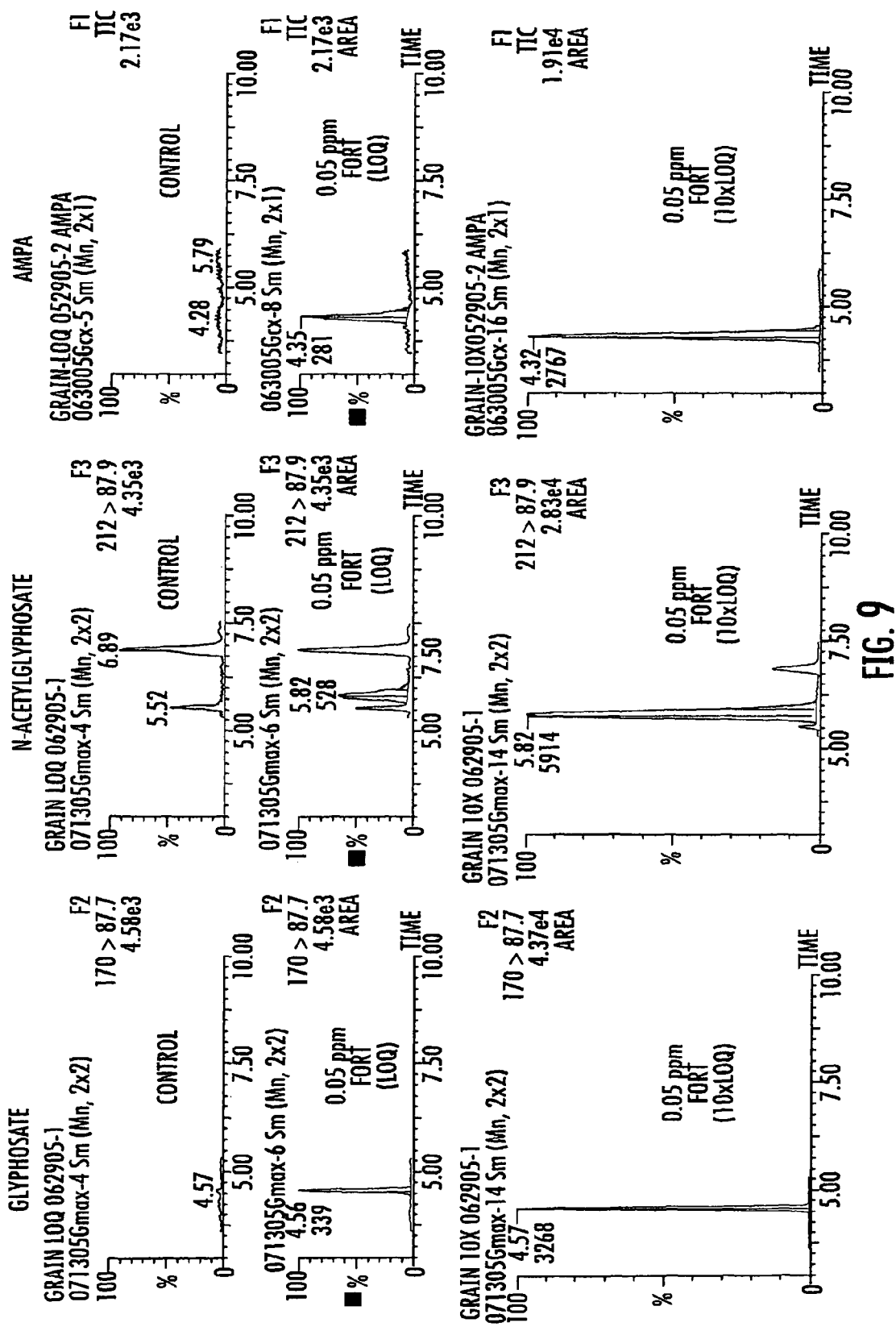
FIG. 9 provides representative corn grain chromatograms.
Figure 10:
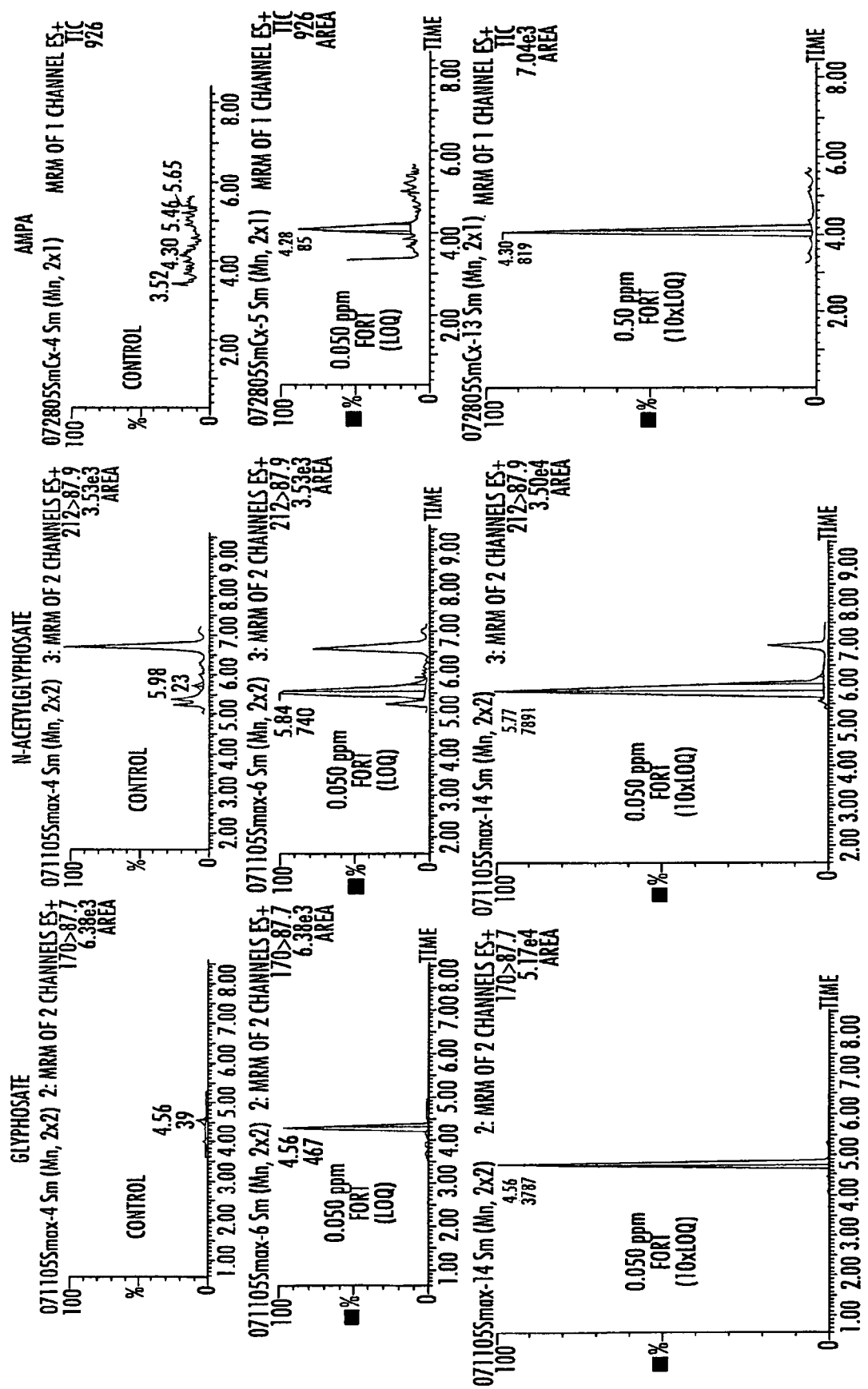
FIG. 10 provides representative corn stover chromatograms.
Figure 11:
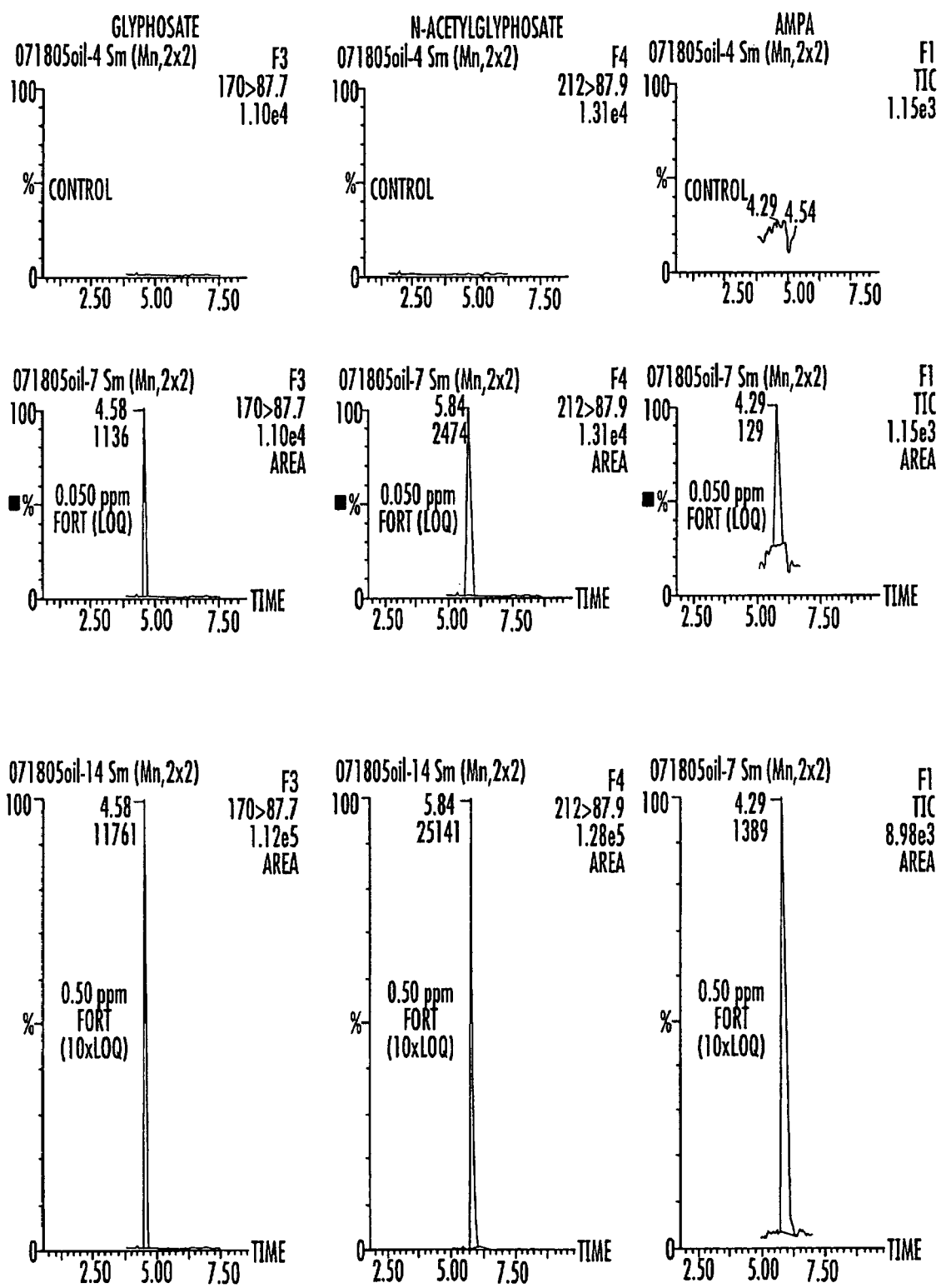
FIG. 11 provides representative corn oil chromatograms.
Figure 12:
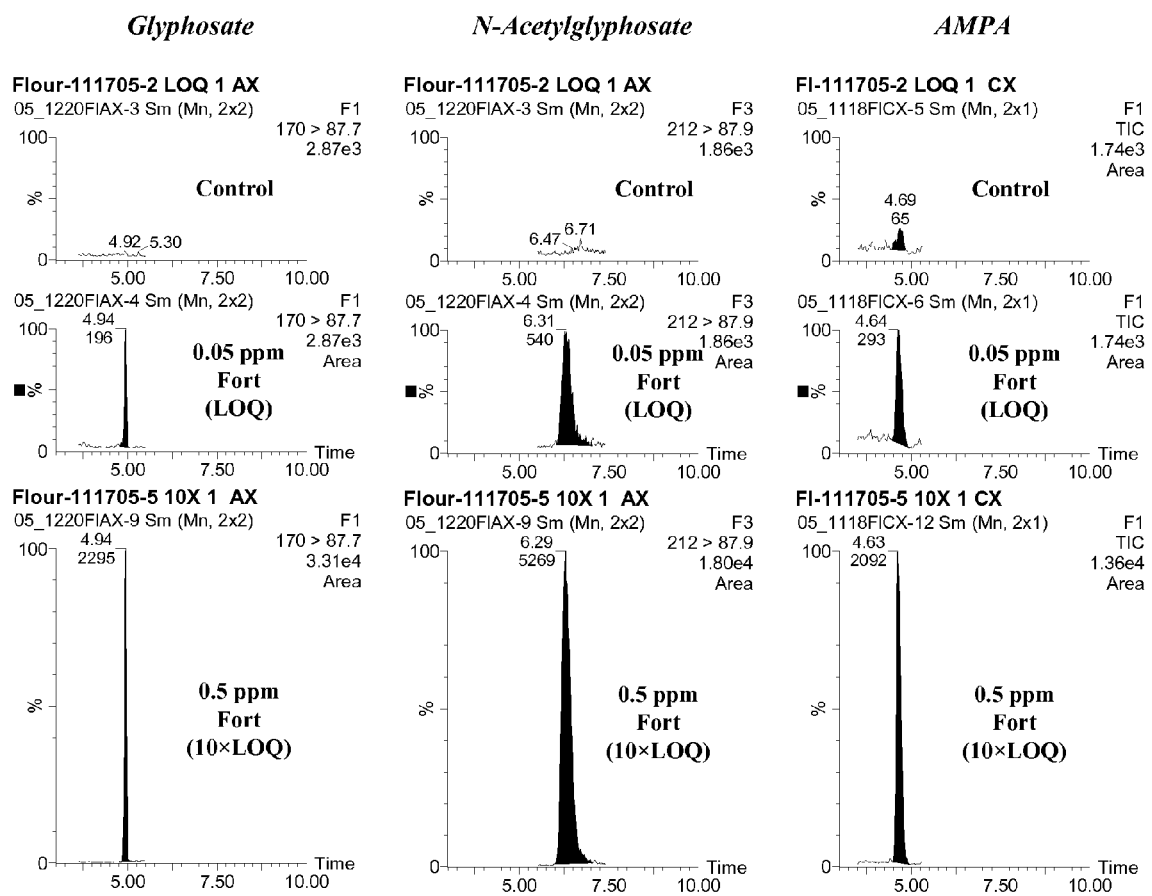
FIG. 12 provides representative corn flour chromatograms.
Figure 13:
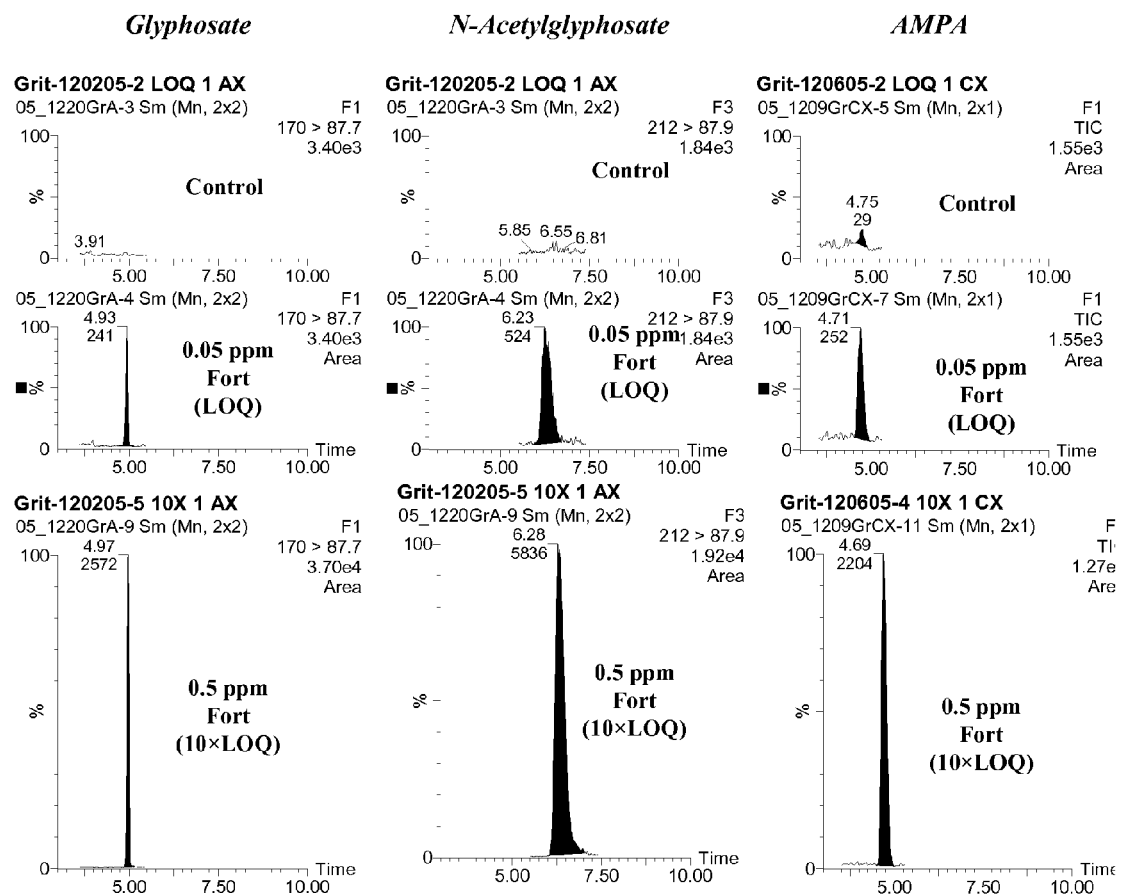
FIG. 13 provides representative corn grits chromatograms.
Figure 14:
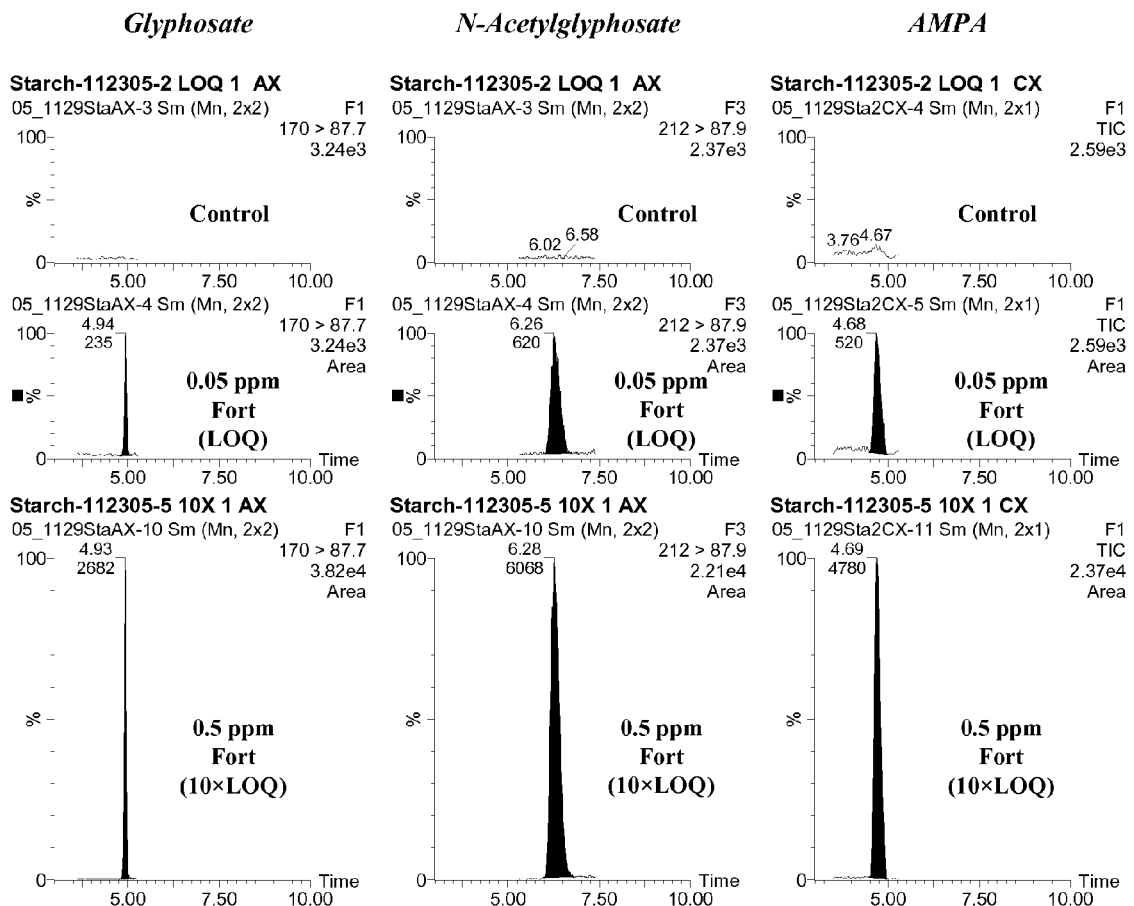
FIG. 14 provides representative corn starch chromatograms.
Figure 15:
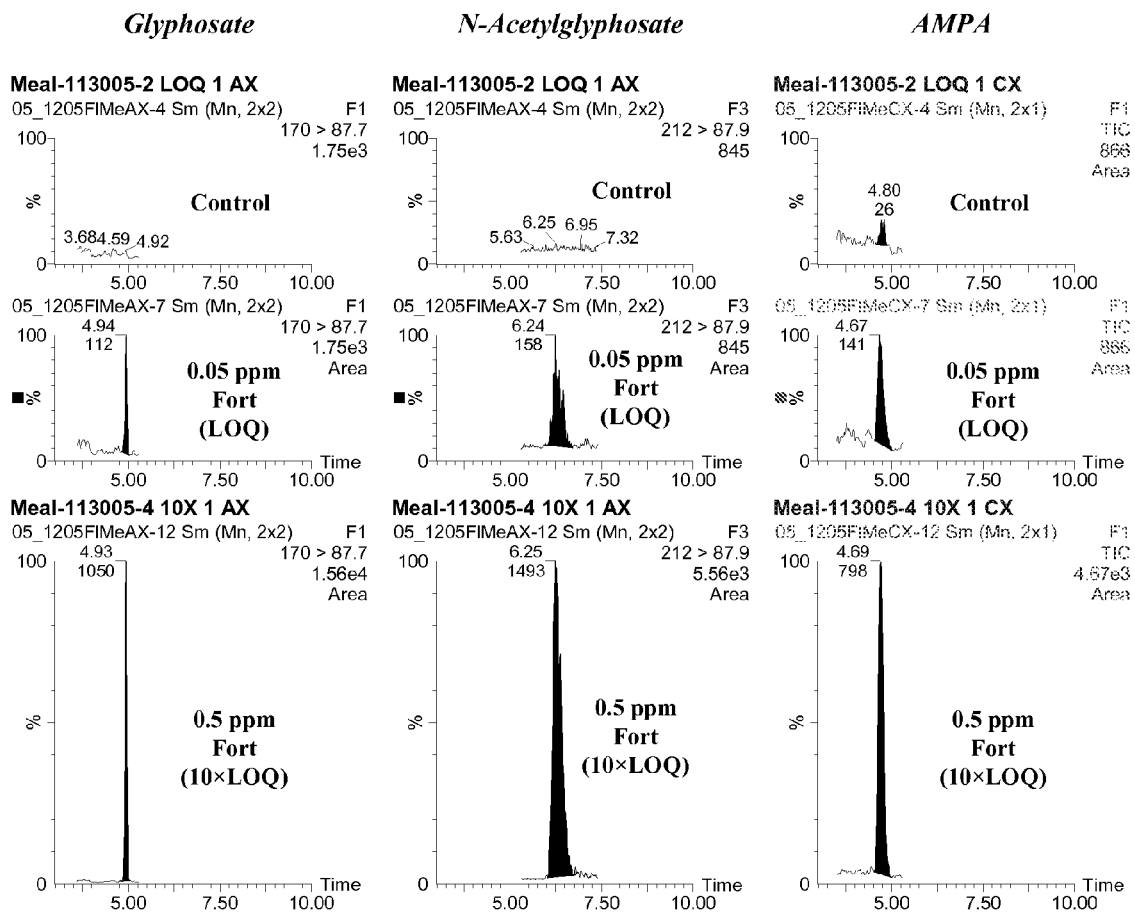
FIG. 15 provides representative corn meal chromatograms.

N-acetylglyphosate in corn grain sample: Grain 10X 062905-1
(Reference: Table 2, FIG. 8, Tables 30-40)

$$\frac{5914 \text{ area}}{602 \text{ area/ng/mL}} \times \frac{10.0 \text{ mL} \times 100 \text{ mL}}{4.0 \text{ mL} \times 5.0 \text{ g}} \times \frac{\text{mg} \cdot \text{g}}{1000 \text{ ng} \cdot \text{kg}} =$$
$$0.491 = 0.49 \text{ mg/kg}$$

Note: Control sample area of 39 substracted from fortified sample area $$\% \text{ Recovery} = \frac{0.491 \text{ mg/kg analyte found}}{0.50 \text{ mg/kg analyte fortified}} \times 100 = 98\%$$

AMPA in corn grain sample: Grain-LOQ052905-3
(Reference: Table 2, FIG. 8, Table 30-40)

$$\frac{283 \text{ area} \times 5.0 \text{ mL} \times 100 \text{ mL}}{137 \text{ area/ng/mL} \times 4.0 \text{ mL} \times 5.0 \text{ g}} \times \frac{\text{mg} \cdot \text{g}}{1000 \text{ ng} \cdot \text{kg}} = 0.0516 = 0.052 \text{ mg/kg}$$

$$\% \text{ Recovery} = \frac{0.0516 \text{ mg/kg analyte found}}{0.050 \text{ mg/kg analyte fortified}} \times 100 = 103\%$$

Examples With Internal Standard

Figure 16:
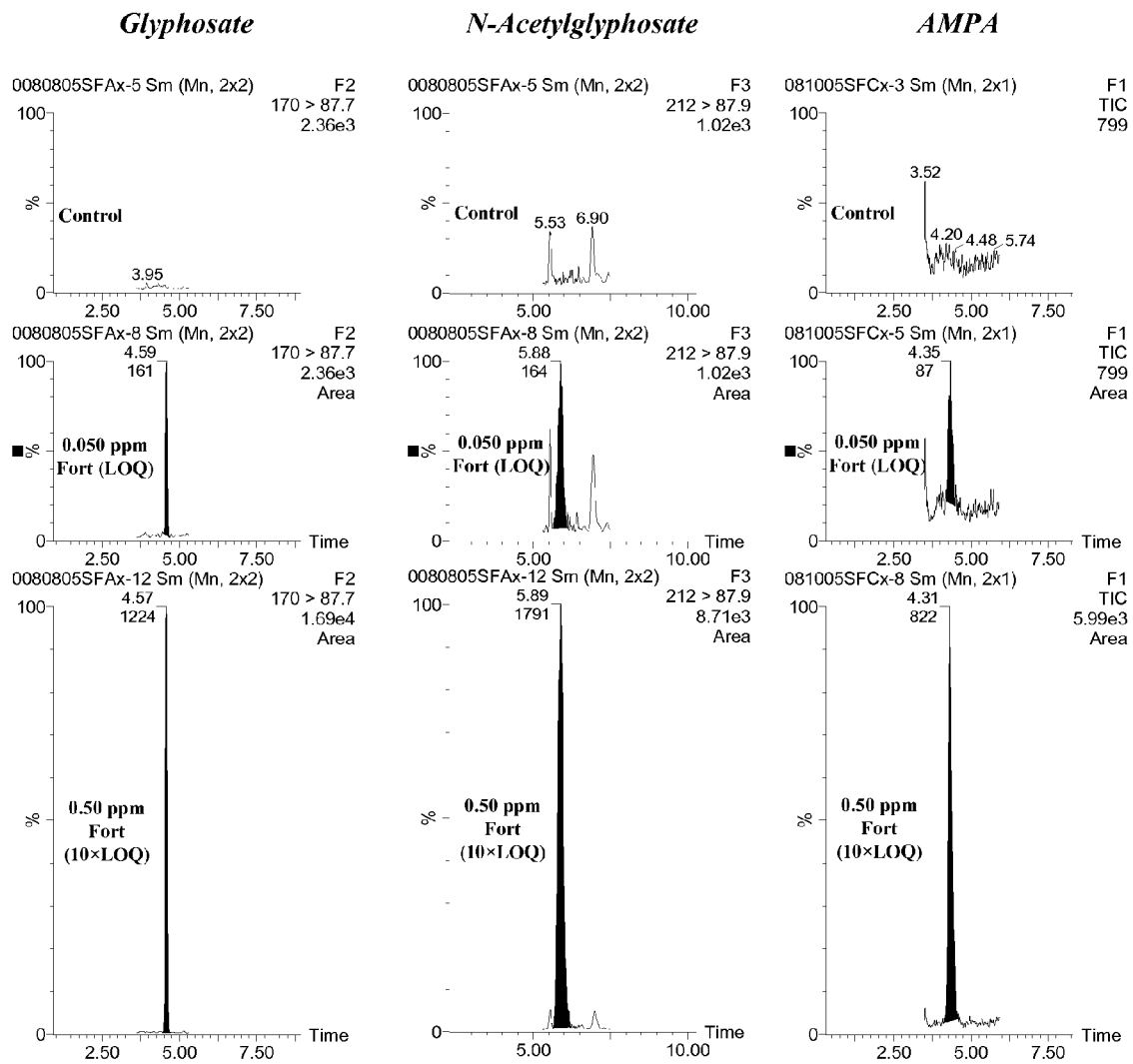
FIG. 16 provides representative soybean forage chromatograms.
Figure 17:
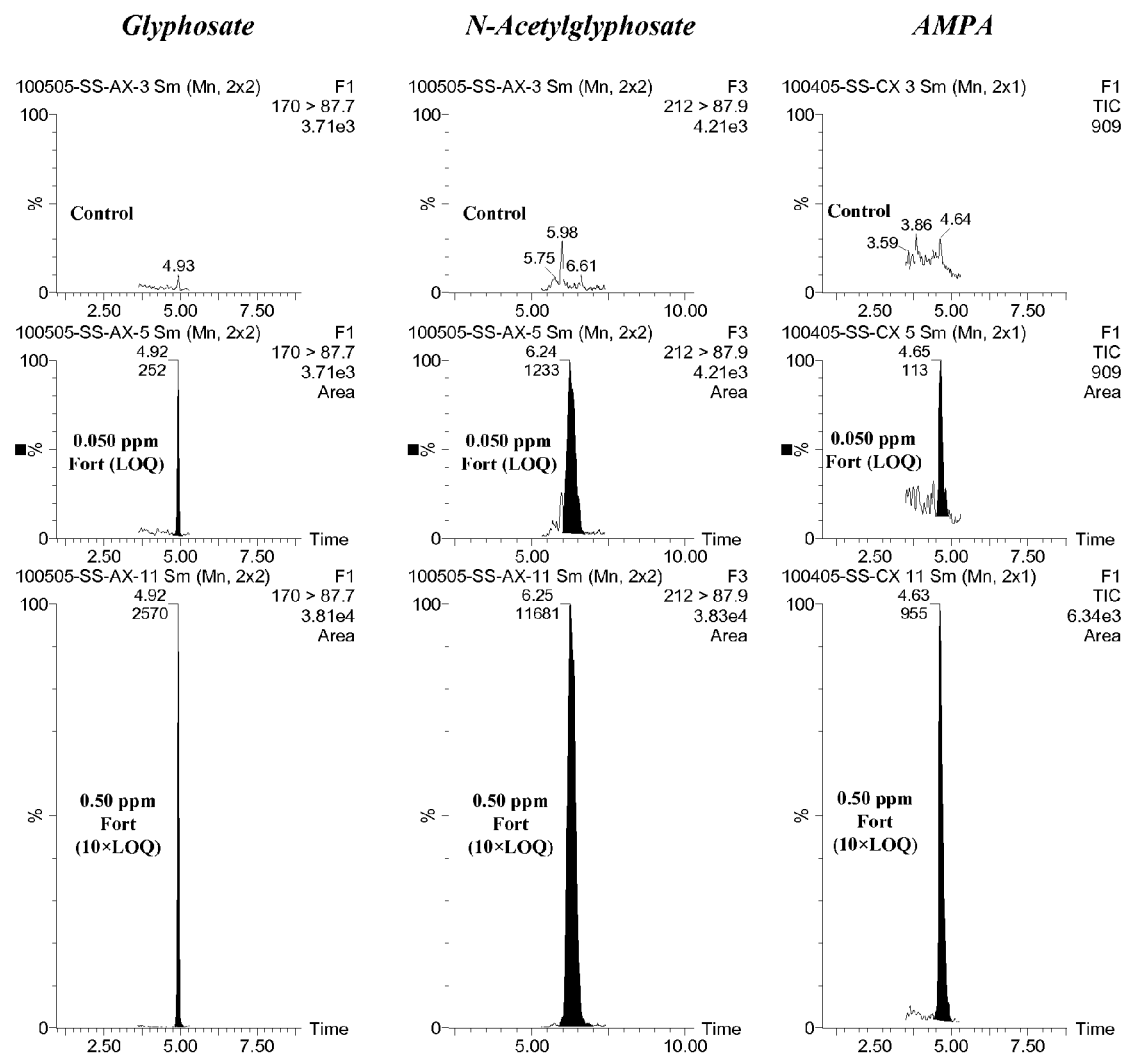
FIG. 17 provides representative soybean seed chromatograms.
Figure 18:
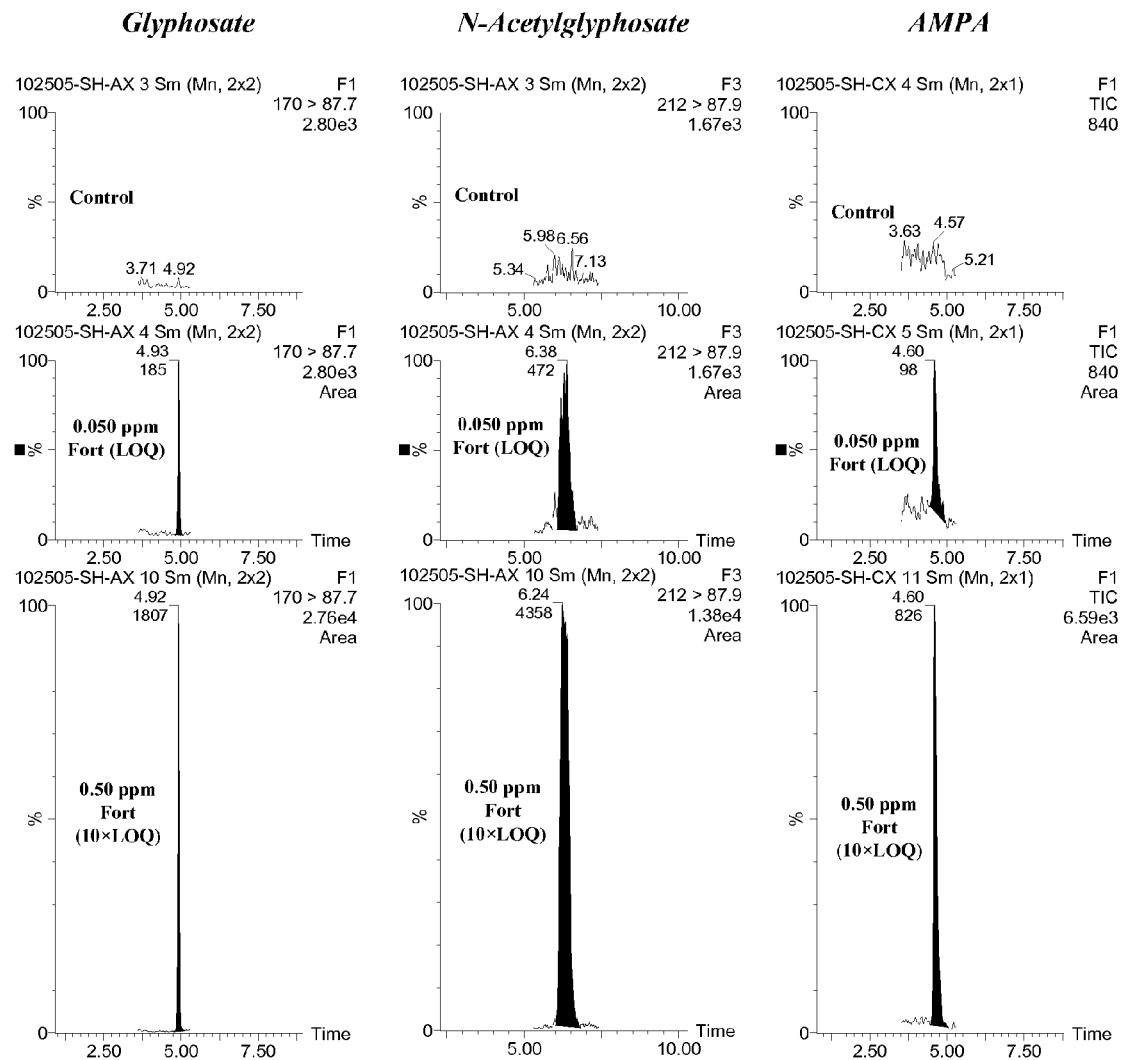
FIG. 18 provides representative soybean hay chromatograms.
Figure 19:
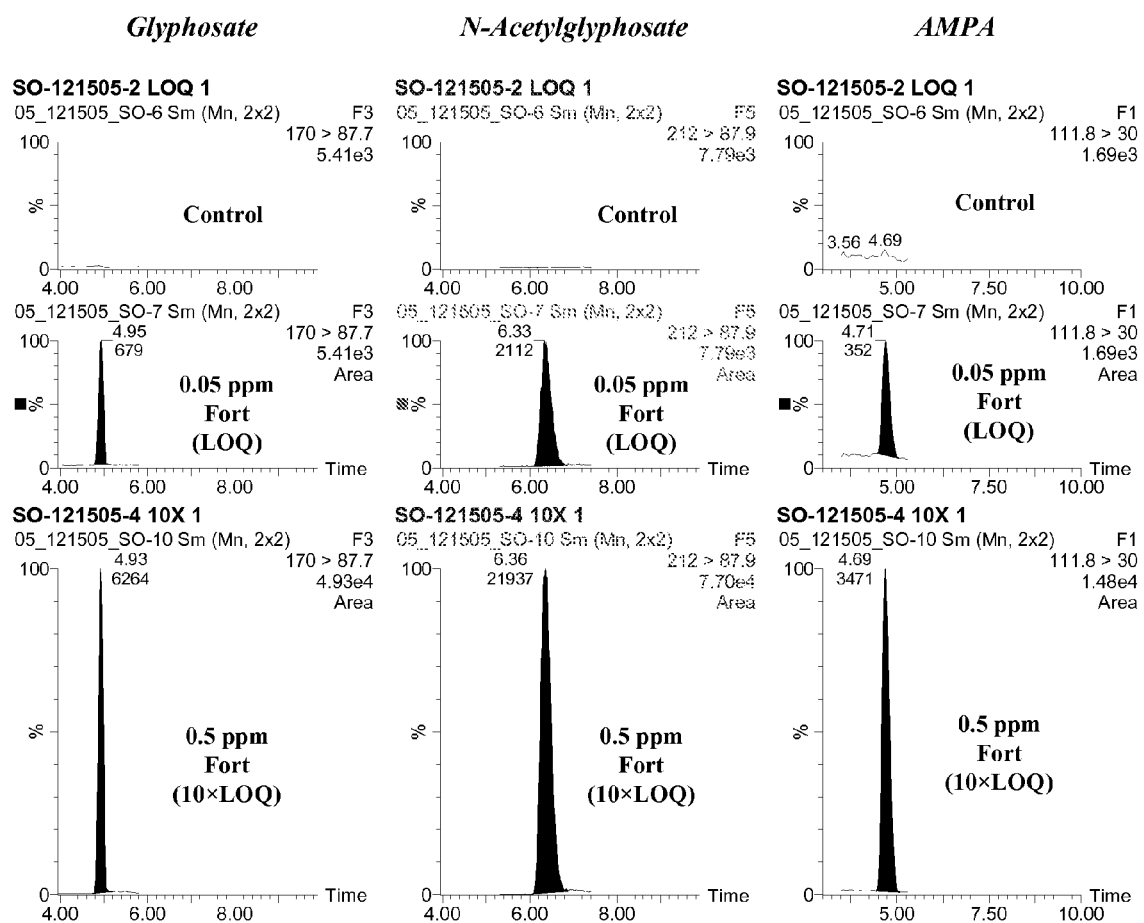
FIG. 19 provides representative soybean oil chromatograms.
Figure 20:
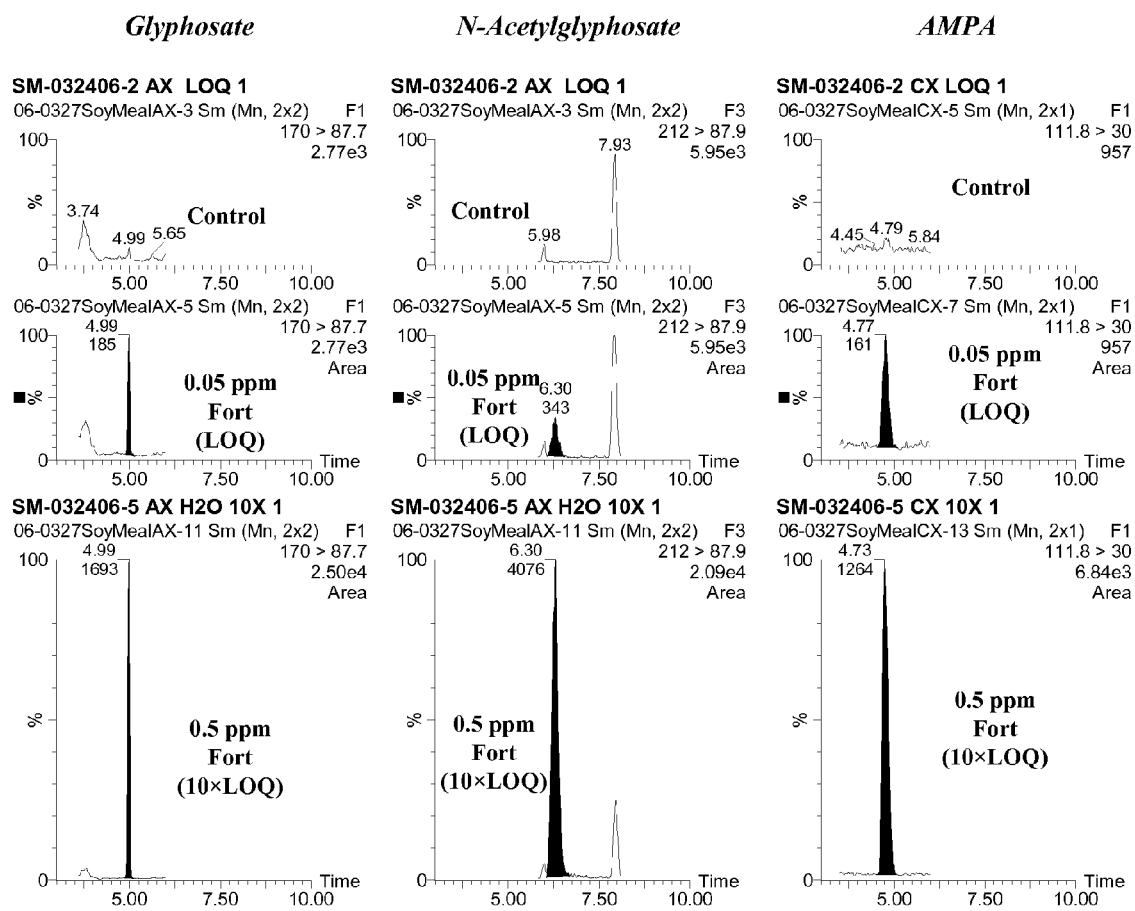
FIG. 20 provides representative soybean meal chromatograms.
Figure 21:
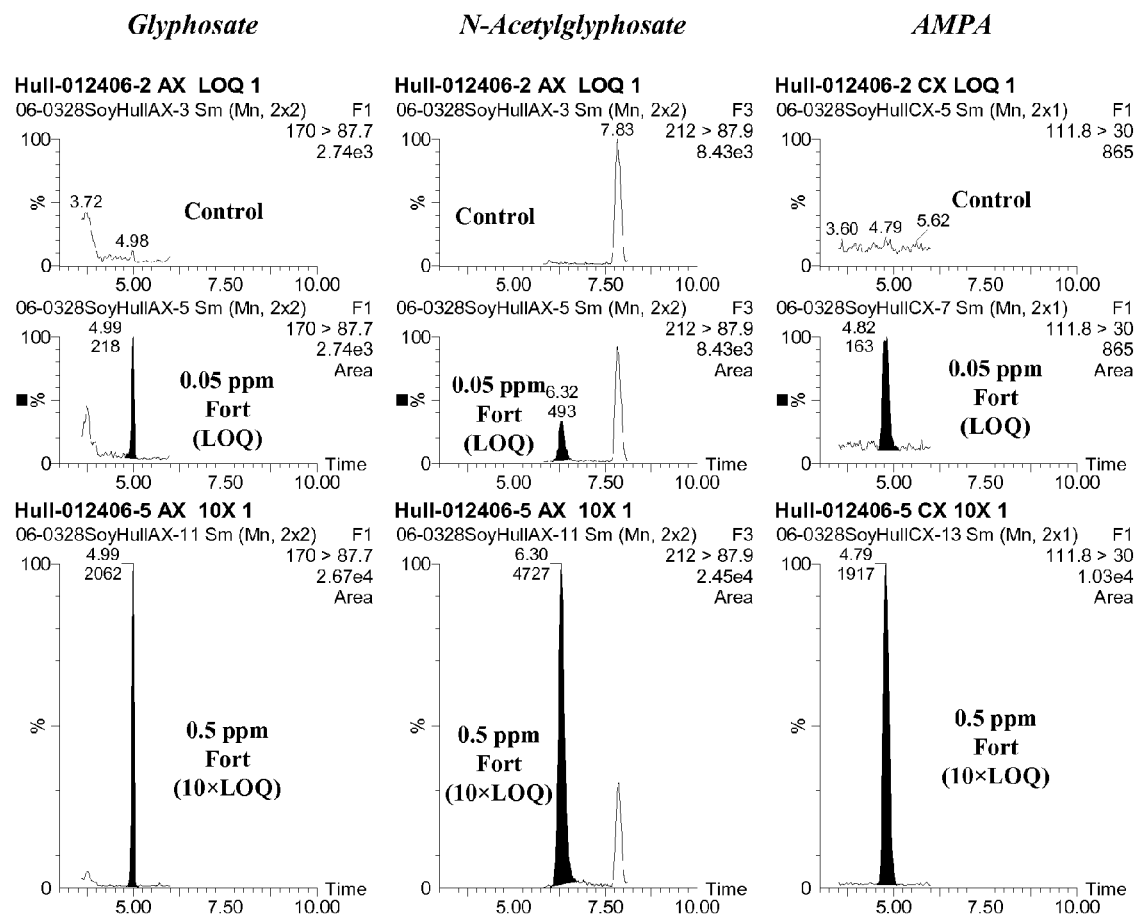
FIG. 21 provides representative soybean hulls chromatograms.
Figure 22A:
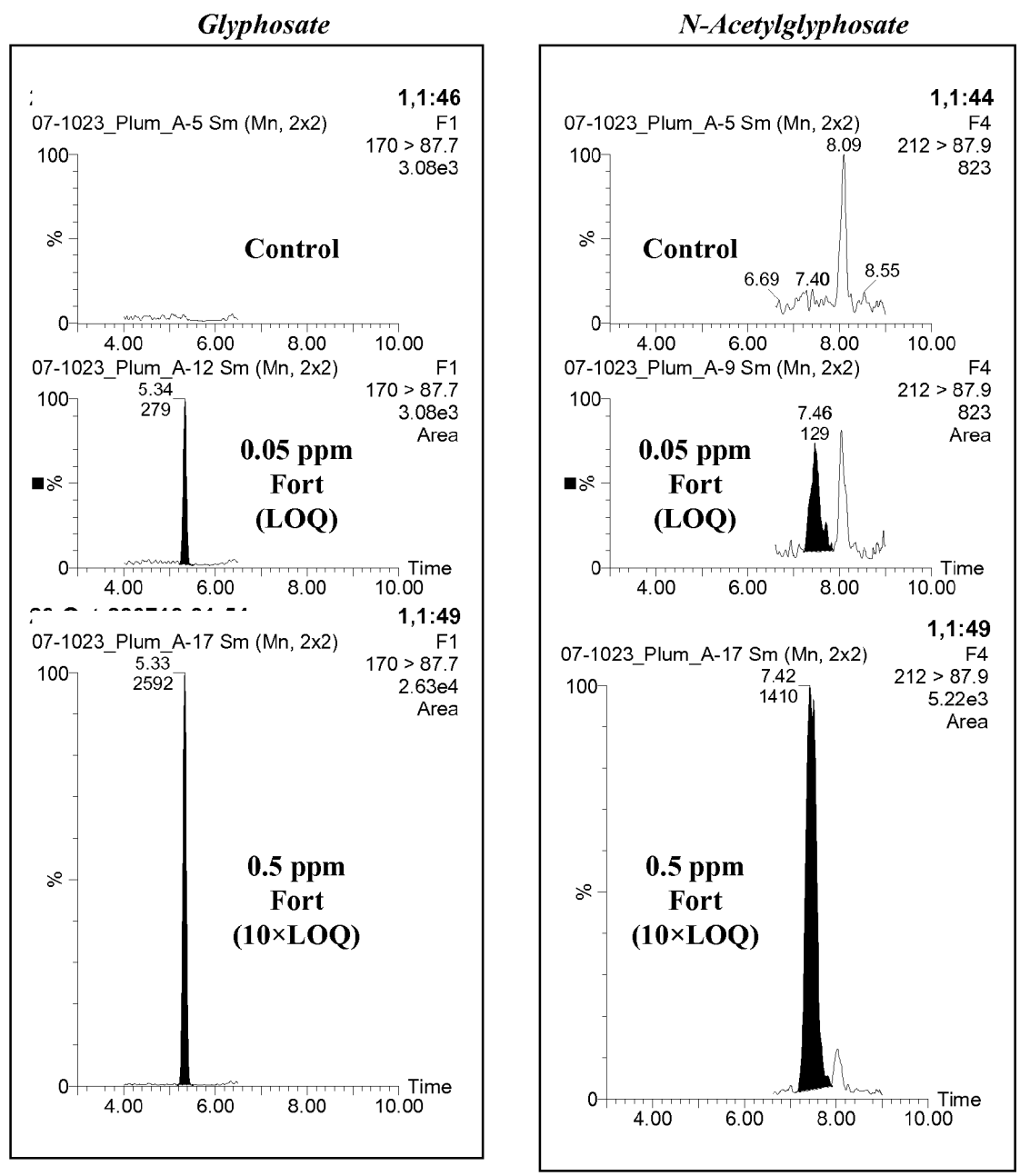
FIGS. 22A and B provide representative plum chromatograms.
Figure 22B:
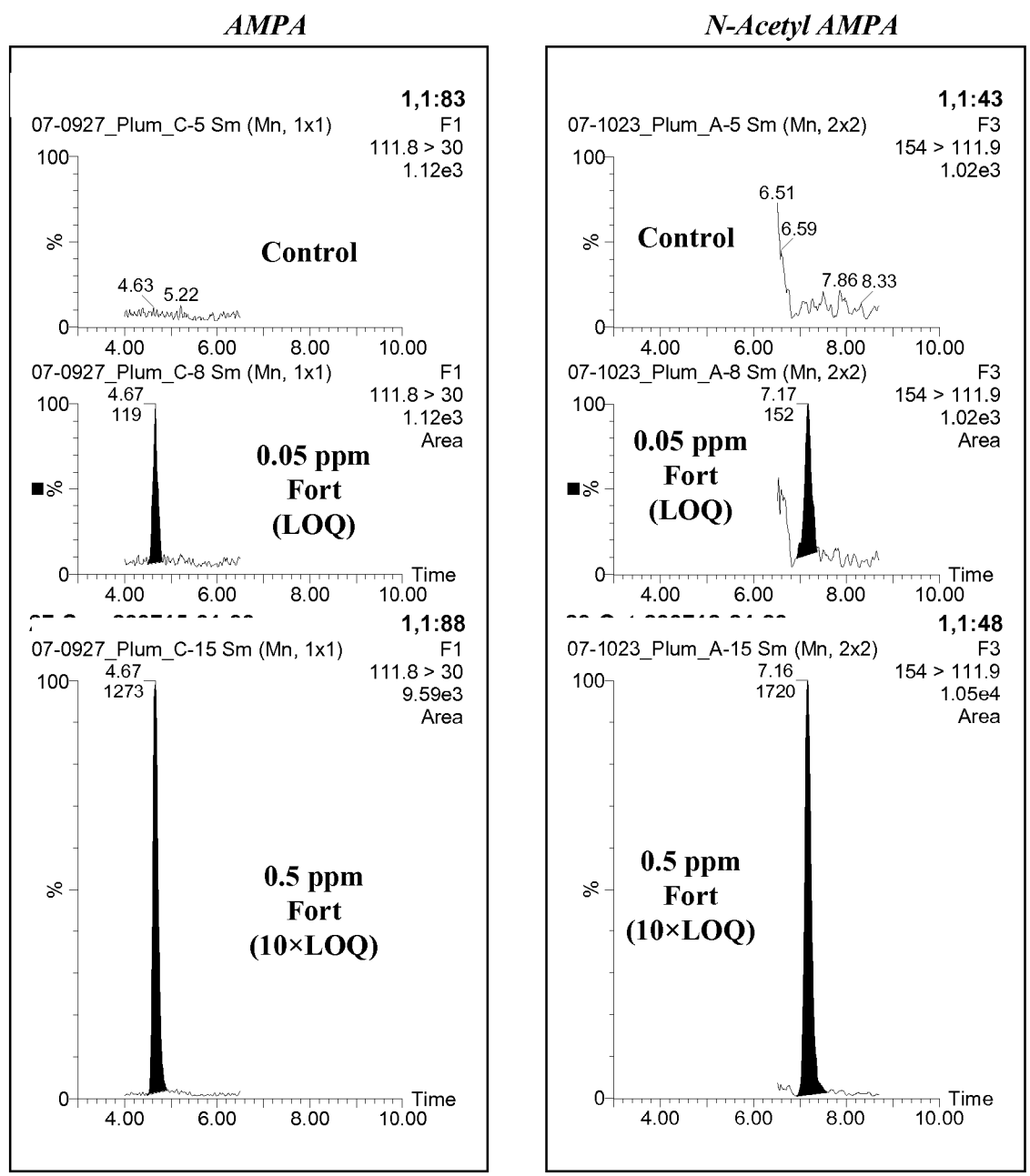
Figure 23A:
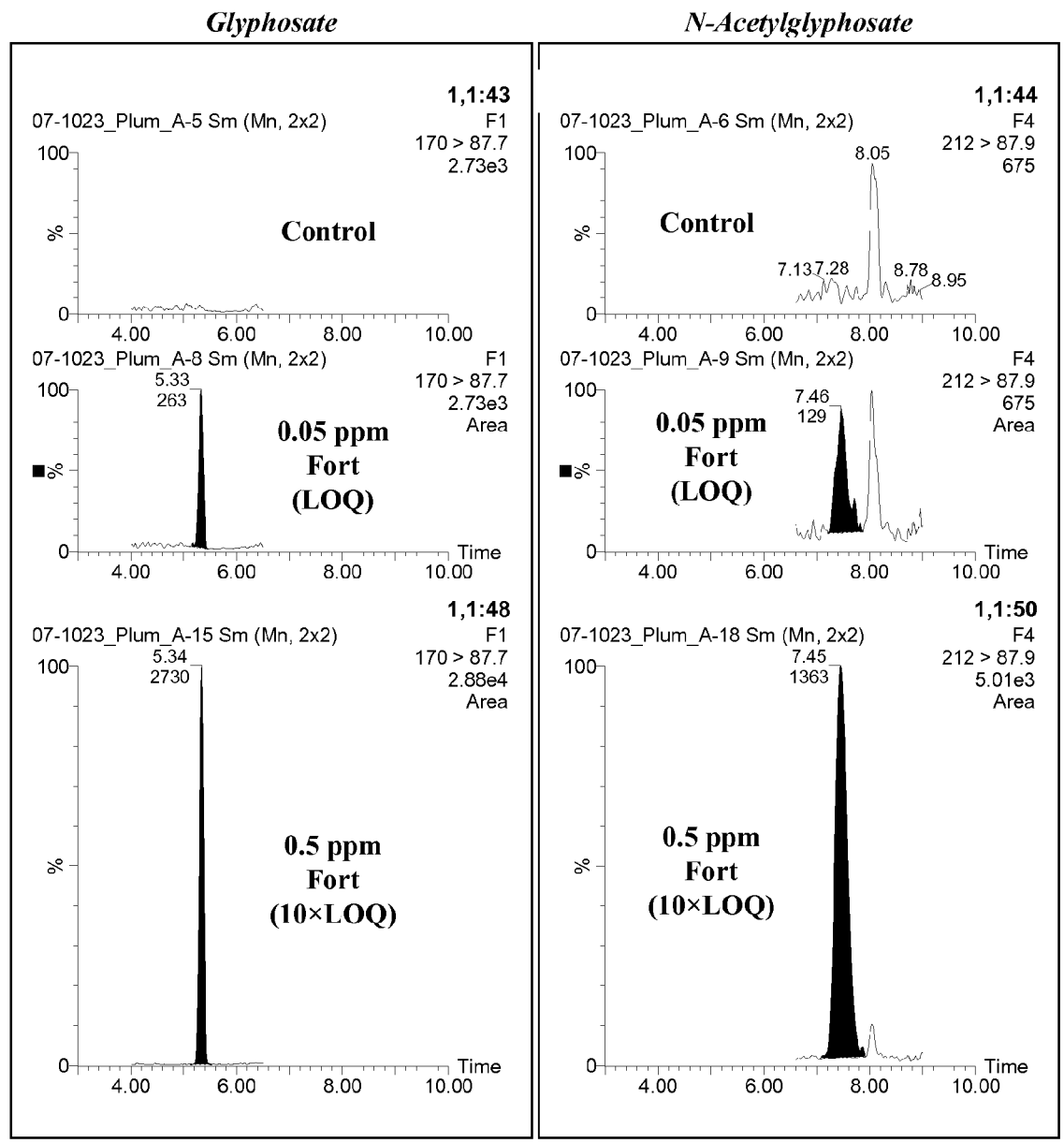
FIGS. 23A and B provide representative lime chromatograms.
Figure 23B:
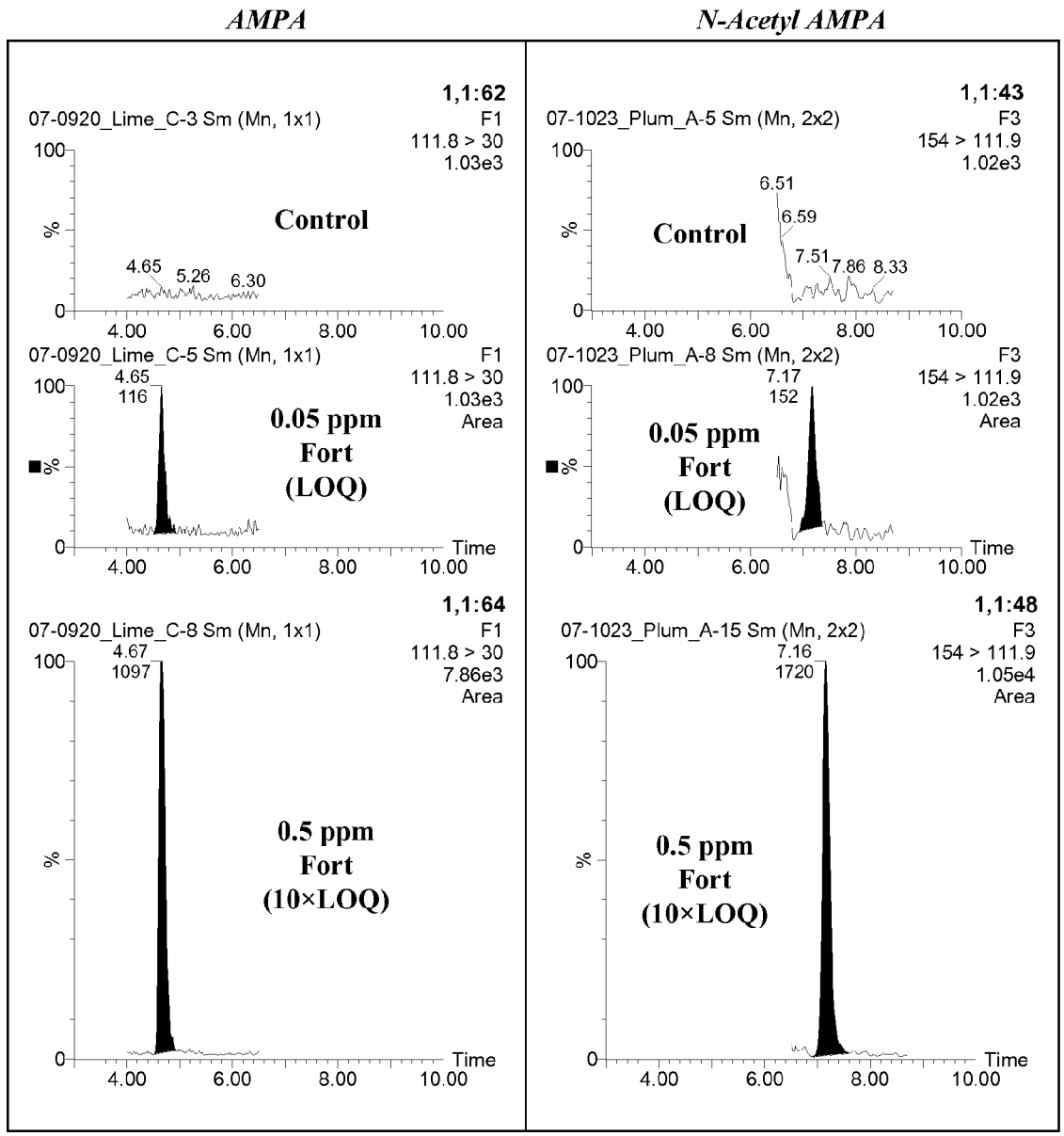
Figure 24:
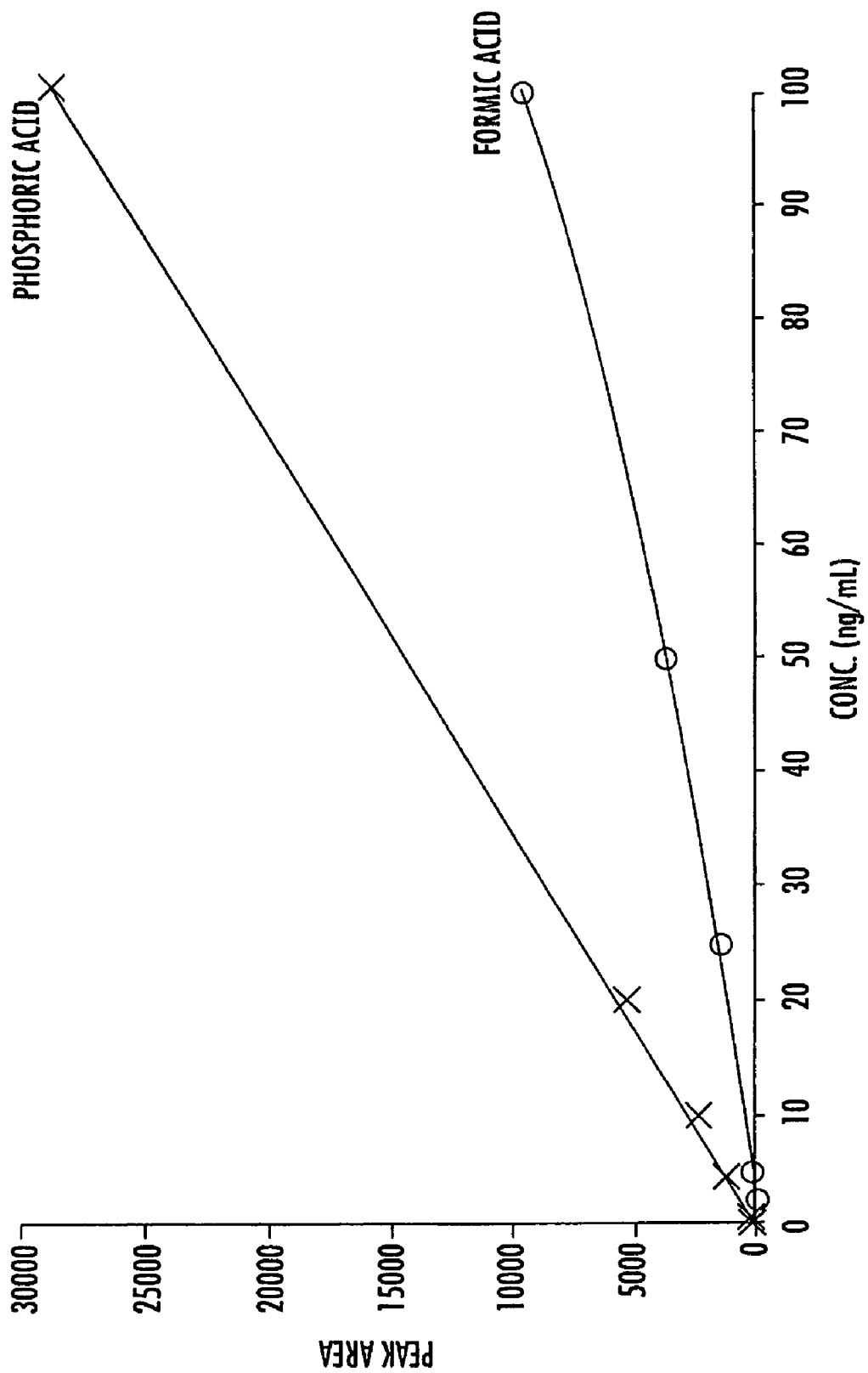
FIG. 24 provides the acid modifier effects on glyphosate LC/MS/MS response.

Glyphosate in soybean seed sample: Soy Seed AX 10X1 1004
(Reference: Table 10, FIG. 16, Table 30-40)

$$\frac{2570/1208 \text{ area}}{0.2501 \text{ area/ng/mL}} \times \frac{10.0 \text{ mL} \times 100 \text{ mL}}{4.0 \text{ mL} \times 5.0 \text{ g}} \times \frac{\text{mg} \cdot \text{g}}{1000 \text{ ng} \cdot \text{kg}} =$$
$$0.425 = 0.43 \text{ mg/kg}$$

$$\% \text{ Recovery} = \frac{0.0425 \text{ mg/kg analyte found}}{0.50 \text{ mg/kg analyte fortified}} \times 100 = 85\%$$

AMPA in soybean seed sample: Soy Seed CX L1 1004
(Reference: Table 10, FIG. 16, Table 30-40)

$$\frac{113/204 \text{ area}}{0.5927 \text{ area/ng/mL}} \times \frac{10.0 \text{ mL} \times 100 \text{ mL}}{4.0 \text{ mL} \times 5.0 \text{ g}} \times \frac{\text{mg} \cdot \text{g}}{1000 \text{ ng} \cdot \text{kg}} =$$
$$0.467 = 0.47 \text{ mg/kg}$$

$$\% \text{ Recovery} = \frac{0.0467 \text{ mg/kg analyte found}}{0.050 \text{ mg/kg analyte fortified}} \times 100 = 93\%$$

TABLE 30

Corn Grain - glyphosate and N-acetylglyphosate

Matrix: Corn Grain
Quantitation Ions: glyphosate: glyphosate: 170 > 87.7, N-acetylglyphosate: 212 > 87.9

| | Sample Information | | | SW | XV | AV | FV | Analyte Response | | | |
|---|---|---|---|---|---|---|---|---|---|---|---|
| | | | | | | | | glyphosate | | NA-Gly | |
| Run ID | Type | ppb | Identification | g | ml | ml | ml | Area | RF | Area | RF |
| 071305Gmax-3 | S | 0.5 | 0.5 MM Cal Std | | | | | 222 | 444 | 295 | 590 |
| 071305Gmax-4 | C | | Grain Ctrl 062905 | | | | | | | | |
| 071305Gmax-6 | F | 50 | Grain LOQ 062905-1 | 5 | 100 | 4 | 10 | 339 | | 470 | |
| 071305Gmax-7 | F | 50 | Grain LOQ 062905-2 | 5 | 100 | 4 | 10 | 328 | | 573 | |
| 071305Gmax-8 | S | 1 | 1.0 MM Cal Std | 5 | 100 | 4 | 10 | 452 | 452 | 555 | 555 |
| 071305Gmax-9 | F | 50 | Grain LOQ 062905-3 | 5 | 100 | 4 | 10 | 323 | | 491 | |
| 071305Gmax-10 | F | 50 | Grain LOQ 062905-4 | 5 | 100 | 4 | 10 | 328 | | 589 | |
| 071305Gmax-12 | F | 50 | Grain LOQ 062905-5 | 5 | 100 | 4 | 10 | 312 | | 485 | |
| 071305Gmax-13 | S | 4 | 4.0 MM Cal Std | 5 | 100 | 4 | 10 | 1763 | 441 | 2515 | 629 |
| 071305Gmax-14 | F | 500 | Grain 10X 062905-1 | 5 | 100 | 4 | 10 | 3268 | | 5914 | |
| 071305Gmax-15 | F | 500 | Grain 10X 062905-2 | 5 | 100 | 4 | 10 | 3182 | | 5457 | |
| 071305Gmax-17 | F | 500 | Grain 10X 062905-3 | 5 | 100 | 4 | 10 | 3119 | | 5432 | |
| 071305Gmax-18 | F | 500 | Grain 10X 062905-4 | 5 | 100 | 4 | 10 | 3085 | | 5654 | |
| 071305Gmax-19 | S | 10 | 10.0 MM Cal Std | 5 | 100 | 4 | 10 | 4213 | 421 | 5917 | 592 |
| 071305Gmax-21 | F | 500 | Grain 10X 062905-5 | 5 | 100 | 4 | 10 | 3080 | | 5468 | |
| 071305Gmax-22 | S | 20 | 20.0 MM Cal Std | | | | | 8793 | 440 | 12917 | 646 |
| Calibration Standards Statistics | | | | | | | Slope = | 2.286E−03 | | 1.551E−03 | |
| | | | | | | | Intercept = | 4.011E−02 | | 2.132E−01 | |
| | | | | | | | RSQ = | 0.99947 | | 0.99819 | |
| Quantified by Average Response Factor | | | | | | | Average RF = | 440 | | 602 | |
| | | | | | | | RF STDEV = | 11 | | 36 | |
| | | | | | | | RF % RSD = | 3% | | 6% | |

| | Sample Information | | | SW | XV | AV | FV | Recoveries | | | |
|---|---|---|---|---|---|---|---|---|---|---|---|
| | | | | | | | | glyphosate | | NA-Gly | |
| Run ID | Type | mg/kg | Identification | ml | ml | ml | ml | mg/kg | % Rec | mg/kg | % Rec |
| 071305Gmax-4 | C | 0 | Grain Ctrl 062905 | 5 | 100 | 4 | 10 | nd | | nd | |
| 071305Gmax-6 | F | 0.05 | Grain LOQ 062905-1 | 5 | 100 | 4 | 10 | 0.039 | 77% | 0.039 | 78% |
| 071305Gmax-7 | F | 0.05 | Grain LOQ 062905-2 | 5 | 100 | 4 | 10 | 0.037 | 75% | 0.048 | 95% |
| 071305Gmax-9 | F | 0.05 | Grain LOQ 062905-3 | 5 | 100 | 4 | 10 | 0.037 | 73% | 0.041 | 82% |
| 071305Gmax-10 | F | 0.05 | Grain LOQ 062905-4 | 5 | 100 | 4 | 10 | 0.037 | 75% | 0.049 | 98% |
| 071305Gmax-12 | F | 0.05 | Grain LOQ 062905-5 | 5 | 100 | 4 | 10 | 0.035 | 71% | 0.040 | 81% |

TABLE 30-continued

Corn Grain - glyphosate and N-acetylglyphosate

| 071305Gmax-14 | F | 0.5 | Grain 10X 062905-1 | 5 | 100 | 4 | 10 | 0.372 | 74% | 0.491 | 98% |
| 071305Gmax-15 | F | 0.5 | Grain 10X 062905-2 | 5 | 100 | 4 | 10 | 0.362 | 72% | 0.453 | 91% |
| 071305Gmax-17 | F | 0.5 | Grain 10X 062905-3 | 5 | 100 | 4 | 10 | 0.355 | 71% | 0.451 | 90% |
| 071305Gmax-18 | F | 0.5 | Grain 10X 062905-4 | 5 | 100 | 4 | 10 | 0.351 | 70% | 0.469 | 94% |
| 071305Gmax-21 | F | 0.5 | Grain 10X 062905-5 | 5 | 100 | 4 | 10 | 0.350 | 70% | 0.454 | 91% |

TABLE 31

Corn Grain - AMPA

Matrix: Corn Grain
Quantitation Ions: glyphosate: AMPA: 111.9 > 30

| | | | Sample Information | SW | XV | AF | FV | Analyte Response AMPA | |
|---|---|---|---|---|---|---|---|---|---|
| Run ID | Type | 1 ppb | Identification | g | ml | ml | ml | Area | RF |
| 063005Gcx-2 | S | 1 | 1 ppb Cal Std | | | | | 162 | 162 |
| 063005Gcx-3 | S | 1 | 1 ppb Cal Std | | | | | 156 | 156 |
| 063005Gcx-4 | C | | Grain Ctrl 052905-1 | 5 | 100 | 4 | 5 | | |
| 063005Gcx-5 | C | | Grain Ctrl 052905-2 | 5 | 100 | 4 | 5 | | |
| 063005Gcx-6 | S | 2 | 2 ppb Cal Std | | | | | 287 | 144 |
| 063005Gcx-7 | F | 50 | Grain-LOQ052905-1 AMPA | 5 | 100 | 4 | 5 | 310 | |
| 063005Gcx-8 | F | 50 | Grain-LOQ052905-2 AMPA | 5 | 100 | 4 | 5 | 281 | |
| 063005Gcx-9 | S | 2 | 2 ppb Cal Std | | | | | 276 | 138 |
| 063005Gcx-10 | F | 50 | Grain-LOQ052905-3 AMPA | 5 | 100 | 4 | 5 | 283 | |
| 063005Gcx-11 | F | 50 | Grain-LOQ052905-4 AMPA | 5 | 100 | 4 | 5 | 329 | |
| 063005Gcx-12 | S | 10 | 10 ppb Cal Std | | | | | 1254 | 125 |
| 063005Gcx-13 | F | 50 | Grain-LOQ052905-5 AMPA | 5 | 100 | 4 | 5 | 294 | |
| 063005Gcx-14 | F | 500 | Grain-10X052905-1 AMPA | 5 | 100 | 4 | 5 | 2799 | |
| 063005Gcx-15 | S | 20 | 20 ppb Cal Std | | | | | 2471 | 124 |
| 063005Gcx-16 | F | 500 | Grain-10X052905-2 AMPA | 5 | 100 | 4 | 5 | 2767 | |
| 063005Gcx-17 | F | 500 | Grain-10X052905-3 AMPA | 5 | 100 | 4 | 5 | 2762 | |
| 063005Gcx-18 | S | 20 | 20 ppb Cal Std | | | | | 2505 | 125 |
| 063005Gcx-19 | F | 500 | Grain-10X052905-4 AMPA | 5 | 100 | 4 | 5 | 2907 | |
| 063005Gcx-20 | F | 500 | Grain-10X052905-5 AMPA | 5 | 100 | 4 | 5 | 2595 | |
| 063005Gcx-21 | S | 50 | 50 ppb Cal Std | | | | | 6230 | 125 |

Calibration Standards Statistics  
Slope = 8.079E−03  
Intercept = −2.221E−01  
RSQ = 0.99995  
Quantified by Average Response Factor  
Average RF = 137  
RF STDEV = 15  
RF % RSD = 11%

| | | | Sample Information | SW | XV | AF | FV | AMPA | |
|---|---|---|---|---|---|---|---|---|---|
| Run ID | Type | mg/kg | Identification | ml | ml | ml | ml | mg/kg | % Rec |
| 063005Gcx-4 | C | 0 | Grain Ctrl 052905-1 | 5 | 100 | 4 | 5 | nd | |
| 063005Gcx-5 | C | 0 | Grain Ctrl 052905-2 | 5 | 100 | 4 | 5 | nd | |
| 063005Gcx-7 | F | 0.05 | Grain-LOQ052905-1 AMPA | 5 | 100 | 4 | 5 | 0.050 | 113% |
| 063005Gcx-8 | F | 0.05 | Grain-LOQ052905-2 AMPA | 5 | 100 | 4 | 5 | 0.051 | 102% |
| 063005Gcx-10 | F | 0.05 | Grain-LOQ052905-3 AMPA | 5 | 100 | 4 | 5 | 0.052 | 103% |
| 063005Gcx-11 | F | 0.05 | Grain-LOQ052905-4 AMPA | 5 | 100 | 4 | 5 | 0.060 | 120% |
| 063005Gcx-13 | F | 0.05 | Grain-LOQ052905-5 AMPA | 5 | 100 | 4 | 5 | 0.054 | 107% |
| 063005Gcx-14 | F | 0.5 | Grain-10X052905-1 AMPA | 5 | 100 | 4 | 5 | 0.510 | 102% |
| 063005Gcx-16 | F | 0.5 | Grain-10X052905-2 AMPA | 5 | 100 | 4 | 5 | 0.504 | 101% |
| 063005Gcx-17 | F | 0.5 | Grain-10X052905-3 AMPA | 5 | 100 | 4 | 5 | 0.503 | 101% |
| 063005Gcx-19 | F | 0.5 | Grain-10X052905-4 AMPA | 5 | 100 | 4 | 5 | 0.529 | 106% |
| 063005Gcx-20 | F | 0.5 | Grain-10X052905-5 AMPA | 5 | 100 | 4 | 5 | 0.473 | 95% |

TABLE 32

Corn Oil - glyphosate, N-acetylglyphosate and AMPA

Matrix: Corn Oils - Dry and Wet Milled
Quantitation Ions: glyphosate: 170 > 87.7, N-acetylglyphosate: 212 > 87.9, AMPA: 111.9 > 30.0

| | | | | | | | | Analyte Response | | | | |
|---|---|---|---|---|---|---|---|---|---|---|---|---|
| | Sample Information | | | SW | XV | AV | FV | glyphosate | | NA-Gly | | AMPA | |
| Run ID | Type | ppb | Identification | g | ml | ml | ml | Area | RF | Area | RF | Area | RF |
| 071805oil-3 | S | 1 | 1 ppb Cal Std 0718 | | | | | 494 | 494 | 960 | 960 | 55 | 55 |
| 071805oil-4 | C | | Dry Oil Control 0718 | 2 | 40 | 40 | 40 | | | | | | |
| 071805oil-5 | C | | Wet Oil Control 0718 | 2 | 40 | 40 | 40 | | | | | | |
| 071805oil-6 | S | 2.5 | 2.5 ppb Cal Std 0718 | | | | | 1301 | 520 | 2387 | 955 | 168 | 67 |
| 071805oil-7 | F | 50 | Dry Oil LOQ 1 0718 | 2 | 40 | 40 | 40 | 1136 | | 2474 | | 129 | |
| 071805oil-8 | F | 50 | Dry Oil LOQ 2 0718 | 2 | 40 | 40 | 40 | 1229 | | 2437 | | 166 | |
| 071805oil-9 | S | 2.5 | 2.5 ppb Cal Std 0718 | | | | | 1178 | 471 | 2443 | 977 | 170 | 68 |
| 071805oil-10 | F | 50 | Wet Oil LOQ 1 0718 | 2 | 40 | 40 | 40 | 1176 | | 2448 | | 132 | |
| 071805oil-11 | F | 50 | Wet Oil LOQ 2 0718 | 2 | 40 | 40 | 40 | 1203 | | 2429 | | 191 | |
| 071805oil-12 | S | 10 | 10 ppb Cal Std 0718 | | | | | 4862 | 486 | 9568 | 957 | 591 | 59 |
| 071805oil-13 | F | 50 | Wet Oil LOQ 3 0718 | 2 | 40 | 40 | 40 | 1199 | | 2404 | | 128 | |
| 071805oil-14 | F | 500 | Dry Oil 10X 1 0718 | 2 | 40 | 40 | 40 | 11761 | | 25141 | | 1389 | |
| 071805oil-15 | S | 25 | 25 ppb Cal Std 0718 | | | | | 12158 | 486 | 25496 | 1020 | 1530 | 61 |
| 071805oil-16 | F | 500 | Dry Oil 10X 2 0718 | 2 | 40 | 40 | 40 | 12631 | | 24939 | | 1495 | |
| 071805oil-17 | F | 500 | Dry Oil 10X 3 0718 | 2 | 40 | 40 | 40 | 11706 | | 24007 | | 1403 | |
| 071805oil-18 | S | 25 | 25 ppb Cal Std 0718 | | | | | 11877 | 475 | 24473 | 979 | 1539 | 62 |
| 071805oil-19 | F | 500 | Wet Oil 10X 1 0718 | 2 | 40 | 40 | 40 | 12172 | | 24142 | | 1316 | |
| 071805oil-20 | F | 500 | Wet Oil 10X 2 0718 | 2 | 40 | 40 | 40 | 13146 | | 24840 | | 1395 | |
| 071805oil-21 | S | 50 | 50 ppb Cal Std 0718 | | | | | 25074 | 501 | 49707 | 994 | 2626 | 53 |
| Calibration Standards Statistics | | | | | | | Slope = | 2.007E−03 | | 1.002E−03 | | 1.846E−02 | |
| | | | | | | | Intercept = | 2.407E−01 | | 1.081E−01 | | −1.043E+00 | |
| | | | | | | | RSQ = | 0.99923 | | 0.99965 | | 0.99049 | |
| Quantified by Average Response Factor | | | | | | | Average RF = | 491 | | 977 | | 61 | |
| | | | | | | | RF STDEV = | 17 | | 24 | | 6 | |
| | | | | | | | RF % RSD = | 3% | | 2% | | 9% | |

| | | | | | | | | Recoveries | | | | | |
|---|---|---|---|---|---|---|---|---|---|---|---|---|---|
| | Sample Information | | | SW | XV | AV | FV | glyphosate | | NA-Gly | | AMPA | |
| Run ID | Type | mg/kg | Identification | g | ml | ml | ml | mg/kg | % Rec | mg/kg | % Rec | mg/kg | % Rec |
| 071805oil-4 | C | 0 | Dry Oil Control 0718 | 2 | 40 | 40 | 40 | nd | | nd | | nd | |
| 071805oil-5 | C | 0 | Wet Oil Control 0718 | 2 | 40 | 40 | 40 | nd | | nd | | nd | |
| 071805oil-7 | F | 0.05 | Dry Oil LOQ 1 0718 | 2 | 40 | 40 | 40 | 0.046 | 93% | 0.051 | 101% | 0.043 | 85% |
| 071805oil-8 | F | 0.05 | Dry Oil LOQ 2 0718 | 2 | 40 | 40 | 40 | 0.050 | 100% | 0.050 | 100% | 0.055 | 109% |
| 071805oil-10 | F | 0.05 | Wet Oil LOQ 1 0718 | 2 | 40 | 40 | 40 | 0.048 | 96% | 0.050 | 100% | 0.044 | 87% |
| 071805oil-11 | F | 0.05 | Wet Oil LOQ 2 0718 | 2 | 40 | 40 | 40 | 0.049 | 98% | 0.050 | 99% | 0.063 | 126% |
| 071805oil-13 | F | 0.05 | Wet Oil LOQ 3 0718 | 2 | 40 | 40 | 40 | 0.049 | 98% | 0.049 | 98% | 0.042 | 84% |
| 071805oil-14 | F | 0.5 | Dry Oil 10X 1 0718 | 2 | 40 | 40 | 40 | 0.479 | 96% | 0.514 | 103% | 0.458 | 92% |
| 071805oil-16 | F | 0.5 | Dry Oil 10X 2 0718 | 2 | 40 | 40 | 40 | 0.515 | 103% | 0.510 | 102% | 0.493 | 99% |
| 071805oil-17 | F | 0.5 | Dry Oil 10X 3 0718 | 2 | 40 | 40 | 40 | 0.477 | 95% | 0.491 | 98% | 0.463 | 93% |
| 071805oil-19 | F | 0.5 | Wet Oil 10X 1 0718 | 2 | 40 | 40 | 40 | 0.496 | 99% | 0.494 | 99% | 0.434 | 87% |
| 071805oil-20 | F | 0.5 | Wet Oil 10X 2 0718 | 2 | 40 | 40 | 40 | 0.536 | 107% | 0.508 | 102% | 0.460 | 92% |

TABLE 33

Soybean Seed - glyphosate and N-acetylglyphosate

C18: 10 ml X + 10 ml 5% H2O/MeOH; MAX: 8 ml C18 eluate +
160 µL NH4OH/20 ml in methanol
Matrix: Soybean Seed
Quantitation Ions: glyphosate: 170 > 87.7, n-acetyl glyphosate: 212 > 87.9

| | | | | | | | | Analyte Response | | | | |
|---|---|---|---|---|---|---|---|---|---|---|---|---|
| | Sample Information | | | SW | XV | AF | FV | glyphosate | | | NA-Gly | |
| Run ID | Type | ppb | Identification | g | ml | ml | ml | Area | IS | RF | Area | RF |
| 100505-SS-AX-1 | S | 0.5 | 0.5 CS + IS 1004 | | | | | 231 | 1994 | 0.2317 | 647 | 1294 |
| 100505-SS-AX-2 | S | 0.5 | 0.5 CS + IS 1004 | | | | | 253 | 1867 | 0.2710 | 622 | 1244 |
| 100505-SS-AX-3 | C | | Soy Seed AX Cont 1004 | 5 | 100 | 4 | 10 | | 1165 | | | |
| 100505-SS-AX-4 | S | 1 | 1 CS + IS 1004 | | | | | 494 | 1845 | 0.2678 | 1256 | 1256 |
| 100505-SS-AX-5 | F | 50 | Soy Seed AX L1 1004 | 5 | 100 | 4 | 10 | 252 | 1144 | | 1233 | |
| 100505-SS-AX-6 | S | 2 | 2 CS + IS 1004 | | | | | 876 | 1821 | 0.2405 | 2549 | 1275 |

TABLE 33-continued

Soybean Seed - glyphosate and N-acetylglyphosate

| 100505-SS-AX-7 | F | 50 | Soy Seed AX L2 1004 | 5 | 100 | 4 | 10 | 268 | 1199 | | 1219 | |
|---|---|---|---|---|---|---|---|---|---|---|---|---|
| 100505-SS-AX-8 | S | 5 | 5 CS + IS 1004 | | | | | 2168 | 1892 | 0.2292 | 6309 | 1262 |
| 100505-SS-AX-9 | F | 50 | Soy Seed AX L3 1004 | 5 | 100 | 4 | 10 | 282 | 1245 | | 1191 | |
| 100505-SS-AX-10 | S | 10 | 10 CS + IS 1004 | | | | | 4537 | 1751 | 0.2591 | 12576 | 1258 |
| 100505-SS-AX-11 | F | 500 | Soy Seed AX 10X1 1004 | 5 | 100 | 4 | 10 | 2570 | 1208 | | 11681 | |
| 100505-SS-AX-12 | S | 20 | 20 CS + IS 1004 | | | | | 9121 | 1827 | 0.2496 | 25180 | 1259 |
| 100505-SS-AX-13 | F | 500 | Soy Seed AX 10X2 1004 | 5 | 100 | 4 | 10 | 2441 | 1218 | | 11651 | |
| 100505-SS-AX-14 | S | 50 | 50 CS + IS 1004 | | | | | 22316 | 1769 | 0.2523 | 63580 | 1272 |

Calibration Standards Statistics  
Slope = 2.237E-03    7.869E-04  
Intercept = -5.949E-02    3.773E-02  
RSQ = 0.99990    0.99998  
Quantified by Average Response Factor  
Average RF = 0.2501    1265  
STDEV = 0.0156    15  
% RSD = 6%    1%

| | | | | | | | | Recoveries | | | |
|---|---|---|---|---|---|---|---|---|---|---|---|
| | Sample Information | | | SW | XV | AF | FV | glyphosate | | NA-Gly | |
| Run ID | Type | mg/kg | Identification | ml | ml | ml | ml | mg/kg | % Rec | mg/kg | % Rec |
| 100505-SS-AX-3 | C | 0 | Soy Seed AX Cont 1004 | 5 | 100 | 4 | 10 | nd | | nd | |
| 100505-SS-AX-5 | F | 0.05 | Soy Seed AX L1 1004 | 5 | 100 | 4 | 10 | 0.044 | 88% | 0.049 | 97% |
| 100505-SS-AX-7 | F | 0.05 | Soy Seed AX L2 1004 | 5 | 100 | 4 | 10 | 0.045 | 89% | 0.048 | 96% |
| 100505-SS-AX-9 | F | 0.05 | Soy Seed AX L3 1004 | 5 | 100 | 4 | 10 | 0.045 | 91% | 0.047 | 94% |
| 100505-SS-AX-11 | F | 0.5 | Soy Seed AX 10X1 1004 | 5 | 100 | 4 | 10 | 0.425 | 85% | 0.462 | 92% |
| 100505-SS-AX-13 | F | 0.5 | Soy Seed AX 10X2 1004 | 5 | 100 | 4 | 10 | 0.401 | 80% | 0.461 | 92% |

TABLE 34

Soybean Seed - AMPA

C18: 2 ml X to waste, collect 5 ml X; MCX: 4 ml X + 2 ml MeOH  
Matrix: Soybean Seed  
Quantitation Ions: AMPA: 111.9 > 30, AMPA IS: 113.9 > 32

| | | | | | | | | Analyte Response AMPA | | |
|---|---|---|---|---|---|---|---|---|---|---|
| | Sample Information | | | SW | XV | AF | FV | | | |
| Run ID | Type | ppb | Identification | g | ml | ml | ml | Area | IS Area | RF |
| 100405-SS-CX 1 | S | 0.5 | 0.5 CS + IS 1004 | | | | | 276 | 793 | 0.6961 |
| 100405-SS-CX 2 | S | 0.5 | 0.5 CS + IS 1004 | | | | | 269 | 804 | 0.6692 |
| 100405-SS-CX 3 | C | | Soy Seed CX Cont 1004 | 5 | 100 | 4 | 10 | | 216 | |
| 100405-SS-CX 4 | S | 1 | 1 CS + IS 1004 | | | | | 498 | 755 | 0.6596 |
| 100405-SS-CX 5 | F | 50 | Soy Seed CX L1 1004 | 5 | 100 | 4 | 10 | 113 | 204 | |
| 100405-SS-CX 6 | S | 2 | 2 CS + IS 1004 | | | | | 883 | 755 | 0.5848 |
| 100405-SS-CX 7 | F | 50 | Soy Seed CX L2 1004 | 5 | 100 | 4 | 10 | 109 | 240 | |
| 100405-SS-CX 8 | S | 5 | 5 CS + IS 1004 | | | | | 2063 | 791 | 0.5216 |
| 100405-SS-CX 9 | F | 50 | Soy Seed CX L3 1004 | 5 | 100 | 4 | 10 | 129 | 202 | |
| 100405-SS-CX 10 | S | 10 | 10 CS + IS 1004 | | | | | 3961 | 743 | 0.5331 |
| 100405-SS-CX 11 | F | 500 | Soy Seed CX 10X1 1004 | 5 | 100 | 4 | 10 | 955 | 190 | |
| 100405-SS-CX 12 | S | 20 | 20 CS + IS 1004 | | | | | 8615 | 789 | 0.5459 |
| 100405-SS-CX 13 | F | 500 | Soy Seed CX 10X2 1004 | 5 | 100 | 4 | 10 | 968 | 222 | |
| 100405-SS-CX 14 | S | 50 | 50 CS + IS 1004 | | | | | 20602 | 775 | 0.5317 |

Calibration Standards Statistics  
Slope = 2.424E-03  
Intercept = -1.364E-01  
RSQ = 0.99956  
Quantified by Average Response Factor  
Average RF = 0.5927  
STDEV = 0.0713  
% RSD = 12%

| | | | | | | | | Recoveries AMPA | |
|---|---|---|---|---|---|---|---|---|---|
| | Sample Information | | | SW | XV | AF | FV | | |
| Run ID | Type | mg/kg | Identification | ml | ml | ml | ml | mg/kg | % Rec |
| 100405-SS-CX 3 | C | 0 | Soy Seed CX Cont 1004 | 5 | 100 | 4 | 10 | nd | |
| 100405-SS-CX 5 | F | 0.05 | Soy Seed CX L1 1004 | 5 | 100 | 4 | 10 | 0.047 | 93% |
| 100405-SS-CX 7 | F | 0.05 | Soy Seed CX L2 1004 | 5 | 100 | 4 | 10 | 0.038 | 77% |
| 100405-SS-CX 9 | F | 0.05 | Soy Seed CX L3 1004 | 5 | 100 | 4 | 10 | 0.054 | 108% |
| 100405-SS-CX 11 | F | 0.5 | Soy Seed CX 10X1 1004 | 5 | 100 | 4 | 10 | 0.424 | 85% |
| 100405-SS-CX 13 | F | 0.5 | Soy Seed CX 10X2 1004 | 5 | 100 | 4 | 10 | 0.368 | 74% |

TABLE 35

Soybean Meal - glyphosate and N-acetylglyphosate

Matrix: Soybean Meal
Quantitation Ions: glyphosate: 170 > 87.7, n-acetyl glyphosate: 212 > 87.9

| | Sample Information | | | | | | | Analyte Response | | | | |
|---|---|---|---|---|---|---|---|---|---|---|---|---|
| | | | | | | | | glyphosate | | | NA-Gly | |
| Run ID | Type | ppb | Identification | SW g | XV ml | AF ml | FV ml | Area | IS | $RF_{IS}$ | Area | RF |
| 06-0327SoyMealAX-1 | S | 0.5 | 0.5 CS + IS 0327 | | | | | 153 | 1350 | 0.2267 | 257 | 514 |
| 06-0327SoyMealAX-2 | S | 0.5 | 0.5 CS + IS 0327 | | | | | 149 | 1336 | 0.2231 | 226 | 452 |
| 06-0327SoyMealAX-3 | C | | SM-032406-1 AX Cont | 5 | 100 | 2 | 5 | | 898 | | | |
| 06-0327SoyMealAX-4 | S | 1 | 1.0 CS + IS 0327 | | | | | 301 | 1315 | 0.2289 | 473 | 473 |
| 06-0327SoyMealAX-5 | F | 50 | SM-032406-2 AX LOQ 1 | 5 | 100 | 2 | 5 | 185 | 921 | | 343 | |
| 06-0327SoyMealAX-6 | S | 1 | 1.0 CS + IS 0327 | | | | | 328 | 1387 | 0.2365 | 384 | 384 |
| 06-0327SoyMealAX-7 | F | 50 | SM-032406-3 AX LOQ 2 | 5 | 100 | 2 | 5 | 176 | 901 | | 424 | |
| 06-0327SoyMealAX-8 | S | 2 | 2 CS + IS 0327 | | | | | 602 | 1351 | 0.2228 | 910 | 455 |
| 06-0327SoyMealAX-9 | F | 50 | SM-032406-4 AX LOQ 3 | 5 | 100 | 2 | 5 | 195 | 899 | | 414 | |
| 06-0327SoyMealAX-10 | S | 5 | 5 CS + IS 0327 | | | | | 1556 | 1389 | 0.2240 | 2339 | 468 |
| 06-0327SoyMealAX-11 | F | 500 | SM-032406-5 AX H2O 10X 1 | 5 | 100 | 2 | 5 | 1693 | 954 | | 4076 | |
| 06-0327SoyMealAX-12 | S | 10 | 10 CS + IS 0327 | | | | | 3014 | 1284 | 0.2347 | 4658 | 466 |
| 06-0327SoyMealAX-13 | F | 500 | SM-032406-6 AX H2O 10X 2 | 5 | 100 | 2 | 5 | 1707 | 966 | | 4038 | |
| 06-0327SoyMealAX-14 | S | 20 | 20 CS + IS 0327 | | | | | 5911 | 1443 | 0.2048 | 9355 | 468 |

| Calibration Standards Statistics | Slope = | 3.380E−03 | 2.135E−03 |
|---|---|---|---|
| | Intercept = | −7.603E−02 | 3.653E−02 |
| | RSQ = | 0.99979 | 0.99990 |
| Quantified by Average Response Factor | Average RF = | 0.2252 | 460 |
| | STDEV = | 0.0097 | 36 |
| | % RSD = | 4% | 8% |

| | Sample Information | | | SW | | | | Recoveries | | | |
|---|---|---|---|---|---|---|---|---|---|---|---|
| | | | | | | | | glyphosate | | NA-Gly | |
| Run ID | Type | mg/kg | Identification | ml | XV ml | AF ml | FV ml | mg/kg | % Rec | mg/kg | % Rec |
| 06-0327SoyMealAX-3 | C | 0 | SM-032406-1 AX Cont | 5 | 100 | 2 | 5 | nd | | nd | |
| 06-0327SoyMealAX-5 | F | 0.05 | SM-032406-2 AX LOQ 1 | 5 | 100 | 2 | 5 | 0.045 | 89% | 0.037 | 75% |
| 06-0327SoyMealAX-7 | F | 0.05 | SM-032406-3 AX LOQ 2 | 5 | 100 | 2 | 5 | 0.043 | 87% | 0.046 | 92% |
| 06-0327SoyMealAX-9 | F | 0.05 | SM-032406-4 AX LOQ 3 | 5 | 100 | 2 | 5 | 0.048 | 96% | 0.045 | 90% |
| 06-0327SoyMealAX-11 | F | 0.5 | SM-032406-5 AX H2O 10X 1 | 5 | 100 | 2 | 5 | 0.394 | 79% | 0.443 | 89% |
| 06-0327SoyMealAX-13 | F | 0.5 | SM-032406-6 AX H2O 10X 2 | 5 | 100 | 2 | 5 | 0.392 | 78% | 0.439 | 88% |

TABLE 36

Soybean Meal - AMPA

Matrix: Soybean Meal
Quantitation Ions: AMPA: 111.9 > 30, AMPAIS: 113.9 > 32

| | Sample Information | | | | | | | Analyte Response AMPA | | |
|---|---|---|---|---|---|---|---|---|---|---|
| Run ID | Type | ppb | Identification | SW g | XV ml | AF ml | FV ml | Area | IS Area | $RF_{IS}$ |
| 06-0327SoyMealCX-3 | S | 1 | 1.0 CS + IS 0327 | | | | | 129 | 367 | 0.3515 |
| 06-0327SoyMealCX-4 | S | 1 | 1.0 CS + IS 0327 | | | | | 124 | 370 | 0.3351 |
| 06-0327SoyMealCX-5 | C | | SM-032406-1 CX Cont | 5 | 100 | 4 | 5 | | 282 | |
| 06-0327SoyMealCX-6 | S | 2 | 2.0 CS + IS 0327 | | | | | 238 | 417 | 0.2854 |
| 06-0327SoyMealCX-7 | F | 50 | SM-032406-2 CX LOQ 1 | 5 | 100 | 4 | 5 | 161 | 302 | |
| 06-0327SoyMealCX-8 | S | 5 | 5.0 CS + IS 0327 | | | | | 607 | 417 | 0.2911 |
| 06-0327SoyMealCX-9 | F | 50 | SM-032406-3 CX LOQ 2 | 5 | 100 | 4 | 5 | 135 | 267 | |
| 06-0327SoyMealCX-10 | S | 10 | 10 CS + IS 0327 | | | | | 1025 | 353 | 0.2904 |
| 06-0327SoyMealCX-11 | F | 50 | SM-032406-4 CX LOQ 3 | 5 | 100 | 4 | 5 | 164 | 295 | |
| 06-0327SoyMealCX-12 | S | 20 | 20 CS + IS 0327 | | | | | 2111 | 357 | 0.2957 |

TABLE 36-continued

Soybean Meal - AMPA

| 06-0327SoyMealCX-13 | F | 500 | SM-032406-5 CX 10X 1 | 5 | 100 | 4 | 5 | 1264 | 281 | |
|---|---|---|---|---|---|---|---|---|---|---|
| 06-0327SoyMealCX-14 | F | 500 | SM-032406-6 CX 10X 2 | 5 | 100 | 4 | 5 | 1278 | 272 | |
| 06-0327SoyMealCX-15 | S | 50 | 50 CS + IS 0327 | | | | | 5296 | 349 | 0.3035 |

| Calibration Standards Statistics | Slope = | 9.501E−03 |
|---|---|---|
| | Intercept = | −2.201E−01 |
| | RSQ = | 0.99970 |
| Quantified by Average Response Factor | Average RF = | 0.3075 |
| | STDEV = | 0.0255 |
| | % RSD = | 8% |

| | Sample Information | | | | | | Recoveries AMPA | |
|---|---|---|---|---|---|---|---|---|
| Run ID | Type | mg/kg | Identification | SW ml | XV ml | AF ml | FV ml | mg/kg | % Rec |
| 06-0327SoyMealCX-5 | C | 0 | SM-032406-1 CX Cont | 5 | 100 | 4 | 5 | nd | |
| 06-0327SoyMealCX-7 | F | 0.05 | SM-032406-2 CX LOQ 1 | 5 | 100 | 4 | 5 | 0.043 | 87% |
| 06-0327SoyMealCX-9 | F | 0.05 | SM-032406-3 CX LOQ 2 | 5 | 100 | 4 | 5 | 0.041 | 82% |
| 06-0327SoyMealCX-11 | F | 0.05 | SM-032406-4 CX LOQ 3 | 5 | 100 | 4 | 5 | 0.045 | 90% |
| 06-0327SoyMealCX-13 | F | 0.5 | SM-032406-5 CX 10X 1 | 5 | 100 | 4 | 5 | 0.366 | 73% |
| 06-0327SoyMealCX-14 | F | 0.5 | SM-032406-6 CX 10X 2 | 5 | 100 | 4 | 5 | 0.382 | 76% |

TABLE 37

Plum - glyphosate, N-acetylglyphosate and N-acetyl AMPA

Water dilution, Ab2-1b2 inlet conditions, 15 μL injection
Matrix: Plums
Quantitation Ions: glyphosate: 170 > 87.7, glyphosate IS 173 > 90.7,
N-acetylglyphosate: 212 > 87.9, N-acetyl AMPA 154 > 111.9

| | Sample Information | | | SW | XV | AF | | Analyte Response | | | | | |
|---|---|---|---|---|---|---|---|---|---|---|---|---|---|
| | | | | | | | | glyphosate | | | NA-AMPA | | NA-Gly | |
| Run ID | Type | ppb | Identification | g | ml | ml | FV ml | Area | IS | RF$_{IS}$ | Area | RF | Area | RF |
| 07-1010_Plum_A-4 | S | 0.5 | 0.5 ppb CS 100507 | | | | | 152 | 1296 | 0.2346 | 93 | 186 | 75 | 150 |
| 07-1010_Plum_A-5 | C | | Plum 1 CONTROL 092507 | 5 | 100 | 2 | 5 | | 1169 | | | | | |
| 07-1010_Plum_A-6 | C | | Plum 7 CONTROL 092607 | 5 | 100 | 2 | 5 | | 1197 | | | | | |
| 07-1010_Plum_A-7 | S | 1 | 1.0 ppb CS 100507 | | | | | 309 | 1239 | 0.2494 | 131 | 131 | 167 | 167 |
| 07-1010_Plum_A-8 | F | 50 | Plum 2 LOQ 092507 | 5 | 100 | 2 | 5 | 263 | 1283 | | 152 | | 155 | |
| 07-1010_Plum_A-9 | F | 50 | Plum 3 LOQ 092507 | 5 | 100 | 2 | 5 | 253 | 1156 | | 163 | | 129 | |
| 07-1010_Plum_A-10 | S | 2 | 2.0 ppb CS 100507 | | | | | 609 | 1267 | 0.2403 | 314 | 157 | 267 | 134 |
| 07-1010_Plum_A-11 | F | 50 | Plum 8 LOQ 092607 | 5 | 100 | 2 | 5 | 277 | 1269 | | 168 | | 132 | |
| 07-1010_Plum_A-12 | F | 50 | Plum 9 LOQ 092607 | 5 | 100 | 2 | 5 | 279 | 1237 | | 151 | | 149 | |
| 07-1010_Plum_A-13 | S | 5 | 5.0 ppb CS 100507 | | | | | 1447 | 1311 | 0.2207 | 761 | 152 | 707 | 141 |
| 07-1010_Plum_A-14 | F | 50 | Plum 10 LOQ 092607 | 5 | 100 | 2 | 5 | 289 | 1284 | | 154 | | 155 | |
| 07-1010_Plum_A-15 | F | 500 | Plum 4 10x LOQ 092507 | 5 | 100 | 2 | 5 | 2730 | 1315 | | 1720 | | 1384 | |
| 07-1010_Plum_A-16 | S | 10 | 10 ppb CS 100507 | | | | | 2876 | 1341 | 0.2145 | 1531 | 153 | 1403 | 140 |
| 07-1010_Plum_A-17 | F | 500 | Plum 5 10x LOQ 092507 | 5 | 100 | 2 | 5 | 2592 | 1209 | | 1542 | | 1410 | |
| 07-1010_Plum_A-18 | F | 500 | Plum 6 10x LOQ 092507 | 5 | 100 | 2 | 5 | 2632 | 1198 | | 1574 | | 1363 | |
| 07-1010_Plum_A-19 | S | 20 | 20 ppb CS 100507 | | | | | 5344 | 1196 | 0.2234 | 2855 | 143 | 2537 | 127 |
| 07-1010_Plum_A-20 | F | 500 | Plum 11 10x LOQ 092607 | 5 | 100 | 2 | 5 | 2235 | 1095 | | 1365 | | 1228 | |
| 07-1010_Plum_A-21 | F | 500 | Plum 12 10x LOQ 092607 | 5 | 100 | 2 | 5 | 2099 | 1080 | | 1525 | | 1159 | |
| 07-1010_Plum_A-22 | S | 50 | 50 ppb CS 100507 | | | | | 12669 | 1155 | 0.2194 | 7850 | 157 | 6480 | 130 |

| Calibration Standards Statistics | Slope = | | 3.962E−03 | 6.397E−03 | 7.769E−03 |
|---|---|---|---|---|---|
| | Intercept = | | −6.054E−01 | 2.747E−01 | −2.706E−01 |
| | RSQ = | | 0.99918 | 0.99862 | 0.99956 |
| Quantified by Average Response Factor | Average RF = | 1258 | 0.2289 | 154 | 141 |
| | STDEV = | 66 | 0.0128 | 17 | 14 |
| | % RSD = | 5% | 6% | 11% | 10% |

| | Sample Information | | | | | | | Recoveries | | | | | |
|---|---|---|---|---|---|---|---|---|---|---|---|---|---|
| | | | | | | | | glyphosate | | NA-AMPA | | NA-Gly | |
| Run ID | Type | mg/kg | Identification | SW ml | XV ml | AF ml | FV ml | mg/kg | % Rec | mg/kg | % Rec | mg/kg | % Rec |
| 07-1010_Plum_A-5 | C | 0 | Plum 1 CONTROL 092507 | 5 | 100 | 2 | 5 | nd | | nd | | nd | |
| 07-1010_Plum_A-6 | C | 0 | Plum 7 CONTROL 092607 | 5 | 100 | 2 | 5 | nd | | nd | | nd | |
| 07-1010_Plum_A-8 | F | 0.05 | Plum 2 LOQ 092507 | 5 | 100 | 2 | 5 | 0.045 | 90% | 0.049 | 99% | 0.055 | 110% |

TABLE 37-continued

Plum - glyphosate, N-acetylglyphosate and N-acetyl AMPA

| 07-1010_Plum_A-9  | F | 0.05 | Plum 3 LOQ 092507       | 5 | 100 | 2 | 5 | 0.048 | 96% | 0.053 | 106%     | 0.046 | 91%  |
| 07-1010_Plum_A-11 | F | 0.05 | Plum 8 LOQ 092607       | 5 | 100 | 2 | 5 | 0.048 | 95% | 0.054 | 109%     | 0.047 | 93%  |
| 07-1010_Plum_A-12 | F | 0.05 | Plum 9 LOQ 092607       | 5 | 100 | 2 | 5 | 0.049 | 99% | 0.049 | 98%      | 0.053 | 105% |
| 07-1010_Plum_A-14 | F | 0.05 | Plum 10 LOQ 092607      | 5 | 100 | 2 | 5 | 0.049 | 98% | 0.050 | 100%     | 0.055 | 110% |
| 07-1010_Plum_A-15 | F | 0.5  | Plum 4 10x LOQ 092507   | 5 | 100 | 2 | 5 | 0.453 | 91% | 0.558 | *112%*| 0.490 | 98%  |
| 07-1010_Plum_A-17 | F | 0.5  | Plum 5 10x LOQ 092507   | 5 | 100 | 2 | 5 | 0.468 | 94% | 0.500 | 100%     | 0.499 | 100% |
| 07-1010_Plum_A-18 | F | 0.5  | Plum 6 10x LOQ 092507   | 5 | 100 | 2 | 5 | 0.480 | 96% | 0.511 | 102%     | 0.483 | 97%  |
| 07-1010_Plum_A-20 | F | 0.5  | Plum 11 10x LOQ 092607  | 5 | 100 | 2 | 5 | 0.446 | 89% | 0.443 | 89%      | 0.435 | 87%  |
| 07-1010_Plum_A-21 | F | 0.5  | Plum 12 10x LOQ 092607  | 5 | 100 | 2 | 5 | 0.425 | 85% | 0.495 | 99%      | 0.410 | 82%  |

COMMENTS:

Bold italics: % Rec outside 70-110%

Underlined area detected in control subtracted from area detected in sample.

Type (B: blank, S: standard, IS: internal standard, C: control sample, F: fortified control sample, T: treated sample, FS: fort standard). SW: sample weight, XV: extract volume, AF: aliquot factor, FV: final volume, RFIS: response factor normalized to IS (analyte area/IS area/analyte ppb), RF: response factor (analyte area/analyte ppb).

mg/kg Found = (Area/Average RF) × (FV × XV)/(AF × SW × 1000);

mg/kg Found (IS) = (Area/IS Area/Average RFIS) × (FV × XV)/(AF × SW × 1000).

TABLE 38

Plum - AMPA

Matrix: Plums  
Quantitation Ions: AMPA: 111.8 > 30, AMPA IS: 113.8 > 32

| | Sample Information | | | | | | | Analyte Response AMPA | | |
|---|---|---|---|---|---|---|---|---|---|---|
| Run ID | Type | ppb | Identification | SW g | XV ml | AF ml | FV ml | Area | IS | RF$_{IS}$ |
| 07-0927_Plum_C-4  | S | 0.5 | 0.5 ppb CS 091907       |   |     |   |   | 41   | 259 | 0.3166 |
| 07-0927_Plum_C-5  | C |     | Plum 1 CONTROL 092507   | 5 | 100 | 4 | 5 |      | 230 |        |
| 07-0927_Plum_C-6  | C |     | Plum 7 CONTROL 092607   | 5 | 100 | 4 | 5 |      | 243 |        |
| 07-0927_Plum_C-7  | S | 1   | 1.0 ppb CS 091907       |   |     |   |   | 64   | 257 | 0.2490 |
| 07-0927_Plum_C-8  | F | 50  | Plum 2 LOQ 092507       | 5 | 100 | 4 | 5 | 119  | 251 |        |
| 07-0927_Plum_C-9  | F | 50  | Plum 3 LOQ 092507       | 5 | 100 | 4 | 5 | 123  | 274 |        |
| 07-0927_Plum_C-10 | S | 2   | 2.0 ppb CS 091907       |   |     |   |   | 139  | 293 | 0.2372 |
| 07-0927_Plum_C-11 | F | 50  | Plum 8 LOQ 092607       | 5 | 100 | 4 | 5 | 115  | 251 |        |
| 07-0927_Plum_C-12 | F | 50  | Plum 9 LOQ 092607       | 5 | 100 | 4 | 5 | 138  | 282 |        |
| 07-0927_Plum_C-13 | S | 5   | 5.0 ppb CS 091907       |   |     |   |   | 333  | 261 | 0.2552 |
| 07-0927_Plum_C-14 | F | 50  | Plum 10 LOQ 092607      | 5 | 100 | 4 | 5 | 134  | 243 |        |
| 07-0927_Plum_C-15 | F | 500 | Plum 4 10x LOQ 092507   | 5 | 100 | 4 | 5 | 1273 | 268 |        |
| 07-0927_Plum_C-16 | S | 10  | 10 ppb CS 091907        |   |     |   |   | 708  | 280 | 0.2529 |
| 07-0927_Plum_C-17 | F | 500 | Plum 5 10x LOQ 092507   | 5 | 100 | 4 | 5 | 1214 | 251 |        |
| 07-0927_Plum_C-18 | F | 500 | Plum 6 10x LOQ 092507   | 5 | 100 | 4 | 5 | 1266 | 231 |        |
| 07-0927_Plum_C-19 | S | 20  | 20 ppb CS 091907        |   |     |   |   | 1373 | 294 | 0.2335 |
| 07-0927_Plum_C-20 | F | 500 | Plum 11 10x LOQ 092607  | 5 | 100 | 4 | 5 | 1266 | 221 |        |
| 07-0927_Plum_C-21 | F | 500 | Plum 12 10x LOQ 092607  | 5 | 100 | 4 | 5 | 1246 | 264 |        |
| 07-0927_Plum_C-22 | S | 50  | 50 ppb CS 091907        |   |     |   |   | 3472 | 284 | 0.2445 |

| Calibration Standards Statistics | | | Slope = | | | | 1.441E−02 |
| | | | Intercept = | | | | 2.718E−02 |
| | | | RSQ = | | | | 0.99993 |
| Quantified by Average Response Factor | | | Average RF = | | | 275 | 0.2556 |
| | | | STDEV = | | | 16 | 0.0281 |
| | | | % RSD = | | | 6% | 11% |

| | Sample Information | | | | | | | Recoveries AMPA | |
|---|---|---|---|---|---|---|---|---|---|
| Run ID | Type | mg/kg | Identification | SW g | XV ml | AF ml | FV ml | mg/kg | % Rec |
| 07-0927_Plum_C-5  | C | 0    | Plum 1 CONTROL 092507 | 5 | 100 | 4 | 5 | nd    |      |
| 07-0927_Plum_C-6  | C | 0    | Plum 7 CONTROL 092607 | 5 | 100 | 4 | 5 | nd    |      |
| 07-0927_Plum_C-8  | F | 0.05 | Plum 2 LOQ 092507     | 5 | 100 | 4 | 5 | 0.046 | 93%  |
| 07-0927_Plum_C-9  | F | 0.05 | Plum 3 LOQ 092507     | 5 | 100 | 4 | 5 | 0.044 | 88%  |
| 07-0927_Plum_C-11 | F | 0.05 | Plum 8 LOQ 092607     | 5 | 100 | 4 | 5 | 0.045 | 90%  |
| 07-0927_Plum_C-12 | F | 0.05 | Plum 9 LOQ 092607     | 5 | 100 | 4 | 5 | 0.048 | 96%  |
| 07-0927_Plum_C-14 | F | 0.05 | Plum 10 LOQ 092607    | 5 | 100 | 4 | 5 | 0.054 | 108% |
| 07-0927_Plum_C-15 | F | 0.5  | Plum 4 10x LOQ 092507 | 5 | 100 | 4 | 5 | 0.465 | 93%  |

TABLE 38-continued

Plum - AMPA

| 07-0927_Plum_C-17 | F | 0.5 | Plum 5 10x LOQ 092507 | 5 | 100 | 4 | 5 | 0.473 | 95% |
| 07-0927_Plum_C-18 | F | 0.5 | Plum 6 10x LOQ 092507 | 5 | 100 | 4 | 5 | 0.536 | 107% |
| 07-0927_Plum_C-20 | F | 0.5 | Plum 11 10x LOQ 092607 | 5 | 100 | 4 | 5 | 0.560 | *112%* |
| 07-0927_Plum_C-21 | F | 0.5 | Plum 12 10x LOQ 092607 | 5 | 100 | 4 | 5 | 0.462 | 92% |

COMMENTS:
Bold italics: % Rec outside 70-110%,
Underlined: area detected in control subtracted from area detected in sample.

Type (B: blank, S: standard, IS: internal standard, C: control sample, F: fortified control sample, T: treated sample, FS: fort standard). SW: sample weight, XV: extract volume, AF: aliquot factor, FV: final volume, $RF_{IS}$: response factor normalized to IS (analyte area/IS area/analyte ppb), RF: response factor (analyte area/analyte ppb).

mg/kg Found = (Area/Average RF) × (FV × XV)/(AF × SW × 1000);
mg/kg Found (IS) = (Area/IS Area/Average $RF_{IS}$) × (FV × XV)/(AF × SW × 1000).

TABLE 39

Limes-glyphosate, N-acetylglyphosate, N-acetyl AMPA

TEA base adjustment
Matrix: LIMES
Quantitation Ions: glyphosate: 170 > 87.7, glyphosate IS: 173 > 90.7, N-acetylglyphosate: 212 > 87.9,
N-acetyl AMPA: 154 > 111.9

| | | | Sample Information | SW | XV | AF | FV | glyphosate | | | NA-AMPA | | NA-Gly | |
|---|---|---|---|---|---|---|---|---|---|---|---|---|---|---|
| Run ID | Type | ppb | Identification | g | ml | ml | ml | Area | IS | $RF_{IS}$ | Area | RF | Area | RF |
| 07-0924_Lime_A-4 | S | 0.5 | 0.5 ppb CS 091907 | | | | | 157 | 1457 | 0.2155 | 100 | 200 | 72 | 144 |
| 07-0924_Lime_A-5 | C | | Lime 1 CONTROL 091707 | 5 | 100 | 1 | 2.5 | 42 | 1230 | | | | | |
| 07-0924_Lime_A-6 | C | | Lime 7 CONTROL 092107 | 5 | 100 | 1 | 2.5 | 19 | 1255 | | | | | |
| 07-0924_Lime_A-7 | S | 1 | 1.0 ppb CS 091907 | | | | | 287 | 1410 | 0.2035 | 173 | 173 | 152 | 152 |
| 07-0924_Lime_A-8 | F | 50 | Lime 2 LOQ 091707 | 5 | 100 | 1 | 2.5 | 282 | 1197 | | 152 | | 131 | |
| 07-0924_Lime_A-9 | F | 50 | Lime 3 LOQ 091707 | 5 | 100 | 1 | 2.5 | 275 | 1254 | | 179 | | 154 | |
| 07-0924_Lime_A-10 | S | 2 | 2.0 ppb CS 091907 | | | | | 641 | 1450 | 0.2210 | 348 | 174 | 354 | 177 |
| 07-0924_Lime_A-11 | F | 50 | Lime 8 LOQ 092107 | 5 | 100 | 1 | 2.5 | 286 | 1159 | | 204 | | 132 | |
| 07-0924_Lime_A-12 | F | 50 | Lime 9 LOQ 092107 | 5 | 100 | 1 | 2.5 | 288 | 1272 | | 202 | | 141 | |
| 07-0924_Lime_A-13 | S | 5 | 5.0 ppb CS 091907 | | | | | 1517 | 1501 | 0.2021 | 976 | 195 | 886 | 177 |
| 07-0924_Lime_A-14 | F | 50 | Lime 10 LOQ 092107 | 5 | 100 | 1 | 2.5 | 288 | 1219 | | 172 | | 166 | |
| 07-0924_Lime_A-15 | F | 500 | Lime 4 10x LOQ 091707 | 5 | 100 | 1 | 2.5 | 2554 | 1229 | | 1833 | | 1426 | |
| 07-0924_Lime_A-16 | S | 10 | 10 ppb CS 091907 | | | | | 3324 | 1565 | 0.2124 | 2012 | 201 | 1724 | 172 |
| 07-0924_Lime_A-17 | F | 500 | Lime 5 10x LOQ 091707 | 5 | 100 | 1 | 2.5 | 2508 | 1300 | | 2332 | | 1532 | |
| 07-0924_Lime_A-18 | F | 500 | Lime 6 10x LOQ 091707 | 5 | 100 | 1 | 2.5 | 2633 | 1250 | | 2069 | | 1620 | |
| 07-0924_Lime_A-19 | S | 20 | 20 ppb CS 091907 | | | | | 6286 | 1511 | 0.2080 | 4064 | 203 | 3514 | 176 |
| 07-0924_Lime_A-20 | F | 500 | Lime 11 10x LOQ 092107 | 5 | 100 | 1 | 2.5 | 2779 | 1228 | | 2172 | | 1645 | |
| 07-0924_Lime_A-21 | F | 500 | Lime 12 10x LOQ 092107 | 5 | 100 | 1 | 2.5 | 2517 | 1155 | | 1933 | | 1469 | |
| 07-0924_Lime_A-22 | S | 50 | 50 ppb CS 091907 | | | | | 16228 | 1524 | 0.2130 | 10369 | 207 | 8997 | 180 |
| 07-0924_Lime_A-4 | S | 0.5 | 0.5 ppb CS 091907 | | | | | 157 | 1457 | 0.2155 | 100 | 200 | 72 | 144 |
| 07-0924_Lime_A-7 | S | 1 | 1.0 ppb CS 091907 | | | | | 287 | 1410 | 0.2035 | 173 | 173 | 152 | 152 |
| 07-0924_Lime_A-10 | S | 2 | 2.0 ppb CS 091907 | | | | | 641 | 1450 | 0.2210 | 348 | 174 | 354 | 177 |
| 07-0924_Lime_A-13 | S | 5 | 5.0 ppb CS 091907 | | | | | 1517 | 1501 | 0.2021 | 976 | 195 | 886 | 177 |
| 07-0924_Lime_A-16 | S | 10 | 10 ppb CS 091907 | | | | | 3324 | 1565 | 0.2124 | 2012 | 201 | 1724 | 172 |
| 07-0924_Lime_A-19 | S | 20 | 20 ppb CS 091907 | | | | | 6286 | 1511 | 0.2080 | 4064 | 203 | 3514 | 176 |
| 07-0924_Lime_A-22 | S | 50 | 50 ppb CS 091907 | | | | | 16228 | 1524 | 0.2130 | 10369 | 207 | 8997 | 180 |

| Calibration Standards Statistics | | Slope = | | | | | 3.082E−03 | | | 4.808E−03 | | 5.552E−03 | |
| | | Intercept = | | | | | 1.214E−01 | | | 2.517E−01 | | 1.909E−01 | |
| | | RSQ = | | | | | 0.99975 | | | 0.99993 | | 0.99989 | |
| Quantified by Average Response Factor | | Average RF = | | | 1488 | | 0.2108 | | | 193 | | 168 | |
| | | STDEV = | | | 52 | | 0.0067 | | | 14 | | 14 | |
| | | % RSD = | | | 4% | | 3% | | | 7% | | 8% | |

| | | | Sample Information | SW | XV | AF | FV | Recoveries | | | | | | |
|---|---|---|---|---|---|---|---|---|---|---|---|---|---|---|
| | | mg/ | | | | | | glyphosate | | NA-AMPA | | NA-Gly | | |
| Run ID | Type | kg | Identification | ml | ml | ml | ml | mg/kg | % Rec | mg/kg | % Rec | mg/kg | % Rec | |
| 07-0924_Lime_A-5 | C | 0 | Lime 1 CONTROL 091707 | 5 | 100 | 1 | 2.5 | 0.008 | | nd | | nd | | |
| 07-0924_Lime_A-6 | C | 0 | Lime 7 CONTROL 092107 | 5 | 100 | 1 | 2.5 | 0.004 | | nd | | nd | | |
| 07-0924_Lime_A-8 | F | 0.05 | Lime 2 LOQ 091707 | 5 | 100 | 1 | 2.5 | <u>0.048</u> | 96% | 0.039 | 79% | 0.039 | 78% | |
| 07-0924_Lime_A-9 | F | 0.05 | Lime 3 LOQ 091707 | 5 | 100 | 1 | 2.5 | <u>0.044</u> | 88% | 0.046 | 93% | 0.046 | 91% | |
| 07-0924_Lime_A-11 | F | 0.05 | Lime 8 LOQ 092107 | 5 | 100 | 1 | 2.5 | <u>0.055</u> | 110% | 0.053 | 105% | 0.039 | 78% | |
| 07-0924_Lime_A-12 | F | 0.05 | Lime 9 LOQ 092107 | 5 | 100 | 1 | 2.5 | <u>0.050</u> | 100% | 0.052 | 104% | 0.042 | 84% | |
| 07-0924_Lime_A-14 | F | 0.05 | Lime 10 LOQ 092107 | 5 | 100 | 1 | 2.5 | <u>0.052</u> | 105% | 0.044 | 89% | 0.049 | 99% | |
| 07-0924_Lime_A-15 | F | 0.5 | Lime 4 10x LOQ 091707 | 5 | 100 | 1 | 2.5 | <u>0.485</u> | 97% | 0.474 | 95% | 0.424 | 85% | |

TABLE 39-continued

Limes-glyphosate, N-acetylglyphosate, N-acetyl AMPA

| | | | | | | | | | | | | |
|---|---|---|---|---|---|---|---|---|---|---|---|---|
| 07-0924_Lime_A-17 | F | 0.5 | Lime 5 10x LOQ 091707 | 5 | 100 | 1 | 2.5 | 0.450 | 90% | 0.603 | 121% | 0.455 | 91% |
| 07-0924_Lime_A-18 | F | 0.5 | Lime 6 10x LOQ 091707 | 5 | 100 | 1 | 2.5 | 0.492 | 98% | 0.535 | 107% | 0.481 | 96% |
| 07-0924_Lime_A-20 | F | 0.5 | Lime 11 10x LOQ 092107 | 5 | 100 | 1 | 2.5 | 0.533 | 107% | 0.561 | 112% | 0.489 | 98% |
| 07-0924_Lime_A-21 | F | 0.5 | Lime 12 10x LOQ 092107 | 5 | 100 | 1 | 2.5 | 0.513 | 103% | 0.500 | 100% | 0.436 | 87% |

COMMENTS:

Bold italics: % Rec outside 70-110%,

Underlined: area detected in control subtracted from area detected in sample. Type (B: blank, S: standard, IS: internal standard, C: control sample, F: fortified control sample, T: treated sample, FS: fort standard). SW: sample weight, XV: extract volume, AF: aliquot factor, FV: final volume, $RF_{IS}$: response factor normalized to IS (analyte area/IS area/analyte ppb), RF: response factor (analyte area/analyte ppb).

mg/kg Found = (Area/Average RF) × (FV × XV)/(AF × SW × 1000);

mg/kg Found (IS) = (Area/IS Area/Average $RF_{IS}$) × (FV × XV)/(AF × SW × 1000).

TABLE 40

Limes - AMPA

Matrix: LIMES
Quantitation Ions: AMPA: 111.8 > 30, AMPA IS: 113.8 > 32

| Sample Information | | | | | | | | Analyte Response AMPA | | |
|---|---|---|---|---|---|---|---|---|---|---|
| Run ID | Type | ppb | Identification | SW g | XV ml | AF ml | FV ml | Area | IS | $RF_{IS}$ |
| 07-0924_Lime_C-2 | S | 0.5 | 0.5 ppb CS 091907 | | | | | 37 | 299 | 0.2475 |
| 07-0924_Lime_C-3 | C | | Lime 7 CONTROL 092107 | 5 | 100 | 4 | 5 | | 245 | |
| 07-0924_Lime_C-4 | S | 1 | 1.0 ppb CS 091907 | | | | | 64 | 275 | 0.2327 |
| 07-0924_Lime_C-5 | F | 50 | Lime 8 LOQ 092107 | 5 | 100 | 4 | 5 | 121 | 265 | |
| 07-0924_Lime_C-6 | F | 50 | Lime 9 LOQ 092107 | 5 | 100 | 4 | 5 | 109 | 254 | |
| 07-0924_Lime_C-7 | S | 2 | 2.0 ppb CS 091907 | | | | | 135 | 260 | 0.2596 |
| 07-0924_Lime_C-8 | F | 50 | Lime 10 LOQ 092107 | 5 | 100 | 4 | 5 | 129 | 247 | |
| 07-0924_Lime_C-9 | F | 500 | Lime 11 10x LOQ 092107 | 5 | 100 | 4 | 5 | 1040 | 230 | |
| 07-0924_Lime_C-10 | S | 5 | 5.0 ppb CS 091907 | | | | | 353 | 269 | 0.2625 |
| 07-0924_Lime_C-11 | F | 500 | Lime 12 10x LOQ 092107 | 5 | 100 | 4 | 5 | 1279 | 258 | |
| 07-0924_Lime_C-12 | S | 10 | 10 ppb CS 091907 | | | | | 684 | 258 | 0.2651 |
| 07-0924_Lime_C-13 | S | 20 | 20 ppb CS 091907 | | | | | 1367 | 277 | 0.2468 |
| 07-0924_Lime_C-14 | S | 50 | 50 ppb CS 091907 | | | | | 3385 | 269 | 0.2517 |
| 07-0924_Lime_C-2 | S | 0.5 | 0.5 ppb CS 091907 | | | | | 37 | 299 | 0.2475 |
| 07-0924_Lime_C-4 | S | 1 | 1.0 ppb CS 091907 | | | | | 64 | 275 | 0.2327 |
| 07-0924_Lime_C-7 | S | 2 | 2.0 ppb CS 091907 | | | | | 135 | 260 | 0.2596 |
| 07-0924_Lime_C-10 | S | 5 | 5.0 ppb CS 091907 | | | | | 353 | 269 | 0.2625 |
| 07-0924_Lime_C-12 | S | 10 | 10 ppb CS 091907 | | | | | 684 | 258 | 0.2651 |
| 07-0924_Lime_C-13 | S | 20 | 20 ppb CS 091907 | | | | | 1367 | 277 | 0.2468 |
| 07-0924_Lime_C-14 | S | 50 | 50 ppb CS 091907 | | | | | 3385 | 269 | 0.2517 |

| Calibration Standards Statistics | Slope = | | 1.477E−02 | |
|---|---|---|---|---|
| | Intercept = | | −7.279E−02 | |
| | RSQ = | | 0.99997 | |
| Quantified by Average Response Factor | Average RF = | 272 | 0.2523 | |
| | STDEV = | 14 | 0.0112 | |
| | % RSD = | 5% | 4% | |

| Sample Information | | | | | | | | Recoveries AMPA | |
|---|---|---|---|---|---|---|---|---|---|
| Run ID | Type | mg/kg | Identification | SW ml | XV ml | AF ml | FV ml | mg/kg | % Rec |
| 07-0924_Lime_C-3 | C | 0 | Lime 7 CONTROL 092107 | 5 | 100 | 4 | 5 | nd | |
| 07-0924_Lime_C-5 | F | 0.05 | Lime 8 LOQ 092107 | 5 | 100 | 4 | 5 | 0.045 | 91% |
| 07-0924_Lime_C-6 | F | 0.05 | Lime 9 LOQ 092107 | 5 | 100 | 4 | 5 | 0.043 | 85% |
| 07-0924_Lime_C-8 | F | 0.05 | Lime 10 LOQ 092107 | 5 | 100 | 4 | 5 | 0.052 | 104% |
| 07-0924_Lime_C-9 | F | 0.5 | Lime 11 10x LOQ 092107 | 5 | 100 | 4 | 5 | 0.448 | 90% |
| 07-0924_Lime_C-11 | F | 0.5 | Lime 12 10x LOQ 092107 | 5 | 100 | 4 | 5 | 0.491 | 98% |

COMMENTS:

Bold italics: % Rec outside 70-110%,

Underlined: area detected in control subtracted from area detected in sample.

Type (B: blank, S: standard, IS: internal standard, C: control sample, F: fortified control sample, T: treated sample, FS: fort standard). SW: sample weight, XV: extract volume, AF: aliquot factor, FV: final volume, $RF_{IS}$: response factor normalized to IS (analyte area/IS area/analyte ppb), RF: response factor (analyte area/analyte ppb).

mg/kg Found = (Area/Average RF) × (FV × XV)/(AF × SW × 1000);

mg/kg Found (IS) = (Area/IS Area/Average $RF_{IS}$) × (FV × XV)/(AF × SW × 1000).

Results
Detector Response

Figure 2:
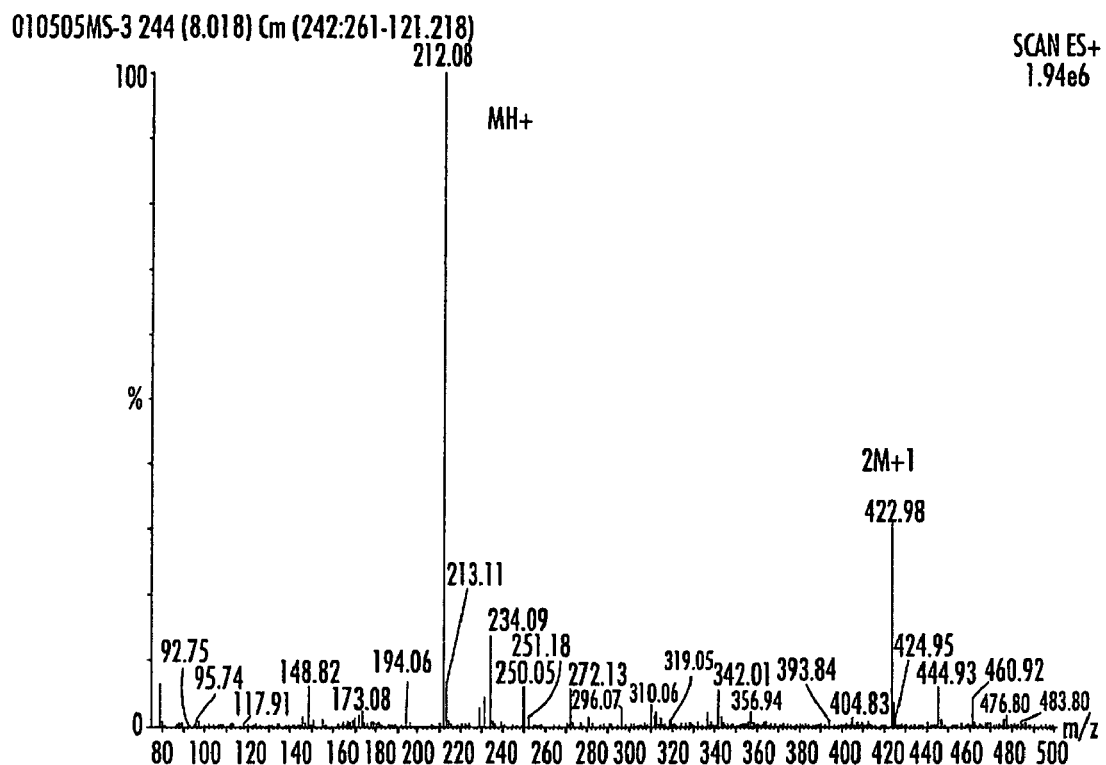
FIG. 2 provides representative N-acetylglyphosate mass spectra.
Figure 2:
Figure 2:
Figure 2:
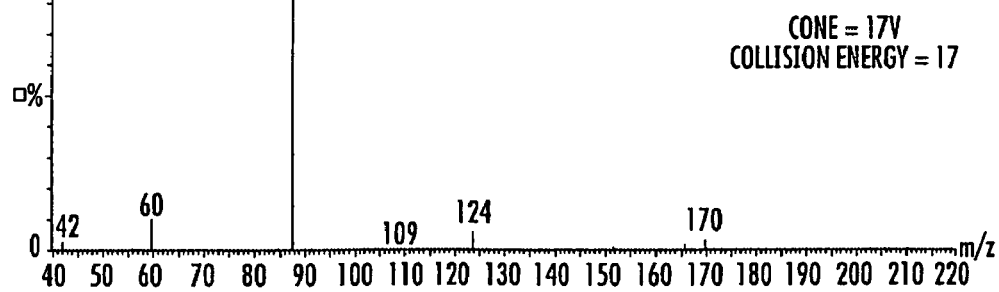
Figure 3:
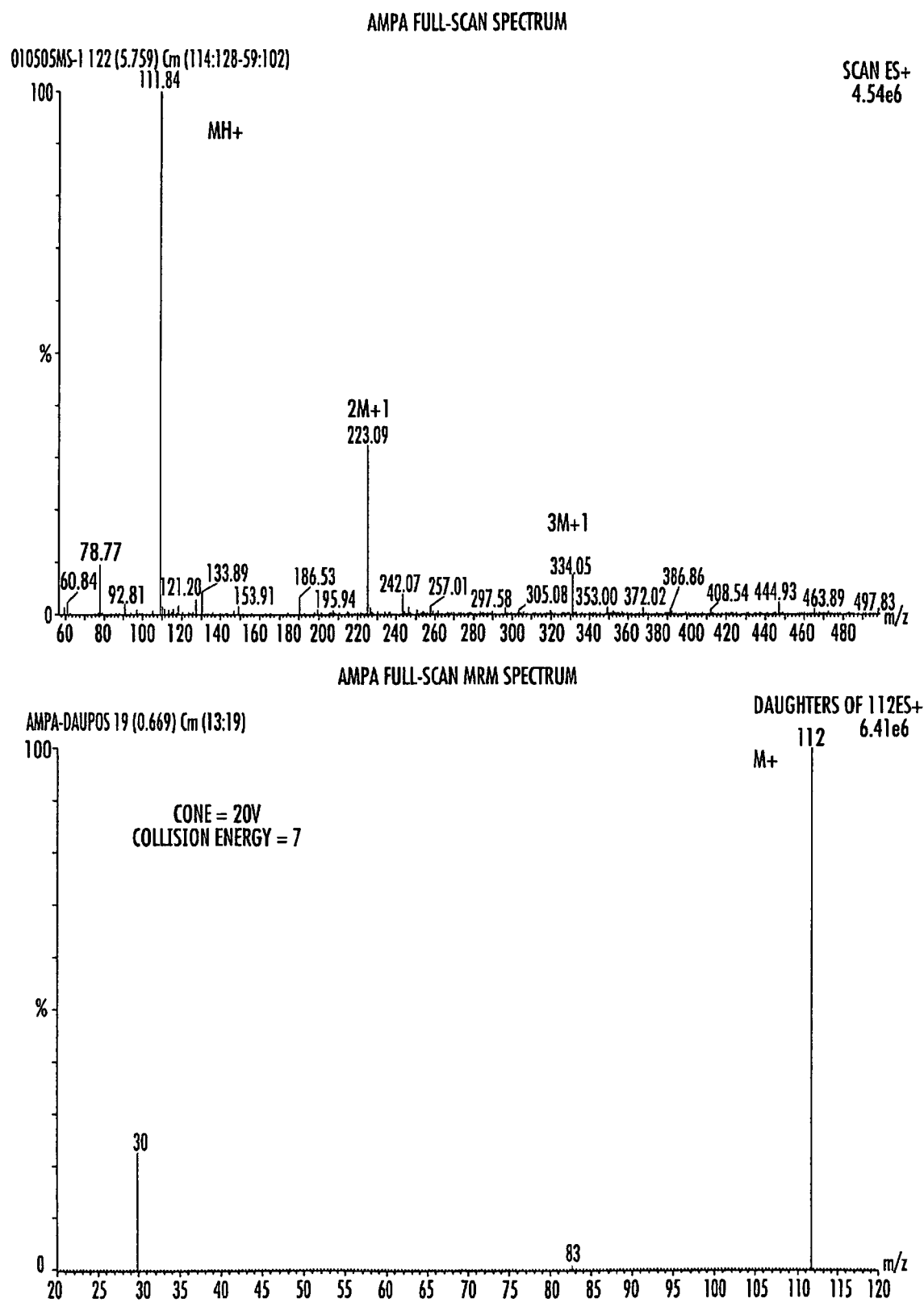
FIG. 3 provides representative AMPA mass spectra.

A triple quadrupole mass spectrometer using positive ion ESI and tandem mass spectrometry detection was used for sample extract analysis. Full-Scan total ion and MRM spectra for glyphosate, N-acetylglyphosate, and AMPA and N-acetyl AMPA from analysis of standard solutions are provided in FIG. 1-FIG. 3, respectively.

Figure 4:
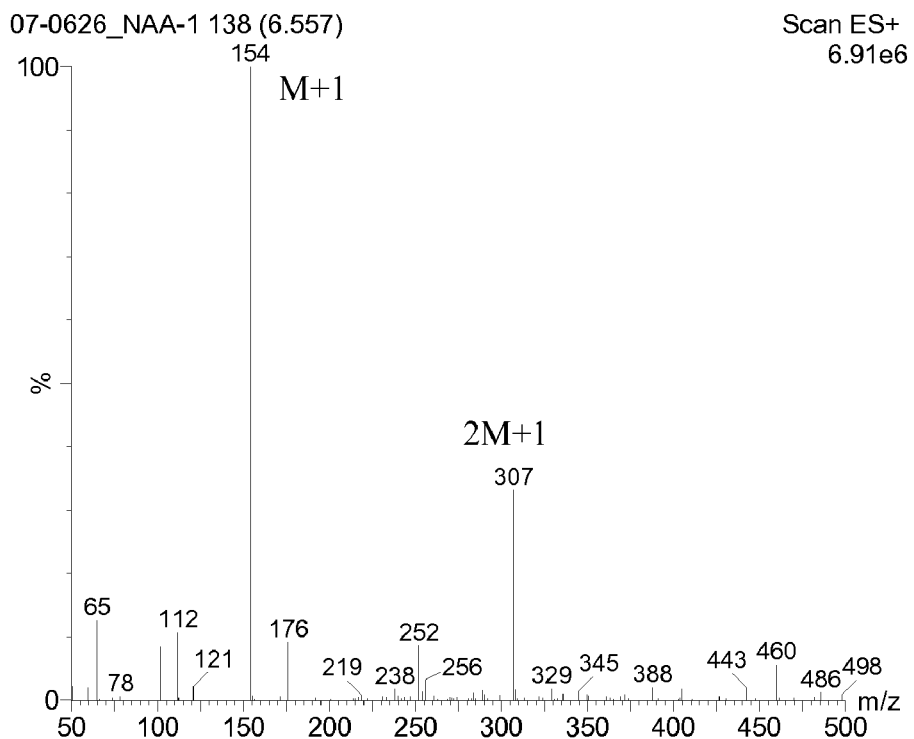
FIG. 4 provides representative N-acetyl AMPA mass spectra.
Figure 4:
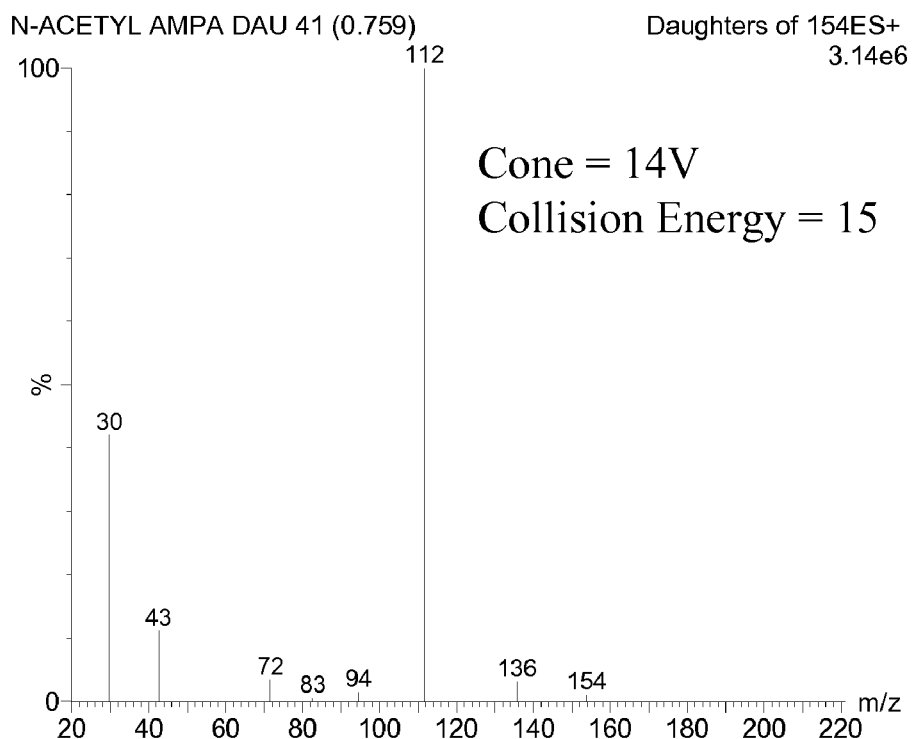
Figure 5:
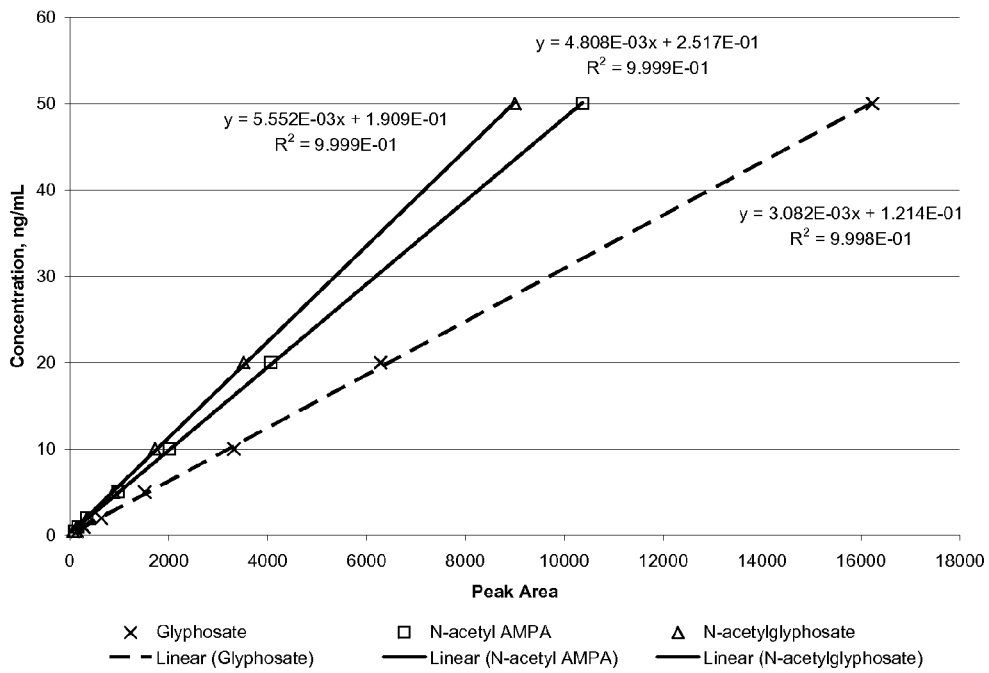
FIG. 5 provides representative calibration curves.
Figure 5:
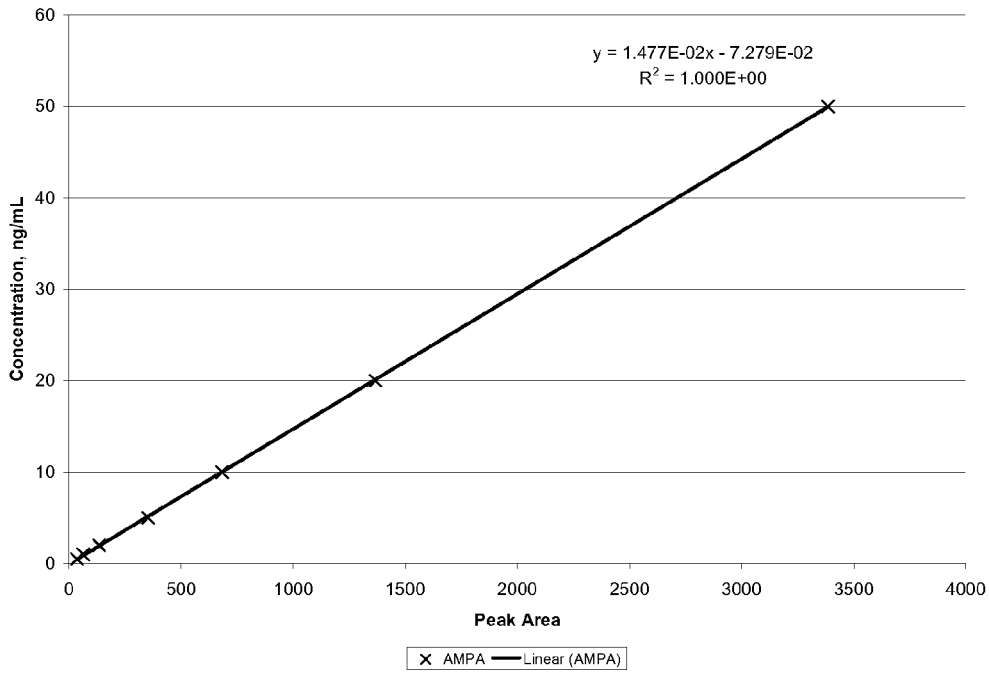
Figure 6A:
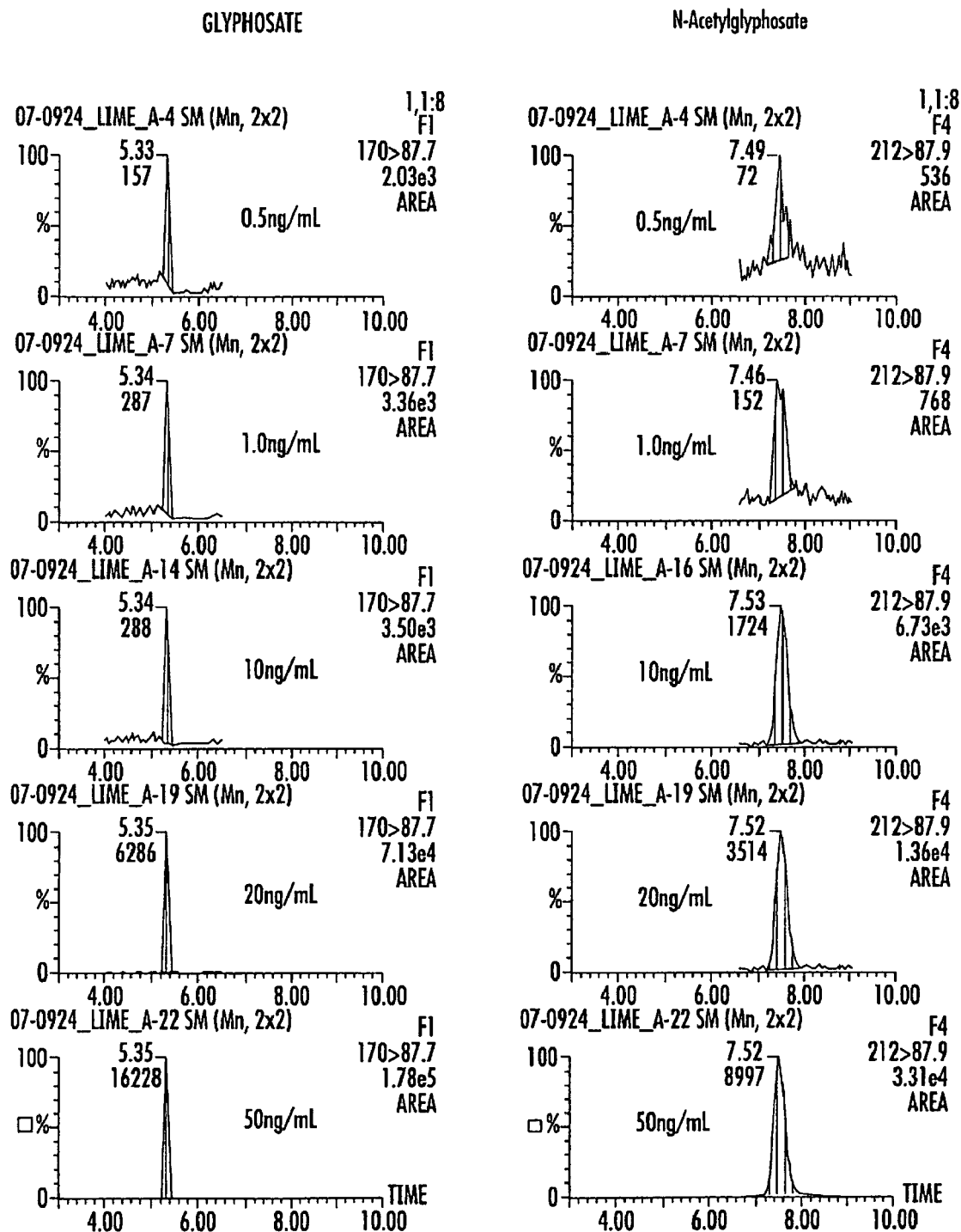
FIGS. 6A and B provides representative calibration standard chromatograms.
Figure 6B:
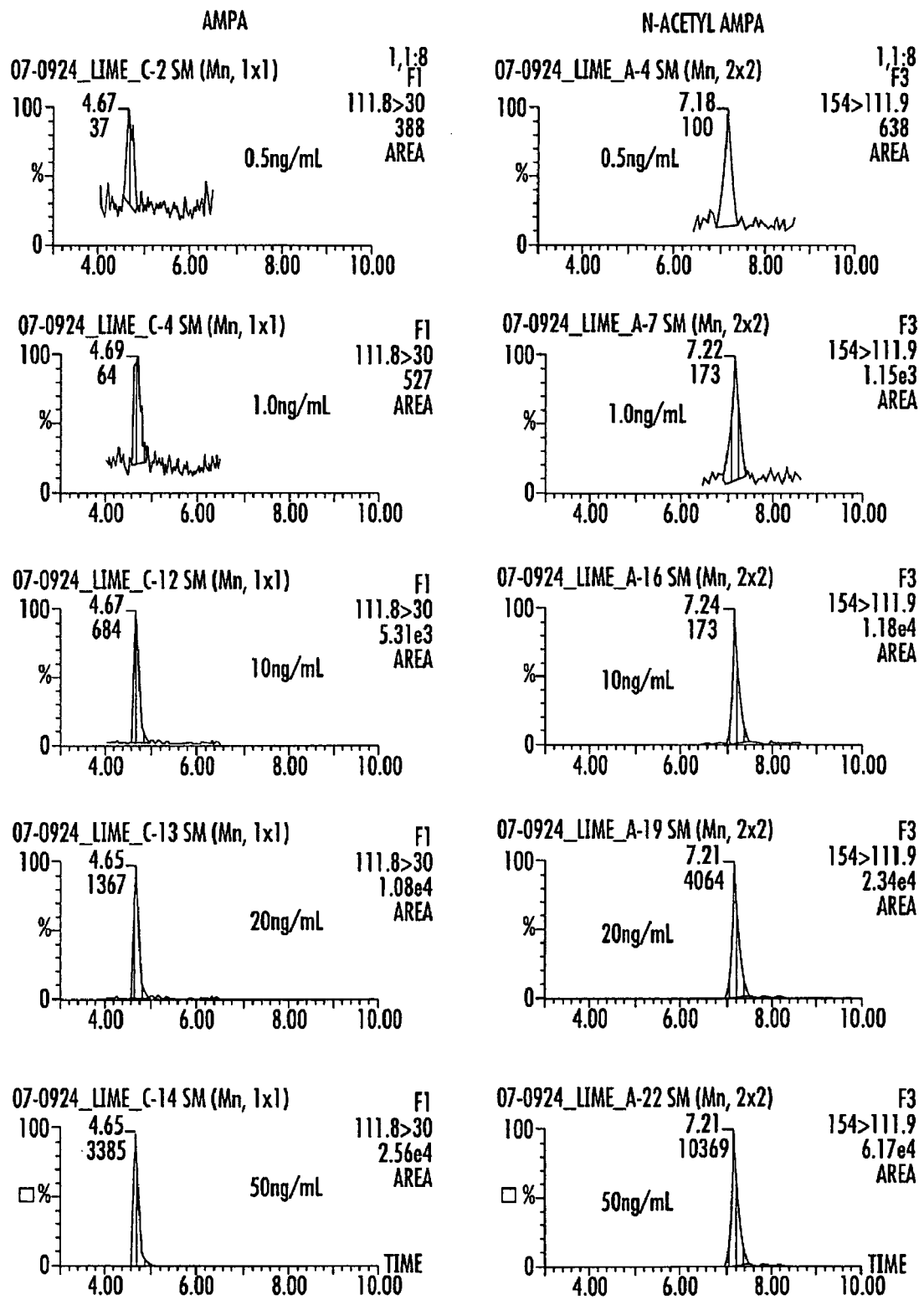
Figure 7:
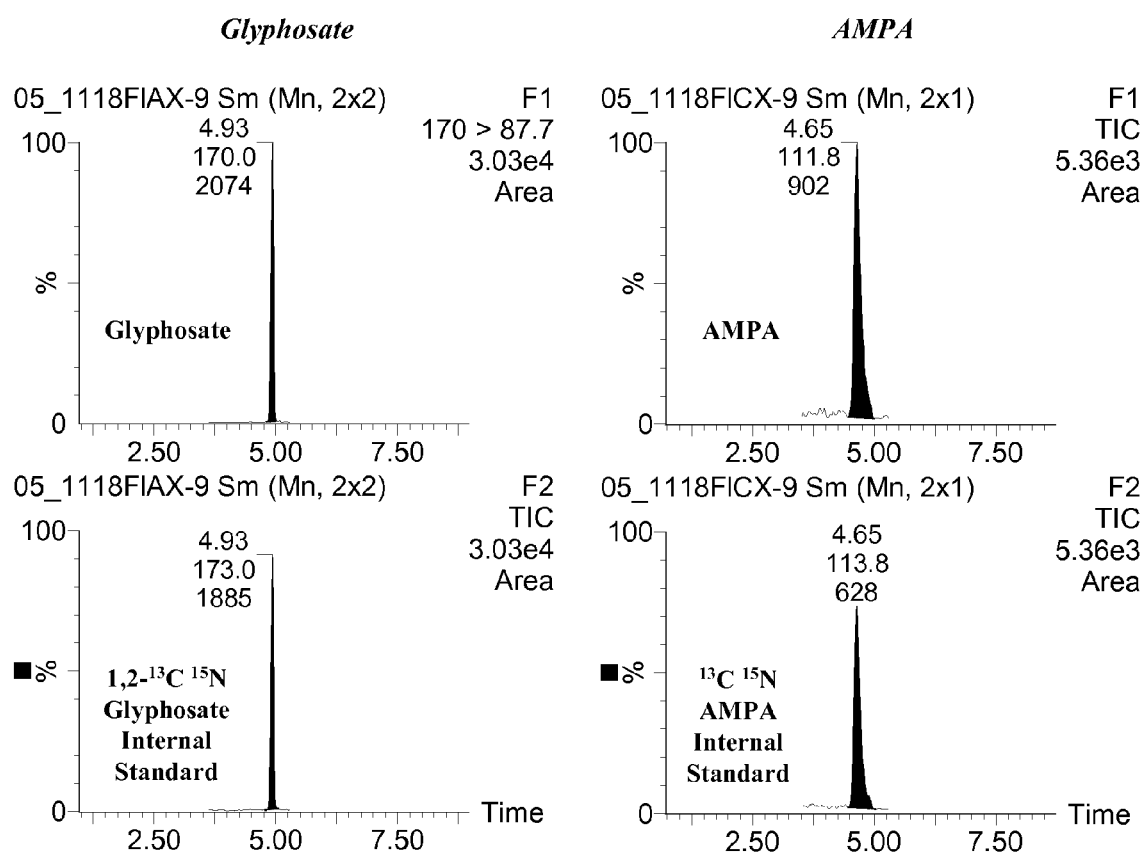
FIG. 7 provides representative 5 ng/ml glyphosate and AMPA chromatograms with stable isotope internal standard. Glyphosate and glyphosate 1,2-$^{13}$C$^{15}$N stable isotope are equivalent at 5 ng/ml and showed consistent peak area responses (2074, 1885). Since AMPA is 5 ng/ml in glyphosate equivalents and AMPA $^{13}$C$^{15}$N is 5 ng/ml, the isotope peak response was consistent with the molar ratio of AMPA/glyphosate (111/169=0.66≈628/902).

Calibration standards typically yielded a linear response ($r^2 > 0.99$) with % RSD<20% for calibration standard response factors (peak area/concentration) over the range of 0.5-20 ng/ml for glyphosate and N-acetylglyphosate or 1.0-50 ng/ml for AMPA. Representative calibration curves for each analyte were constructed using calibration standards from validation sets including expanded range of 0.5-100 ng/ml and are presented in FIG. 4 Representative ion chromatograms of Calibration Standards are provided in FIG. 6. Representative ion chromatograms of stable isotope glyphosate and AMPA standards are provided in FIG. 25.

Representative chromatograms of extracts from an untreated control sample, a 0.050 ppm (LOQ) fortification sample, and a 0.50 ppm fortification sample are provided in FIG. 8-FIG. 21 for corn and soybean matrices.

Controls

No significant matrix interference was observed at the chromatographic retention times of glyphosate, AMPA, or N-acetylglyphosate elution in chromatograms of control extracts for corn and soybean matrices. Because genetically modified plants and glyphosate containing herbicides are widely used in soybean crop grown in the U.S., commercially available samples (including organic) generally contain glyphosate and AMPA residues. Soybean control samples used in this study were untreated controls from field plots in regulatory studies.

Recoveries (Accuracy & Precision)

Recovery results for corn matrices are provided in Tables 1-Table 8 (forage, grain, stover, oil, flour, grits, starch, and meal, respectively). Recovery results for soybean matrices are provided in Table 9-Table 14 (forage, seed, hay, oil, meal, and hulls, respectively). The average results at the 0.050 mg/kg (LOQ) and 0.50 mg/kg fortification levels with overall results in corn and soybean matrices are provided in tables in the Summary section. Representative recovery results from individual sample set analyses for corn grain, corn oil, soybean seed, and soybean meal are provided in Tables 30-40.

TABLE 1

Corn Forage Validation Results

| Matrix | Fort Level (ppm) | Sample ID | Glyphosate % Rec | N-acetyl-glyphosate % Rec | |
|---|---|---|---|---|---|
| Corn Forage | 0.050 | Forage LOQ1 11-8 | 100% | 92% | |
| | 0.050 | Forage LOQ2 11-8 | 87% | 93% | |
| | 0.050 | Forage LOQ3 11-8 | 95% | 97% | |
| | 0.50 | Forage 10X 1 11-8 | 100% | 89% | |
| | 0.50 | Forage 10X 2 11-8 | 83% | 92% | |
| | 0.050 | Forage LOQ1 11-11 | 92% | 82% | * |
| | 0.050 | Forage LOQ2 11-11 | 95% | 84% | * |
| | 0.50 | Forage 10X 1 11-11 | 85% | 82% | * |
| | 0.50 | Forage 10X 2 11-11 | 90% | 83% | * |
| | 0.50 | Forage 10X 3 11-11 | 88% | 78% | * |
| | 0.050 | Forage L1 0408 | 74% | 93% | |
| | 0.050 | Forage L2 0408 | 74% | 95% | |
| | 0.050 | Forage L3 0408 | 72% | 93% | |
| | 0.50 | Forage 10X1 0408 | 66% | 71% | |
| | 0.50 | Forage 10X2 0408 | 69% | 91% | |
| | 0.050 | Forage LOQ 070105-1 | 79% | 87% | |

TABLE 1-continued

Corn Forage Validation Results

| | Fort Level (ppm) | Sample ID | Glyphosate % Rec | N-acetyl-glyphosate % Rec |
|---|---|---|---|---|
| | 0.050 | Forage LOQ 070105-2 | 73% | 75% |
| | 0.050 | Forage LOQ 070105-3 | 82% | 93% |
| | 0.050 | Forage LOQ 070105-4 | 77% | 95% |
| | 0.050 | Forage LOQ 070105-5 | 83% | 95% |
| | 0.50 | Forage 10X 0670105-1 | 73% | 83% |
| | 0.50 | Forage 10X 0670105-2 | 75% | 96% |
| | 0.50 | Forage 10X 0670105-3 | 75% | 91% |
| | 0.50 | Forage 10X 0670105-4 | 78% | 90% |
| | 0.50 | Forage 10X 0670105-5 | 76% | 89% |
| Recovery Statistics | 0.050 | Average | 83% | 90% |
| | | Stdev | 10% | 6% |
| | | RSD | 11% | 7% |
| | | n | 13 | 13 |
| | | min | 72% | 75% |
| | | max | 100% | 97% |
| | 0.50 | Average | 80% | 86% |
| | | Stdev | 10% | 7% |
| | | RSD | 12% | 8% |
| | | n | 12 | 12 |
| | | min | 66% | 71% |
| | | max | 100% | 96% |

* Average results from multiple analyses.

| Matrix | Fort Level (ppm) | Sample ID | AMPA % Rec |
|---|---|---|---|
| Corn Forage | 0.050 | Forage-LOQ-1 AMPA | 89% |
| | 0.050 | Forage-LOQ-2 AMPA | 94% |
| | 0.050 | Forage-LOQ-3 AMPA | 93% |
| | 0.050 | Forage-LOQ-4 AMPA | 88% |
| | 0.050 | Forage-LOQ-5 AMPA | 87% |
| | 0.50 | Forage-10X1 AMPA | 98% |
| | 0.50 | Forage-10X2 AMPA | 93% |
| | 0.50 | Forage-10X3 AMPA | 83% |
| | 0.50 | Forage-10X4 AMPA | 85% |
| | 0.50 | Forage-10X5 AMPA | 87% |
| | 0.050 | Forage LOQ 070105-1 | 96% |
| | 0.050 | Forage LOQ 070105-2 | 117% |
| | 0.050 | Forage LOQ 070105-3 | 100% |
| | 0.050 | Forage LOQ 070105-4 | 102% |
| | 0.050 | Forage LOQ 070105-5 | 109% |
| | 0.50 | Forage 10X 070105-1 | 93% |
| | 0.50 | Forage 10X 070105-2 | 92% |
| | 0.50 | Forage 10X 070105-3 | 90% |
| | 0.50 | Forage 10X 070105-4 | 93% |
| | 0.50 | Forage 10X 070105-5 | 94% |
| Recovery Statistics | 0.050 | Average | 98% |
| | | Stdev | 10% |
| | | RSD | 10% |
| | | n | 10 |
| | | min | 87% |
| | | max | 117% |
| | 0.50 | Average | 91% |
| | | Stdev | 4% |
| | | RSD | 5% |
| | | n | 10 |
| | | min | 83% |
| | | max | 98% |

| Matrix | Fort Level | Data Source | Recovery (%) N-acetyl AMPA |
|---|---|---|---|
| Corn Forage | 0.050 | | 84 |
| | 0.050 | | 90 |
| | 0.500 | | 73 |
| | 0.500 | | 91 |
| | 0.050 | | 93 |
| | 0.050 | | 114 |
| | 5.000 | | 91 |
| | 5.000 | | 99 |
| | 5.000 | | 83 |
| | 0.050 | | 94 |
| | 5.000 | | 92 |
| | 0.050 | | 122 |
| | 0.050 | | 93 |
| | 0.050 | | 69 |
| | 5.000 | | 88 |
| | 5.000 | | 102 |

TABLE 1-continued

Corn Forage Validation Results

|  |  |  |  |
|---|---|---|---|
|  | 5.000 |  | 112 |
|  | 0.050 |  | 83 |
|  | 5.000 |  | 87 |
|  | 0.050 |  | 83 |
|  | 5.000 |  | 93 |
|  | 0.050 |  | 80 |
|  | 5.000 |  | 83 |
|  | 0.050 |  | 87 |
|  | 0.050 |  | 78 |
|  | 0.050 |  | 87 |
|  | 5.000 |  | 99 |
|  | 5.000 |  | 86 |
|  | 5.000 |  | 81 |
|  | 0.050 |  | 90 |
|  | 5.000 |  | 95 |
|  | 0.050 |  | 78 |
|  | 5.000 |  | 95 |
|  | 0.050 |  | 81 |
|  | 0.050 |  | 87 |
|  | 0.050 |  | 82 |
|  | 5.000 |  | 101 |
|  | 5.000 |  | 72 |
|  | 5.000 |  | 86 |
|  | 0.050 |  | 69 |
|  | 5.000 |  | 86 |
|  | 0.050 |  | 70 |
|  | 0.050 |  | 90 |
|  | 5.000 |  | 81 |
|  | 5.000 |  | 92 |
| Recovery Statistics | 0.050 | AVERAGE | 87 |
|  |  | STDEV | 13 |
|  |  | % RSD | 15 |
|  |  | COUNT | 22 |
|  |  | MIN | 69 |
|  |  | MAX | 122 |
|  | 0.500 | Avg | 82 |
|  |  | n | 2 |
|  |  | min | 73 |
|  |  | max | 91 |
|  | 5.000 | Avg | 91 |
|  |  | StDev | 9 |
|  |  | % RSD | 10 |
|  |  | n | 21 |
|  |  | min | 72 |
|  |  | max | 112 |

TABLE 2

CORN GRAIN VALIDATION RESULTS

| Matrix | Fort Level (ppm) | Sample ID | Glyphosate % Rec | N-acetyl-glyphosate % Rec |  |
|---|---|---|---|---|---|
| Corn Grain | 0.050 | Grain LOQ1 11-5 | 88% | 85% |  |
|  | 0.050 | Grain LOQ2 11-5 | 78% | 83% |  |
|  | 0.050 | Grain LOQ3 11-5 | 95% | 84% |  |
|  | 0.050 | Grain LOQ1 11-8 | 0.77 | 83% | * |
|  | 0.050 | Grain LOQ2 11-8 | 0.73 | 91% | * |
|  | 0.50 | Grain 10X 1 11-5 | 80% | 83% |  |
|  | 0.50 | Grain 10X 2 11-5 | 90% | 83% |  |
|  | 0.50 | Grain 10X 1 11-8 | 87% | 86% |  |
|  | 0.50 | Grain 10X 2 11-8 | 97% | 84% |  |
|  | 0.50 | Grain 10X 3 11-8 | 97% | 86% |  |
|  | 0.050 | Grain L1 040805 | 74% | 92% | * |
|  | 0.050 | Grain L2 040805 | 71% | 93% | * |
|  | 0.50 | Grain 10X1 040805 | 72% | 91% | * |
|  | 0.50 | Grain 10X2 040805 | 73% | 92% | * |
|  | 0.050 | Grain LOQ 062905-1 | 77% | 78% |  |
|  | 0.050 | Grain LOQ 062905-2 | 75% | 95% |  |
|  | 0.050 | Grain LOQ 062905-3 | 73% | 82% |  |
|  | 0.050 | Grain LOQ 062905-4 | 75% | 98% |  |
|  | 0.050 | Grain LOQ 062905-5 | 71% | 81% |  |
|  | 0.50 | Grain 10X 062905-1 | 74% | 98% |  |
|  | 0.50 | Grain 10X 062905-2 | 72% | 91% |  |
|  | 0.50 | Grain 10X 062905-3 | 71% | 90% |  |
|  | 0.50 | Grain 10X 062905-4 | 70% | 94% |  |
|  | 0.50 | Grain 10X 062905-5 | 70% | 91% |  |
| Recovery Statistics | 0.050 | Average | 77% | 87% |  |
|  |  | Stdev | 7% | 6% |  |
|  |  | RSD | 9% | 7% |  |
|  |  | n | 12 | 12 |  |
|  |  | min | 71% | 78% |  |
|  |  | max | 95% | 98% |  |
|  | 0.50 | Average | 79% | 89% |  |
|  |  | Stdev | 10% | 5% |  |
|  |  | RSD | 13% | 5% |  |
|  |  | n | 12 | 12 |  |
|  |  | min | 70% | 83% |  |
|  |  | max | 97% | 98% |  |

* Average results from multiple analyses

| Matrix | Fort Level (ppm) | Sample ID | AMPA % Rec |
|---|---|---|---|
| Corn Grain | 0.050 | Grain L1 0214 | 97% |
|  | 0.050 | Grain L2 0214 | 109% |
|  | 0.050 | Grain L3 0214 | 104% |
|  | 0.50 | Grain 10X1 0214 | 85% |
|  | 0.50 | Grain 10X2 0214 | 83% |
|  | 0.050 | Grain-LOQ-1 AMPA | 106% |
|  | 0.050 | Grain-LOQ-2 AMPA | 115% |
|  | 0.050 | Grain-LOQ-4 AMPA | 129% |
|  | 0.050 | Grain-LOQ-5 AMPA | 105% |
|  | 0.50 | Grain-10X1 AMPA | 89% |
|  | 0.50 | Grain-10X2 AMPA | 93% |
|  | 0.50 | Grain-10X3 AMPA | 103% |
|  | 0.50 | Grain-10X4 AMPA | 102% |
|  | 0.50 | Grain-10X5 AMPA | 102% |
|  | 0.050 | Grain-LOQ052905-1 AMPA | 113% |
|  | 0.050 | Grain-LOQ052905-2 AMPA | 102% |
|  | 0.050 | Grain-LOQ052905-3 AMPA | 103% |
|  | 0.050 | Grain-LOQ052905-4 AMPA | 120% |
|  | 0.050 | Grain-LOQ052905-5 AMPA | 107% |
|  | 0.50 | Grain-10X052905-1 AMPA | 102% |
|  | 0.50 | Grain-10X052905-2 AMPA | 101% |
|  | 0.50 | Grain-10X052905-3 AMPA | 101% |
|  | 0.50 | Grain-10X052905-4 AMPA | 106% |
|  | 0.50 | Grain-10X052905-5 AMPA | 95% |
| Recovery Statistics | 0.050 | Average | 109% |
|  |  | Stdev | 9% |
|  |  | RSD | 8% |
|  |  | n | 12 |
|  |  | min | 97% |
|  |  | max | 129% |
|  | 0.50 | Average | 97% |
|  |  | Stdev | 8% |
|  |  | RSD | 8% |
|  |  | n | 12 |
|  |  | min | 83% |
|  |  | max | 106% |

| Matrix | Fort Level | Data Source | Recovery (%) N-acetyl AMPA |
|---|---|---|---|
| Corn Grain | 0.050 |  | 89 |
|  | 0.050 |  | 92 |
|  | 0.500 |  | 98 |
|  | 0.500 |  | 95 |
|  | 0.050 |  | 77 |
|  | 0.050 |  | 74 |
|  | 0.500 |  | 80 |
|  | 0.050 |  | 100 |
|  | 0.500 |  | 80 |
|  | 0.050 |  | 75 |
|  | 0.500 |  | 79 |
|  | 0.050 |  | 79 |
|  | 0.500 |  | 81 |
|  | 0.050 |  | 89 |
|  | 0.500 |  | 88 |
|  | 0.050 |  | 91 |
|  | 0.500 |  | 85 |
|  | 0.050 |  | 90 |

TABLE 2-continued

CORN GRAIN VALIDATION RESULTS

| | | | |
|---|---|---|---|
| | 0.500 | | 82 |
| | 0.050 | | 91 |
| | 0.500 | | 97 |
| | 0.050 | | 94 |
| | 0.500 | | 84 |
| | 0.050 | | 86 |
| | 0.500 | | 77 |
| Recovery Statistics | 0.050 | AVERAGE | 87 |
| | | STDEV | 8 |
| | | % RSD | 9 |
| | | COUNT | 13 |
| | | MIN | 74 |
| | | MAX | 100 |
| | 0.500 | AVERAGE | 85 |
| | | StDev | 7 |
| | | % RSD | 9 |
| | | COUNT | 12 |
| | | MIN | 77 |
| | | MAX | 98 |

TABLE 3

CORN STOVER VALIDATION RESULTS

| Matrix | Fort Level (ppm) | Sample ID | Glyphosate % Rec | N-acetyl-glyphosate % Rec |
|---|---|---|---|---|
| Corn Stover | 0.050 | LOQ-1 Stover 2-11 | 74% | 92% |
| | 0.050 | LOQ-2 Stover 2-11 | 86% | 89% |
| | 0.050 | LOQ-3 Stover 2-11 | 78% | 94% |
| | 0.050 | LOQ-4 Stover 3-7 | 73% | 86% |
| | 0.050 | LOQ-5 Stover 3-7 | 91% | 92% |
| | 0.50 | 10X-1 Stover 2-11 | 79% | 92% |
| | 0.50 | 10X-2 Stover 2-11 | 84% | 84% |
| | 0.50 | 10X-3 Stover 3-7 | 88% | 91% |
| | 0.50 | 10X-4 Stover | 87% | 87% |
| | 0.50 | 10X-5 Stover 3-7 | 84% | 102% |
| | 0.050 | Stover LOQ 063005-1 | 90% | 81% |
| | 0.050 | Stover LOQ 063005-2 | 78% | 90% |
| | 0.050 | Stover LOQ 063005-3 | 77% | 92% |
| | 0.050 | Stover LOQ 063005-4 | 87% | 96% |
| | 0.050 | Stover LOQ 063005-5 | 83% | 97% |
| | 0.50 | Stover 10X 063005-1 | 79% | 89% |
| | 0.50 | Stover 10X 063005-2 | 81% | 90% |
| | 0.50 | Stover 10X 063005-3 | 84% | 91% |
| | 0.50 | Stover 10X 063005-4 | 83% | 90% |
| | 0.50 | Stover 10X 063005-5 | 76% | 87% |
| Recovery Statistics | 0.050 | Average | 82% | 91% |
| | | Stdev | 7% | 5% |
| | | RSD | 8% | 5% |
| | | n | 10 | 10 |
| | | min | 73% | 81% |
| | | max | 91% | 97% |
| | 0.50 | Average | 83% | 90% |
| | | Stdev | 4% | 5% |
| | | RSD | 4% | 5% |
| | | n | 10 | 10 |
| | | min | 76% | 84% |
| | | max | 88% | 102% | nd: not detected

| Matrix | Fort Level (ppm) | Sample ID | AMPA % Rec |
|---|---|---|---|
| Corn Stover | 0.050 | Stover-LOQ-1 AMPA | 96% |
| | 0.050 | Stover-LOQ-2 AMPA | 102% |
| | 0.050 | Stover-LOQ-3 AMPA | 106% |
| | 0.050 | Stover-LOQ-4 AMPA | 86% |
| | 0.050 | Stover-LOQ-5 AMPA | 94% |
| | 0.50 | Stover-10X1 AMPA | 97% |
| | 0.50 | Stover-10X2 AMPA | 96% |
| | 0.50 | Stover-10X3 AMPA | 83% |
| | 0.50 | Stover-10X4 AMPA | 76% |
| | 0.50 | Stover-10X5 AMPA | 76% |

TABLE 3-continued

CORN STOVER VALIDATION RESULTS

| | | | |
|---|---|---|---|
| | 0.050 | Stover LOQ 063005-1 | 93% |
| | 0.050 | Stover LOQ 063005-2 | 97% |
| | 0.050 | Stover LOQ 063005-3 | 103% |
| | 0.050 | Stover LOQ 063005-4 | 99% |
| | 0.050 | Stover LOQ 063005-5 | 95% |
| | 0.50 | Stover 10X 063005-1 | 90% |
| | 0.50 | Stover 10X 063005-2 | 92% |
| | 0.50 | Stover 10X 063005-3 | 99% |
| | 0.50 | Stover 10X 063005-4 | 100% |
| | 0.50 | Stover 10X 063005-5 | 92% |
| Recovery Statistics | 0.050 | Average | 97% |
| | | Stdev | 6% |
| | | RSD | 6% |
| | | n | 10 |
| | | min | 86% |
| | | max | 106% |
| | 0.50 | Average | 90% |
| | | Stdev | 9% |
| | | RSD | 10% |
| | | n | 10 |
| | | min | 76% |
| | | max | 100% |

| Matrix | Fort Level | Data Source | Recovery (%) N-acetyl AMPA |
|---|---|---|---|
| Corn Stover | 0.05 | | 98 |
| | 0.05 | | 86 |
| | 0.50 | | 89 |
| | 0.50 | | 85 |
| | 0.05 | | 87 |
| | 10 | | 95 |
| | 0.05 | | 85 |
| | 0.05 | | 88 |
| | 0.05 | | 96 |
| | 10 | | 88 |
| | 10 | | 85 |
| | 10 | | 94 |
| | 0.05 | | 80 |
| | 0.05 | | 89 |
| | 0.05 | | 82 |
| | 10 | | 91 |
| | 10 | | 94 |
| | 0.05 | | 82 |
| | 10 | | 81 |
| | 0.05 | | 66 |
| | 10 | | 85 |
| | 0.05 | | 75 |
| | 10 | | 95 |
| | 0.05 | | 84 |
| | 10 | | 97 |
| | 0.05 | | 74 |
| | 0.05 | | 87 |
| | 0.05 | | 80 |
| | 10 | | 92 |
| | 10 | | 89 |
| | 0.05 | | 87 |
| | 0.05 | | 89 |
| | 10 | | 93 |
| | 0.05 | | 82 |
| | 0.05 | | 68 |
| | 10 | | 89 |
| | 0.05 | | 85 |
| | 10 | | 97 |
| | 0.05 | | 76 |
| | 0.05 | | 88 |
| | 0.05 | | 84 |
| | 10 | | 75 |
| | 10 | | 92 |
| Recovery Statistics | 0.050 | AVERAGE | 83 |
| | | STDEV | 8 |
| | | % RSD | 9 |
| | | COUNT | 24 |
| | | MIN | 66 |
| | | MAX | 98 |
| | 0.50 | Avg | 87 |
| | | min | 85 |
| | | max | 89 |

TABLE 3-continued

CORN STOVER VALIDATION RESULTS

| | | |
|---|---|---|
| 10.0 | Avg | 90 |
| | StDev | 6 |
| | % RSD | 7 |
| | n | 17 |
| | min | 75 |
| | max | 97 |

TABLE 4

CORN OIL VALIDATION RESULTS

| Matrix | Fort Level (mg/kg) | Sample ID | Glyphosate % Rec | N-acetyl glyphosate % Rec | AMPA % Rec |
|---|---|---|---|---|---|
| Corn Oil | 0.050 | Dry Oil LOQ 1 0718 | 93% | 101% | 85% |
| | 0.050 | Dry Oil LOQ 2 0718 | 100% | 100% | 109% |
| | 0.050 | Dry Oil LOQ 3 0719 | 102% | 100% | 107% |
| | 0.050 | Dry Oil LOQ 4 0719 | 99% | 99% | 130% |
| | 0.050 | Dry Oil LOQ 5 0719 | 98% | 93% | 94% |
| | 0.050 | Wet Oil LOQ 1 0718 | 96% | 100% | 87% |
| | 0.050 | Wet Oil LOQ 2 0718 | 98% | 99% | 126% |
| | 0.050 | Wet Oil LOQ 3 0718 | 98% | 98% | 84% |
| | 0.050 | Wet Oil LOQ 4 0719 | 106% | 97% | 120% |
| | 0.050 | Wet Oil LOQ 5 0719 | 103% | 99% | 77% |
| | 0.50 | Dry Oil 10x 1 0718 | 96% | 103% | 92% |
| | 0.50 | Dry Oil 10X 2 0718 | 103% | 102% | 99% |
| | 0.50 | Dry Oil 10X 3 0718 | 95% | 98% | 93% |
| | 0.50 | Dry Oil 10X 4 0719 | 103% | 101% | 91% |
| | 0.50 | Dry Oil 10X 5 0719 | 101% | 98% | 88% |
| | 0.50 | Wet Oil 10X 1 0718 | 99% | 99% | 87% |
| | 0.50 | Wet Oil 10X 2 0718 | 107% | 102% | 92% |
| | 0.50 | Wet Oil 10X 3 0719 | 97% | 91% | 77% |
| | 0.50 | Wet Oil 10X 4 0719 | 104% | 102% | 90% |
| | 0.50 | Wet Oil 10X 5 0719 | 107% | 102% | 98% |
| Statistical Analysis | 0.050 ppm | Average | 99% | 99% | 102% |
| | | St Dev | 4% | 2% | 19% |
| | | % RSD | 4% | 2% | 19% |
| | | n | 10 | 10 | 10 |
| | | min | 93% | 93% | 77% |
| | | max | 106% | 101% | 130% |
| | 0.50 ppm | Average | 101% | 100% | 90% |
| | | St Dev | 4% | 4% | 6% |
| | | % RSD | 4% | 4% | 7% |
| | | n | 10 | 10 | 10 |
| | | min | 95% | 91% | 77% |
| | | max | 107% | 103% | 99% |

| Matrix | Fort Level | Data Source | Recovery (%) N-acetyl AMPA |
|---|---|---|---|
| Corn Oil | 0.05 | | 101 |
| | 0.05 | | 109 |
| | 0.5 | | 97 |
| | 0.5 | | 100 |
| Soybean Oil | 0.05 | | 108 |
| | 0.05 | | 96 |
| | 0.5 | | 100 |
| | 0.5 | | 105 |
| | 0.05 | | 97 |
| | 0.05 | | 97 |
| | 0.5 | | 99 |
| | 0.5 | | 104 |
| Recovery Statistics | 0.05 | AVERAGE | 101 |
| | | St Dev | 6 |
| | | % RSD | 6 |
| | | COUNT | 6 |
| | | MIN | 96 |
| | | MAX | 109 |
| | 0.5 | AVERAGE | 101 |
| | | StDev | 3 |
| | | % RSD | 3 |
| | | COUNT | 6 |
| | | MIN | 97 |
| | | MAX | 105 |

Corn and Soybean Oil validation recoveries combined for N-acetyl AMPA

TABLE 5

CORN FLOUR VALIDATION RESULTS

| Matrix | Fort Level (mg/kg) | Sample ID | Glyphosate % Rec | N-acetylglyphosate % Rec | AMPA % Rec |
|---|---|---|---|---|---|
| Corn Flour | 0.050 | Fl-111705-2 LOQ 1 | 86% | 80% | 86% |
| | 0.050 | Fl-111705-3 LOQ 2 | 101% | 82% | 86% |
| | 0.050 | Fl-111705-4 LOQ 3 | 83% | 81% | 74% |
| | 0.50 | Fl-111705-5 10X 1 | 93% | 78% | 76% |
| | 0.50 | Fl-111705-6 10X 2 | 90% | 72% | 77% |
| | 0.050 | Flour-113005-2 LOQ 1 | 87% | 89% | 89% |
| | 0.050 | Flour-113005-3 LOQ 2 | 100% | 95% | 100% |
| | 0.50 | Flour-113005-4 10X 1 | 72% | 86% | 71% |
| | 0.50 | Flour-113005-5 10X 2 | 69% | 91% | 81% |
| | 0.50 | Flour-113005-6 10X 3 | 73% | 85% | 77% |
| Recovery Statistics | 0.050 | Avg | 91% | 85% | 87% |
| | | St Dev | 8% | 7% | 9% |
| | | % RSD | 9% | 8% | 10% |
| | | n | 5 | 5 | 5 |
| | | min | 83% | 80% | 74% |
| | | max | 101% | 95% | 100% |
| | 0.50 | Avg | 79% | 83% | 76% |
| | | St Dev | 12% | 7% | 4% |
| | | % RSD | 15% | 9% | 5% |
| | | n | 5 | 5 | 5 |
| | | min | 69% | 72% | 71% |
| | | max | 93% | 91% | 81% |

Glyphosate and AMPA stable isotopes used as internal standards.

TABLE 6

CORN GRITS VALIDATION RESULTS

| Matrix | Fort Level (mg/kg) | Sample ID | Glyphosate % Rec | N-acetylglyphosate % Rec | AMPA % Rec |
|---|---|---|---|---|---|
| Corn Grits | 0.050 | Grit-120205-2 LOQ 1 | 82% | 79% | 87% |
| | 0.050 | Grit-120205-3 LOQ 2 | 93% | 79% | 90% |
| | 0.050 | Grit-120205-4 LOQ 3 | 88% | 83% | 89% |
| | 0.50 | Grit-120205-5 10X 1 | 81% | 88% | 82% |
| | 0.50 | Grit-120205-6 10X 2 | 79% | 75% | 78% |
| | 0.050 | Grit-120605-2 LOQ 1 | 80% | 81% | 87% |
| | 0.050 | Grit-120605-3 LOQ 2 | 88% | 81% | 94% |
| | 0.50 | Grit-120605-4 10X 1 | 74% | 78% | 79% |
| | 0.50 | Grit-120605-5 10X 2 | 99% | 106% | 83% |
| | 0.50 | Grit-120605-6 10X 3 | 75% | 76% | 77% |
| Recovery Statistics | 0.050 | Avg | 86% | 81% | 90% |
| | | St Dev | 5% | 2% | 3% |
| | | % RSD | 6% | 2% | 3% |
| | | n | 5 | 5 | 5 |
| | | min | 80% | 79% | 87% |
| | | max | 93% | 83% | 94% |
| | 0.50 | Avg | 82% | 85% | 80% |
| | | St Dev | 10% | 13% | 3% |
| | | % RSD | 12% | 15% | 3% |
| | | n | 5 | 5 | 5 |
| | | min | 74% | 75% | 77% |
| | | max | 99% | 106% | 83% |

Glyphosate and AMPA stable isotopes used as internal standards.

TABLE 7

CORN STARCH VALIDATION RESULTS

| Matrix | Fort Level (mg/kg) | Sample ID | Glyphosate % Rec | N-acetylglyphosate % Rec | AMPA % Rec |
|---|---|---|---|---|---|
| Corn Starch | 0.050 | Starch-112305-2 LOQ 1 | 81% | 95% | 103%* |
| | 0.050 | Starch-112305-3 LOQ 2 | 83% | 90% | 94%* |
| | 0.050 | Starch-112305-4 LOQ 3 | 74% | 99% | 95%* |
| | 0.50 | Starch-112305-5 10X 1 | 88% | 93% | 94%* |
| | 0.50 | Starch-112305-6 10X 2 | 85% | 94% | 92%* |
| | 0.050 | Starch-120205-2 LOQ 1 | 74% | 96% | 100% |

TABLE 7-continued

CORN STARCH VALIDATION RESULTS

| Matrix | Fort Level (mg/kg) | Sample ID | Glyphosate % Rec | N-acetylglyphosate % Rec | AMPA % Rec |
|---|---|---|---|---|---|
| | 0.050 | Starch-120205-3 LOQ 2 | 76% | 94% | 101% |
| | 0.50 | Starch-120205-4 10X 1 | 71% | 93% | 88% |
| | 0.50 | Starcht-120205-5 10X 2 | 77% | 95% | 94% |
| | 0.50 | Starch-120205-6 10X 3 | 77% | 94% | 93% |
| Recovery Statistics | 0.050 | Avg | 78% | 95% | 98% |
| | | St Dev | 4% | 3% | 4% |
| | | % RSD | 5% | 3% | 4% |
| | | n | 5 | 5 | 5 |
| | | min | 74% | 90% | 94% |
| | | max | 83% | 99% | 103% |
| | 0.50 | Avg | 80% | 94% | 92% |
| | | St Dev | 7% | 1% | 2% |
| | | % RSD | 8% | 1% | 3% |
| | | n | 5 | 5 | 5 |
| | | min | 71% | 93% | 88% |
| | | max | 88% | 95% | 94% |

Glyphosate and AMPA stable isotopes used as internal standards.
*AMPA results are average of 2 injections of same extracts (25 μL & 50 μL injection volumes)

TABLE 8

CORN MEAL VALIDATION RESULTS

| Matrix | Fort Level (mg/kg) | Sample ID | Glyphosate % Rec | N-acetylglyphosate % Rec | AMPA % Rec |
|---|---|---|---|---|---|
| Corn Meal | 0.050 | Me-111705-2 LOQ 1 | 100% | 82% | 105% |
| | 0.050 | Me-111705-3 LOQ 2 | 116% | 65% | 113% |
| | 0.050 | Me-1117054 LOQ 3 | 98% | 73% | 111% |
| | 0.50 | Me-111705-5 10X 1 | 100% | 78% | 91% |
| | 0.50 | Me-111705-6 10X 2 | 99% | 81% | 89% |
| | 0.050 | Meal-113005-2 LOQ 1 | 83% | 89% | 86% |
| | 0.050 | Meal-113005-3 LOQ 2 | 100% | 91% | 80% |
| | 0.50 | Meal-113005-4 10X 1 | 85% | 84% | 75% |
| | 0.50 | Meal-113005-5 10X 2 | 91% | 83% | 74% |
| | 0.50 | Meal-113005-6 10X 3 | 86% | 79% | 78% |
| Recovery Statistics | 0.050 | Avg | 99% | 80% | 99% |
| | | St Dev | 12% | 11% | 15% |
| | | % RSD | 12% | 14% | 15% |
| | | n | 5 | 5 | 5 |
| | | min | 83% | 65% | 80% |
| | | max | 116% | 91% | 113% |
| | 0.50 | Avg | 92% | 81% | 81% |
| | | St Dev | 7% | 3% | 8% |
| | | % RSD | 8% | 3% | 10% |
| | | n | 5 | 5 | 5 |
| | | min | 85% | 78% | 74% |
| | | max | 100% | 84% | 91% |

Glyphosate and AMPA stable isotopes used as internal standards.

TABLE 9

SOYBEAN FORAGE VALIDATION RESULTS

| Matrix | Fort Level (mg/kg) | Sample ID | Glyphosate % Rec | N-acetylglyphosate % Rec | AMPA % Rec |
|---|---|---|---|---|---|
| Soybean Forage | 0.050 | Soy Forage LOQ 072005-1 | 88% | 89% | 90% |
| | 0.050 | Soy Forage LOQ 072005-2 | 86% | 92% | 72% |
| | 0.050 | Soy Forage LOQ 072005-3 | 91% | 108% | 85% |
| | 0.500 | Soy Forage 10X 072005-1 | 92% | 96% | 72% |
| | 0.500 | Soy Forage 10X 072005-2 | 89% | 98% | 75% |
| | 0.050 | Soy Forage LOQ 0808-4 | 124% | 89% | 105% |
| | 0.050 | Soy Forage LOQ 0808-5 | 90% | 93% | 91% |
| | 0.500 | Soy Forage 10X 0808-3 | 94% | 97% | 99% |
| | 0.500 | Soy Forage 10X 0808-4 | 103% | 98% | 94% |
| | 0.500 | Soy Forage 10X 0808-5 | 89% | 100% | 95% |
| | 0.050 | SF-010306-2 LOQ 1 | 87% | 85% | 93%* |

TABLE 9-continued

SOYBEAN FORAGE VALIDATION RESULTS

| | 0.050 | SF-010306-3 LOQ 2 | 115% | 84% | 90%* |
|---|---|---|---|---|---|
| | 0.050 | SF-010306-4 LOQ 3 | 106% | 85% | 91%* |
| | 0.500 | SF-010306-5 10X 1 | 98% | 80% | 80%* |
| | 0.500 | SF-010306-6 10X 2 | 94% | 80% | 78%* |
| Recovery | 0.050 | Avg | 98% | 91% | 90% |
| Statistics | | St Dev | 15% | 8% | 9% |
| | | % RSD | 15% | 9% | 10% |
| | | n | 8 | 8 | 8 |
| | | min | 86% | 84% | 72% |
| | | max | 124% | 108% | 105% |
| | 0.50 | Avg | 94% | 93% | 85% |
| | | St Dev | 5% | 9% | 11% |
| | | % RSD | 5% | 9% | 13% |
| | | n | 7 | 7 | 7 |
| | | min | 89% | 80% | 72% |
| | | max | 103% | 100% | 99% |

| Matrix | Fort Level | Data Source | Recovery (%) N-acetyl AMPA |
|---|---|---|---|
| Soybean Forage | 0.050 | | 92 |
| | 0.050 | | 96 |
| | 0.050 | | 80 |
| | 0.050 | | 77 |
| | 0.50 | | 96 |
| | 0.50 | | 82 |
| | 0.050 | | 83 |
| | 0.050 | | 88 |
| | 0.50 | | 89 |
| | 0.50 | | 91 |
| | 0.50 | | 81 |
| | 0.50 | | 82 |
| | 0.50 | | 87 |
| | 0.50 | | 87 |
| | 0.50 | | 74 |
| | 0.50 | | 82 |
| Recovery | 0.050 | AVERAGE | 86 |
| Statistics | | ST DEV | 7 |
| | | % RSD | 8 |
| | | COUNT | 6 |
| | | MIN | 77 |
| | | MAX | 96 |
| | 0.5 | AVERAGE | 85 |
| | | St Dev | 6 |
| | | % RSD | 7 |
| | | COUNT | 10 |
| | | MIN | 74 |
| | | MAX | 96 |

Underlined indicate peak area in control sample was subtracted from peak area in sample to determine final results.
*Glyphosate and AMPA stable isotopes used as internal standards. Glyphosate and N-acetylglyphosate results are average of analyses of the same final extract processed 2 times.

TABLE 10A

SOYBEAN SEED VALIDATION RESULTS

| Matrix | Fort Level (mg/kg) | Sample ID | Glyphosate % Rec | N-acetyl-glyphosate % Rec | AMPA % Rec |
|---|---|---|---|---|---|
| Soybean Seed | 0.050 | SS-100405-1 | 88% | 97% | 93% |
| | 0.050 | SS-100405-2 | 89% | 96% | 77% |
| | 0.050 | SS-100405-3 | 91% | 94% | 108% |
| | 0.50 | SS-100405-4 | 85% | 92% | 85% |
| | 0.50 | SS-100405-5 | 80% | 92% | 74% |
| | 0.050 | SS-101005-1 | 80% | 100% | 102% |
| | 0.050 | SS-101005-2 | 78% | 98% | 90% |
| | 0.50 | SS-101005-3 | 72% | 96% | 83% |
| | 0.50 | SS-101005-4 | 81% | 94% | 77% |
| | 0.50 | SS-101005-5 | 73% | 99% | 73% |
| Recovery | 0.050 | Avg | 85% | 97% | 94% |
| Statistics | | StDev | 6% | 2% | 12% |
| | | % RSD | 7% | 2% | 13% |
| | | n | 5 | 5 | 5 |
| | | min | 78% | 94% | 77% |
| | | max | 91% | 100% | 108% |
| | 0.50 | Avg | 78% | 95% | 78% |
| | | StDev | 5% | 3% | 5% |
| | | % RSD | 7% | 3% | 7% |
| | | n | 5 | 5 | 5 |
| | | min | 72% | 92% | 73% |
| | | max | 85% | 99% | 85% |

| Matrix | Fort Level | Data Source | Recovery (%) N-acetyl AMPA |
|---|---|---|---|
| Soybean Seed | 0.050 | | 96 |
| | 0.050 | | 100 |
| | 0.50 | | 95 |
| | 0.50 | | 91 |
| | 0.050 | | 86 |
| | 0.050 | | 87 |
| | 0.50 | | 81 |
| | 0.50 | | 79 |
| | 0.50 | | 70 |
| | 0.50 | | 71 |

TABLE 10A-continued

SOYBEAN SEED VALIDATION RESULTS

| | | | | |
|---|---|---|---|---|
| | 0.50 | 75 | | |
| | 0.50 | 73 | | |
| | 0.050 | 82 | | |
| | 0.050 | 96 | | |
| | 0.050 | 88 | | |
| | 0.050 | 82 | | |
| | 0.050 | 105 | | |
| | 0.050 | 113 | | |
| | 0.050 | 92 | | |
| | 0.050 | 87 | | |
| | 0.050 | 66 | | |
| | 0.050 | 83 | | |
| Recovery Statistics | 0.050 | AVERAGE | 90 | |
| | | STDEV | 12 | |
| | | % RSD | 13 | |
| | | COUNT | 14 | |
| | | MIN | 66 | |
| | | MAX | 113 | |
| | 0.50 | AVERAGE | 79 | |
| | | StDev | 9 | |
| | | % RSD | 12 | |
| | | COUNT | 8 | |
| | | MIN | 70 | |
| | | MAX | 95 | |

Glyphosate and AMPA isotopes used as internal standards.

TABLE 11A

SOYBEAN HAY VALIDATION RESULTS

| Matrix | Fort Level (mg/kg) | Sample ID | Glyphosate % Rec | N-acetylglyphosate % Rec | AMPA % Rec | |
|---|---|---|---|---|---|---|
| Soybean Hay | 0.050 | SH-102105-2 | 90% | 92% | 113% | * |
| | 0.050 | SH-102105-3 | 99% | 105% | 95% | * |
| | 0.050 | SH-102105-4 | 83% | 88% | 95% | * |
| | 0.50 | SH-102105-5 | 76% | 85% | 76% | * |
| | 0.50 | SH-102105-6 | 78% | 84% | 74% | * |
| | 0.050 | SS-102605-2 | 91% | 87% | 94% | * |
| | 0.050 | SS-102605-3 | 107% | 100% | 98% | * |
| | 0.50 | SS-102605-4 | 83% | 85% | 80% | * |
| | 0.50 | SS-102605-5 | 78% | 87% | 82% | * |
| | 0.50 | SS-102605-6 | 86% | 88% | 85% | * |
| Recovery Statistics | 0.050 | Avg | 94% | 94% | 99% | |
| | | StDev | 9% | 8% | 8% | |
| | | % RSD | 10% | 8% | 8% | |
| | | n | 5 | 5 | 5 | |
| | | min | 83% | 87% | 94% | |
| | | max | 107% | 105% | 113% | |
| | 0.50 | Avg | 80% | 86% | 79% | |
| | | StDev | 4% | 2% | 5% | |
| | | % RSD | 5% | 2% | 6% | |
| | | n | 5 | 5 | 5 | |
| | | min | 76% | 84% | 74% | |
| | | max | 86% | 88% | 85% | |

| Matrix | Fort Level | Data Source | Recovery (%) N-acetyl AMPA |
|---|---|---|---|
| Soybean Hay | 0.50 | | 82 |
| | 0.50 | | 83 |
| | 0.50 | | 81 |
| | 0.50 | | 74 |
| | 0.50 | | 75 |
| | 0.50 | | 71 |
| | 0.05 | | 79 |
| | 0.05 | | 72 |
| | 0.05 | | 78 |
| | 0.05 | | 78 |
| | 0.05 | | 83 |
| | 0.05 | | 77 |
| | 0.05 | | 86 |
| | 0.05 | | 73 |
| | 0.05 | | 78 |
| | 0.05 | | 71 |
| | 0.05 | | 70 |
| | 0.05 | | 61 |
| | 0.05 | | 77 |
| | 0.05 | | 62 |
| | 0.05 | | 80 |
| | 0.05 | | 73 |
| | 0.05 | | 68 |
| | 0.05 | | 80 |
| | 0.05 | | 92 |
| | 0.05 | | 71 |
| | 0.05 | | 67 |
| | 0.05 | | 71 |
| | 0.05 | | 66 |

TABLE 11A-continued

SOYBEAN HAY VALIDATION RESULTS

| | | | |
|---|---|---|---|
| Recovery | 0.050 | AVERAGE | 75 |
| Statistics | | STDEV | 7 |
| | | % RSD | 10 |
| | | COUNT | 23 |
| | | MIN | 61 |
| | | MAX | 92 |
| | 0.5 | AVERAGE | 78 |
| | | StDev | 5 |
| | | % RSD | 6 |
| | | COUNT | 6 |
| | | MIN | 71 |
| | | MAX | 83 |

Glyphosate and AMPA isotopes used as internal standards.
* average of 2 analyses of same extract (repurified)

TABLE 12

SOYBEAN OIL VALIDATION RESULTS

| Matrix | Fort Level (mg/kg) | Sample ID | Glyphosate % Rec | N-acetylglyphosate % Rec | AMPA % Rec |
|---|---|---|---|---|---|
| Soybean Oil | 0.050 | SO-112205-2 LOQ 1 | 100% | 94% | 98% |
| | 0.050 | SO-112205-3 LOQ 2 | 102% | 92% | 100% |
| | 0.050 | SO-112205-4 LOQ 3 | 91% | 93% | 118% |
| | 0.50 | SO-112205-5 10X 1 | 95% | 101% | 95% |
| | 0.50 | SO-112205-6 10X 2 | 83% | 98% | 95% |
| | 0.050 | SO-121505-2 LOQ 1 | 105% | 94% | 101% |
| | 0.050 | SO-121505-3 LOQ 2 | 96% | 97% | 116% |
| | 0.50 | SO-121505-4 10X 1 | 101% | 98% | 94% |
| | 0.50 | SO-121505-5 10X 2 | 101% | 96% | 96% |
| | 0.50 | SO-121505-6 10X 3 | 85% | 97% | 96% |
| Recovery | 0.050 | Avg | 99% | 94% | 107% |
| Statistics | | StDev | 6% | 2% | 9% |
| | | % RSD | 6% | 2% | 9% |
| | | n | 5 | 5 | 5 |
| | | min | 91% | 92% | 98% |
| | | max | 105% | 97% | 118% |
| | 0.50 | Avg | 93% | 98% | 95% |
| | | StDev | 9% | 2% | 1% |
| | | % RSD | 9% | 2% | 1% |
| | | n | 5 | 5 | 5 |
| | | min | 83% | 96% | 94% |
| | | max | 101% | 101% | 96% |

Glyphosate and AMPA stable isotopes used as internal standards.
See Table 4 for N-acetyl AMPA recovery data

TABLE 13

SOYBEAN MEAL VALIDATION RESULTS

| Matrix | Fort Level (mg/kg) | Sample ID | Glyphosate % Rec | N-acetyl-glyphosate % Rec | AMPA % Rec |
|---|---|---|---|---|---|
| Soybean Meal | 0.050 | LOQ-1 | 91% | 97% | 84% |
| | 0.050 | LOQ-2 | 102% | 90% | 76% |
| | 0.050 | 10xLOQ-1 | 78% | 96% | 74% |
| | 0.50 | 10xLOQ-2 | 81% | 100% | 75% |
| | 0.50 | 10xLOQ-3 | 77% | 93% | 72% |
| | 0.050 | LOQ-3 | 89% | 75% | 87% |
| | 0.050 | LOQ-4 | 87% | 92% | 82% |
| | 0.50 | LOQ-5 | 96% | 90% | 90% |
| | 0.50 | 10xLOQ-4 | 79% | 89% | 73% |
| | 0.50 | 10xLOQ-5 | 78% | 88% | 76% |
| Recovery | 0.050 | Avg | 93% | 89% | 84% |
| Statistics | | StDev | 6% | 8% | 5% |
| | | % RSD | 7% | 9% | 6% |
| | | n | 5 | 5 | 5 |
| | | min | 87% | 75% | 76% |
| | | max | 102% | 97% | 90% |
| | 0.50 | Avg | 79% | 93% | 74% |
| | | StDev | 2% | 5% | 2% |
| | | % RSD | 2% | 5% | 2% |
| | | n | 5 | 5 | 5 |
| | | min | 77% | 88% | 72% |
| | | max | 81% | 100% | 76% |

Glyphosate and AMPA stable isotopes used as internal standards.
* Different sample set for AMPA analysis

TABLE 14

SOYBEAN HULLS VALIDATION RESULTS

| Matrix | Fort Level (mg/kg) | Sample ID | Glyphosate % Rec | N-acetylglyphosate % Rec | AMPA % Rec | |
|---|---|---|---|---|---|---|
| Soybean Hulls | 0.050 | Hu-012406-2 CX LOQ 1 | 92% | 104% | 84% | * |
| | 0.050 | Hu-012406-3 CX LOQ 2 | 93% | 95% | 96% | * |
| | 0.050 | Hu-012406-4 CX LOQ 3 | 87% | 98% | 84% | * |
| | 0.50 | Hu-012406-5 CX 10X 1 | 78% | 100% | 81% | * |
| | 0.50 | Hu-012406-6 CX 10X 2 | 71% | 99% | 83% | * |
| | 0.050 | Hu-020706-2 CX LOQ 4 | 75% | 93% | 84% | |
| | 0.050 | Hu-020706-3 CX LOQ 5 | 72% | 104% | 90% | |
| | 0.50 | Hu-020706-4 CX 10X 3 | 74% | 102% | 84% | |
| | 0.50 | Hu-020706-5 CX 10X 4 | 77% | 95% | 72% | |
| | 0.50 | Hu-020706-6 CX 10X 5 | 74% | 102% | 81% | |
| Recovery Statistics | 0.050 | Avg | 84% | 99% | 87% | |
| | | StDev | 10% | 5% | 5% | |
| | | % RSD | 12% | 5% | 6% | |
| | | n | 5 | 5 | 5 | |
| | | min | 72% | 93% | 84% | |
| | | max | 93% | 104% | 96% | |
| | 0.50 | Avg | 75% | 100% | 80% | |
| | | StDev | 3% | 3% | 5% | |
| | | % RSD | 3% | 3% | 6% | |
| | | n | 5 | 5 | 5 | |
| | | min | 71% | 95% | 72% | |
| | | max | 78% | 102% | 84% | |

Glyphosate and AMPA stable isotopes used as internal standards.
* Average of 2 analyses of same extract for AMPA

TABLE 15

PLUM VALIDATION RESULTS

| | Fort Level | Recovery (%) | | | |
|---|---|---|---|---|---|
| Matrix | (mg/kg) | Glyphosate | N-acetylglyphosate | AMPA | N-acetyl AMPA |
| | 0.050 | 90% | 110% | 93% | 99% |
| | | 96% | 91% | 88% | 106% |
| | | 95% | 93% | 90% | 109% |
| | | 99% | 105% | 96% | 98% |
| | | 98% | 110% | 108% | 100% |
| | 0.50 | 91% | 98% | 93% | 112% |
| | | 94% | 100% | 95% | 100% |
| | | 96% | 97% | 107% | 102% |
| | | 89% | 87% | 112% | 89% |
| | | 85% | 82% | 92% | 99% |
| Recovery Statistics | 0.050 | Avg | 95% | 102% | 95% | 102% |
| | | StDev | 4% | 9% | 8% | 5% |
| | | % RSD | 4% | 9% | 8% | 5% |
| | | n | 5 | 5 | 5 | 5 |
| | | min | 90% | 91% | 88% | 98% |
| | | max | 99% | 110% | 108% | 109% |
| | 0.50 | Avg | 91% | 93% | 100% | 100% |
| | | StDev | 4% | 8% | 9% | 8% |
| | | % RSD | 5% | 8% | 9% | 8% |
| | | n | 5 | 5 | 5 | 5 |
| | | min | 85% | 82% | 92% | 89% |
| | | max | 96% | 100% | 112% | 112% |

TABLE 16

LIME VALIDATION RESULTS

| | Fort Level | Recovery (%) | | | |
|---|---|---|---|---|---|
| Matrix | (mg/kg) | Glyphosate | N-acetylglyphosate | AMPA | N-acetyl AMPA |
| Limes | 0.050 | 96% | 78% | 100% | 79% |
| | | 88% | 91% | 96% | 93% |
| | | 110% | 78% | 91% | 105% |
| | | 100% | 84% | 85% | 104% |
| | | 105% | 99% | 104% | 89% |

TABLE 16-continued

LIME VALIDATION RESULTS

| Matrix | Fort Level (mg/kg) | | Recovery (%) | | | |
|---|---|---|---|---|---|---|
| | | | Glyphosate | N-acetylglyphosate | AMPA | N-acetyl AMPA |
| | 0.50 | | 97% | 85% | 101% | 95% |
| | | | 90% | 91% | 101% | 121% |
| | | | 98% | 96% | 101% | 107% |
| | | | 107% | 98% | 90% | 112% |
| | | | 103% | 87% | 98% | 100% |
| Recovery Statistics | 0.050 | Avg | 100% | 86% | 95% | 94% |
| | | StDev | 8% | 9% | 7% | 11% |
| | | % RSD | 9% | 10% | 8% | 12% |
| | | n | 5 | 5 | 5 | 5 |
| | | min | 88% | 78% | 85% | 79% |
| | | max | 110% | 99% | 104% | 105% |
| | 0.50 | Avg | 99% | 91% | 98% | 107% |
| | | StDev | 6% | 6% | 5% | 10% |
| | | % RSD | 6% | 6% | 5% | 9% |
| | | n | 5 | 5 | 5 | 5 |
| | | min | 90% | 85% | 90% | 95% |
| | | max | 107% | 98% | 101% | 121% |

Extraction Efficiency

In the metabolism study, corn forage, grain, or stover samples were extracted 3 times in 0.1% formic acid/methanol (96/4, v:v) using tissumizer homogenization and wrist-action shaker. The greatest extract to sample ratio applied in the procedure was 6 to 1 (150 ml to 25 g), although the ratio varied by commodity and extraction repetition.

In this residue analytical method, the sample size was reduced to 5.0 g and the solvent to sample ratio for each commodity and repetition was at least 5 to 1. Table 41 contrasts the sample amounts and ratios used in metabolism and residue methods for each matrix.

TABLE 41

| Method | Matrix | Sample (g) | Extract Volumes (ratios) | | | | | |
|---|---|---|---|---|---|---|---|---|
| | | | 1st | | 2nd | | 3rd | |
| Metabolism | Forage | 25 | 150 | (6) | 100 | (4) | 100 | (4) |
| Residue | Forage | 5 | 50 | (10) | 25 | (5) | 25 | (5) |
| Metabolism | Grain | 50 | 100 | (2) | 50 | (1) | 50 | (1) |
| Residue | Grain | 5 | 50 | (10) | 25 | (5) | 25 | (5) |
| Metabolism | Stover | 25 | 150 | (6) | 100 | (4) | 100 | (4) |
| Residue | Stover | 5 | 100 | (20) | 50 | (10) | 50 | (10) |

The extraction procedure in this residue analytical method is consistent with or exceeds the extraction procedure applied to quantitatively extract glyphosate related residues from crops.

Incurred residue samples from regulatory field studies were analyzed for glyphosate and AMPA residues by a post-column derivatization fluorescence (PCD-fluor) method (Cowell et al. (1986) *J. Agric. Food Chem.* 34:955-960) in the original studies and by this LC/MS/MS method. The corn in these studies contained the EPSPS enzyme variant genetic modification and therefore the N-acetylglyphosate metabolite was not formed. Table 42 summarizes results in mg/kg (ppm) glyphosate free-acid equivalents for untreated (control) and treated corn grain samples collected from 2 test sites.

TABLE 42

| | | glyphosate | | AMPA | |
|---|---|---|---|---|---|
| Sample | Sample Type | PCD-fluor | LC/MS/MS | PCD-fluor | LC/MS/MS |
| S00227147 | Control | nd | nd | 0.080 | nd* |
| S00227081 | Control | nd | nd | nd | nd |
| S00227054 | Treated | 0.12 | 0.12 | 0.03 | 0.02 |
| S00227149 | Treated | 0.058 | 0.051 | 0.090 | 0.02* |
| S00227154 | Treated | 0.054 | 0.053 | 0.081 | 0.03* |

*S00227147 (control), S00227149, and S00227154 samples were collected from the same test site and interference was observed using post-column derivatization fluorescence detection that contributed to the AMPA residue.

Table 43 summarizes results in mg/kg (ppm) glyphosate free-acid equivalents for untreated (control) and treated corn grain, forage, and stover samples collected from 2 test sites of the field study.

TABLE 43

| | | | glyphosate | | AMPA | |
|---|---|---|---|---|---|---|
| Matrix | Sample | Sample Type | PCD-fluor | LC/MS/MS | PCD-fluor | LC/MS/MS |
| Corn Grain | S00227444 | Control | nd | nd | nd | nd |
| | S00227543 | Control | nd | nd | nd | nd |
| | S00227450 | Treated | 0.13 | 0.10 | nd | 0.01 |
| | S00227549 | Treated | 0.064 | 0.049 | nd | 0.01 |
| Corn Forage | S00227433 | Control | nd | nd | nd | nd |
| | S00227532 | Control | nd | nd | nd | nd |
| | S00227440 | Treated | 1.2 | 1.0 | 0.04 | 0.02 |
| | S00227539 | Treated | 0.37 | 0.52 | 0.03 | 0.02 |

TABLE 43-continued

| Matrix | Sample | Sample Type | glyphosate | | AMPA | |
|---|---|---|---|---|---|---|
| | | | PCD-fluor | LC/MS/MS | PCD-fluor | LC/MS/MS |
| Corn Stover | S00227445 | Control | nd | nd | nd | nd |
| | S00227544 | Control | nd | nd | nd | nd |
| | S00227453 | Treated | 3.1 | 2.7 | 0.074 | 0.024 |
| | S00227551 | Treated | 14 | 6.0 | 0.16 | 0.022 |

Analytical results from both methods indicate consistent results for glyphosate and AMPA in corn and support the extraction efficiency for the analytical method.

Limit of Quantitation (LOQ)

The LOQ validated in this method was 0.050 ppm (mg/kg) for glyphosate, N-acetylglyphosate, and AMPA in corn and soybean matrices. The LOQ is defined as the lowest fortification level at which average recoveries of 70-120% and a RSD<20% are achieved. In addition, at this fortification level, the analyte peak consistently represents a signal-to-noise ratio of approximately 5-20 to 1 for the least responsive analyte, AMPA.

Background Evaluation

Background levels experienced in tandem mass spectrometry analyses are minimal. Generally, the chromatographic profiles of a sample extract solution and a calibration standard solution appear the same. The control sample chromatograms for each matrix tested are provided in FIG. 9-FIG. 21.

Limit of Detection (LOD)

The LOD is defined as the analyte concentration in matrix with a response equivalent to a signal-to-noise ratio (s/n) of approximately 3 to 1. The LOD was estimated from the s/n response determined in a LOQ fortification sample using the following equation for each analyte.

$$\frac{LOD\ s/n\ \text{response}(3/1)}{\text{Observed}\ LOQ\ s/n\ \text{response}} \times \text{mg/kg found} = LOD(\text{mg/kg})$$

Figure 26:
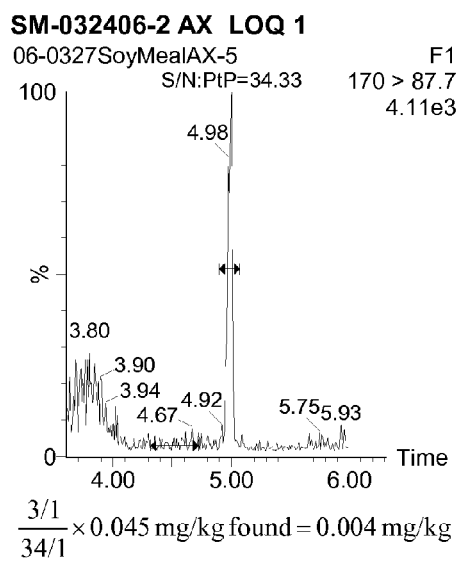
FIG. 26 provides signal to noise and LOD determinations for soybean meal LOQ fortification samples.
Figure 26:
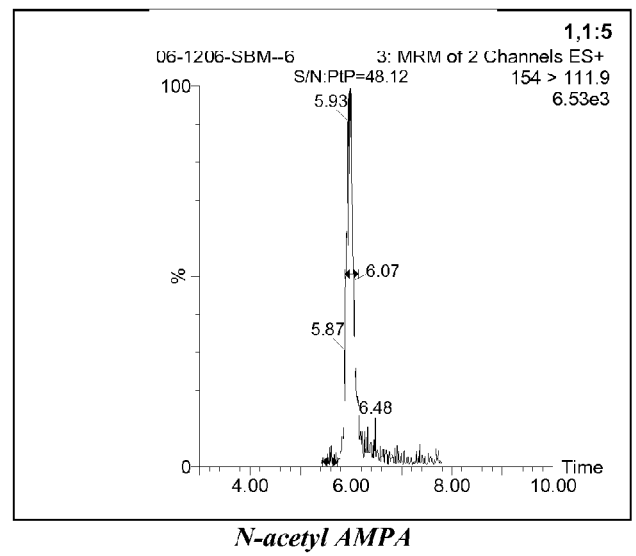
Figure 26:
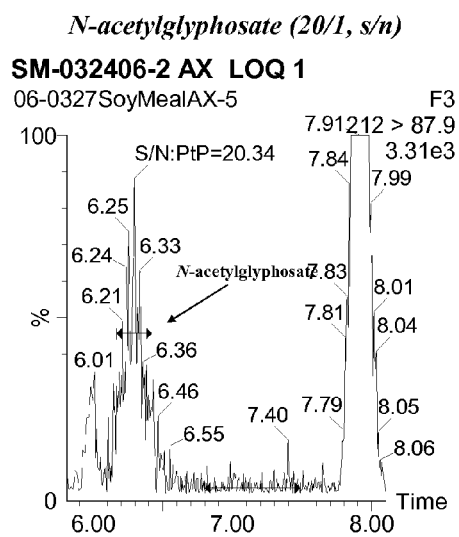
Figure 26:
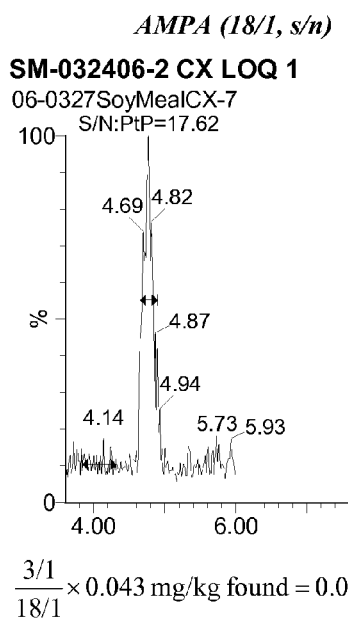
Figure 27:
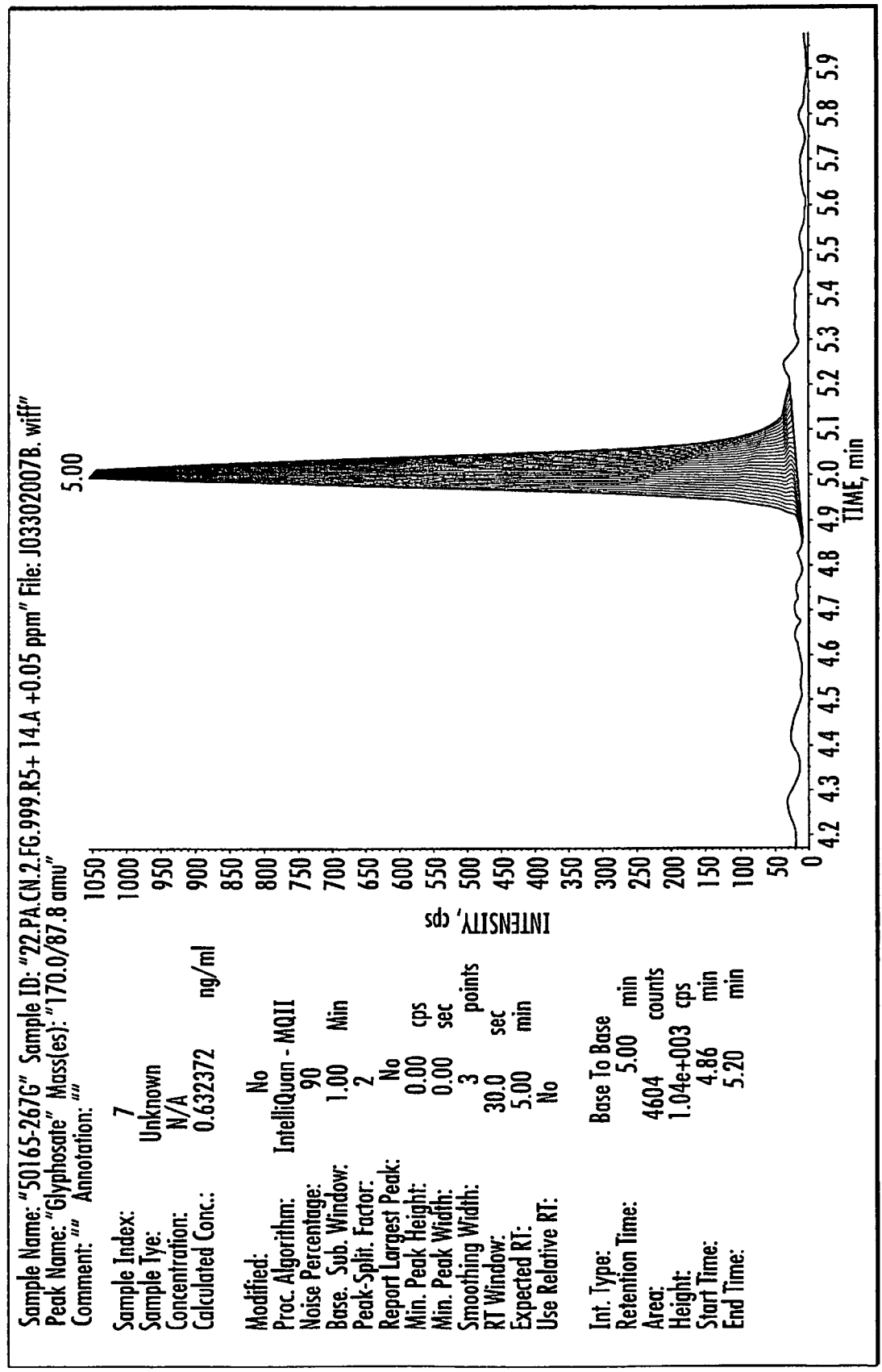
FIG. 27 provides a representative API 4000 LC/MS/MS Chromatogram for glyphosate 0.050 ppm corn forage fortification sample.
Figure 28:
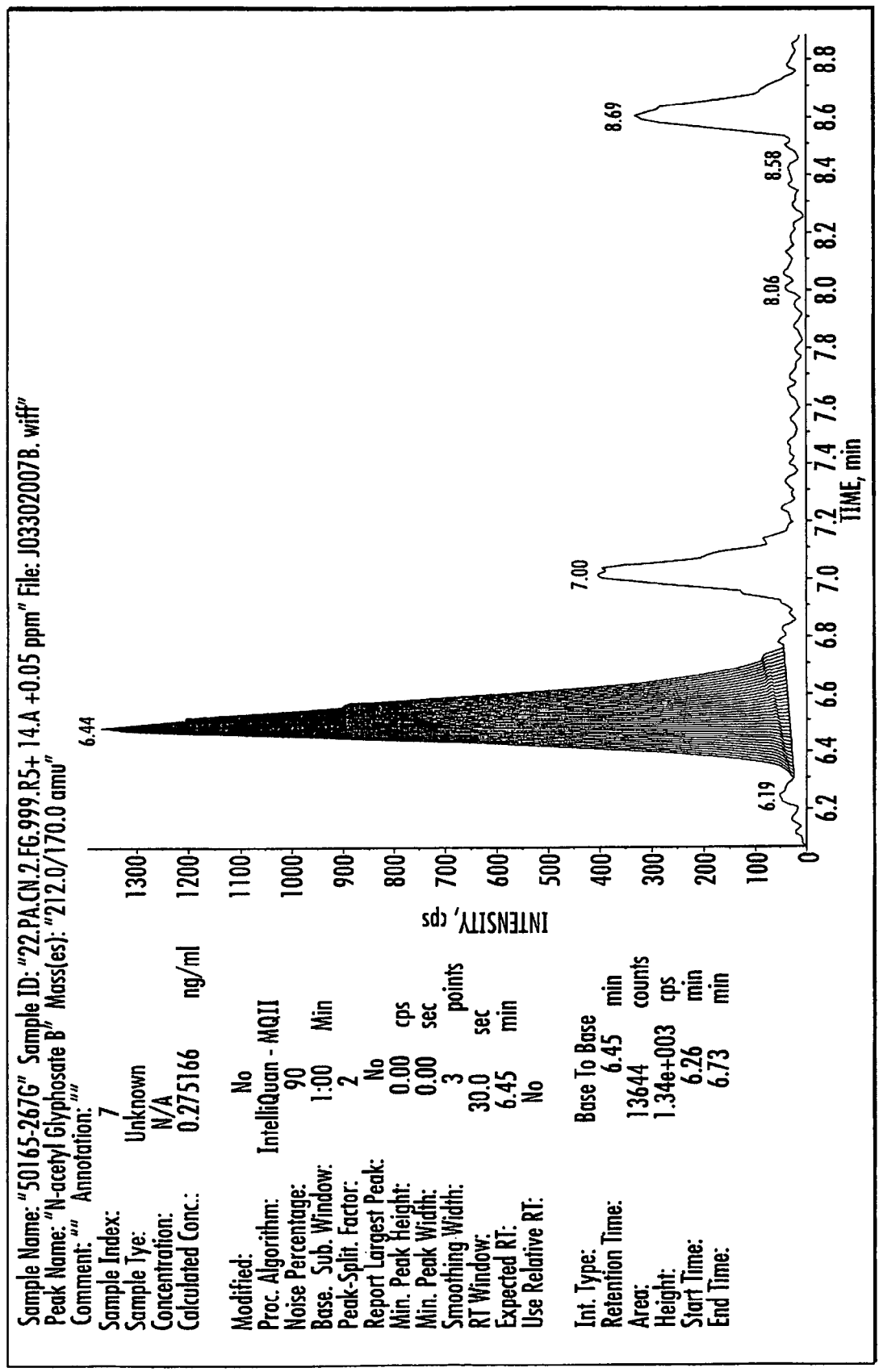
FIG. 28 provides a representative API 4000 LC/MS/MS Chromatogram for N-acetylglyphosate 0.050 ppm corn forage fortification sample.
Figure 29:
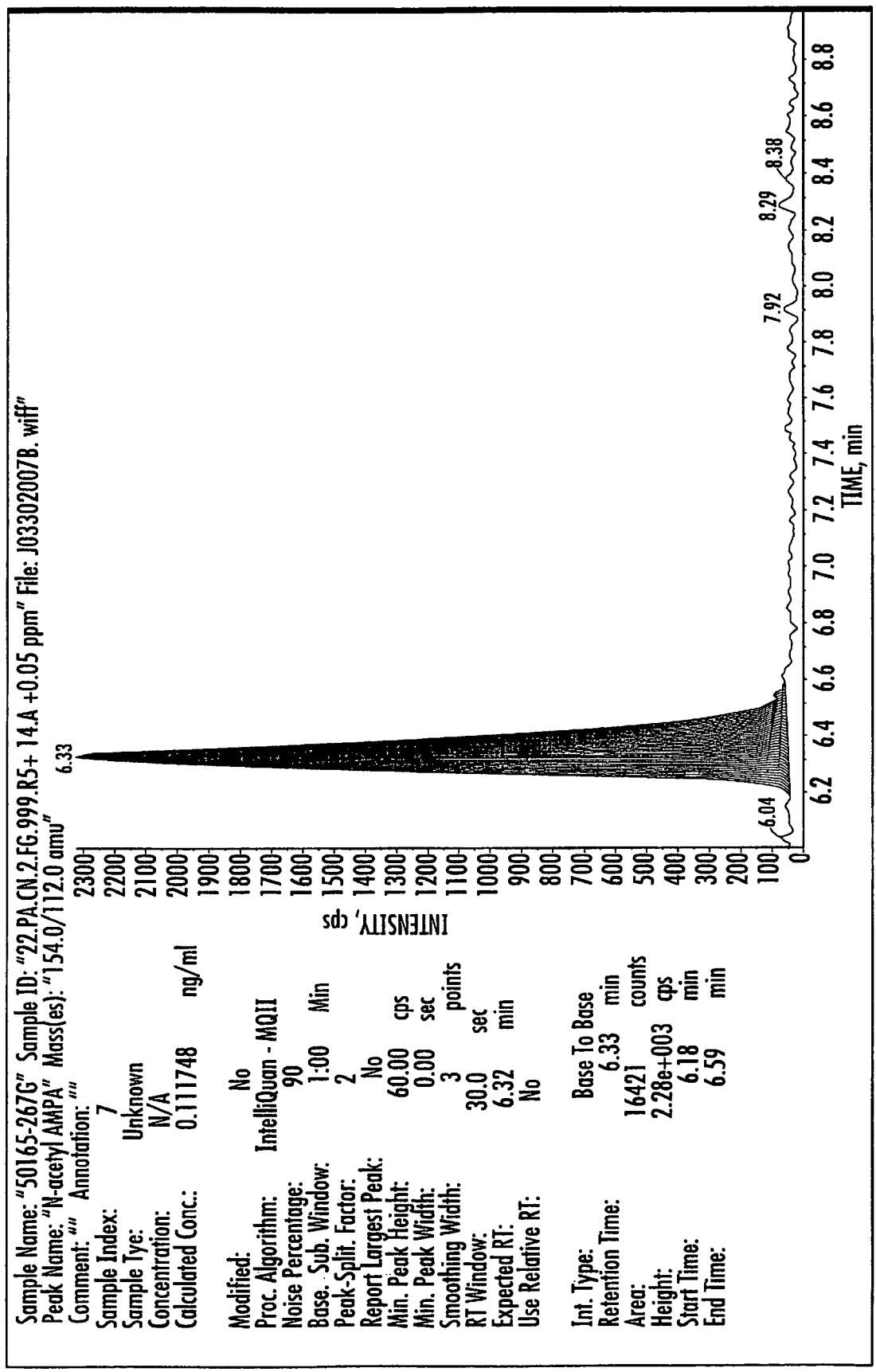
FIG. 29 provides a representative API 4000 LC/MS/MS Chromatogram for N-acetyl AMPA 0.05 ppm corn forage fortification sample.
Figure 30:
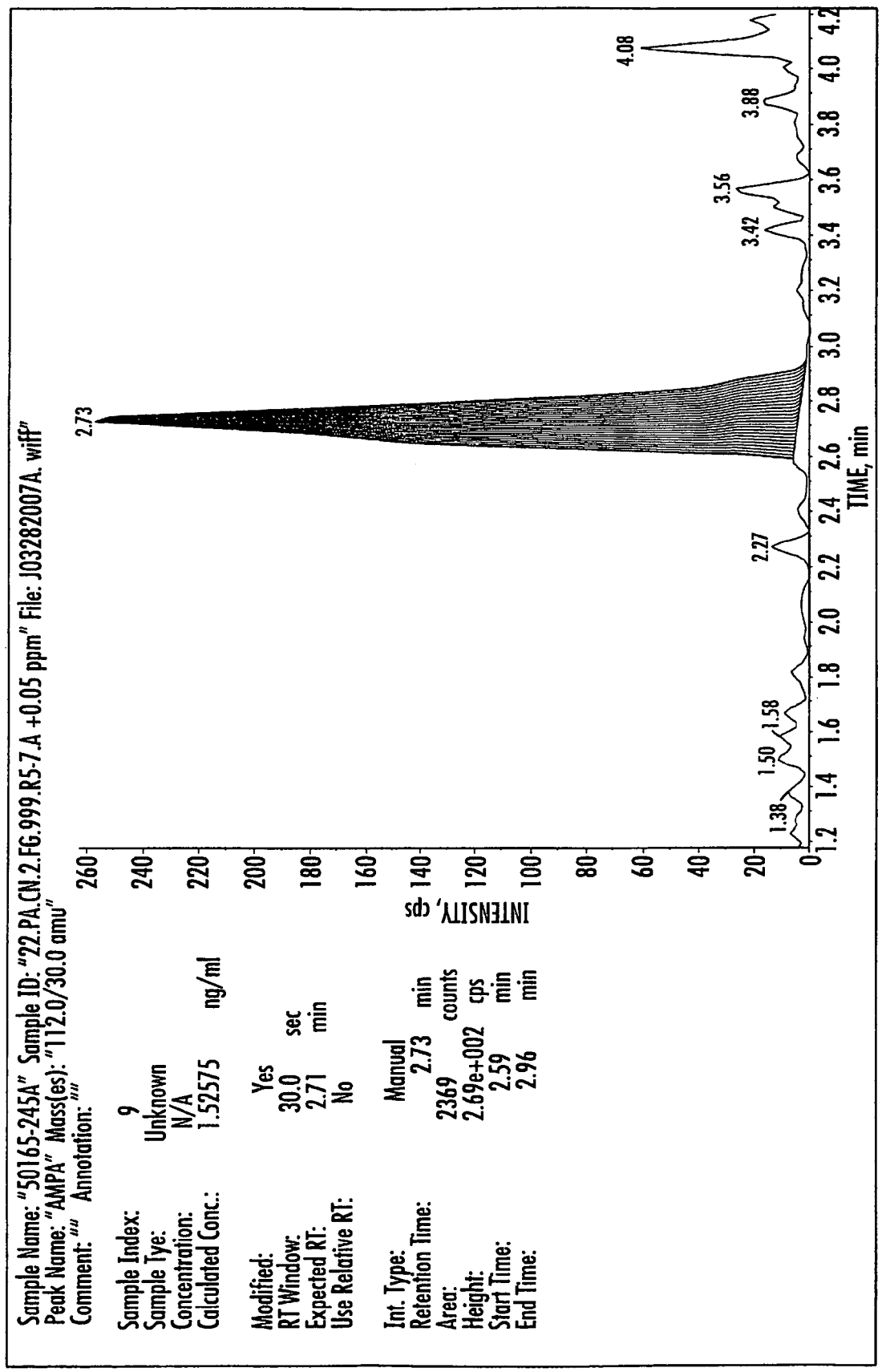
FIG. 30 provides a representative API 4000 LC/MS/MS Chromatogram for AMPA 0.05 ppm corn forage fortification sample.

The LOD estimates for were 0.004 mg/kg for glyphosate, 0.006 mg/kg for N-acetylglyphosate, and 0.007 mg/kg for AMPA and 0.006 mg/kg for N-acetyl AMPA. The individual chromatograms showing s/n determination and calculated estimates for each analyte are provided in FIG. 26. Variation in the LOD was observed and each lab using this method should estimate an LOD value.

Two independent MS/MS transitions of the molecular ion for glyphosate and N-acetylglyphosate were monitored. The relative response ratios of the two fragment ions (base peak/secondary peak) were determined from calibration standard responses for confirmation of analyte in matrix samples. Acceptable confirmation criteria are a co-eluting peak (±5%) and equivalent ion ratio (±30%) compared to the average response observed in calibration standards at or above the LOQ equivalent concentration concurrently analyzed with the samples. The calculated response ratios and retention times for each analyte determined in an analysis set are shown in Tables 43-48. Confirmation for glyphosate and AMPA can be determined using existing regulatory methods. See, for example, Cowell et al. (1986) *J. Agric. Food Chem.* 34: 955-960; Alferness et al. (Apr. 3, 1993) "Touchdown: Determination of Glyphosate and Aminomethylphosphonic Acid in Corn Grain, Corn Forage, and Corn Fodder by Gas Chromatography and Mass-Selective Detection". Zeneca Ag Products Analytical Method RR 92-042B, Available at U.S. EPA Pesticides: Analytical Methods & Procedures website (www.epa.gov/oppbead1/methods/ram12b.htm); and, Method No. 405 in Manual of Pesticide Residue Analysis Volume I and II available from BfR Federal Institute for Risk Assessment, Official analytical methods for residues of plant protection products and pesticides (L 00.00 16) (www.bfr.bund.de/cd/1652).

TABLE 43

Corn Forage: Representative glyphosate and N-acetylglyphosate confirmation results.
Matrix: Corn Forage
Confirmation Ions: Glyphosate: TIC (170 > 87.7, 60.1), N-acetylglyphosate: TIC (212 > 169.9, 87.7)

| Sample Information | | | Analyte Response (Fragment Ions peak areas; Ratio = base peak/minor peak; RT = peak retention time, min) | | | | | | | |
|---|---|---|---|---|---|---|---|---|---|---|
| | | | Glyphosate | | | | N-acetylglyphosate | | | |
| Run ID | ng/g or ppb | Identification | 170 > 88 | 170 > 60 | Ratio | RT | 212 > 170 | 212 > 88 | Ratio | RT |
| 071205Fmax-5 | 1 | 1 ppb Cal Std | 448 | 98 | 4.59 | 4.56 | 426 | 711 | 0.60 | 5.79 |
| 071205Fmax-11 | 5 | 5.0 ppb Cal Std | 2283 | 527 | 4.33 | 4.57 | 1983 | 3335 | 0.59 | 5.78 |
| 071205Fmax-16 | 10 | 10 ppb Cal Std | 4514 | 980 | 4.61 | 4.57 | 4002 | 6708 | 0.60 | 5.79 |
| 071205Fmax-20 | 20 | 20 ppb Cal Std | 8888 | 2062 | 4.31 | 4.57 | 7926 | 13421 | 0.59 | 5.8 |
| 071205Fmax-6 | 50 | Forage LOQ 070105-1 | 337 | 104 | 3.24 | 4.56 | 368 | 533 | 0.69 | 5.8 |
| 071205Fmax-7 | 50 | Forage LOQ 070105-2 | 328 | 76 | 4.29 | 4.57 | 385 | 598 | 0.64 | 5.82 |
| 071205Fmax-9 | 50 | Forage LOQ 070105-3 | 322 | 93 | 3.46 | 4.56 | 362 | 555 | 0.65 | 5.84 |
| 071205Fmax-10 | 50 | Forage LOQ 070105-4 | 320 | 94 | 3.39 | 4.56 | 382 | 657 | 0.58 | 5.83 |
| 071205Fmax-12 | 50 | Forage LOQ 070105-5 | 312 | 82 | 3.79 | 4.56 | 384 | 549 | 0.70 | 5.78 |
| 071205Fmax-14 | 500 | Forage 10X 0670105-1 | 3268 | 762 | 4.29 | 4.56 | 3562 | 5914 | 0.60 | 5.81 |
| 071205Fmax-15 | 500 | Forage 10X 0670105-2 | 3182 | 668 | 4.77 | 4.56 | 3474 | 5663 | 0.61 | 5.8 |
| 071205Fmax-17 | 500 | Forage 10X 0670105-3 | 3113 | 714 | 4.36 | 4.57 | 3431 | 5432 | 0.63 | 5.82 |

TABLE 43-continued

Corn Forage: Representative glyphosate and N-acetylglyphosate confirmation results.
Matrix: Corn Forage
Confirmation Ions: Glyphosate: TIC (170 > 87.7, 60.1), N-acetylglyphosate: TIC (212 > 169.9, 87.7)

| Run ID | Sample Information | | Glyphosate | | | | N-acetylglyphosate | | | |
|---|---|---|---|---|---|---|---|---|---|---|
| | ng/g or ppb | Identification | 170 > 88 | 170 > 60 | Ratio | RT | 212 > 170 | 212 > 88 | Ratio | RT |
| 071205Fmax-18 | 500 | Forage 10X 0670105-4 | 3085 | 739 | 4.18 | 4.57 | 3452 | 5654 | 0.61 | 5.82 |
| 071205Fmax-21 | 500 | Forage 10X 0670105-5 | 3080 | 654 | 4.71 | 4.56 | 3427 | 5468 | 0.63 | 5.8 |
| | Average | | | | 4.46 | 4.57 | | | 0.60 | 5.79 |
| | St Dev | | | | 0.16 | 0.01 | | | 0.00 | 0.01 |
| | % RSD | | | | 4% | 0.1% | | | 1% | 0.1% |
| | Lower Limit (avg. × 0.7) | | | | 3.12 | 4.34 | | | 0.42 | 5.50 |
| | Upper Limit (avg. × 1.3) | | | | 5.80 | 4.80 | | | 0.77 | 6.08 |

Ratio: Lower Limit = 0.7 ´ Average ratio, Upper Limit = 1.3 ´ Average ratio
Retention Time (RT): Upper Limit = Average × 0.95, Upper Limit = Average × 1.05

TABLE 44

Corn Grain: representative glyphosate and N-acetylglyphosate confirmation results.
Matrix: Corn Grain
Confirmation Ions: Glyphosate: TIC (170 > 87.7, 60.1), N-acetylglyphosate: TIC (212 > 169.9, 87.7)

| Run ID | Sample Information | | Glyphosate | | | | N-acetylglyphosate | | | |
|---|---|---|---|---|---|---|---|---|---|---|
| | ng/g or ppb | Identification | 170 > 88 | 170 > 60 | Ratio | RT | 212 > 170 | 212 > 88 | Ratio | RT |
| 071305Gmax-5 | 1 | 1 ppb Cal Std | 448 | 98 | 4.59 | 4.57 | 426 | 711 | 0.60 | 5.81 |
| 071305Gmax-11 | 5 | 5.0 ppb Cal Std | 2283 | 527 | 4.33 | 4.57 | 1983 | 3335 | 0.59 | 5.81 |
| 071305Gmax-16 | 10 | 10 ppb Cal Std | 4514 | 980 | 4.61 | 4.57 | 4002 | 6708 | 0.60 | 5.81 |
| 071305Gmax-20 | 20 | 20 ppb Cal Std | 8888 | 2062 | 4.31 | 4.57 | 7926 | 13421 | 0.59 | 5.81 |
| 071305Gmax-6 | 50 | Grain LOQ 062905-1 | 337 | 104 | 3.24 | 4.56 | 368 | 533 | 0.69 | 5.83 |
| 071305Gmax-7 | 50 | Grain LOQ 062905-2 | 328 | 76 | 4.29 | 4.56 | 385 | 598 | 0.64 | 5.77 |
| 071305Gmax-9 | 50 | Grain LOQ 062905-3 | 322 | 93 | 3.46 | 4.56 | 362 | 555 | 0.65 | 5.81 |
| 071305Gmax-10 | 50 | Grain LOQ 062905-4 | 320 | 94 | 3.39 | 4.56 | 382 | 657 | 0.58 | 5.82 |
| 071305Gmax-12 | 50 | Grain LOQ 062905-5 | 312 | 82 | 3.79 | 4.57 | 384 | 549 | 0.70 | 5.78 |
| 071305Gmax-14 | 500 | Grain 10X 062905-1 | 3268 | 762 | 4.29 | 4.57 | 3562 | 5914 | 0.60 | 5.82 |
| 071305Gmax-15 | 500 | Grain 10X 062905-2 | 3182 | 668 | 4.77 | 4.56 | 3474 | 5663 | 0.61 | 5.8 |
| 071305Gmax-17 | 500 | Grain 10X 062905-3 | 3113 | 714 | 4.36 | 4.56 | 3431 | 5432 | 0.63 | 5.78 |
| 071305Gmax-18 | 500 | Grain 10X 062905-4 | 3085 | 739 | 4.18 | 4.56 | 3452 | 5654 | 0.61 | 5.81 |
| 071305Gmax-21 | 500 | Grain 10X 062905-5 | 3080 | 654 | 4.71 | 4.56 | 3427 | 5468 | 0.63 | 5.8 |
| | Average | | | | 4.46 | 4.57 | | | 0.60 | 5.81 |
| | St Dev | | | | 0.16 | 0.00 | | | 0.00 | 0.00 |
| | % RSD | | | | 4% | 0.0% | | | 1% | 0.0% |
| | Lower Limit | | | | 3.12 | 4.34 | | | 0.42 | 5.52 |
| | Upper Limit | | | | 5.80 | 4.80 | | | 0.77 | 6.10 |

Ratio: Lower Limit = 0.7 ´ Average ratio, Upper Limit = 1.3 ´ Average ratio
Retention Time (RT): Upper Limit = Average × 0.95, Upper Limit = Average × 1.05

TABLE 45

Corn Stover: representative glyphosate and N-acetylglyphosate confirmation results.
Matrix: Corn Stover
Confirmation Ions: Glyphosate: TIC (170 > 87.7, 60.1), N-acetylglyphosate: TIC (212 > 169.9, 87.7)

| Run ID | Sample Information | | Glyphosate | | | | N-acetylglyphosate | | | |
|---|---|---|---|---|---|---|---|---|---|---|
| | ng/g or ppb | Identification | 170 > 88 | 170 > 60 | Ratio | RT | 212 > 170 | 212 > 88 | Ratio | RT |
| 071105Smax-5 | 1 | 1 ppb Cal Std | 448 | 98 | 4.59 | 4.57 | 426 | 711 | 0.60 | 5.81 |
| 071105Smax-11 | 5 | 5.0 ppb Cal Std | 2283 | 527 | 4.33 | 4.57 | 1983 | 3335 | 0.59 | 5.78 |
| 071105Smax-16 | 10 | 10 ppb Cal Std | 4514 | 980 | 4.61 | 4.57 | 4002 | 6708 | 0.60 | 5.79 |
| 071105Smax-20 | 20 | 20 ppb Cal Std | 8888 | 2062 | 4.31 | 4.57 | 7926 | 13421 | 0.59 | 5.82 |
| 071305Gmax-6 | 50 | Grain LOQ 062905-1 | 337 | 104 | 3.24 | 4.56 | 368 | 533 | 0.69 | 5.81 |
| 071305Gmax-7 | 50 | Grain LOQ 062905-2 | 328 | 76 | 4.29 | 4.56 | 385 | 598 | 0.64 | 5.75 |

TABLE 45-continued

Corn Stover: representative glyphosate and N-acetylglyphosate confirmation results.
Matrix: Corn Stover
Confirmation Ions: Glyphosate: TIC (170 > 87.7, 60.1), N-acetylglyphosate: TIC (212 > 169.9, 87.7)

| | Sample Information | | Analyte Response (Fragment Ions peak areas; Ratio = base peak/minor peak; RT = peak retention time, min) | | | | | | | |
|---|---|---|---|---|---|---|---|---|---|---|
| | | | Glyphosate | | | | N-acetylglyphosate | | | |
| Run ID | ng/g or ppb | Identification | 170 > 88 | 170 > 60 | Ratio | RT | 212 > 170 | 212 > 88 | Ratio | RT |
| 071305Gmax-9 | 50 | Grain LOQ 062905-3 | 322 | 93 | 3.46 | 4.56 | 362 | 555 | 0.65 | 5.8 |
| 071305Gmax-10 | 50 | Grain LOQ 062905-4 | 320 | 94 | 3.39 | 4.56 | 382 | 657 | 0.58 | 5.84 |
| 071305Gmax-12 | 50 | Grain LOQ 062905-5 | 312 | 82 | 3.79 | 4.56 | 384 | 549 | 0.70 | 5.8 |
| 071305Gmax-14 | 500 | Grain 10X 062905-1 | 3268 | 762 | 4.29 | 4.56 | 3562 | 5914 | 0.60 | 5.81 |
| 071305Gmax-15 | 500 | Grain 10X 062905-2 | 3182 | 668 | 4.77 | 4.56 | 3474 | 5663 | 0.61 | 5.79 |
| 071305Gmax-17 | 500 | Grain 10X 062905-3 | 3113 | 714 | 4.36 | 4.56 | 3431 | 5432 | 0.63 | 5.8 |
| 071305Gmax-18 | 500 | Grain 10X 062905-4 | 3085 | 739 | 4.18 | 4.56 | 3452 | 5654 | 0.61 | 5.83 |
| 071305Gmax-21 | 500 | Grain 10X 062905-5 | 3080 | 654 | 4.71 | 4.56 | 3427 | 5468 | 0.63 | 5.81 |
| | Average | | | | 4.46 | 4.57 | | | 0.60 | 5.80 |
| | St Dev | | | | 0.16 | 0.00 | | | 0.00 | 0.02 |
| | % RSD | | | | 4% | 0.0% | | | 1% | 0.3% |
| | Lower Limit | | | | 3.12 | 4.34 | | | 0.42 | 5.51 |
| | Upper Limit | | | | 5.80 | 4.80 | | | 0.77 | 6.09 |

Ratio: Lower Limit = 0.7 ′ Average ratio, Upper Limit = 1.3 ′ Average ratio
Retention Time (RT): Upper Limit = Average × 0.95, Upper Limit = Average × 1.05

TABLE 46

Soybean forage: representative glyphosate and N-acetylglyphosate confirmation results.
Matrix: Soybean Forage
Confirmation Ions: Glyphosate: TIC (170 > 87.7, 60.1), N-acetylglyphosate: TIC (212 > 169.9, 87.7)

| | Sample Information | | Analyte Response (Fragment Ions peak areas; Ratio = base peak/minor peak; RT = peak retention time, min) | | | | | | | |
|---|---|---|---|---|---|---|---|---|---|---|
| | | | Glyphosate | | | | N-acetylglyphosate | | | |
| Run ID | ng/g or ppb | Identification | 170 > 88 | 170 > 60 | Ratio | RT | 212 > 170 | 212 > 88 | Ratio | RT |
| 072105SFax-6 | 1 | 1 ppb Cal Std | 428 | 103 | 4.18 | 4.57 | 383 | 645 | 0.59 | 5.81 |
| 072105SFax-11 | 5 | 5.0 ppb Cal Std | 1954 | 463 | 4.22 | 4.57 | 2123 | 3297 | 0.64 | 5.81 |
| 072105SFax-13 | 10 | 10 ppb Cal Std | 4045 | 970 | 4.17 | 4.57 | 4132 | 6792 | 0.61 | 5.82 |
| 072105SFax-17 | 20 | 20 ppb Cal Std | 7486 | 1666 | 4.49 | 4.57 | 8362 | 13359 | 0.63 | 5.8 |
| 072105SFax-8 | 50 | Soy Forage LOQ 072005-1 | 440 | 120 | 3.67 | 4.57 | 359 | 639 | 0.56 | 5.83 |
| 072105SFax-9 | 50 | Soy Forage LOQ 072005-2 | 432 | 112 | 3.85 | 4.56 | 348 | 586 | 0.59 | 5.86 |
| 072105SFax-12 | 50 | Soy Forage LOQ 072005-3 | 455 | 115 | 3.96 | 4.57 | 349 | 719 | 0.49 | 5.8 |
| 072105SFax-15 | 500 | Soy Forage 10X 072005-1 | 3813 | 867 | 4.39 | 4.57 | 3903 | 6421 | 0.61 | 5.83 |
| 072105SFax-16 | 500 | Soy Forage 10X 072005-2 | 3688 | 825 | 4.47 | 4.57 | 4004 | 6557 | 0.61 | 5.85 |
| | Average | | | | 4.26 | 4.57 | | | 0.62 | 5.81 |
| | St Dev | | | | 0.15 | 0.00 | | | 0.02 | 0.01 |
| | % RSD | | | | 4% | 0.0% | | | 4% | 0.1% |
| | Lower Limit | | | | 2.98 | 4.34 | | | 0.43 | 5.52 |
| | Upper Limit | | | | 5.54 | 4.80 | | | 0.80 | 6.10 |

Ratio: Lower Limit = 0.7 ′ Average ratio, Upper Limit = 1.3 ′ Average ratio
Retention Time (RT): Upper Limit = Average × 0.95, Upper Limit = Average × 1.05

TABLE 47

Soybean seed: representative glyphosate and N-acetylglyphosate confirmation results.
Matrix: Soybean Seed
Confirmation Ions: Glyphosate: TIC (170 > 87.7, 60.1), N-acetylglyphosate: TIC (212 > 169.9, 87.7)

| | Sample Information | | Analyte Response (Fragment Ions peak areas; Ratio = base peak/minor peak; RT = peak retention time, min) | | | | | | | |
|---|---|---|---|---|---|---|---|---|---|---|
| | | | Glyphosate | | | | N-acetylglyphosate | | | |
| Run ID | ng/g or ppb | Identification | 170 > 88 | 170 > 60 | Ratio | RT | 212 > 170 | 212 > 88 | Ratio | RT |
| 100505-SS-AX-4 | 1 | 1 CS + IS 1004 | 494 | 97 | 5.08 | 4.93 | 706 | 1144 | 0.62 | 6.28 |
| 100505-SS-AX-6 | 2 | 2 CS + IS 1004 | 876 | 177 | 4.96 | 4.93 | 1467 | 2496 | 0.59 | 6.28 |
| 100505-SS-AX-8 | 5 | 5 CS + IS 1004 | 2168 | 470 | 4.61 | 4.94 | 3702 | 6090 | 0.61 | 6.24 |
| 100505-SS-AX-10 | 10 | 10 CS + IS 1004 | 4537 | 955 | 4.75 | 4.93 | 7232 | 12357 | 0.59 | 6.27 |
| 100505-SS-AX-12 | 20 | 20 CS + IS 1004 | 9121 | 1939 | 4.70 | 4.94 | 15173 | 24642 | 0.62 | 6.26 |

TABLE 47-continued

Soybean seed: representative glyphosate and N-acetylglyphosate confirmation results.
Matrix: Soybean Seed
Confirmation Ions: Glyphosate: TIC (170 > 87.7, 60.1), N-acetylglyphosate: TIC (212 > 169.9, 87.7)

| Run ID | Sample Information | | Analyte Response (Fragment Ions peak areas; Ratio = base peak/minor peak; RT = peak retention time, min) | | | | | | | |
|---|---|---|---|---|---|---|---|---|---|---|
| | | | Glyphosate | | | | N-acetylglyphosate | | | |
| | ng/g or ppb | Identification | 170 > 88 | 170 > 60 | Ratio | RT | 212 > 170 | 212 > 88 | Ratio | RT |
| 100505-SS-AX-14 | 50 | 50 CS + IS 1004 | 22316 | 4965 | 4.49 | 4.94 | 37434 | 62891 | 0.60 | 6.26 |
| 100505-SS-AX-5 | 50 | Soy Seed AX L1 1004 | 252 | 45 | 5.56 | 4.92 | 606 | 1128 | 0.54 | 5.83 |
| 100505-SS-AX-7 | 50 | Soy Seed AX L2 1004 | 268 | 61 | 4.42 | 4.92 | 627 | 1158 | 0.54 | 5.86 |
| 100505-SS-AX-9 | 50 | Soy Seed AX L3 1004 | 275 | 61 | 4.49 | 4.93 | 673 | 1091 | 0.62 | 5.8 |
| 100505-SS-AX-11 | 500 | Soy Seed AX 10X1 1004 | 2570 | 556 | 4.63 | 4.92 | 6694 | 11048 | 0.61 | 5.83 |
| 100505-SS-AX-13 | 500 | Soy Seed AX 10X2 1004 | 2441 | 565 | 4.32 | 4.94 | 6844 | 11108 | 0.62 | 5.85 |
| | Average | | | | 4.77 | 4.94 | | | 0.60 | 6.27 |
| | St Dev | | | | 0.22 | 0.01 | | | 0.01 | 0.02 |
| | % RSD | | | | 5% | 0.1% | | | 2% | 0.2% |
| | Lower Limit | | | | 3.34 | 4.69 | | | 0.42 | 5.95 |
| | Upper Limit | | | | 6.20 | 5.18 | | | 0.78 | 6.58 |

Ratio: Lower Limit = 0.7 ′ Average ratio, Upper Limit = 1.3 ′ Average ratio
Retention Time (RT): Upper Limit = Average × 0.95, Upper Limit = Average × 1.05

TABLE 48

Soybean hay: representative glyphosate and N-acetylglyphosate confirmation results.
Matrix: Soybean Hay
Confirmation Ions: Glyphosate: TIC (170 > 87.7, 60.1), N-acetylglyphosate: TIC (212 > 169.9, 87.7)

| Run ID | Sample Information | | Analyte Response (Fragment Ions peak areas; Ratio = base peak/minor peak; RT = peak retention time, min) | | | | | | | |
|---|---|---|---|---|---|---|---|---|---|---|
| | | | Glyphosate | | | | N-acetylglyphosate | | | |
| | ng/g or ppb | Identification | 170 > 88 | 170 > 60 | Ratio | RT | 212 > 170 | 212 > 88 | Ratio | RT |
| 102505-SH-AX 5 | 1 | 1 CS + IS 1024 | 290 | 73 | 3.99 | 4.94 | 278 | 466 | 0.60 | 6.24 |
| 102505-SH-AX 7 | 2 | 2 CS + IS 1024 | 609 | 104 | 5.85 | 4.94 | 513 | 969 | 0.53 | 6.31 |
| 102505-SH-AX 9 | 5 | 5 CS + IS 1024 | 1549 | 378 | 4.10 | 4.93 | 1532 | 2532 | 0.61 | 6.28 |
| 102505-SH-AX 11 | 10 | 10 CS + IS 1024 | 2824 | 652 | 4.33 | 4.93 | 3055 | 4989 | 0.61 | 6.29 |
| 102505-SH-AX 13 | 20 | 20 CS + IS 1024 | 5890 | 1272 | 4.63 | 4.93 | 6265 | 9900 | 0.63 | 6.27 |
| 102505-SH-AX 4 | 50 | SH-102105-2 LOQ 1 | 185 | 51 | 3.61 | 4.93 | 230 | 402 | 0.57 | 6.38 |
| 102505-SH-AX 6 | 50 | SH-102105-3 LOQ 2 | 211 | 51 | 4.11 | 4.92 | 258 | 507 | 0.51 | 6.36 |
| 102505-SH-AX 8 | 50 | SH-102105-4 LOQ 3 | 190 | 46 | 4.10 | 4.95 | 236 | 400 | 0.59 | 6.3 |
| 102505-SH-AX 10 | 500 | SH-102105-5 10X 1 | 1807 | 361 | 5.01 | 4.92 | 2531 | 4131 | 0.61 | 6.24 |
| 102505-SH-AX 12 | 500 | SH-102105-6 10X 2 | 1775 | 394 | 4.50 | 4.92 | 2545 | 4028 | 0.63 | 6.24 |
| | Average | | | | 4.58 | 4.93 | | | 0.60 | 6.28 |
| | St Dev | | | | 0.75 | 0.01 | | | 0.04 | 0.03 |
| | % RSD | | | | 16% | 0.1% | | | 7% | 0.4% |
| | Lower Limit | | | | 3.20 | 4.69 | | | 0.42 | 5.96 |
| | Upper Limit | | | | 5.95 | 5.18 | | | 0.77 | 6.59 |

Ratio: Lower Limit = 0.7 ′ Average ratio, Upper Limit = 1.3 ′ Average ratio
Retention Time (RT): Upper Limit = Average × 0.95, Upper Limit = Average × 1.05

Additional validation trials for this method were conducted. Glyphosate, N-acetylglyphosate, and AMPA were fortified at 0.050 and 0.50 ppm levels in corn (forage, grain, and stover) and soybean (forage, seed, and hay) matrices. A VirTishear™ (Virtis Company Inc., Gardiner, N.Y.) homogenizer was used instead of a Tissumizer™ homogenizer to macerate tissues during extraction. An Applied Biosystems/MDS SCIEX API 4000 mass spectrometer was used instead of the Quattro Premier. Injection volumes were increased to compensate for decreased mass spectrometer sensitivity. Acceptable results were found. Data not shown. The API 4000 LC-MS/MS System instrumental conditions are provided in Table 49 and FIG. 27-30.

TABLE 49

API 4000 LC/MS/MS Conditions and Chromatograms
Applied Biosystems/MDS SCIEX API 4000 Acquisition Parameters (ESI interface, MRM mode)

| Period (min) | Analyte | Polarity (+/−) | Q1 (m/z) | Q3 (m/z) | Dwell (msecs) | CUR (psi) | GS1 (psi) | GS2 (psi) | TEM (°C.) | ihe | IS (V) | CAD (psi) | DP (V) | EP (V) | CE (V) | CXP (V) |
|---|---|---|---|---|---|---|---|---|---|---|---|---|---|---|---|---|
| 3.3–6.0 | AMPA | + | 111.90 | 30.00 | 700.00 | 10.00 | 20.00 | 50.00 | 400.00 | on | 4500 | 4.00 | 40.00 | 5.00 | 17.00 | 15.00 |
| | AMPA 13C 15N | | 113.90 | 32.00 | | | | | | | | | | | | |

TABLE 49-continued

API 4000 LC/MS/MS Conditions and Chromatograms
Applied Biosystems/MDS SCIEX API 4000 Acquisition Parameters (ESI interface, MRM mode)

| Period (min) | Analyte | Polarity (+/−) | Q1 (m/z) | Q3 (m/z) | Dwell (msecs) | CUR (psi) | GS1 (psi) | GS2 (psi) | TEM (°C.) | ihe | IS (V) | CAD (psi) | DP (V) | EP (V) | CE (V) | CXP (V) |
|---|---|---|---|---|---|---|---|---|---|---|---|---|---|---|---|---|
| 3.6-6.0 | glyphosate | + | 170.00 | 87.80 | 50.00 | 10.00 | 20.00 | 50.00 | 350.00 | on | 4500 | 4.00 | 28.00 | 5.00 | 13.00 | 10.00 |
|  |  |  | 170.00 | 59.80 |  |  |  |  |  |  |  |  | 32.00 | 4.50 | 24.00 | 10.00 |
| 3.6-6.0 | glyphosate 1,2-13C 15N |  | 173.00 | 90.80 |  |  |  |  |  |  |  |  | 28.00 | 5.00 | 13.00 | 15.00 |
| 5.8-8.2 | N-acetyl glyphosate | + | 212.00 | 170.00 | 400.00 | 10.00 | 20.00 | 50.00 | 350 | on | 4500 | 4.00 | 32.00 | 10.00 | 14.50 | 15.00 |
|  |  |  | 212.00 | 88.00 |  |  |  |  |  |  |  |  | 35.00 | 8.00 | 23.00 |  |

Period (min) values were adjusted to be consistent with times reported in Section 4.3.2 for HPLC using a guard column.

In summary, the analytical methods presently disclosed are suitable for the quantitation of glyphosate, N-acetylglyphosate, and AMPA and N-acetyl AMPA residues in corn and soybean matrices. The results support an LOQ of 0.050 mg/kg (ppm) with estimated LOD values of 0.004 mg/kg for glyphosate, 0.006 mg/kg for N-acetylglyphosate, and 0.007 mg/kg for AMPA.

This analytical method procedure was successfully applied to plum and lime matrices to demonstrate suitability in watery and acidic crop matrices, respectively, even though these crop types do not contain the gat trait and N-acetylglyphosate.

Overall average recoveries for each analyte and matrix in the validation trials ranged from 75% (glyphosate in soybean hulls) to 109% (AMPA in soybean oil) with maximum RSD of 19% (AMPA in corn oil).

Residue confirmation for glyphosate and N-acetylglyphosate was demonstrated at 0.050 mg/kg (LOQ) and 0.50 mg/kg fortification levels based on retention time and the relative ratios of two MS/MS parent-to-fragment ion transitions detected during sample analysis.

Example 6

Summary

N-acetylglyphosate, aminomethyl-phosphonic acid (AMPA), and N-acetyl aminomethylphosphonic acid (N-acetyl AMPA) were examined. This study was designed to demonstrate the utility, ruggedness, and efficiency of the method. The method is designed to measure glyphosate and metabolites in plant matrices with a limit of quantitation (LOQ) of 0.05 ppm. The method's reported LOQ of 0.05 ppm in glyphosate equivalents for both glyphosate and metabolites was confirmed by obtaining individual recoveries within the acceptable range of 70 to 120% for controls fortified five times at 0.05 ppm in grapes and soybean seed.

Performance of the subject method was successfully validated for the quantitation of glyphosate and metabolites in grapes and soybean seed at the method LOQ and respective tolerance levels for each matrix. The method was successfully validated in grapes with one trial. Two trials were required for successful validation of soybean seed. A summary of the results is presented in the following table.

TABLE 54

Summary of Recoveries

| SAMPLE MATRIX | LEVEL (PPM) | GLYPHOSATE AVERAGE % | RANGE | AMPA AVERAGE % | RANGE | N-ACETYL GLYPHOSATE AVERAGE % | RANGE | N-ACETYL AMPA AVERAGE % | RANGE | N |
|---|---|---|---|---|---|---|---|---|---|---|
| Soybean Seed | 0.050 (LOQ) | 96 ± 13 | 83-113 | 91 ± 10 | 78-105 | 84 ± 3.8 | 81-90 | 96 ± 5.0 | 88-102 | 5 |
|  | 20.0 | 85 ± 7.0 | 73-90 | 89 ± 10 | 74-99 | 90 ± 4.3 | 83-95 | 111 ± 16 | 86-126 | 5 |
| Overall Average |  | 90 ± 12 | 73-113 | 90 ± 9.3 | 74-105 | 87 ± 4.9 | 81-95 | 103 ± 14 | 86-126 | 10 |
| Grapes | 0.050 (LOQ) | 81 ± 8.3 | 72-93 | 81 ± 3.1 | 76-84 | 95 ± 3.5 | 92-99 | 93 ± 9.0 | 80-101 | 5 |
|  | 0.20 | 80 ± 7.3 | 70-89 | 73 ± 3.3 | 70-78 | 86 ± 3.7 | 80-90 | 82 ± 4.7 | 77-88 | 5 |
| Overall Average |  | 81 ± 7.4 | 70-93 | 77 ± 5.1 | 70-84 | 91 ± 6.0 | 80-99 | 88 ± 9.0 | 77-101 | 10 |

A minor method modification made during the course of this method was to dilute the final soybean seed extracts of the 20 ppm fortification samples 100-fold prior to LC/MS/MS analysis to adjust residue concentrations within the calibration curve. Instrument parameters were also adjusted to increase sensitivity.

This LC/MS/MS method with multiple reaction monitoring (MRM) detection was free of interferences at the retention times corresponding to glyphosate and metabolites in unfortified samples. Acceptable recoveries (70 to 120%) were achieved for five replicate analyses of control samples fortified at two levels in grapes and soybean seed. One recovery of 126% of N-acetyl AMPA in soybean seed was accepted on the basis that recoveries for soybean seed were consistent and average recoveries of this metabolite at each fortification level were within the acceptable range of 70 to 120%.

For all matrices, unfortified control samples showed no detectable residues of glyphosate or metabolites.

Fortification levels in this study were chosen to provide method performance data at the method LOQ and at the proposed tolerance levels. The LOQ was 0.050 ppm in glyphosate equivalents for all analytes in all matrices. Grapes were fortified with all analytes at the proposed tolerance level of 0.20 ppm in glyphosate equivalents while soybean seed was fortified at the proposed tolerance level of 20.0 ppm in glyphosate equivalents. Results presented in the summary tables reflect the actual concentration of each compound; not glyphosate equivalents.

The analytical method was performed without any significant modifications. Successful validation sets were achieved on the second attempt for soybean seed and the first attempt for grapes. This independent laboratory validation study demonstrated that the analytical method is acceptable for the quantitation of glyphosate and metabolites in soybean seed and grapes.

Test System

The subject method is applicable for the quantitation of glyphosate and glyphosate metabolites in various crop matrices. Grapes and soybean seed were chosen to validate the analytical method. The grape control matrix was purchased from an outside source (organic food store). The sample was stored frozen and processed prior to being analyzed to verify that the control was free of interferences at the appropriate retention times. The soybean seed control matrix was provided by ABC Laboratories, Inc., 7200 E. ABC Lane, Columbia, Mo.

Equipment

The following equipment items were used in the conduct of this independent laboratory validation.

Instrumentation/Chromatography:

MDS Sciex API 4000 LC-MS/MS System, comprised of:
MDS Sciex API 4000 MS/MS, Serial No. V04560403 (Applied Biosystems Group, Foster City, Calif.), equipped with a TurboIonSpray interface and Analyst software version 1.4
HPLC Column: 4.6 mm i.d.×150 mm, Phenomenex Luna Phenyl Hexyl, Serial No. 208752-1, 3-µm diameter packing Part No. 00F-4256-E0 (Phenomenex, Torrance, Calif.)
Ten Port Electrically Actuated Valve, Serial No. EM2M06183 (Valco Instruments Co. Inc., Houston, Tex.)
Shimadzu LC-10ADVP HPLC pumps, Serial Nos. C2096 41 53748US and C2096 41 53747 US (Shimadzu US Manufacturing Inc., Columbia, Md.)
Shimadzu SiL-HTC Autosampler, Serial No. L2002 42 50137US (Shimadzu US Manufacturing Inc., Columbia, Md.)
Shimadzu CTO-10AVP Column Oven, Serial No. C2102 41 50408 (Shimadzu US Manufacturing Inc., Columbia, Md.)
Shimadzu DGU-14A Degasser, Serial No. SS132668 (Shimadzu US Manufacturing Inc., Columbia, Md.)
Phenomenex $C_{18}$ Guard Column, 4×3 mm, Part No. AJO-4287

Solid-Phase Extraction Equipment/Supplies:

24-port SPE vacuum manifold (Burdick and Jackson, Muskegon, Mich.)
Bond Elute SPE cartridges: $C_{18}$, 500 mg/6 cc, Cat No. 12102052, Lot No. 0723704 (Varian, Inc. Palo Alto, Calif.)
Oasis MAX SPE cartridges, 500 mg/6 ml, Cat. No. 1860000865, Lot No. 001336341A (Waters Corporation, Millford, Mass.)
Oasis MCX SPE cartridges, 500 mg/6 ml, Cat. No. 1860000776, Lot No. 002236322A (Waters Corporation, Millford, Mass.)

Labware 15 ml Polypropylene Centrifuge Tubes, Part No. 20171-024 (VWR, West Chester, Pa. 19380)
50 ml Polypropylene Centrifuge Tubes, Part No. 89004-367 (VWR, West Chester, Pa. 19380)
Borosilicate glass scintillation vials with cap, 20 ml Part No. 986546 (Wheaton, Millville N.J. 08332)
HPLC vials, 2 ml, Part No. 5182-0716 (Agilent Technologies, Palo Alto, Calif. 94306)
HPLC vial caps, Part No. 5182-0717 (Agilent Technologies, Palo Alto, Calif. 94306)
Disposable Transfer Pipettes, 3 ml, Part No. 16001-176 (VWR, West Chester, Pa. 19380)
Pyrex graduated cylinders, 100 ml, with stoppers, Part Nos. CLS2982250 and CLS3022250 (Sigma-Aldrich, St. Louis, Mo. 63103)
HDPE widemouth polypropylene bottles, 250 ml, with linerless cap, Part No. 209548SP (Wheaton, Millville, N.J. 08332)
Syringe filter, Nylon 0.45 µm, 30-mm diameter filter unit, Part. No. F2500-1 (National Scientific, Rockwood, Tenn. 37854)
Syringe filter, Nylon 0.20 µm, 17-mm diameter filter unit, Part. No. F2513-2 (National Scientific, Rockwood, Tenn. 37854)

Reagents

Acetone—HPLC-grade, Catalog No. AX0115-1, EMD (Chemicals, Gibbstown, N.J.)
Acetic Acid—Glacial, Catalog No. 9515-03 (J. T. Baker, Philipsburg, N.J.)
Acetonitrile—HPLC-grade, Catalog No. AX0145-1 (used for LC/MS/MS needle rinse only) (EMD Chemicals, Gibbstown, N.J.)
Ammonium Hydroxide—28% $NH_3$ in water 99.99+% pure (Sigma-Aldrich, St. Louis, Mo. 63103)
Methylene Chloride —HPLC-grade, Catalog No. DXO838-1 (EMD chemicals, Gibbstown, N.J.)
Formic acid, 99.0% pure, Fluka, Catalog No. 06440 (Sigma-Aldrich, St. Louis, Mo. 63103)
Methanol-HPLC-grade Catalog No. MX0475-1 (EMD Chemicals, Gibbstown, N.J.)
Phosphoric acid—Baker Analyzed 86.0% pure, Catalog No. 7664-38-2 (J. T. Baker, Philipsburg, N.J.)
Trifluoroacetic acid, 99.0% pure, Fluka, Catalog No. 91703 (Sigma-Aldrich, St. Louis, Mo. 63103)
Water—Ultra high purity, obtained from Purelab Classic UV UHP Water System Principles of the Analytical Method Glyphosate, N-acetylglyphosate, AMPA, and N-acetyl AMPA were extracted from grape and soybean seed samples into dilute aqueous acid/methanol (96/4, v/v) using a probe homogenizer. Three extractions were made for quantitative recovery of analytes and then continued with purification and analysis.

Purification of glyphosate and N-acetylglyphosate: An aliquot of extract was partitioned with methylene chloride and the aqueous fraction was recovered and filtered to remove particulates. Approximately 10 ml of the aqueous fraction was collected following filtration through a $C_{18}$ SPE cartridge. An aliquot of the eluate collected from the $C_{18}$ SPE was diluted and applied to a MAX SPE cartridge. The analytes were eluted from the MAX sorbent in 1% TFA in methanol/water (90/10) solution following several solution rinses. The MAX eluate was evaporated to dryness and redissolved in aqueous 0.02 M aqueous phosphoric acid, filtered, and analyzed for glyphosate and N-acetylglyphosate. Following partitioning, soybean seed samples were subjected to a steam bath for approximately 15 minutes to precipitate additional material in the extract prior to particulate filtration.

Purification of AMPA and N-acetyl AMPA: A second aliquot of the eluate, collected from the $C_{18}$ SPE described above, was processed through a MCX SPE cartridge.

Samples were applied to the cartridge, and then eluted with water and methanol. An N-Evap is used to blow down solvents; a concentrated aqueous solution of phosphoric acid was added so that the final solution equals 0.02 M aqueous phosphoric acid. The samples were then analyzed for AMPA and N-acetyl AMPA. Soybean seed samples were diluted in methanol before application to the cartridge.

Modifications, Interpretations, and Critical Steps

A minor method modification was made for the validation of glyphosate in soybean seed. The final extracts were diluted 100-fold prior to LC/MS/MS analysis to incorporate residues within the calibration curve.

Some API 4000 LC/MS/MS instrumental parameters were modified to optimize sensitivity. The modifications included: increasing source temperature, adjusting collision energy potential and adjusting gas flow settings.

In Step 2.2 of example 4A of the method, the temperature for the steam bath was not specified. During correspondence with the Sponsor, a temperature of 85° C. was recommended to more effectively precipitate protein from the matrix.

In Step 5.0 of example 4C, use of a 50 ml or 20 ml collection container with a flat or gently sloped bottom was recommended. From this, it was assumed that a 15-ml centrifuge tube would be adequate. However, based upon the low recoveries obtained in soybean seed Trial 1, Set 3, it was determined that a 20-ml scintillation vial, which has a flatter bottom and more surface area, is necessary for effective evaporation.

Instrumentation

Chromatography: Reversed-phase liquid chromatography was used to separate glyphosate and its metabolites from co-extractants. A Phenomenex Luna Phenyl Hexyl column was selected.

TABLE 55

HPLC Conditions

| | | | | | |
|---|---|---|---|---|---|
| System: | MDX Sciex API 4000 LC/MS/MS | | | | |
| Column: | Phenomenex Luna Phenyl Hexyl, 4.6 × 150 mm, 3 µm diameter packing | | | | |
| Column Temperature: | 40° C. | | | | |
| Injection Volume: | 50-100 µL | | | | |
| Conditions: | A: aqueous 0.2M formic acid<br>B: methanol | | | | |
| | Time | % A | % B | Flowrate (ml/min) | Comments |
| | 0.0 | 95 | 5 | 0.35 | No post-column split to MS |
| | 10.0 | 40 | 60 | 0.35 | |
| | 10.05 | 1 | 99 | 0.35 | |
| | 10.1 | 1 | 99 | 0.35 | |
| | 10.2 | 1 | 99 | 0.5 | |
| | 13.0 | 1 | 99 | 0.5 | |
| | 13.1 | 95 | 5 | 0.5 | Column re-equilibration |
| | 18.0 | 95 | 5 | 0.5 | End run |
| Glyphosate Retention Time: | ~3.6-6.0 min | | | | |
| AMPA Retention Time: | ~3.3-6.0 min | | | | |
| N-AMPA Retention Time: | ~5.8-8.2 min | | | | |
| N-acetylglyphosate Retention Time: | ~5.8-8.2 min | | | | |
| Total Run Time: | 18.0 min | | | | |

LC/MS/MS Analysis

Analysis of glyphosate and its metabolites was performed using a MDS Sciex API 4000 LC/MS/MS, equipped with a TurboIonSpray source, and operated in MRM, positive ion mode. Quantitation was based on the integrated area of a single ion transition for each analyte using a linear regression with a 1/x weighting on Analyst software version 1.4. A summary of representative experimental conditions is provided in Table 56.

TABLE 56

MDS Sciex API 4000 MS/MS Mass Spectrometer Conditions

| ANALYTES | IONS MONITORED | CXP (COLLISION CELL EXIT POTENTIAL) | DP (DECLUSTERING POTENTIAL) | DWELL TIME (MSEC) | COLLISION ENERGY |
|---|---|---|---|---|---|
| Glyphosate | 170.0→ 87.3 AMU | 15 V | 50 V | 200 | 13 |
| Glyphosate | 170.0→ 60.0 AMU | 10 V | 50 V | 200 | 25 |
| AMPA | 112.1→ 30.2 AMU | 5.0 V | 45 V | 200 | 17.5 |
| N-acetylglyphosate | 212.0→ 170.2 AMU | 14 V | 30 V | 200 | 15 |
| N-acetylglyphosate | 212.0→ 87.9 AMU | 14 V | 37 V | 200 | 25 |
| N-acetyl AMPA | 154.0→ 112.1 AMU | 16 V | 20 V | 200 | 13 |

TABLE 56-continued

MDS Sciex API 4000 MS/MS Mass Spectrometer Conditions

| ANALYTES | IONS MONITORED | CXP (COLLISION CELL EXIT POTENTIAL) | DP (DECLUSTERING POTENTIAL) | DWELL TIME (MSEC) | COLLISION ENERGY |
|---|---|---|---|---|---|
| N-acetyl AMPA | 154.0 → 30.2 AMU | 10 V | 23 V | 200 | 38 |
| AMPA IS | 113.1 → 30.2 AMU | 5 V | 45 V | 200 | 17.5 |
| Glyphosate IS | 173.1 → 91.0 AMU | 18 V | 30 V | 200 | 15 |

TABLE 56

| ANALYTES | ION SPRAY VOLTAGE | CEM VOLTAGE | SOURCE TEMPERATURE | CURTAIN GAS SETTING | GS1 SETTING | GS2 SETTING | CAD SETTING |
|---|---|---|---|---|---|---|---|
| Glyphosate | 4500 V | 2500 V | 550° C. | 20 | 20 | 20 | 12 |
| AMPA | 4500 V | 2500 V | 450° C. | 10 | 35 | 50 | 4 |

Calibration Procedure

Calibration standards were embedded with samples in each set and typically progressed from low to high concentrations. The response factor of each calibration standard was calculated by dividing the analyte peak area of each standard by the analyte concentration for that standard. The average response was calculated for calibration standards injected with each set.

Results and Discussion

Detector Response

Calibration standards were analyzed over the range of 0.5 to 100 ng/ml. The response of the MS/MS detector was linear with 1/x weighting over the range of standards analyzed. Detector response was stable throughout the course of each analytical run as was demonstrated by standard accuracy values.

Control Samples

There were no interference peaks detected at the retention time for either glyphosate or its metabolites in duplicate unfortified control samples analyzed concurrently with each validation trial.

Trial 1, Soybean Seed

The first trial for soybean seed (Set 3) failed due to low recoveries observed for glyphosate and each metabolite. Results of Trial 1 are summarized in table 57.

Following the analysis of the first trial for soybean seed it was determined that the low recoveries of glyphosate were likely due to samples not being completely dry from blow down, and the lack of internal standard. The no detection of N-acetyl AMPA was likely related to retention time shift from residual TFA in final solution due to samples not being completely dry from blow down. Further all method development and validation work had been performed at temperatures of at least 80° C. during the steam bath steps. The temperature of the steam bath in the first trial for soybean seed was 45° C. This may have not promoted proteins within the matrix to precipitate out, which could have suppressed the analytes during LCMS/MS analysis. The addition of glyphosate and AMPA internal standards would also adjust for suppression and drift during LCMS/MS analysis.

Trial 2, Soybean Seed

The second soybean seed trial (Set 4) was analyzed according to the procedure given in the analytical method with clarifications in correspondence following the failure of the first trial. A set of new calibration standards, with the internal standards incorporated, were prepared for analysis of the second tryout. The glyphosate extracts were blown down in 20-ml glass scintillation vials to ensure complete dryness. Internal standard was added to all samples before analysis.

Recoveries for glyphosate, AMPA, and N-acetylglyphosate were within the acceptable range of 70 to 120%. N-acetyl AMPA had one recovery of 126%, which is above the acceptable range of 70 to 120%. However, these results were

TABLE 57

Summary of Recoveries for Failed Soybean Seed: Trial 1

| SAMPLE MATRIX | LEVEL (PPM) | GLYPHOSATE AVERAGE % | RANGE | AMPA AVERAGE % | RANGE | N-ACETYL GLYPHOSATE AVERAGE % | RANGE | N-ACETYL AMPA AVERAGE % | RANGE | N |
|---|---|---|---|---|---|---|---|---|---|---|
| Soybean Seed | 0.050 (LOQ) | 81 ± 6.9 | 70-89 | 71 ± 3.6 | 67-76 | 68 ± 4.4 | 65-76 | 0 | 0 | 5 |
| | 20.0 | 54 ± 7.4 | 43-62 | 47 ± 2.8 | 43-51 | 61 ± 12 | 44-73 | 0 | 0 | 5 |
| Overall Average | | 67 ± 16 | 43-89 | 59 ± 13 | 43-76 | 65 ± 9.7 | 44-76 | 0 | 0 | 10 |

The first trial for soybean seed was analyzed according to the procedure given in the analytical method, except that glyphosate and AMPA stable isotopes were not used as internal standards and the collection vessel for MAX SPE was not consistent with the larger volume and dimensions recommended in the method.

accepted on the basis that they were consistent, and the average recovery values for each fortification level were within the acceptable range of 70 to 120%, thus establishing successful method validation for the analysis of glyphosate and metabolites in soybean seed. Calibration data and exemplary chromatograms are not shown. The recovery data for glyphosate and metabolites are presented in table 58.

TABLE 58

Summary of Glyphosate Recoveries for Successful Soybean Seed: Trial 2

| SAMPLE MATRIX | LEVEL (PPM) | GLYPHOSATE AVERAGE % | RANGE | AMPA AVERAGE % | RANGE | N-ACETYL GLYPHOSATE AVERAGE % | RANGE | N-ACETYL AMPA AVERAGE % | RANGE | N |
|---|---|---|---|---|---|---|---|---|---|---|
| Soybean Seed | 0.050 (LOQ) | 96 ± 13 | 83-113 | 91 ± 10 | 78-105 | 84 ± 3.8 | 81-90 | 96 ± 5.0 | 88-102 | 5 |
| | 20.0 | 85 ± 7.0 | 73-90 | 89 ± 10 | 74-99 | 90 ± 4.3 | 83-95 | 111 ± 16 | 86-126 | 5 |
| Overall Average | | 90 ± 12 | 73-113 | 90 ± 9.3 | 74-105 | 87 ± 4.9 | 81-95 | 103 ± 14 | 86-126 | 10 |

Trial 1, Grapes

Figure 31:
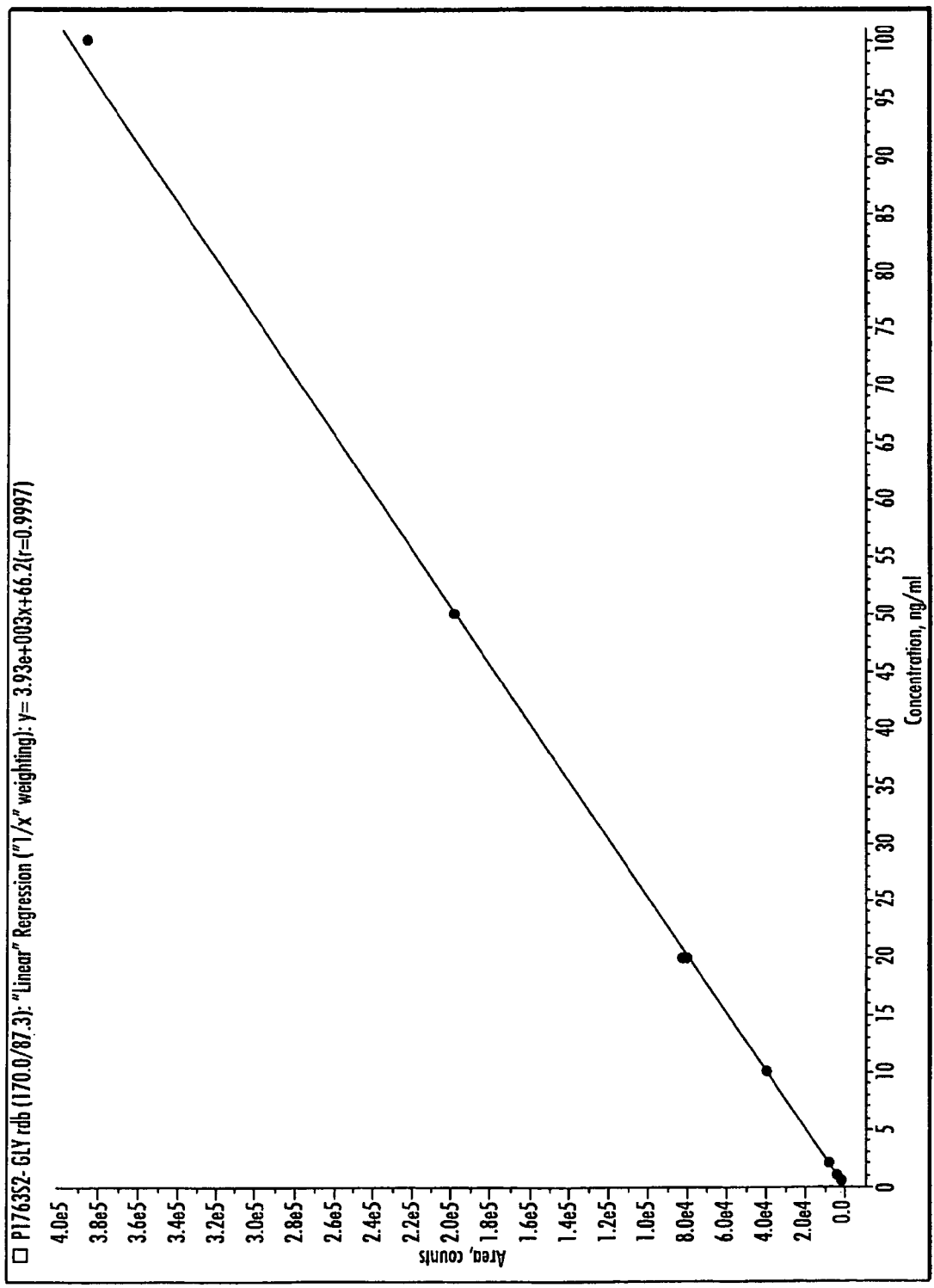
FIG. 31 provides a calibration curve for glyphosate, grapes, Trial 1, Set 2.
Figure 32:
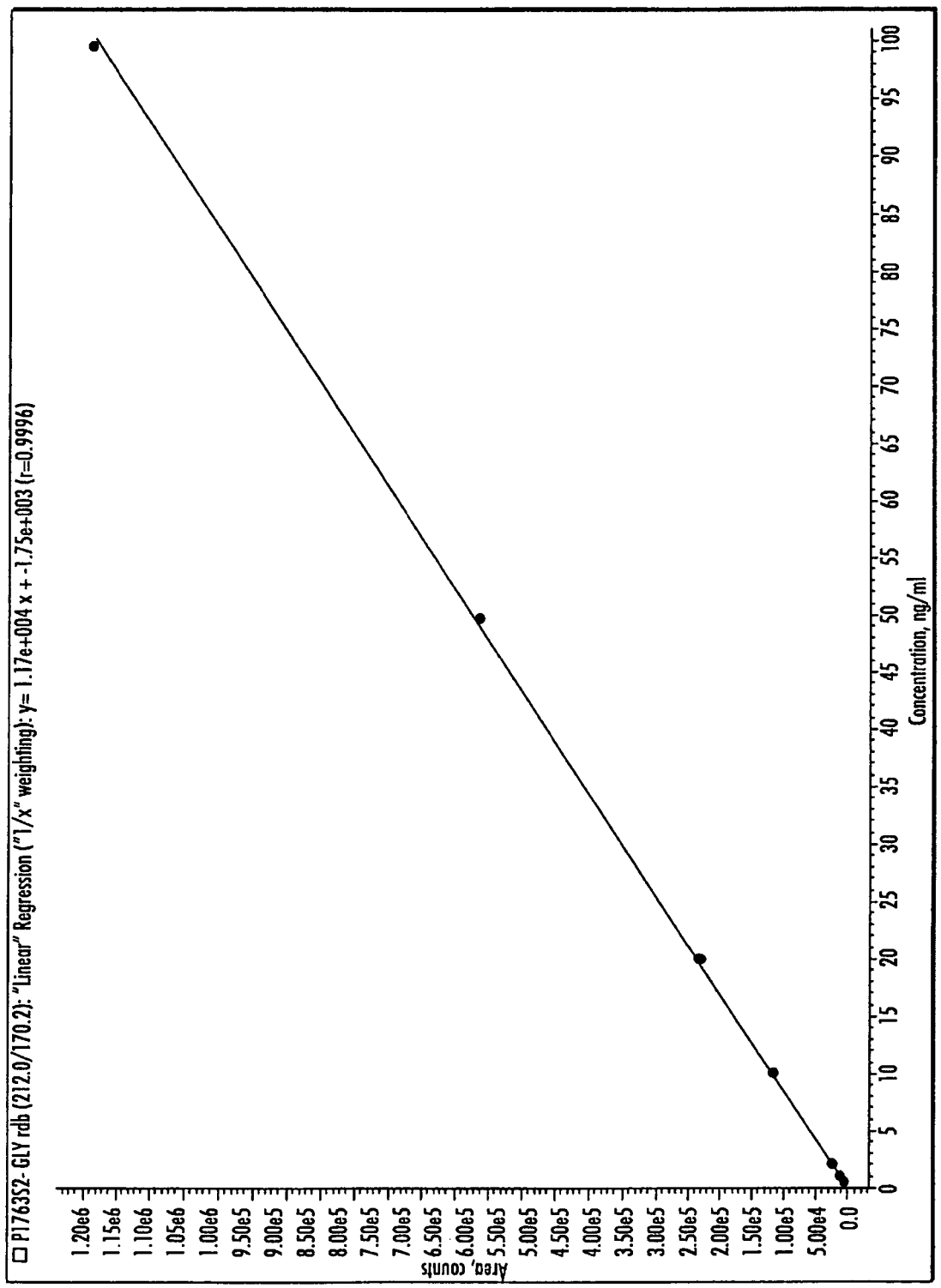
FIG. 32 provides a calibration curve for N-Acetylglyphosate, grapes, Trial 1, Set 2.
Figure 33:
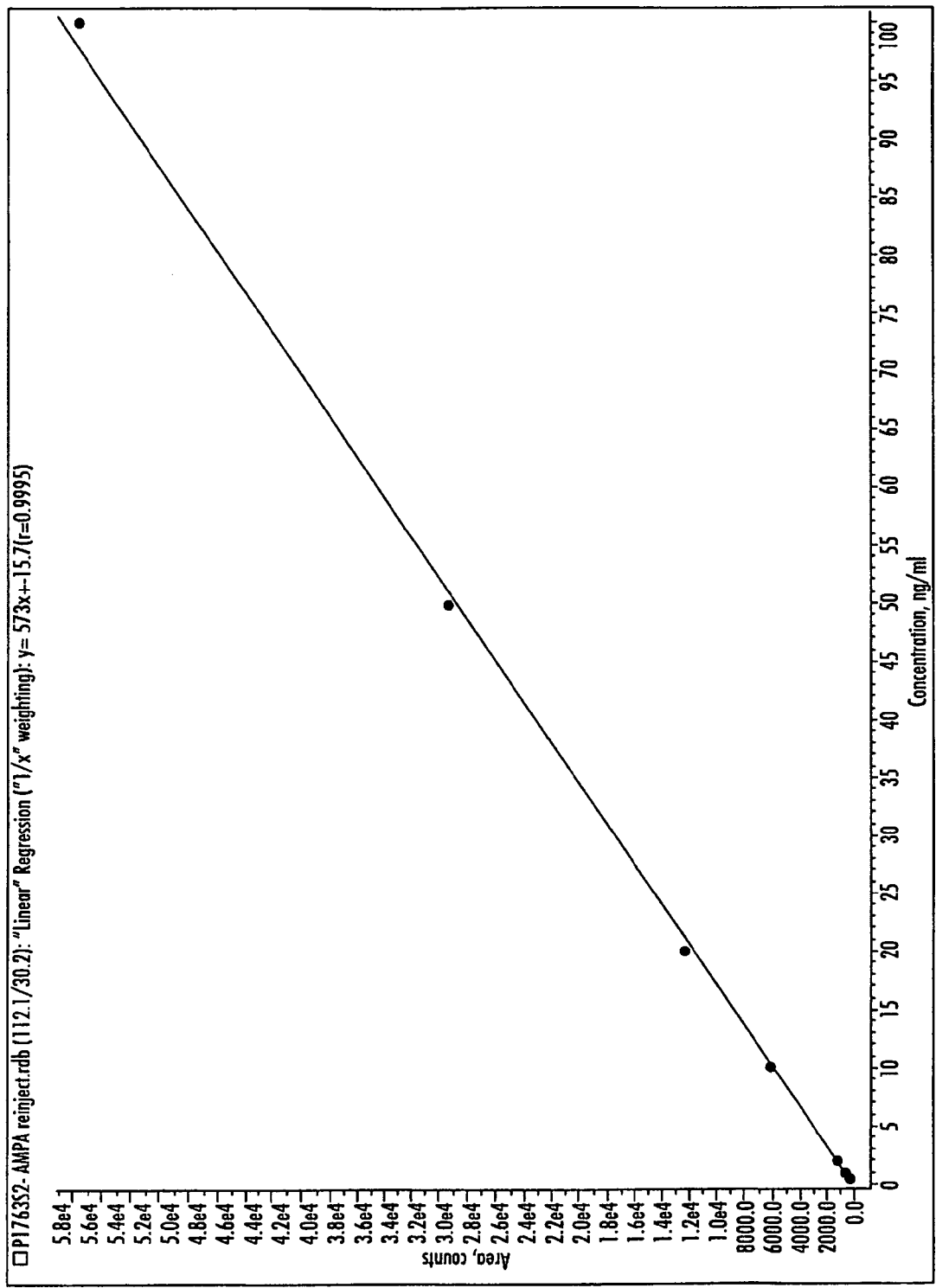
FIG. 33 provides a calibration curve for AMPA, grapes, Trial 1, Set 2.
Figure 34:
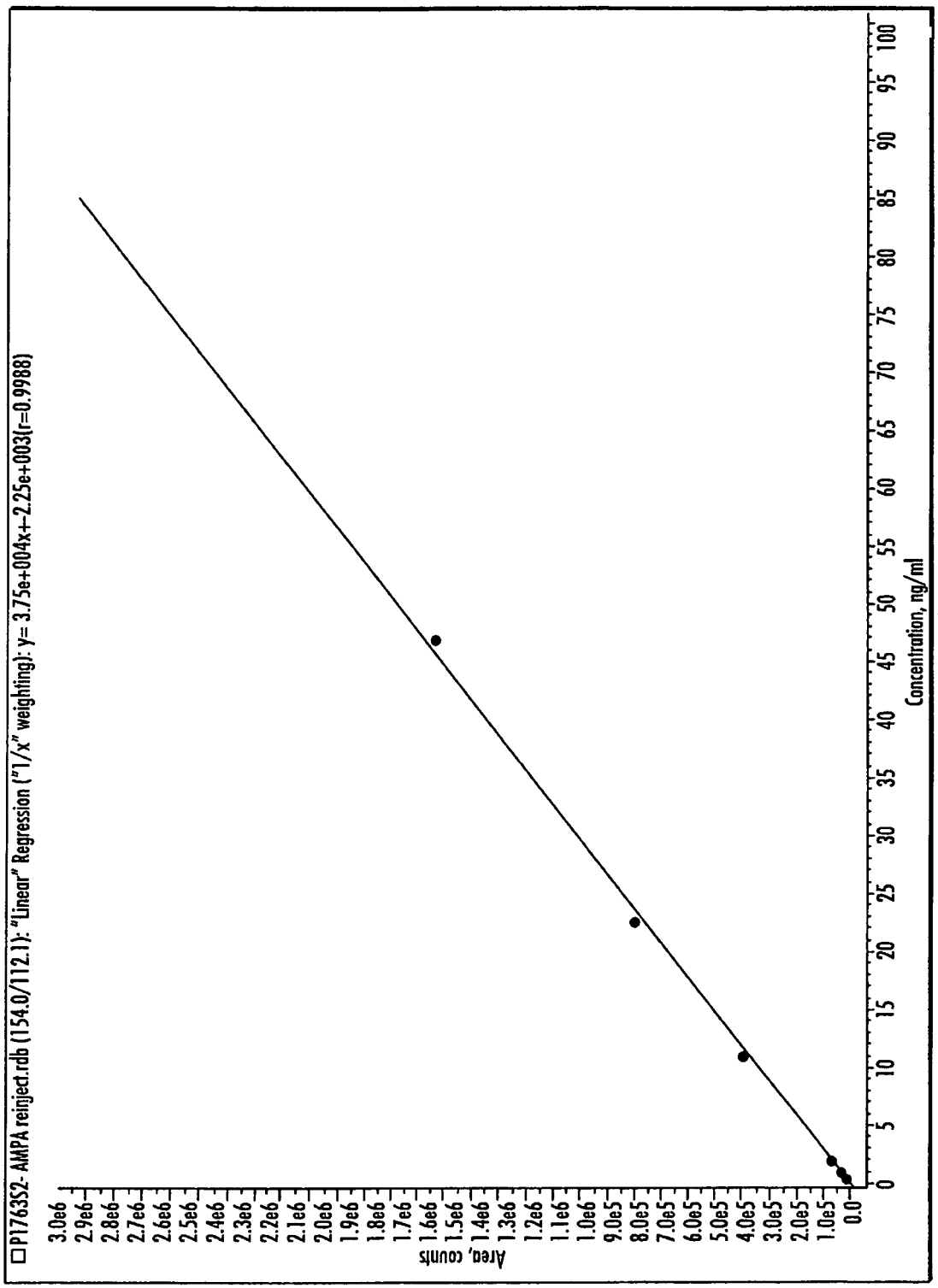
FIG. 34 provides a calibration curve for N-Acetyl AMPA, grapes, Trial 1, Set 2.
Figure 35:
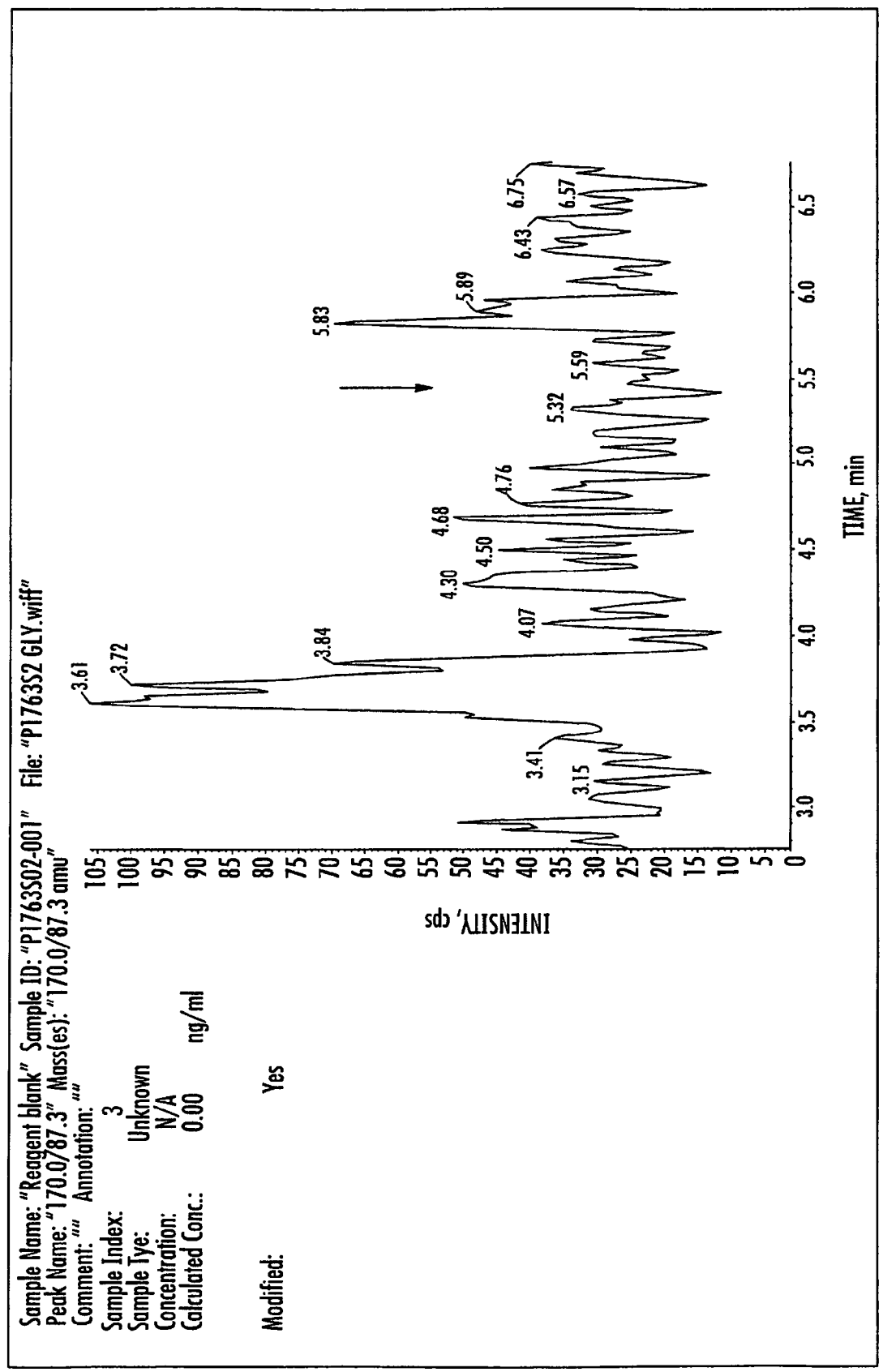
FIG. 35 provides a representative chromatogram for reagent blank, glyphosate, grapes, Trial 1, Set 2.
Figure 36:
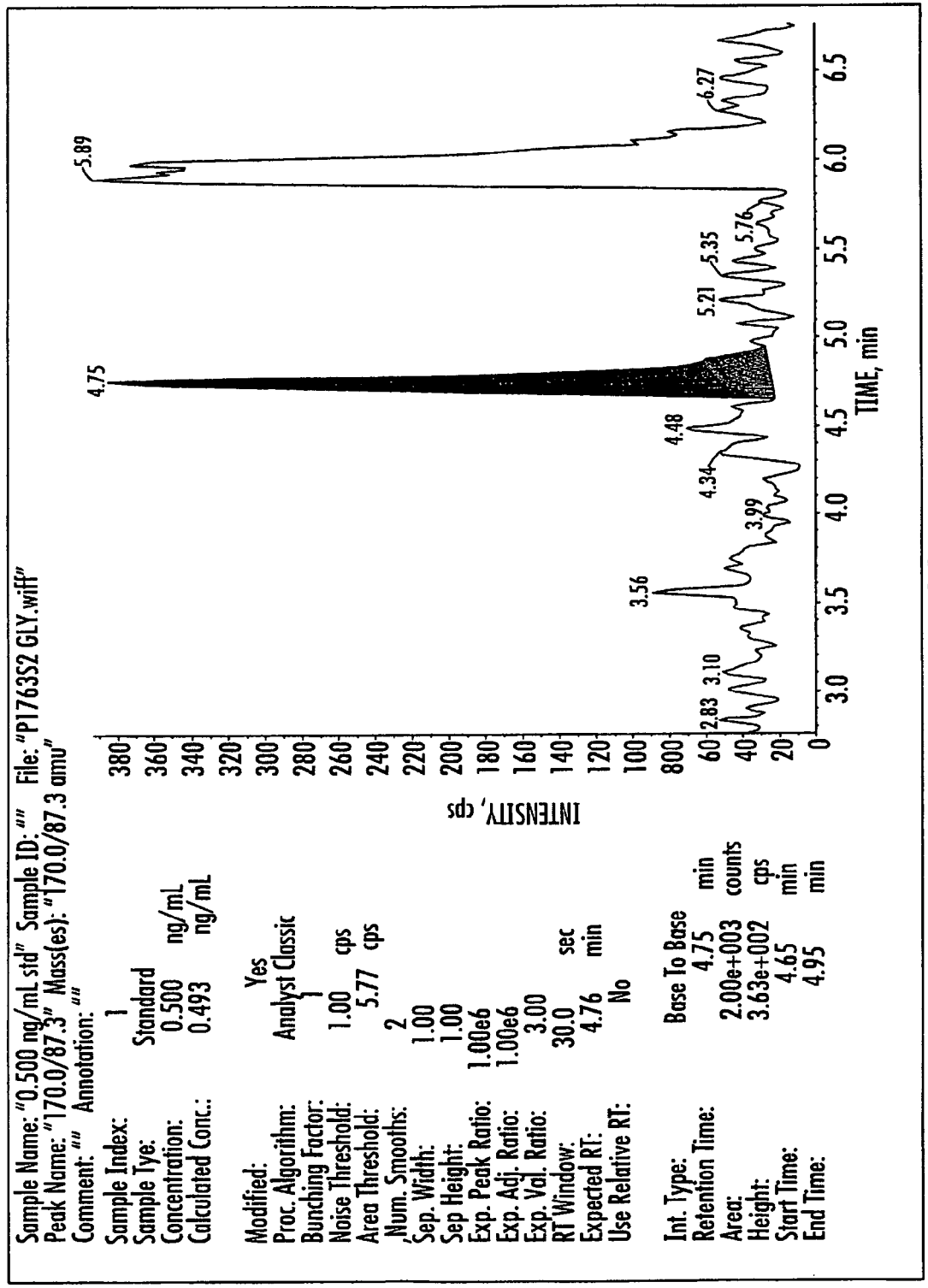
FIG. 36 provides a representative chromatogram for 0.500 ng/ml calibration standard, glyphosate, grapes, Trial 1, Set 2.
Figure 37:
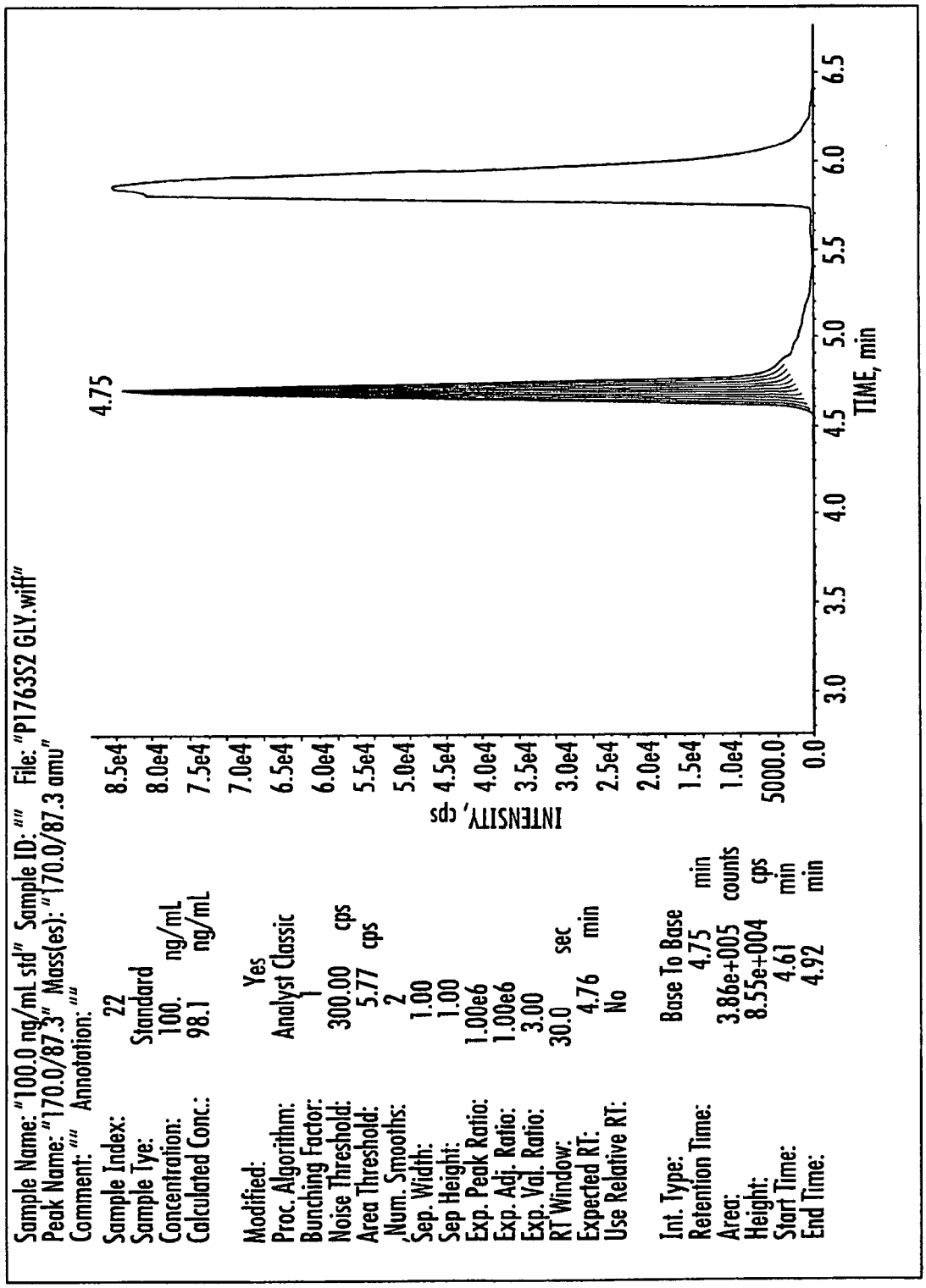
FIG. 37 provides a representative chromatogram for 100 ng/ml calibration standard, glyphosate, grapes, Trial 1, Set 2.
Figure 38:
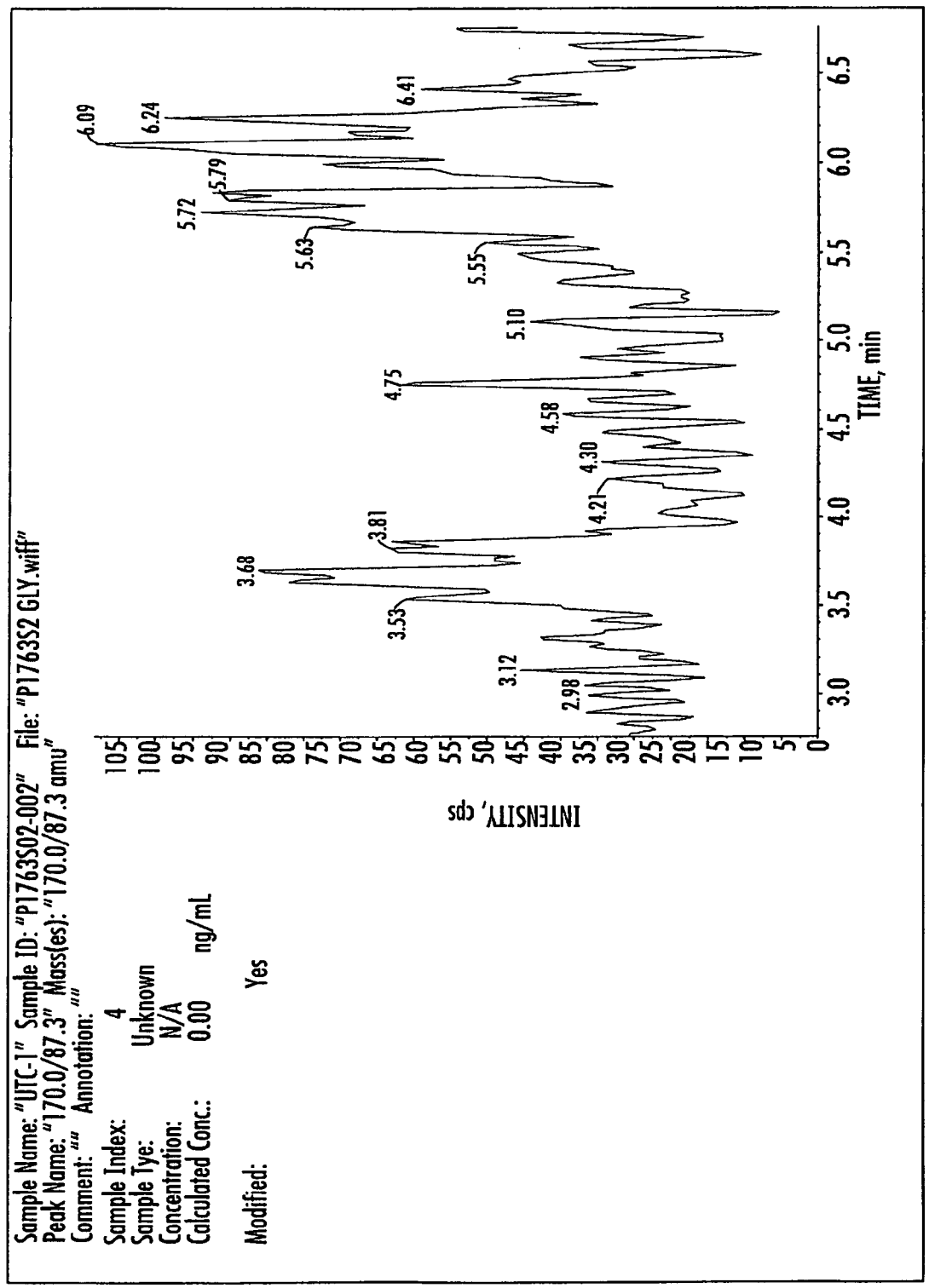
FIG. 38 provides a representative chromatogram for P1763S02-002, untreated control sample, glyphosate, grapes, Trial 1, Set 2.
Figure 39:
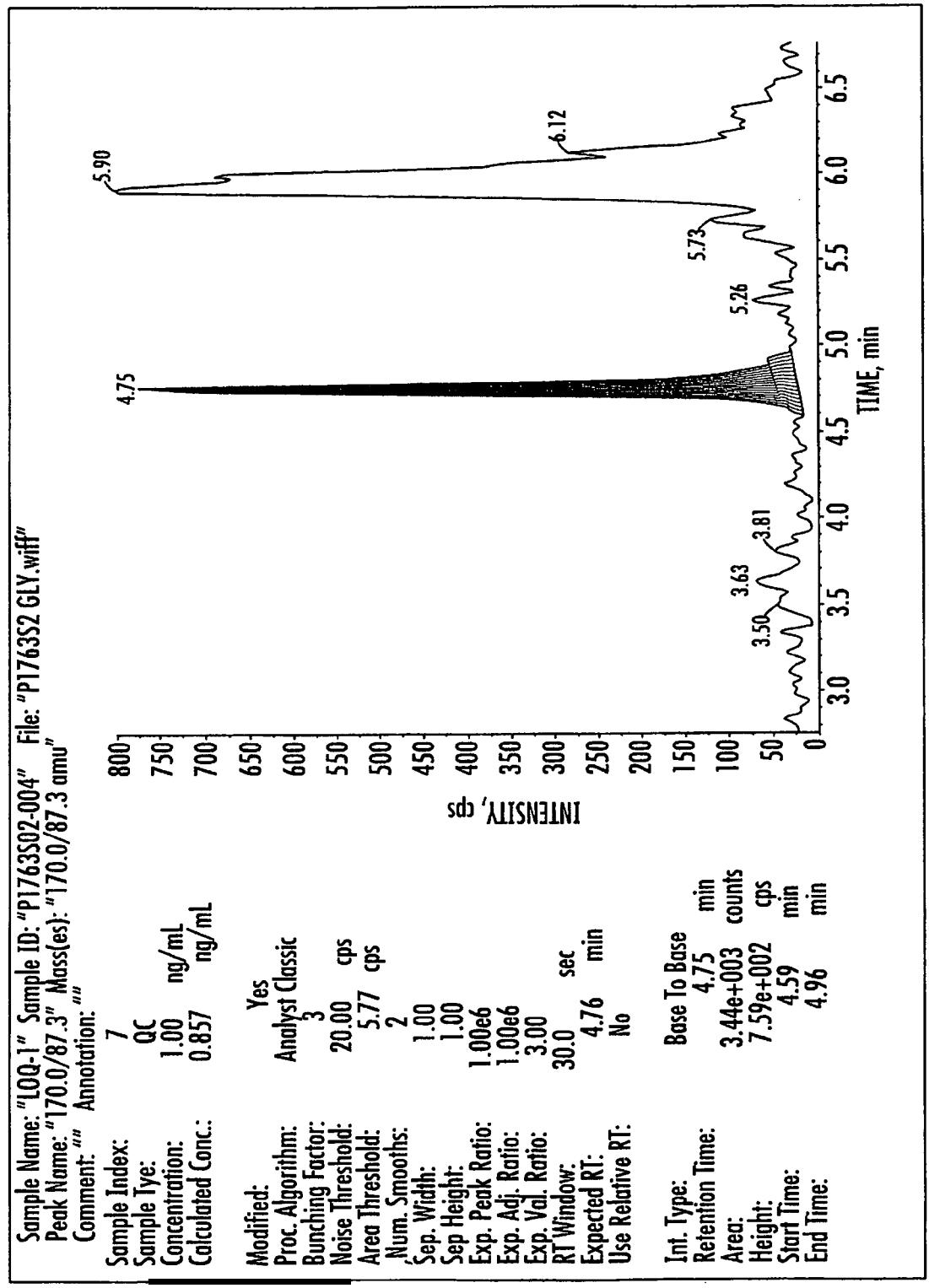
FIG. 39 provides representative chromatogram for P1763S02-004, sample fortified at LOQ, glyphosate, grapes, Trial 1, Set 2.
Figure 40:
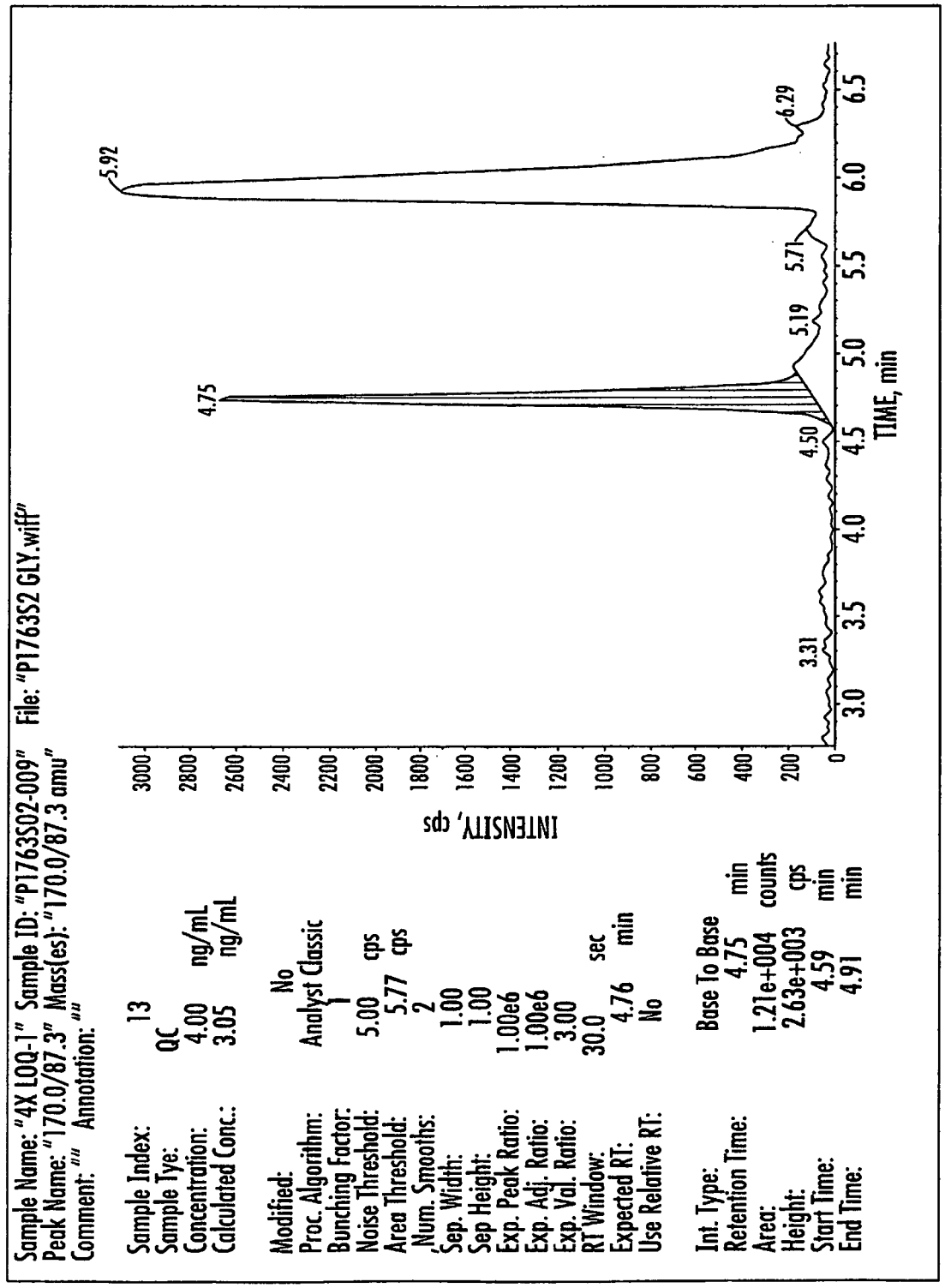
FIG. 40 provides representative chromatogram for P1763S02-009, sample fortified at 4×LOQ, glyphosate, grapes, Trial 1, Set 2.
Figure 41:
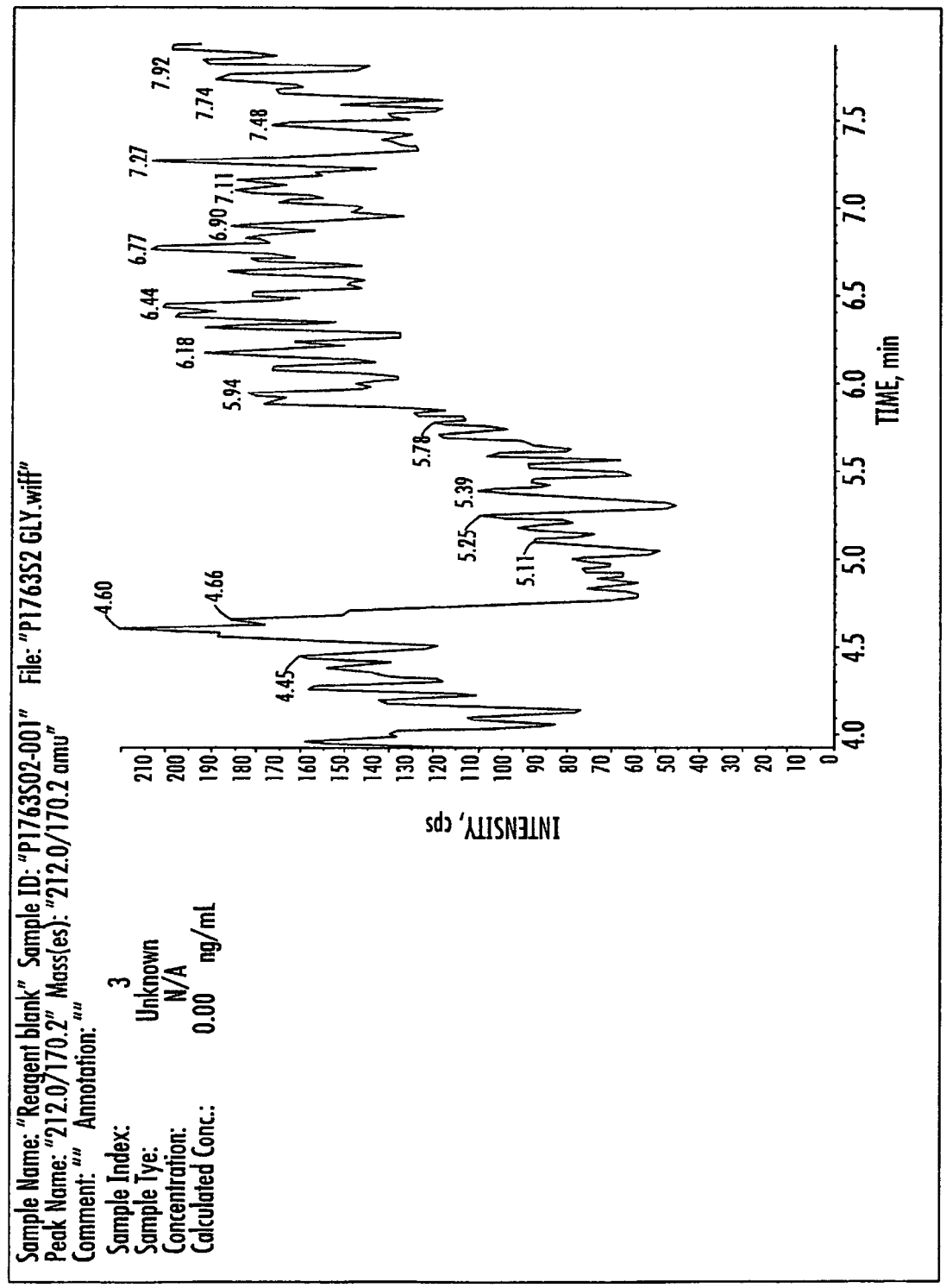
FIG. 41 provides representative chromatogram for reagent blank, N-acetylglyphosate, grapes, Trial 1, Set 2.
Figure 42:
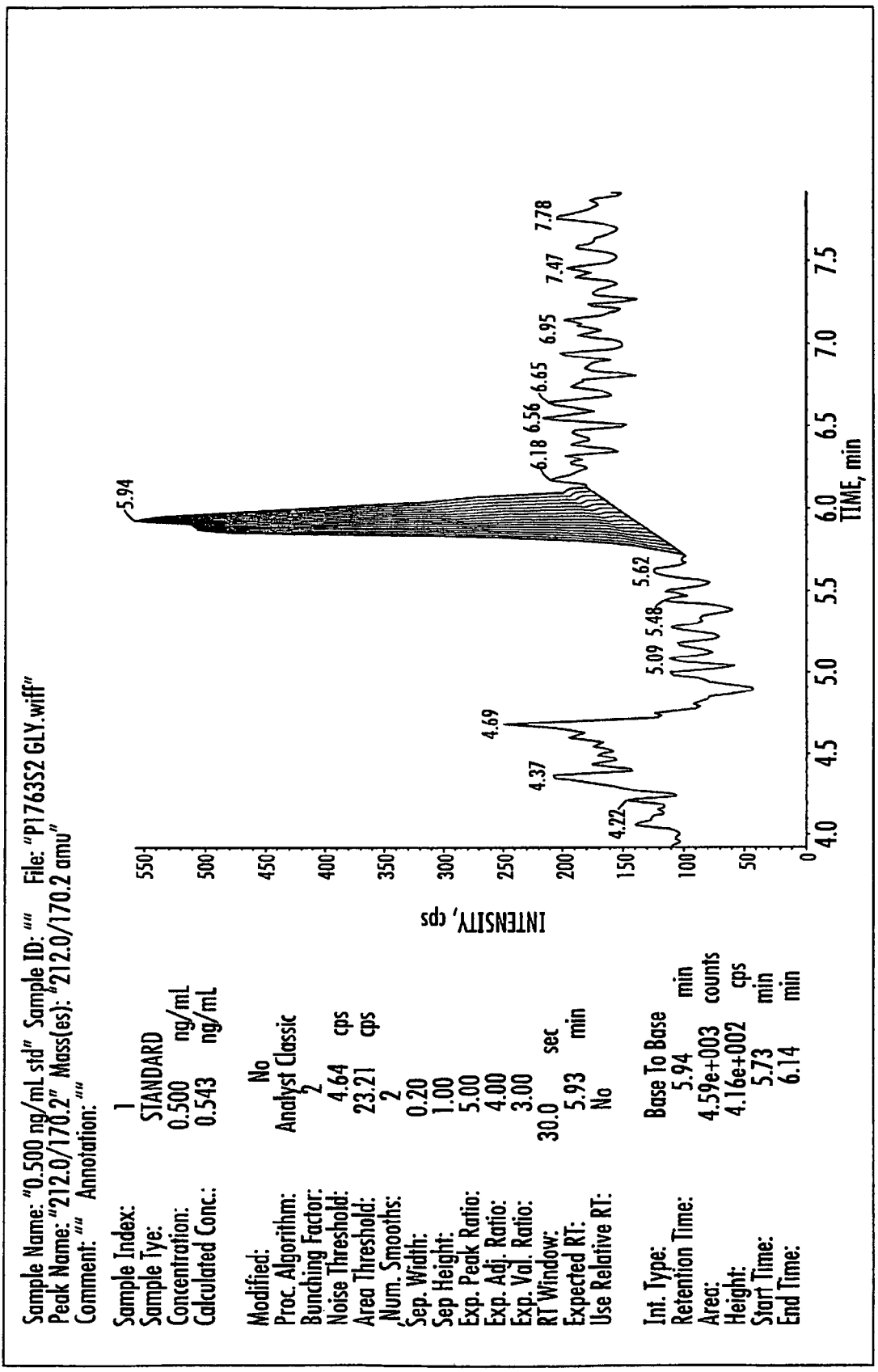
FIG. 42 provides representative chromatogram for 0.500 ng/ml calibration standard, N-acetylglyphosate, grapes, Trial 1, Set 2.
Figure 43:
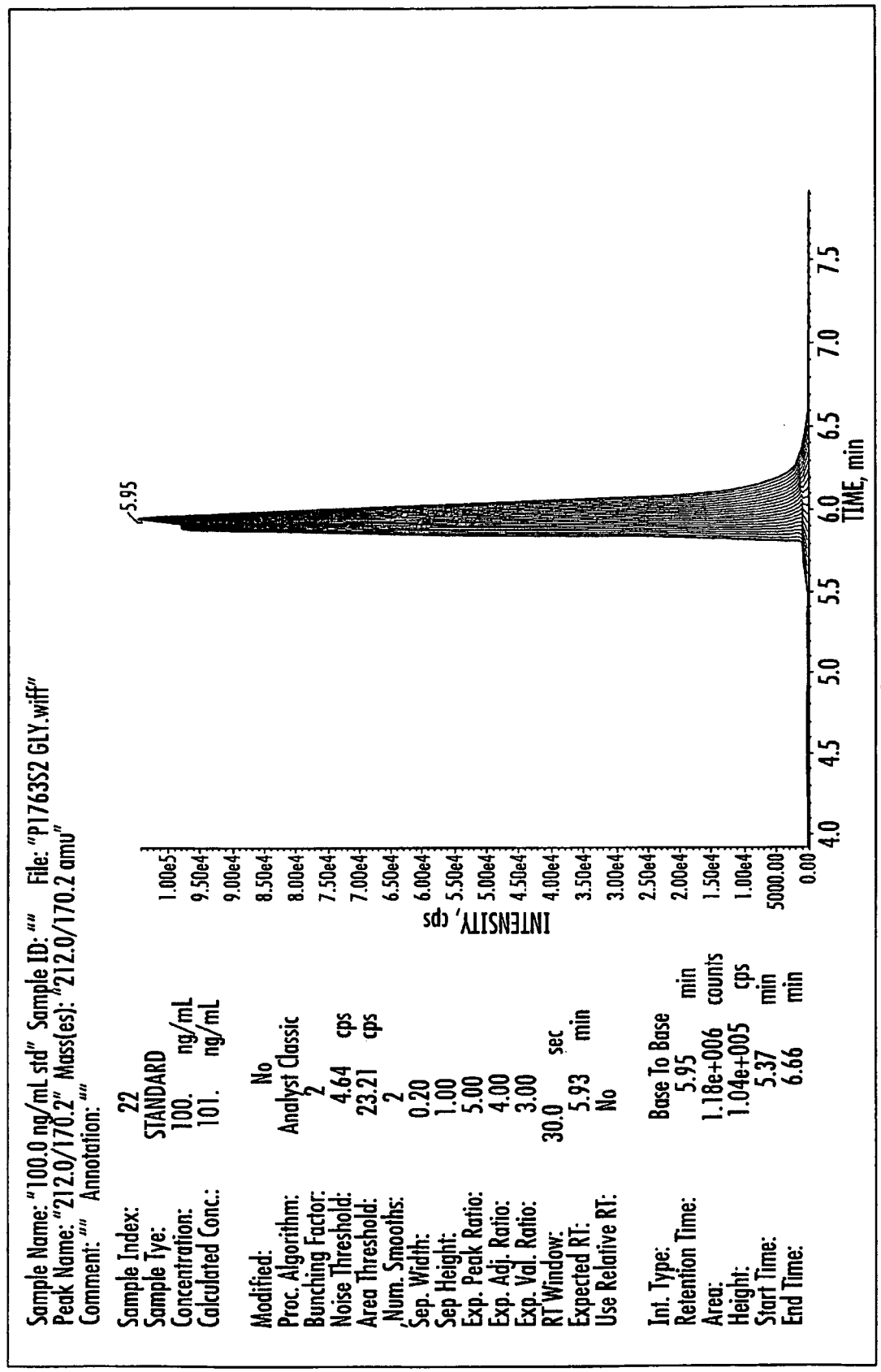
FIG. 43 provides representative chromatogram for 100 ng/ml calibration standard, N-acetylglyphosate, grapes, Trial 1, Set 2.
Figure 44:
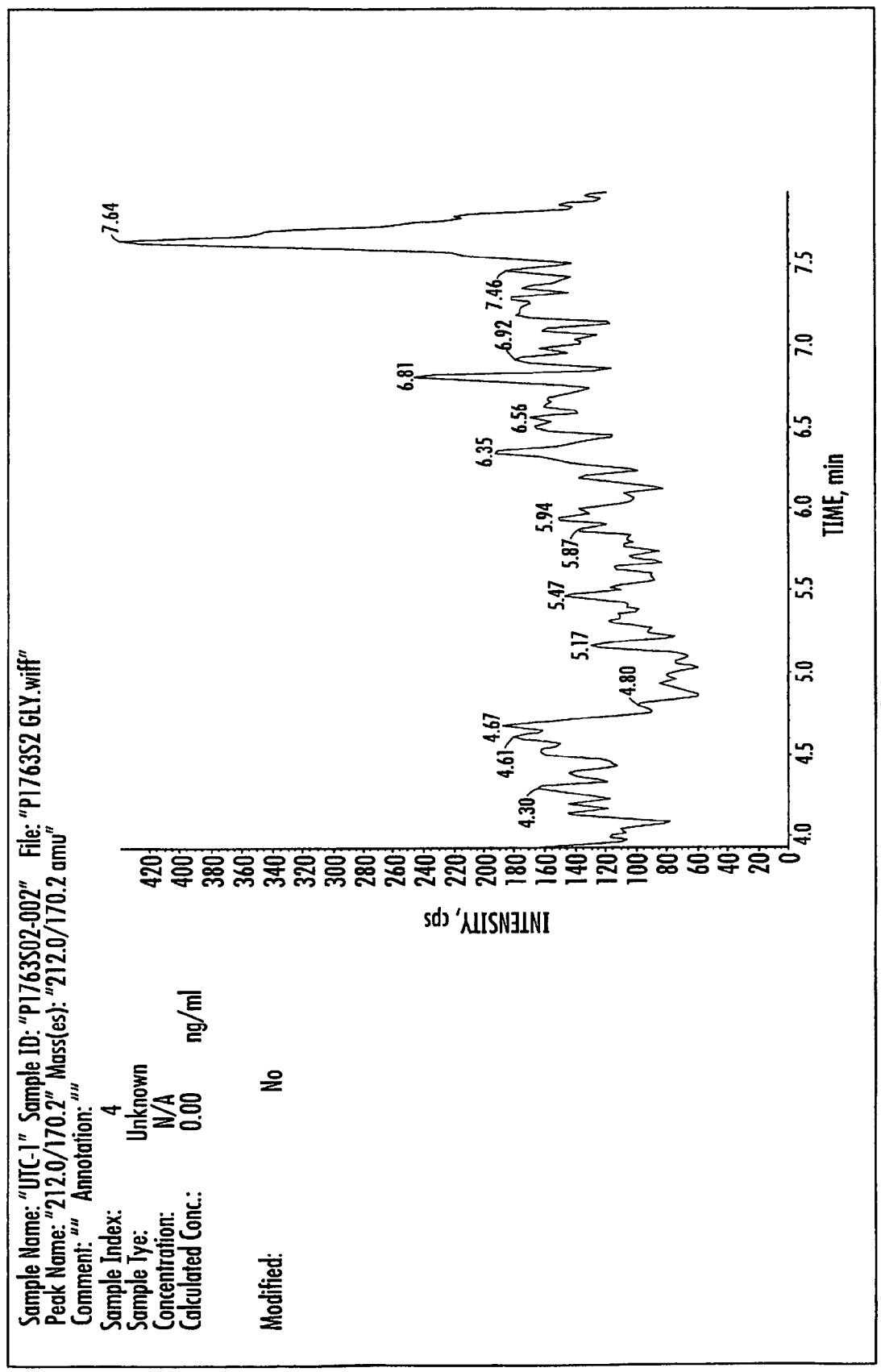
FIG. 44 provides representative chromatogram for P1763S02-002, untreated control sample, N-acetylglyphosate, grapes, Trial 1, Set 2.
Figure 45:
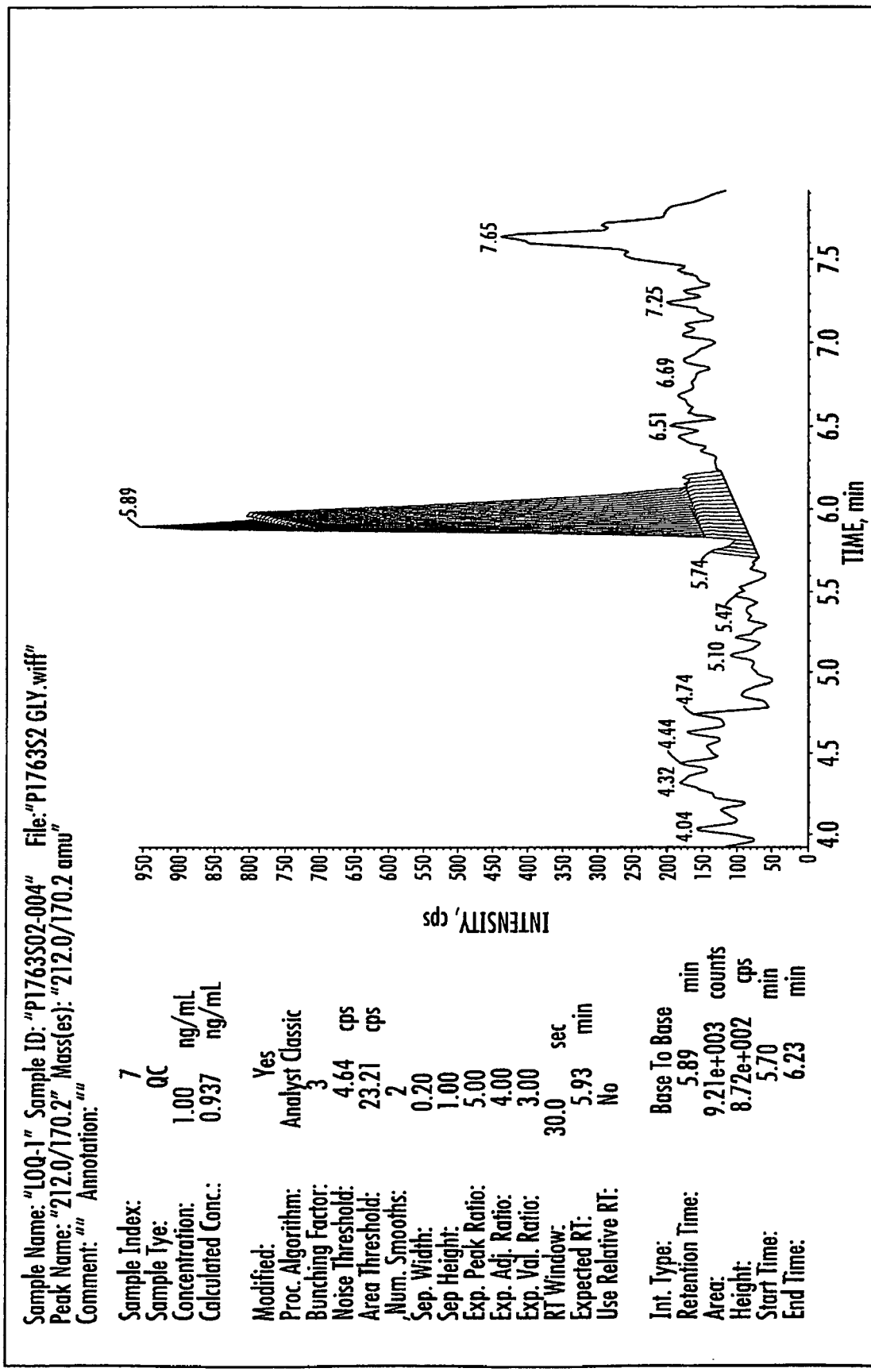
FIG. 45 provides representative chromatogram for P1763S02-004, sample fortified at LOQ, N-acetylglyphosate, grapes, Trial 1, Set 2.
Figure 46:
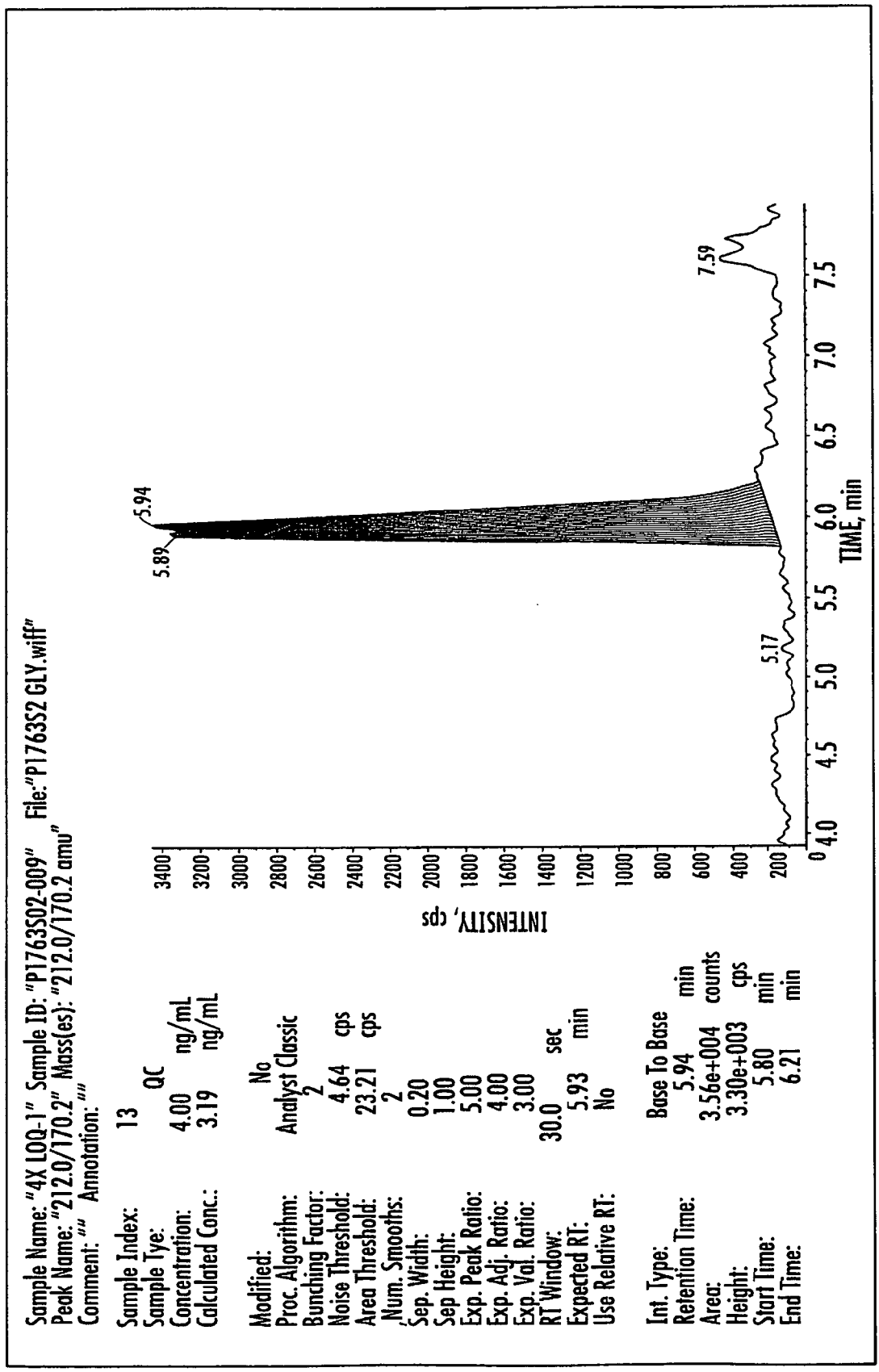
FIG. 46 provides representative chromatogram for P1763S02-009, sample fortified at 4×LOQ, N-acetylglyphosate, grapes, Trial 1, Set 2.
Figure 47:
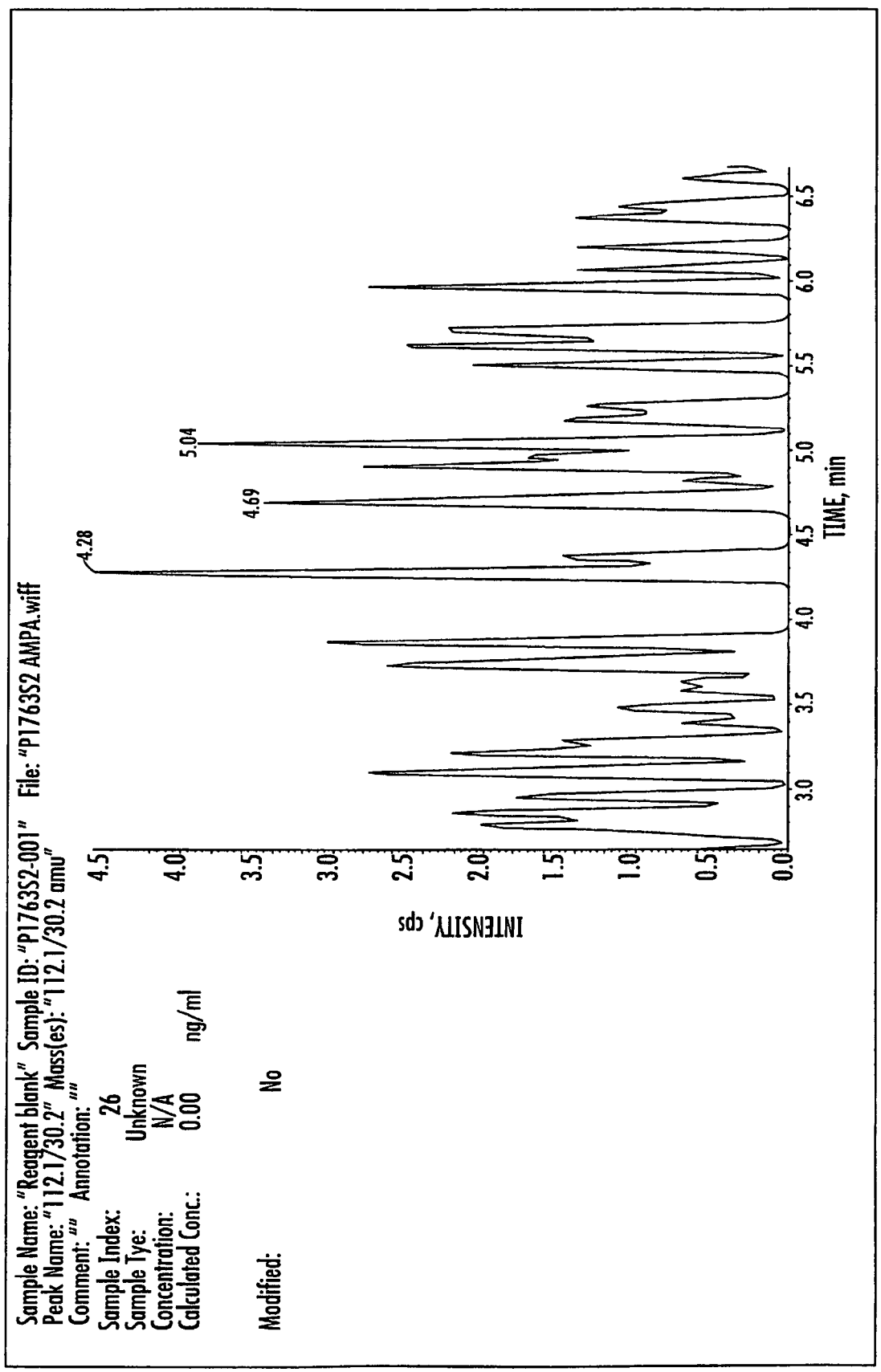
FIG. 47 provides representative chromatogram for reagent blank, AMPA, grapes, Trial 1, Set 2.
Figure 48:
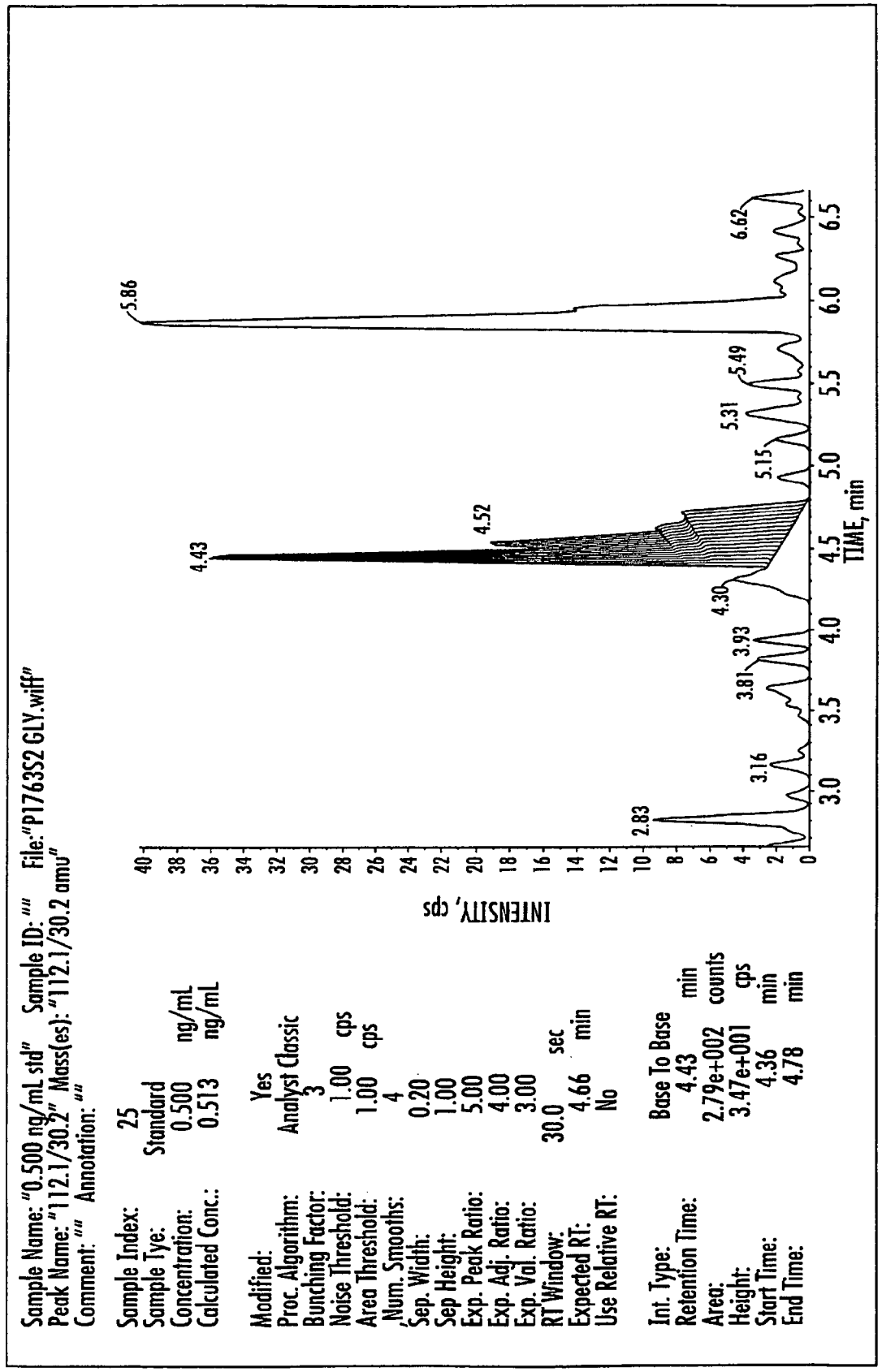
FIG. 48 provides representative chromatogram for 0.500 ng/ml calibration standard, AMPA, grapes, Trial 1, Set 2.
Figure 49:
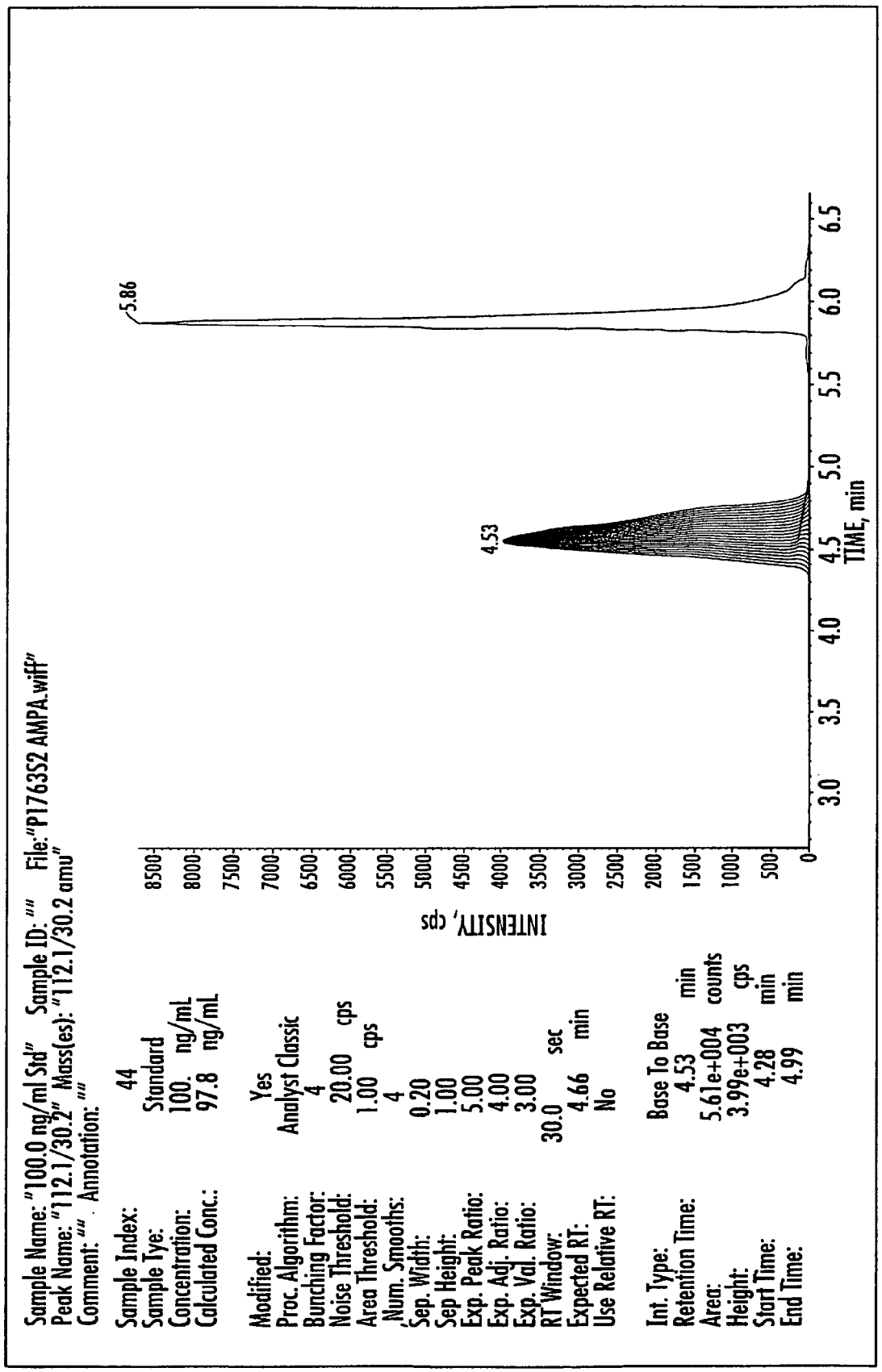
FIG. 49 provides representative chromatogram for 100 ng/ml calibration standard, AMPA, grapes, Trial 1, Set 2.
Figure 50:
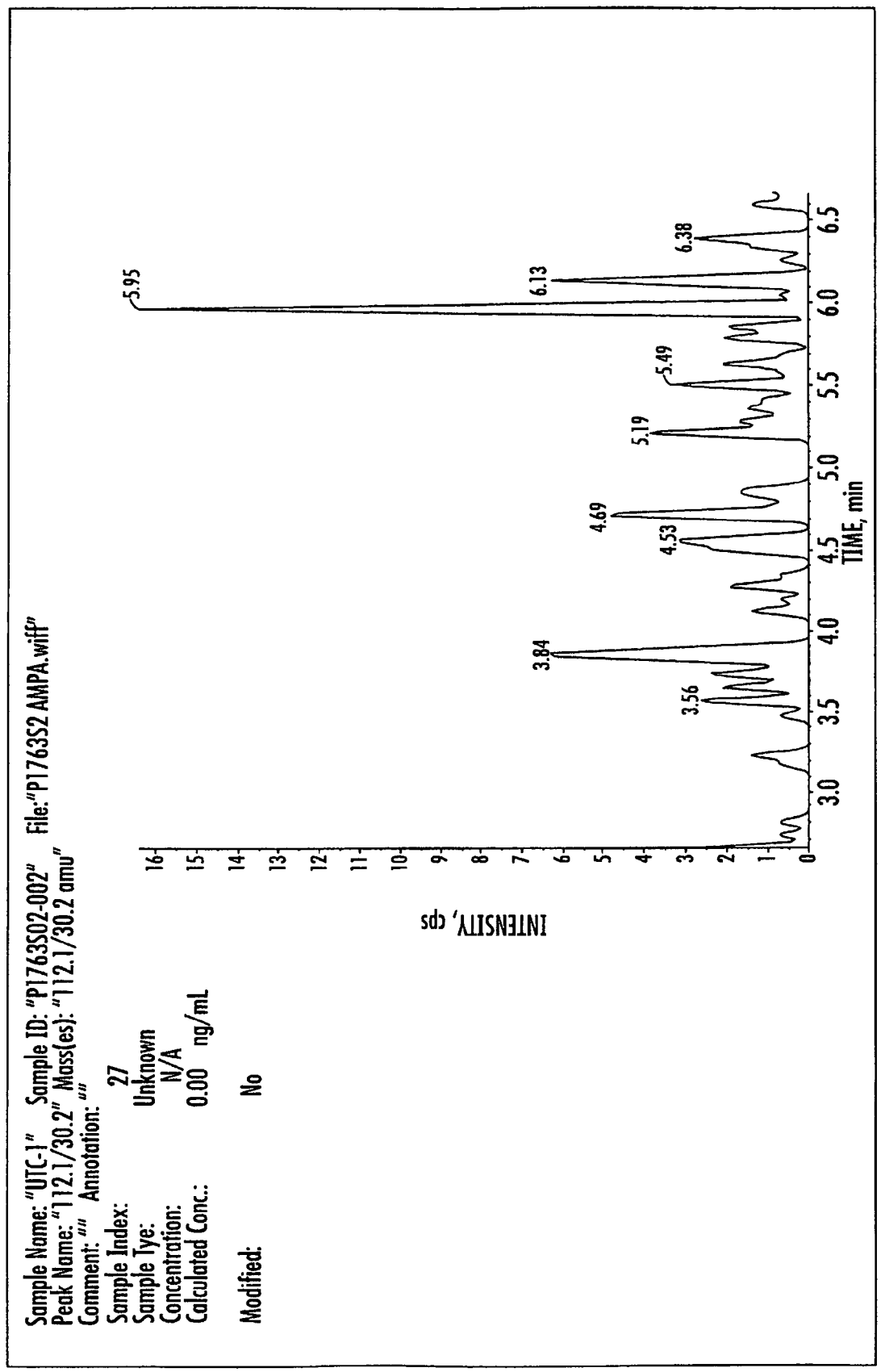
FIG. 50 provides representative chromatogram for P1763S02-002, untreated control sample, AMPA, grapes, Trial 1, Set 2.
Figure 51:
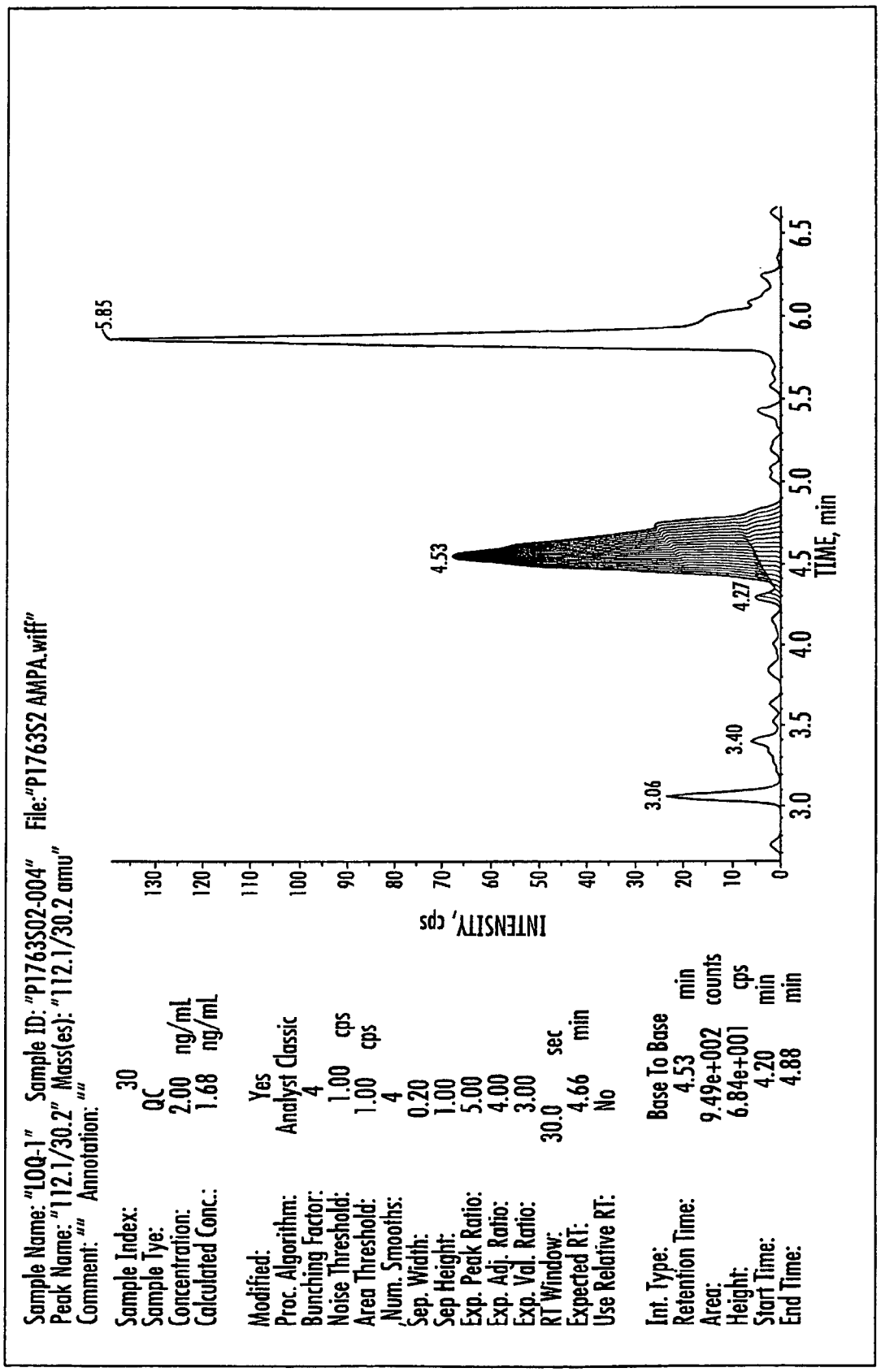
FIG. 51 provides representative chromatogram for P1763S02-004, sample fortified at LOQ, AMPA, grapes, Trial 1, Set 2.
Figure 52:
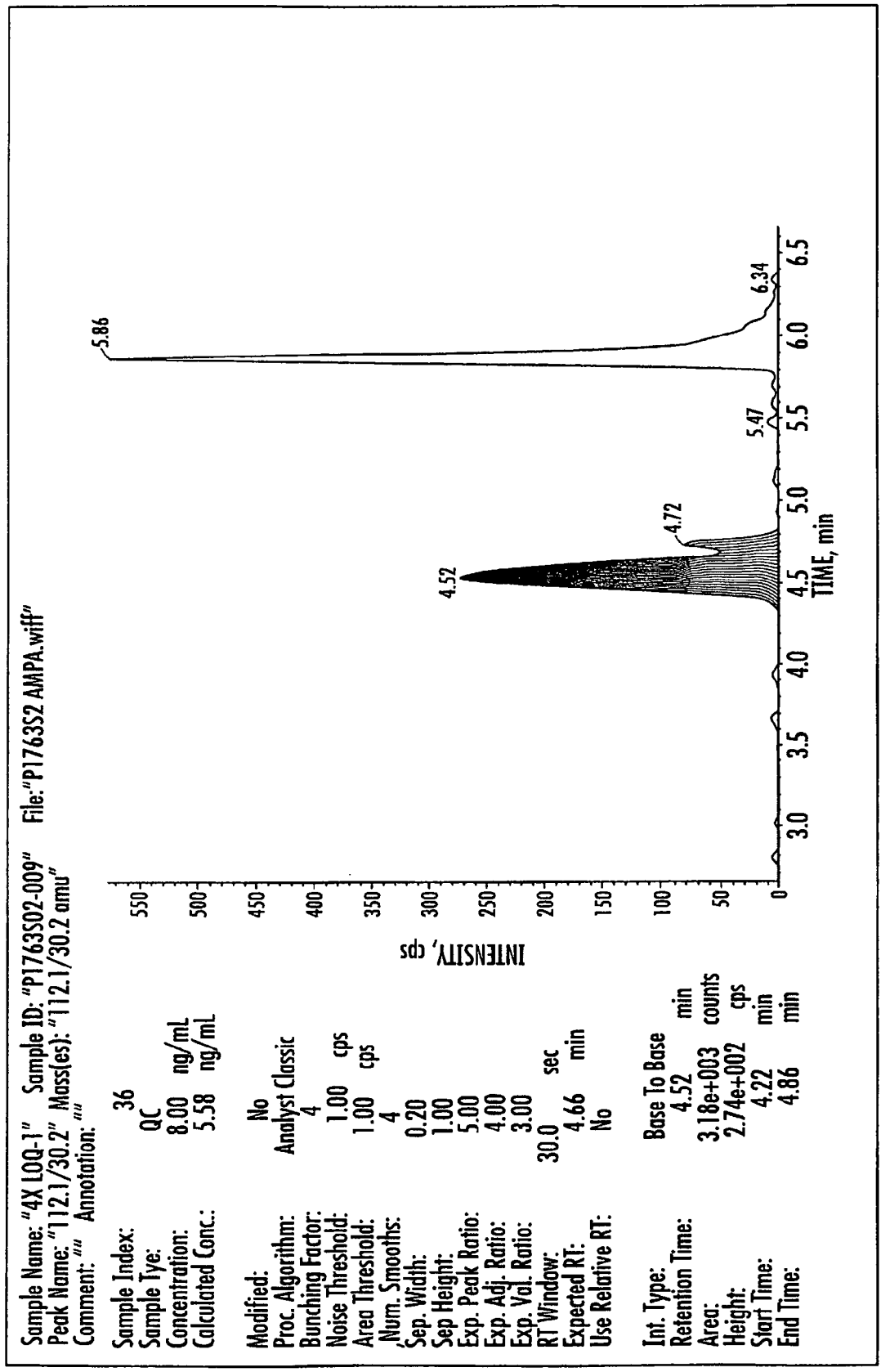
FIG. 52 provides representative chromatogram for P1763S02-009, sample fortified at 4×LOQ, AMPA, grapes, Trial 1, Set 2.
Figure 53:
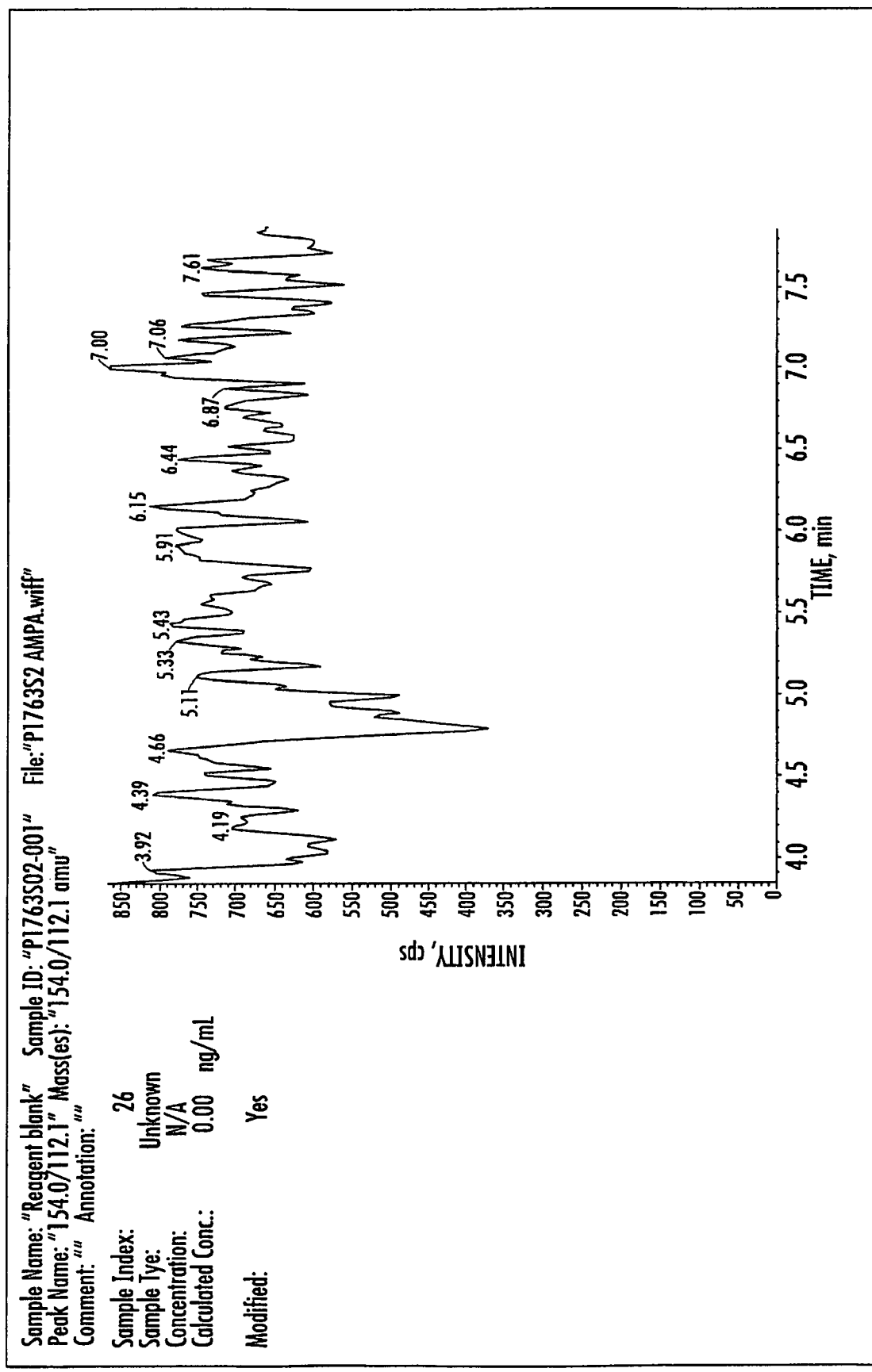
FIG. 53 provides representative chromatogram for reagent blank, N-Acetyl AMPA, grapes, Trial 1, Set 2.
Figure 54:
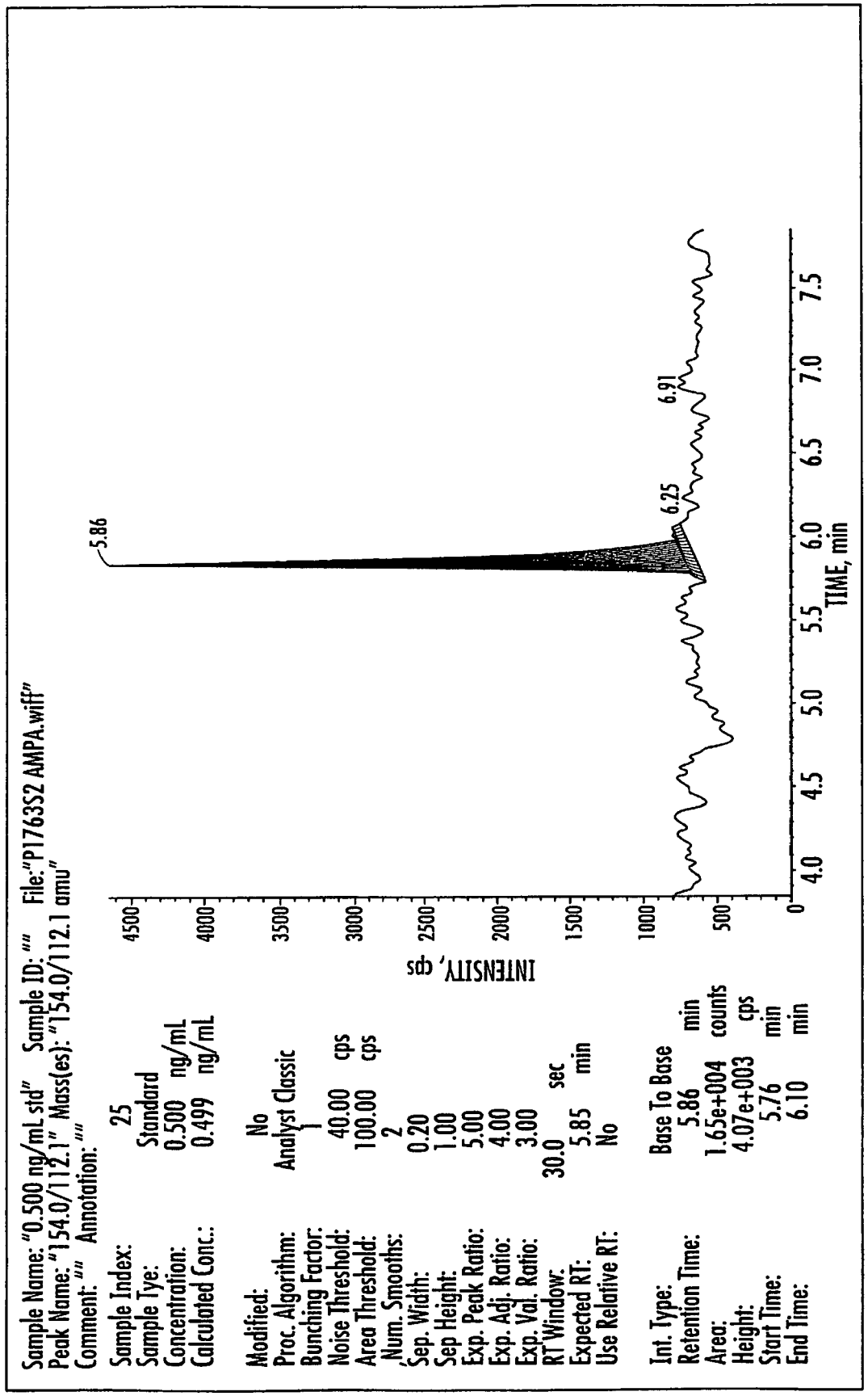
FIG. 54 provides representative chromatogram for 0.500 ng/ml calibration standard, N-Acetyl AMPA, grapes, Trial 1, Set 2.
Figure 55:
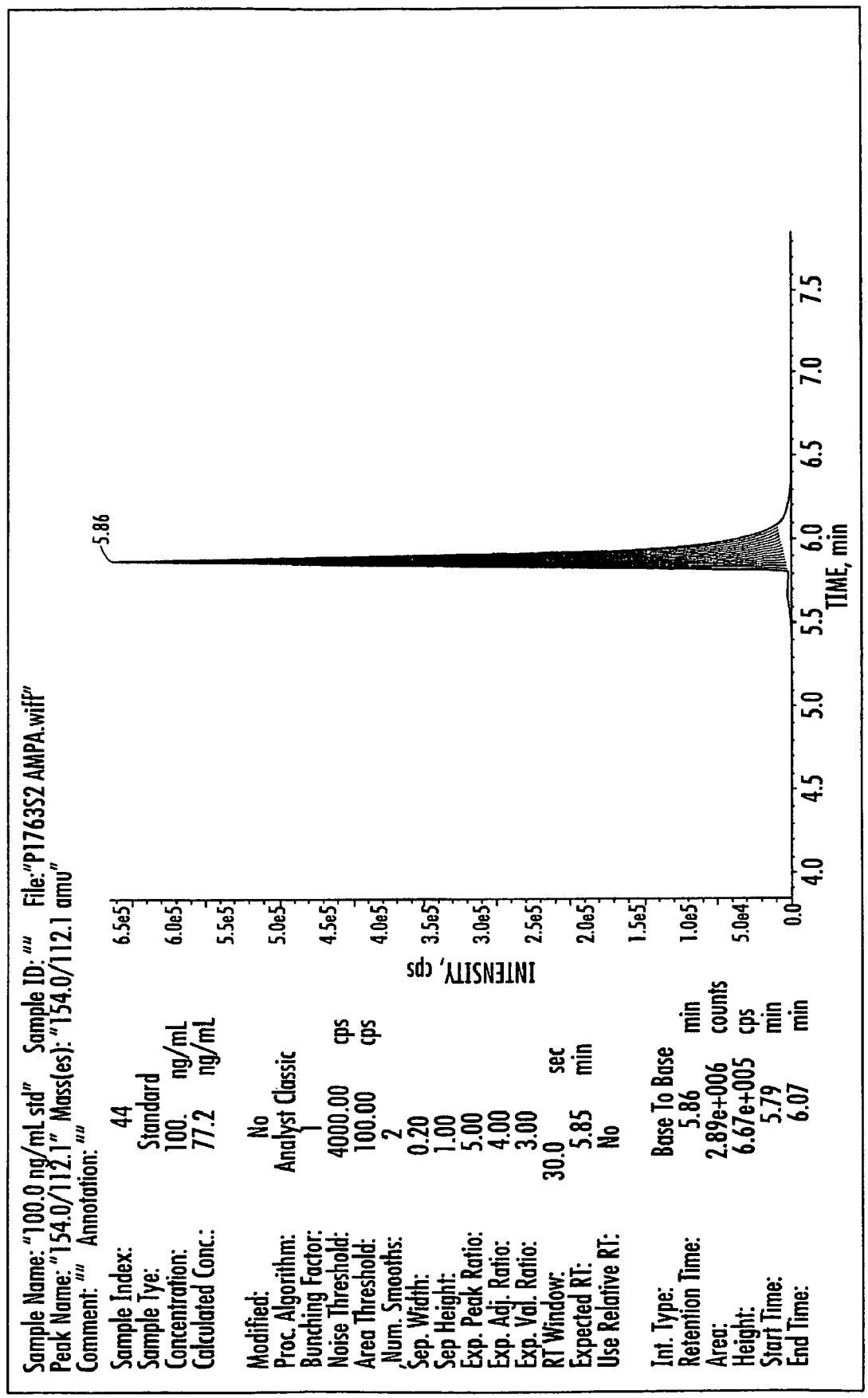
FIG. 55 provides representative chromatogram for 100 ng/ml calibration standard, N-Acetyl AMPA, grapes, Trial 1, Set 2.
Figure 56:
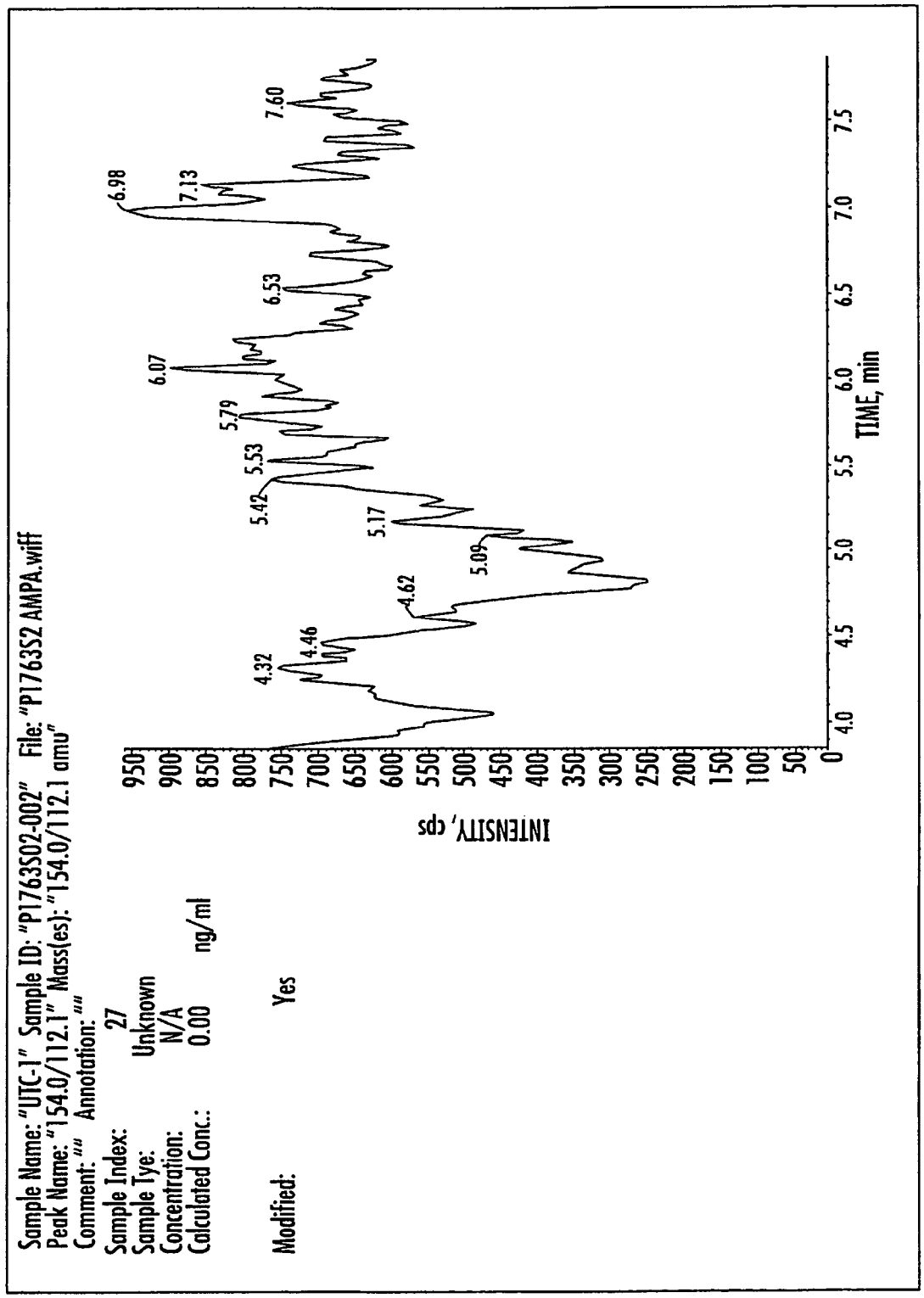
FIG. 56 provides representative chromatogram for P1763S02-002, untreated control sample, N-Acetyl AMPA, grapes, Trial 1, Set 2.
Figure 57:
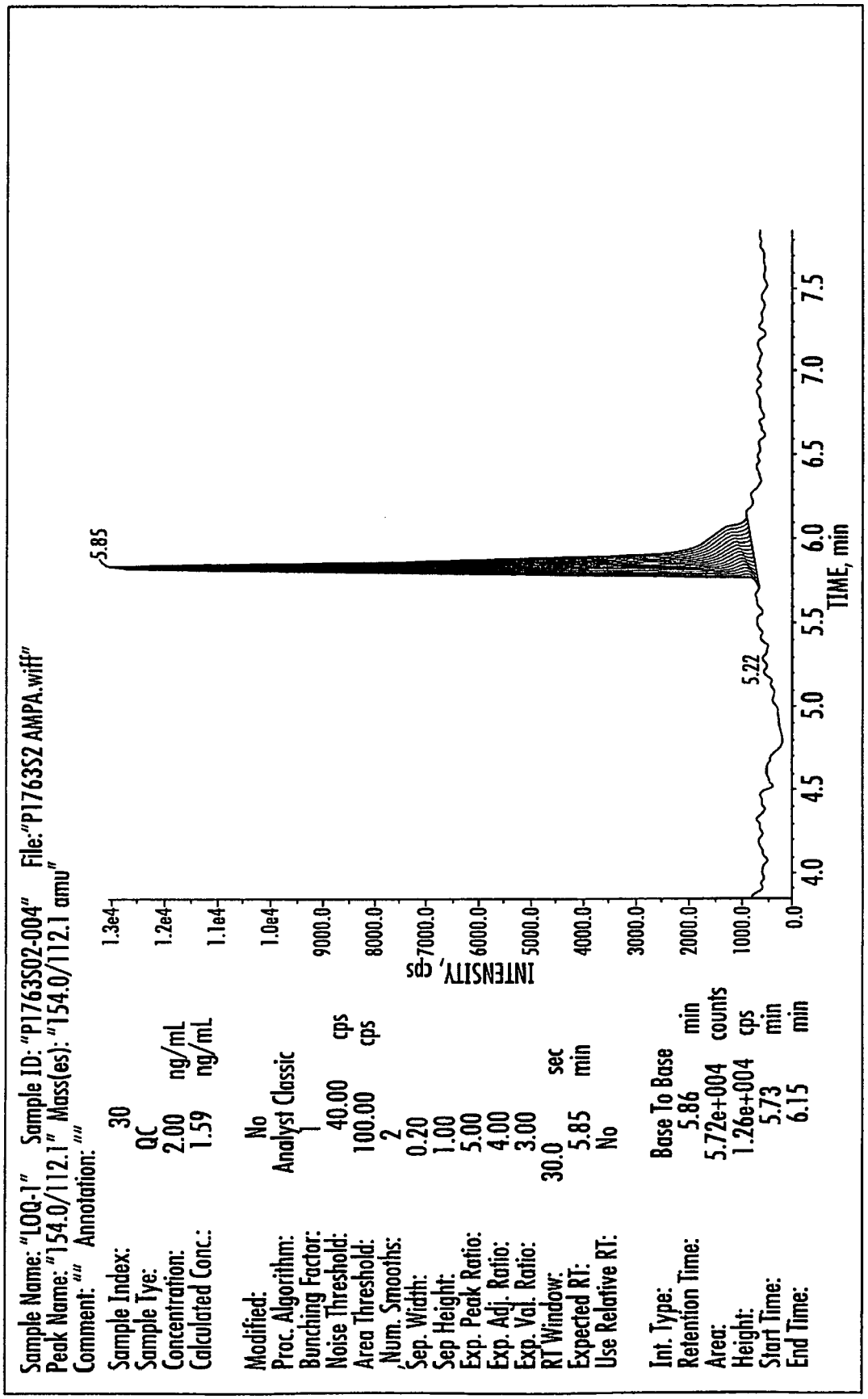
FIG. 57 provides representative chromatogram for P1763S02-004, sample fortified at LOQ, N-Acetyl AMPA, grapes, Trial 1, Set 2.
Figure 58:
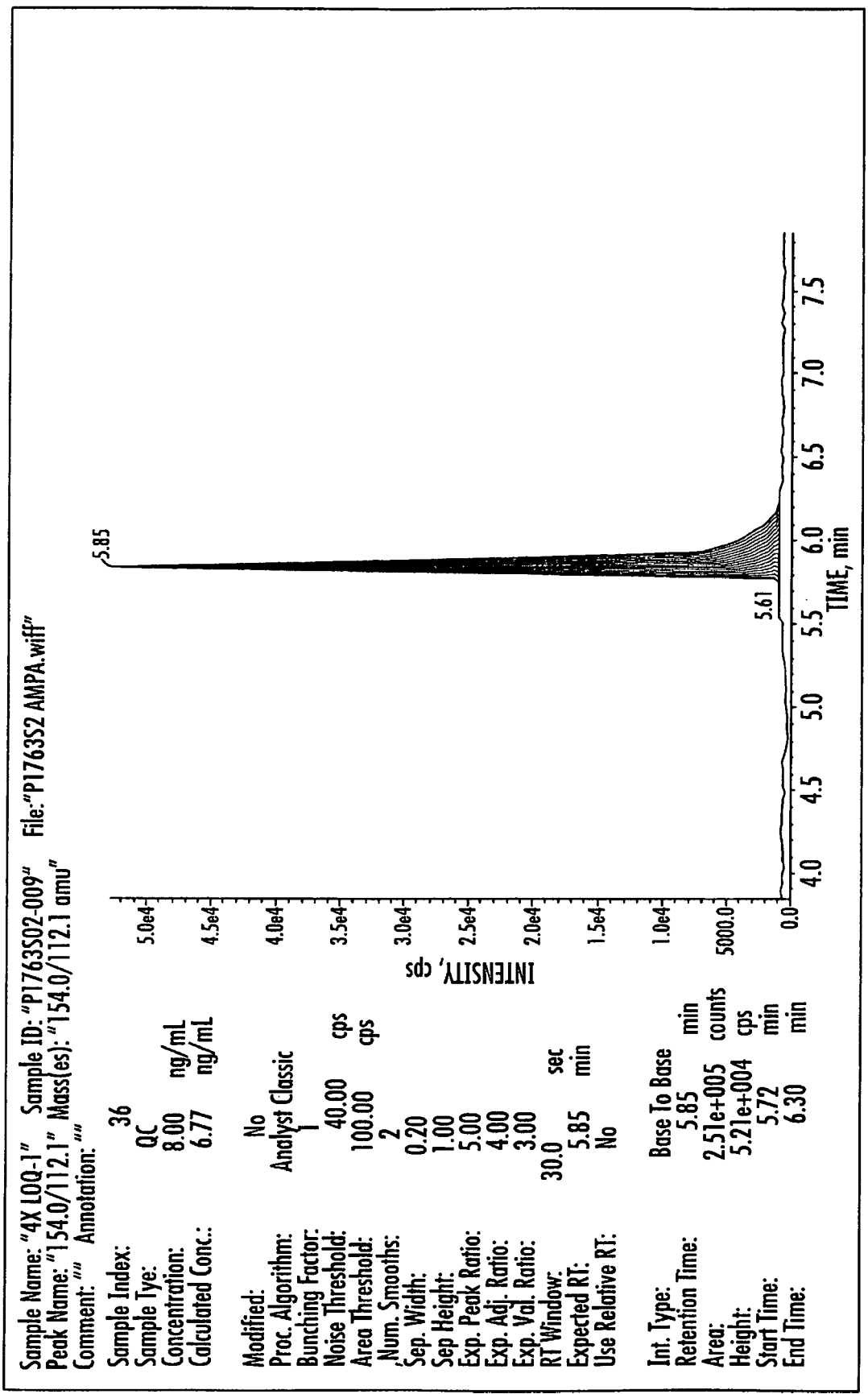
FIG. 58 provides representative chromatogram for P1763S02-009, sample fortified at 4×LOQ, N-Acetyl AMPA, grapes, Trial 1, Set 2.
Figure 59:
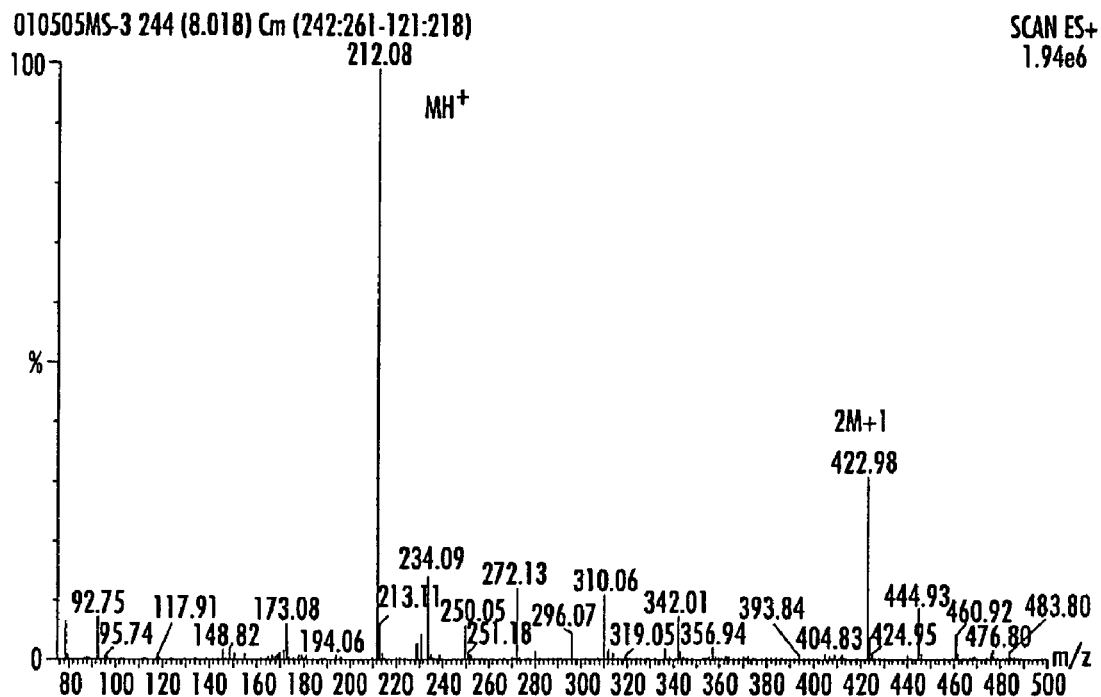
FIG. 59 provides a representative N-acetylglyphosate mass spectra.
Figure 59:
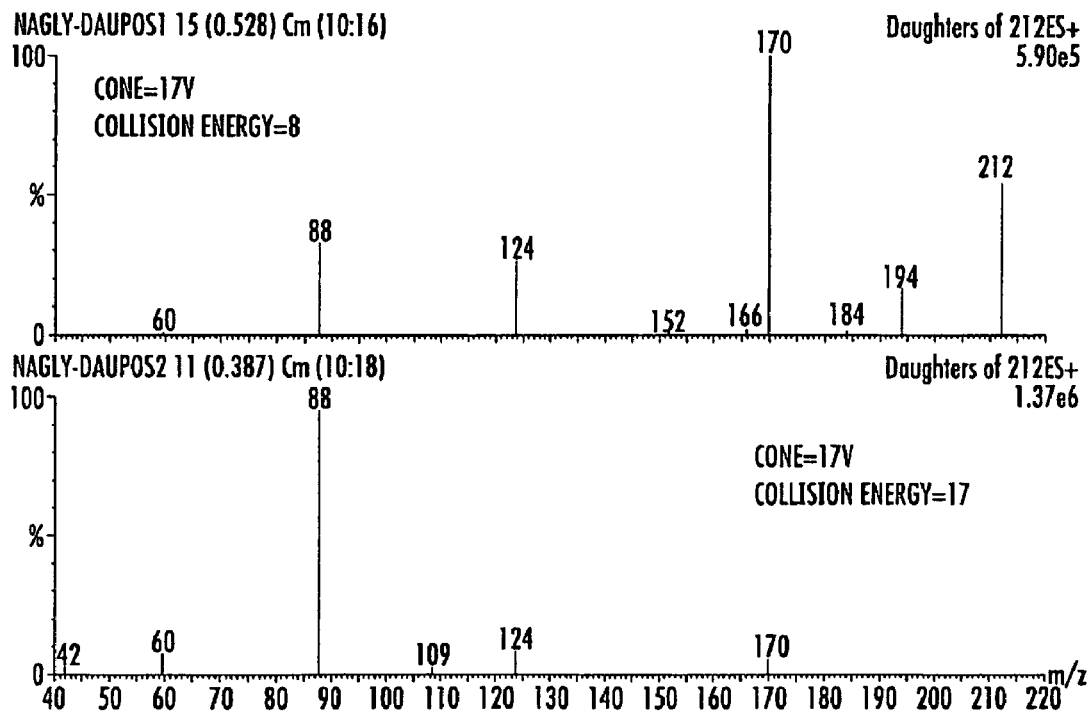
Figure 60:
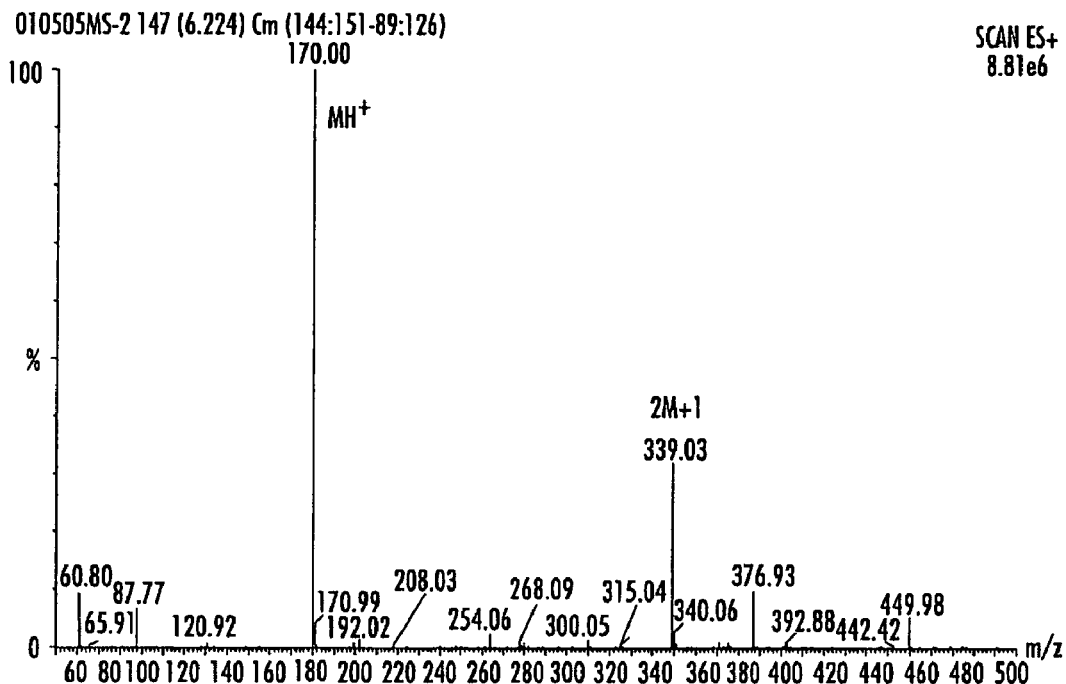
FIG. 60 provides a representative glyphosate mass spectra.
Figure 60:
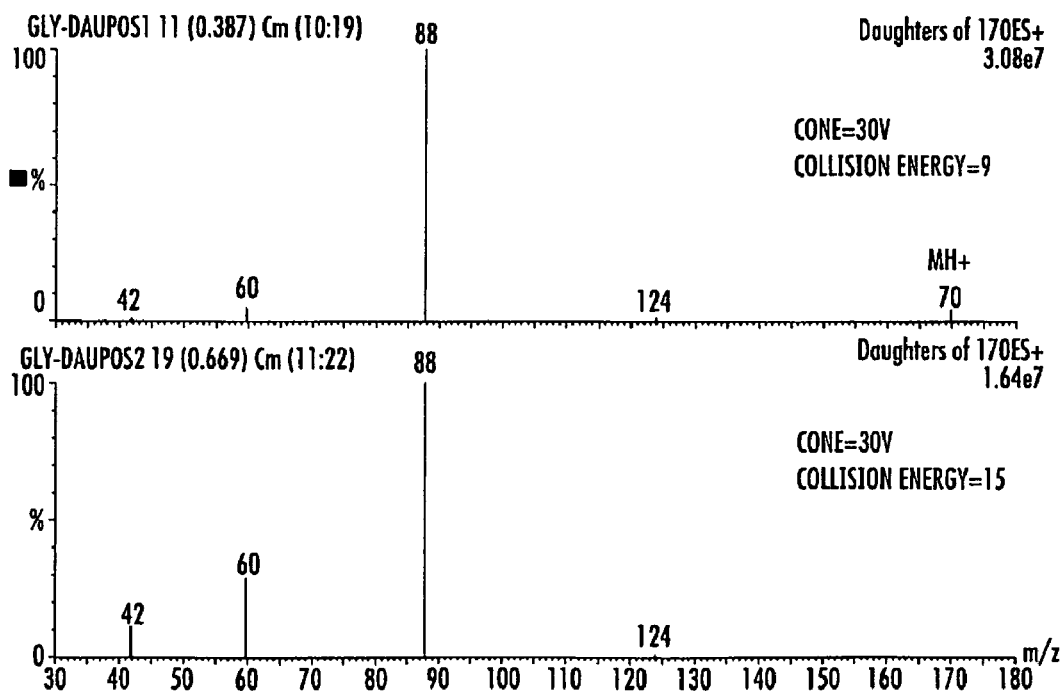
Figure 61:
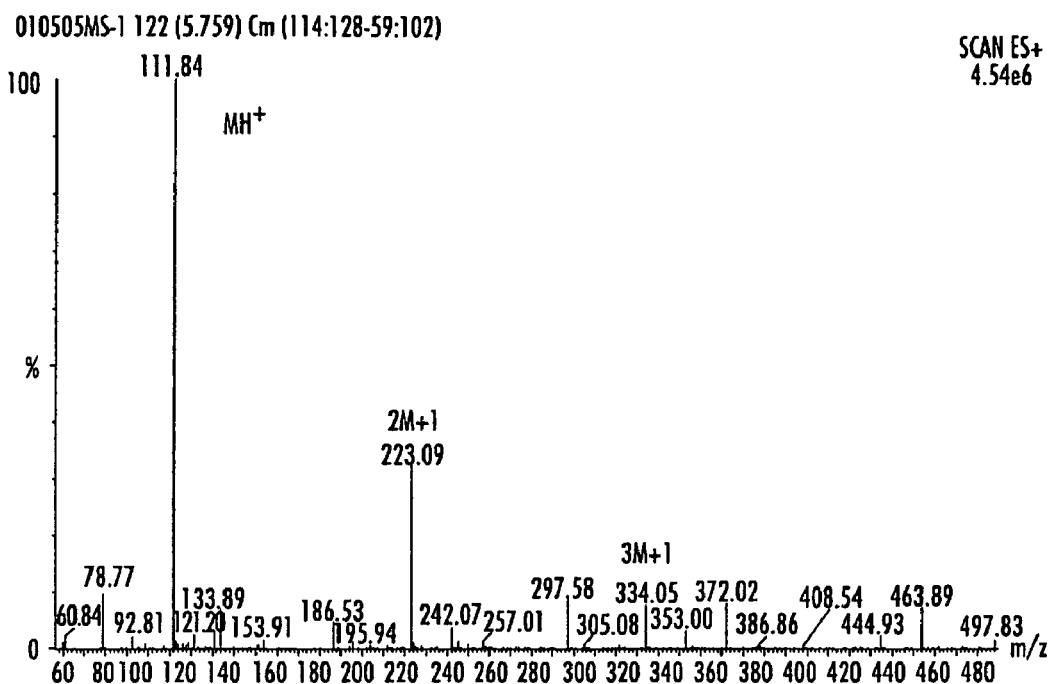
FIG. 61 provides a representative AMPA mass spectra.
Figure 61:
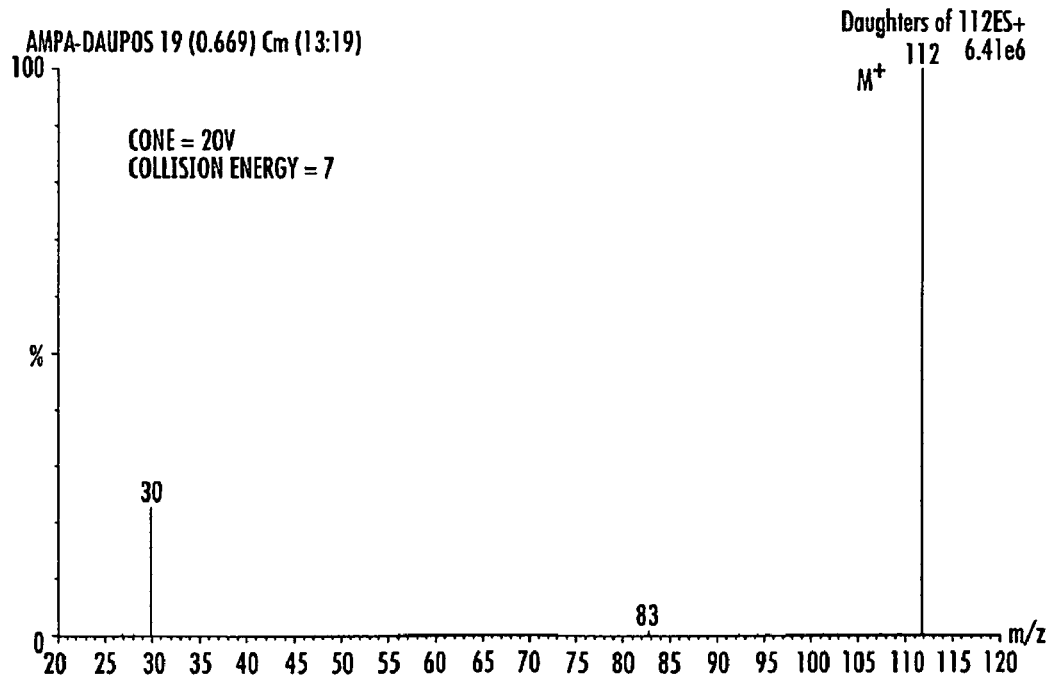
Figure 62:
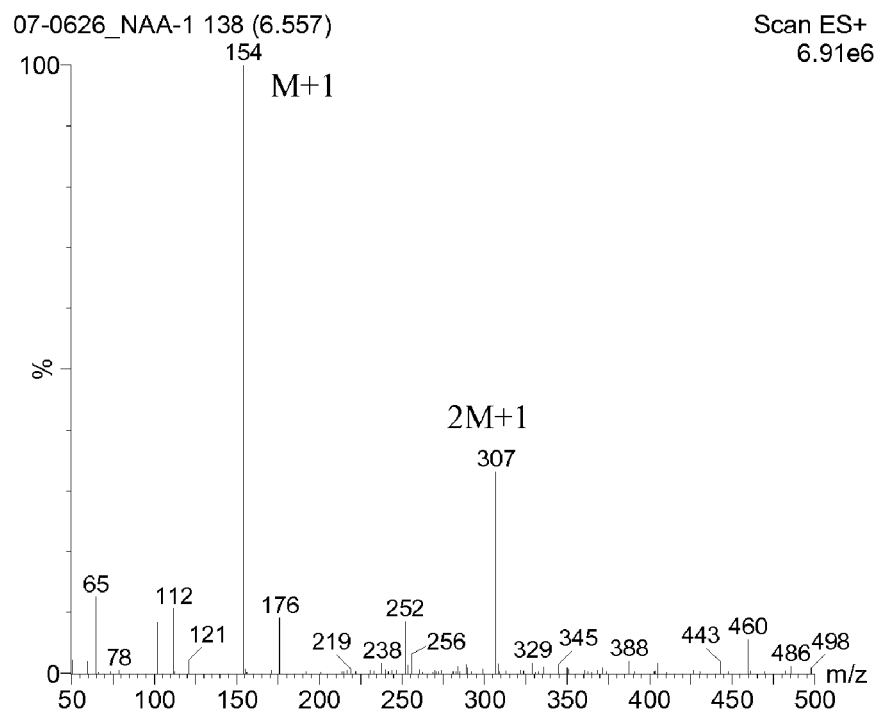
FIG. 62 provides a representative N-acetyl AMPA mass spectra.
Figure 62:
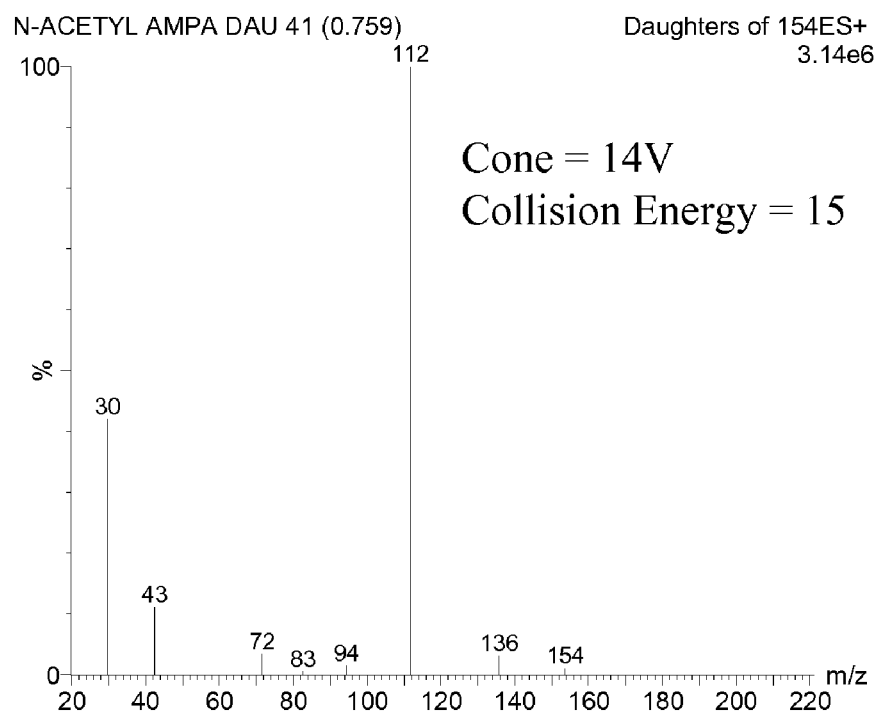

Successful recovery data were obtained for grapes in the first trial (Set 2). Refer to FIG. 31 though FIG. 34 for plots of calibration data and FIG. 35 through FIG. 58 for example chromatograms from Trial 1 for grapes. The recovery data for these validation trials are presented in table 59.

TABLE 59

Summary of Recoveries for Successful Grapes Trials

| SAMPLE MATRIX | LEVEL (PPM) | GLYPHOSATE AVERAGE % | RANGE | AMPA AVERAGE % | RANGE | N-ACETYL GLYPHOSATE AVERAGE % | RANGE | N-ACETYL AMPA AVERAGE % | RANGE | N |
|---|---|---|---|---|---|---|---|---|---|---|
| Grapes | 0.050 (LOQ) | 81 ± 8.3 | 72-93 | 81 ± 3.1 | 76-84 | 95 ± 3.5 | 92-99 | 93 ± 9.0 | 80-101 | 5 |
| | 0.20 | 80 ± 7.3 | 70-89 | 73 ± 3.3 | 70-78 | 86 ± 3.7 | 80-90 | 82 ± 4.7 | 77-88 | 5 |
| Overall Average | | 81 ± 7.4 | 70-93 | 77 ± 5.1 | 70-84 | 91 ± 6.0 | 80-99 | 88 ± 9.0 | 77-101 | 10 |

CONCLUSION

This study demonstrated that the analytical method is acceptable for the quantitation of glyphosate and metabolites in soybean seed and grapes. The method's stated LOQ of 0.05 ppm was demonstrated by acceptable recovery values from controls fortified at this level in both matrices. Acceptable method performance at the proposed tolerance limits for glyphosate in grapes (0.2 ppm) and soybean seed (20 ppm) was demonstrated by acceptable recoveries obtained from control samples fortified at these levels in each matrix. A summary of the data appears in Tables 50-67.

TABLE 50

SUMMARY OF GLYPHOSATE AND N-ACETYLGLYPHOSATE FORTIFICATION (RECOVERY) DATA IN GRAPES

| SAMPLE ID NO. | SET NO. | FORTIFICATION LEVEL (PPM) | GLYPHOSATE FOUND (PPM) | % RECOVERY | N-ACETYL GLYPHOSATE FOUND (PPM) | % RECOVERY |
|---|---|---|---|---|---|---|
| P1763S02-004 | Set 2 | 0.050 | 0.043 | 86 | 0.47 | 94 |
| P1763S02-005 | Set 2 | 0.050 | 0.047 | 93 | 0.050 | 99 |
| P1763S02-006 | Set 2 | 0.050 | 0.036 | 72 | 0.046 | 92 |
| P1763S02-007 | Set 2 | 0.050 | 0.039 | 79 | 0.049 | 99 |
| P1763S02-008 | Set 2 | 0.050 | 0.038 | 76 | 0.046 | 92 |
| P1763S02-009 | Set 2 | 0.20 | 0.15 | 76 | 0.16 | 80 |
| P1763S02-010 | Set 2 | 0.20 | 0.18 | 89 | 0.18 | 88 |
| P1763S02-011 | Set 2 | 0.20 | 0.17 | 85 | 0.17 | 86 |
| P1763S02-012 | Set 2 | 0.20 | 0.16 | 80 | 0.17 | 86 |
| P1763S02-013 | Set 2 | 0.20 | 0.14 | 70 | 0.18 | 90 |
| Overall Mean % Recovery ± SD (n = 10) = | | | | 81 ± 7.4 | | 91 ± 6.0 |
| RSD = | | | | 9.2 | | 6.6 |

Residue values carried to an excessive number of significant figures were used to calculate % Recovery.

After calculation, % Recovery values were rounded to the nearest whole number and reported.

TABLE 51

SUMMARY OF AMPA AND N-ACETYL AMPA FORTIFICATION (RECOVERY) DATA IN GRAPES

| SAMPLE ID NO. | SET NO. | FORTIFICATION LEVEL (PPM) | AMPA FOUND (PPM) | % RECOVERY | N-ACETYL AMPA FOUND (PPM) | % RECOVERY |
|---|---|---|---|---|---|---|
| P1763S02-004 | Set 2 | 0.050 | 0.042 | 84 | 0.040 | 78 |
| P1763S02-005 | Set 2 | 0.050 | 0.038 | 76 | 0.051 | 101 |
| P1763S02-006 | Set 2 | 0.050 | 0.040 | 80 | 0.049 | 98 |
| P1763S02-007 | Set 2 | 0.050 | 0.041 | 83 | 0.044 | 89 |
| P1763S02-008 | Set 2 | 0.050 | 0.041 | 82 | 0.050 | 99 |
| P1763S02-009 | Set 2 | 0.20 | 0.14 | 70 | 0.17 | 85 |
| P1763S02-010 | Set 2 | 0.20 | 0.15 | 74 | 0.18 | 88 |
| P1763S02-011 | Set 2 | 0.20 | 0.15 | 73 | 0.16 | 80 |
| P1763S02-012 | Set 2 | 0.20 | 0.16 | 78 | 0.15 | 77 |
| P1763S02-013 | Set 2 | 0.20 | 0.14 | 70 | 0.16 | 80 |
| Overall Mean % Recovery ± SD (n = 10) = | | | | 77 ± 5.1 | | 88 ± 9.0 |
| RSD = | | | | 6.7 | | 10 |

Residue values carried to an excessive number of significant figures were used to calculate % Recovery.
After calculation, % Recovery values were rounded to the nearest whole number and reported.

TABLE 52

SUMMARY OF GLYPHOSATE AND N-ACETYLGLYPHOSATE FORTIFICATION (RECOVERY) DATA IN SOYBEAN SEED

| SAMPLE ID NO. | SET NO. | FORTIFICATION LEVEL (PPM) | GLYPHOSATE FOUND (PPM) | % RECOVERY | N-ACETYL GLYPHOSATE FOUND (PPM) | % RECOVERY |
|---|---|---|---|---|---|---|
| P1763S04-004 | Set 4 | 0.050 | 0.049 | 98 | 0.041 | 81 |
| P1763S04-005 | Set 4 | 0.050 | 0.052 | 103 | 0.042 | 84 |
| P1763S04-006 | Set 4 | 0.050 | 0.057 | 113 | 0.042 | 83 |
| P1763S04-007 | Set 4 | 0.050 | 0.042 | 83 | 0.040 | 81 |
| P1763S04-008 | Set 4 | 0.050 | 0.042 | 84 | 0.045 | 90 |
| P1763S04-009 | Set 4 | 20 | 18 | 89 | 17 | 83 |
| P1763S04-010 | Set 4 | 20 | 17 | 87 | 18 | 88 |
| P1763S04-011 | Set 4 | 20 | 18 | 90 | 18 | 90 |
| P1763S04-012 | Set 4 | 20 | 17 | 85 | 19 | 95 |
| P1763S04-013 | Set 4 | 20 | 15 | 73 | 18 | 91 |
| Overall Mean % Recovery ± SD (n = 10) = | | | | 90 ± 12 | | 87 ± 4.9 |
| RSD = | | | | 13 | | 5.6 |

Residue values carried to an excessive number of significant figures were used to calculate % Recovery.
After calculation, % Recovery values were rounded to the nearest whole number and reported.

TABLE 53

SUMMARY OF AMPA AND N-ACETYL AMPA FORTIFICATION (RECOVERY) DATA IN SOYBEAN SEED

| SAMPLE ID NO. | SET NO. | FORTIFICATION LEVEL (PPM) | AMPA FOUND (PPM) | % RECOVERY | N-ACETYL AMPA FOUND (PPM) | % RECOVERY |
|---|---|---|---|---|---|---|
| P1763S04-004 | Set 4 | 0.050 | 0.039 | 78 | 0.044 | 88 |
| P1763S04-005 | Set 4 | 0.050 | 0.043 | 86 | 0.051 | 102 |
| P1763S04-006 | Set 4 | 0.050 | 0.047 | 95 | 0.049 | 98 |
| P1763S04-007 | Set 4 | 0.050 | 0.046 | 91 | 0.048 | 96 |

TABLE 53-continued

SUMMARY OF AMPA AND N-ACETYL AMPA FORTIFICATION
(RECOVERY) DATA IN SOYBEAN SEED

| SAMPLE ID NO. | SET NO. | FORTIFICATION LEVEL (PPM) | AMPA FOUND (PPM) | % RECOVERY | N-ACETYL AMPA FOUND (PPM) | % RECOVERY |
|---|---|---|---|---|---|---|
| P1763S04-008 | Set 4 | 0.050 | 0.052 | 105 | 0.048 | 95 |
| P1763S04-009 | Set 4 | 20 | 18 | 87 | 17 | 86 |
| P1763S04-010 | Set 4 | 20 | 19 | 96 | 24 | 120 |
| P1763S04-011 | Set 4 | 20 | 20 | 99 | 24 | 118 |
| P1763S04-012 | Set 4 | 20 | 18 | 91 | 25 | 126 |
| P1763S04-013 | Set 4 | 20 | 15 | 74 | 21 | 105 |
| Overall Mean % Recovery ± SD (n = 10) = | | | | 90 ± 9.3 | | 103 ± 14 |
| RSD = | | | | 10 | | 14 |

Residue values carried to an excessive number of significant figures were used to calculate % Recovery.
After calculation, % Recovery values were rounded to the nearest whole number and reported.

TABLE 60

DATA SHEET FOR GLYPHOSATE, GRAPES, TRIAL 1, SET 2

| Project: | 1763 | Fit | Linear | Weighting | 1/x |
|---|---|---|---|---|---|
| Set: | 2 | Intercept | 66.2 | | |
| | | Slope | 3.93E+03 | | |
| | | Correlation coefficient | 0.9997 | | |
| | | Q1/Q3 Masses: | 170.00/87.30 amu | | |
| Matrix: | Grapes | | | | |
| Analyte: | Glyphosate | | | | |

| Sample Name | Sample ID | Sample Weight | Peak Area | Fortified Concentration (µg/g) | Volume 1 (mL) | Aliquot from Vol. 1 (mL) | Final Vol. (mL) | Dilution Factor | Conc. From curve (ng/mL)* | Calculated µg/sample | Accuracy (%) | Recovery (%) |
|---|---|---|---|---|---|---|---|---|---|---|---|---|
| 0.500 ng/mL std | — | — | 2.00E+03 | — | — | — | — | — | 0.493 | — | 98.6 | — |
| 0.500 ng/mL std | — | — | 1.93E+03 | — | — | — | — | — | 0.474 | — | 94.1 | — |
| Reagent blank | P1763S02-001 | — | 0.00E+00 | — | 100 | 2.00 | 5.00 | — | 0.00 | — | — | — |
| UTC-1 | P1763S02-002 | 5.01 | 0.00E+00 | — | 100 | 2.00 | 5.00 | — | 0.00 | 0.00 | — | — |
| UTC-2 | P1763S02-003 | 4.99 | 0.00E+00 | — | 100 | 2.00 | 5.00 | — | 0.00 | 0.00 | — | — |
| 1.00 ng/mL std | — | — | 4.06E+03 | — | — | — | — | — | 1.02 | — | 102 | — |
| LOQ-1 | P1763S02-004 | 5.01 | 3.44E+03 | 0.0499 | 100 | 2.00 | 5.00 | — | 0.857 | 0.0428 | — | 66.7 |
| LOQ-2 | P1763S02-005 | 4.98 | 3.73E+03 | 0.0502 | 100 | 2.00 | 5.00 | — | 0.931 | 0.0467 | — | 50.1 |
| LOQ-3 | P1763S02-006 | 5.02 | 2.91E+03 | 0.0498 | 100 | 2.00 | 5.00 | — | 0.724 | 0.0361 | — | 72.4 |
| 2.00 ng/mL std | — | — | 7.80E+03 | — | — | — | — | — | 1.97 | — | 98.5 | — |
| LOQ-4 | P1763S02-007 | 5.02 | 3.17E+03 | 0.0498 | 100 | 2.00 | 5.00 | — | 0.788 | 0.0392 | — | 76.6 |
| LOQ-5 | P1763S02-008 | 4.99 | 3.04E+03 | 0.0501 | 100 | 2.00 | 5.00 | — | 0.757 | 0.0379 | — | 75.7 |
| 4X LOQ-1 | P1763S02-009 | 5.00 | 1.21E+04 | 0.200 | 100 | 2.00 | 5.00 | — | 3.05 | 0.153 | — | 76.3 |
| 10.0 ng/mL std | — | — | 3.97E+04 | — | — | — | — | — | 10.1 | — | 101 | 89.3 |
| 4X LOQ-2 | P1763S02-010 | 5.00 | 1.41E+04 | 0.200 | 100 | 2.00 | 5.00 | — | 3.57 | 0.179 | — | 84.8 |
| 4X LOQ-3 | P1763S02-011 | 5.00 | 1.34E+04 | 0.200 | 100 | 2.00 | 5.00 | — | 3.39 | 0.170 | — | 79.9 |
| 4X LOQ-4 | P1763S02-012 | 4.99 | 1.26E+04 | 0.200 | 100 | 2.00 | 5.00 | — | 3.19 | 0.160 | — | — |
| 20.0 ng/mL std | — | — | 8.27E+04 | — | — | — | — | — | 21.0 | — | 106 | 70.4 |
| 4X LOQ-5 | P1763S02-013 | 5.01 | 1.12E+04 | 0.200 | 100 | 2.00 | 5.00 | — | 2.82 | 0.141 | — | — |
| 20.0 ng/mL std | — | — | 8.02E+04 | — | — | — | — | — | 20.4 | — | 102 | — |
| 50.0 ng/mL std | — | — | 1.99E+05 | — | — | — | — | — | 50.5 | NA | 10.1 | — |
| 100.0 ng/mL std | — | — | 3.86E+05 | — | — | — | — | — | 98.1 | — | 98.1 | — |
| Solvent blank | — | — | 0.00E+00 | — | — | — | — | — | No Peak | — | — | — |
| | | | | | | | | Average Std Accuracy | | | 100 | Std. Dev. |
| | | | | | | | | LOQ Average % Recovery | | | 81.1 | 8.3 |
| | | | | | | | | 4XLOQ Average % Recovery | | | 80.1 | 7.3 |
| | | | | | | | | Total Average % Recovery | | | 80.6 | 7.4 |

TABLE 61

DATA SHEET FOR N-ACETYLGLYPHOSATE, GRAPES, TRIAL 1, SET 2

| Project: | 1763 | Fit | Linear | Weighting | 1/x |
|---|---|---|---|---|---|
| Set: | 2 | Intercept | −1.76E+03 | | |
| Title | Validation-tryout 1 | Slope | 1.17E+04 | | |
| | | Correlation coefficient | 0.9999 | | |
| | | Q1/Q3 Masses: 212.00/170.20 amu | | | |
| Matrix: | Grapes | | | | |
| Analyte: | n-acetyl-Glyphosate | | | | |

| Sample Name | Sample ID | Sample Weight | Peak Area | Fortified Concentration (μg/g) | Volume 1 (mL) | Aliquot from Vol. 1 (mL) | Final Vol. (mL) | Dilution Factor | Conc. From curve (ng/mL)* | Calculated μg/sample | Accuracy (%) | Recovery (%) |
|---|---|---|---|---|---|---|---|---|---|---|---|---|
| 0.500 ng/mL std | — | — | 4.59E+03 | — | — | — | — | — | 0.543 | — | 109 | — |
| 0.500 ng/mL std | — | — | 3.94E+03 | — | — | — | — | — | 0.487 | — | 97.4 | — |
| Reagent blank | P1763S02-001 | — | 0.00E+00 | — | 100 | 2.00 | 5.00 | — | 0.00 | — | — | — |
| UTC-1 | P1763S02-002 | 5.01 | 0.00E+00 | — | 100 | 2.00 | 5.00 | — | 0.00 | 0.00 | — | — |
| UTC-2 | P1763S02-003 | 4.99 | 0.00E+00 | — | 100 | 2.00 | 5.00 | — | 0.00 | 0.00 | — | — |
| 1.00 ng/mL std | — | — | 1.06E+04 | — | — | — | — | — | 1.05 | — | 105 | — |
| LOQ-1 | P1763S02-004 | 5.01 | 9.21E+03 | 0.0499 | 100 | 2.00 | 5.00 | — | 0.937 | 0.0468 | — | 93.7 |
| LOQ-2 | P1763S02-005 | 4.98 | 9.82E+03 | 0.0502 | 100 | 2.00 | 5.00 | — | 0.989 | 0.0496 | — | 98.9 |
| LOQ-3 | P1763S02-006 | 5.02 | 9.01E+03 | 0.0498 | 100 | 2.00 | 5.00 | — | 0.920 | 0.0458 | — | 92.0 |
| 2.00 ng/mL std | — | — | 1.92E+04 | — | — | — | — | — | 1.79 | — | 89.5 | — |
| LOQ-4 | P1763S02-007 | 5.02 | 9.82E+03 | 0.0498 | 100 | 2.00 | 5.00 | — | 0.989 | 0.0493 | — | 98.9 |
| LOQ-5 | P1763S02-008 | 4.99 | 9.04E+03 | 0.0501 | 100 | 2.00 | 5.00 | — | 0.922 | 0.0462 | — | 92.2 |
| 4X LOQ-1 | P1763S02-009 | 5.00 | 3.56E+04 | 0.200 | 100 | 2.00 | 5.00 | — | 3.19 | 0.160 | — | 79.8 |
| 10.0 ng/mL std | — | — | 1.17E+05 | — | — | — | — | — | 10.1 | — | 101 | — |
| 4X LOQ-2 | P1763S02-010 | 5.00 | 3.93E+04 | 0.200 | 100 | 2.00 | 5.00 | — | 3.51 | 0.176 | — | 87.8 |
| 4X LOQ-3 | P1763S02-011 | 5.00 | 3.85E+04 | 0.200 | 100 | 2.00 | 5.00 | — | 3.43 | 0.172 | — | 85.8 |
| 4X LOQ-4 | P1763S02-012 | 4.99 | 3.87E+04 | 0.200 | 100 | 2.00 | 5.00 | — | 3.45 | 0.173 | — | 86.4 |
| 20.0 ng/mL std | — | — | 2.28E+05 | — | — | — | — | — | 19.6 | — | 98.0 | — |
| 4X LOQ-5 | P1763S02-013 | 5.01 | 4.03E+04 | 0.200 | 100 | 2.00 | 5.00 | — | 3.59 | 0.179 | — | 89.6 |
| 20.0 ng/mL std | — | — | 2.32E+05 | — | — | — | — | — | 20.0 | — | 100 | — |
| 50.0 ng/mL std | — | — | 5.77E+05 | — | — | — | — | — | 49.4 | NA | 98.8 | — |
| 100.0 ng/mL std | — | — | 1.18E+06 | — | — | — | — | — | 101 | — | 101 | — |
| Solvent blank | — | — | 0.00E+00 | — | — | — | — | — | No Peak | — | — | — |
| | | | | | | | Average Std Accuracy | | 100 | | Std. Dev. | % RSD |
| | | | | | | | LOQ Average % Recovery | | 95.1 | | 3.5 | 3.7 |
| | | | | | | | 4XLOQ Average % Recovery | | 85.8 | | 3.7 | 4.3 |
| | | | | | | | Total Average % Recovery | | 90.5 | | 6.0 | 6.6 |

TABLE 62

DATA SHEET FOR AMPA, GRAPES, TRIAL 1, SET 2

| Project: | 1763 | Fit | Linear | Weighting | 1/x |
|---|---|---|---|---|---|
| Set: | 2 | Intercept | −15.7 | | |
| Title | Validation-tryout 1 | Slope | 573 | | |
| | | Correlation coefficient | 0.9995 | | |
| | | Q1/Q3 Masses: 112.10/30.20 amu | | | |
| Matrix: | Grapes | | | | |
| Analyte: | AMPA | | | | |

| Sample Name | Sample ID | Sample Weight | Peak Area | Fortified Concentration (μg/g) | Volume 1 (mL) | Aliquot from Vol. 1 (mL) | Final Vol. (mL) | Dilution Factor | Conc. From curve (ng/mL)* | Calculated μg/sample | Accuracy (%) | Recovery (%) |
|---|---|---|---|---|---|---|---|---|---|---|---|---|
| 0.500 ng/mL std | — | — | 2.79E+02 | — | — | — | — | — | 0.513 | — | 103 | — |
| Reagent blank | P1763S02-001 | — | 0.00E+00 | — | 100 | 4.00 | 5.00 | — | 0.00 | — | — | — |
| UTC-1 | P1763S02-002 | 5.01 | 0.00E+00 | — | 100 | 4.00 | 5.00 | — | 0.00 | 0.00 | — | — |
| UTC-2 | P1763S02-003 | 4.99 | 0.00E+00 | — | 100 | 4.00 | 5.00 | — | 0.00 | 0.00 | — | — |
| 1.00 ng/mL std | — | — | 5.62E+02 | — | — | — | — | — | 1.01 | — | 101 | — |
| LOQ-1 | P1763S02-004 | 5.01 | 9.49E+02 | 0.0499 | 100 | 4.00 | 5.00 | — | 1.68 | 0.0419 | — | 84.0 |

TABLE 62-continued

DATA SHEET FOR AMPA, GRAPES, TRIAL 1, SET 2

| | | | | | | | | | | | | | |
|---|---|---|---|---|---|---|---|---|---|---|---|---|---|
| LOQ-2 | P1763S02-005 | 4.98 | 8.57E+02 | 0.0502 | 100 | 4.00 | 5.00 | — | 1.52 | 0.0382 | — | 76.0 |
| LOQ-3 | P1763S02-006 | 5.02 | 9.04E+02 | 0.0498 | 100 | 4.00 | 5.00 | — | 1.60 | 0.0398 | — | 80.0 |
| 2.00 ng/mL std | — | — | 1.01E+03 | — | — | — | — | — | 1.79 | — | 89.5 | — |
| LOQ-4 | P1763S02-007 | 5.02 | 9.32E+02 | 0.0498 | 100 | 4.00 | 5.00 | — | 1.65 | 0.0411 | — | 82.5 |
| LOQ-5 | P1763S02-008 | 4.99 | 9.19E+02 | 0.0501 | 100 | 4.00 | 5.00 | — | 1.63 | 0.0408 | — | 81.5 |
| 4X LOQ-1 | P1763S02-009 | 5.00 | 3.18E+03 | 0.200 | 100 | 4.00 | 5.00 | — | 5.58 | 0.140 | — | 69.8 |
| 10.0 ng/mL std | — | — | 5.80E+03 | — | — | — | — | — | 10.1 | — | 101 | — |
| 4X LOQ-2 | P1763S02-010 | 5.00 | 3.39E+03 | 0.200 | 100 | 4.00 | 5.00 | — | 5.94 | 0.149 | — | 74.3 |
| 4X LOQ-3 | P1763S02-011 | 5.00 | 3.31E+03 | 0.200 | 100 | 4.00 | 5.00 | — | 5.80 | 0.145 | — | 72.5 |
| 4X LOQ-4 | P1763S02-012 | 4.99 | 3.54E+03 | 0.200 | 100 | 4.00 | 5.00 | — | 6.20 | 0.155 | — | 77.7 |
| 20.0 ng/mL std | — | — | 1.21E+04 | — | — | — | — | — | 21.2 | — | 106 | — |
| 4X LOQ-5 | P1763S02-013 | 5.01 | 3.21E+03 | 0.200 | 100 | 4.00 | 5.00 | — | 5.62 | 0.140 | — | 70.1 |
| 50.0 ng/mL std | — | — | 2.93E+04 | — | — | — | — | — | 51.1 | — | 102 | — |
| 100.0 ng/mL std | — | — | 5.61E+04 | — | — | — | — | — | 97.8 | NA | 97.8 | — |
| Solvent blank | — | — | 0.00E+00 | — | — | — | — | — | 0.00 | — | — | — |

|  |  | Std. Dev. | % RSD |
|---|---|---|---|
| Average Std Accuracy | 100 |  |  |
| LOQ Average % Recovery | 80.8 | 3.1 | 3.8 |
| 4XLOQ Average % Recovery | 72.9 | 3.3 | 4.5 |
| Total Average % Recovery | 76.8 | 5.1 | 6.7 |

TABLE 63

DATA SHEET FOR N-ACETYL AMPA, GRAPES, TRIAL 1, SET 2

| | | | | | |
|---|---|---|---|---|---|
| Project: | 1763 | Fit | Linear | Weighting | 1/x |
| Set: | 2 | Intercept | −2.25E+03 | | |
| Title | Validation-tryout 1 | Slope | 3.75E+04 | | |
| | | Correlation coefficient | 0.9988 | | |
| | | Q1/Q3 Masses: | 154.00/112.10 amu | | |
| Matrix: | Grapes | | | | |
| Analyte: | n-acetylAMPA | | | | |

| Sample Name | Sample ID | Sample Weight | Peak Area | Fortified Concentration (µg/g) | Volume 1 (mL) | Aliquot from Vol. 1 (mL) | Final Vol. (mL) | Dilution Factor | Conc. From curve (ng/mL)* | Calculated µg/sample | Accuracy (%) | Recovery (%) |
|---|---|---|---|---|---|---|---|---|---|---|---|---|
| 0.500 ng/mL std | — | — | 1.65E+04 | — | — | — | — | — | 0.499 | — | 100 | — |
| Reagent blank | P1763S02-001 | — | 0.00E+00 | — | 100 | 4.00 | 5.00 | — | 0.00 | — | — | — |
| UTC-1 | P1763S02-002 | 5.01 | 0.00E+00 | — | 100 | 4.00 | 5.00 | — | 0.00 | 0.00 | — | — |
| UTC-2 | P1763S02-003 | 4.99 | 0.00E+00 | — | 100 | 4.00 | 5.00 | — | 0.00 | 0.00 | — | — |
| 1.00 ng/mL std | — | — | 3.22E+04 | — | — | — | — | — | 0.919 | — | 91.9 | — |
| LOQ-1 | P1763S02-004 | 5.01 | 5.72E+04 | 0.0499 | 100 | 4.00 | 5.00 | — | 1.59 | 0.0397 | — | 79.5 |
| LOQ-2 | P1763S02-005 | 4.98 | 7.35E+04 | 0.0502 | 100 | 4.00 | 5.00 | — | 2.02 | 0.0507 | — | 101 |
| LOQ-3 | P1763S02-006 | 5.02 | 7.08E+04 | 0.0498 | 100 | 4.00 | 5.00 | — | 1.95 | 0.0486 | — | 97.5 |
| 2.00 ng/mL std | — | — | 7.22E+04 | — | — | — | — | — | 1.99 | — | 99.5 | — |
| LOQ-4 | P1763S02-007 | 5.02 | 6.42E+04 | 0.0498 | 100 | 4.00 | 5.00 | — | 1.77 | 0.0441 | — | 88.5 |
| LOQ-5 | P1763S02-008 | 4.99 | 7.19E+04 | 0.0501 | 100 | 4.00 | 5.00 | — | 1.98 | 0.0496 | — | 99.0 |
| 4X LOQ-1 | P1763S02-009 | 5.00 | 2.51E+05 | 0.200 | 100 | 4.00 | 5.00 | — | 6.77 | 0.169 | — | 84.6 |
| 10.0 ng/mL std | — | — | 3.97E+05 | — | — | — | — | — | 10.7 | — | 107 | — |
| 4X LOQ-2 | P1763S02-010 | 5.00 | 2.63E+05 | 0.200 | 100 | 4.00 | 5.00 | — | 7.07 | 0.177 | — | 88.4 |
| 4X LOQ-3 | P1763S02-011 | 5.00 | 2.36E+05 | 0.200 | 100 | 4.00 | 5.00 | — | 6.36 | 0.159 | — | 79.5 |
| 4X LOQ-4 | P1763S02-012 | 4.99 | 2.27E+05 | 0.200 | 100 | 4.00 | 5.00 | — | 6.11 | 0.153 | — | 76.5 |
| 20.0 ng/mL std | — | — | 7.91E+05 | — | — | — | — | — | 21.2 | — | 106 | — |
| 4X LOQ-5 | P1763S02-013 | 5.01 | 2.39E+05 | 0.200 | 100 | 4.00 | 5.00 | — | 6.42 | 0.160 | — | 80.1 |
| 50.0 ng/mL std | — | — | 1.81E+06 | — | — | — | — | — | 48.3 | — | 96.6 | — |

TABLE 63-continued

DATA SHEET FOR N-ACETYL AMPA, GRAPES, TRIAL 1, SET 2

| | | | | | | | | | | | | |
|---|---|---|---|---|---|---|---|---|---|---|---|---|
| 100.0 ng/mL std* | — | — | 2.89E+06 | — | — | — | — | — | 77.2 | NA | 77.2 | — |
| Solvent blank | — | — | 0.00E+00 | — | — | — | — | — | 0.00 | — | — | — |
| | | | | | | | Average Std Accuracy | | 97 | Std. Dev. | % RSD | |
| | | | | | | | LOQ Average % Recovery | | 93.1 | 9.0 | 9.6 | |
| | | | | | | | 4XLOQ Average % Recovery | | 81.8 | 4.7 | 5.7 | |
| | | | | | | | Total Average % Recovery | | 87.5 | 9.0 | 10.3 | |

*Standard was not utilized due to not meeting specifications

TABLE 64

DATA SHEET FOR GLYPHOSATE, SOYBEAN SEED, TRIAL 2, SET 4

| Project: | 1763 | Fit | Linear | Weighting | 1/x |
|---|---|---|---|---|---|
| Set: | 4 | Intercept | −0.0384 | | |
| Title | Validation-tryout 2 | Slope | 0.25 | | |
| | | Correlation coefficient | 0.9992 | Use as Internal Standard | |
| | | Q1/Q3 Masses: 170.00/87.30 amu | | Q1/Q3 Masses: 173.10/91.00 amu | |
| Matrix: | Soya Seed | | | | |
| Analyte: | Glyphosate | | | | |

| Sample Name | Sample ID | Sample Weight | Analyte Peak Area | I.S. Peak Area | Fortified Concentration (μg/g) | Volume 1 (mL) | Aliquot from Vol. 1 (mL) | Final Vol. (mL) | Dilution Factor | Conc. From curve (ng/mL) | Calculated μg/sample | Accuracy (%) | Recovery (%) |
|---|---|---|---|---|---|---|---|---|---|---|---|---|---|
| 0.500 ng/mL std | — | — | 1.09E+04 | 1.09E+05 | — | — | — | — | — | 0.554 | — | 111 | — |
| Reagent blank | P1763S04-001 | — | 0.00E+00 | 9.48E+04 | — | 100 | 2.00 | 5.00 | — | No Peak | — | — | — |
| UTC-1 | P1763S04-002 | 5.00 | 0.00E+00 | 9.69E+04 | — | 100 | 2.00 | 5.00 | — | No Peak | 0.00 | — | — |
| UTC-2 | P1763S04-003 | 5.00 | 0.00E+00 | 9.03E+04 | — | 100 | 2.00 | 5.00 | — | No Peak | 0.00 | — | — |
| 1.00 ng/mL std | — | — | 2.41E+04 | 1.10E+05 | — | — | — | — | — | 1.03 | — | 103 | — |
| LOQ-1 | P1763S04-004 | 5.00 | 1.94E+04 | 9.38E+04 | 0.0500 | 100 | 2.00 | 5.00 | — | 0.983 | 0.0492 | — | 98.3 |
| LOQ-2 | P1763S04-005 | 5.00 | 2.03E+04 | 9.29E+04 | 0.0500 | 100 | 2.00 | 5.00 | — | 1.030 | 0.0515 | — | 103 |
| LOQ-3 | P1763S04-006 | 5.00 | 2.27E+04 | 9.33E+04 | 0.0500 | 100 | 2.00 | 5.00 | — | 1.13 | 0.0565 | — | 113 |
| 2.00 ng/mL std | — | — | 4.32E+04 | 1.11E+05 | — | — | — | — | — | 1.72 | — | 86.0 | — |
| LOQ-4 | P1763S04-007 | 5.00 | 1.70E+04 | 1.01E+05 | 0.0500 | 100 | 2.00 | 5.00 | — | 0.831 | 0.0416 | — | 83.1 |
| 2.00 ng/mL std | — | — | 4.35E+04 | 9.66E+04 | — | 100 | 2.00 | 5.00 | — | 1.96 | — | 98.0 | — |
| LOQ-5 | P1763S04-008 | 5.00 | 1.68E+04 | 9.81E+04 | 0.0500 | 100 | 2.00 | 5.00 | — | 0.84 | 0.0420 | — | 84.0 |
| 400X LOQ-1 | P1763S04-009 | 5.00 | 9.51E+04 | 1.12E+05 | 20.0 | 100 | 2.00 | 5.00 | 100 | 3.55 | 17.8 | — | 88.8 |
| 5.00 ng/mL std | — | — | 1.25E+05 | 1.03E+05 | — | — | — | — | — | 5.03 | — | 101 | — |
| 400X LOQ-2 | P1763S04-010 | 5.00 | 1.01E+05 | 1.22E+05 | 20.0 | 100 | 2.00 | 5.00 | 100 | 3.47 | 17.4 | — | 86.8 |
| 400X LOQ-3 | P1763S04-011 | 5.00 | 1.05E+05 | 1.23E+05 | 20.0 | 100 | 2.00 | 5.00 | 100 | 3.59 | 18.0 | — | 89.8 |
| 400X LOQ-4 | P1763S04-012 | 5.00 | 1.00E+05 | 1.24E+05 | 20.0 | 100 | 2.00 | 5.00 | 100 | 3.41 | 17.1 | — | 85.3 |
| 10.0 ng/mL std | — | — | 2.88E+05 | 1.16E+05 | — | — | — | — | — | 10.1 | — | 101.0 | — |
| 400X LOQ-5 | P1763S04-013 | 5.00 | 8.79E+04 | 1.28E+05 | 20.0 | 100 | 2.00 | 5.00 | 100 | 2.9 | 14.5 | — | 72.5 |
| 20.0 ng/mL std | — | — | 5.36E+05 | 1.08E+05 | — | — | — | — | — | 20.1 | NA | 101 | — |
| Solvent blank | — | — | 0.00E+00 | 0.00E+00 | — | — | — | — | — | No Peak | — | — | — |
| | | | | | | | Average Std Accuracy | | 100 | Std. Dev. | % RSD | | |
| | | | | | | | LOQ Average % Recovery | | 96.3 | 12.8 | 13.3 | | |
| | | | | | | | 400XLOQ Average % Recovery | | 84.6 | 7.0 | 8.3 | | |
| | | | | | | | Total Average % Recovery | | 90.4 | 11.5 | 12.7 | | |

TABLE 65

DATA SHEET FOR N-ACETYLGLYPHOSATE, SOYBEAN SEED, TRIAL 2, SET 4

Project: 1763  
Set: 4  
Title: Validation-tryout 2  
Fit: Linear  Weighting: 1/x  
Intercept: −4810  
Slope: 3.00E+04  
Correlation coefficient: 0.9984  
Q1/Q3 Masses: 212.00/170.20 amu  
Matrix: Soya Seed  
Analyte: n-acetylGlyphosate

| Sample Name | Sample ID | Sample Weight | Analyte Peak Area | Fortified Concentration (µg/g) | Volume 1 (mL) | Aliquot from Vol. 1 (mL) | Final Vol. (mL) | Dilution Factor | Conc. From curve (ng/mL) | Calculated µg/sample | Accuracy (%) | Recovery (%) |
|---|---|---|---|---|---|---|---|---|---|---|---|---|
| 0.500 ng/mL std | — | — | 1.24E+04 | — | — | — | — | — | 0.573 | — | 115 | — |
| Reagent blank | P1763S04-001 | — | 0.00E+00 | — | 100 | 2.00 | 5.00 | — | No Peak | — | — | — |
| UTC-1 | P1763S04-002 | 5.00 | 0.00E+00 | — | 100 | 2.00 | 5.00 | — | No Peak | 0.00 | — | — |
| UTC-2 | P1763S04-003 | 5.00 | 0.00E+00 | — | 100 | 2.00 | 5.00 | — | No Peak | 0.00 | — | — |
| 1.00 ng/mL std | — | — | 2.44E+04 | — | — | — | — | — | 0.973 | — | 97.3 | — |
| LOQ-1 | P1763S04-004 | 5.00 | 1.95E+04 | 0.0500 | 100 | 2.00 | 5.00 | — | 0.809 | 0.0405 | — | 80.9 |
| LOQ-2 | P1763S04-005 | 5.00 | 2.04E+04 | 0.0500 | 100 | 2.00 | 5.00 | — | 0.842 | 0.0421 | — | 84.2 |
| LOQ-3 | P1763S04-006 | 5.00 | 2.01E+04 | 0.0500 | 100 | 2.00 | 5.00 | — | 0.831 | 0.0416 | — | 83.1 |
| 2.00 ng/mL std | — | — | 5.29E+04 | — | — | — | — | — | 1.92 | — | 96.0 | — |
| LOQ-4 | P1763S04-007 | 5.00 | 1.93E+04 | 0.0500 | 100 | 2.00 | 5.00 | — | 0.805 | 0.0403 | — | 80.5 |
| 2.00 ng/mL std | — | — | 5.36E+04 | — | 100 | 2.00 | 5.00 | — | 1.94 | — | 97.0 | — |
| LOQ-5 | P1763S04-008 | 5.00 | 2.22E+04 | 0.0500 | 100 | 2.00 | 5.00 | — | 0.899 | 0.0450 | — | 89.9 |
| 400X LOQ-1 | P1763S04-009 | 5.00 | 9.52E+04 | 20.0 | 100 | 2.00 | 5.00 | 100 | 3.33 | 16.7 | — | 83.3 |
| 5.00 ng/mL std | — | — | 1.29E+05 | — | — | — | — | — | 4.47 | — | 89.4 | — |
| 400X LOQ-2 | P1763S04-010 | 5.00 | 1.01E+05 | 20.0 | 100 | 2.00 | 5.00 | 100 | 3.52 | 17.6 | — | 88.0 |
| 400X LOQ-3 | P1763S04-011 | 5.00 | 1.03E+05 | 20.0 | 100 | 2.00 | 5.00 | 100 | 3.61 | 18.1 | — | 90.3 |
| 400X LOQ-4 | P1763S04-012 | 5.00 | 1.09E+05 | 20.0 | 100 | 2.00 | 5.00 | 100 | 3.79 | 19.0 | — | 94.8 |
| 10.0 ng/mL std | — | — | 3.08E+05 | — | — | — | — | — | 10.4 | — | 104 | — |
| 400X LOQ-5 | P1763S04-013 | 5.00 | 1.05E+05 | 20.0 | 100 | 2.00 | 5.00 | 100 | 3.7 | 18.3 | — | 91.3 |
| 20.0 ng/mL std | — | — | 6.01E+05 | — | — | — | — | — | 20.2 | NA | 101 | — |
| Solvent blank | — | — | 0.00E+00 | — | — | — | — | — | No Peak | — | — | — |

|  |  |  |
|---|---|---|
| Average Std Accuracy | 100 | Std. Dev. / % RSD |
| LOQ Average % Recovery | 83.7 | 3.8 / 4.5 |
| 400XLOQ Average % Recovery | 89.5 | 4.3 / 4.8 |
| Total Average % Recovery | 86.6 | 4.9 / 5.6 |

TABLE 66

DATA SHEET FOR AMPA, SOYBEAN SEED, TRIAL 2, SET 4

Project: 1763  
Set: 4  
Title: Validation-tryout 2  
Matrix: Soya Seed  
Analyte: AMPA Fit: Linear  
Intercept: −0.0104  
Slope: 1.13  
Correlation coefficient: 0.9996  
Q1/Q3 Masses: 112.10/30.20 amu Weighting: 1/x  
Use as Internal Standard  
Q1/Q3 Masses: 113.10/30.20 amu

| Sample Name | Sample ID | Sample Weight | Analyte Peak Area | I.S. Peak Area | Fortified Concentration (µg/g) | Volume 1 (mL) | Aliquot from Vol. 1 (mL) | Final Vol. (mL) | Dilution Factor | Conc. From curve (ng/mL) | Calculated µg/sample | Accuracy (%) | Recovery (%) |
|---|---|---|---|---|---|---|---|---|---|---|---|---|---|
| 1.00 ng/mL std | — | — | 9.51E+02 | 4.34E+03 | — | — | — | — | — | 1.01 | — | 101 | — |
| Reagent blank | P1763S04-001 | — | 0.00E+00 | 5.77E+03 | — | 100 | 4.00 | 5.00 | — | No Peak | — | — | — |
| UTC-1 | P1763S04-002 | 5.00 | 0.00E+00 | 2.46E+03 | — | 100 | 4.00 | 5.00 | — | No Peak | 0.00 | — | — |
| UTC-2 | P1763S04-003 | 5.00 | 0.00E+00 | 2.66E+03 | — | 100 | 4.00 | 5.00 | — | No Peak | 0.00 | — | — |
| 2.00 ng/mL std | — | — | 2.29E+03 | 5.07E+03 | — | — | — | — | — | 2.04 | — | 102 | — |
| LOQ-1 | P1763S04-004 | 5.00 | 8.32E+02 | 2.43E+03 | 0.0500 | 100 | 4.00 | 5.00 | — | 1.55 | 0.0388 | — | 77.5 |
| LOQ-2 | P1763S04-005 | 5.00 | 1.05E+03 | 2.78E+03 | 0.0500 | 100 | 4.00 | 5.00 | — | 1.71 | 0.0428 | — | 85.5 |
| LOQ-3 | P1763S04-006 | 5.00 | 1.21E+03 | 2.89E+03 | 0.0500 | 100 | 4.00 | 5.00 | — | 1.89 | 0.0473 | — | 94.5 |
| 5.00 ng/mL std | — | — | 5.44E+03 | 4.74E+03 | — | — | — | — | — | 5.11 | — | 102 | — |
| LOQ-4 | P1763S04-007 | 5.00 | 9.68E+02 | 2.41E+03 | 0.0500 | 100 | 4.00 | 5.00 | — | 1.82 | 0.0455 | — | 91.0 |
| LOQ-5 | P1763S04-008 | 5.00 | 1.10E+03 | 2.38E+03 | 0.0500 | 100 | 4.00 | 5.00 | — | 2.09 | 0.0523 | — | 105 |
| 400X LOQ-1 | P1763S04-009 | 5.00 | 8.24E+03 | 5.23E+03 | 20.0 | 100 | 4.00 | 5.00 | 100 | 6.99 | 17.5 | — | 87.4 |
| 10.0 ng/mL std | — | — | 1.12E+04 | 5.04E+03 | — | — | — | — | — | 9.79 | — | 97.9 | — |
| 400X LOQ-2 | P1763S04-010 | 5.00 | 1.71E+04 | 9.88E+03 | 20.0 | 100 | 4.00 | 5.00 | 100 | 7.68 | 19.2 | — | 96.0 |
| 400X LOQ-3 | P1763S04-011 | 5.00 | 1.82E+04 | 1.02E+04 | 20.0 | 100 | 4.00 | 5.00 | 100 | 7.91 | 19.8 | — | 98.9 |
| 400X LOQ-4 | P1763S04-012 | 5.00 | 1.80E+04 | 1.10E+04 | 20.0 | 100 | 4.00 | 5.00 | 100 | 7.24 | 18.1 | — | 90.5 |
| 20.0 ng/mL std | — | — | 4.39E+04 | 9.56E+03 | — | — | — | — | — | 20.3 | — | 102 | — |
| 400X LOQ-5 | P1763S04-013 | 5.00 | 1.46E+04 | 1.09E+04 | 20.0 | 100 | 4.00 | 5.00 | 100 | 5.94 | 14.9 | — | 74.3 |
| 5.00 ng/mL std | — | — | 1.04E+04 | 9.70E+03 | — | — | — | — | — | 4.77 | — | 95.4 | — |

|  |  | Std. Dev. | % RSD |
|---|---|---|---|
| Average Std Accuracy | 100 |  |  |
| LOQ Average % Recovery | 90.6 | 10 | 11 |
| 400XLOQ Average % Recovery | 89.4 | 9.6 | 11 |
| Total Average % Recovery | 90.0 | 9.3 | 10 |

TABLE 67

DATA SHEET FOR N-ACETYL AMPA, SOYBEAN SEED, TRIAL 2, SET 4

| | | | | |
|---|---|---|---|---|
| Project: | 1763 | Fit | Linear | Weighting 1/x |
| Set: | 4 | Intercept | −500 | |
| Title | Validation-tryout 2 | Slope | 2.59E+03 | |
| | | Correlation coefficient | 0.9994 | |
| | | Q1/Q3 Masses: 154.00/30.2 amu | | |
| Matrix: | Soya Seed | | | |
| Analyte: | n-acetylAMPA | | | |

| Sample Name | Sample ID | Sample Weight | Analyte Peak Area | Fortified Concentration (µg/g) | Volume 1 (mL) | Aliquot from Vol. 1 (mL) | Final Vol. (mL) | Dilution Factor | Conc. From curve (ng/mL) | Calculated µg/sample | Accuracy (%) | Recovery (%) |
|---|---|---|---|---|---|---|---|---|---|---|---|---|
| 1.00 ng/mL std | — | — | 2.20E+03 | — | — | — | — | — | 1.04 | — | 104 | — |
| Reagent blank | P1763S04-001 | — | 0.00E+00 | — | 100 | 4.00 | 5.00 | — | No Peak | — | — | — |
| UTC-1 | P1763S04-002 | 5.00 | 0.00E+00 | — | 100 | 4.00 | 5.00 | — | No Peak | 0.00 | — | — |
| UTC-2 | P1763S04-003 | 5.00 | 0.00E+00 | — | 100 | 4.00 | 5.00 | — | No Peak | 0.00 | — | — |
| 2.00 ng/mL std | — | — | 4.26E+03 | — | — | — | — | — | 1.84 | — | 92.0 | — |
| LOQ-1 | P1763S04-004 | 5.00 | 4.04E+03 | 0.0500 | 100 | 4.00 | 5.00 | — | 1.76 | 0.0440 | — | 88.0 |
| LOQ-2 | P1763S04-005 | 5.00 | 4.76E+03 | 0.0500 | 100 | 4.00 | 5.00 | — | 2.03 | 0.0508 | — | 102 |
| LOQ-3 | P1763S04-006 | 5.00 | 4.58E+03 | 0.0500 | 100 | 4.00 | 5.00 | — | 1.96 | 0.0490 | — | 98.0 |
| 5.00 ng/mL std* | — | — | 9.39E+03 | — | — | — | — | — | 3.82 | — | 76.4 | — |
| LOQ-4 | P1763S04-007 | 5.00 | 4.44E+03 | 0.0500 | 100 | 4.00 | 5.00 | — | 1.91 | 0.0478 | — | 95.5 |
| LOQ-5 | P1763S04-008 | 5.00 | 4.42E+03 | 0.0500 | 100 | 4.00 | 5.00 | — | 1.90 | 0.0475 | — | 95.0 |
| 400X LOQ-1 | P1763S04-009 | 5.00 | 1.72E+04 | 20.0 | 100 | 4.00 | 5.00 | 100 | 6.84 | 17.1 | — | 85.5 |
| 10.0 ng/mL std* | — | — | 1.98E+04 | — | — | — | — | — | 7.86 | — | 78.6 | — |
| 400X LOQ-2 | P1763S04-010 | 5.00 | 2.44E+04 | 20.0 | 100 | 4.00 | 5.00 | 100 | 9.63 | 24.1 | — | 120 |
| 400X LOQ-3 | P1763S04-011 | 5.00 | 2.40E+04 | 20.0 | 100 | 4.00 | 5.00 | 100 | 9.45 | 23.6 | — | 118 |
| 400X LOQ-4 | P1763S04-012 | 5.00 | 2.56E+04 | 20.0 | 100 | 4.00 | 5.00 | 100 | 10.10 | 25.3 | — | 126 |
| 20.0 ng/mL std | — | — | 5.10E+04 | — | — | — | — | — | 19.9 | — | 100 | — |
| 400X LOQ-5 | P1763S04-013 | 5.00 | 2.13E+04 | 20.0 | 100 | 4.00 | 5.00 | 100 | 8.41 | 21.0 | — | 105 |
| 5.00 ng/mL std | — | — | 1.30E+04 | — | — | — | — | — | 5.21 | — | 104 | — |
| | | | | | | | Average Std Accuracy | | | 92 | Std. Dev. | % RSD |
| | | | | | | | LOQ Average % Recovery | | | 96 | 5.0 | 5.2 |
| | | | | | | | 400XLOQ Average % Recovery | | | 111 | 16 | 15 |
| | | | | | | | Total Average % Recovery | | | 103 | 14 | 14 |

*Standard not utilized due to not meeting specifications

Example 5

Analytical Method for the Determination of N-acetylglyphosate and Other Analytes in Various Matrices using LC/MS/MS

Summary

An analytical method was developed for the determination of N-acetylglyphosate, glyphosate, AMPA, and N-acetyl AMPA in animal matrices including milk, eggs, muscle, kidney, liver, and fat. The method target limit of quantitation (LOQ) in glyphosate equivalents for each analyte was 0.025 mg/kg in egg, milk, and muscle matrices and 0.050 mg/kg in kidney, liver, and fat matrices. The method was validated at the respective LOQ and 10×LOQ level. Milk and egg matrices were validated at 0.025 mg/kg (LOQ), 0.050 mg/kg (2×LOQ), and 0.5 mg/kg (20×LOQ). For each matrix using a LC/MS/MS system operating with an electrospray interface (ESI) in positive or negative ion mode detection. This analytical method was developed to support residue data collection in livestock feeding studies required for registration of genetically modified crops.

For milk and egg matrices, matrix samples were diluted in aqueous 0.1% formic acid/methanol (96/4, v/v) and shaken to dilute sample in aqueous medium. Samples may be stored frozen or extracted promptly without freezing. The dilute sample was partitioned with hexane (after thawing if frozen) and the hexane layer discarded. The remaining aqueous fraction was partitioned with methylene chloride and the aqueous layer was collected. The methylene chloride fraction was back extracted with additional 0.1% formic acid/methanol (96/4, v/v) for quantitative recovery of analytes. The aqueous fractions were combined and diluted to final volume 50 mL. An aliquot of the aqueous fraction was filtered through a C18 SPE cartridge. The C18 filtered extract was further purified by solid phase extraction using polymeric anion exchange (MAX) SPE cartridge and/or polymeric cation exchange (MCX) SPE cartridge, depending on matrix and analytes to be examined. Glyphosate and/or AMPA stable isotope standards used as internal standards were added to extracts prior to ion exchange SPE purification. Final extracts were filtered prior to LC/MS/MS analysis.

For animal tissue matrices, matrix samples were initially blended with $C_{18}$ sorbent material (matrix solid phase dispersion) prior to extraction in 0.1N HCl solution (96% water/4% methanol) followed by water for final extract volume of 50 mL. An aliquot of the extract was diluted in acetonitrile and methanol to precipitate proteins, then purified by solid phase extraction using polymeric anion exchange (MAX) SPE cartridge and/or polymeric cation exchange (MCX) SPE cartridge, depending on matrix and analytes to be examined. Glyphosate and/or AMPA stable isotope standards used as internal standards were added to extracts prior to ion exchange SPE purification. Final extracts were filtered prior to LC/MS/MS analysis.

Final extract and calibration standard solutions were adjusted to 0.02M phosphoric acid. Samples and standards were analyzed using HPLC with reverse phase chromatography and a triple quadrupole mass spectrometer with an electrospray source, operating in positive ion LC/MS/MS mode.

The recoveries from matrix samples fortified at the respective LOQ and higher levels support the satisfactory performance of this method. Tables 68-71 summarize the average recovery results for N-acetylglyphosate, glyphosate, N-acetyl AMPA, and AMPA in sample matrices. Liver, fat, and muscle include samples from cow and chicken. Cow was source of kidney samples.

TABLE 68

| MATRIX | FORTIFICATION LEVEL IN PPM (MG/KG) | SAMPLE SIZE (N) | RECOVERIES (%) | MEAN ± STD. DEV. (% ± %) |
|---|---|---|---|---|
| N-ACETYLGLYPHOSATE | | | | |
| Whole Milk | 0.025 | 9 | 81, 78, 78, 75, 77, 75, 84, 83, 91 | 80 ± 5 |
| | 0.05 | 7 | 83, 75, 77, 79, 79, 81, 77 | 78 ± 3 |
| | 0.5 | 7 | 83, 79, 78, 76, 75, 83, 78 | 79 ± 3 |
| Skim Milk | 0.025 | 5 | 94, 93, 94, 98, 95 | 95 ± 2 |
| | 0.05 | 5 | 90, 81, 103, 98, 93 | 93 ± 8 |
| | 0.5 | 5 | 86, 86, 90, 96, 97 | 91 ± 5 |
| Cream | 0.025 | 5 | 81, 80, 78, 77, 74 | 78 ± 3 |
| | 0.05 | 5 | 83, 86, 75, 83, 82 | 82 ± 4 |
| | 0.5 | 5 | 86, 85, 81, 80, 81 | 82 ± 3 |
| Whole Egg | 0.025 | 5 | 102, 80, 111, 104, 85 | 97 ± 13 |
| | 0.05 | 5 | 88, 83, 97, 82, 86 | 87 ± 6 |
| | 0.5 | 5 | 81, 88, 91, 85, 91 | 87 ± 4 |
| Egg Yolks | 0.025 | 5 | 83, 98, 86, 85, 87 | 88 ± 6 |
| | 0.05 | 5 | 85, 88, 88, 97, 88 | 90 ± 5 |
| | 0.5 | 5 | 111, 93, 92, 83, 96 | 95 ± 10 |
| Egg Whites | 0.025 | 5 | 87, 105, 108, 105, 107 | 103 ± 9 |
| | 0.05 | 5 | 88, 107, 106, 89, 90 | 96 ± 10 |
| | 0.5 | 5 | 98, 93, 96, 95, 92 | 95 ± 2 |
| Liver | 0.05 | 11 | 82, 87, 87, 98, 80, 105, 93, 75, 92, 84, 112 | 90 ± 11 |
| | 0.5 | 9 | 89, 109, 90, 92, 94, 81, 86, 78, 76 | 89 ± 10 |
| Kidney | 0.05 | 6 | 97, 106, 103, 94, 112, 80 | 99 ± 11 |
| | 0.5 | 7 | 82, 84, 85, 88, 73, 82, 87 | 83 ± 5 |
| Fat | 0.05 | 6 | 99, 93, 91, 107, 104, 104 | 100 ± 6 |
| | 0.5 | 6 | 93, 97, 83, 86, 87, 96 | 90 ± 6 |
| Muscle | 0.025 | 7 | 90, 93, 78, 102, 93, 113, 76 | 92 ± 13 |
| | 0.25 | 7 | 84, 92, 70, 81, 87, 78, 73 | 81 ± 8 |

TABLE 69

| | FORTIFICATION LEVEL IN PPM (MG/KG) | SAMPLE SIZE (N) | RECOVERIES (%) | MEAN ± STD. DEV. (% ± %) |
|---|---|---|---|---|
| GLYPHOSATE | | | | |
| Whole Milk | 0.025 | 9 | 87, 82, 119, 87, 95, 99, 93, 90, 119 | 97 ± 14 |
| | 0.05 | 7 | 104, 87, 97, 94, 93, 101, 126 | 100 ± 13 |
| | 0.5 | 7 | 78, 71, 77, 80, 79, 94, 84 | 80 ± 7 |
| Skim Milk | 0.025 | 5 | 82, 94, 97, 81, 111 | 93 ± 12 |
| | 0.05 | 5 | 89, 83, 85, 88, 79 | 85 ± 4 |
| | 0.5 | 5 | 87, 95, 78, 82, 85 | 85 ± 7 |
| Cream | 0.025 | 5 | 109, 79, 94, 113, 101 | 99 ± 13 |
| | 0.05 | 5 | 94, 91, 91, 95, 103 | 95 ± 5 |
| | 0.5 | 5 | 80, 84, 90, 77, 84 | 83 ± 5 |
| Whole Egg | 0.025 | 5 | 93, 79, 89, 89, 92 | 88 ± 6 |
| | 0.05 | 5 | 89, 101, 87, 84, 86 | 89 ± 7 |
| | 0.5 | 5 | 85, 87, 87, 84, 82 | 85 ± 2 |
| Egg Yolks | 0.025 | 5 | 95, 89, 115, 92, 100 | 98 ± 10 |
| | 0.05 | 5 | 87, 85, 84, 104, 90 | 90 ± 8 |
| | 0.5 | 5 | 99, 92, 85, 83, 86 | 89 ± 7 |
| Egg Whites | 0.025 | 5 | 74, 85, 94, 81, 81 | 83 ± 7 |
| | 0.05 | 5 | 90, 89, 91, 84, 85 | 88 ± 3 |
| | 0.5 | 5 | 81, 86, 95, 93, 90 | 89 ± 6 |
| Liver | 0.05 | 11 | 93, 98, 74, 105, 92, 90, 78, 80, 102, 84, 92 | 90 ± 10 |
| | 0.5 | 9 | 86, 85, 79, 86, 85, 88, 82, 71, 76 | 82 ± 5 |
| Kidney | 0.05 | 6 | 116, 78, 96, 113, 88, 99 | 98 ± 15 |
| | 0.5 | 7 | 81, 84, 92, 91, 86, 84, 89 | 87 ± 4 |

TABLE 69-continued

|  | FORTIFICATION LEVEL IN PPM (MG/KG) | SAMPLE SIZE (N) | RECOVERIES (%) | MEAN ± STD. DEV. (% ± %) |
|---|---|---|---|---|
| Fat | 0.05 | 6 | 98, 110, 88, 113, 86, 91 | 98 ± 11 |
|  | 0.5 | 6 | 92, 86, 96, 95, 97, 98 | 94 ± 4 |
| Muscle | 0.025 | 7 | 96, 102, 82, 89, 77, 94, 103 | 92 ± 10 |
|  | 0.25 | 7 | 82, 88, 78, 91, 81, 82, 86 | 84 ± 4 |

TABLE 70

| MATRIX | FORTIFICATION LEVEL IN PPM (MG/KG) | SAMPLE SIZE (N) | RECOVERIES (%) | MEAN ± STD. DEV. (% ± %) |
|---|---|---|---|---|
| N-ACETYL AMPA | | | | |
| Whole Milk | 0.025 | 9 | 75, 77, 91, 81, 84, 85, 74, 72, 89 | 81 ± 7 |
|  | 0.05 | 7 | 79, 76, 85, 82, 77, 78, 74 | 79 ± 4 |
|  | 0.5 | 7 | 86, 83, 83, 84, 82, 81, 76 | 82 ± 3 |
| Skim Milk | 0.025 | 5 | 100, 101, 82, 97, 96 | 95 ± 8 |
|  | 0.05 | 5 | 94, 91, 97, 103, 107 | 99 ± 7 |
|  | 0.5 | 5 | 100, 100, 98, 105, 104 | 101 ± 3 |
| Cream | 0.025 | 5 | 108, 68, 85, 88, 85 | 87 ± 14 |
|  | 0.05 | 5 | 82, 71, 92, 89, 84 | 83 ± 8 |
|  | 0.5 | 5 | 98, 86, 94, 94, 94 | 93 ± 5 |
| Whole Egg | 0.025 | 5 | 80, 84, 93, 101, 101 | 92 ± 9 |
|  | 0.05 | 5 | 93, 90, 103, 102, 109 | 99 ± 8 |
|  | 0.5 | 5 | 89, 93, 97, 101, 104 | 97 ± 6 |
| Egg Yolks | 0.025 | 5 | 91, 101, 87, 95, 93 | 93 ± 5 |
|  | 0.05 | 5 | 97, 94, 93, 99, 97 | 96 ± 2 |
|  | 0.5 | 5 | 105, 109, 106, 99, 112 | 106 ± 5 |
| Egg Whites | 0.025 | 5 | 96, 86, 91, 89, 89 | 90 ± 4 |
|  | 0.05 | 5 | 92, 94, 91, 77, 81 | 87 ± 8 |
|  | 0.5 | 5 | 92, 100, 92, 85, 92 | 92 ± 5 |
| Liver | 0.05 | 10 | 96, 100, 58, 93, 107, 76, 71, 72, 71, 86 | 83 ± 16 |
|  | 0.5 | 9 | 81, 94, 85, 95, 93, 73, 81, 63, 68 | 81 ± 12 |
| Kidney | 0.05 | 6 | 93, 94, 69, 80, 75, 79 | 82 ± 10 |
|  | 0.5 | 6 | 87, 93, 71, 75, 71, 76 | 79 ± 9 |
| Fat | 0.05 | 6 | 82, 85, 85, 95, 94, 86 | 88 ± 5 |
|  | 0.5 | 6 | 90, 92, 71, 90, 93, 89 | 87 ± 8 |
| Muscle | 0.025 | 6 | 77, 77, 69, 93, 96, 84 | 83 ± 10 |
|  | 0.25 | 5 | 80, 88, 86, 80, 64 | 80 ± 9 |

TABLE 71

| MATRIX | FORTIFICATION LEVEL IN PPM (MG/KG) | SAMPLE SIZE (N) | RECOVERIES (%) | MEAN ± STD. DEV. (% ± %) |
|---|---|---|---|---|
| AMPA | | | | |
| Whole Milk | 0.025 | 9 | 88, 93, 86, 85, 86, 86, 84, 82, 90 | 87 ± 3 |
|  | 0.05 | 7 | 90, 96, 83, 73, 83, 89, 84 | 85 ± 7 |
|  | 0.5 | 7 | 81, 86, 78, 77, 71, 87, 82 | 80 ± 6 |
| Skim Milk | 0.025 | 2 | 93, 96 | 94 |
|  | 0.05 | 2 | 87, 81 | 84 |
|  | 0.5 | 2 | 76, 76 | 76 |
| Cream | 0.025 | 5 | 88, 98, 94, 87, 97 | 93 ± 5 |
|  | 0.05 | 5 | 95, 78, 86, 88, 96 | 88 ± 8 |
|  | 0.5 | 5 | 84, 81, 87, 80, 75 | 82 ± 4 |
| Whole Egg | 0.025 | 5 | 110, 92, 110, 107, 107 | 105 ± 7 |
|  | 0.05 | 5 | 80, 97, 97, 98, 107 | 96 ± 10 |
|  | 0.5 | 5 | 79, 85, 86, 86, 83 | 84 ± 3 |
| Egg Yolks | 0.025 | 2 | 106, 114 | 110 |
|  | 0.05 | 2 | 80, 100 | 90 |
|  | 0.5 | 2 | 97, 91 | 94 |
| Egg Whites | 0.025 | 4 | 74, 86, 94, 111 | 91 ± 16 |
|  | 0.05 | 5 | 90, 92, 103, 91, 97 | 94 ± 5 |
|  | 0.5 | 5 | 87, 84, 87, 89, 84 | 86 ± 2 |
| Liver | 0.05 | 10 | 95, 92, 86, 77, 101, 103, 118, 94, 95, 111 | 97 ± 12 |
|  | 0.5 | 9 | 105, 110, 91, 85, 86, 97, 92, 81, 98 | 94 ± 10 |

TABLE 71-continued

| MATRIX | FORTIFICATION LEVEL IN PPM (MG/KG) | SAMPLE SIZE (N) | RECOVERIES (%) | MEAN ± STD. DEV. (% ± %) |
|---|---|---|---|---|
| Kidney | 0.05 | 6 | 76, 83, 100, 113, 101, 77 | 92 ± 15 |
|  | 0.5 | 7 | 77, 71, 95, 88, 84, 98, 108 | 89 ± 13 |
| Fat | 0.05 | 5 | 109, 105, 109, 97, 95 | 103 ± 6 |
|  | 0.5 | 5 | 89, 94, 91, 92, 97 | 93 ± 3 |
| Muscle | 0.025 | 6 | 101, 101, 84, 84, 88, 103 | 94 ± 9 |
|  | 0.25 | 5 | 91, 95, 85, 101, 99 | 94 ± 6 |

Materials

TABLE 72

Equipment

| EQUIPMENT DESCRIPTION | PRODUCT ID | SUPPLIER |
|---|---|---|
| Freezer | Labline ® Frigid-Cab ® | Labline Instruments, Inc. (Melrose Park, Ill.) |
| Refrigerator | 6FAR | Marvel Industries, Inc. (Richmond, Ind.) |
| Analytical Balance | AE163 Dual Range Balance PDPX0 Toploading Balance | Mettler Instrument Corp. (Hightstown, NJ) |
| Sonication | Bransonic ® 52-H, 0.75 gal. capacity | Branson Ultrasonics Corp. (Danbury, Conn.) |
| Vortex Mixer | Vortex Genie ® K-550-G or Vortex-2 Genie ® | VWR, Inc. (West Chester, PA) |
| Filtration | Pall Acrodisc ® nylon syringe filters: 13 mm × 0.2 µm (#4427T), 25 mm × 0.2 µm (#4436T) | VWR (Bridgeport, N.J.) |
| Solid Phase Extraction | Oasis ™ MAX SPE cartridge, 500 mg/6 mL, Cat. No. 186000865 | Waters Corporation (Milford, Mass.) |
|  | Oasis ™ MCX SPE cartridge, 500 mg/6 mL, Cat. No. 186000776 | Waters Corporation (Milford, Mass.) |
|  | Bond Elut ™ SPE cartridge: C18, 500 mg/6 cc, Cat. No. 12102052; Reservoir Adapters, Cat. No. 12131003; 60 mL reservoir Cat. No. 12131012. | Varian, Inc. (Palo Alto, CA) |
|  | Supelco Visiprep ™ SPE Vacuum Manifold standard, 12-port model, Cat No. 57030-U | Sigma-Aldrich Corp. (St. Louis, MO) |
|  | Frit, polethylene, 20 µm for 60 mL reservoir: VWR Cat No. BJ9444 (Frit, fits 75 mL) or Varian #12131024 | VWR (Bridgeport, NJ) |
| Centrifuge | Sorvall ® Centrifuge, Model RT7 with a RTH750 rotor | Sorvall Instruments (Wilmington, DE) |
| Analytical Evaporator | N-Evap ® Model 112 (with stainless steel luer fit needles) | Organomation Assoc. (South Berlin, Mass.) |
| Labware | Pyrex ® Brand Single Metric Scale Graduated Cylinders, 50-mL Cat. No. 24707-061; Samco Transfer Pipets, Cat. No. 336 B/B-PET | VWR (Bridgeport, NJ) |
| Labware | Electronic 10-mL variable volume Pipettor | Rainin (Walnut Creek, CA.) |
| Variable Volume Pipettors | Mechanical, positive displacement, 100-µL, 250-µL and 1000-µL Pipettors | Gilson Inc. (Middletown, Wis.) |
| Labware | Falcon ® 2098 (50 mL), 2096 (15 mL) Polypropylene Centrifuge Tubes; 3-mL Disposable Syringe, Cat. No. BD309585; 10-mL Disposable Syringe, Cat. No. BD309604 | Becton Dickinson (Franklin Lakes, NJ) |

TABLE 73

HPLC/MS SYSTEM

| HPLC | HP1100: G1322A degasser, G1311A quaternary pump; G1330A chilled well plate autosampler; G1316A column unit; G1314A variable wavelength detector | Agilent Technologies, Inc. (Palo Alto, CA) |
|---|---|---|
| Autosampler Vials | 100 PK, Cat. No. 5182-0556, 5182-0715, or 5182-0725 | Agilent Technologies, Inc. (Palo Alto, CA) |
| HPLC Column | Luna ® Phenyl-Hexyl; 4.6 mm × 150 mm, 3-µm particle size diameter, P.N. 00F-4256-E0 | Phenomenex ® (Torrance, CA) |
| Triple Quadrupole MS | MicroMass Quattro Premier triple quadrupole mass spectrometer using an electrospray (ESI) interface and MassLynx XP version 4.0 software | Waters Corporation (Milford, Mass.) |
|  | AB Sciex API 5000: ESI interface, Analyst Version 1.42 software using an ESI interface and Analyst Version 1.42 software | Applied Biosystems (Foster City, CA) |

Reagents and Standards

TABLE 74

Reagents

| REAGENTS | PRODUCT DESCRIPTION | PRODUCT ID | SUPPLIER |
| --- | --- | --- | --- |
| Formic Acid | GR, ACS, 98% or 98-100% Analar ® | FX0440-11 B10115-74 | EMD Science (Gibbstown, NJ) |
| Glacial Acetic Acid | OmniTrace ®, Ultra High Purity, 99% | AX0077-1 | EMD Science (Gibbstown, NJ) |
| Hydrochloric Acid | Hydrochloric Acid GR ACS (36.5-38% assay) | HX0603-4 | EMD Chemicals (Gibbstown, NJ) |
| Phosphoric Acid | 'Baker Analyzed', 500 mL or HPLC grade | 0260-02 PX0996-6 | JT Baker (Phillipsburg, NJ) EM Science (Gibbstown, NJ) |
| Trifluoroacetic Acid | 'Baker Analyzed', 100 mL | W729-05 | JT Baker (Phillipsburg, NJ) |
| Methanol | OmniSolv ®, 4 L | MX0488-1 | EMD Science (Gibbstown, NJ) |
| Water | OmniSolv ® HPLC grade, 4 L | WX0004-1 | EMD Science (Gibbstown, NJ) |
| Methylene Chloride | OmniSolv ®, 1 L | DX0831-6 | EMD Science (Gibbstown, NJ) |
| Ammonium Hydroxide Solution | EM SupraPur ®, min 25%, 250 mL or EM GR ACS, 28-30%, 500 mL | 5428-1 AX1303-13 | EMD Science (Gibbstown, NJ) |
| Trietylamine (TEA) | Sigma-Aldrich Triethylamine, ≧99.5% | 471283-100 mL | VWR (Bridgeport, NJ) |
| Bulk $C_{18}$ sorbent | Bakerbond ® Octadecyl ($C_{18}$), 40 µm Prep LC Packing, 1 Kg | 7025-01 | JT Baker (Phillipsburg, NJ) |

Reference Analytical Standards

Reference standards were supplied by DuPont Crop Protection, E. I. du Pont de Nemours and Company, Wilmington, Del. Information pertaining to the characterization and stability of the reference standards along with chemical retain samples are archived by E. I. du Pont de Nemours and Company, DuPont Crop Protection, Newark, Del. The reference standards in solid form were stored at room temperature in a dessicator typically in the presence of desiccant. Stable isotope standards of glyphosate and AMPA used for internal standards were acquired from Dr. Ehrenstorfer GmbH (Atlanta, Ga.).

Principle of the Analytical Method

For milk and egg commodities, matrix samples (2 g) were diluted in aqueous 0.1% formic acid/methanol (96/4, v/v) and shaken to dilute sample in aqueous medium. The dilute sample was partitioned with hexane and the hexane layer discarded. The remaining aqueous fraction was partitioned with methylene chloride and the aqueous layer was collected. The methylene chloride fraction was back extracted with additional 0.1% formic acid/methanol (96/4, v/v) for quantitative recovery of analytes. The aqueous fractions were combined and diluted to final volume of 50 mL. An aliquot of the aqueous fraction was filtered through a C18 SPE cartridge. The C18 purified extract was further purified by solid phase extraction using polymeric anion exchange (MAX) SPE cartridge and/or polymeric cation exchange (MCX) SPE cartridge, depending on matrix and analytes to be examined. For MAX SPE, an aliquot of the C18 eluate and internal standard were diluted to 20 mL with water and applied to a conditioned SPE cartridge. The MAX sorbent is sequentially rinsed with methanol/water (80/20), 0.1M acetic acid in methanol/water (80/20) and methanol/water (95/5). The analytes were eluted in 1% TFA in 90% methanol/10% water solution and the eluate was evaporated to dryness then restored in final solution for LC/MS/MS following mixing and filtration for the analysis of glyphosate and N-acetylglyphosate and/or N-acetyl AMPA. For MCX SPE, an aliquot of the C18 eluate and internal standard were eluted through a conditioned SPE cartridge followed by methanol rinse. The load and methanol rinse from the MCX SPE cartridge were collected and the methanol was evaporated, then extract was diluted to final volume containing 0.02M phosphoric acid, mixed, and filtered for LC/MS/MS for the analysis N-acetylglyphosate, AMPA, and/or N-acetyl AMPA depending on the sample matrix.

For animal tissue commodities, samples (2 g) were blended with $C_{18}$ sorbent material (4 g) until tissue was macerated and homogenized (matrix solid phase dispersion). Prepped samples were extracted in 25 mL of 0.1N HCl solution (96% water/4% methanol) using vortexing and mechanical shaking. The extraction solution was decanted from sample after centrifugation, then sample was re-extracted with water for quantitative transfer of analytes to final extract volume of 50 mL. Aliquots of the extract were purified by solid phase extraction using polymeric anion exchange (MAX) SPE cartridge and/or polymeric cation exchange (MCX) SPE cartridge, depending on matrix and analytes to be examined. For MAX SPE purification, an aliquot of the extract was diluted in acetonitrile and methanol in the presence of triethylamine (adjusts pH basic to promote protein precipitation and prepare analytes for loading on anion exchange medium). Following centrifugation to isolate precipitants in a pellet, the extract solution was diluted with methanol to approximately 20 mL and loaded onto a conditioned MAX SPE cartridge. The MAX sorbent was sequentially rinsed with methanol/water (80/20), 0.1M acetic acid in methanol/water (80/20) and methanol/water (95/5). The analytes were eluted in 1% TFA in 90% methanol/10% water solution and the eluate was evaporated to dryness then restored in final solution for LC/MS/MS following mixing and filtration for the analysis of glyphosate and N-acetylglyphosate and/or N-acetyl AMPA. For MCX SPE, an aliquot of the extract was diluted in acetonitrile and methanol to promote protein precipitation. Following centrifugation to isolate precipitants in a pellet, the extract solution was diluted with methanol to approximately 20 mL and loaded onto a conditioned MCX SPE cartridge. The MCX sorbent was rinsed with methanol, then the analytes were eluted in water (4 mL) followed by methanol (4 mL) for quantitative recovery. The methanol in the collected eluate was evaporated and solution was adjusted to final volume containing 0.02M phosphoric acid, mixed, and filtered for LC/MS/MS for the analysis AMPA.

Glyphosate and/or AMPA stable isotope standards used as internal standards were added to extracts prior to ion exchange SPE purification. Final extracts were prepared in aqueous 0.02M phosphoric acid and filtered (0.2 μm) prior to LC/MS/MS analysis to remove particulates as preventive maintenance measure for the HPLC system. Phosphoric acid acts a weak ion-pairing agent on HPLC polymeric stationery phase and was used as the final solution to improve glyphosate LC/MS/MS performance (response and linearity). The analytes were resolved by HPLC reverse-phase chromatography using a phenyl-hexyl column coupled to electrospray ionization in with MS/MS detection to acquire 2 molecular ion transitions (only 1 ion transition is monitored for AMPA in positive ion mode). Quantitative analysis was accomplished using a single molecular ion transition. The relative abundance of the 2 MS/MS fragment ions provided confirmatory evidence for glyphosate, N-acetylglyphosate, N-acetyl AMPA, and AMPA (negative mode).

Analytical Procedure
Preparation & Stability of Reagent Solutions

The following procedures may be adjusted to prepare different volumes.

Aqueous 0.1% formic acid/methanol (96/4, v/v) Extraction Solution: Per liter volume, add 40 mL of methanol followed by 0.96 mL of formic acid to a 1-L graduated cylinder and dilute to final volume with HPLC grade purified water. Transfer solution to a clean bottle and cap. The solution may be stored at room temperature and should be prepared at least monthly.

0.1N HCl in water/methanol (96/4, v/v) Extraction Solution: Per liter volume, add water in a 1-L graduated cylinder to at least half volume followed by 8.3 mL of concentrated HCl. Add 40 mL of methanol and dilute to final volume of 1-L with HPLC grade purified water. Transfer solution to a clean bottle and cap. The solution may be stored at room temperature and should be prepared at least weekly.

80% or 95% Methanol in Water Solution: Per liter volume, add 800 mL or 950 mL, respectively, of methanol to a 1-L graduated cylinder and dilute to final volume with HPLC grade purified water. Transfer solution to a clean bottle and cap. The solution may be stored at room temperature and should be prepared at least monthly.

0.1M Acetic Acid in 80% Methanol/Water Solution: Per liter volume, add 5.73 mL acetic acid to 200 mL of HPLC grade purified water in a 1-L graduated cylinder and dilute to final volume with methanol. Transfer solution to a clean bottle and cap. The solution may be stored at room temperature and should be prepared at least monthly.

0.25% Ammonium Hydroxide in Water: Per liter volume, add 10 mL of ammonium hydroxide solution (minimum 25%) to small volume of HPLC grade purified water, then dilute to final volume with HPLC grade purified water. This is a conditioning solution for egg and milk MAX SPE (12 mL/sample, dilution in water procedure). The solution may be stored at room temperature and should be prepared at least monthly. Note: 1 mL of 25% ammonium hydroxide diluted to 100 mL≈0.25% NH$_4$OH 0.1% Triethylamine (TEA) in methanol/acetonitrile (75/25, v/v): Per liter volume, add 1.0 mL of TEA to 750-mL methanol in a 1 L graduated cylinder and dilute to final volume with acetonitrile. This is a conditioning solution for tissues MAX SPE (12 mL/sample, dilution in methanol procedure). The solution may be stored at room temperature and should be prepared at least monthly.

Elution Solution, 1% TFA in 90% methanol/10% water: Prepare sufficient volume needed for analysis. For 100 mL volume, add 1 mL of trifluoroacetic acid to about 10 mL of methanol in a 100 mL graduated cylinder, followed by 10 mL of HPLC grade purified water, then dilute to final volume with methanol. Transfer solution to a clean bottle and cap. 8 mL of the Elution Solution is required for each sample (100 mL preparation is consistent with 12 samples requiring 96 mL). Prepare as needed, do not store.

1.0M Phosphoric Acid Solution: Per 10 mL volume, add 0.67 mL of concentrated phosphoric acid (min. 85%) to HPLC grade purified water in a 15-mL polypropylene centrifuge tube and dilute to final volume using gradations on tube with HPLC grade purified water. The solution may be stored at room temperature and should be prepared at least monthly.

Sample and Standard Final Solution, aqueous 0.02M phosphoric acid: Per liter volume, add 1.34 mL concentrated phosphoric acid (min. 85%) to HPLC grade purified water in a 1-L graduated cylinder and dilute to final volume of 1000 mL with HPLC grade purified water. Transfer solution to a clean bottle and cap. The solution may be stored at room temperature and should be prepared at least monthly.

Aqueous 0.2M Formic Acid, aqueous mobile phase: Per liter volume, add 8.3 mL concentrated formic acid (98%) to HPLC grade purified water in a 1-L graduated cylinder and dilute to final volume of 1000 mL with HPLC grade purified water. Transfer solution to a clean bottle and cap. The solution may be stored at room temperature and should be prepared at least monthly.

Stock Standard Preparation and Stability

If possible standards with purity greater than 95% were used. A minimum of approximately 10 mg of standard was weighed on an analytical balance that provides a weight precision to three significant figures, or the amount of standard should be increased to satisfy this condition.

Since residue tolerances were established in glyphosate free-acid equivalents, stock standard solutions for each analyte were prepared in glyphosate free-acid equivalents so that fortifications and recoveries can be determined in parent free acid equivalents. As needed, individual parent free-acid equivalent stock standards solutions for N-acetylglyphosate, glyphosate, N-acetyl AMPA, or AMPA were prepared by adding appropriate amounts of standard to a 100-mL volumetric flask and diluting to final volume with water. Water refers to HPLC grade or equivalent water. The following calculation and example provide guidance for the preparation of 100 mL of a 100 μg/mL stock solution in glyphosate equivalents for each analyte.

$$\left(\frac{100 \text{ μg/mL}}{1000 \text{ μg/mg}}\right) \times \left(\frac{\text{MW analyte}}{\text{MW glyphosate free acid}}\right) / \left(\frac{\% \text{ Purity}}{100}\right) \times 100 \text{ mL} =$$

mg analyte

N-acetylglyphosate Example $$\left(\frac{100 \text{ μg/mL}}{1000 \text{ μg/mg}}\right) \times \left(\frac{211.11 \text{ g/mole}}{169.07 \text{ g/mole}}\right) / \left(\frac{63}{100}\right) \times 100 \text{ mL} = 19.8 \text{ mg}$$

Amounts weighed for each analyte should be at least 10 mg. Individual analyte stock solution concentrations can exceed 100 μg/mL in glyphosate equivalents. Stock standard solutions may be prepared at higher concentrations (not to exceed 1 mg/mL). A minimum standard weight of approximately 10 mg and final standard volume of at least 10 mL should be observed.

Internal Standard Preparation and Stability

Figure 74:
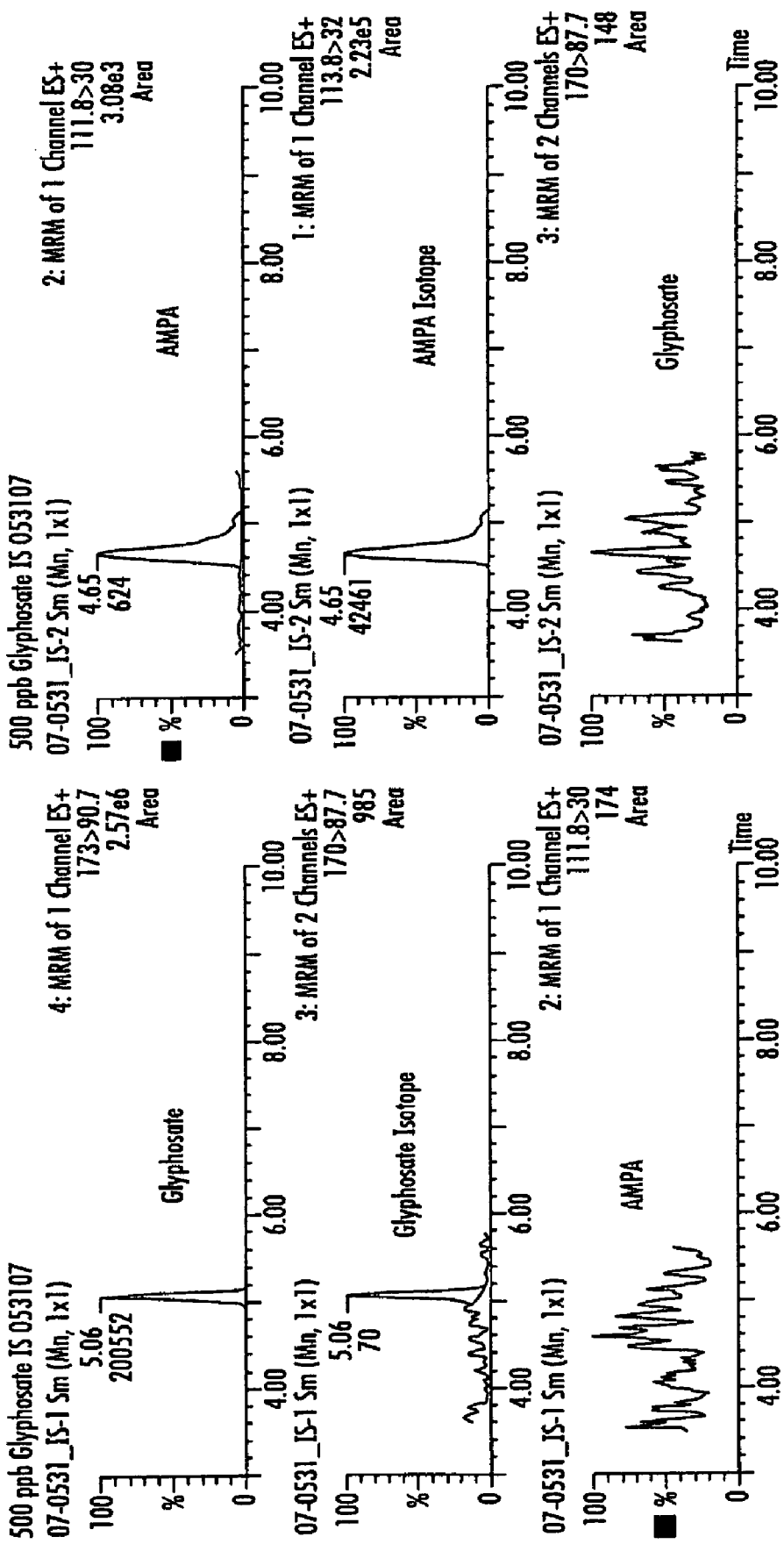
FIG. 74 shows the isotopic purity evaluation of glyphosate 1,2-13C2 15N and AMPA 13C 15N Standards. Glyphosate impurity (70 area) observed for glyphosate 1,2-13C2 15N standard represents 70×100/200552=0.03% impurity. AMPA impurity (624 area) observed for AMPA 13C 15N standard represents 624×100/42461=1.5% impurity.
Figure 75:
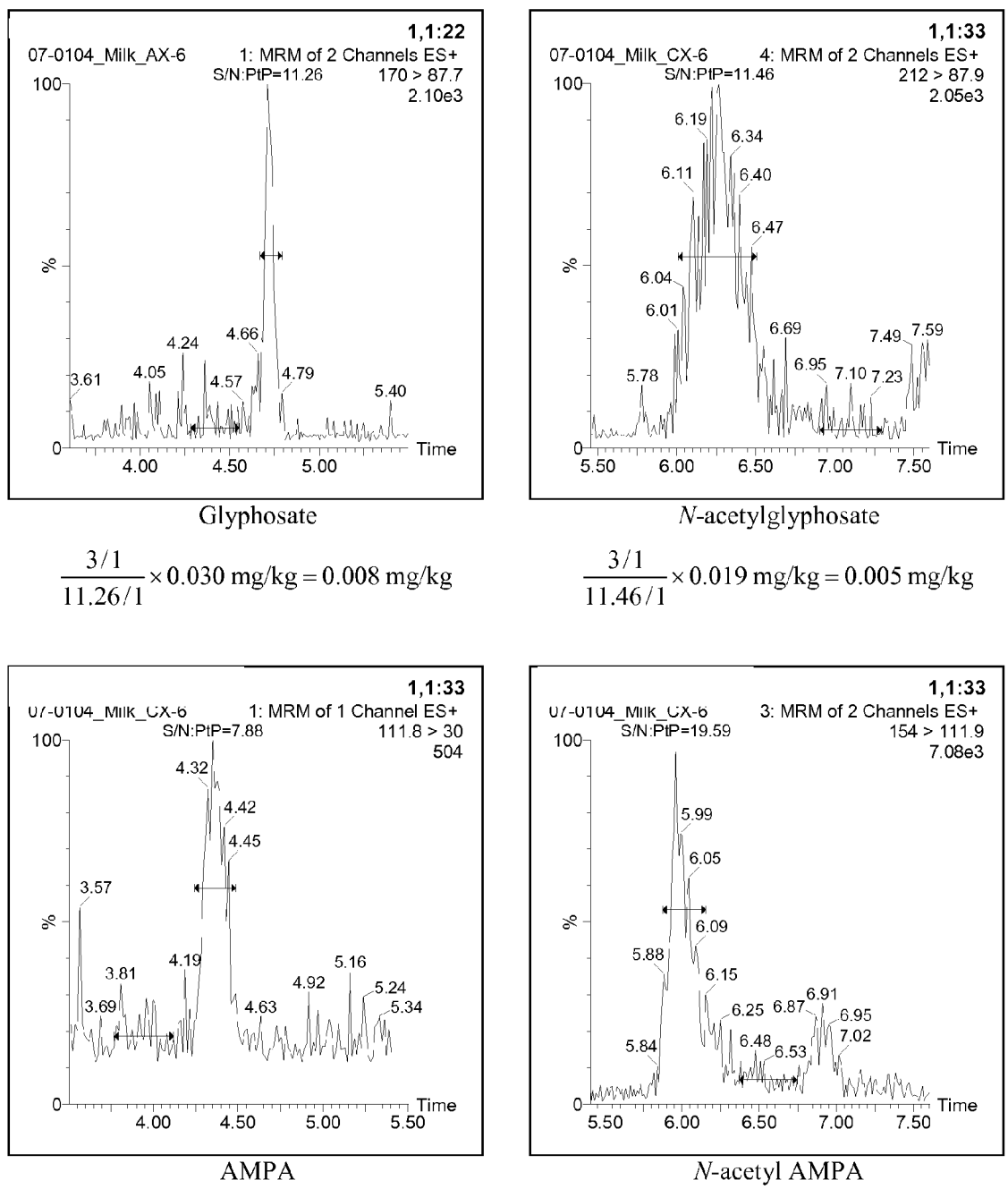
FIG. 75 provides a signal-to-noise and LOD determination for a milk matrix.
Figure 76:
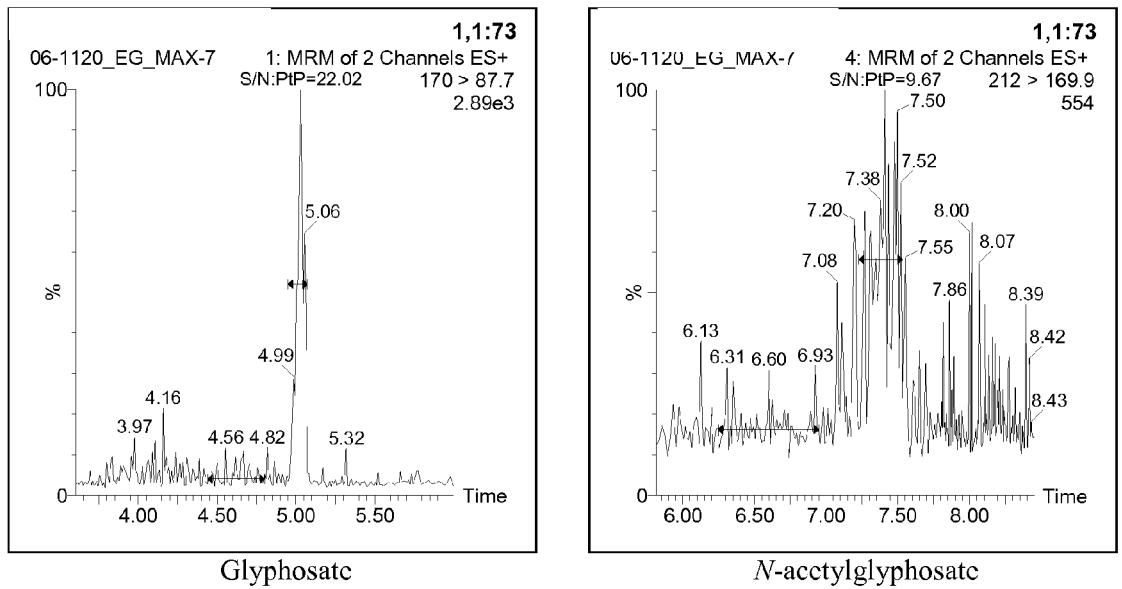
FIG. 76 provides a signal-to-noise and LOD determination for an egg matrix.
Figure 76:
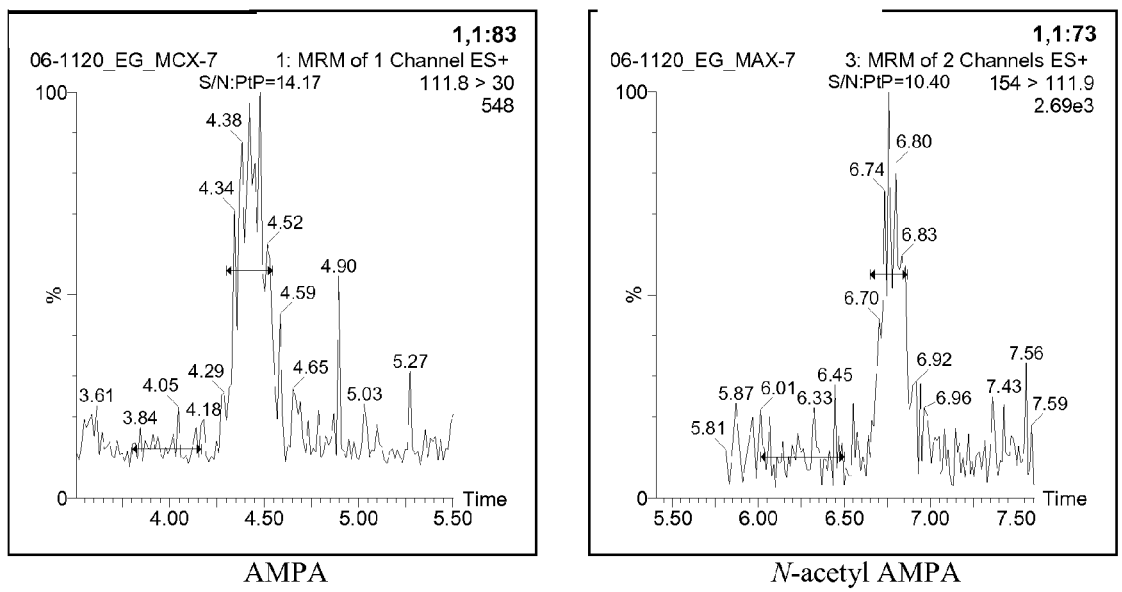
Figure 77:
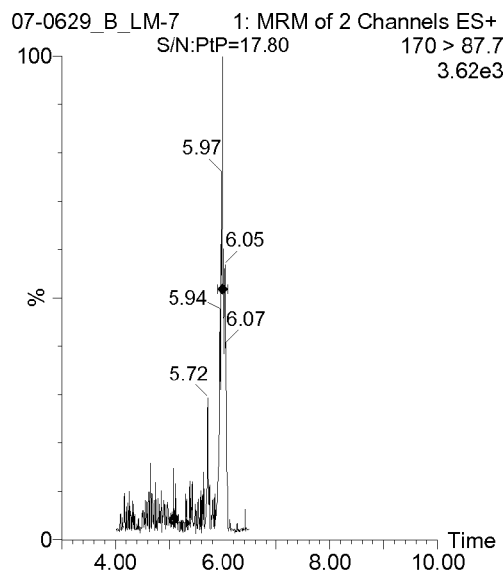
FIG. 77 provides a signal-to-noise and LOD determination for a liver matrix.
Figure 77:
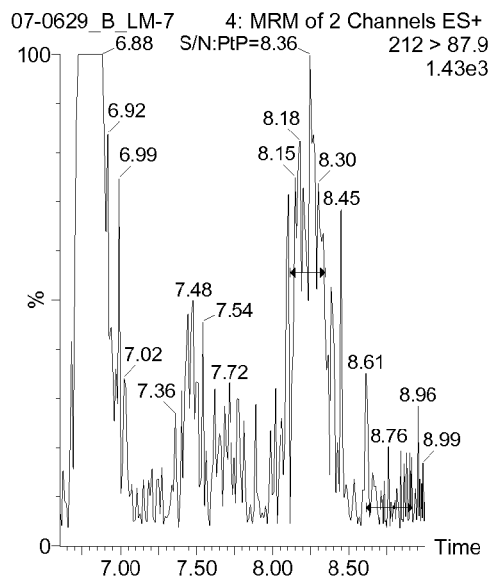
Figure 77:
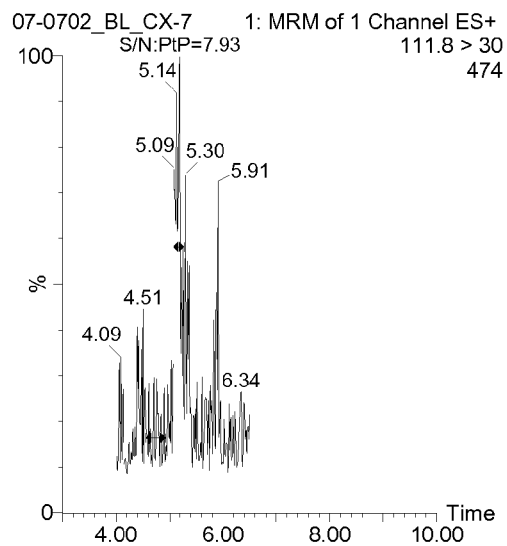
Figure 77:
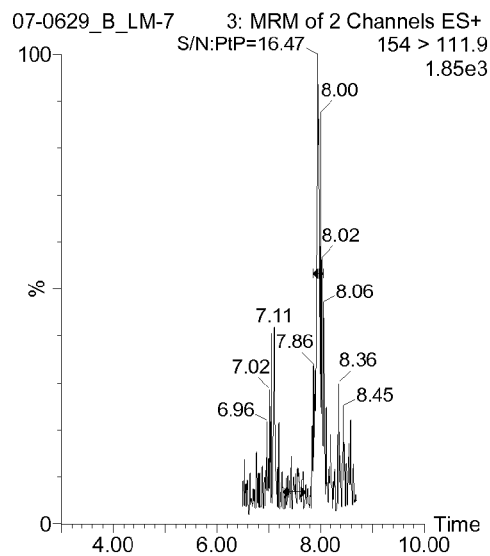
Figure 78:
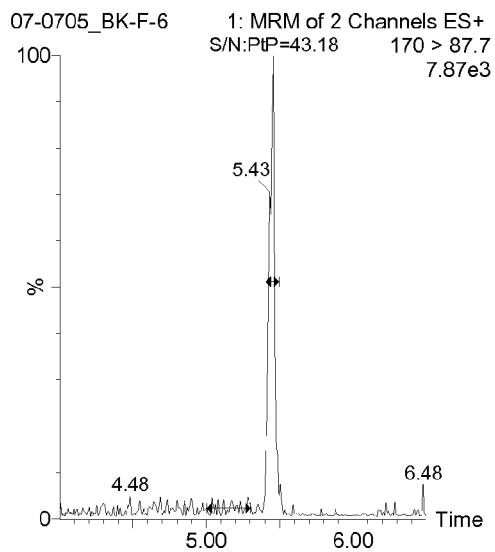
FIG. 78 provides a signal-to-noise and LOD determination for a kidney matrix.
Figure 78:
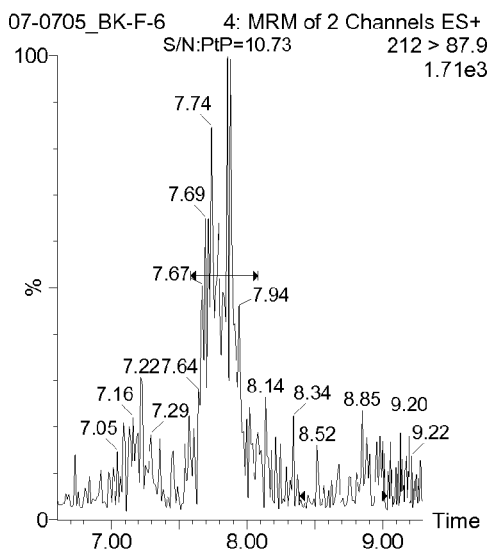
Figure 78:
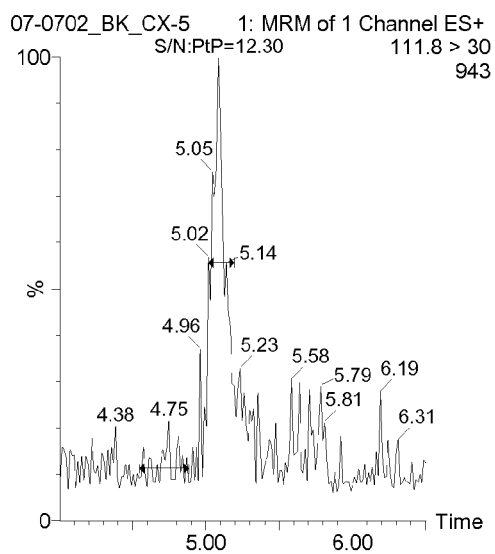
Figure 78:
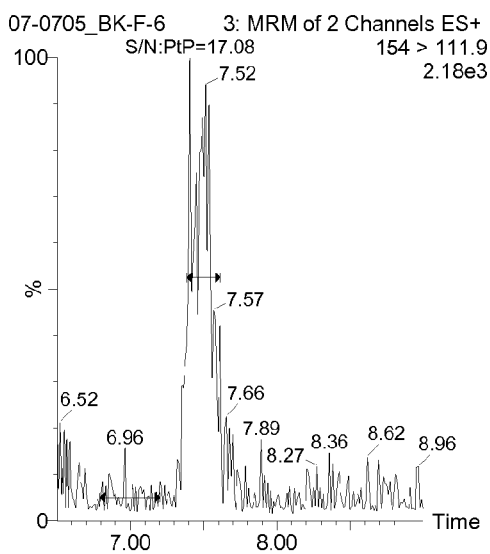
Figure 79:
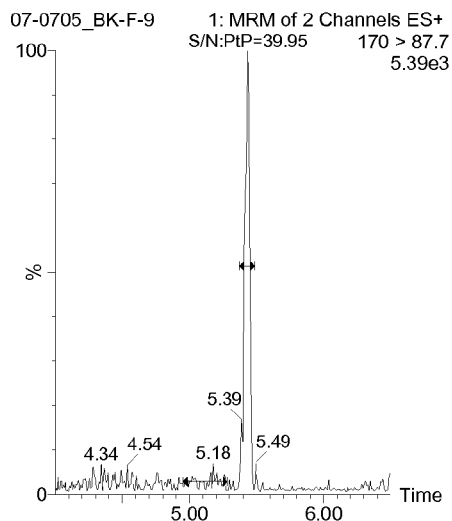
FIG. 79 provides a signal-to-noise and LOD determination for a fat matrix.
Figure 79:
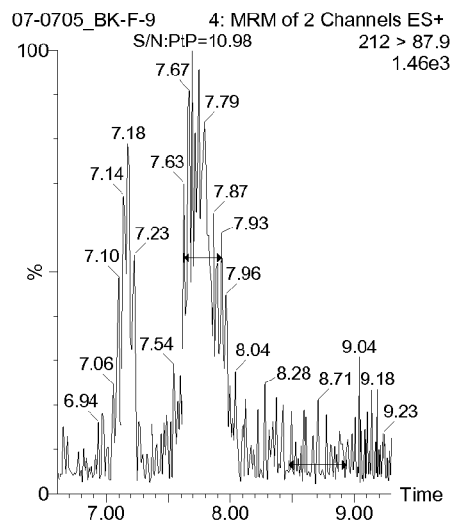
Figure 79:
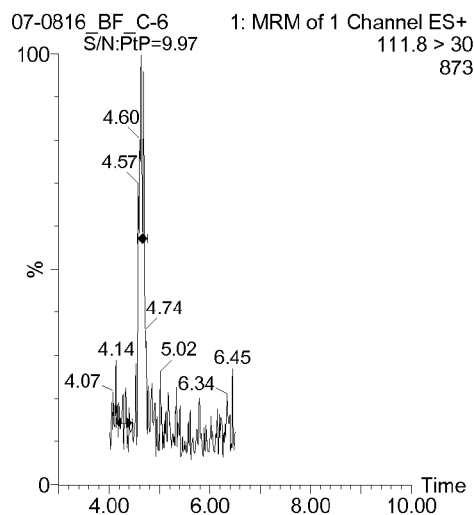
Figure 79:
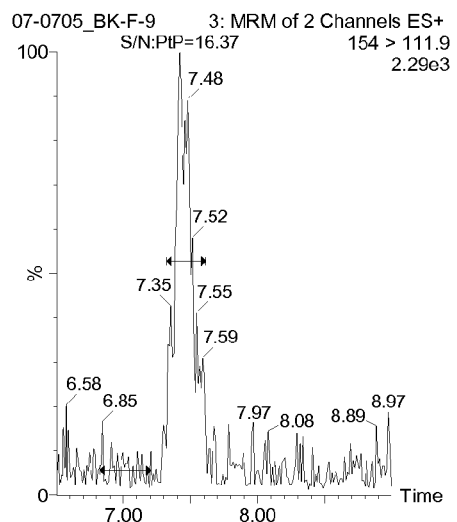
Figure 80:
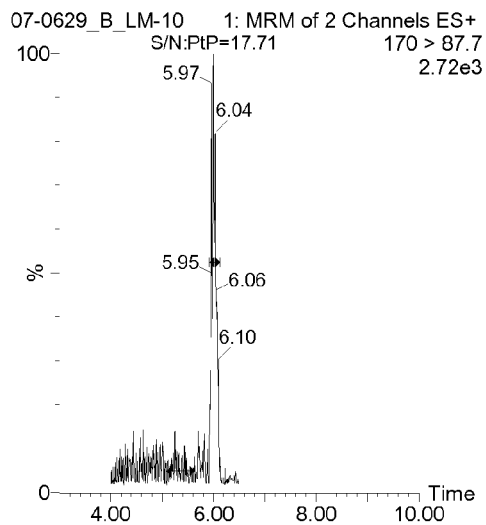
FIG. 80 provides a signal-to-noise and LOD determination for a muscle matrix.
Figure 80:
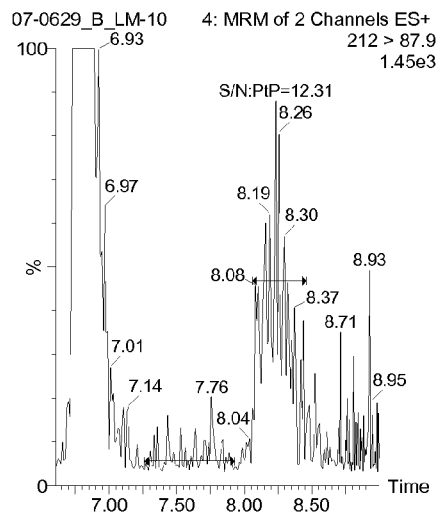
Figure 80:
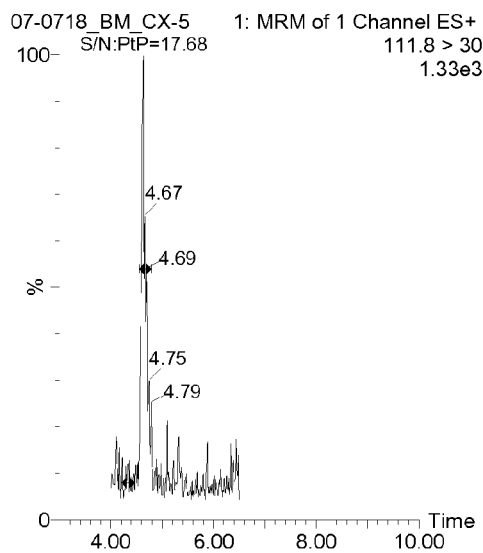
Figure 80:
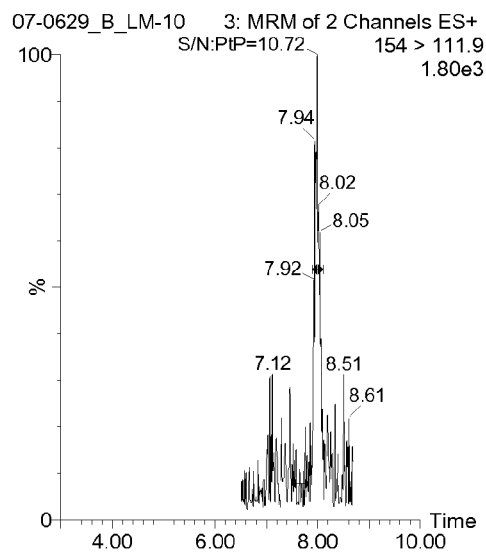

Glyphosate 1,2-$^{13}C_2^{15}N$ and aminomethyl phosphonic acid $^{13}C^{15}N$ (AMPA) stable isotope standards were supplied in amber ampules containing 1.1 mL of aqueous solution at a nominal concentration of 100 mg/L (μg/mL). Each standard solution was transferred to a 15 mL polypropylene centrifuge tube and diluted to 5 mL volume with HPLC grade water rinses of the original container for quantitative transfer of the standard material. Final concentration for stock standard solution was approximately 20 μg/mL. The isotopic purity was verified for each standard by analysis of an approximately 500 ng/mL solution. See, FIG. 74.

An intermediate 100 ng/mL internal standard solution containing glyphosate and AMPA isotopes was prepared by diluting 100 μg/mL stock solution at a rate of 0.1 mL in 100 mL of aqueous 0.02M phosphoric acid or HPLC grade purified water. Internal standards were included in final extract and calibration standard solutions at a rate of 50 μL/mL. Each 100 mL of a 100 ng/mL standard solution can be used in up to 400 samples when 250 μL of internal standard is applied in 5 mL of final extract.

Specifically, individually transfer the 100 μg/mL standards to a 15 mL polypropylene centrifuge tube and dilute to 5 mL volume with HPLC grade water rinses of the original container for quantitative transfer of the standard material. Final concentration for stock standard solution were approximately 20 μg/mL. For each stock solution, 0.025 mL of the 20 μg/mL standard solution was transferred to a autosampler vial and dilute to 1 mL volume with 0.975 mL of 0.02M H3PO4 to prepare separate solutions at approximately 500 ng/mL for purity evaluation.

Next, 1.00 mL aliquot of each 20 μg/mL standard stock solution was combined in a single 250 mL graduated cylinder and diluted to final volume with 0.02M H3PO4 to prepare a mixed solution at 100 ng/mL. 100 ng/mL IS solution was transferred to a 250 mL bottle. Solution was store refrigerated (~4° C.).

Intermediate and Fortification Standards Preparation and Stability

Stock solution for each analyte was diluted appropriately into a common volumetric flask, dilute to volume with HPLC grade purified water, cap, and mix well. For example, 1.00 mL of a 100 μg/mL stock solution for each required analyte was combined in a 10-mL volumetric flask and diluted to final volume with water, cap, and mix well. It was store at or below 4° C. and replaced monthly.

Stock solutions concentrations will vary and the required volume of each analyte stock solution used to prepare fortification solution was adjusted for correct final concentration as determined using the following calculation.

$$\frac{\text{Final Concentration, }\mu g/ml \times \text{Final Volume, mL}}{\text{Stock Solution Concentration, }\mu g/mL} =$$

Aliquot(mL) of Stock Solution added

For example, to prepare 50 mL of a 10 μg/mL fortification solution from glyphosate, N-acetylglyphosate, N-acetyl AMPA, and AMPA stock solutions prepared respectively at 115 μg/mL, 186 μg/mL, 143 μg/mL, and 206 μg/mL in glyphosate free-acid equivalent concentrations the following stock solution volumes were added to a 50-mL volumetric flask.

Glyphosate=10 μg/mL×50 mL/115 μg/mL=4.35 mL stock solution

N-acetylglyphosate=10 μg/mL×50 mL/186 μg/mL=2.69 mL stock solution

N-acetyl AMPA=10 μg/mL×50 mL/143 μg/mL=3.50 mL stock solution

AMPA=10 μg/mL×50 mL/206 μg/mL=2.42 mL stock solution 10.0 μg/mL Fortification Solution Each stock solution was diluted appropriately with water into a volumetric flask, cap and mix well. For example, 1.00 mL of a 100 μg/mL stock solution was combined in a 10-mL volumetric flask and diluted to final volume with water, cap and mix well. It was stored at or below 4° C. and replaced monthly.

1.0 μg/mL Fortification Solution 10.0 μg/mL fortification solution (preferred) or the stock solution for each analyte was diluted appropriately with water into a volumetric flask. For example, 1.0 mL of the 10.0 μg/mL fortification solution was transferred to a 10-mL volumetric flask, diluted to volume with water, capped and mixed well. It was stored at or below 4° C. and replaced monthly.

Chromatographic Standard Preparation and Stability

Calibration standards were prepared from dilutions of fortification standards or individual stock standards. A minimum of 5 calibration standards over a range from approximately 50% of LOQ equivalent final concentration to $\geq$120% of the highest expected final sample concentration is recommended for quantification. The LOQ equivalent final concentration for N-acetylglyphosate was 1.0 ng/mL.

For example, calibration standards of 10.0 ng/mL and 100 ng/mL were prepared from the 1.0 and 10.0 μg/mL fortification solutions, respectively, by diluting a 100 μL aliquot to final volume of 10.0 mL in aqueous 0.02M phosphoric acid (this simulates sample fortification). Calibration standards were prepared concurrently with sample fortifications using this procedure.

Source (& Characterization) of Samples

Raw milk was obtained from the University of Delaware Agricultural Farm. Milk commodities (whole, skim, and heavy cream), and eggs were obtained from local supermarket. Beef liver, kidney, fat, and muscle were obtained from a cattle feeding study. Poultry liver, fat, and muscle were obtained from a laying hen feeding study.

Storage & Preparation of Samples

Whole eggs were beaten prior to subsampling. Egg whites and yolks were separated and beaten prior to subsampling. Egg commodity subsamples (2 g) were weighed into tarred 50-mL polypropylene centrifuge tubes. If subsamples were not analyzed promptly, 25 mL of aqueous 0.1% formic acid/methanol (96/4, v/v) was added, capped, mixed, and the sample was frozen.

Raw, whole, skim, or heavy cream milk subsamples (2 g) were weighed into tarred 50-mL polypropylene centrifuge tubes. If subsamples were not analyzed promptly, 25 mL of aqueous 0.1% formic acid/methanol (96/4, v/v) was added, capped, mixed, and the sample was frozen.

Animal tissue samples were ground with dry ice using a Warning commercial food processor (Lab Micronizer Model 31FP93) prior to freezer storage. Samples were mixed extensively during the grinding process to ensure fine maceration and homogeneity. The dry ice was allowed to sublime in a fume hood or overnight in freezer prior to subsampling and freezer storage.

All frozen samples were stored at −20±5° C. prior to sample extraction, and analysis.

Sample Fortification Procedure

Untreated matrix control samples in extraction containers (50-mL centrifuge tubes) were fortified as required. The 10.0 and 1.0 µg/mL Fortification Standards (see above) were used to fortify test samples. Table 75 is provided as an example for the fortifications made in this study.

TABLE 75

| SAMPLE IDENTIFICATION | AMOUNT (G) | FORTIFICATION SOLUTION | | FORTIFICATION (MG/KG) |
|---|---|---|---|---|
| | | µG/ML | ML | |
| MILK, EGG, AND MUSCLE MATRICES | 2.0 ± 0.1 | 1.0 | 0.050 | 0.025 |
| MILK, EGG, AND TISSUE MATRICES | 2.0 ± 0.1 | 1.0 | 0.100 | 0.050 |
| MUSCLE MATRIX | 2.0 ± 0.1 | 10.0 | 0.050 | 0.25 |
| MILK, EGG, AND TISSUE MATRICES | 2.0 ± 0.1 | 10.0 | 0.100 | 0.50 |

For each matrix sample, 2.0±0.1 g was weighed into a clean 50-mL centrifuge tube. For milk and egg commodities, the sample was gently swirled or vortexed after fortification to disperse the analyte in the sample. For animal tissue commodities, samples were allowed to stand in fume hood for approximately 15 minutes to allow fortification solution to dissipate. Following fortification, milk and egg samples were diluted in 25 mL of aqueous 0.1% formic acid/methanol (96/4, v/v), frozen, and stored prior to extraction and analysis.

Analyte Extraction Procedures

Separate analyte extraction procedures are provided for milk/eggs and animal tissue commodities.

Milk and Egg Commodities 1.0 For freshly prepared samples, the samples were fortified as appropriate and gently swirled or vortexed mixed after fortification to disperse the analyte in the sample.

2.0 For freshly prepared samples, 25 mL of aqueous 0.1% formic acid/methanol (96/4, v/v) was added to each sample, capped, vortex mixed for approximately 5 seconds. Samples can be stored frozen for later analysis.

3.0 If samples were stored frozen, sample were thawed in an ultrasonic bath (approximately 15 min). Note: Samples may be shaken together in a sample rack by holding a cover in place over tops of the tubes.

4.0 20 mL of hexane was added to sample, capped, and shaken gently for at least 30 seconds.

5.0 Samples were centrifuged for 10 minutes at speed sufficient to resolve partitions (upper hexane, aqueous, and formed precipitates).

6.0 As much of the upper hexane fraction was pipetted as possible without disturbing the lower aqueous layer and discard (remaining hexane will be incorporated in the methylene chloride fraction in the next step).

7.0 20 mL of methylene chloride was added to remaining sample, capped, and shook gently for at least 30 seconds.

8.0 Samples were centrifuged for 10 minutes at speed sufficient to resolve partitions (upper aqueous, formed precipitates, and lower methylene chloride).

9.0 As much of the upper aqueous fraction was transferred to a clean 50 mL graduated cylinder (TC) as possible without disturbing the lower precipitates and methylene chloride fraction.

10.0 20 mL of aqueous 0.1% formic acid/methanol (96/4, v/v) was added to each sample, capped, and shaken gently for at least 30 seconds.

11.0 Steps 8.0 and 9.0 were repeated and extract was combined with first extract in 50 mL graduated cylinder.

12.0 The combined extract was diluted to 50 mL with aqueous 0.1% formic acid/methanol (96/4, v/v) in graduated cylinder or if extract volume exceeds 50 mL, the volume was adjusted to mL reading and final volume was recorded.

13.0 The aqueous extracts were transferred to a clean 50-mL tube or bottle, by poring extract back and forth and finally to clean container to mix.

Meat Tissue Commodities 1.0 2.0±0.1 g of homogenized tissue was weighed in a tarred 50-mL polypropylene centrifuge tube.

2.0 Approximately 4 g of C18 sorbent was added to sample tube (4 g sorbent equivalent to 7 mL fill in a 15-mL centrifuge tube).

3.0 Sample and C18 sorbent were mixed well with spatula for solid phase dispersion of matrix.

4.0 25 mL of 0.1N HCl in 96% water/4% methanol was added, vortexed, and shaken on wrist action shaker for 15 min.

5.0 10 min (3500 rpm minimum) of centrifugation was performed and supernatant was decanted through reservoir equipped with polyethylene frit into 50 mL polypropylene centrifuge tube. Vacuum was briefly after all extracts have been added to start filtration then vacuum was broken.

6.0 20 mL of water was added to sample pellet, the sample was vortexed to re-suspend sample, centrifuged, then the sample solution was decanted through reservoir with paper frit into respective 50 mL polypropylene centrifuge tube. If needed, vacuum was applied briefly after all extracts have been added to start filtration then vacuum was broken.

7.0 Common volume of water was added to each sample pellet to achieve final extract near, but less than 50 mL for all extracts (generally 8-10 mL). The sample was vortexed and poured into reservoir, vacuum was applied to collect final rinse. Sample collection tube was removed and final volume was adjusted to 50 mL with water. Sample extract can be centrifuged and decanted into reservoir after vortexing to prevent frit plugging. This option is recommended for muscle extracts.

Analyte Purification Procedures

C18 SPE filtration, MAX SPE and MCX SPE filtration procedures were applied to milk (except skim) and egg commodity sample extracts.

C18 SPE Filtration (Whole Milk, Cream, & Egg Commodities)

1.0 Waste collection tubes were installed in vacuum manifold to collect conditioning solutions and initial sample load volume (waste collection tubes were used to contain analyte containing eluate and prevent cross-contamination).

2.0 C18 SPE (6 cc/500 mg, Varian #12102052) cartridges was conditioned with ~1 mL of methanol, followed by 2 CV's (CV≈6 mL) of aqueous 0.1% formic acid/methanol (96/4, v/v). Vacuum or positive pressure was applied as needed for slow drip rate (1-2 mL/min).

3.0 As last of conditioning solution entered the sorbent, 4.0 mL of aqueous sample extract from Analyte Extraction Procedure step 13.0 was added onto SPE column.

4.0 After dripping stops, waste collection tubes were removed and clean 15 mL centrifuge tubes were installed. 10 mL of aqueous sample extract from Analyte Extraction Procedure step 13.0 was added, eluted, and eluate collected. Extract was capped and vortex mixed. Sample can be centrifuged to partially clarify the solution (fine particulates require higher centrifugation speed, e.g., 7000 rpm).

MAX SPE Purification (Milk and Egg Commodities)

Analysis of glyphosate, N-acetylglyphosate, and N-acetyl AMPA in egg matrices and skim milk. Analysis of glyphosate only in whole milk or cream.

1.0 0.25 mL of internal standard+2.5 mL of C18 purified extract was transferred to a 50-mL graduated centrifuge tube and diluted to approximately 20 mL with HPLC grade water.

2.0 MAX SPE (6 cc/500 mg) cartridges were conditioned with 1 CV (column volume, ~6 mL) of methanol, followed by 2 CV's of 0.25% ammonium hydroxide in HPLC grade water.

3.0 As the last of the conditioning solution enters the sorbent, sample extract solution was loaded. A slight vacuum may need to be applied, but the drip rate is kept slow.

4.0 After the last of the sample solution enters the sorbent, sequentially 10 mL of 80% methanol/water, 10 mL of 0.1M acetic acid in 80% methanol/water, and 10 mL of 95% methanol/water was added to rinse the SPE cartridge. Note: The 10 mL of 80% methanol/water and the 10 mL of 0.1M acetic acid was sequentially added to and dispensed from respective emptied sample extract tubes for quantitative transfer of sample extract to the SPE cartridges. The final 10 mL of 95% methanol/water rinse was applied directly to the SPE cartridge in 2×5 mL aliquots.

5.0 After dripping stops, the vacuum was increased briefly to remove excess solution from SPE sorbent, then collection vial or tubes in vacuum manifold was installed.

6.0 Analytes were eluted in 2×4 mL aliquots of Elution Solution (1% TFA in methanol/water, 90/10) by gravity feed. At least 5 minutes were waited after first aliquot passes through SPE cartridge before adding the second aliquot. Positive pressure or vacuum was applied to recover methanol remaining on SPE cartridge.

7.0 Samples were removed from SPE tank and evaporated to complete dryness on N-Evap at 45-50° C. Note: An additional 15 minutes of drying was allowed to insure TFA is completely evaporated.

8.0 5.0 mL of aqueous 0.02M phosphoric acid to sample was added. Capped, vortex mixed, sonicated at least 5 min, and vortex mixed.

9.0 An aliquot of the final extract solutions was added into a autosampler vial for LC/MS/MS analysis.

MAX SPE Purification (Meat Tissue Commodities)

Analysis of glyphosate, N-acetylglyphosate, and N-acetyl AMPA in liver and kidney sample extracts. Analysis of glyphosate and N-acetylglyphosate in muscle sample extracts.

1.0 1.25 mL (fat, kidney, or liver) or 2.5 mL (muscle) extract was transferred to a 15-mL polypropylene centrifuge tube and 0.1 mL of triethylamine (TEA) was added to the sample. Note: For fat and kidney samples Steps 1.0-3.0 can be combined and all dilutions performed in the 50 mL tube (Step 3.0) since little or no precipitate forms for these matrices.

2.0 5 mL of acetonitrile was added to extract aliquot, capped, and vortexed solution. 5 mL of methanol was added to sample solution, capped, vortexed, and sample was rested for 10 min.

3.0 Samples were centrifuged 10 min at a speed sufficient to form sample pellet and decanted into clean 50 mL polypropylene centrifuge tube containing 0.125 mL of internal standard. Original tube was rinsed with 7-8 mL of methanol and combined with extract in 50 mL tube for a final volume of approximately 20 mL.

4.0 MAX SPE (6 cc/500 mg) cartridges were conditioned with 1 CV (column volume, ~6 mL) of methanol, followed by 2 CV's of 0.1% TEA in methanol/acetonitrile (75/25). Note: Approximately 12 mL/sample of the TEA solution was required.

5.0 As the last of the conditioning solution enters the sorbent, loading of the sample extract solution began. Gravity elution was preferred, but slight vacuum may need to be applied for slow drip.

6.0 After the last of the sample solution enters the sorbent, 10 mL of 80% methanol/water, 10 mL of 0.1M acetic acid in 80% methanol/water, and 10 mL of 95% methanol/water was sequentially added to rinse the SPE cartridge. Note: The 10 mL of 80% methanol/water and the 10 mL of 0.1M acetic acid should be sequentially added to and dispensed from respective emptied sample extract tubes for quantitative transfer of sample extract to the SPE cartridges. The final 10 mL of 95% methanol/water rinse was applied directly to the SPE cartridge in 2×5 mL aliquots.

7.0 After dripping stops, vacuum is briefly increased to remove excess solution from SPE sorbent, then collection vial or tubes was installed in vacuum manifold. A flat, rounded, or gently sloped bottom can be used for fastest evaporation.

8.0 Analytes in 2×4 mL aliquots of Elution Solution (1% TFA in methanol/water, 90/10) were eluted by gravity feed. At least 5 minutes was waited after first aliquot passes through SPE cartridge before adding the second aliquot. Positive pressure or vacuum was applied to recover methanol remaining on SPE cartridge.

9.0 Samples from SPE tank were removed and evaporated to complete dryness on N-Evap at 45-50° C. Note: An additional 15 minutes of drying was allowed to insure TFA is completely evaporated.

10.0 2.5 mL of aqueous 0.02M phosphoric acid to sample was added. The sample was capped, vortex mixed, sonicated at least 5 min, and vortex mixed.

11.0 An aliquot of the final extract solutions was filtered (0.2 μm nylon) into an autosampler vial for LC/MS/MS analysis.

MCX SPE Filtration Purification

Analysis of AMPA in eggs and skim milk. Analysis of AMPA, N-acetylglyphosate, and N-acetyl AMPA in whole milk or cream.

1.0 Oasis MCX SPE cartridge (6 cc/500 mg, Waters#186000776) was conditioned sequentially with 1 CV (CV≈6 mL) of methanol and 1 CV aqueous 0.1% formic acid/methanol (96/4, v/v). Slight vacuum can be applied to control elution at slow drip (1-2 mL/min). Vacuum was applied or continued just until dripping stops.

2.0 15 mL graduated centrifuge tubes was installed under SPE cartridges in vacuum manifold.

3.0 0.25 mL of internal standard (only for AMPA analysis)+4.0 mL of the C18 filtered extract was applied to MCX SPE cartridge. After dripping stops, 4.0 mL of methanol was applied to MCX SPE cartridge. A slight vacuum can be applied, if necessary. Positive pressure or vacuum was applied to recover methanol remaining on SPE cartridge.

4.0 Samples were recovered from vacuum manifold and sample was evaporated to less than 4 mL on N-Evap at 45-50° C.

5.0 0.1 mL of aqueous 1.0 M phosphoric acid was added and diluted to final volume of with 5 mL water. Final extract was capped and vortexed. Final volume may be adjusted to meet sensitivity requirements for instrument, e.g., final volume of 4 mL including 0.08 mL of aqueous 1.0M phosphoric acid with earlier addition of 0.20 mL of 100 ng/mL internal standard would adjust final concentration at LOQ to 2.0 ng/mL.

6.0 An aliquot of the final extract for LC/MS/MS analysis was filtered (0.2 μm nylon). Final solution may be stored at or below 4° C.

MCX SPE Purification (Meat Tissue Commodities)

Analysis of AMPA in muscle, liver, kidney, or fat commodities.

1.0 2.5 of extract were transferred to a 50-mL polypropylene centrifuge tube. 5 mL of acetonitrile was added to extract aliquot and the sample was capped, and vortexed. The sample was centrifuged for 10 min. Note: No significant precipitation may be observed in this solution because the solution is not adjusted to basic pH.

2.0 For muscle: 0.125 mL of internal standard (only for AMPA analysis) was added and diluted to approximately 20 mL with methanol.

For liver, kidney, or fat: 0.25 mL of internal standard (only for AMPA analysis) was added and dilute to approximately 20 mL with methanol.

3.0 Oasis MCX SPE cartridge (6 cc/500 mg, Waters#186000776) was conditioned sequentially with 1 CV (CV≈6 mL) of methanol and 1 CV aqueous 0.1N HCl in 96% water/4% methanol. Slight vacuum may be applied to control elution at slow drip (1-2 mL/min). The slight vacuum can be applied just until dripping stops.

4.0 Dilute sample was applied to MCX SPE cartridge. Vacuum may be applied, if necessary.

5.0 2 mL of methanol was added to sample tube, mixed and added to SPE cartridge for quantitative transfer and sorbent rinse. Vacuum or positive pressure was applied just until dripping stops.

6.0 15-mL centrifuge tubes were installed under SPE cartridges in vacuum manifold.

7.0 4.0 mL of HPLC grade water to MCX SPE cartridge was added. After dripping stops, 4.0 mL of methanol to MCX SPE cartridge was applied. Slight vacuum may be applied, if necessary. Positive pressure or vacuum was applied to recover methanol remaining on SPE cartridge.

8.0 For muscle: Samples from vacuum manifold were recovered and sample was evaporated to less than 2.5 mL on N-Evap at 45-50° C.

For liver, kidney, or fat: Samples from vacuum manifold were recovered and sample was evaporated to less than 4 mL on N-Evap at 45-50° C.

9.0 For muscle: 0.05 mL of aqueous 1M phosphoric acid was added and sample was diluted to final volume of 2.5 mL with water. Final extract was capped and vortexed.

For liver, kidney, or fat: 0.1 mL of aqueous 1M phosphoric acid was added and sample was diluted to final volume of 5.0 mL with water. Final extract was capped and vortexed.

10.0 An aliquot of the final extract for LC/MS/MS analysis was filtered (0.2 μm nylon). Final solution may be stored at or below 4° C.

Instrumentation

An Agilent HP1100 HPLC and a Waters Quattro Premier or AB Sciex API 5000 triple quadrupole mass spectrometer were used for LC/MS/MS analysis.

Typical equipment components and operating conditions are as follows:

| | |
|---|---|
| Agilent HP1100 HPLC: | G1322A vacuum degasser, G1311A quaternary pump, G1367A chilled autosampler, G1330A chiller, G1316A column compartment |
| Injection Volume: | 25 μL (may be varied to correct for MS sensitivity) |
| HPLC Column: | Phenomenex Luna Phenyl-Hexyl (15.0 cm ± 4.6 mm i.d., 3 μm diameter particle) |
| Column Temperature: | 40° C. |
| Mobile Phases: | A = aqueous 0.2M formic acid (positive ion) or 0.05% formic acid (negative ion) B = methanol |
| Waters Quattro Premier: | ESI interface, MassLynx Version 4 SP4 software |
| AB Sciex API 5000: | ESI interface, Analyst Version 1.42 software |
| Interface: | electrospray (ESI) |
| Polarity: | Positive or negative ion |
| Mode: | MRM |

TABLE 76

HPLC Conditions:

| TIME (MIN) | FLOWRATE (ML/MIN) | % A | % B | COMMENTS |
|---|---|---|---|---|
| Initial | 0.5 | 95 | 5 | No post-column split to MS |
| 0.0 | 0.35 | 95 | 5 | |
| 10.0 | 0.35 | 50 | 50 | |
| 10.1 | 0.5 | 1 | 99 | |
| 13.0 | 0.5 | 1 | 99 | |
| 13.1 | 0.5 | 95 | 5 | |
| 18.0-20.0 | 0.5 | 95 | 5 | End Run (20 min for additional equilibration time) |

Approximate Analyte Retention Times (ordered by retention time) are as follows:

| | 0.2M formic | 0.05% formic |
|---|---|---|
| AMPA = | 4.4 min | 4.4 min |
| glyphosate = | 4.9 min | 7.0 min |
| N-acetyl AMPA = | 6.5 min | 10.0 min |
| N-acetylglyphosate = | 6.7 min | 11.0 min |

TABLE 77

Waters Quattro Premier Mass Spectrometer Conditions:

| Tune File: Gly050205pos.IPR | | | Ionization Mode: ESI+ | | | |
|---|---|---|---|---|---|---|
| Voltages | | | Temperatures | | Gas Flow | |
| Capillary (kV) | Extractor (V) | RF Lens (V) | Source (° C.) | Desolv. (° C.) | Desolv. (L/hr) | Cone (L/hr) |
| 1.00 | 4.2 | 0.1 | 125 | 350 | 700 | 100 |

TABLE 77-continued

Waters Quattro Premier Mass Spectrometer Conditions:

| Q1 | | Q2 | | | Q3 | |
|---|---|---|---|---|---|---|
| LM Res | 12.0 | Entrance | Exit | | 12.0 | LM Res |
| HM Res | 12.0 | 1 | 1 | | 12.0 | HM Res |
| Ion Energy | 0.3 | | | | 3.0 | Ion Energy |

Collison Cell: 0.35 mL/min 3.10E−03 mbar

MRM Functions

| Analyte (acquisition_time) | Parent (m/z) | Daughter (m/z) | Dwell (secs) | Cone (volts) | Energy (eV) |
|---|---|---|---|---|---|
| AMPA (3.3-6.0 min) | 111.80 | 30.00 | 0.30 | 12.00 | 8.00 |
| AMPA 13C 15N | 113.80 | 32.00 | 0.30 | 12.00 | 8.00 |
| Glyphosate (3.6-6.0 min) | 170.00 | 60.10 | 0.10 | 14.00 | 17.00 |
|  | 170.00 | 87.70 | 0.10 | 14.00 | 9.00 |
| Glyphosate 1,2-13C 15N | 173.00 | 90.70 | 0.10 | 14.00 | 9.00 |
| N-acetyl AMPA (5.8-7.8 min) | 154.00 | 30.00 | 0.10 | 14.00 | 15.00 |
|  | 154.00 | 111.90 | 0.10 | 14.00 | 9.00 |
| N-acetylglyphosate (5.8-8.5 min) | 212.00 | 87.90 | 0.10 | 17.00 | 17.00 |
|  | 212.00 | 169.90 | 0.10 | 17.00 | 10.00 |

Mass assignment on other instruments may vary ± 0.5 amu.
Dwell time may be adjusted to optimize response.

Instrument calibration was based on the average response factor (analyte peak area response/analyte concentration) of external calibration standards using Excel® functions AVERAGE, STDEV, and RSD. For average response factor calibration, a % RSD of less than or equal to 20% should be observed. The linear regression response of external calibration standards using Excel® functions SLOPE, INTERCEPT, and RSQ were monitored to establish calibration curve linearity. Acceptance criteria for valid quantitation are: (1) RSQ value >0.99 for calibration curve and (2) the % RSD≦20% for the individual calibration standard response factors. Alternative approaches including linear regression with or without weighting (e.g., 1/x) may be used if they provide an equivalent or more consistent fit of sample response to the response of calibration standards.

The LC/MS/MS calibrated range was 0.25 ng/mL to 50.0 ng/mL for N-acetylglyphosate, glyphosate, and N-acetyl AMPA. The LC/MS/MS calibrated range was 0.5 ng/mL to 50.0 ng/mL for AMPA. Generally, a minimum of 5 calibration solutions were analyzed for quantitative LC/MS/MS analysis.

Net recoveries may be calculated for fortified samples only (not acceptable for field samples). If residues in the control sample can be integrated with signal-to-noise response of at least 3-to-1, then net recoveries may be calculated by sub-

TABLE 78

Applied Biosystems/MDS Sciex API 5000 Mass Spectrometer Conditions:
Applied Biosystems/MDS SCIEX API 5000 Acquisition Parameters (ESI interface, MRM mode)

| Period (min) | Analyte | Polarity (+/−) | Q1 (m/z) | Q3 (m/z) | Dwell (msecs) | CUR (psi) | GS1 (psi) | GS2 (psi) | TEM (° C.) | ihe | IS (V) | CAD (psi) | DP (V) | EP (V) | CE (V) | CXP (V) |
|---|---|---|---|---|---|---|---|---|---|---|---|---|---|---|---|---|
| Negative Ion Parameters | | | | | | | | | | | | | | | | |
| 3.3-6.0 | AMPA | − | 110.00 | 63.10 | 200.00 | 10.00 | 70.00 | 30.00 | 400.00 | on | 4500 | 10.00 | 80.00 | 7.00 | 25.00 | 9.00 |
|  |  |  | 110.00 | 79.10 |  |  |  |  |  |  |  |  |  | 4.00 | 30.00 | 10.0 |
|  | AMPA 13C 15N |  | 112.00 | 63.00 |  |  |  |  |  |  |  |  |  | 7.00 | 25.00 | 9.00 |
| 3.6-6.0 | glyphosate | − | 168.00 | 62.90 | 200.00 | 10.00 | 70.00 | 30.00 | 400.00 | on | 4500 | 10.00 | 25.00 | 6.00 | 45.00 | 12.00 |
|  |  |  | 168.00 | 78.90 |  |  |  |  |  |  |  |  | 25.00 | 6.00 | 45.00 | 12.00 |
| 3.6-6.0 | glyphosate 1,2-13C 15N |  | 171.00 | 62.90 |  |  |  |  |  |  |  |  | 150.00 | 10.00 | 52.00 | 15.00 |
| 5.8-8.2 | N-acetyl AMPA | − | 152.00 | 63.00 | 200.00 | 10.00 | 70.00 | 40.00 | 400 | on | 4000 | 4.00 | 75.00 | 10.00 | 35.00 | 10.00 |
|  |  |  | 152.00 | 79.00 |  |  |  |  |  |  |  |  | 75.00 | 10.00 | 30.00 | 10.00 |
| 5.8-8.2 | N-acetyl glyphosate | − | 210.00 | 79.00 | 200.00 | 10.00 | 70.00 | 40.00 | 400 | on | 4500 | 4.00 | 67.00 | 6.00 | 35.00 | 20.00 |
|  |  |  | 210.00 | 124.00 |  |  |  |  |  |  |  |  | 67.00 | 6.00 | 35.00 | 20.00 |
| Positive Ion Parameters | | | | | | | | | | | | | | | | |
| 3.3-6.0 | AMPA | + | 112.00 | 30.10 | 200.00 | 10.00 | 50.00 | 30.00 | 300.00 | on | 4500 | 10.00 | 85.00 | 12.00 | 24.00 | 5.00 |
|  | AMPA 13C 15N |  | 114.00 | 32.10 |  |  |  |  |  |  |  |  |  |  |  |  |
| 3.6-6.0 | glyphosate | + | 170.00 | 60.10 | 200.00 | 10.00 | 50.00 | 30.00 | 300.00 | on | 4500 | 10.00 | 25.00 | 12.00 | 23.00 | 10.00 |
|  |  |  | 170.00 | 88.00 |  |  |  |  |  |  |  |  | 25.00 | 12.00 | 15.00 | 17.00 |
| 3.6-6.0 | glyphosate 1,2-13C 15N |  | 173.00 | 91.00 |  |  |  |  |  |  |  |  | 25.00 | 12.00 | 15.00 | 17.00 |
| 5.8-8.2 | N-acetyl AMPA | + | 154.00 | 30.00 | 200.00 | 10.00 | 65.00 | 46.00 | 300.00 | on | 5000 | 10.00 | 50.00 | 4.00 | 29.00 | 13.00 |
|  |  |  | 154.00 | 112.00 |  |  |  |  |  |  |  |  | 50.00 | 4.00 | 16.00 | 14.00 |
| 5.8-8.2 | N-acetyl glyphosate | + | 212.00 | 88.00 | 200.00 | 10.00 | 65.00 | 46.00 | 300.00 | on | 5000 | 10.00 | 50.00 | 5.00 | 26.00 | 12.00 |
|  |  |  | 212.00 | 169.90 |  |  |  |  |  |  |  |  | 55.00 | 4.00 | 14.00 | 18.00 |

Calibration Procedures

Standard mass spectrometer tuning and calibration techniques were used. If confidence in the mass calibration needs to be established (modern mass spectrometers under digital control generally do not need frequent mass calibration, especially for quantitative modes), use vendor recommended calibrating solution. Optimization tuning of MS system may be accomplished by infusion of the test analyte. This method uses external standards, prepared as described above.

tracting mg/kg found in the control sample from mg/kg found in the fortified samples. When the control residues are >50% of the LOQ, the recovery samples prepared at the LOQ using that control are invalidated. If net recoveries are calculated, those results must be uniquely identified or presented in a separate spreadsheet column heading for corrected mg/kg.

Sample Analysis

Preliminary runs of at least 2 calibration standards were routinely made to demonstrate adequate instrument response and insure the LC/MS/MS system was equilibrated. If multiple sets were analyzed, a solvent blank injection was made between the last and first injections of the sets to minimize risk of carryover between sets. Calibration standard analyses preceded the first sample analysis and follow the last sample analysis so sample analyses were contained within the external standard calibration. Generally, the injection sequence was organized from lowest to highest expected analyte concentrations. Calibration standard runs were intermixed with the test samples and were analyzed before and after every 1-3 samples in each analytical set. Extracts and calibration standards were refrigerated if stored. Generally, fortification sample recoveries (70-120%) were required for acceptable quantitation results in an analysis set.

Calculations

Methods

N-acetylglyphosate, glyphosate, N-acetyl AMPA, and AMPA residues were measured as ppm (mg/kg) in glyphosate free acid equivalents for animal matrices. Quantitation was based on an average response factor determined from the multiple calibration standards concurrently analyzed with sample extracts. All calculations were made using unrounded values that were reported to two significant figures. Fortified sample recoveries are reported to the nearest whole number percentage (%).

The calculation to determine mg/kg found in residue samples by average response factor analysis follows:

Without internal standard calibration:

$$\text{ppm found (glyphosate free-acid equivalents)} = \frac{PA \times FV \times XV}{ARF \times AF \times SW} \times UC$$

With internal standard calibration:

$$\text{ppm found (glyphosate free-acid equivalents)} = \frac{(PA/IS) \times FV \times XV}{ARF_{IS} \times AF \times SW} \times UC$$

where,
PA is Analyte Peak Area,
FV is Final extract Volume (mL),
XV is total eXtract Volume (mL),
RF Response Factor $$\left(\frac{\text{peak area}}{\text{ng/mL}}\right),$$

$RF_{IS}$ Response Factor with internal standard $$\left(\frac{PA/IS}{\text{ng/mL}}\right),$$

ARF is Average Response Factor from standards in the analytical set,
IS is peak area of Internal Standard in sample extract,
$ARF_{IS}$ is Average Response Factor with Internal Standard from standards in the analytical set,
AF is Aliquot Factor (mL of XV diluted to FV),
SW is Sample Weight (2.0 g) of sample aliquot extracted, and
UC Units Conversions µg/1000 ng×mg/1000 µg×1000 g/kg=mg·g/1000 ng·kg Percent recoveries (reported to the nearest whole number) from fortified samples were calculated as follows:

$$\% \text{ Recovery} = \frac{\text{mg/kg analyte found}}{\text{mg/kg analyte fortified}} \times 100$$

Examples without Internal Standard
N-acetylglyphosate in Whole Milk LOQ Fortification, MCX cleanup (RM L1 MCX 012307)

$$\frac{529 \text{ area} \times 5 \text{ mL} \times 50 \text{ mL}}{880 \text{ area/ng/mL} \times 4 \text{ mL} \times 2 \text{ g}} \times \frac{\text{mg} \cdot \text{g}}{1000 \text{ ng} \cdot \text{kg}} = 0.0188 = 0.019 \text{ mg/kg}$$

$$\% \text{ Recovery} = \frac{0.0188 \text{ mg/kg analyte found}}{0.025 \text{ mg/kg analyte fortified}} \times 100 = 75\%$$

N-acetyl AMPA in Whole Eggs LOQ Fortification, MAX cleanup (EG-0.025-3)

$$\frac{274 \text{ area} \times 5 \text{ mL} \times 50 \text{ mL}}{587 \text{ area/ng/mL} \times 2.5 \text{ mL} \times 2 \text{ g}} \times \frac{\text{mg} \cdot \text{g}}{1000 \text{ ng} \cdot \text{kg}} = 0.0233 = 0.023 \text{ mg/kg}$$

$$\% \text{ Recovery} = \frac{0.0233 \text{ mg/kg analyte found}}{0.025 \text{ mg/kg analyte fortified}} \times 100 = 93\%$$

Example with Internal Standard
Glyphosate in Whole Milk LOQ Fortification, MAX cleanup $$\frac{84 \text{ area}/953 \text{ area} \times 5 \text{ mL} \times 50 \text{ mL}}{0.1787/\text{ng/mL} \times 2.5 \text{ mL} \times 2\text{g}} \times \frac{\text{mg} \cdot \text{g}}{1000 \text{ ng} \cdot \text{kg}} = 0.0247 = 0.025 \text{ mg/kg}$$

$$\% \text{ Recovery} = \frac{0.0247 \text{ mg/kg analyte found}}{0.025 \text{ mg/kg analyte fortified}} \times 100 = 99\%$$

Results and Discussion

Method Validation Results
Detector Response

A triple quadrupole mass spectrometer using positive or negative ion ESI and tandem mass spectrometry detection was used for sample extract analysis. Full-Scan total ion chromatograms and spectra for N-acetylglyphosate, glyphosate, AMPA, and N-acetyl AMPA from analysis of standard solutions are provided in FIG. 59 through FIG. 62, respectively.

Figure 63:
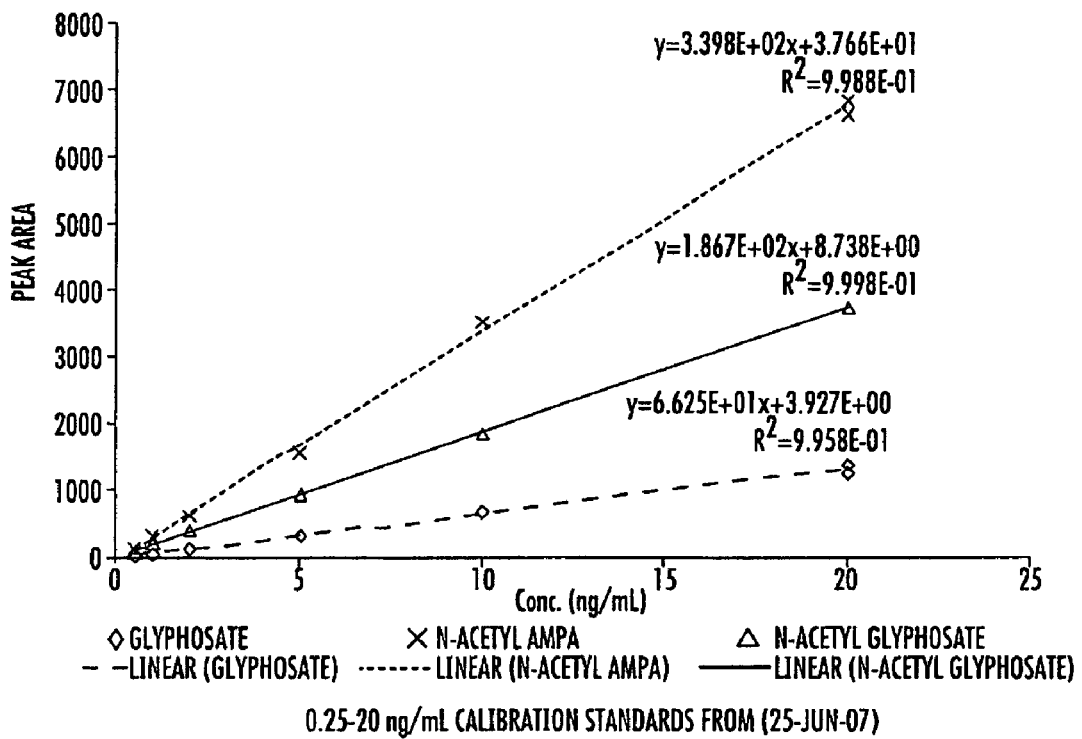
FIG. 63 provides a representative calibration curves.
Figure 63:
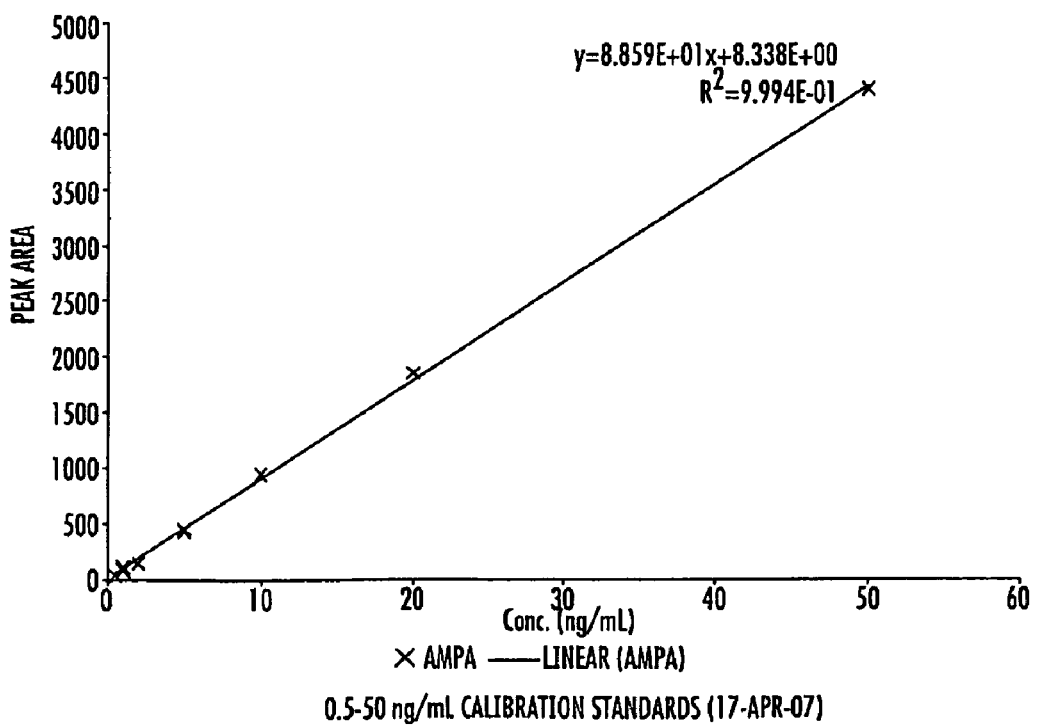
Figure 64:
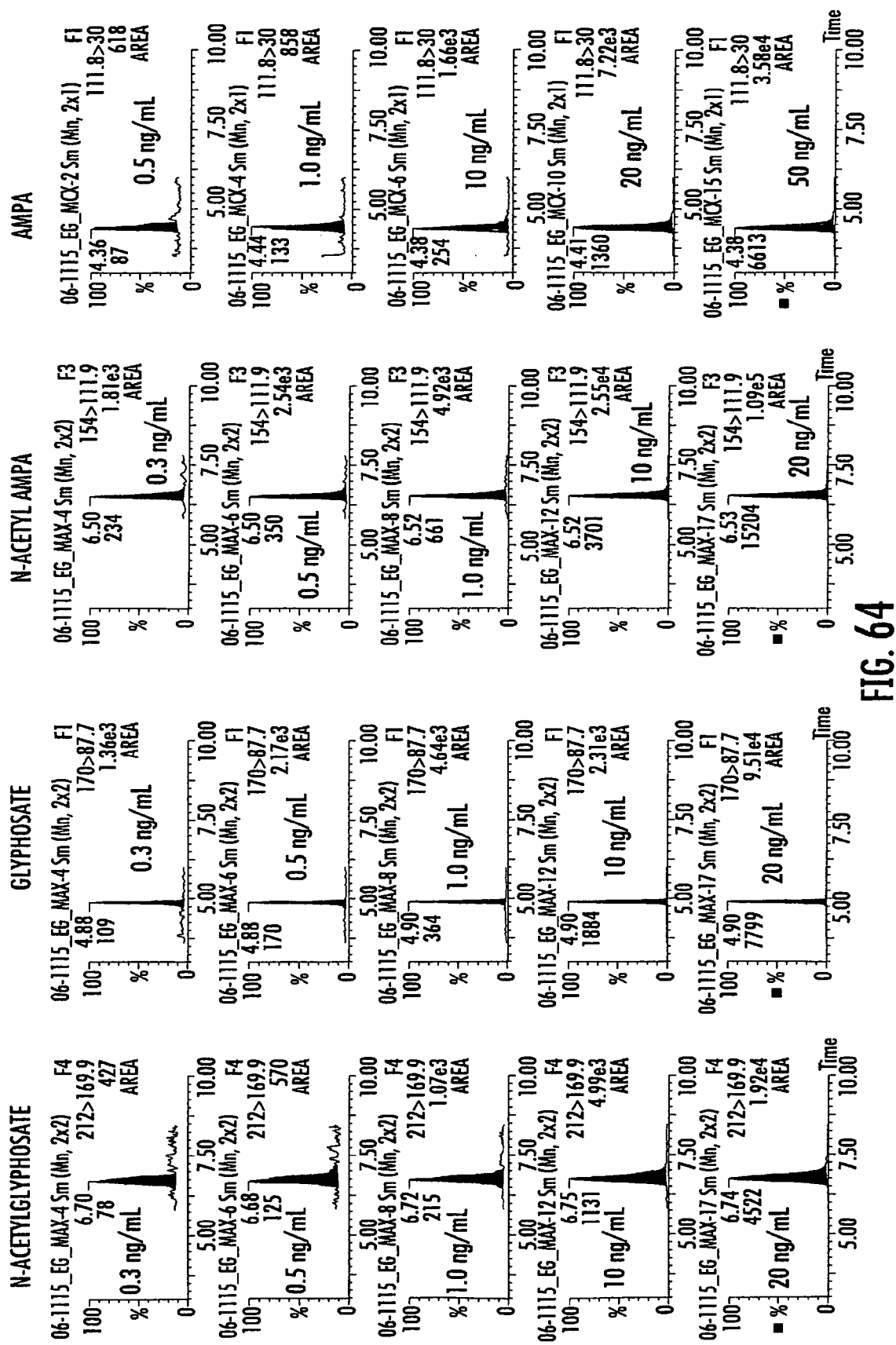
FIG. 64 provides representative calibration standard chromatograms.
Figure 65:
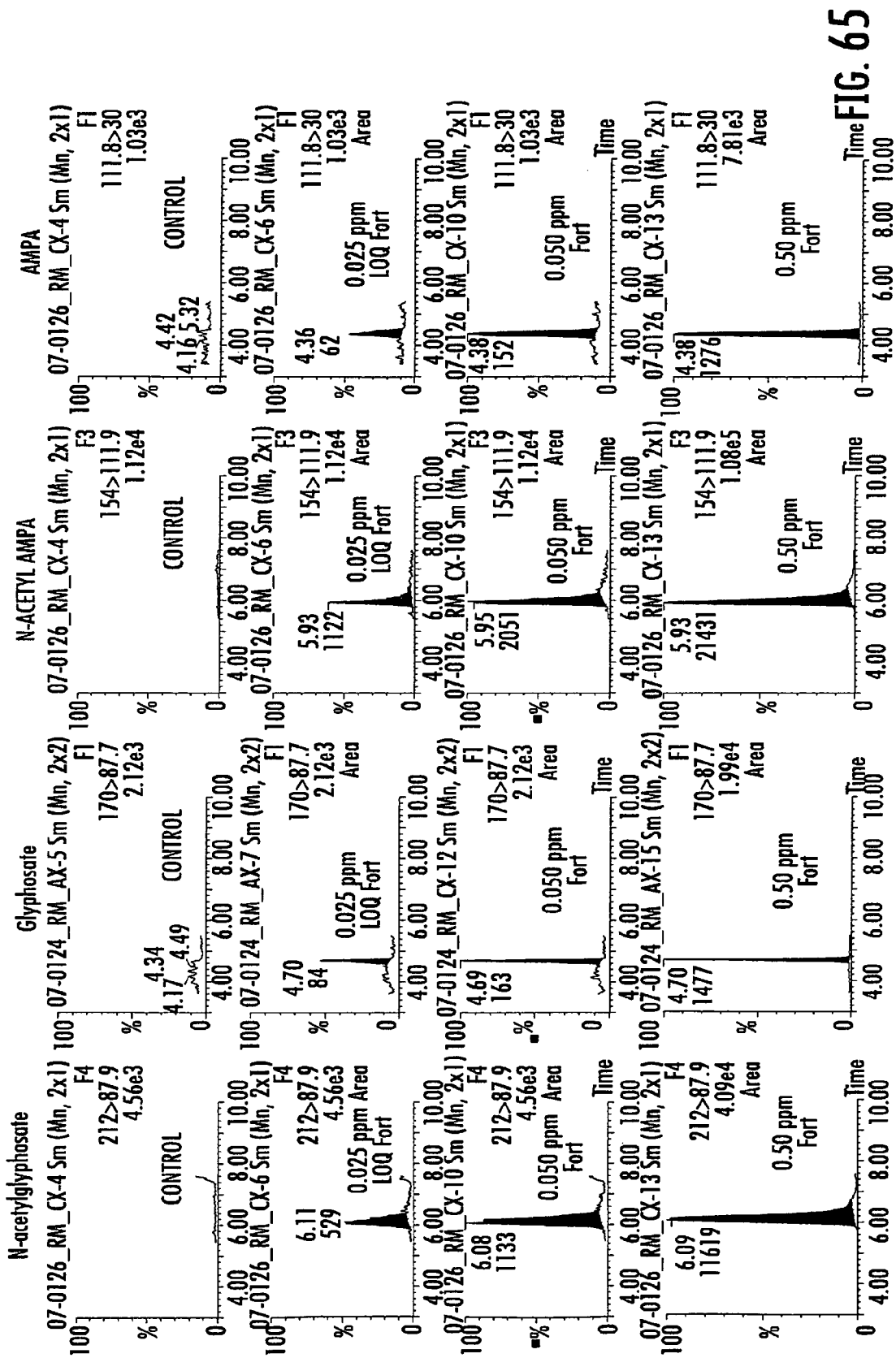
FIG. 65 provides representative milk chromatograms.
Figure 66:
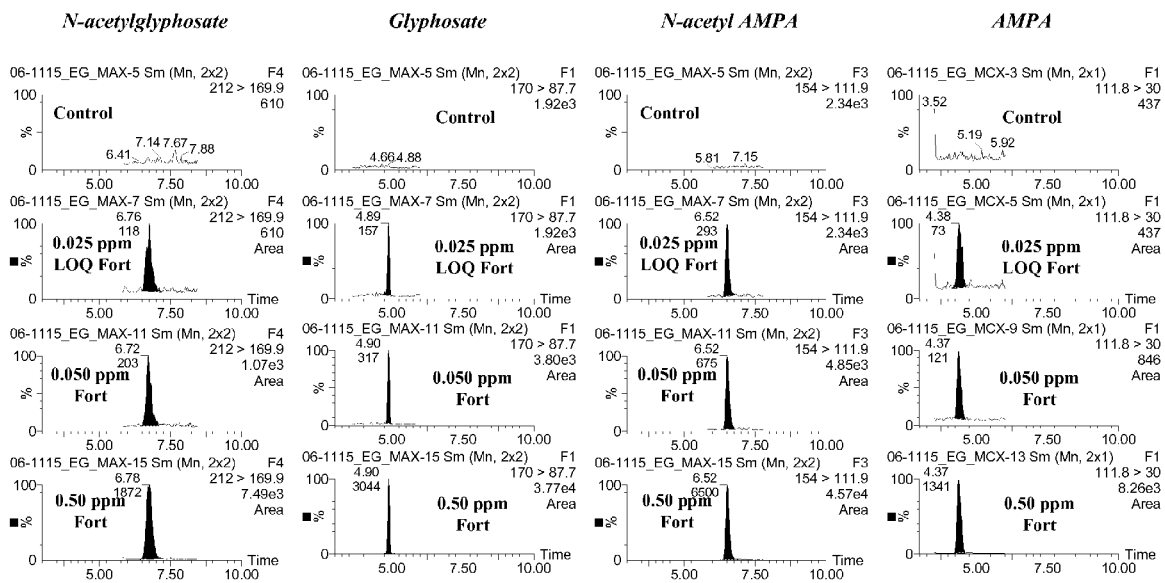
FIG. 66 provides representative egg sample chromatograms.
Figure 67A:
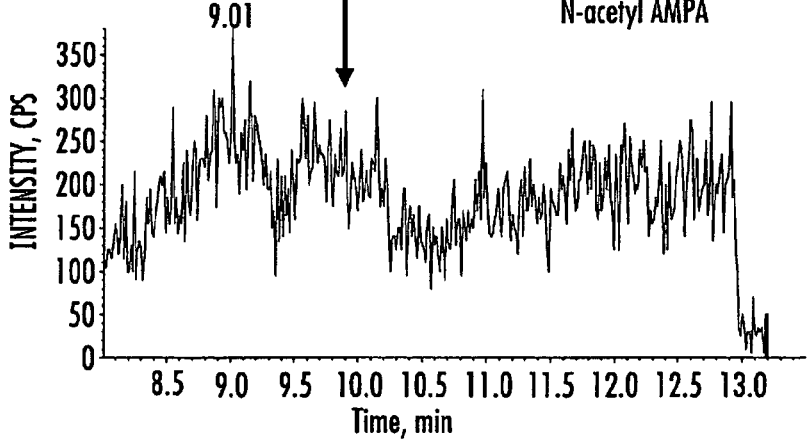
FIGS. 67A, B and C provides representative chicken muscle sample chromatograms.
Figure 67A:
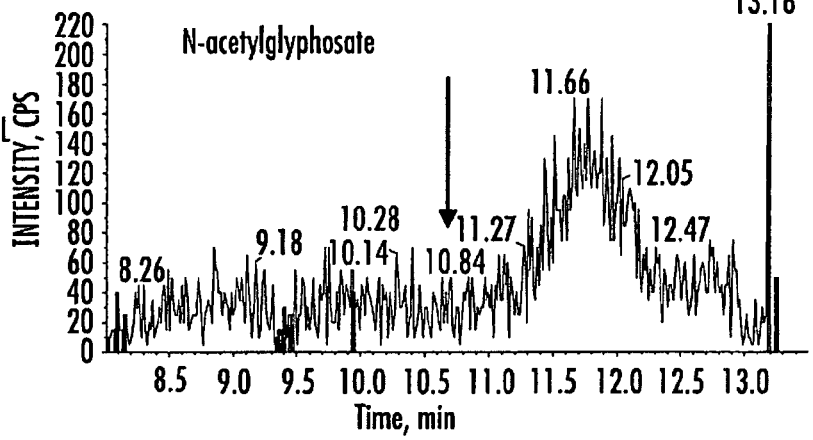
Figure 67A:
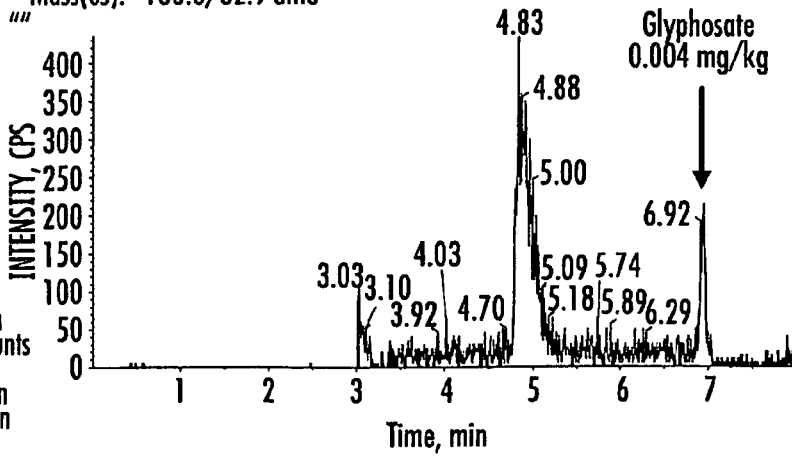
Figure 67B:
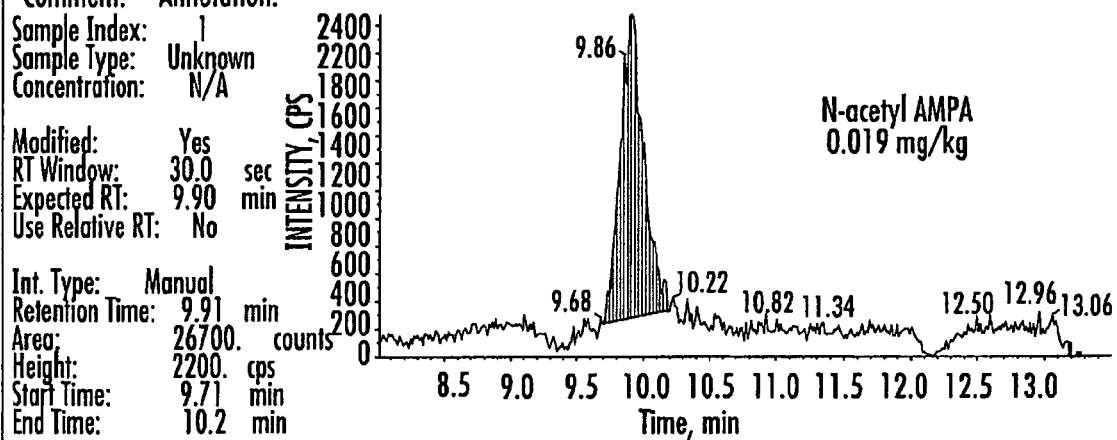
Figure 67B:
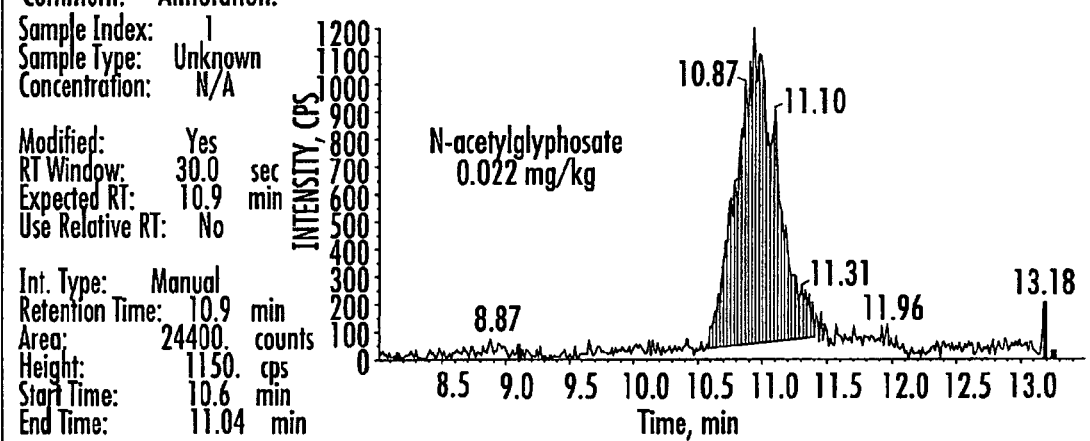
Figure 67B:
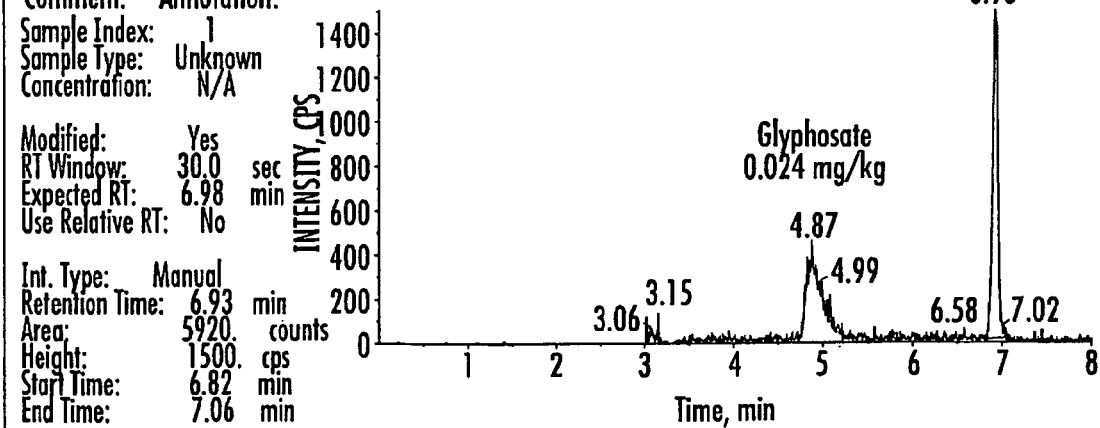
Figure 67C:
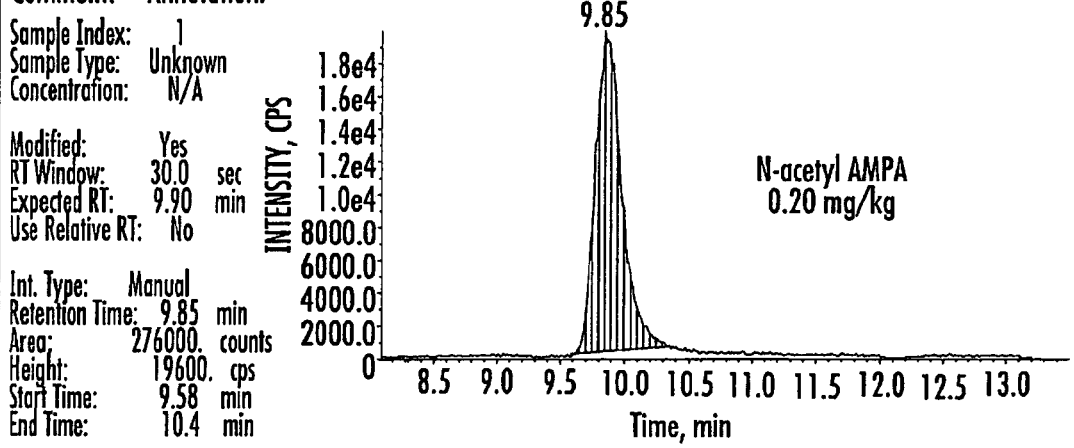
Figure 67C:
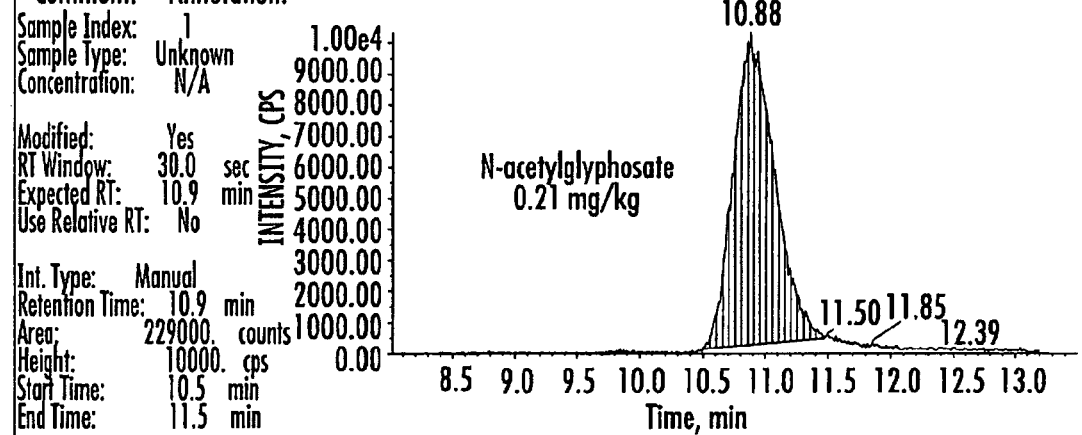
Figure 67C:
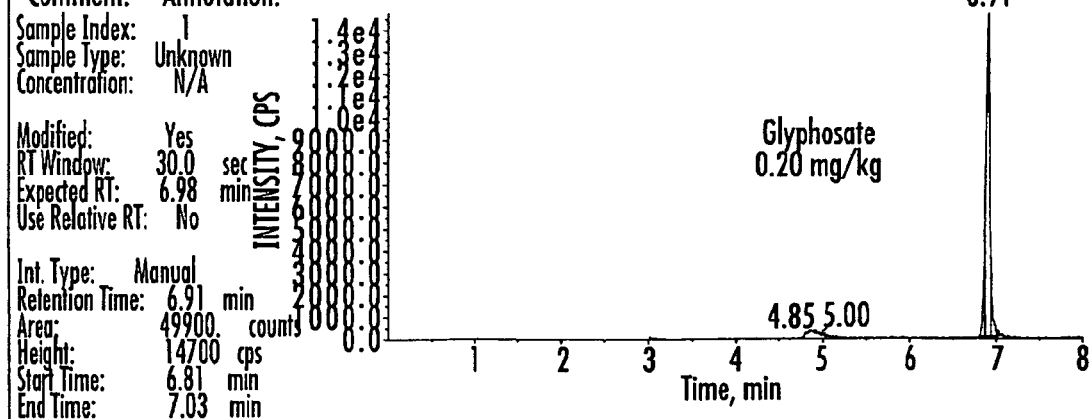
Figure 68:
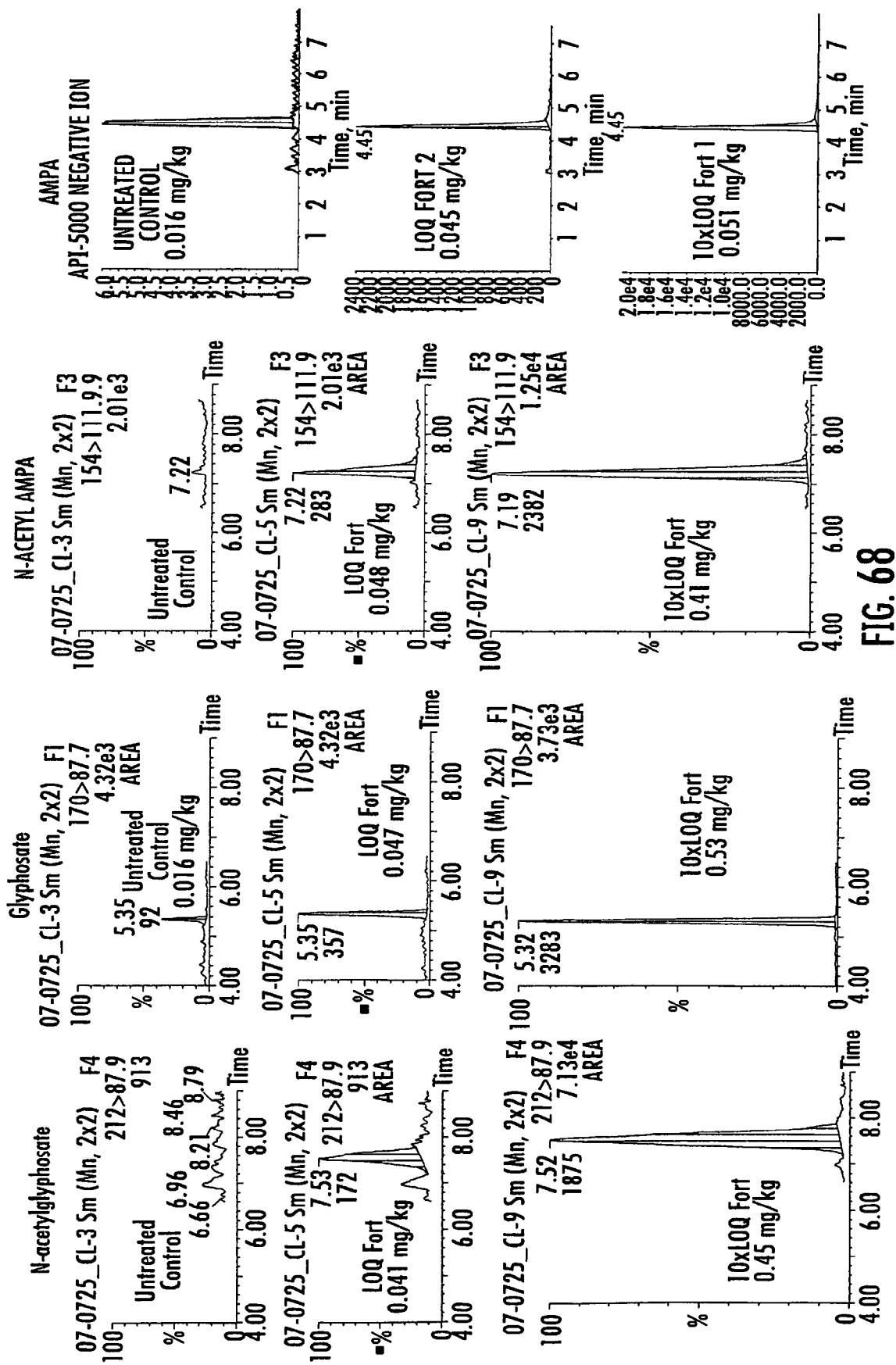
FIG. 68 provides representative chicken liver sample chromatograms.
Figure 69:
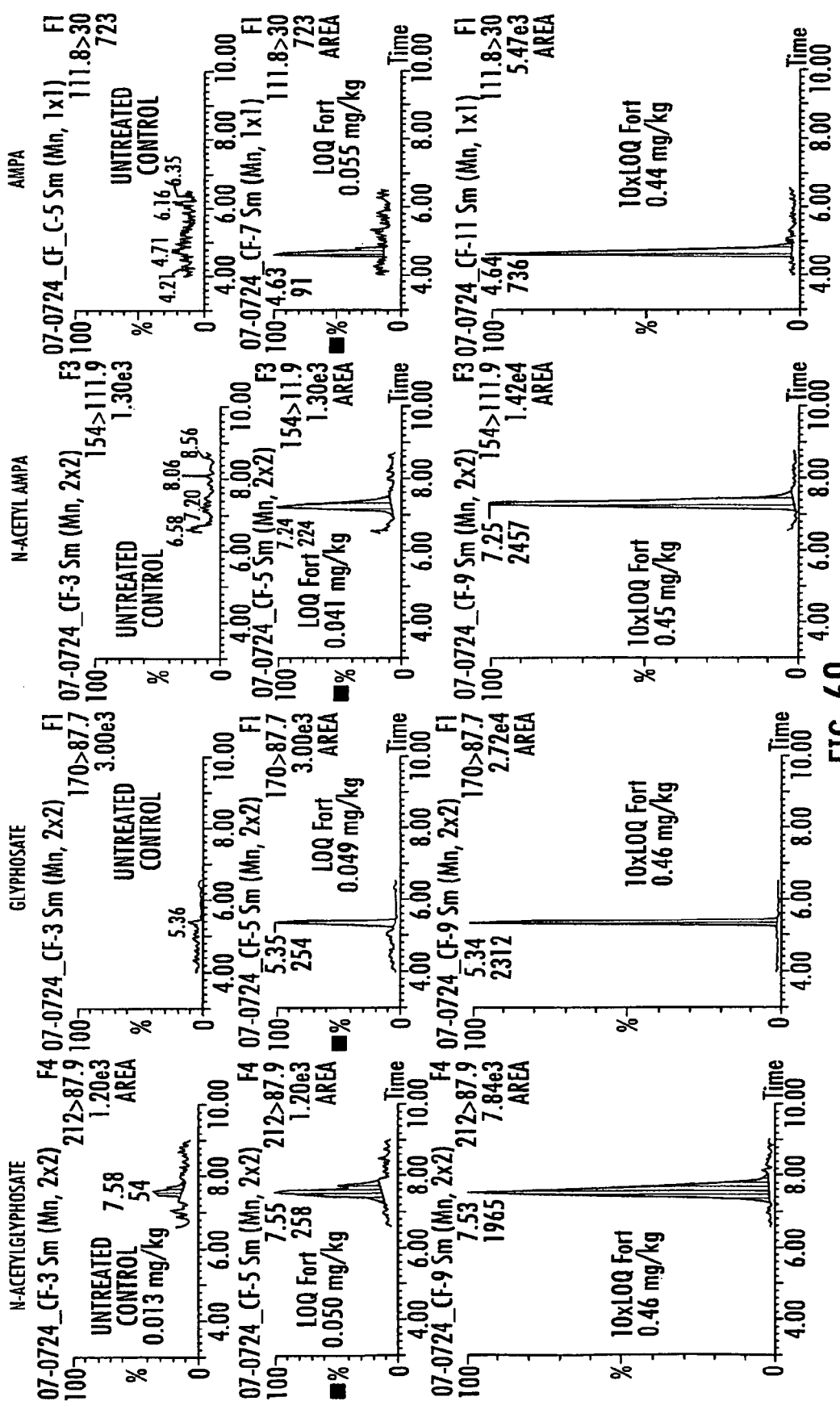
FIG. 69 provides representative chicken fat sample chromatograms.
Figure 70:
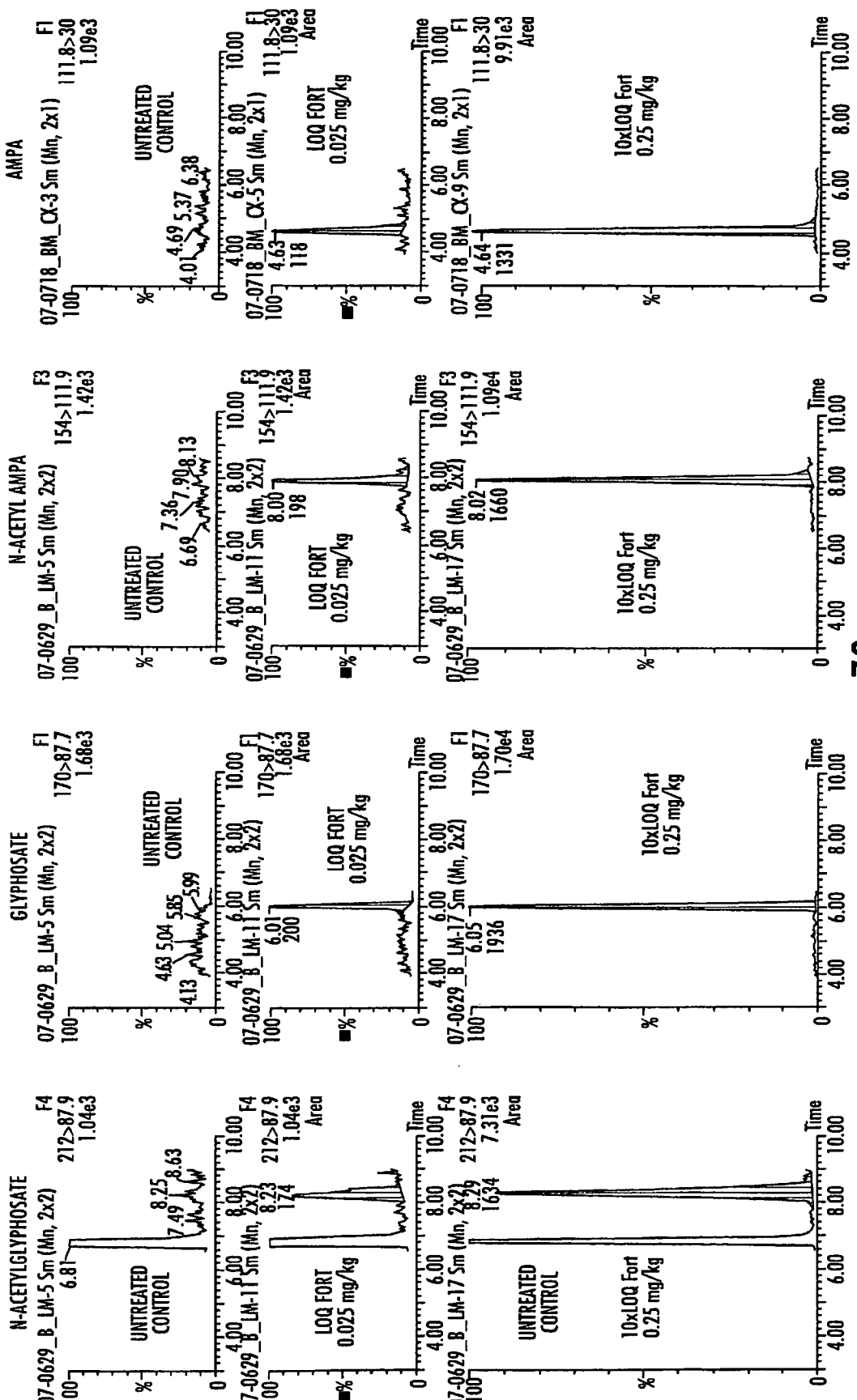
FIG. 70 provides representative cow muscle sample chromatograms.
Figure 71:
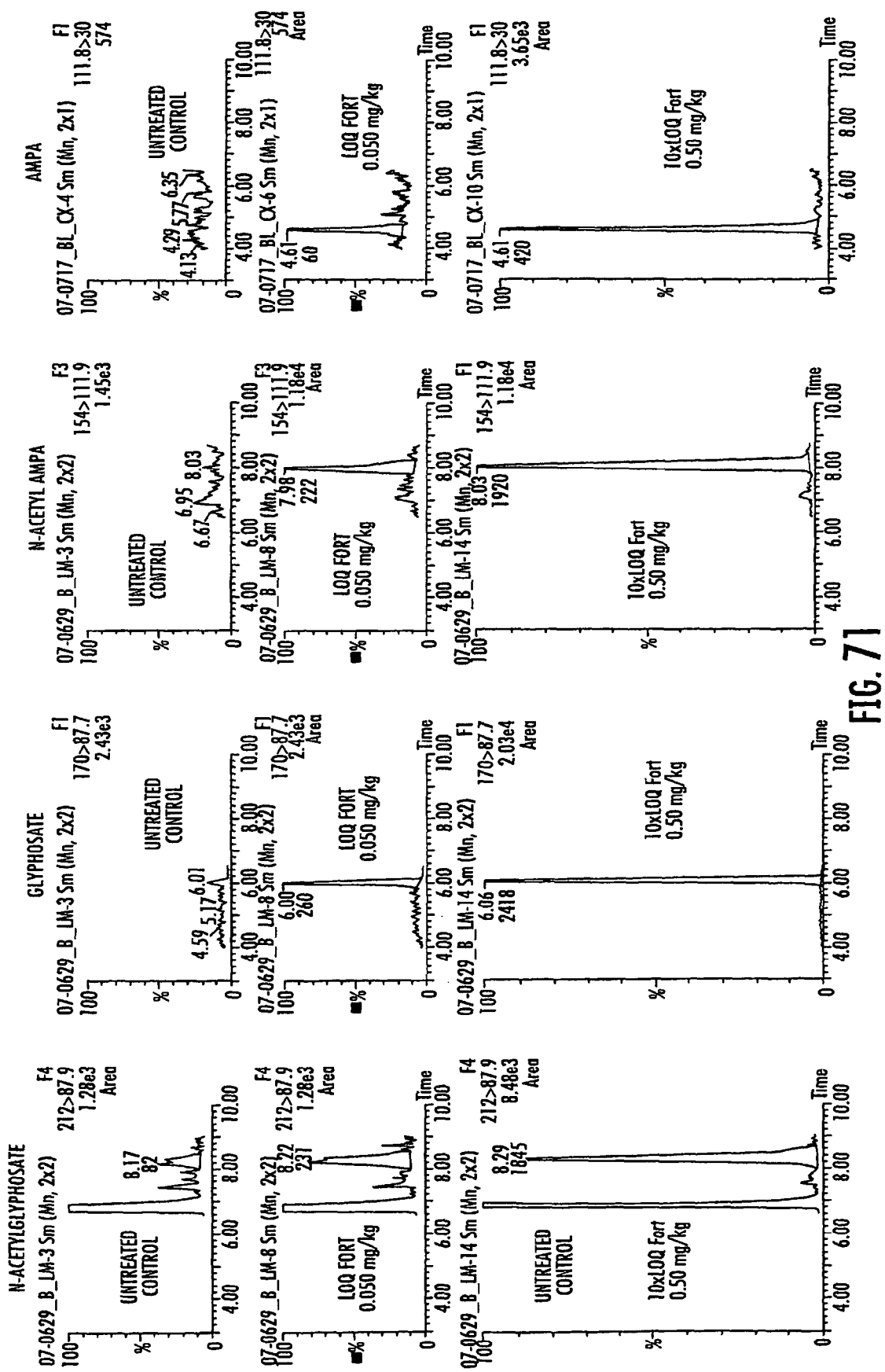
FIG. 71 provides representative cow liver sample chromatograms.
Figure 72:
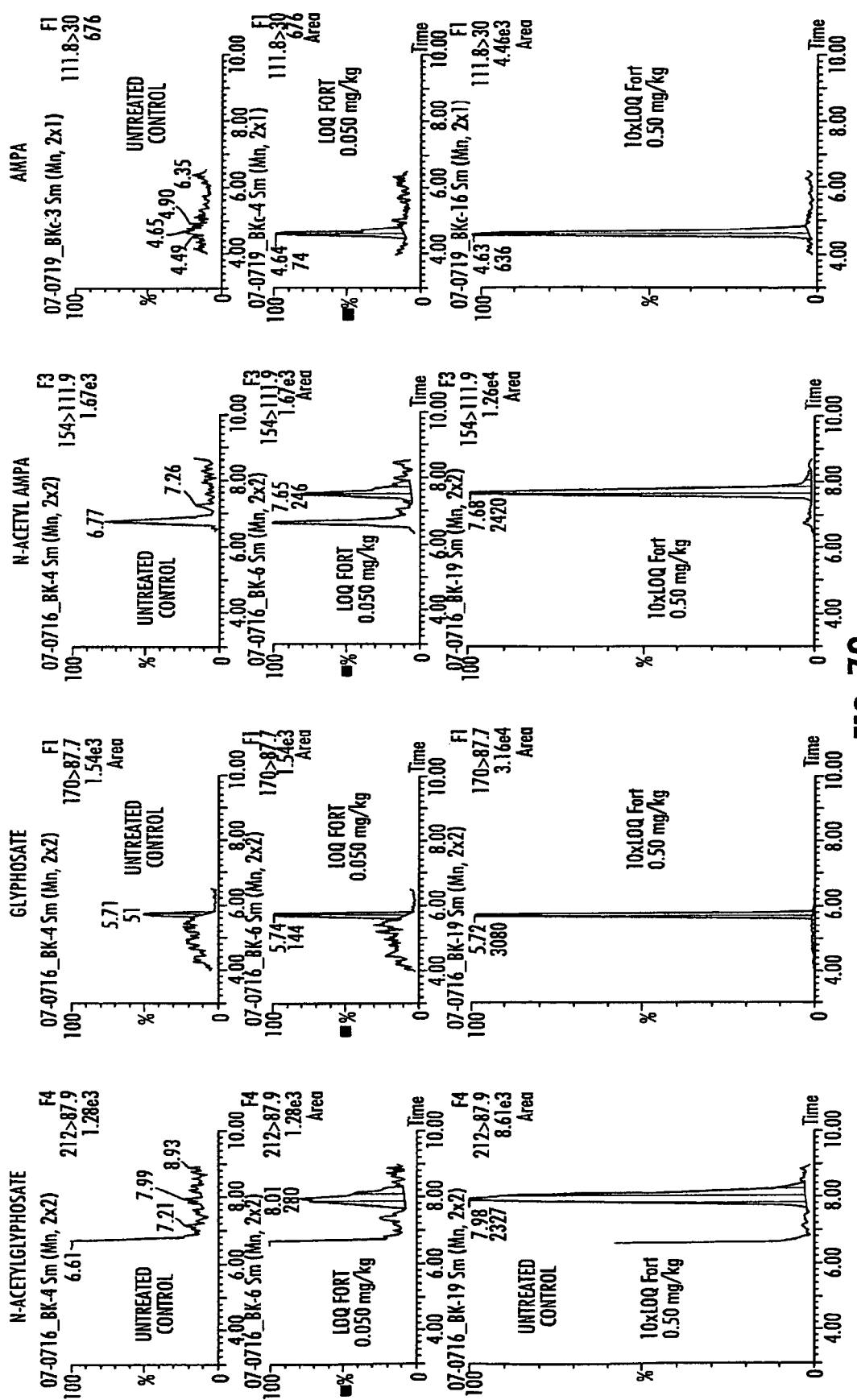
FIG. 72 provides representative cow kidney sample chromatograms.
Figure 73:
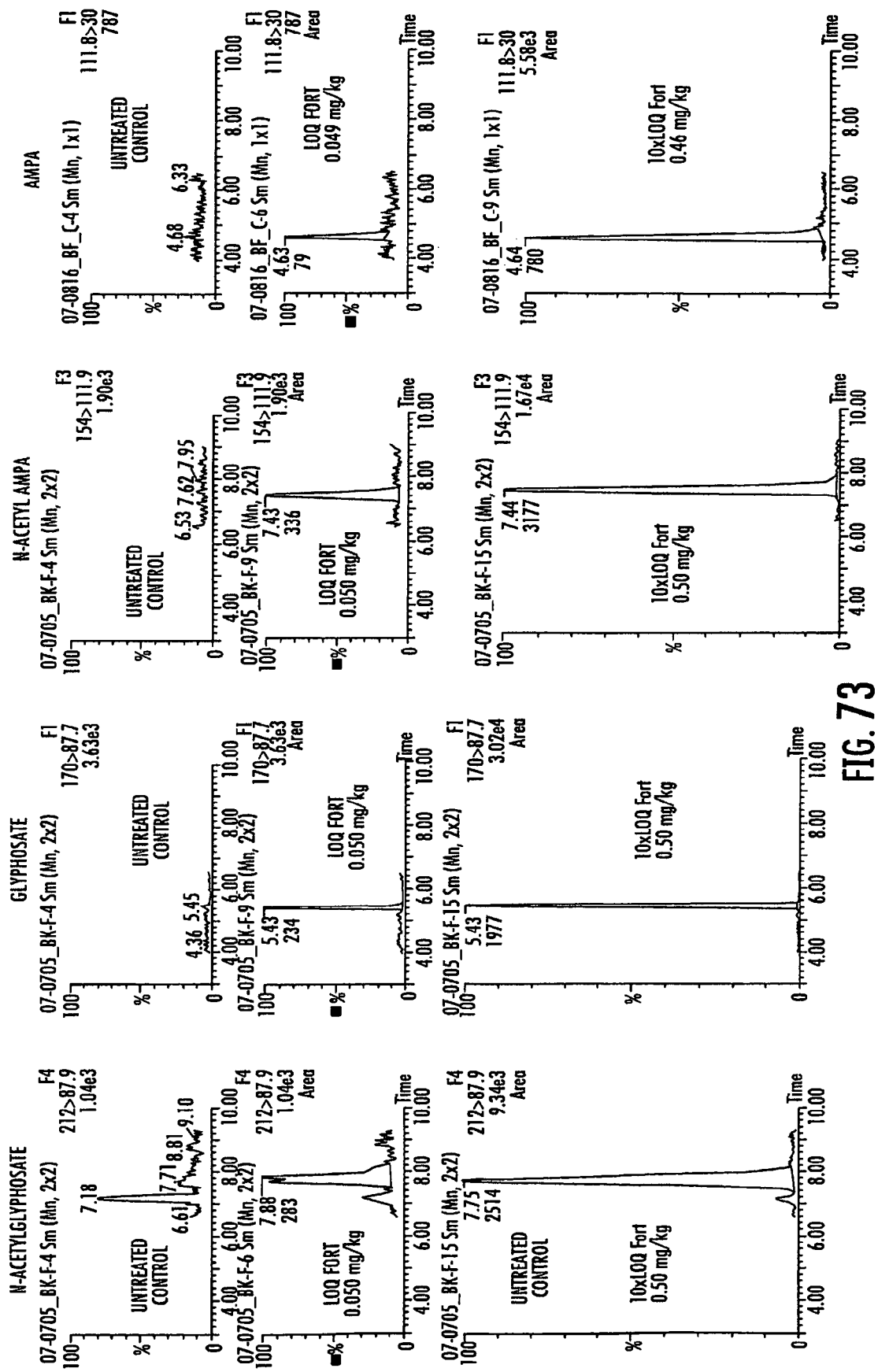
FIG. 73 provides representative cow fat sample chromatograms.

Calibration standards typically yielded a linear response (r-squared >0.99) with % RSD<20% for calibration standard response factors (peak area/concentration) over the range of 0.25-20 ng/mL for Glyphosate, N-acetylglyphosate and N-acetyl AMPA or 0.5-50 ng/mL for AMPA. Representative calibration curves for each analyte were constructed using calibration standards from a validation set and are presented in FIG. 63. Representative ion chromatograms of Calibration Standards are provided in FIG. 64. Representative ion chromatograms of extracts from a Control a LOQ fortification, and 10×LOQ fortification sample extracts for milk, egg, and tissue matrices are provided in FIG. 65 through FIG. 73, respectively.

Controls

No significant matrix interference was observed in the regions of N-acetylglyphosate, glyphosate, or N-acetyl AMPA elution in chromatograms of control extracts from matrix samples. AMPA was found in control chicken liver (0.011 mg/kg) and muscle (0.003 mg/kg) samples.

Recoveries (Accuracy & Precision)

Representative recovery results are provided in Table 80 through Table 82 for milk matrices, Table 83 through Table 85 for egg matrices, and Table 86 through Table 89 for animal tissue matrices. Average recovery results at each fortification level with overall recovery results for each matrix are provided in the summary. Representative results from individual sample set analyses for each commodity including calibration standards statistics are provided in Tables 90-101.

TABLE 80

WHOLE MILK VALIDATION RESULTS

| Matrix | Fort Level (mg/kg) | | N-acetylglyphosate % Rec | Glyphosate % Rec | N-acetyl AMPA % Rec | AMP A % Rec |
|---|---|---|---|---|---|---|
| Whole Milk | 0.025 | | 81% | 87% | 75% | 88% |
| | 0.025 | | 78% | 82% | 77% | 93% |
| | 0.050 | | 83% | 104% | 79% | 90% |
| | 0.050 | | 75% | 87% | 76% | 96% |
| | 0.50 | | 83% | 78% | 86% | 81% |
| | 0.50 | | 79% | 71% | 83% | 86% |
| | 0.025 | | 78% | 119% | 91% | 86% |
| | 0.025 | | 75% | 87% | 81% | 85% |
| | 0.025 | | 77% | 95% | 84% | 86% |
| | 0.050 | | 77% | 97% | 85% | 83% |
| | 0.050 | | 79% | 94% | 82% | 73% |
| | 0.050 | | 79% | 93% | 77% | 83% |
| | 0.50 | | 78% | 77% | 83% | 78% |
| | 0.50 | | 76% | 80% | 84% | 77% |
| | 0.50 | | 75% | 79% | 82% | 71% |
| | 0.025 | | 75% | 99% | 85% | 86% |
| | 0.025 | | 84% | 93% | 74% | 84% |
| | 0.050 | | 81% | 101% | 78% | 89% |
| | 0.050 | | 77% | 126% | 74% | 84% |
| | 0.50 | | 83% | 94% | 81% | 87% |
| | 0.50 | | 78% | 84% | 76% | 82% |
| | 0.025 | | 83% | 90% | 72% | 82% |
| | 0.025 | | 91% | 119% | 89% | 90% |
| | 0.25 | | 85% | 88% | 73% | 83% |
| | 0.25 | | 90% | 83% | 67% | 71% |
| Recovery Statistics | 0.025 | Avg | 80% | 97% | 81% | 87% |
| | | StDev | 5% | 14% | 7% | 3% |
| | | % RSD | 6% | 14% | 8% | 4% |
| | | n | 9 | 9 | 9 | 9 |
| | | min | 75% | 82% | 72% | 82% |
| | | max | 91% | 119% | 91% | 93% |
| | 0.050 | Avg | 78% | 100% | 79% | 85% |
| | | StDev | 3% | 13% | 4% | 7% |
| | | % RSD | 3% | 13% | 4% | 9% |
| | | n | 7 | 7 | 7 | 7 |
| | | min | 75% | 87% | 74% | 73% |
| | | max | 83% | 126% | 85% | 96% |
| | 0.50 | Avg | 79% | 80% | 82% | 80% |
| | | StDev | 3% | 7% | 3% | 6% |
| | | % RSD | 4% | 9% | 4% | 7% |
| | | n | 7 | 7 | 7 | 7 |
| | | min | 75% | 71% | 76% | 71% |
| | | max | 83% | 94% | 86% | 87% |
| | Overall | Avg | 80% | 92% | 80% | 84% |
| | | StDev | 4% | 14% | 6% | 6% |
| | | % RSD | 5% | 15% | 7% | 7% |
| | | n | 25 | 25 | 25 | 25 |
| | | min | 75% | 71% | 67% | 71% |
| | | max | 91% | 126% | 91% | 96% |

Glyphosate and AMPA stable isotopes used as internal standards.

TABLE 81

SKIM MILK VALIDATION RESULTS

| Matrix | Fort Level (mg/kg) | | N-acetylglyphosate % Rec | Glyphosate % Rec | N-acetyl AMPA % Rec | AMPA % Rec |
|---|---|---|---|---|---|---|
| Skim Milk | 0.025 | | 94% | 82% | 100% | 93% |
| | 0.025 | | 93% | 94% | 101% | 96% |
| | 0.050 | | 90% | 89% | 94% | 87% |
| | 0.050 | | 81% | 83% | 91% | 81% |
| | 0.50 | | 86% | 87% | 100% | 76% |
| | 0.50 | | 86% | 95% | 100% | 76% |
| | 0.025 | | 94% | 97% | 82% | na |
| | 0.025 | | 98% | 81% | 97% | na |
| | 0.025 | | 95% | 111% | 96% | na |
| | 0.050 | | 103% | 85% | 97% | na |
| | 0.050 | | 98% | 88% | 103% | na |
| | 0.050 | | 93% | 79% | 107% | na |
| | 0.50 | | 90% | 78% | 98% | na |
| | 0.50 | | 96% | 82% | 105% | na |
| | 0.50 | | 97% | 85% | 104% | na |
| Recovery Statistics | 0.025 | Avg | 95% | 93% | 95% | 94% |
| | | StDev | 2% | 12% | 8% | na |
| | | % RSD | 2% | 13% | 8% | na |
| | | n | 5 | 5 | 5 | 2 |
| | | min | 93% | 81% | 82% | 93% |
| | | max | 98% | 111% | 101% | 96% |
| | 0.050 | Avg | 93% | 85% | 99% | 84% |
| | | StDev | 8% | 4% | 7% | na |
| | | % RSD | 9% | 5% | 7% | na |
| | | n | 5 | 5 | 5 | 2 |
| | | min | 81% | 79% | 91% | 81% |
| | | max | 103% | 89% | 107% | 87% |
| | 0.50 | Avg | 91% | 85% | 101% | 76% |
| | | StDev | 5% | 7% | 3% | na |
| | | % RSD | 6% | 8% | 3% | na |
| | | n | 5 | 5 | 5 | 2 |
| | | min | 86% | 78% | 98% | 76% |
| | | max | 97% | 95% | 105% | 76% |
| | Overall | Avg | 93% | 88% | 98% | 85% |
| | | StDev | 6% | 9% | 6% | 8% |
| | | % RSD | 6% | 10% | 6% | 10% |
| | | n | 15 | 15 | 15 | 6 |
| | | min | 81% | 78% | 82% | 76% |
| | | max | 103% | 111% | 107% | 96% |

Glyphosate and AMPA stable isotopes used as internal standards.
na: not analyzed

TABLE 82

CREAM VALIDATION RESULTS

| Matrix | Fort Level (mg/kg) | Sample ID | N-acetylglyphosate % Rec | Glyphosate % Rec | N-acetyl AMPA % Rec | AMPA % Rec |
|---|---|---|---|---|---|---|
| Heavy Cream | 0.025 | | 81% | 109% | 108% | 88% |
| | 0.025 | | 80% | 79% | 68% | 98% |
| | 0.050 | | 83% | 94% | 82% | 95% |
| | 0.050 | | 86% | 91% | 71% | 78% |
| | 0.50 | | 86% | 80% | 98% | 84% |
| | 0.50 | | 85% | 84% | 86% | 81% |
| | 0.025 | | 78% | 94% | 85% | 94% |
| | 0.025 | | 77% | 113% | 88% | 87% |
| | 0.025 | | 74% | 101% | 85% | 97% |
| | 0.050 | | 75% | 91% | 92% | 86% |
| | 0.050 | | 83% | 95% | 89% | 88% |
| | 0.050 | | 82% | 103% | 84% | 96% |
| | 0.50 | | 81% | 90% | 94% | 87% |
| | 0.50 | | 80% | 77% | 94% | 80% |
| | 0.50 | | 81% | 84% | 94% | 75% |
| Recovery Statistics | 0.025 | Avg | 78% | 99% | 87% | 93% |
| | | StDev | 3% | 13% | 14% | 5% |
| | | % RSD | 4% | 13% | 17% | 5% |
| | | n | 5 | 5 | 5 | 5 |
| | | min | 74% | 79% | 68% | 87% |
| | | max | 81% | 113% | 108% | 98% |

TABLE 82-continued

CREAM VALIDATION RESULTS

| Matrix | Fort Level (mg/kg) | Sample ID | N-acetylglyphosate % Rec | Glyphosate % Rec | N-acetyl AMPA % Rec | AMPA % Rec |
| --- | --- | --- | --- | --- | --- | --- |
| | 0.050 | Avg | 82% | 95% | 83% | 88% |
| | | StDev | 4% | 5% | 8% | 8% |
| | | % RSD | 5% | 5% | 9% | 9% |
| | | n | 5 | 5 | 5 | 5 |
| | | min | 75% | 91% | 71% | 78% |
| | | max | 86% | 103% | 92% | 96% |
| | 0.50 | Avg | 82% | 83% | 93% | 82% |
| | | StDev | 3% | 5% | 5% | 4% |
| | | % RSD | 3% | 6% | 5% | 5% |
| | | n | 5 | 5 | 5 | 5 |
| | | min | 80% | 77% | 86% | 75% |
| | | max | 86% | 90% | 98% | 87% |
| | Overall | Avg | 81% | 92% | 88% | 88% |
| | | StDev | 4% | 11% | 10% | 7% |
| | | % RSD | 5% | 12% | 11% | 8% |
| | | n | 15 | 15 | 15 | 15 |
| | | min | 74% | 77% | 68% | 75% |
| | | max | 86% | 113% | 108% | 98% |

Glyphosate and AMPA stable isotopes used as internal standards.

TABLE 83

WHOLE EGGS VALIDATION RESULTS

| Matrix | Fort Level | | N-acetylglyphosate % Rec | Glyphosate % Rec | N-acetyl AMPA % Rec | AMPA % Rec |
| --- | --- | --- | --- | --- | --- | --- |
| Whole Eggs | 0.025 | | 102% | 93% | 80% | 110% |
| | 0.025 | | 80% | 79% | 84% | 92% |
| | 0.050 | | 88% | 89% | 93% | 80% |
| | 0.050 | | 83% | 101% | 90% | 97% |
| | 0.50 | | 81% | 85% | 89% | 79% |
| | 0.50 | | 88% | 87% | 93% | 85% |
| | 0.025 | | 111% | 89% | 93% | 110% |
| | 0.025 | | 104% | 89% | 101% | 107% |
| | 0.025 | | 85% | 92% | 101% | 107% |
| | 0.050 | | 97% | 87% | 103% | 97% |
| | 0.050 | | 82% | 84% | 102% | 98% |
| | 0.050 | | 86% | 86% | 109% | 107% |
| | 0.50 | | 91% | 87% | 97% | 86% |
| | 0.50 | | 85% | 84% | 101% | 86% |
| | 0.50 | | 91% | 82% | 104% | 83% |
| Recovery Statistics | 0.025 | Avg | 97% | 88% | 92% | 105% |
| | | StDev | 13% | 6% | 9% | 7% |
| | | % RSD | 13% | 7% | 10% | 7% |
| | | n | 5 | 5 | 5 | 5 |
| | | min | 80% | 79% | 80% | 92% |
| | | max | 111% | 93% | 101% | 110% |
| | 0.050 | Avg | 87% | 89% | 99% | 96% |
| | | StDev | 6% | 7% | 8% | 10% |
| | | % RSD | 7% | 7% | 8% | 10% |
| | | n | 5 | 5 | 5 | 5 |
| | | min | 82% | 84% | 90% | 80% |
| | | max | 97% | 101% | 109% | 107% |
| | 0.50 | Avg | 87% | 85% | 97% | 84% |
| | | StDev | 4% | 2% | 6% | 3% |
| | | % RSD | 5% | 3% | 6% | 4% |
| | | n | 5 | 5 | 5 | 5 |
| | | min | 81% | 82% | 89% | 79% |
| | | max | 91% | 87% | 104% | 86% |
| | Overall | Avg | 90% | 88% | 96% | 95% |
| | | StDev | 9% | 5% | 8% | 11% |
| | | % RSD | 10% | 6% | 8% | 12% |
| | | n | 15 | 15 | 15 | 15 |
| | | min | 80% | 79% | 80% | 79% |
| | | max | 111% | 101% | 109% | 110% |

Glyphosate and AMPA stable isotopes used as internal standards.

TABLE 84

EGG WHITES VALIDATION RESULTS

| Matrix | Fort Level | | N-acetylglyphosate % Rec | Glyphosate % Rec | N-acetyl AMPA % Rec | AMPA % Rec |
|---|---|---|---|---|---|---|
| Egg Whites | 0.025 | | 87% | 74% | 96% | 50%* |
| | 0.025 | | 105% | 85% | 86% | 74% |
| | 0.050 | | 88% | 90% | 92% | 90% |
| | 0.050 | | 107% | 89% | 94% | 92% |
| | 0.50 | | 98% | 81% | 92% | 87% |
| | 0.50 | | 93% | 86% | 100% | 84% |
| | 0.025 | | 108% | 94% | 91% | 86% |
| | 0.025 | | 105% | 81% | 89% | 94% |
| | 0.025 | | 107% | 81% | 89% | 111% |
| | 0.050 | | 106% | 91% | 91% | 103% |
| | 0.050 | | 89% | 84% | 77% | 91% |
| | 0.050 | | 90% | 85% | 81% | 97% |
| | 0.50 | | 96% | 95% | 92% | 87% |
| | 0.50 | | 95% | 93% | 85% | 89% |
| | 0.50 | | 92% | 90% | 92% | 84% |
| Recovery Statistics | 0.025 | Avg | 103% | 83% | 90% | 91% |
| | | StDev | 9% | 7% | 4% | 16% |
| | | % RSD | 8% | 9% | 4% | 17% |
| | | n | 5 | 5 | 5 | 4 |
| | | min | 87% | 74% | 86% | 74% |
| | | max | 108% | 94% | 96% | 111% |
| | 0.050 | Avg | 96% | 88% | 87% | 94% |
| | | StDev | 10% | 3% | 8% | 5% |
| | | % RSD | 10% | 4% | 9% | 5% |
| | | n | 5 | 5 | 5 | 5 |
| | | min | 88% | 84% | 77% | 90% |
| | | max | 107% | 91% | 94% | 103% |
| | 0.50 | Avg | 95% | 89% | 92% | 86% |
| | | StDev | 2% | 6% | 5% | 2% |
| | | % RSD | 2% | 6% | 6% | 3% |
| | | n | 5 | 5 | 5 | 5 |
| | | min | 92% | 81% | 85% | 84% |
| | | max | 98% | 95% | 100% | 89% |
| | Overall | Avg | 98% | 87% | 90% | 91% |
| | | StDev | 8% | 6% | 6% | 9% |
| | | % RSD | 8% | 7% | 6% | 10% |
| | | n | 15 | 15 | 15 | 14 |
| | | min | 87% | 74% | 77% | 74% |
| | | max | 108% | 95% | 100% | 111% |

Glyphosate and AMPA stable isotopes used as internal standards.
*AMPA data point outlier, not included in recovery data

TABLE 85

EGG YOLKS VALIDATION RESULTS

| Matrix | Fort Level (mg/kg) | Sample ID | N-acetylglyphosate % Rec | Glyphosate % Rec | N-acetyl AMPA % Rec | AMPA % Rec |
|---|---|---|---|---|---|---|
| Egg Yolks | 0.025 | EY-0.025-3 | 83% | 95% | 91% | 106% |
| | 0.025 | EY-0.025-4 | 98% | 89% | 101% | 114% |
| | 0.050 | EY-0.50-3 | 85% | 87% | 97% | 80% |
| | 0.050 | EY-0.50-4 | 88% | 85% | 94% | 100% |
| | 0.50 | EY-0.050-3 | 111% | 99% | 105% | 97% |
| | 0.50 | EY-0.050-4 | 93% | 92% | 109% | 91% |
| | 0.025 | EY-L3 011707 | 86% | 115% | 87% | na |
| | 0.025 | EY-L4 011707 | 85% | 92% | 95% | na |
| | 0.025 | EY-L5 011707 | 87% | 100% | 93% | na |
| | 0.050 | EY-M3 011707 | 88% | 84% | 93% | na |
| | 0.050 | EY-M4 011707 | 97% | 104% | 99% | na |
| | 0.050 | EY-M5 011707 | 88% | 90% | 97% | na |
| | 0.50 | EY-H3 011707 | 92% | 85% | 106% | na |
| | 0.50 | EY-H4 011707 | 83% | 83% | 99% | na |
| | 0.50 | EY-H5 011707 | 96% | 86% | 112% | na |
| Recovery Statistics | 0.025 | Avg | 88% | 98% | 93% | 110% |
| | | StDev | 6% | 10% | 5% | 6% |
| | | % RSD | 7% | 11% | 5% | 5% |
| | | n | 5 | 5 | 5 | 2 |
| | | min | 83% | 89% | 87% | 106% |
| | | max | 98% | 115% | 101% | 114% |

TABLE 85-continued

EGG YOLKS VALIDATION RESULTS

| Matrix | Fort Level (mg/kg) | Sample ID | N-acetylglyphosate % Rec | Glyphosate % Rec | N-acetyl AMPA % Rec | AMPA % Rec |
|---|---|---|---|---|---|---|
| | 0.050 | Avg | 90% | 90% | 96% | 90% |
| | | StDev | 5% | 8% | 2% | 14% |
| | | % RSD | 5% | 9% | 3% | 16% |
| | | n | 5 | 5 | 5 | 2 |
| | | min | 85% | 84% | 93% | 80% |
| | | max | 97% | 104% | 99% | 100% |
| | 0.50 | Avg | 95% | 89% | 106% | 94% |
| | | StDev | 10% | 7% | 5% | 4% |
| | | % RSD | 11% | 7% | 5% | 4% |
| | | n | 5 | 5 | 5 | 2 |
| | | min | 83% | 83% | 99% | 91% |
| | | max | 111% | 99% | 112% | 97% |

Glyphosate and AMPA stable isotopes used as internal standards.

TABLE 86

LIVER VALIDATION RESULTS

| Matrix | Fort Level (mg/kg)[†] | | N-acetyl glyphosate | Glyphosate | AMPA | N-acetyl AMPA |
|---|---|---|---|---|---|---|
| Chicken Liver | 0.050 | | 82% | 93% | 95%* | 96% |
| | 0.050 | | 87% | 98% | 92%* | 100% |
| | 0.50 | | 89% | 86% | 105%* | 81% |
| | 0.50 | | 109% | 85% | 110%* | 94% |
| | 0.050 | | 87% | 74% | 86% | 58% |
| | 0.50 | | 90% | 79% | 91% | 85% |
| Beef Liver | 0.050 | | 98% | 105% | 77% | 93% |
| | 0.050 | | 80% | 92% | 101% | 107% |
| | 0.50 | | 92% | 86% | 85% | 95% |
| | 0.50 | | 94% | 85% | 86% | 93% |
| | 0.050 | | 105%* | 90%* | 103%* | 76%* |
| | 0.50 | | 81%* | 88%* | 97%* | 73%* |
| | 0.50 | | 86% | 82% | 92% | 81% |
| | 0.050 | | 93% | 78% | 118% | 71% |
| | 0.050 | | 75% | 80% | 94% | 72% |
| | 0.50 | | 78% | 71% | 81% | 63% |
| | 0.50 | | 76% | 76% | 98% | 68% |
| | 0.050 | | 92% | 102% | No Analysis | |
| | 0.050 | | 84% | 84% | 95% | 71% |
| | 0.050 | | 112% | 92% | 111% | 86% |
| Recovery Statistics | 0.050 | Average | 90% | 90% | 97% | 83% |
| | | StDev | 11% | 10% | 12% | 16% |
| | | % RSD | 12% | 11% | 12% | 19% |
| | | Number of Tests | 11 | 11 | 10 | 10 |
| | | Minimum | 75% | 74% | 77% | 58% |
| | | Maximum | 112% | 105% | 118% | 107% |
| | 0.50 | Average | 89% | 82% | 94% | 81% |
| | | StDev | 10% | 5% | 10% | 12% |
| | | % RSD | 11% | 7% | 10% | 14% |
| | | Number of Tests | 9 | 9 | 9 | 9 |
| | | Minimum | 76% | 71% | 81% | 63% |
| | | Maximum | 109% | 88% | 110% | 95% |
| | Overall | Average | 90% | 86% | 96% | 82% |
| | | StDev | 10% | 9% | 11% | 14% |
| | | % RSD | 12% | 10% | 11% | 16% |
| | | Number of Tests | 20 | 20 | 19 | 19 |
| | | Minimum | 75% | 71% | 77% | 58% |
| | | Maximum | 112% | 105% | 118% | 107% |

[†]mg/kg glyphosate equivalents
*Average of 2 analyses of same extract

TABLE 87

KIDNEY VALIDATION RESULTS

| Matrix | Fort Level (mg/kg)† | | N-acetyl glyphosate | Glyphosate | AMPA | N-acetyl AMPA |
|---|---|---|---|---|---|---|
| Beef Kidney | 0.050 | | 97% | 116% | 76% | 93% |
| | 0.050 | | 106% | 78% | 83% | 94% |
| | 0.50 | | 82% | 81% | 77% | 87% |
| | 0.50 | | 84% | 84% | 71% | 93% |
| | 0.050 | | 103%* | 96%* | 100% | 69%* |
| | 0.50 | | 85%* | 92%* | 95%* | 71%* |
| | 0.50 | | 88%* | 91%* | 88% | 75%* |
| | 0.050 | | 94% | 113% | 113% | 80% |
| | 0.50 | | 73% | 86% | 84% | 46%** |
| | 0.050 | | 112% | 88% | 101% | 75% |
| | 0.050 | | 80% | 99% | 77% | 79% |
| | 0.50 | | 82% | 84% | 98% | 71% |
| | 0.50 | | 87% | 89% | 108% | 76% |
| Recovery Statistics | 0.050 | Average | 99% | 98% | 92% | 82% |
| | | StDev | 11% | 15% | 15% | 10% |
| | | % RSD | 11% | 15% | 17% | 12% |
| | | Number of Tests | 6 | 6 | 6 | 6 |
| | | Minimum | 80% | 78% | 76% | 69% |
| | | Maximum | 112% | 116% | 113% | 94% |
| | 0.50 | Average | 83% | 87% | 89% | 79% |
| | | StDev | 5% | 4% | 13% | 9% |
| | | % RSD | 6% | 5% | 14% | 11% |
| | | Number of Tests | 7 | 7 | 7 | 6 |
| | | Minimum | 73% | 81% | 71% | 71% |
| | | Maximum | 88% | 92% | 108% | 93% |
| | Overall | Average | 90% | 92% | 90% | 80% |
| | | StDev | 11% | 11% | 13% | 9% |
| | | % RSD | 13% | 13% | 15% | 11% |
| | | Number of Tests | 13 | 13 | 13 | 12 |
| | | Minimum | 73% | 78% | 71% | 69% |
| | | Maximum | 112% | 116% | 113% | 94% |

†mg/kg glyphosate equivalents
*Average of 2 analyses of same extract
**Result outlier not included in recovery statistics

TABLE 88

FAT VALIDATION RESULTS

| Matrix | Fort Level (mg/kg)† | | N-acetyl glyphosate | Glyphosate | AMPA | N-acetyl AMPA |
|---|---|---|---|---|---|---|
| Chicken Fat | 0.050 | | 99% | 98% | 109% | 82% |
| | 0.050 | | 93% | 110% | 105% | 85% |
| | 0.50 | | 93% | 92% | 89% | 90% |
| | 0.50 | | 97% | 86% | 94% | 92% |
| | 0.050 | | 91% | 88% | 109% | 85% |
| | 0.50 | | 83% | 96% | 91% | 71% |
| Beef Fat | 0.050 | | 107% | 113% | 97% | 95% |
| | 0.050 | | 104% | 86% | 95% | 94% |
| | 0.50 | | 86% | 95% | 92% | 90% |
| | 0.50 | | 87% | 97% | 97% | 93% |
| | 0.050 | | 104% | 91% | No Analysis | 86% |
| | 0.50 | | 96% | 98% | | 89% |
| Recovery Statistics | 0.050 | Average | 100% | 98% | 103% | 88% |
| | | StDev | 6% | 11% | 6% | 5% |
| | | % RSD | 6% | 12% | 6% | 6% |
| | | Number of Tests | 6 | 6 | 5 | 6 |
| | | Minimum | 91% | 86% | 95% | 82% |
| | | Maximum | 107% | 113% | 109% | 95% |
| | 0.50 | Average | 90% | 94% | 93% | 87% |
| | | StDev | 6% | 4% | 3% | 8% |
| | | % RSD | 6% | 5% | 4% | 9% |
| | | Number of Tests | 6 | 6 | 5 | 6 |
| | | Minimum | 83% | 86% | 89% | 71% |
| | | Maximum | 97% | 98% | 97% | 93% |

TABLE 88-continued

FAT VALIDATION RESULTS

| Matrix | Fort Level (mg/kg)† | | Recovery (%) | | | |
|---|---|---|---|---|---|---|
| | | | N-acetyl glyphosate | Glyphosate | AMPA | N-acetyl AMPA |
| | Overall | Average | 95% | 96% | 98% | 88% |
| | | StDev | 8% | 8% | 7% | 7% |
| | | % RSD | 8% | 9% | 7% | 8% |
| | | Number of Tests | 12 | 12 | 10 | 12 |
| | | Minimum | 83% | 86% | 89% | 71% |
| | | Maximum | 107% | 113% | 109% | 95% |

†mg/kg glyphosate equivalents

TABLE 89

MUSCLE VALIDATION RESULTS

| Matrix | Fort Level (mg/kg)† | | Recovery (%) | | | |
|---|---|---|---|---|---|---|
| | | | N-acetyl glyphosate | Glyphosate | AMPA | N-acetyl AMPA |
| Chicken | 0.025 | | 90% | 96% | 101%* | 77% |
| Muscle | 0.025 | | 93% | 102% | 101%* | 77% |
| | 0.25 | | 84% | 82% | 91%* | 80% |
| | 0.25 | | 92% | 88% | 95%* | 88% |
| | 0.025 | | 78% | 82% | 84% | 69% |
| | 0.25 | | 70% | 78% | 85% | 50%** |
| Beef Muscle | 0.025 | | 102% | 89% | 84% | 93% |
| | 0.025 | | 93% | 77% | 88% | 96% |
| | 0.25 | | 81% | 91% | 101% | 86% |
| | 0.25 | | 87% | 81% | 99% | 80% |
| | 0.025 | | 113% | 94% | 103% | 84% |
| | 0.25 | | 78% | 82% | No Analysis | 64% |
| | 0.025 | | 76% | 103% | No Analysis | |
| | 0.25 | | 73% | 86% | | |
| Recovery Statistics | 0.025 | Average | 92% | 92% | 94% | 83% |
| | | StDev | 13% | 10% | 9% | 10% |
| | | % RSD | 14% | 11% | 10% | 13% |
| | | Number of Tests | 7 | 7 | 6 | 6 |
| | | Minimum | 76% | 77% | 84% | 69% |
| | | Maximum | 113% | 103% | 103% | 96% |
| | 0.25 | Average | 81% | 84% | 94% | 80% |
| | | StDev | 8% | 4% | 6% | 9% |
| | | % RSD | 10% | 5% | 7% | 12% |
| | | Number of Tests | 7 | 7 | 5 | 5 |
| | | Minimum | 70% | 78% | 85% | 64% |
| | | Maximum | 92% | 91% | 101% | 88% |
| | Overall | Average | 87% | 88% | 94% | 81% |
| | | StDev | 12% | 8% | 8% | 10% |
| | | % RSD | 14% | 10% | 8% | 12% |
| | | Number of Tests | 14 | 14 | 11 | 11 |
| | | Minimum | 70% | 77% | 84% | 64% |
| | | Maximum | 113% | 103% | 103% | 96% |

†mg/kg glyphosate equivalents
*Average of 2 analyses of same extract
**Result outlier not included in recovery statistics

TABLE 90

REPRESENTATIVE METHOD VALIDATION DATA SHEETS
Whole Milk (glyphosate)
Samples were frozen in 25 mL extraction solution,
then thawed for analysis. 0.1% HCOOH/methanol
(96/4) extraction solution; 25 uL injection
Matrix: RM Raw Milk
Quantitation Ions: glyphosate: 170 > 87.7, glyphosate IS: 173 > 90.7, N-acetylglyphosate: 212 > 87.9, N-acetyl AMPA:

| | Sample Information | | | SW | XV | AF | FV | Analyte Response glyphosate | | |
|---|---|---|---|---|---|---|---|---|---|---|
| Run ID | Type | ppb | Identification | g | mL | mL | mL | Area | IS | $RF_{IS}$ |
| 07-0124_RM_AX-4 | S | 0.3 | 0.3 ppb CS + IS 011807 | | | | | 60 | 1006 | 0.1988 |
| 07-0124_RM_AX-5 | C | | RM C 1 MAX 012307 | 2 | 50 | 2.5 | 5 | | 919 | |
| 07-0124_RM_AX-6 | S | 0.5 | 0.5 ppb CS + IS 011807 | | | | | 81 | 1025 | 0.1580 |
| 07-0124_RM_AX-7 | F | 25 | RM L 1 MAX 012307 | 2 | 50 | 2.5 | 5 | 84 | 953 | |
| 07-0124_RM_AX-9 | S | 1 | 1.0 ppb CS + IS 011807 | | | | | 179 | 988 | 0.1812 |
| 07-0124_RM_AX-10 | F | 25 | RM L 2 MAX 012307 | 2 | 50 | 2.5 | 5 | 85 | 1024 | |
| 07-0124_RM_AX-11 | S | 2 | 2.0 ppb CS + IS 011807 | | | | | 359 | 1036 | 0.1733 |
| 07-0124_RM_AX-12 | F | 50 | RM M 1 MAX 012307 | 2 | 50 | 2.5 | 5 | 163 | 907 | |
| 07-0124_RM_AX-13 | F | 50 | RM M 2 MAX 012307 | 2 | 50 | 2.5 | 5 | 191 | 850 | |
| 07-0124_RM_AX-14 | S | 5 | 5.0 ppb CS + IS 011807 | | | | | 859 | 981 | 0.1751 |
| 07-0124_RM_AX-15 | F | 500 | RM H 1 MAX 012307 | 2 | 50 | 2.5 | 5 | 1477 | 883 | |
| 07-0124_RM_AX-17 | S | 10 | 10 ppb CS + IS 011807 | | | | | 1785 | 973 | 0.1835 |
| 07-0124_RM_AX-18 | F | 500 | RM H 2 MAX 012307 | 2 | 50 | 2.5 | 5 | 1499 | 999 | |
| 07-0124_RM_AX-20 | S | 20 | 20 ppb CS + IS 011807 | | | | | 3505 | 968 | 0.1810 |

| Calibration Standards Statistics | | Slope = | 5.695E−03 | |
|---|---|---|---|---|
| | | Intercept = | −1.206E−02 | |
| | | RSQ = | 0.99986 | |
| Quantified by Average Response Factor | | Average RF = | 997 | 0.1787 |
| | | STDEV = | 26 | 0.0123 |
| | | % RSD = | 3% | 7% |

| | Sample Information | | | SW | XV | AF | FV | Recoveries glyphosate | |
|---|---|---|---|---|---|---|---|---|---|
| Run ID | Type | mg/kg | Identification | mL | mL | mL | mL | mg/kg | % Rec |
| 07-0124_RM_AX-5 | C | 0 | RM C 1 MAX 012307 | 2 | 50 | 2.5 | 5 | nd | |
| 07-0124_RM_AX-7 | F | 0.025 | RM L 1 MAX 012307 | 2 | 50 | 2.5 | 5 | 0.025 | 99% |
| 07-0124_RM_AX-10 | F | 0.025 | RM L 2 MAX 012307 | 2 | 50 | 2.5 | 5 | 0.023 | 93% |
| 07-0124_RM_AX-12 | F | 0.05 | RM M 1 MAX 012307 | 2 | 50 | 2.5 | 5 | 0.050 | 101% |
| 07-0124_RM_AX-13 | F | 0.05 | RM M 2 MAX 012307 | 2 | 50 | 2.5 | 5 | 0.063 | 126% |
| 07-0124_RM_AX-15 | F | 0.5 | RM H 1 MAX 012307 | 2 | 50 | 2.5 | 5 | 0.468 | 94% |
| 07-0124_RM_AX-18 | F | 0.5 | RM H 2 MAX 012307 | 2 | 50 | 2.5 | 5 | 0.420 | 84% |

TABLE 91

Representative Method Validation Data Sheets
Study: DuPont-20009
Extraction Dates: 23 Jan. 2007
Analysis Date: 26 Jan. 2007
Analyst: A. Pentz/F. Bramble
Matrix: RM Raw Milk
Quantitation Ions: AMPA: 111.9 > 30, AMPA IS: 113.9 > 32 N-acetyl glyphosate: 212 > 87.9, N-acetyl AMPA: 154 > 111.9

| | Sample Information | | | SW | XV | AF | FV | Analyte Response | | | | | | |
|---|---|---|---|---|---|---|---|---|---|---|---|---|---|---|
| | | | | | | | | AMPA | | | N-Ac-AMPA | | N-Ac-Gly | |
| | | | | | | | | | IS | | | | | |
| Run ID | Type | ppb | Identification | g | mL | mL | mL | Area | Area | $RF_{IS}$ | Area | $RF_{IS}$ | Area | RF |
| 07-0126_RM_CX-3 | S | 0.5 | 0.5 ppb CS + IS 011807 | | | | | 112 | 671 | 0.3338 | 746 | 1492 | 440 | 880 |
| 07-0126_RM_CX-4 | C | | RM C 1 MCX 012307 | 2 | 50 | 4 | 5 | | 354 | | | | | |
| 07-0126_RM_CX-5 | S | 1 | 1.0 ppb CS + IS 011807 | | | | | 181 | 636 | 0.2846 | 1730 | 1730 | 914 | 914 |
| 07-0126_RM_CX-6 | F | 25 | RM L 1 MCX 012307 | 2 | 50 | 4 | 5 | 62 | 328 | | 1122 | | 529 | |
| 07-0126_RM_CX-7 | S | 2 | 2.0 ppb CS + IS 011807 | | | | | 300 | 583 | 0.2573 | 3562 | 1781 | 1714 | 857 |
| 07-0126_RM_CX-8 | F | 25 | RM L 2 MCX 012307 | 2 | 50 | 4 | 5 | 70 | 379 | | 974 | | 592 | |
| 07-0126_RM_CX-9 | S | 5 | 5.0 ppb CS + IS 011807 | | | | | 783 | 592 | 0.2645 | 8257 | 1651 | 4313 | 863 |
| 07-0126_RM_CX-10 | F | 50 | RM M 1 MCX 012307 | 2 | 50 | 4 | 5 | 152 | 386 | | 2051 | | 1133 | |
| 07-0126_RM_CX-11 | F | 50 | RM M 2 MCX 012307 | 2 | 50 | 4 | 5 | 117 | 316 | | 1966 | | 1079 | |
| 07-0126_RM_CX-12 | S | 10 | 10 ppb CS + IS 011807 | | | | | 1589 | 611 | 0.2601 | 16551 | 1655 | 9094 | 909 |
| 07-0126_RM_CX-13 | F | 500 | RM H 1 MCX 012307 | 2 | 50 | 4 | 5 | 1276 | 333 | | 21431 | | 11619 | |

TABLE 91-continued

Representative Method Validation Data Sheets
Study: DuPont-20009
Extraction Dates: 23 Jan. 2007
Analysis Date: 26 Jan. 2007
Analyst: A. Pentz/F. Bramble
Matrix: RM Raw Milk
Quantitation Ions: AMPA: 111.9 > 30, AMPA IS: 113.9 > 32 N-acetyl glyphosate: 212 > 87.9, N-acetyl AMPA: 154 > 111.9

| Run ID | Type | mg/kg | Identification | SW mL | XV mL | AF mL | FV mL | | | | | | | |
|---|---|---|---|---|---|---|---|---|---|---|---|---|---|---|
| 07-0126_RM_CX-14 | S | 20 | 20 ppb CS + IS 011807 | | | | | 3012 | 598 | 0.2518 | 33049 | 1652 | 17774 | 889 |
| 07-0126_RM_CX-15 | F | 500 | RM H 2 MCX 012307 | 2 | 50 | 4 | 5 | 1136 | 313 | | 19936 | | 11027 | |
| 07-0126_RM_CX-16 | S | 50 | 50 ppb CS + IS 011807 | | | | | 7606 | 555 | 0.2741 | 79457 | 1589 | 42288 | 846 |

| Calibration Standards Statistics | | Slope = | 6.603E−03 | 6.291E−04 | 1.180E−03 |
|---|---|---|---|---|---|
| | | Intercept = | −1.689E−01 | −2.403E−01 | −2.560E−01 |
| | | RSQ = | 0.99988 | 0.99974 | 0.99946 |
| Quantified by Average Response Factor | | Average RF = | 0.2752 | 1650 | 880 |
| | | STDEV = | 0.0281 | 93 | 26 |
| | | % RSD = | 10% | 6% | 3% |

| | | Sample Information | | SW | XV | AF | FV | Recoveries | | | | | |
|---|---|---|---|---|---|---|---|---|---|---|---|---|---|
| | | | | | | | | AMPA | | N-Ac-AMPA | | N-Ac-Gly | |
| Run ID | Type | mg/kg | Identification | mL | mL | mL | mL | mg/kg | % Rec | mg/kg | % Rec | mg/kg | % Rec |
| 07-0126_RM_CX-4 | C | 0 | RM C 1 MCX 012307 | 2 | 50 | 4 | 5 | nd | | nd | | nd | |
| 07-0126_RM_CX-6 | F | 0.025 | RM L 1 MCX 012307 | 2 | 50 | 4 | 5 | 0.021 | 86% | 0.021 | 85% | 0.019 | 75% |
| 07-0126_RM_CX-8 | F | 0.025 | RM L 2 MCX 012307 | 2 | 50 | 4 | 5 | 0.021 | 84% | 0.018 | 74% | 0.021 | 84% |
| 07-0126_RM_CX-10 | F | 0.05 | RM M 1 MCX 012307 | 2 | 50 | 4 | 5 | 0.045 | 89% | 0.039 | 78% | 0.040 | 81% |
| 07-0126_RM_CX-11 | F | 0.05 | RM M 2 MCX 012307 | 2 | 50 | 4 | 5 | 0.042 | 84% | 0.037 | 74% | 0.038 | 77% |
| 07-0126_RM_CX-13 | F | 0.5 | RM H 1 MCX 012307 | 2 | 50 | 4 | 5 | 0.435 | 87% | 0.406 | 81% | 0.413 | 83% |
| 07-0126_RM CX-15 | F | 0.5 | RM H 2 MCX 012307 | 2 | 50 | 4 | 5 | 0.412 | 82% | 0.378 | 76% | 0.392 | 78% |

TABLE 92

Representative Method Validation Data Sheets
Study: DuPont-20009
Extraction Dates: 09 Jan. 2007
Analysis Date: 09 Jan. 2007
Analysts: A. Pentz/F. Bramble
Matrix: Milk, skim
Quantitation Ions: Glyphosate 170 > 87.7; Glyphosate IS 173 > 90.7; N-Acetyl AMPA 154 > 111.9 N-acetyl glyphosate: 212 > 87.9

| | | Sample Information | | SW | XV | AF | FV | Analyte Response | | | | | |
|---|---|---|---|---|---|---|---|---|---|---|---|---|---|
| | | | | | | | | Glyphosate | | | N-Ac-AMPA | | N-Ac-Gly | |
| Run ID | Type | ppb | Identification | g | mL | mL | mL | Area | IS Area | $RF_{IS}$ | Area | RF | Area | RF |
| 07-0109_SM_AX-2 | S | 0.3 | 0.3 ppb CS + IS 010407 | | | | | 55 | 930 | 0.1971 | 263 | 877 | 96 | 320 |
| 07-0109_SM_AX-3 | C | | SM C 1 MAX 010907 | 2 | 50 | 2.5 | 5 | | 987 | | | | | |
| 07-0109_SM_AX-4 | S | 0.5 | 0.5 ppb CS + IS 010407 | | | | | 100 | 919 | 0.2176 | 510 | 1020 | 130 | 260 |
| 07-0109_SM_AX-5 | F | 25 | SM L 1 MAX 010907 | 2 | 50 | 2.5 | 5 | 80 | 1030 | | 492 | | 127 | |
| 07-0109_SM_AX-6 | S | 1 | 1.0 ppb CS + IS 010407 | | | | | 182 | 963 | 0.1890 | 1027 | 1027 | 275 | 275 |
| 07-0109_SM_AX-7 | F | 25 | SM L 2 MAX 010907 | 2 | 50 | 2.5 | 5 | 88 | 991 | | 496 | | 126 | |
| 07-0109_SM_AX-8 | S | 2 | 2.0 ppb CS + IS 010407 | | | | | 378 | 1066 | 0.1773 | 1967 | 984 | 489 | 245 |
| 07-0109_SM_AX-9 | F | 50 | SM M 1 MAX 010907 | 2 | 50 | 2.5 | 5 | 162 | 958 | | 919 | | 244 | |
| 07-0109_SM_AX-10 | F | 50 | SM M 2 MAX 010907 | 2 | 50 | 2.5 | 5 | 162 | 1032 | | 889 | | 218 | |
| 07-0109_SM_AX-11 | S | 5 | 5.0 ppb CS + IS 010407 | | | | | 870 | 955 | 0.1822 | 4678 | 936 | 1300 | 260 |
| 07-0109_SM_AX-12 | F | 500 | SM H 1 MAX 010907 | 2 | 50 | 2.5 | 5 | 1561 | 951 | | 9756 | | 2308 | |
| 07-0109_SM_AX-13 | S | 10 | 10 ppb CS + IS 010407 | | | | | 1930 | 988 | 0.1953 | 9948 | 995 | 2644 | 264 |
| 07-0109_SM_AX-14 | F | 500 | SM H 2 MAX 010907 | 2 | 50 | 2.5 | 5 | 1727 | 955 | | 9840 | | 2325 | |
| 07-0109_SM_AX-15 | S | 20 | 20 ppb CS + IS 010407 | | | | | 3635 | 1073 | 0.1694 | 20371 | 1019 | 5302 | 265 |

| Calibration Standards Statistics | | Slope = | 5.455E−03 | 9.826E−04 | 3.771E−03 |
|---|---|---|---|---|---|
| | | Intercept = | −2.948E−02 | 1.017E−01 | 2.815E−02 |
| | | RSQ = | 0.99882 | 0.99953 | 0.99989 |
| Quantified by Average Response Factor | | Average RF = | 0.1897 | 979 | 270 |
| | | STDEV = | 0.0158 | 55 | 24 |
| | | % RSD = | 8% | 6% | 9% |

TABLE 92-continued

Representative Method Validation Data Sheets
Study: DuPont-20009
Extraction Dates: 09 Jan. 2007
Analysis Date: 09 Jan. 2007
Analysts: A. Pentz/F. Bramble
Matrix: Milk, skim
Quantitation Ions: Glyphosate 170 > 87.7; Glyphosate IS 173 > 90.7; N-Acetyl AMPA 154 > 111.9 N-acetyl glyphosate: 212 > 87.9

| | | | | | | | | | Recoveries | | | |
| --- | --- | --- | --- | --- | --- | --- | --- | --- | --- | --- | --- | --- |
| | | | | | | | | | Glyphosate | | N-Ac-AMPA | N-Ac-Gly |
| | | Sample Information | | SW | XV | AF | FV | | % | | % | mg/ % |
| Run ID | Type | mg/kg | Identification | mL | mL | mL | mL | mg/kg | Rec | mg/kg | Rec | kg Rec |
| 07-0109_SM_AX-3 | C | 0 | SM C 1 MAX 010907 | 2 | 50 | 2.5 | 5 | nd | | nd | | nd |
| 07-0109_SM_AX-5 | F | 0.025 | SM L 1 MAX 010907 | 2 | 50 | 2.5 | 5 | 0.020 | 82% | 0.025 | 100% | 0.024 94% |
| 07-0109_SM_AX-7 | F | 0.025 | SM L 2 MAX 010907 | 2 | 50 | 2.5 | 5 | 0.023 | 94% | 0.025 | 101% | 0.023 93% |
| 07-0109_SM_AX-9 | F | 0.05 | SM M 1 MAX 010907 | 2 | 50 | 2.5 | 5 | 0.045 | 89% | 0.047 | 94% | 0.045 90% |
| 07-0109_SM_AX-10 | F | 0.05 | SM M 2 MAX 010907 | 2 | 50 | 2.5 | 5 | 0.041 | 83% | 0.045 | 91% | 0.040 81% |
| 07-0109_SM_AX-12 | F | 0.5 | SM H 1 MAX 010907 | 2 | 50 | 2.5 | 5 | 0.433 | 87% | 0.498 | 100% | 0.428 86% |
| 07-0109_SM_AX-14 | F | 0.5 | SM H 2 MAX 010907 | 2 | 50 | 2.5 | 5 | 0.477 | 95% | 0.502 | 100% | 0.431 86% |

TABLE 93

Representative Method Validation Data Sheets
Study: DuPont-20009
Extraction Dates: 09 Jan. 2007
Analysis Date: 09 Jan. 2007
Analyst: A. Pentz/F. Bramble
Matrix: Milk, SKIM
Quantitation Ions: AMPA: 111.9 > 30, AMPA IS: 113.9 > 32 N-acetyl glyphosate: 212 > 87.9

| | | | | | | | | | | | | | Analyte Response | | |
| --- | --- | --- | --- | --- | --- | --- | --- | --- | --- | --- | --- | --- | --- | --- | --- |
| | | | | | | | | | AMPA | | | | | | |
| | | Sample Information | | SW | XV | AF | FV | | IS | | N-Ac-AMPA | | N-Ac-Gly | | |
| Run ID | Type | ppb | Identification | g | mL | mL | mL | Area | Area | $RF_{IS}$ | Area | $RF_{IS}$ | Area | RF | |
| 07-0109_SM_CX-4 | S | 0.3 | 0.3 ppb CS + IS 010407 | | | | | 57 | 502 | 0.3785 | 454 | 1513 | 267 | 890 | |
| 07-0109_SM_CX-5 | C | | SM C 1 MCX 010907 | 2 | 50 | 4 | 5 | | 268 | | | | | | |
| 07-0109_SM_CX-6 | S | 0.5 | 0.5 ppb CS + IS 010407 | | | | | 78 | 522 | 0.2989 | 816 | 1632 | 411 | 822 | |
| 07-0109_SM_CX-7 | F | 25 | SM L 1 MCX 010907 | 2 | 50 | 4 | 5 | 66 | 296 | | 964 | | 495 | | |
| 07-0109_SM_CX-8 | S | 1 | 1.0 ppb CS + IS 010407 | | | | | 160 | 562 | 0.2847 | 1582 | 1582 | 831 | 831 | |
| 07-0109_SM_CX-9 | F | 25 | SM L 2 MCX 010907 | 2 | 50 | 4 | 5 | 68 | 293 | | 988 | | 561 | | |
| 07-0109_SM_CX-10 | S | 2 | 2.0 ppb CS + IS 010407 | | | | | 315 | 545 | 0.2890 | 3069 | 1535 | 1596 | 798 | |
| 07-0109_SM_CX-11 | F | 50 | SM M 1 MCX 010907 | 2 | 50 | 4 | 5 | 119 | 284 | | 2074 | | 1067 | | |
| 07-0109_SM_CX-12 | S | 5 | 5.0 ppb CS + IS 010407 | | | | | 774 | 506 | 0.3059 | 7882 | 1576 | 3903 | 781 | |
| 07-0109_SM_CX-13 | F | 50 | SM M 2 MCX 010907 | 2 | 50 | 4 | 5 | 115 | 296 | | 2199 | | 1153 | | |
| 07-0109_SM_CX-14 | S | 10 | 10 ppb CS + IS 010407 | | | | | 1555 | 528 | 0.2945 | 16637 | 1664 | 8026 | 803 | |
| 07-0109_SM_CX-15 | F | 500 | SM H 1 MCX 010907 | 2 | 50 | 4 | 5 | 1100 | 300 | | 21303 | | 11002 | | |
| 07-0109_SM_CX-16 | S | 20 | 20 ppb CS + IS 010407 | | | | | 2967 | 528 | 0.2810 | 33497 | 1675 | 16726 | 836 | |
| 07-0109_SM_CX-17 | F | 500 | SM H 2 MCX 010907 | 2 | 50 | 4 | 5 | 1118 | 289 | | 22001 | | 11694 | | |
| 07-0109_SM_CX-18 | S | 50 | 50 ppb CS + IS 010407 | | | | | 7381 | 532 | 0.2775 | 83062 | 1661 | 42723 | 854 | |
| Calibration Standards Statistics | | | | | | | Slope = | | 6.788E−03 | | 6.004E−04 | | 1.169E−03 | | |
| | | | | | | | Intercept = | | −1.747E−01 | | 6.790E−02 | | 2.117E−01 | | |
| | | | | | | | RSQ = | | 0.99990 | | 0.99995 | | 0.99979 | | |
| Quantified by Average Response Factor | | | | | | | Average RF = | | 0.3012 | | 1605 | | 827 | | |
| | | | | | | | STDEV = | | 0.0326 | | 62 | | 35 | | |
| | | | | | | | % RSD = | | 11% | | 4% | | 4% | | |

| | | | | | | | | | Recoveries | | | |
| --- | --- | --- | --- | --- | --- | --- | --- | --- | --- | --- | --- | --- |
| | | | | | | | | | AMPA | | N-Ac-AMPA | N-Ac-Gly |
| | | Sample Information | | SW | XV | AF | FV | | % | | % | % |
| Run ID | Type | mg/kg | Identification | mL | mL | mL | mL | mg/kg | Rec | mg/kg | Rec | mg/kg Rec |
| 07-0109_SM_CX-5 | C | 0 | SM C 1 MCX 010907 | 2 | 50 | 4 | 5 | nd | | nd | | nd |
| 07-0109_SM_CX-7 | F | 0.025 | SM L 1 MCX 010907 | 2 | 50 | 4 | 5 | 0.023 | 93% | 0.019 | 75% | 0.019 75% |
| 07-0109_SM_CX-9 | F | 0.025 | SM L 2 MCX 010907 | 2 | 50 | 4 | 5 | 0.024 | 96% | 0.019 | 77% | 0.021 85% |
| 07-0109_SM_CX-11 | F | 0.05 | SM M 1 MCX 010907 | 2 | 50 | 4 | 5 | 0.043 | 87% | 0.040 | 81% | 0.040 81% |

TABLE 93-continued

Representative Method Validation Data Sheets
Study: DuPont-20009
Extraction Dates: 09 Jan. 2007
Analysis Date: 09 Jan. 2007
Analyst: A. Pentz/F. Bramble
Matrix: Milk, SKIM
Quantitation Ions: AMPA: 111.9 > 30, AMPA IS: 113.9 > 32 N-acetyl glyphosate: 212 > 87.9

| 07-0109_SM_CX-13 | F | 0.05 | SM M 2 MCX 010907 | 2 | 50 | 4 | 5 | 0.040 | 81% | 0.043 | 86% | 0.044 | 87% |
| 07-0109_SM_CX-15 | F | 0.5 | SM H 1 MCX 010907 | 2 | 50 | 4 | 5 | 0.380 | 76% | 0.415 | 83% | 0.416 | 83% |
| 07-0109_SM_CX-17 | F | 0.5 | SM H 2 MCX 010907 | 2 | 50 | 4 | 5 | 0.382 | 76% | 0.428 | 86% | 0.442 | 88% |

TABLE 94

Representative Method Validation Data Sheets
Study: DuPont-20009
Extraction Dates: 04 Jan. 2007
Analysis Date: 05 Jan. 2007
Analyst: A. Pentz/F. Bramble
Matrix: HC: Milk, Heavy Cream
Quantitation Ions: AMPA: 111.9 > 30, AMPA IS: 113.9 > 32 N-acetylglyphosate: 212 > 87.9

| | | | | | | | | Analyte Response | | | | | |
| --- | --- | --- | --- | --- | --- | --- | --- | --- | --- | --- | --- | --- | --- |
| | | | | | | | | AMPA | | | | | |
| | | Sample Information | | SW | XV | AF | FV | | IS | | N-Ac-AMPA | | N-Ac-Gly |
| Run ID | Type | ppb | Identification | g | mL | mL | mL | Area | Area | $RF_{IS}$ | Area | $RF_{IS}$ | Area | RF |
| 07-0105_HC_CX-1 | S | 0.3 | 0.3 ppb CS + IS 010407 | | | | | 41 | 544 | 0.2512 | 411 | 1370 | 266 | 887 |
| 07-0105_HC_CX-2 | S | 0.5 | 0.5 ppb CS + IS 010407 | | | | | 93 | 514 | 0.3619 | 652 | 1304 | 452 | 904 |
| 07-0105_HC_CX-3 | C | | HC C 2 MCX 010407 | 2 | 50 | 4 | 5 | | 330 | | | | | |
| 07-0105_HC_CX-4 | F | 25 | HC L 3 MCX 010407 | 2 | 50 | 4 | 5 | 64 | 290 | | 1026 | | 547 | |
| 07-0105_HC_CX-5 | S | 1 | 1.0 ppb CS + IS 010407 | | | | | 173 | 519 | 0.3333 | 1367 | 1367 | 833 | 833 |
| 07-0105_HC_CX-6 | F | 25 | HC L 4 MCX 010407 | 2 | 50 | 4 | 5 | 62 | 301 | | 1065 | | 536 | |
| 07-0105_HC_CX-7 | F | 25 | HC L 5 MCX 010407 | 2 | 50 | 4 | 5 | 79 | 344 | | 1026 | | 515 | |
| 07-0105_HC_CX-8 | S | 2 | 2.0 ppb CS + IS 010407 | | | | | 309 | 543 | 0.2845 | 3032 | 1516 | 1763 | 882 |
| 07-0105_HC_CX-9 | F | 50 | HC M 3 MCX 010407 | 2 | 50 | 4 | 5 | 126 | 312 | | 2216 | | 1053 | |
| 07-0105_HC_CX-10 | F | 50 | HC M 4 MCX 010407 | 2 | 50 | 4 | 5 | 142 | 342 | | 2147 | | 1168 | |
| 07-0105_HC_CX-11 | S | 5 | 5.0 ppb CS + IS 010407 | | | | | 780 | 557 | 0.2801 | 8066 | 1613 | 4477 | 895 |
| 07-0105_HC_CX-12 | F | 50 | HC M 5 MCX 010407 | 2 | 50 | 4 | 5 | 148 | 328 | | 2027 | | 1155 | |
| 07-0105_HC_CX-13 | F | 500 | HC H 3 MCX 010407 | 2 | 50 | 4 | 5 | 1255 | 304 | | 22679 | | 11313 | |
| 07-0105_HC_CX-14 | S | 10 | 10 ppb CS + IS 010407 | | | | | 1572 | 562 | 0.2797 | 16048 | 1605 | 8762 | 876 |
| 07-0105_HC_CX-15 | F | 500 | HC H 4 MCX 010407 | 2 | 50 | 4 | 5 | 1259 | 316 | | 22736 | | 11158 | |
| 07-0105_HC_CX-16 | S | 20 | 20 ppb CS + IS 010407 | | | | | 2883 | 504 | 0.2860 | 32828 | 1641 | 17002 | 850 |
| 07-0105_HC_CX-17 | F | 500 | HC H 5 MCX 010407 | 2 | 50 | 4 | 5 | 1219 | 326 | | 22783 | | 11349 | |
| 07-0105_HC_CX-18 | S | 50 | 50 ppb CS + IS 010407 | | | | | 7317 | 517 | 0.2831 | 84195 | 1684 | 43962 | 879 |

| Calibration Standards Statistics | Slope = | 6.864E−03 | 5.930E−04 | 1.141E−03 |
| --- | --- | --- | --- | --- |
| | Intercept = | −1.974E−01 | 2.338E−01 | 4.857E−02 |
| | RSQ = | 0.99971 | 0.99989 | 0.99981 |
| Quantified by Average Response Factor | Average RF = | 0.2950 | 1513 | 876 |
| | STDEV = | 0.0351 | 146 | 23 |
| | % RSD = | 12% | 10% | 3% |

| | | | | | | | | Recoveries | | | | | |
| --- | --- | --- | --- | --- | --- | --- | --- | --- | --- | --- | --- | --- | --- |
| | | | | | | | | AMPA | | N-Ac-AMPA | | N-Ac-Gly | |
| | | Sample Information | | SW | XV | AF | FV | | % | | % | | % |
| Run ID | Type | mg/kg | Identification | mL | mL | mL | mL | mg/kg | Rec | mg/kg | Rec | mg/kg | Rec |
| 07-0105_HC_CX-3 | C | 0 | HC C 2 MCX 010407 | 2 | 50 | 4 | 5 | nd | | nd | | nd | |
| 07-0105_HC_CX-4 | F | 0.025 | HC L 3 MCX 010407 | 2 | 50 | 4 | 5 | 0.023 | 94% | 0.021 | 85% | 0.020 | 78% |
| 07-0105_HC_CX-6 | F | 0.025 | HC L 4 MCX 010407 | 2 | 50 | 4 | 5 | 0.022 | 87% | 0.022 | 88% | 0.019 | 77% |
| 07-0105_HC_CX-7 | F | 0.025 | HC L 5 MCX 010407 | 2 | 50 | 4 | 5 | 0.024 | 97% | 0.021 | 85% | 0.018 | 74% |
| 07-0105_HC_CX-9 | F | 0.05 | HC M 3 MCX 010407 | 2 | 50 | 4 | 5 | 0.043 | 86% | 0.046 | 92% | 0.038 | 75% |
| 07-0105_HC_CX-10 | F | 0.05 | HC M 4 MCX 010407 | 2 | 50 | 4 | 5 | 0.044 | 88% | 0.044 | 89% | 0.042 | 83% |
| 07-0105_HC_CX-12 | F | 0.05 | HC M 5 MCX 010407 | 2 | 50 | 4 | 5 | 0.048 | 96% | 0.042 | 84% | 0.041 | 82% |
| 07-0105_HC_CX-13 | F | 0.5 | HC H 3 MCX 010407 | 2 | 50 | 4 | 5 | 0.437 | 87% | 0.469 | 94% | 0.404 | 81% |
| 07-0105_HC_CX-15 | F | 0.5 | HC H 4 MCX 010407 | 2 | 50 | 4 | 5 | 0.402 | 80% | 0.470 | 94% | 0.398 | 80% |
| 07-0105_HC_CX-17 | F | 0.5 | HC H 5 MCX 010407 | 2 | 50 | 4 | 5 | 0.377 | 75% | 0.471 | 94% | 0.405 | 81% |

TABLE 95

Representative Method Validation Data Sheets
Study: DuPont-20009
Extraction Dates: 04 Jan. 2007
Analysis Date: 05 Jan. 2007
Analyst: A. Pentz/F. Bramble
Matrix: HC: Milk, heavy cream
Quantitation Ions: Glyphosate 170 > 87.7; Glyphosate IS 173 > 90.7; N-Acetyl AMPA 154 > 111.9 N-acetyl glyphosate: 212 > 87

| | | | | | | | | Analyte Response | | | | | |
| | | | | | | | | Glyphosate | | | N-Ac-AMPA | | N-Ac-Gly | |
| | | Sample Information | | SW | XV | AF | FV | | IS | | | | | |
| Run ID | Type | ppb | Identification | g | mL | mL | mL | Area | Area | $RF_{IS}$ | Area | RF | Area | RF |
|---|---|---|---|---|---|---|---|---|---|---|---|---|---|---|
| 07-0105_HC_AX-2 | S | 0.3 | 0.3 ppb CS + IS 010407 | | | | | 61 | 1003 | 0.2027 | 292 | 973 | 90 | 300 |
| 07-0105_HC_AX-3 | C | | HC C 2 MAX 010407 | 2 | 50 | 2.5 | 5 | | 950 | | | | | |
| 07-0105_HC_AX-4 | F | 25 | HC L 3 MAX 010407 | 2 | 50 | 2.5 | 5 | 92 | 1002 | | 483 | | 140 | |
| 07-0105_HC_AX-5 | S | 0.5 | 0.5 ppb CS + IS 010407 | | | | | 102 | 1020 | 0.2000 | 531 | 1062 | 161 | 322 |
| 07-0105_HC_AX-6 | F | 25 | HC L 4 MAX 010407 | 2 | 50 | 2.5 | 5 | 108 | 980 | | 454 | | 95 | |
| 07-0105_HC_AX-7 | F | 25 | HC L 5 MAX 010407 | 2 | 50 | 2.5 | 5 | 94 | 957 | | 449 | | 123 | |
| 07-0105_HC_AX-8 | S | 1 | 1.0 ppb CS + IS 010407 | | | | | 188 | 935 | 0.2011 | 993 | 993 | 297 | 297 |
| 07-0105_HC_AX-9 | F | 50 | HC M 3 MAX 010407 | 2 | 50 | 2.5 | 5 | 162 | 910 | | 1020 | | 233 | |
| 07-0105_HC_AX-10 | F | 50 | HC M 4 MAX 010407 | 2 | 50 | 2.5 | 5 | 183 | 988 | | 914 | | 246 | |
| 07-0105_HC_AX-11 | S | 2 | 2.0 ppb CS + IS 010407 | | | | | 368 | 957 | 0.1923 | 1952 | 976 | 541 | 271 |
| 07-0105_HC_AX-12 | F | 50 | HC M 5 MAX 010407 | 2 | 50 | 2.5 | 5 | 205 | 1027 | | 1013 | | 263 | |
| 07-0105_HC_AX-13 | F | 500 | HC H 3 MAX 010407 | 2 | 50 | 2.5 | 5 | 1702 | 967 | | 9962 | | 2435 | |
| 07-0105_HC_AX-14 | S | 5 | 5.0 ppb CS + IS 010407 | | | | | 814 | 860 | 0.1893 | 4889 | 978 | 1417 | 283 |
| 07-0105_HC_AX-15 | F | 500 | HC H 4 MAX 010407 | 2 | 50 | 2.5 | 5 | 1540 | 984 | | 9948 | | 2463 | |
| 07-0105_HC_AX-16 | S | 10 | 10 ppb CS + IS 010407 | | | | | 1591 | 860 | 0.1850 | 10810 | 1081 | 2789 | 279 |
| 07-0105_HC_AX-17 | F | 500 | HC H 5 MAX 010407 | 2 | 50 | 2.5 | 5 | 1647 | 1010 | | 10155 | | 2438 | |
| 07-0105_HC_AX-18 | S | 20 | 20 ppb CS + IS 010407 | | | | | 3596 | 937 | 0.1919 | 21332 | 1067 | 5797 | 290 |

| Calibration Standards Statistics | | |
|---|---|---|
| Slope = | 5.644E-03 | 9.315E-04 | 3.466E-03 |
| Intercept = | 1.244E-01 | 1.139E-01 | 5.041E-02 |
| RSQ = | 0.99619 | 0.99946 | 0.99959 |
| Quantified by Average Response Factor — Average RF = | 0.1946 | 1019 | 292 |
| STDEV = | 0.0067 | 49 | 17 |
| % RSD = | 3% | 5% | 6% |

| | | | | | | | | Recoveries | | | | |
| | | | | | | | | Glyphosate | | N-Ac-AMPA | | N-Ac-Gly | |
| | | Sample Information | | SW | XV | AF | FV | mg/ | | | % | mg/ | % |
| Run ID | Type | mg/kg | Identification | mL | mL | mL | mL | kg | % Rec | mg/kg | Rec | kg | Rec |
|---|---|---|---|---|---|---|---|---|---|---|---|---|---|
| 07-0105_HC_AX-3 | C | 0 | HC C 2 MAX 010407 | 2 | 50 | 2.5 | 5 | nd | | nd | | nd | |
| 07-0105_HC_AX-4 | F | 0.025 | HC L 3 MAX 010407 | 2 | 50 | 2.5 | 5 | 0.024 | 94% | 0.024 | 95% | 0.024 | 96% |
| 07-0105_HC_AX-6 | F | 0.025 | HC L 4 MAX 010407 | 2 | 50 | 2.5 | 5 | 0.028 | 113% | 0.022 | 89% | 0.016 | 65% |
| 07-0105_HC_AX-7 | F | 0.025 | HC L 5 MAX 010407 | 2 | 50 | 2.5 | 5 | 0.025 | 101% | 0.022 | 88% | 0.021 | 84% |
| 07-0105_HC_AX-9 | F | 0.05 | HC M 3 MAX 010407 | 2 | 50 | 2.5 | 5 | 0.046 | 91% | 0.050 | 100% | 0.040 | 80% |
| 07-0105_HC_AX-10 | F | 0.05 | HC M 4 MAX 010407 | 2 | 50 | 2.5 | 5 | 0.048 | 95% | 0.045 | 90% | 0.042 | 84% |
| 07-0105_HC_AX-12 | F | 0.05 | HC M 5 MAX 010407 | 2 | 50 | 2.5 | 5 | 0.051 | 103% | 0.050 | 99% | 0.045 | 90% |
| 07-0105_HC_AX-13 | F | 0.5 | HC H 3 MAX 010407 | 2 | 50 | 2.5 | 5 | 0.452 | 90% | 0.489 | 98% | 0.417 | 83% |
| 07-0105_HC_AX-15 | F | 0.5 | HC H 4 MAX 010407 | 2 | 50 | 2.5 | 5 | 0.383 | 77% | 0.488 | 98% | 0.422 | 84% |
| 07-0105_HC_AX-17 | F | 0.5 | HC H 5 MAX 010407 | 2 | 50 | 2.5 | 5 | 0.419 | 84% | 0.499 | 100% | 0.418 | 84% |

TABLE 96

Representative Method Validation Data Sheets
Whole Eggs - AMPA Analysis

Samples were frozen in 25 mL extraction solution, then thawed for analysis. A: 0.1% HCOOH/methanol (96/4) extraction solution;
Matrix: Ey Egg yolks
Quantitation Ions: AMPA: 111.9 > 30, AMPA IS: 113.9 > 32

| | Sample Information | | | SW | XV | AF | FV | Analyte Response AMPA | | |
|---|---|---|---|---|---|---|---|---|---|---|
| Run ID | Type | ppb | Identification | g | mL | mL | mL | Area | IS Area | $RF_{IS}$ |
| 06-1120_EG_MCX-2 | S | 0.5 | 0.5 ppb CS + IS 111506 | | | | | 75 | 478 | 0.3138 |
| 06-1120_EG_MCX-3 | C | | EG-C-2 | 2 | 50 | 4 | 5 | | 359 | |
| 06-1120_EG_MCX-4 | S | 1 | 1.0 ppb CS + IS 111506 | | | | | 140 | 466 | 0.3004 |
| 06-1120_EG_MCX-5 | F | 25 | EG-0.025-3 | 2 | 50 | 4 | 5 | 68 | 274 | |
| 06-1120_EG_MCX-6 | S | 2 | 2.0 ppb CS + IS 111506 | | | | | 265 | 452 | 0.2931 |
| 06-1120_EG_MCX-7 | F | 25 | EG-0.025-4 | 2 | 50 | 4 | 5 | 76 | 314 | |
| 06-1120_EG_MCX-8 | F | 25 | EG-0.025-5 | 2 | 50 | 4 | 5 | 83 | 344 | |
| 06-1120_EG_MCX-9 | S | 5 | 5.0 ppb CS + IS 111506 | | | | | 678 | 473 | 0.2867 |
| 06-1120_EG_MCX-10 | F | 50 | EG-0.050-3 | 2 | 50 | 4 | 5 | 154 | 352 | |
| 06-1120_EG_MCX-11 | S | 10 | 10 ppb CS + IS 111506 | | | | | 1283 | 487 | 0.2634 |
| 06-1120_EG_MCX-12 | F | 50 | EG-0.050-4 | 2 | 50 | 4 | 5 | 149 | 335 | |
| 06-1120_EG_MCX-13 | F | 50 | EG-0.050-5 | 2 | 50 | 4 | 5 | 170 | 353 | |
| 06-1120_EG_MCX-14 | S | 20 | 20 ppb CS + IS 111506 | | | | | 2307 | 442 | 0.2610 |
| 06-1120_EG_MCX-15 | F | 500 | EG-0.50-3 | 2 | 50 | 4 | 5 | 1204 | 310 | |
| 06-1120_EG_MCX-16 | F | 500 | EG-0.50-4 | 2 | 50 | 4 | 5 | 1236 | 317 | |
| 06-1120_EG_MCX-17 | S | 20 | 20 ppb CS + IS 111506 | | | | | 2446 | 459 | 0.2664 |
| 06-1120_EG_MCX-18 | F | 500 | EG-0.50-5 | 2 | 50 | 4 | 5 | 1208 | 320 | |
| 06-1120_EG_MCX-19 | S | 50 | 50 ppb CS + IS 111506 | | | | | 6297 | 457 | 0.2756 |

Calibration Standards Statistics
Quantified by Average Response Factor

Slope = 8.020E−03
Intercept = 3.800E−02
RSQ = 0.99850
Average RF = 0.2826
STDEV = 0.0191
% RSD = 7%

| | Sample Information | | | SW | XV | AF | FV | Recoveries AMPA | |
|---|---|---|---|---|---|---|---|---|---|
| Run ID | Type | mg/kg | Identification | mL | mL | mL | mL | mg/kg | % Rec |
| 06-1120_EG_MCX-3 | C | 0 | EG-C-2 | 2 | 50 | 4 | 5 | nd | |
| 06-1120_EG_MCX-5 | F | 0.025 | EG-0.025-3 | 2 | 50 | 4 | 5 | 0.027 | 110% |
| 06-1120_EG_MCX-7 | F | 0.025 | EG-0.025-4 | 2 | 50 | 4 | 5 | 0.027 | 107% |
| 06-1120_EG_MCX-8 | F | 0.025 | EG-0.025-5 | 2 | 50 | 4 | 5 | 0.027 | 107% |
| 06-1120_EG_MCX-10 | F | 0.05 | EG-0.050-3 | 2 | 50 | 4 | 5 | 0.048 | 97% |
| 06-1120_EG_MCX-12 | F | 0.05 | EG-0.050-4 | 2 | 50 | 4 | 5 | 0.049 | 98% |
| 06-1120_EG_MCX-13 | F | 0.05 | EG-0.050-5 | 2 | 50 | 4 | 5 | 0.053 | 107% |
| 06-1120_EG_MCX-15 | F | 0.5 | EG-0.50-3 | 2 | 50 | 4 | 5 | 0.430 | 86% |
| 06-1120_EG_MCX-16 | F | 0.5 | EG-0.50-4 | 2 | 50 | 4 | 5 | 0.431 | 86% |
| 06-1120_EG_MCX-18 | F | 0.5 | EG-0.50-5 | 2 | 50 | 4 | 5 | 0.417 | 83% |

TABLE 97

Representative Method Validation Data Sheets
Whole Egg- N-acetylglyphosphate, Glyphosphate, and N-acetyl AMPA analysis
Study: DuPont-20009
Extraction Dates: 20 Nov. 2006
Analysis Date: 20 Nov. 2006
Analyst: A. Pentz/F. Bramble
Matrix: EG: Whole Egg
Quantitation Ions: glyphosate: 170 > 87.7, glyphosate IS: 173 > 90.7, N-acetylglyphosate: 212 > 87.9, N-acetyl AMPA: 154 > 111.9

| | Sample Information | | | SW | XV | AF | FV | Analyte Response | | | | | | |
|---|---|---|---|---|---|---|---|---|---|---|---|---|---|---|
| | | | | | | | | glyphosate | | | NA-Gly | | NA-AMPA | |
| Run ID | Type | ppb | Identification | g | mL | mL | mL | Area | IS | $RF_{IS}$ | Area | RF | Area | RF |
| 06-1120_EG_MAX-2 | S | 0.3 | 0.3 ppb CS + IS 111506 | | | | | 97 | 1628 | 0.1986 | 58 | 193 | 203 | 677 |
| 06-1120_EG_MAX-3 | C | | EG-C-2 | 2 | 50 | 2.5 | 5 | | 1698 | | | | | |
| 06-1120_EG_MAX-4 | S | 0.5 | 0.5 ppb CS + IS 111506 | | | | | 145 | 1624 | 0.1786 | 73 | 146 | 274 | 548 |

TABLE 97-continued

Representative Method Validation Data Sheets
Whole Egg- N-acetylglyphosphate, Glyphosphate, and N-acetyl AMPA analysis
Study: DuPont-20009
Extraction Dates: 20 Nov. 2006
Analysis Date: 20 Nov. 2006
Analyst: A. Pentz/F. Bramble
Matrix: EG: Whole Egg
Quantitation Ions: glyphosate: 170 > 87.7, glyphosate IS: 173 > 90.7, N-acetylglyphosate: 212 > 87.9, N-acetyl AMPA: 154 > 111.9

| Run ID | Type | mg/kg | Identification | SW mL | XV mL | AF mL | FV mL | Area | IS | RF | Area | RF | Area | RF |
|---|---|---|---|---|---|---|---|---|---|---|---|---|---|---|
| 06-1120_EG_MAX-5 | F | 25 | EG-0.025-3 | 2 | 50 | 2.5 | 5 | 142 | 1758 | | 88 | 274 | | |
| 06-1120_EG_MAX-6 | S | 1 | 1.0 ppb CS + IS 111506 | | | | | 316 | 1746 | 0.1810 | 154 | 154 | 582 | 582 |
| 06-1120_EG_MAX-7 | F | 25 | EG-0.025-4 | 2 | 50 | 2.5 | 5 | 144 | 1781 | | 83 | 296 | | |
| 06-1120_EG_MAX-8 | F | 25 | EG-0.025-5 | 2 | 50 | 2.5 | 5 | 132 | 1575 | | 68 | 296 | | |
| 06-1120_EG_MAX-9 | S | 2 | 2.0 ppb CS + IS 111506 | | | | | 647 | 1696 | 0.1907 | 311 | 156 | 188 | 594 |
| 06-1120_EG_MAX-10 | F | 50 | EG-0.050-3 | 2 | 50 | 2.5 | 5 | 271 | 1720 | | 154 | 604 | | |
| 06-1120_EG_MAX-11 | S | 5 | 5.0 ppb CS + IS 111506 | | | | | 1487 | 1644 | 0.1809 | 760 | 152 | 892 | 578 |
| 06-1120_EG_MAX-12 | F | 50 | EG-0.050-4 | 2 | 50 | 2.5 | 5 | 269 | 1759 | | 131 | 599 | | |
| 06-1120_EG_MAX-13 | F | 50 | EG-0.050-5 | 2 | 50 | 2.5 | 5 | 279 | 1783 | | 137 | 640 | | |
| 06-1120_EG_MAX-14 | S | 10 | 10 ppb CS + IS 111506 | | | | | 3087 | 1728 | 0.1786 | 1544 | 1558 | 838 | 584 |
| 06-1120_EG_MAX-15 | F | 500 | EG-0.50-3 | 2 | 50 | 2.5 | 5 | 2750 | 1733 | | 1451 | 5696 | | |
| 06-1120_EG_MAX-16 | F | 500 | EG-0.50-4 | 2 | 50 | 2.5 | 5 | 2712 | 1785 | | 1359 | 5902 | | |
| 06-1120_EG_MAX-17 | S | 10 | 10 ppb CS + IS 111506 | | | | | 3051 | 1752 | 0.1741 | 1575 | 1558 | 782 | 578 |
| 06-1120_EG_MAX-18 | F | 500 | EG-0.50-5 | 2 | 50 | 2.5 | 5 | 2597 | 1739 | | 1443 | 6128 | | |
| 06-1120_EG_MAX-19 | S | 20 | 20 ppb CS + IS 111506 | | | | | 6026 | 1766 | 0.1706 | 3199 | 1510 | 041 | 552 |

Calibration Standards Statistics
Quantified by Average Response Factor

| | | |
|---|---|---|
| Slope = | 3.312E−03 | 6.276E−03 | 1.796E−03 |
| Intercept = | −5.003E−02 | 8.015E−02 | −1.408E−01 |
| RSQ = | 0.99978 | 0.99962 | 0.99905 |
| Average RF = | 1698 | 0.1817 | 159 | 587 |
| STDEV = | 59 | 0.0090 | 14 | 40 |
| % RSD = | 3% | 5% | 9% | 7% |

| | | | | | | | | Recoveries | | | | | |
|---|---|---|---|---|---|---|---|---|---|---|---|---|---|
| | Sample Information | | | SW | XV | AF | FV | glyphosate | | NA-Gly | | NA-AMPA | |
| Run ID | Type | mg/kg | Identification | mL | mL | mL | mL | mg/kg | % Rec | mg/kg | % Rec | mg/kg | % Rec |
| 06-1120_EG_MAX-3 | C | 0 | EG-C-2 | 2 | 50 | 2.5 | 5 | nd | | nd | | nd | |
| 06-1120_EG_MAX-5 | F | 0.025 | EG-0.025-3 | 2 | 50 | 2.5 | 5 | 0.022 | 89% | 0.028 | 111% | 0.023 | 93% |
| 06-1120_EG_MAX-7 | F | 0.025 | EG-0.025-4 | 2 | 50 | 2.5 | 5 | 0.022 | 89% | 0.026 | 104% | 0.025 | 101% |
| 06-1120_EG_MAX-8 | F | 0.025 | EG-0.025-5 | 2 | 50 | 2.5 | 5 | 0.023 | 92% | 0.021 | 85% | 0.025 | 101% |
| 06-1120_EG_MAX-10 | F | 0.05 | EG-0.050-3 | 2 | 50 | 2.5 | 5 | 0.043 | 87% | 0.048 | 97% | 0.051 | 103% |
| 06-1120_EG_MAX-12 | F | 0.05 | EG-0.050-4 | 2 | 50 | 2.5 | 5 | 0.042 | 84% | 0.041 | 82% | 0.051 | 102% |
| 06-1120_EG_MAX-13 | F | 0.05 | EG-0.050-5 | 2 | 50 | 2.5 | 5 | 0.043 | 86% | 0.043 | 86% | 0.055 | 109% |
| 06-1120_EG_MAX-15 | F | 0.5 | EG-0.50-3 | 2 | 50 | 2.5 | 5 | 0.437 | 87% | 0.456 | 91% | 0.485 | 97% |
| 06-1120_EG_MAX-16 | F | 0.5 | EG-0.50-4 | 2 | 50 | 2.5 | 5 | 0.418 | 84% | 0.427 | 85% | 0.503 | 101% |
| 06-1120_EG_MAX-18 | F | 0.5 | EG-0.50-5 | 2 | 50 | 2.5 | 5 | 0.411 | 82% | 0.454 | 91% | 0.522 | 104% |

Whole Egg - N-acetylglyphosate, Glyphosate, and N-acetyl AMPA Analysis

TABLE 98

Representative Method Validation Data Sheets
Cow Muscle and Liver - N-acetylglyphosate, Glyphosate, and N-acetyl AMPA Analysis
Matrix: BEEF LIVER & MUSCLE
Quantitation Ions: glyphosate: 170 > 87.7, glyphosate IS: 173 > 90.7, N-acetylglyphosate: 212 > 87.9, N-acetyl AMPA: 154 > 111.9

| | | | | | | | | Analyte Response | | | | | | |
|---|---|---|---|---|---|---|---|---|---|---|---|---|---|---|
| | Sample Information | | | SW | XV | AF | FV | glyphosate | | | NA-AMPA | | NA-Gly | |
| Run ID | Type | ppb | Identification | g | mL | mL | mL | Area | IS | $RF_{IS}$ | Area | RF | Area | RF |
| 07-0629_B_LM-2 | S | 0.5 | 0.5 ppb CS 062907 | | | | | 191 | 1545 | 0.2472 | 113 | 226 | 115 | 230 |
| 07-0629_B_LM-3 | C | | BL Control 062807 | 2 | 50 | 1.25 | 2.5 | | 1210 | | | | 82 | |
| 07-0629_B_LM-4 | S | 1 | 1.0 ppb CS 062907 | | | | | 382 | 1706 | 0.2239 | 197 | 197 | 183 | 183 |
| 07-0629_B_LM-5 | C | | BM Control 062807 | 2 | 50 | 2.5 | 2.5 | | 1185 | | | | | |

TABLE 98-continued

Representative Method Validation Data Sheets
Cow Muscle and Liver - N-acetylglyphosate, Glyphosate, and N-acetyl AMPA Analysis
Matrix: BEEF LIVER & MUSCLE
Quantitation Ions: glyphosate: 170 > 87.7, glyphosate IS: 173 > 90.7, N-acetylglyphosate: 212 > 87.9, N-acetyl AMPA: 154 > 111.9

| Run ID | Type | | | | | | | | | | | | |
|---|---|---|---|---|---|---|---|---|---|---|---|---|---|
| 07-0629_B_LM-6 | S | 2 | 2.0 ppb CS 062907 | | | | | 713 | 1663 | 0.2144 | 391 | 196315 | 158 |
| 07-0629_B_LM-7 | F | 50 | BL LOQ 1 062807 | 2 | 50 | 1.25 | 2.5 | 296 | 1298 | | 192 | 265 | |
| 07-0629_B_LM-8 | F | 50 | BL LOQ 2 062807 | 2 | 50 | 1.25 | 2.5 | 260 | 1297 | | 222 | 231 | |
| 07-0629_B_LM-9 | S | 5 | 5.0 ppb CS 062907 | | | | | 1722 | 1706 | 0.2019 | 987 | 197913 | 183 |
| 07-0629_B_LM-10 | F | 25 | BM LOQ 1 062807 | 2 | 50 | 2.5 | 2.5 | 239 | 1227 | | 193 | 191 | |
| 07-0629_B_LM-11 | F | 25 | BM LOQ 2 062807 | 2 | 50 | 2.5 | 2.5 | 200 | 1192 | | 198 | 174 | |
| 07-0629_B_LM-12 | S | 10 | 10 ppb CS 062907 | | | | | 3721 | 1748 | 0.2129 | 2072 | 207852 | 185 |
| 07-0629_B_LM-13 | F | 500 | BL 10X 1 062807 | 2 | 50 | 1.25 | 2.5 | 2340 | 1254 | | 1965 | 1809 | |
| 07-0629_B_LM-14 | F | 500 | BL 10X 2 062807 | 2 | 50 | 1.25 | 2.5 | 2418 | 1305 | | 1920 | 1845 | |
| 07-0629_B_LM-15 | S | 20 | 20 ppb CS 062907 | | | | | 7532 | 1753 | 0.2148 | 4343 | 213792 | 190 |
| 07-0629_B_LM-16 | F | 250 | BM 10X 1 062807 | 2 | 50 | 2.5 | 2.5 | 1833 | 927 | | 1781 | 1522 | |
| 07-0629_B_LM-17 | F | 250 | BM 10X 2 062807 | 2 | 50 | 2.5 | 2.5 | 1936 | 1102 | | 1660 | 1634 | |
| 07-0629_B_LM-18 | S | 50 | 50 ppb CS 062907% | | | | | 18943 | 1792 | 0.2114 | 10296 | 208985 | 180 |

| | Calibration Standards Statistics | Quantified by Average Response Factor | | | Slope = | | | | | 2.634E-03 | 4.827E-03 | 5.540E-03 |
|---|---|---|---|---|---|---|---|---|---|---|---|---|
| | | | | | Intercept = | | | | | 1.509E-01 | -4.502E-02 | -1.433E-01 |
| | | | | | RSQ = | | | | | 0.99992 | 0.99944 | 0.99944 |
| | | | | | Average RF = | | | | 1702 | 0.2181 | 207 | 187 |
| | | | | | STDEV = | | | | 81 | 0.0144 | 11 | 22 |
| | | | | | % RSD = | | | | 5% | 7% | 6% | 12% |

| | Sample Information | | | SW | XV | AF | FV | glyphosate | | NA-AMPA | | NA-Gly | |
|---|---|---|---|---|---|---|---|---|---|---|---|---|---|
| Run ID | Type | mg/kg | Identification | g | mL | mL | mL | mg/kg | % Rec | mg/kg | % Rec | mg/kg | % Rec |
| 07-0629_B_LM-3 | C | 0 | BL Control 062807 | 2 | 50 | 1.25 | 2.5 | nd | | nd | | 0.022 | |
| 07-0629_B_LM-5 | C | 0 | BM Control 062807 | 2 | 50 | 2.5 | 2.5 | nd | | nd | | nd | |
| 07-0629_B_LM-7 | F | 0.05 | BL LOQ 1 062807 | 2 | 50 | 1.25 | 2.5 | 0.052 | 105% | 0.046 | 93% | 0.049 | 98% |
| 07-0629_B_LM-8 | F | 0.05 | BL LOQ 2 062807 | 2 | 50 | 1.25 | 2.5 | 0.046 | 92% | 0.054 | 107% | 0.040 | 80% |
| 07-0629_B_LM-10 | F | 0.025 | BM LOQ 1 062807 | 2 | 50 | 2.5 | 2.5 | 0.022 | 89% | 0.023 | 93% | 0.026 | 102% |
| 07-0629_B_LM-11 | F | 0.025 | BM LOQ 2 062807 | 2 | 50 | 2.5 | 2.5 | 0.019 | 77% | 0.024 | 96% | 0.023 | 93% |
| 07-0629_B_LM-13 | F | 0.5 | BL 10X 1 062807 | 2 | 50 | 1.25 | 2.5 | 0.428 | 86% | 0.476 | 95% | 0.462 | 92% |
| 07-0629_B_LM-14 | F | 0.5 | BL 10X 2 062807 | 2 | 50 | 1.25 | 2.5 | 0.425 | 85% | 0.465 | 93% | 0.472 | 94% |
| 07-0629_B_LM-16 | F | 0.25 | BM 10X 1 062807 | 2 | 50 | 2.5 | 2.5 | 0.227 | 91% | 0.216 | 86% | 0.204 | 81% |
| 07-0629_B_LM-17 | F | 0.25 | BM 10X 2 062807 | 2 | 50 | 2.5 | 2.5 | 0.201 | 81% | 0.201 | 80% | 0.219 | 87% |

COMMENTS:
Bold italics: % Rec outside 70-110%,
Underlined: area detected in control subtracted from area detected in sample.
Type (B: blank, S: standard, IS: internal standard, C: control sample, F: fortified control sample, T: treated sample, FS: fort standard).
SW: sample weight,
XV: extract volume,
AF: aliquot factor,
FV: final volume,
$RF_{IS}$: response factor normalized to IS (analyte area/IS area/analyte ppb),
RF: response factor (analyte area/analyte ppb).
mg/kg Found = (Area/Average RF) × (FV × XV)/(AF × SW × 1000);
mg/kg Found (IS) = (Area/IS Area/Average $RF_{IS}$) × (FV × XV)/(AF × SW × 1000).

TABLE 99

Representative Method Validation Data Sheets
Cow Muscle-AMPA Analysis
Matrix: BEEF muscle
Quantitaitive Ions: AMPA 111.9 > 30

| | Sample Information | | | SW | XV | AF | FV | Analyte Response AMPA | | |
|---|---|---|---|---|---|---|---|---|---|---|
| Run ID | Type | ppb | Identification | g | mL | mL | mL | Area | IS | $RF_{IS}$ |
| 07-0718_BM_CX-1 | S | 0.25 | 0.25 ppb CS + IS 071607 | | | | | 23 | 331 | 0.2779 |
| 07-0718_BM_CX-2 | S | 0.5 | 0.5 ppb CS + IS 071607 | | | | | 44 | 326 | 0.2699 |
| 07-0718_BM_CX-3 | C | | BM Control 062807 | 2 | 50 | 2.5 | 2.5 | | 262 | |
| 07-0718_BM_CX-4 | S | 1 | 1.0 ppb CS + IS 071607 | | | | | 75 | 297 | 0.2525 |
| 07-0718_BM_CX-5 | F | 50 | BM LOQ 1 062807 | 2 | 50 | 2.5 | 2.5 | 118 | 278 | |
| 07-0718_BM_CX-6 | S | 2 | 2.0 ppb CS + IS 071607 | | | | | 156 | 312 | 0.2500 |
| 07-0718_BM_CX-7 | F | 50 | BM LOQ 2 062807 | 2 | 50 | 2.5 | 2.5 | 119 | 269 | |
| 07-0718_BM_CX-8 | S | 5 | 5.0 ppb CS + IS 071607 | | | | | 376 | 296 | 0.2541 |
| 07-0718_BM_CX-9 | F | 500 | BM 10X 1 062807 | 2 | 50 | 2.5 | 2.5 | 133 | 1262 | |
| 07-0718_BM_CX-10 | S | 10 | 10 ppb CS + IS 071607 | | | | | 741 | 341 | 0.2173 |
| 07-0718_BM_CX-11 | F | 500 | BM 10X 2 062807 | 2 | 50 | 2.5 | 2.5 | 136 | 2274 | |
| 07-0718_BM_CX-12 | S | 20 | 20 ppb CS + IS 071607 | | | | | 150 | 9317 | 0.2380 |
| | | | Calibration Standards Statistics | | Slope = | | | | | 1.332E−02 |
| | | | | | Intercept = | | | | | −3.007E−02 |
| | | | | | RSQ = | | | | | 0.99988 |
| | | | | | Average RF = | | | | 317 | 0.2514 |
| | | | Quantified by Average Response Factor | | STDEV = | | | | 17 | 0.0200 |
| | | | | | % RSD = | | | | 5% | 8% |

| | Sample Information | | | SW | XV | AF | FV | Recoveries AMPA | |
|---|---|---|---|---|---|---|---|---|---|
| Run ID | Type | mg/kg | Identification | g | mL | mL | mL | mg/kg | % Rec |
| 07-0718_BM_CX-3 | C | 0 | BM Control 062807 | 2 | 50 | 2.5 | 2.5 | nd | |
| 07-0718_BM_CX-5 | F | 0.05 | BM LOQ 1 062807 | 2 | 50 | 2.5 | 2.5 | 0.042 | 84% |
| 07-0718_BM_CX-7 | F | 0.05 | BM LOQ 2 062807 | 2 | 50 | 2.5 | 2.5 | 0.044 | 88% |
| 07-0718_BM_CX-9 | F | 0.5 | BM 10X 1 062807 | 2 | 50 | 2.5 | 2.5 | 0.505 | 101% |
| 07-0718_BM_CX-11 | F | 0.5 | BM 10X 2 062807 | 2 | 50 | 2.5 | 2.5 | 0.494 | 99% |

Comments:
Bold italics: % Rec outside 70-110%
Underlined: area detected in control subtracted from area detected in sample.
Type (B: blank, S: standard, IS: internal standard, C: control sample, F: fortified control sample, FS: Fort standard).
SW: sample weight,
XV: extract volume,
AF: aliquot factor,
FV: final volume,
RF IS: response factor normalized to IS (analyte area/IS area/analyte ppb),
RF: response factor (analyte area/analyte ppb).
mg/kg Found = (Area/Average RF) × (FV × XV)/(AF × SW × 1000);
mg/kg Found (IS) = (Area/Average RF IS) × (FV × XV)/(AF × SW × 1000).

TABLE 100

Representative Method Validation Data Sheets
Cow Kidney and Fat - N-acetylglyphosate, Glyphosate, and N-acetyl AMPA Analysis
Matrix: BEEF FAT & KIDNEY
Quantitation Ions: glyphosate: 170 > 87.7, glyphosate IS: 173 > 90.7, N-acetylglyphosate: 212 > 87.9, N-acetyl AMPA: 154 > 111.9

| | Sample Information | | | SW | XV | AF | FV | Analyte Response | | | | | |
|---|---|---|---|---|---|---|---|---|---|---|---|---|---|
| | | | | | | | | glyphosate | | | NA-AMPA | | NA-Gly |
| Run ID | Type | ppb | Identification | g | mL | mL | mL | Area | IS | $RF_{IS}$ | Area | RF | Area | RF |
| 07-0705_BK-F-1 | S | 0.5 | 0.5 ppb CS 062907 | | | | | 253 | 2309 | 0.2191 | 180 | 360 | 141 | 282 |
| 07-0705_BK-F-2 | C | 0 | BK Control 062807 | 2 | 50 | 1.25 | 2.5 | 72 | 1019 | | | | | |
| 07-0705_BK-F-3 | S | 1 | 1.0 ppb CS 062907 | | | | | 511 | 2260 | 0.2261 | 337 | 337 | 324 | 324 |
| 07-0705_BK-F-4 | C | 0 | BF Control 062807 | 2 | 50 | 1.25 | 2.5 | | 969 | | | | | |
| 07-0705_BK-F-5 | S | 2 | 2.0 ppb CS 062907 | | | | | 955 | 2342 | 0.2039 | 736 | 368 | 568 | 284 |
| 07-0705_BK-F-6 | F | 50 | BK LOQ 1 062907 | 2 | 50 | 1.25 | 2.5 | 327 | 1031 | | 328 | | 283 | |

TABLE 100-continued

Representative Method Validation Data Sheets
Cow Kidney and Fat - N-acetylglyphosate, Glyphosate, and N-acetyl AMPA Analysis
Matrix: BEEF FAT & KIDNEY
Quantitation Ions: glyphosate: 170 > 87.7, glyphosate IS: 173 > 90.7, N-acetylglyphosate: 212 > 87.9, N-acetyl AMPA: 154 > 111.9

| Run ID | Type | | Identification | | | | | | | | | | | |
|---|---|---|---|---|---|---|---|---|---|---|---|---|---|---|
| 07-0705_BK-F-7 | F | 50 | BK LOQ 2 062907 | 2 | 50 | 1.25 | 2.5 | 242 | 1025 | | 332 | | 309 | |
| 07-0705_BK-F-8 | S | 5 | 5.0 ppb CS 062907 | | | | | 2378 | 2239 | 0.2124 | 1707 | 341 | 1431 | 286 |
| 07-0705_BK-F-9 | F | 50 | BF LOQ 1 062907 | 2 | 50 | 1.25 | 2.5 | 234 | 973 | | 336 | | 311 | |
| 07-0705_BK-F-10 | F | 50 | BF LOQ 2 062907 | 2 | 50 | 1.25 | 2.5 | 184 | 1002 | | 332 | | 302 | |
| 07-0705_BK-F-11 | S | 10 | 10 ppb CS 062907 | | | | | 4783 | 2277 | 0.2101 | 3676 | 368 | 2987 | 299 |
| 07-0705_BK-F-12 | F | 500 | BK 10X 1 062907 | 2 | 50 | 1.25 | 2.5 | 1906 | 1062 | | 3066 | | 2381 | |
| 07-0705_BK-F-13 | F | 500 | BK 10X 2 062907 | 2 | 50 | 1.25 | 2.5 | 1932 | 1035 | | 3268 | | 2446 | |
| 07-0705_BK-F-14 | S | 20 | 20 ppb CS 062907 | | | | | 9979 | 2422 | 0.2060 | 6870 | 344 | 5675 | 284 |
| 07-0705_BK-F-15 | F | 500 | BF 10X 1 062907 | 2 | 50 | 1.25 | 2.5 | 1977 | 977 | | 3177 | | 2514 | |
| 07-0705_BK-F-16 | F | 500 | BF 10X 2 062907 | 2 | 50 | 1.25 | 2.5 | 2158 | 1043 | | 3282 | | 2530 | |
| 07-0705_BK-F-17 | S | 50 | 50 ppb CS 062907 | | | | | 24362 | 2290 | 0.2128 | 17587 | 352 | 14041 | 281 |

Calibration Standards Statistics
Quantified by Average Response Factor

| | | | |
|---|---|---|---|
| Slope = | 2.047E-03 | 2.849E-03 | 3.566E-03 |
| Intercept = | 2.506E-03 | -9.933E-03 | -1.776E-01 |
| RSQ = | 0.99986 | 0.99977 | 0.99984 |
| Average RF = | 2306 / 0.2129 | 353 | 291 |
| STDEV = | 61 / 0.0076 | 13 | 16 |
| % RSD = | 3% / 4% | 4% | 5% |

| | Sample Information | | | SW | XV | AF | FV | Recoveries | | | | | |
|---|---|---|---|---|---|---|---|---|---|---|---|---|---|
| | | | | | | | | glyphosate | | NA-AMPA | | NA-Gly | |
| Run ID | Type | mg/kg | Identification | g | mL | mL | mL | mg/kg | % Rec | mg/kg | % Rec | mg/kg | % Rec |
| 07-0705_BK-F-2 | C | 0 | BK Control 062807 | 2 | 50 | 1.25 | 2.5 | 0.017 | | nd | | nd | |
| 07-0705_BK-F-4 | C | 0 | BF Control 062907 | 2 | 50 | 1.25 | 2.5 | nd | | nd | | nd | |
| 07-0705_BK-F-6 | F | 0.05 | BK LOQ 1 062907 | 2 | 50 | 1.25 | 2.5 | <u>0.058</u> | _116%_ | 0.046 | 93% | 0.049 | 97% |
| 07-0705_BK-F-7 | F | 0.05 | BK LOQ 2 062907 | 2 | 50 | 1.25 | 2.5 | <u>0.039</u> | 78% | 0.047 | 94% | 0.053 | 106% |
| 07-0705_BK-F-9 | F | 0.05 | BF LOQ 1 062907 | 2 | 50 | 1.25 | 2.5 | 0.056 | _113%_ | 0.048 | 95% | 0.053 | 107% |
| 07-0705_BK-F-10 | F | 0.05 | BF LOQ 2 062907 | 2 | 50 | 1.25 | 2.5 | 0.043 | 86% | 0.047 | 94% | 0.052 | 104% |
| 07-0705_BK-F-12 | F | 0.5 | BK 10X 1 062907 | 2 | 50 | 1.25 | 2.5 | <u>0.405</u> | 81% | 0.435 | 87% | 0.409 | 82% |
| 07-0705_BK-F-13 | F | 0.5 | BK 10X 2 062907 | 2 | 50 | 1.25 | 2.5 | <u>0.422</u> | 84% | 0.463 | 93% | 0.420 | 84% |
| 07-0705_BK-F-15 | F | 0.5 | BF 10X 1 062907 | 2 | 50 | 1.25 | 2.5 | 0.475 | 95% | 0.450 | 90% | 0.431 | 86% |
| 07-0705_BK-F-16 | F | 0.5 | BF 10X 2 062907 | 2 | 50 | 1.25 | 2.5 | 0.486 | 97% | 0.465 | 93% | 0.434 | 87% |

COMMENTS:
Bold italics: % Rec outside 70-110%,
Underlined: area detected in control subtracted from area detected in sample.
Type (B:blank, S: standard, IS: internal standard, C: control sample, F: fortified control sample, T: treated sample, FS: fort standard).
SW: sample weight,
XV: extract volume,
AF: aliquot factor,
FV: final volume,
$RF_{IS}$: response factor normalized to IS (analyte area/IS area/analyte ppb),
RF: response factor (analyte area/analyte ppb).
mg/kg Found = (Area/Average RF) × (FV × XV)/(AF × SW × 1000);
mg/kg Found (IS) = (Area/ISArea/Average $RF_{IS}$) × (FV × XV)/(AF × SW × 1000).

TABLE 101

Representative Method Validation Data Sheets
Cow Kidney-AMPA Analysis
Matrix: BEEF
Quantitation Ions: AMPA 111.9 > 30

| Run ID | Sample Information | | | SW | XV | AF | FV | Analyte Response AMPA | | |
|---|---|---|---|---|---|---|---|---|---|---|
| | Type | ppb | Identification | g | mL | mL | mL | Area | IS | $RF_{IS}$ |
| 07-0702_BK_CX-1 | S | 0.25 | 0.5 ppb CS + IS 062907 | | | | | 39 | 542 | 0.2878 |
| 07-0702_BK_CX-2 | S | 0.5 | 0.5 ppb CS + IS 062907 | | | | | 82 | 502 | 0.3267 |
| 07-0702_BK_CX-3 | C | | BK Control 062907 | 2 | 50 | 4 | 5 | 37 | 250 | |
| 07-0702_BK_CX-4 | S | 1 | 1.0 ppb CS + IS 061407 | | | | | 123 | 457 | 0.2691 |
| 07-0702_BK_CX-5 | F | 50 | BK LOQ 1 062907 | 2 | 50 | 4 | 5 | 117 | 253 | |
| 07-0702_BK_CX-6 | S | 2 | 2.0 ppb CS + IS 062907 | | | | | 220 | 487 | 0.2259 |
| 07-0702_BK_CX-7 | F | 50 | BK LOQ 2 062907 | 2 | 50 | 4 | 5 | 131 | 266 | |
| 07-0702_BK_CX-8 | S | 5 | 5.0 ppb CS + IS 062907 | | | | | 568 | 502 | 0.2263 |
| 07-0702_BK_CX-9 | F | 500 | BK 10X 1 062907 | 2 | 50 | 4 | 5 | 901 | 270 | |
| 07-0702_BK_CX-10 | S | 10 | 10 ppb CS + IS 062907 | | | | | 118 | 4468 | 0.2530 |
| 07-0702_BK_CX-11 | F | 500 | BK 10X 2 062907 | 2 | 50 | 4 | 5 | 816 | 264 | |
| 07-0702_BK_CX-12 | S | 20 | 20 ppb CS + IS 062907 | | | | | 222 | 2479 | 0.2319 |
| Calibration Standards Statistics | | | | | | | Slope = | | | 8.971E-03 |
| | | | | | | | Intercept = | | | -1.521E-01 |
| | | | | | | | RSQ = | | | 0.99900 |
| | | | | | | | Average RF = | | 491 | 0.2601 |
| Quantified by Average Response Factor | | | | | | | STDEV = | | 28 | 0.0375 |
| | | | | | | | % RSD = | | 6% | 14% |

| Run ID | Sample Information | | | SW | XV | AF | FV | Recoveries AMPA | |
|---|---|---|---|---|---|---|---|---|---|
| | Type | mg/kg | Identification | g | mL | mL | mL | mg/kg | % Rec |
| 07-0702_BK_CX-3 | C | 0 | BK Control 062907 | 2 | 50 | 4 | 5 | 0.018 | |
| 07-0702_BK_CX-5 | F | 0.05 | BK LOQ 1 062907 | 2 | 50 | 4 | 5 | <u>0.038</u> | 76% |
| 07-0702_BK_CX-7 | F | 0.05 | BK LOQ 2 062907 | 2 | 50 | 4 | 5 | <u>0.041</u> | 83% |
| 07-0702_BK_CX-9 | F | 0.5 | BK 10X 1 062907 | 2 | 50 | 4 | 5 | <u>0.383</u> | 77% |
| 07-0702_BK_CX-11 | F | 0.5 | BK 10X 2 062907 | 2 | 50 | 4 | 5 | <u>0.354</u> | 71% |

COMMENTS:
Bold italics: % Rec outside 70-110%
Underlined: area detected in control subtracted from area detected in sample.
Type (B: blank, S: standard, IS: internal standard, C: control sample, F: fortified control sample, FS: fort standard).
SW: sample weight,
XV: extract volume,
AF: aliquot factor,
FV: final volume,
RFIS: repsonse factor normalized to IS (analyte area/IS area/analyte ppb),
RF: response factor (analyte area/analyte ppb).
mg/kg Found = (Area/Average RF) × (FV × XV)/(AF × SW × 1000);
mg/kg Found (IS) = (Area/Average RF IS) × (FV × XV)/(AF × SW × 1000).

Extraction Efficiency

Chicken liver, fat, and muscle samples treated with $^{14}C$ N-acetylglyphosate in a poultry metabolism study were extracted using procedures in described herein for radiochemical validation of the extraction efficiency. Duplicate 2 g subsamples from each matrix were extracted and aliquots from each extract were analyzed by liquid scintillation counting (LSC) for radioactive recovery. Radioactive recovery results (dpm/g) were converted using specific activity of original $^{14}C$ N-acetylglyphosate test substance (13.83 µCi/mg=30703 dpm/µg) to µg/g concentrations for comparison with reported recoveries in the poultry metabolism study. The respective recovery results for liver, fat, and muscle were 98%, 88%, and 104% of the µg/g concentrations found in the metabolism study extractions. LSC data and results are provided in Table 102.

TABLE 102

Extraction efficiency determinations

Protocol #: 37
COUNTER #14

| LSC Counter Data | | | | | | | | Sample Information and Calculated Recoveries | | | | |
|---|---|---|---|---|---|---|---|---|---|---|---|---|
| PID | S# | A: 2S % | tSIE | CPMA | TIME | % EFF | DPM1 | SAMPLE | Extract (mL) | Sample Wt. (g) | Aliquot (mL) | Total dpm | dpm/g |
| 13 | 1 | 10.26 | 392 | 19 | 20 | 86 | 22 | BKG | | | | | |
| 13 | 2 | 3.26 | 238 | 188 | 20 | 77 | 245 | Fat-1A | 50 | 1.984 | 4 | 2788 | 1405 |

TABLE 102-continued

| | | | | | | | | | | | | | |
|---|---|---|---|---|---|---|---|---|---|---|---|---|---|
| 13 | 3 | 3.01 | 239 | 221 | 20 | 77 | 288 | Fat-2A | 50 | 2.006 | 4 | 3325 | 1658 |
| 13 | 4 | 2.03 | 305 | 483 | 20 | 82 | 590 | Liver-1A | 50 | 2.019 | 1 | 28400 | 14066 |
| 13 | 5 | 2.01 | 301 | 495 | 20 | 82 | 607 | Liver-2A | 50 | 2.005 | 1 | 29250 | 14589 |
| 13 | 6 | 5.05 | 290 | 78 | 20 | 81 | 97 | Muscle-1A | 50 | 1.989 | 2 | 1875 | 943 |
| 13 | 7 | 5.35 | 294 | 70 | 20 | 81 | 86 | Muscle-2A | 50 | 2.017 | 2 | 1600 | 793 |
| 13 | 8 | 3.61 | 252 | 153 | 20 | 78 | 197 | Fat-1B | 50 | 1.984 | 4 | 2188 | 1103 |
| 13 | 9 | 3.07 | 237 | 212 | 20 | 77 | 277 | Fat-2B | 50 | 2.006 | 4 | 3188 | 1589 |
| 13 | 10 | 2.01 | 304 | 494 | 20 | 82 | 604 | Liver-1B | 50 | 2.019 | 1 | 29100 | 14413 |
| 13 | 11 | 1.96 | 302 | 520 | 20 | 82 | 636 | Liver-2B | 50 | 2.005 | 1 | 30700 | 15312 |
| 13 | 12 | 4.87 | 288 | 84 | 20 | 81 | 104 | Muscle-1B | 50 | 1.989 | 2 | 2050 | 1031 |
| 15 | 13 | 5 | 286 | 80 | 20 | 81 | 99 | Muscle-2B | 50 | 2.017 | 2 | 1925 | 954 |

| Matrix | Extraction Efficiency Analyses | | Metabolism | Extraction Efficiency % of |
|---|---|---|---|---|
| | Average dpm/g | µg/g | Study* µg/g | Metabolism Value |
| Liver | 14595 | 0.475 | 0.483 | 98% |
| Fat | 1439 | 0.047 | 0.053 | 88% |
| Muscle | 930 | 0.030 | 0.029 | 104% |

Total dpm = (extract dpm − BKG dpm)/Aliquot (mL) × Extract (mL)
dpm/g = Total dpm/Sample Wt (g)
µg/g = (Average dpm/g)/(30703 dpm/µg)
Specific Activity = 13.83 µCi/mg = 30703 dpm/µg
Calculation:
13.83 µCi/mg × 2220000 dpm/µCi × 1 mg/1000 µg = 30703 dpm/µg
2.22E+06 dpm/µCi
2 replicate samples (-1, -2) of each matrix were extracted and 2 aliquots of each extract were analyzed by LSC (-1A, -1B).

Milk and egg samples are generally liquid matrices that were diluted in aqueous solution prior to purification procedures of partitioning and solid phase extraction SPE. No extraction efficiency testing was conducted for these matrices.

Limit of Quantitation (LOQ)

The LOQ determined in this method was 0.025 mg/kg (ppm) in milk, egg, and muscle matrices and 0.050 mg/kg in kidney, liver, and fat matrices for the analysis of glyphosate, N-acetylglyphosate, AMPA, and N-acetyl AMPA. The LOQ is defined as the lowest fortification level at which average recoveries of 70-110% and a RSD<20% are achieved. In addition, at this fortification level, the analyte peak consistently represents a signal-to-noise ratio of approximately 5-20 to 1 for N-acetylglyphosate.

Background Evaluation

Background levels experienced in tandem mass spectrometry analyses are minimal. Generally, the chromatographic profiles of a sample extract solution and a calibration standard solution appear the same. Representative matrix chromatograms are provided in FIG. 65 through FIG. 73.

Limit of Detection (LOD)

The LOD is defined as the analyte concentration in matrix with a response equivalent to a signal-to-noise ratio (s/n) of approximately 3 to 1. The LOD was estimated from the s/n response determined in a LOQ fortification sample using the following equation for each analyte.

$$\frac{LOD\ s/n\ \text{response}(3/1)}{\text{Observed}\ LOQ\ s/n\ \text{response}} \times mg/kg\ \text{found} = LOD(mg/kg)$$

The individual chromatograms showing s/n determination and calculated estimates for each analyte are provided in FIGS. 75-80. The LOD estimates for each analyte and matrix examined with are summarized in the table 79.

TABLE 79

ESTIMATED LOD
(MG/KG GLYPHOSATE EQUIVALENTS)

| MATRIX | GLYPHOSATE | N-ACETYL GLYPHOSATE | AMPA | N-ACETYL AMPA |
|---|---|---|---|---|
| MILK | 0.008 | 0.005 | 0.008 | 0.008 |
| EGG | 0.003 | 0.008 | 0.006 | 0.007 |
| LIVER | 0.009 | 0.018 | 0.019 | 0.008 |
| KIDNEY | 0.004 | 0.014 | 0.009 | 0.008 |
| FAT | 0.008 | 0.015 | 0.015 | 0.009 |
| MUSCLE | 0.004 | 0.006 | 0.008 | 0.006 |

Variation in the LOD was observed and each lab using this method should estimate LOD values. Sample extracts stored frozen should be thawed and sonicated approximately 15 minutes prior to re-purification or analysis. Routinely, a LC/MS/MS end run was setup so that high percentage organic solvent (99% methanol) would continue overnight at a low flowrate (0.025 mL/min) after the final analysis to keep the HPLC pump and column in good condition.

The stability of the analyte stock standards prepared in distilled water and stored at approximately 4° C. were shown to be stable for more than a year. Data not shown. Fortification Standards, also prepared in distilled water, should be stable for same time period as the stock solutions. Calibration standards were prepared in aqueous 0.02M phosphoric acid or 80% control matrix/20% aqueous 0.02M phosphoric acid were shown to be stable for at least 2.7 months when stored at approximately 4° C.

No interferences attributable to glassware, reagents, or matrices were observed to co-elute with test analytes. A peak was observed in the m/z 212→88 MRM transition channel eluting just after N-acetylglyphosate that was attributable to MAX SPE sorbent.

Confirmatory Procedure

Two independent MS/MS transitions of the molecular ion for N-acetylglyphosate, glyphosate, and N-acetyl AMPA were monitored in ESI positive or negative ion mode. Two independent MS/MS transitions of the molecular ion for AMPA were monitored in ESI negative mode only. The relative response ratios of the two fragment ions (base peak/secondary peak) were determined from calibration standard responses for confirmation of analyte in matrix samples. Acceptable confirmation criteria are a co-eluting peak (±5%) and equivalent ion ratio (±30%) compared to the average response observed in calibration standards at or above the LOQ equivalent concentration concurrently analyzed with the samples. Representative confirmatory analyses showing calculated response ratios and retention times for each analyte are provided in tables 103-106.

TABLE 103

Representative Confirmatory Analysis
Whole Milk
Glyphosate, N-acetylglyhosate, N-acetyl AMPA

| | Sample Information | | | N-acetyl AMPA | | | | N-acetylglyphosate | | | |
|---|---|---|---|---|---|---|---|---|---|---|---|
| Run ID | Type | ng/g or ppb | Identification | 154 > 112 | 154 > 30 | Ratio | RT | 212 > 170 | 212 > 88 | Ratio | RT |
| 07-0126_RM_CX-5 | S | 1 | 1.0 ppb CS + IS 011807 | 1730 | 316 | 5.47 | 5.96 | 914 | 486 | 0.53 | 6.13 |
| 07-0126_RM_CX-7 | S | 2 | 2.0 ppb CS + IS 011807 | 3562 | 612 | 5.82 | 5.98 | 1714 | 1119 | 0.65 | 6.17 |
| 07-0126_RM_CX-9 | S | 5 | 5.0 ppb CS + IS 011807 | 8257 | 1577 | 5.24 | 5.98 | 4313 | 2712 | 0.63 | 6.14 |
| 07-0126_RM_CX-12 | S | 10 | 10 ppb CS + IS 011807 | 16551 | 3286 | 5.04 | 5.98 | 9094 | 5790 | 0.64 | 6.15 |
| 07-0126_RM_CX-14 | S | 20 | 20 ppb CS + IS 011807 | 33049 | 6289 | 5.26 | 5.98 | 17774 | 11121 | 0.63 | 6.16 |
| 07-0126_RM_CX-16 | S | 50 | 50 ppb CS + IS 011807 | 79457 | 16189 | 4.91 | 5.98 | 42288 | 26478 | 0.63 | 6.15 |
| 07-0126_RM_CX-6 | F | 25 | RM L 1 MCX 012307 | 1122 | 205 | 5.47 | 5.93 | 529 | 338 | 0.64 | 6.11 |
| 07-0126_RM_CX-8 | F | 25 | RM L 2 MCX 012307 | 974 | 186 | 5.24 | 5.96 | 592 | 304 | 0.51 | 6.15 |
| 07-0126_RM_CX-10 | F | 50 | RM M 1 MCX 012307 | 2051 | 444 | 4.62 | 5.95 | 1133 | 726 | 0.64 | 6.08 |
| 07-0126_RM_CX-11 | F | 50 | RM M 2 MCX 012307 | 1966 | 406 | 4.84 | 5.92 | 1079 | 661 | 0.61 | 6.13 |
| 07-0126_RM_CX-13 | F | 250 | RM H 1 MCX 012307 | 21431 | 4320 | 4.96 | 5.93 | 11619 | 7181 | 0.62 | 6.09 |
| 07-0126_RM_CX-15 | F | 250 | RM H 2 MCX 012307 | 19936 | 3907 | 5.10 | 5.94 | 11027 | 6933 | 0.63 | 6.11 |
| | Average | | | | | 5.29 | 5.98 | | | 0.62 | 6.15 |
| | StDev | | | | | 0.33 | 0.01 | | | 0.04 | 0.01 |
| | % RSD | | | | | 6% | 0.1% | | | 7% | 0.2% |
| | Lower Limit | | | | | 3.70 | 5.68 | | | 0.43 | 5.84 |
| | Upper Limit | | | | | 6.88 | 6.28 | | | 0.80 | 6.46 |

| | Sample Information | | | Glyphosate | | | |
|---|---|---|---|---|---|---|---|
| Run ID | Type | ng/g or ppb | Identification | 170 > 88 | 170 > 60 | Ratio | RT |
| 07-0124_RM_AX-9 | S | 1 | 1.0 ppb CS + IS 011807 | 179 | 37 | 0.21 | 4.71 |
| 07-0124_RM_AX-11 | S | 2 | 2.0 ppb CS + IS 011807 | 359 | 90 | 0.25 | 4.7 |
| 07-0124_RM_AX-14 | S | 5 | 5.0 ppb CS + IS 011807 | 859 | 176 | 0.20 | 4.7 |
| 07-0124_RM_AX-17 | S | 10 | 10 ppb CS + IS 011807 | 1785 | 392 | 0.22 | 4.7 |
| 07-0124_RM_AX-20 | S | 20 | 20 ppb CS + IS 011807 | 3505 | 808 | 0.23 | 4.7 |
| 07-0124_RM_AX-7 | F | 25 | RM L 1 MAX 012307 | 84 | 19 | 0.23 | 4.68 |
| 07-0124_RM_AX-10 | F | 25 | RM L 2 MAX 012307 | 85 | 20 | 0.24 | 4.7 |
| 07-0124_RM_AX-12 | F | 50 | RM M 1 MAX 012307 | 163 | 39 | 0.24 | 4.69 |
| 07-0124_RM_AX-13 | F | 50 | RM M 2 MAX 012307 | 191 | 48 | 0.25 | 4.7 |
| 07-0124_RM_AX-15 | F | 250 | RM H 1 MAX 012307 | 1477 | 345 | 0.23 | 4.7 |
| 07-0124_RM_AX-18 | F | 250 | RM H 2 MAX 012307 | 1499 | 307 | 0.20 | 4.7 |
| | Average | | | | | 0.22 | 4.70 |
| | StDev | | | | | 0.02 | 0.00 |
| | % RSD | | | | | 8% | 0.1% |
| | Lower Limit | | | | | 0.16 | 4.47 |
| | Upper Limit | | | | | 0.29 | 4.94 |

TABLE 104

Whole Eggs
Glyphosate, N-acetylglyhosate, N-acetyl AMPA, AMPA
Matrix: Whole egg

Analyte Response (Fragment Ions peak areas; Ratio = base peak/minor peak; RT = peak retention time, min)

| Sample Information | | AMPA (neg ion) | | | | Glyphosate (pos ion) | | | |
|---|---|---|---|---|---|---|---|---|---|
| Identification | ng/g or ppb | 110 > 63.1 | 110 > 79.1 | Ratio | RT | 170 > 60.1 | 170 > 88 | Ratio | RT |
| 1.0 ppb Std. | 1 | 10900 | 8430 | 1.29 | 4.46 | 1270 | 3780 | 0.34 | 5.52 |
| 2.0 ppb Std. | 2 | 21400 | 16600 | 1.29 | 4.47 | 2770 | 8790 | 0.32 | 5.51 |
| 5.0 ppb Std. | 5 | 52900 | 38600 | 1.37 | 4.46 | 6140 | 18200 | 0.34 | 5.51 |
| 10.0 ppb Std. | 10 | 107000 | 80400 | 1.33 | 4.47 | 12600 | 43800 | 0.29 | 5.52 |
| 20.0 ppb Std. | 20 | 204000 | 156000 | 1.31 | 4.46 | 24300 | 81800 | 0.30 | 5.52 |
| 50.0 ppb Std. | 50 | 559000 | 404000 | 1.38 | 4.47 | | | | |
| EG 2 L 1 033007 | 25 | 7170 | 5530 | 1.30 | 4.46 | 354 | 1370 | 0.26 | 5.47 |
| EG 3 L 2 033007 | 25 | 7450 | 5230 | 1.42 | 4.46 | 356 | 1520 | 0.23 | 5.48 |
| EG 4 10X 1 033007 | 250 | 74200 | 53600 | 1.38 | 4.47 | 3970 | 12000 | 0.33 | 5.48 |

TABLE 104-continued

Whole Eggs
Glyphosate, N-acetylglyhosate, N-acetyl AMPA, AMPA
Matrix: Whole egg

| | | | | | | | | | |
|---|---|---|---|---|---|---|---|---|---|
| EG 5 10X 2 033007 | 250 | 68900 | 50900 | 1.35 | 4.46 | 3690 | 12500 | 0.30 | 5.48 |
| Average | | | | 1.33 | 4.47 | | | 0.31 | 5.52 |
| StDev | | | | 0.04 | 0.01 | | | 0.02 | 0.01 |
| % RSD | | | | 3% | 0.1% | | | 7% | 0.1% |
| Lower Limit | | | | 0.93 | 4.24 | | | 0.22 | 5.24 |
| Upper Limit | | | | 1.73 | 4.69 | | | 0.41 | 5.79 |

| | | Analyte Response (Fragment Ions peak areas; Ratio = base peak/ minor peak; RT = peak retention time, min) | | | | | | | |
|---|---|---|---|---|---|---|---|---|---|
| Sample Information | | N-acetyl AMPA (pos ion) | | | | N-acetylglyphosate (pos ion) | | | |
| Identification | ng/g or ppb | 154 > 30 | 154 > 112 | Ratio | RT | 212 > 88 | 212 > 169.9 | Ratio | RT |
| 1.0 ppb Std. | 1 | 5880 | 20100 | 0.29 | 8.10 | 40100 | 20600 | 1.95 | 8.58 |
| 2.0 ppb Std. | 2 | 12000 | 41500 | 0.29 | 8.10 | 72800 | 39500 | 1.84 | 8.63 |
| 5.0 ppb Std. | 5 | 30700 | 103000 | 0.30 | 8.07 | 177000 | 91100 | 1.94 | 8.57 |
| 10.0 ppb Std. | 10 | 60300 | 201000 | 0.30 | 8.07 | 342000 | 187000 | 1.83 | 8.64 |
| 20.0 ppb Std. | 20 | 118000 | 399000 | 0.30 | 8.08 | 689000 | 393000 | 1.75 | 8.61 |
| 50.0 ppb Std. | 50 | | | | | | | | |
| EG 2 L 1 033007 | 25 | 3300 | 11300 | 0.29 | 8.07 | 15900 | 8570 | 1.86 | 8.60 |
| EG 3 L 2 033007 | 25 | 3030 | 9550 | 0.32 | 8.07 | 17700 | 9120 | 1.94 | 8.53 |
| EG 4 10X 1 033007 | 250 | 29700 | 97700 | 0.30 | 8.06 | 165000 | 91100 | 1.81 | 8.56 |
| EG 5 10X 2 033007 | 250 | 28500 | 97800 | 0.29 | 8.06 | 155000 | 85900 | 1.80 | 8.58 |
| Average | | | | 0.30 | 8.08 | | | 1.86 | 8.61 |
| StDev | | | | 0.00 | 0.02 | | | 0.08 | 0.03 |
| % RSD | | | | 1% | 0.2% | | | 4% | 0.4% |
| Lower Limit | | | | 0.21 | 7.68 | | | 1.30 | 8.18 |
| Upper Limit | | | | 0.38 | 8.49 | | | 2.42 | 9.04 |

TABLE 105

Chicken Liver and Muscle
AMPA

| | Sample Information | | | AMPA | | | |
|---|---|---|---|---|---|---|---|
| Batch ID | Type | ng/g or ppb | Identification | 110 > 63 | 110 > 79 | Ratio | RT |
| AMPA073107 | S | 0.5 | 0.5 ppb CS071607 | 10100 | 7890 | 0.78 | 4.46 |
| | S | 0.5 | 0.5 ppb CS071607 | 9020 | 6470 | 0.72 | 4.46 |
| | S | 1 | 1.0 ppb CS071607 | 17100 | 12800 | 0.75 | 4.46 |
| | S | 2 | 2.0 ppb CS071607 | 34300 | 25500 | 0.74 | 4.45 |
| | S | 5 | 5.0 ppb CS071607 | 91800 | 71200 | 0.78 | 4.46 |
| | S | 10 | 10.0 ppb CS071607 | 191000 | 143000 | 0.75 | 4.46 |
| | S | 20 | 20.0 ppb CS0716079 | 380000 | 288000 | 0.76 | 4.45 |
| | S | 50 | 50.0 ppb CS071607 | 939000 | 709000 | 0.76 | 4.45 |
| | F | 25 | R2-G6-LOQ 1 Muscle 072507 | 15700 | 11900 | 0.76 | 4.46 |
| | F | 25 | R2-G6-LOQ 2 Muscle 072507 | 16300 | 13400 | 0.82 | 4.45 |
| | F | 50 | R2-G6-LOQ 1 Liver 072507 | 15700 | 12600 | 0.80 | 4.45 |
| | F | 50 | R2-G6-LOQ 2 Liver 072507 | 16300 | 12200 | 0.75 | 4.45 |
| | F | 250 | R2-G6-10X 1 Muscle 072507 | 144000 | 111000 | 0.77 | 4.45 |
| | F | 250 | R2-G6-10X 2 Muscle 072507 | 152000 | 120000 | 0.79 | 4.46 |
| | F | 500 | R2-G6-10X 1 Liver 072507 | 142000 | 108000 | 0.76 | 4.44 |
| | F | 500 | R2-G6-10X 2 Liver 072507 | 148000 | 115000 | 0.78 | 4.45 |
| | | | Average | | | 0.75 | 4.46 |
| | | | StDev | | | 0.02 | 0.01 |
| | | | % RSD | | | 3% | 0.1% |
| | | | Lower Limit | | | 0.53 | 4.23 |
| | | | Upper Limit | | | 0.98 | 4.68 |

TABLE 106

Beef Liver and Muscle
Glyphosate, N-acetylglyhosate, N-acetyl AMPA

| | Sample Information | | | Analyte Response (Fragment Ions peak areas; Ratio = base peak/minor peak; RT = peak retention time, min) | | | | | | | |
|---|---|---|---|---|---|---|---|---|---|---|---|
| | | | | Glyphosate | | | | N-acetyl AMPA | | | |
| Batch ID | Type | ng/g or ppb | Identification | 170 > 88 | 170 > 60 | Ratio | RT | 154 > 112 | 154 > 30 | Ratio | RT |
| 080707cm-2 | S | 1 | 1.0 ppb CS 062907 | 382 | 76 | 5.03 | 6.01 | 197 | 48 | 4.10 | 8 |
| | S | 2 | 2.0 ppb CS 062907 | 713 | 142 | 5.02 | 6.04 | 391 | 88 | 4.44 | 7.97 |
| | S | 5 | 5.0 ppb CS 062907 | 1722 | 396 | 4.35 | 6.01 | 987 | 199 | 4.96 | 7.99 |
| | S | 10 | 10 ppb CS 062907 | 3721 | 693 | 5.37 | 6.03 | 2072 | 323 | 6.41 | 7.98 |
| | S | 20 | 20 ppb CS 062907 | 7532 | 1415 | 5.32 | 6.10 | 4343 | 816 | 5.32 | 8.07 |
| | S | 50 | 50 ppb CS 062907 | 18943 | 3519 | 5.38 | 6.07 | 10296 | 1886 | 5.46 | 8.03 |
| | F | 50 | BL LOQ 1 062807 | 296 | 63 | 4.70 | 6.00 | 192 | 36 | 5.33 | 7.96 |
| | F | 50 | BL LOQ 2 062807 | 260 | 57 | 4.56 | 6.00 | 222 | 40 | 5.55 | 7.98 |
| | F | 50 | BM LOQ 1 062807 | 239 | 51 | 4.69 | 6.01 | 193 | 41 | 4.71 | 7.99 |
| | F | 50 | BM LOQ 2 062807 | 200 | 47 | 4.26 | 6.01 | 198 | 40 | 4.95 | 8 |
| | F | 500 | BL 10X 1 062807 | 2340 | 470 | 4.98 | 6.05 | 1965 | 366 | 5.37 | 8.03 |
| | F | 500 | BL 10X 2 062807 | 2418 | 439 | 5.51 | 6.06 | 1920 | 357 | 5.38 | 8.03 |
| | F | 500 | BM 10X 1 062807 | 1833 | 354 | 5.18 | 6.07 | 1781 | 357 | 4.99 | 8 |
| | F | 500 | BM 10X 2 062807 | 1936 | 379 | 5.11 | 6.05 | 1660 | 326 | 5.09 | 8.02 |
| | Average | | | | | 5.08 | 6.04 | | | 5.12 | 8.01 |
| | StDev | | | | | 0.39 | 0.04 | | | 0.82 | 0.04 |
| | % RSD | | | | | 8% | 0.6% | | | 16% | 0.5% |
| | Lower Limit | | | | | 3.55 | 5.74 | | | 3.58 | 7.61 |
| | Upper Limit | | | | | 6.60 | 6.35 | | | 6.65 | 8.41 |

| | Sample Information | | | Analyte Response (Fragment Ions peak areas; Ratio = base peak/minor peak; RT = peak retention time, min) N-acetylglyphosate | | | |
|---|---|---|---|---|---|---|---|
| Batch ID | Type | ng/g or ppb | Identification | 212 > 170 | 212 > 88 | Ratio | RT |
| 080707cm-2 | S | 1 | 1.0 ppb CS 062907 | 183 | 114 | 0.62 | 8.27 |
| | S | 2 | 2.0 ppb CS 062907 | 315 | 210 | 0.67 | 8.24 |
| | S | 5 | 5.0 ppb CS 062907 | 913 | 526 | 0.58 | 8.24 |
| | S | 10 | 10 ppb CS 062907 | 1852 | 1141 | 0.62 | 8.23 |
| | S | 20 | 20 ppb CS 062907 | 3792 | 2283 | 0.60 | 8.34 |
| | S | 50 | 50 ppb CS 062907 | 8985 | 5661 | 0.63 | 8.29 |
| | F | 50 | BL LOQ 1 062807 | 265 | 142 | 0.54 | 8.23 |
| | F | 50 | BL LOQ 2 062807 | 231 | 140 | 0.61 | 8.29 |
| | F | 50 | BM LOQ 1 062807 | 191 | 105 | 0.55 | 8.27 |
| | F | 50 | BM LOQ 2 062807 | 174 | 111 | 0.64 | 8.34 |
| | F | 500 | BL 10X 1 062807 | 1809 | 1024 | 0.57 | 8.31 |
| | F | 500 | BL 10X 2 062807 | 1845 | 1060 | 0.57 | 8.28 |
| | F | 500 | BM 10X 1 062807 | 1522 | 910 | 0.60 | 8.26 |
| | F | 500 | BM 10X 2 062807 | 1634 | 927 | 0.57 | 8.26 |
| | Average | | | | | 0.62 | 8.27 |
| | StDev | | | | | 0.03 | 0.04 |
| | % RSD | | | | | 5% | 0.5% |
| | Lower Limit | | | | | 0.43 | 7.85 |
| | Upper Limit | | | | | 0.80 | 8.68 |

CONCLUSIONS

This analytical method is suitable for the quantitation of glyphosate, N-acetylglyphosate, AMPA, and N-acetyl AMPA residues in milk, egg, and animal tissue matrices. The results support an LOQ of 0.025 mg/kg glyphosate equivalents in milk, egg, and muscle matrices, and an LOQ of 0.050 mg/kg in liver, kidney, and fat matrices. The estimated LOD values for all analytes were less than or equal to 0.008 mg/kg glyphosate equivalents in milk, egg, and muscle matrices, and less than or equal to 0.019 mg/kg glyphosate equivalents in liver, kidney, and fat matrices. The estimated LOD for glyphosate in all matrices examined was less than or equal to 0.009 mg/kg glyphosate equivalents.

The mean recoveries for individual fortification levels of each analyte and matrix in the validation trials ranged from 76% (AMPA in skim milk at 0.50 mg/kg) to 110% (AMPA in Egg Yolks at 0.025 mg/kg). The maximum standard deviation for individual fortification levels was 16% (N-acetyl AMPA in liver at 0.050 mg/kg).

Residue confirmation for glyphosate, N-acetylglyphosate, AMPA, and N-acetyl AMPA was demonstrated at the LOQ and 10×LOQ fortification levels based on retention time and the relative ratios of two MS/MS parent-to-fragment ion transitions detected during sample analysis.

The articles "a" and "an" are used herein to refer to one or more than one (i.e., to at least one) of the grammatical object of the article. By way of example, "an element" means one or more element. As used herein, the term "about," when referring to a value is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of determining the presence or amount of N-acetylglyphosate in a test sample comprising:
    a) providing said test sample suspected of containing said N-acetylglyphosate;
    b) extracting a composition comprising the N-acetylglyphosate from said test sample;
    c) adding a sufficient concentration of phosphoric acid to the composition comprising the N-acetylglyphosate, wherein said sufficient concentration allows for an improved response and linearity of N-acetylglyphosate during detection;
    d) chromatographically separating said N-acetylglyphosate from other constituents in said composition by a high performance liquid chromatography (HPLC) column; and,
    e) analyzing by a tandem mass spectrometer the chromatographically separated N-acetylglyphosate to determine the presence or amount of the N-acetylglyphosate in the test sample.

2. The method of claim 1, wherein the mass spectrometer is operated in positive ion mode.

3. The method of claim 1, wherein prior to chromatographically separating the N-acetylglyphosate from the other constituents in said composition, the composition comprising the N-acetylglyphosate is in aqueous 0.02M phosphoric acid.

4. The method of claim 1, wherein extracting the composition comprising the N-acetylglyphosate from said test sample comprises the steps selected from the group consisting of:
    a) i) extracting the composition comprising the N-acetylglyphosate from the test sample by liquid-liquid extraction; and,
       ii) disposing said extracted composition comprising the N-acetylglyphosate onto at least one extraction column and eluting the composition comprising the N-acetylglyphosate therefrom;
       or,
    b) i) mixing said test sample with a solid phase extraction sorbent under conditions that allow the solid phase extraction sorbent to bind said N-acetylglyphosate; and,
       ii) extracting the solid phase extraction sorbent and the bound N-acetylglyphosate from the sample by liquid/liquid extraction; and,
       iii) eluting said N-acetylglyphosate from the solid phase extraction sorbent.

5. The method of claim 4, wherein said liquid-liquid extraction comprises an extraction with an aqueous mixture comprising methanol and a dilute acid.

6. The method of claim 4, further comprising disposing the eluted composition comprising the N-acetylglyphosate from step 6(a)(ii) or 6(b)(iii) onto an anion exchange extraction column and eluting the N-acetylglyphosate therefrom.

7. The method of claim 1, wherein derivatization of said N-acetylglyphosate does not occur.

8. The method of claim 1, further comprising determining the presence or amount of aminomethyl phosphonic acid (AMPA), N-acetyl AMPA or glyphosate in the test sample.

9. The method of claim 1, wherein said test sample is from an animal or an environmental sample.

10. The method of claim 1, wherein said test sample is from a plant.

11. The method of claim 10, wherein said test sample comprises forage, grain, stover, a plant tissue, a solid process fraction matrix, flour, a meal process fractions, hay, hulls, a seed, meal, grits, or starch.

12. The method of claim 11, wherein said test sample comprises a solid matrix sample.

13. The method of claim 10, wherein said plant is a dicot.

14. The method of claim 10, wherein said plant is a monocot.

15. The method of claim 1, wherein said method has a limit of quantitation of about 0.05 mg/kg to about 0.5 mg/kg.

16. A method of determining the presence or amount of N-acetylaminomethylphosphonic acid (N-acetyl AMPA) in a test sample comprising:
    a) providing said test sample suspected of containing said N-acetyl AMPA;
    b) extracting a composition comprising the N-acetyl AMPA from said test sample;
    c) adding a sufficient concentration of phosphoric acid to the composition comprising the N-acetyl AMPA, wherein said sufficient concentration allows for an improved response and linearity of N-acetyl AMPA during detection;
    d) separating said N-acetyl AMPA from other constituents in said composition by a high performance liquid chromatography (HPLC) column; and,
    e) analyzing by a tandem mass spectrometer the separated N-acetyl AMPA to determine the presence or amount of the in the test sample.

17. The method of claim 16, wherein the mass spectrometer is operated in positive ion mode.

18. The method of claim 16, wherein prior to chromatographically separating the N-acetyl AMPA from the other constituents in said composition, the composition comprising the N-acetyl AMPA is in aqueous 0.02M phosphoric acid.

19. The method of claim 16, wherein extracting the composition comprising the N-acetyl AMPA from said test sample comprises the steps selected from the group consisting of:
    a) i) extracting the composition comprising the N-acetyl AMPA from the test sample using an aqueous dilute acid/methanol solution; and,
       ii) disposing said extracted composition comprising the N-acetyl AMPA onto at least one extraction column and eluting the composition comprising the N-acetyl AMPA therefrom;
       or,
    b) i) mixing said test sample with a solid phase extraction sorbent under conditions which allow said solid phase extraction sorbent to bind the N-acetyl AMPA; and,
       ii) extracting the solid phase extraction sorbent and the N-acetyl AMPA from the sample by liquid/liquid extraction; and,
       iii) eluting said N-acetyl AMPA from the solid phase extraction sorbent.

20. The method of claim 19, further comprising disposing the eluted composition comprising the N-acetyl AMPA from step 23(a)(ii) or (b)(iii) onto an anion exchange extraction column and eluting the N-acetyl AMPA therefrom.

21. The method of claim 16, wherein derivatization of said N-acetyl AMPA does not occur.

22. The method of claim 16, further comprising determining the presence or amount of aminomethyl phosphonic acid (AMPA), glyphosate or N-acetyl glyphosate in the test sample.

23. The method of claim 16, wherein said test sample is from an animal, a plant, or an environmental sample.

24. The method of claim 23, wherein said test sample comprises forage, grain, stover, a plant tissue, a solid process fraction matrix, flour, a meal process fractions, hay, hulls, a seed, meal, grits, or starch.

25. The method of claim 24, wherein said test sample comprises a solid matrix sample.

26. The method of claim 23, wherein said plant is a dicot.

27. The method of claim 23, wherein said plant is a monocot.

28. The method of claim 16, wherein said method has a limit of quantitation of about 0.05 mg/kg to about 0.5 mg/kg.

29. A method of determining the presence or amount of N-acetylglyphosate or N-acetyl AMPA in a test sample comprising:
 a) providing said test sample suspected of containing said N-acetylglyphosate or N-acetyl AMPA;
 b) extracting the composition comprising the N-acetylglyphosate or N-acetyl AMPA from the test sample, said extracting comprising the steps selected from the group consisting of:
  1) i) extracting said N-acetylglyphosate or said N-acetyl AMPA from the test sample by liquid-liquid extraction;
   ii) disposing said extracted composition comprising the N-acetylglyphosate or N-acetyl AMPA of step (b) onto a $C_{18}$ extraction column and eluting the N-acetylglyphosate or N-acetyl AMPA therefrom; or,
  2) i) mixing said test sample with a solid phase extraction sorbent under conditions which allow said solid phase extraction sorbent to bind the N-acetyl AMPA or N-acetylglyphosate;
   ii) extracting the solid phase extraction sorbent and the N-acetyl AMPA or the N-acetylglyphosate from the sample by liquid/liquid extraction; and,
   iii) eluting said bound N-acetyl AMPA or said bound N-acetylglyphosate from the solid phase extraction sorbent;
 c) disposing the eluted N-acetylglyphosate or N-acetyl AMPA from step (b) onto an anion exchange column comprising a surface functionally of m-divinylbenzene and N-vinylpyrrolidone copolymer having quaternary amines and eluting the N-acetylglyphosate therefrom;
 d) adding a sufficient concentration of phosphoric acid to said eluted N-acetylglyphosate of step (c), wherein said sufficient concentration allows for an improved response and linearity of N-acetylglyphosate during detection;
 e) chromatographically separating said N-acetylglyphosate or said N-acetyl AMPA from other constituents of step (d) using a phenyl-hexyl high performance liquid chromatography (HPLC) analytical column; and,
 f) analyzing the chromatographically separated sample of step (e) to determine the presence or amount of the N-acetylglyphosate or the N-acetyl AMPA in the test sample by a tandem quadrupole mass spectrometer operated in positive ion mode.

30. The method of claim 29, wherein said liquid-liquid extraction comprises the use of an aqueous dilute acid and methanol solution.

31. A method for determining the presence or amount of glyphosate in a test sample comprising
 a) providing the test sample suspected of containing the glyphosate;
 b) extracting a composition comprising the glyphosate from said test sample;
 c) adding a sufficient concentration of phosphoric acid to the composition comprising said glyphosate of step (b), wherein said sufficient concentration allows for an improved response and linearity of glyphosate during detection;
 d) chromatographically separating the glyphosate from other constituents in the composition by a high performance liquid chromatography (HPLC) column; and,
 e) analyzing by a tandem mass spectrometer the chromatographically separated glyphosate of step (d) to determine the presence or amount of the glyphosate in the test sample;
 wherein detection of said glyphosate occurs without derivatization of said glyphosate.

32. A method for determining the presence or amount of glyphosate in a test sample comprising
 a) providing the test sample suspected of containing the glyphosate;
 b) extracting a composition comprising the glyphosate from said test sample using a dilute aqueous acid/methanol solution.
 c) chromatographically separating the glyphosate from other constituents in the composition by a high performance liquid chromatography (HPLC) column; and,
 d) analyzing by a tandem mass spectrometer the chromatographically separated glyphosate of step (c) to determine the presence or amount of the glyphosate in the test sample;
 wherein detection of said glyphosate occurs without derivatization of said glyphosate.

33. The method of claim 32, wherein following step (b) and prior to step (c) a sufficient concentration of phosphoric acid is added to the composition comprising said glyphosate of step (b), wherein said sufficient concentration allows for an improved response and linearity of glyphosate during detection.

34. The method of claim 33, wherein the mass spectrometer is operated in positive ion mode.

35. The method of claim 33, wherein extracting the composition comprising the glyphosate from said test sample comprises the steps selected from the group consisting of:
 a) i) extracting the composition comprising the glyphosate from the test sample by liquid-liquid extraction; and,
   ii) disposing said extracted composition comprising the glyphosate onto at least one extraction column and eluting the composition comprising the glyphosate therefrom;
   or,
 b) i) mixing said test sample with a solid phase extraction sorbent under conditions which allow the solid phase extraction sorbent to bind the glyphosate; and,
   ii) extracting the solid phase extraction sorbent and the bound glyphosate from the sample by liquid/liquid extraction; and,
   iii) eluting said glyphosate from the solid phase extraction sorbent.

36. The method of claim 35, further comprising disposing the eluate of the extraction column or the solid phase extraction sorbent onto an anion exchange extraction column and eluting the glyphosate therefrom.

37. The method of claim 33, wherein said test sample is from an animal, a plant or an environmental sample.

38. The method of claim 37, wherein said test sample comprises forage, grain, stover, a plant tissue, a solid process fraction matrix, flour, a meal process fractions, hay, hulls, a seed, meal, grits, or starch.

39. The method of claim 38, wherein said test sample comprises a solid matrix sample.

40. The method of claim 37, wherein said plant is a dicot.

41. The method of claim 37, wherein said plant is a monocot.

42. A method of determining the presence or amount of glyphosate in a test sample comprising:
   a) providing said test sample suspected of containing glyphosate;
   b) extracting the composition comprising the glyphosate from the test sample, said extracting comprising the steps selected from the group consisting of:
      1) i) extracting said glyphosate from the test sample by liquid-liquid extraction;
         ii) disposing said extracted composition comprising the glyphosate of step (1)(i) onto a $C_{18}$ extraction column and eluting the glyphosate therefrom; or,
      2) i) mixing said test sample with a solid phase extraction sorbent under conditions which allow the solid phase extraction sorbent to bind said glyphosate;
         ii) extracting the solid phase extraction sorbent and the bound glyphosate from the sample by liquid/liquid extraction; and,
         iii) eluting said glyphosate from the solid phase extraction sorbent;
   c) disposing the eluted glyphosate from step (b) onto an anion exchange column comprising a surface functionally of m-divinylbenzene and N-vinylpyrrolidone copolymer having quaternary amines and eluting the glyphosate therefrom;
   d) adding a sufficient concentration of phosphoric acid to said eluted glyphosate of step (c), wherein said sufficient concentration allows for an improved response and linearity of glyphosate during detection;
   e) chromatographically separating said glyphosate from other constituents in the eluate of step (d) using a phenyl-hexyl high performance liquid chromatography (HPLC) analytical column; and,
   f) analyzing the chromatographically separated sample of step (e) to determine the presence or amount of glyphosate in the test sample by a tandem quadrupole mass spectrometer operated in positive ion mode;
   wherein detection of said glyphosate occurs without derivatization of said glyphosate.

43. A method for determining the presence or amount of aminomethyl phosphonic acid (AMPA) in a test sample comprising
   a) providing the test sample suspected of containing the AMPA;
   b) extracting a composition comprising at least one of said AMPA from said test sample;
   c) adding a sufficient concentration of phosphoric acid to the composition comprising the AMPA, wherein said sufficient concentration allows for an improved response and linearity of AMPA during detection;
   d) chromatographically separating the AMPA from other constituents in the composition by a high performance liquid chromatography (HPLC) column; and,
   e) analyzing by a tandem mass spectrometer at least one of the chromatographically separated AMPA of step (c) to determine the presence or amount AMPA in the test sample;
   wherein detection of the AMPA occurs without derivatization of said AMPA.

44. The method of claim 43, wherein the mass spectrometer is operated in positive ion mode.

45. The method of claim 43, wherein prior to chromatographically separating the AMPA from the constituents in said composition, the composition comprising said AMPA is in aqueous 0.02M phosphoric acid.

46. The method of claim 43, wherein extracting the composition comprising the AMPA from said test sample comprises the steps selected from the group consisting of:
   a) i) extracting the composition comprising the AMPA from the test sample by liquid-liquid extraction; and,
      ii) disposing said extracted composition comprising the AMPA onto at least one extraction column and eluting the composition comprising the AMPA therefrom; or,
   b) i) mixing said test sample with a solid phase extraction sorbent under conditions which allow the solid phase extraction sorbent to bind the AMPA; and,
      ii) extracting the solid phase extraction sorbent and the bound AMPA from the sample by liquid/liquid extraction; and,
      iii) eluting said AMPA from the solid phase extraction sorbent.

47. The method of claim 46, wherein said liquid-liquid extraction comprises an extraction with a dilute aqueous acid/methanol solution.

48. The method of claim 46, further comprising disposing the eluate of the extraction column onto a cation exchange extraction column and eluting the AMPA therefrom.

49. The method of claim 43, wherein said test sample is from an animal, a plant, or an environmental sample.

50. The method of claim 49, wherein said test sample comprises forage, grain, stover, a plant tissue, a solid process fraction matrix, flour, a meal process fractions, hay, hulls, a seed, meal, grits, or starch.

51. The method of claim 50, wherein said test sample comprises a solid matrix sample.

52. The method of claim 49, wherein said plant is a dicot.

53. The method of claim 51, wherein said plant is a monocot.

54. A method of determining the presence or amount of aminomethyl phosphonic acid (AMPA) in a test sample comprising:
   a) providing said test sample suspected of containing AMPA;
   b) extracting the composition comprising the AMPA from the test sample, said extracting comprising the steps selected from the group consisting of:
      1) i) extracting said AMPA from the test sample by liquid-liquid extraction;
         ii) disposing said extracted composition comprising the AMPA of step (1)(i) onto a $C_{18}$ extraction column and eluting the AMPA therefrom;
      or,
      2) i) mixing said test sample with a solid phase extraction sorbent under conditions which allow the solid phase extraction sorbent to bind the AMPA;

ii) extracting the solid phase extraction sorbent and the bound AMPA from the sample by liquid/liquid extraction; and, iii) eluting said AMPA from the solid phase extraction sorbent;

c) disposing the eluted AMPA from step (b) onto a cation exchange column comprising a surface functionally of m-divinylbenzene and N-vinylpyrrolidone copolymer having sulfonic acid substituents and eluting the AMPA therefrom;

d) adding a sufficient concentration of phosphoric acid to said eluated AMPA of step (c), wherein said sufficient concentration allows for an improved response and linearity of AMPA during detection;

e) chromatographically separating said AMPA from other constituents in the eluate of step (d) using a phenyl-hexyl high performance liquid chromatography (HPLC) analytical column; and, g) analyzing the chromatographically separated sample of step (e) to determine the presence or amount of AMPA in the test sample by a tandem quadrupole mass spectrometer operated in positive ion mode;

wherein detection of said AMPA occurs without derivatization of said AMPA.

55. A method for determining the presence or amount of at least one of glyphosate, N-acetylglyphosate, N-acetylaminomethylphosphonic acid (N-acetyl AMPA) or aminomethyl phosphonic acid (AMPA) in an oil test sample comprising a) providing the oil test sample suspected of containing at least one the glyphosate, the N-acetylglyphosate, the N-acetyl AMPA or the AMPA;

b) adding a sufficient concentration of phosphoric acid to said test sample of (a) wherein said sufficient concentration allows for an improved response and linearity of the glyphosate, the N-acetylglyphosate, the N-acetyl AMPA or the AMPA during detection;

c) extracting from said test sample a composition comprising at least one of said AMPA, said N-acetylglyphosate, said N-acetyl AMPA or the glyphosate by an aqueous-organic extraction; and, d) detecting at least one of said AMPA, said N-acetylglyphosate, said N-acetyl AMPA or said glyphosate, wherein said detecting comprises (a) chromatographically separating at least one of the AMPA, the N-acetylglyphosate, the N-acetyl AMPA or the glyphosate from the composition by a high performance liquid chromatography (HPLC) column; and, (b) analyzing by a tandem mass spectrometer at least one of the chromatographically separated glyphosate, N-acetylglyphosate, N-acetyl AMPA or AMPA to determine the presence or amount of at least one of the glyphosate, the N-acetylglyphosate, the N-acetyl AMPA or the AMPA in the test sample.

56. The method of claim 55, wherein said aqueous-organic extraction comprises a methylene chloride and phosphoric acid partition.

57. The method of claim 55, wherein the mass spectrometer is operated in positive ion mode.

58. The method of claim 55, wherein said test sample is from an animal, a plant, or an environmental sample.

59. The method of claim 58, wherein said plant is a dicot or a monocot.

60. A method for determining the presence or amount of at least one of glyphosate, N-acetylglyphosate, N-acetylaminomethylphosphonic acid (N-acetyl AMPA) or aminomethyl phosphonic acid (AMPA) in an oil test sample comprising a) providing the test sample suspected of containing at least one of the glyphosate, the N-acetylglyphosate, the N-acetyl AMPA or the AMPA;

b) adding a sufficient concentration of phosphoric acid to said test sample of (a) wherein said sufficient concentration allows for an improved response and linearity of the glyphosate, the N-acetylglyphosate, the N-acetyl AMPA or the AMPA during detection;

c) extracting a composition from said test sample comprising at least one of said AMPA, said N-acetylglyphosate, the N-acetyl AMPA or the glyphosate by an aqueous-organic partition;

d) chromatographically separating at least one of said AMPA, said N-acetylglyphosate, the N-acetyl AMPA or said glyphosate from the composition of step (c) using a phenyl-hexyl high performance liquid chromatography (HPLC) analytical column; and, e) analyzing the chromatographically separated sample of step (d) to determine the presence or amount of at least one of the AMPA, the glyphosate, the N-acetyl AMPA, or the N-acetylglyphosate in the test sample by a tandem quadrupole mass spectrometer operated in positive ion mode.

* * * * *